US011661410B2

(12) United States Patent
Li et al.

(10) Patent No.: US 11,661,410 B2
(45) Date of Patent: May 30, 2023

(54) TRICYCLIC COMPOUNDS AS HISTONE METHYLTRANSFERASE INHIBITORS

(71) Applicant: GLOBAL BLOOD THERAPEUTICS, INC., South San Francisco, CA (US)

(72) Inventors: Zhe Li, San Diego, CA (US); Ming Yu, Foster City, CA (US); Qing Xu, Foster City, CA (US); Manuel Zancanella, San Mateo, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 123 days.

(21) Appl. No.: 16/639,051

(22) PCT Filed: Aug. 13, 2018

(86) PCT No.: PCT/US2018/046541
§ 371 (c)(1),
(2) Date: Feb. 13, 2020

(87) PCT Pub. No.: WO2019/036377
PCT Pub. Date: Feb. 21, 2019

(65) Prior Publication Data
US 2023/0002351 A1 Jan. 5, 2023

Related U.S. Application Data

(60) Provisional application No. 62/712,864, filed on Jul. 31, 2018, provisional application No. 62/545,936, filed on Aug. 15, 2017.

(51) Int. Cl.
| | | |
|---|---|---|
| *C07D 403/12* | (2006.01) | |
| *C07D 401/14* | (2006.01) | |
| *C07D 405/14* | (2006.01) | |
| *C07D 219/10* | (2006.01) | |
| *C07D 221/06* | (2006.01) | |
| *C07D 401/12* | (2006.01) | |
| *C07D 413/12* | (2006.01) | |
| *C07D 471/04* | (2006.01) | |
| *C07D 471/08* | (2006.01) | |
| *C07D 491/044* | (2006.01) | |
| *C07D 491/056* | (2006.01) | |
| *A61K 31/473* | (2006.01) | |
| *A61K 31/4741* | (2006.01) | |
| *A61K 31/4375* | (2006.01) | |
| *A61P 35/00* | (2006.01) | |
| *C07D 215/42* | (2006.01) | |
| *C07B 59/00* | (2006.01) | |
| *C07D 487/04* | (2006.01) | |
| *C07D 453/02* | (2006.01) | |
| *C07D 487/08* | (2006.01) | |

(52) U.S. Cl.
CPC .......... *C07D 401/12* (2013.01); *C07B 59/002* (2013.01); *C07D 215/42* (2013.01); *C07D 401/14* (2013.01); *C07D 405/14* (2013.01); *C07D 413/12* (2013.01); *C07D 453/02* (2013.01); *C07D 487/04* (2013.01); *C07D 487/08* (2013.01); *C07D 491/044* (2013.01); *C07D 491/056* (2013.01); *C07B 2200/05* (2013.01)

(58) Field of Classification Search
CPC .. C07D 403/12; C07D 401/14; C07D 405/14; C07D 219/00; C07D 221/06; C07D 401/12; C07D 413/12; C07D 471/04; C07D 471/08; C07D 491/044; C07D 491/056; A61K 31/473; A61K 31/4741; A61K 31/4375; A61P 35/00
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 11,254,651 B2 | 2/2022 | Yu et al. | |
| 2015/0274660 A1 | 10/2015 | Pliushchev et al. | |
| 2019/0047981 A1 | 2/2019 | Yu et al. | |

FOREIGN PATENT DOCUMENTS

| | | |
|---|---|---|
| WO | WO 2015/085229 A1 | 6/2015 |
| WO | WO 2015/192981 A1 | 12/2015 |
| WO | WO 2017/102677 A1 | 6/2017 |
| WO | WO 2017/142947 A1 | 8/2017 |
| WO | WO 2019/036384 A1 | 2/2019 |

OTHER PUBLICATIONS

Patel et al. (Journal of the Indian Chemical Society (1955), 32, 187-90). Abstract.*
Kshatriya et al. (Journal of the University of Bombay, Science: Physical Sciences, Mathematics, Biological Sciences and Medicine (1948), 17A (Pt. 3), 13-24). Abstarct.*
Petrow, V., "Some amino-derivatives of dihydro-β-quinindene and tetrahydroacridine," Journal of the Chemical Society (resumed), 634-637, (1947).
Indian Application No. 202017010779, Examination report dated Oct. 13, 2021.
Agarwal et al., "G9a inhibition potentiates the anti-tumour activity of DNA double-strand break inducing agents by impairing DNA repair independent of p53 status," Cancer Letters, 280:467-475, (2016).

(Continued)

*Primary Examiner* — Bruck Kifle

(57) ABSTRACT

The present disclosure provides certain tricyclic compounds that are histone methyltransferases G9a and/or GLP inhibitors and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

27 Claims, No Drawings

(56) References Cited

OTHER PUBLICATIONS

Antignano et al., "Methyltransferase G9A regulates T cell differentiation during murine intestinal inflammation," J. Clin. Invest., 124(5):1945-1955, (2014).
Casciello et al., "Functional role of G9a histone methyltransferase in cancer," Front. Immunol., 6:Article 487, 1-12, (2015).
Charache et al., "Hydroxyurea: Effects on Hemoglobin F Production in Patients With Sickle Cell Anemia," Blood, 79(10):2555-2265, (1992).
Galli et al., "Sodium-dependent Norepinephrine-Induced Currents in Norepinephrine-Transporter-Transfected HEK-293 Cells Blocked by Cocaine and Antidepressants," J. Exp. Biol., 198(Pt 10):2197-2212, (1995).
Gao et al., "Synthesis and biological evaluation of benzimidazole acridine derivatives as potential DNA binding and apoptosis inducing agents," Bioorganic and Medicinal Chemistry, 23(8):1800-1807, (2015).
Imai et al., "Involvement of Histone H3 Lysine 9 (H3K9) Methyltransferase G9a in the Maintenance of HIV-1 Latency and Its Reactivation by BIX01294," J. Biol. Chem., 285(22):16538-16545, (2010).
Konshin et al., "2,3-Polymethylenequinolines," Chemistry of Heterocyclic Compounds, 9(4):490-492, (1973).
Korabecny et al., "Comparison of Novel Tacrine and 7-MEOTA Derivatives with Aromatic and Alicyclic Residues: Synthesis, Biological Evaluation and Docking Studies," Letters in Organic Chemistry, 10(4):291-297, (2013).
Krivega et al., "Inhibition of G9a methyltransferase stimulates fetal hemoglobin production by facilitating LCR/y-globin looping," Blood, 126(5):665-672, (2015).
Ling et al., "Lysine methyltransferase G9a methylates the transcription factor MyoD and regulates skeletal muscle differentiation," Proc. Natl. Acad. Sci. USA, 109(3):841-846, (2012).
Liu et al., "Discovery of a 2,4-Diamino-7-aminoalkoxyquinazoline as a Potent and Selective Inhibitor of Histone Lysine Methyltransferase G9," J. Med. Chem., 52(24):7950-7953, (2009).
Liu et al., "Discovery of an in Vivo Chemical Probe of the Lysine Methyltransferases G9a and GLP," J. Med. Chem., 56(21):8931-8942, (2013).
Liu et al., "Optimization of Cellular Activity of G9a Inhibitors 7-Aminoalkoxy-quinazolines," J. Med. Chem., 54(17):6139-6150, (2011).
Liu et al., "Protein Lysine Methyltransferase G9a Inhibitors: Design, Synthesis, and Structure Activity Relationships of 2,4-Diamino-7-aminoalkoxy-quinazolines," J. Med. Chem., 53(15):5844-5857, (2010).
Merkling et al., "The Epigenetic Regulator G9a Mediates Tolerance to RNA Virus Infection in *Drosophila*," PLoS Pathog., 11(4):e1004692, 25 pages, (2015).
Michel et al., "Identification of a Single Alpha 1-adrenoceptor Corresponding to the Alpha 1A-subtype in Rat Submaxillary Gland," Br. J. Pharmacol., 98(3):883-889, (1989).
Nguyen et al., "Functionalized acridin-9-yl phenylamines protected neuronal HT22 cells from glutamate-induced cell death by reducing intracellular levels of free radical species," Bioorganic and Medicinal Chemistry Letters, 24(15):1830-1838, (2014).
Nickel et al., "Antimalarial 6-aminoquinolines. XI. Some 2-, 3-, and 4-alkyl-, aryl-, and arylakyl derivatives (Abstract)," Arzneimittel-Forschung, 28(5):723-731, (1978).
Pitt et al., "Heteroaromatic Rings of the Future," J. Med. Chem., 52(9):2952-2963, (2009).
Pozharskii et al., Heterocycles in Life and Society Wiley, pp. 1-6, (1997).
PubChem SID 540857, Substance Record No. 5438-91-5, Alpha-[(dipropylamino)methyl]-5,6,7,8-tetrahydro-3-Acridinemethanol, Hydrochloride, Deposit Date: Mar. 26, 2005.
Renneville et al., "EHMT1 and EHMT2 inhibition induces fetal hemoglobin expression," Blood, 126(16):1930-1939, (2015).
San José-Enériz et al., "Discovery of first-in-class reversible dual small molecule inhibitors against G9a and DNMTs in hematological malignancies," Nature Communications, 8:15424, 60 pages, (2017).
Sankaran et al., "The Switch from Fetal to Adult Hemoglobin," Cold Spring Harb. Perspect. Med., 3(1):a011643, 14 pages, (2013).
Saucier et al., "Identification of an Endogenous 5-hydroxytryptamine2A Receptor in NIH-3T3 Cells: Agonist-Induced Down-Regulation Involves Decreases in Receptor RNA and Number," J. Neurochem., 68(5):1998-2011, (1997).
Shankar et al., "G9a, a multipotent regulator of gene expression," Epigenetics, 8(1):16-22, (2013).
Shinkai et al., "H3K9 methyltransferase G9a and the related molecule GLP," Genes Dev., 25(8):781-788, (2011).
Skripkina, "Methoxy derivatives of 7-sulfodimethylamidoacridine (Abstract)," Khimiya Geterotsiklicheskikh Soedinenii, 7(1):115-117, (1971).
Sondhi et al., "Synthesis, anti-inflammatory, and anticancer activity evaluation of some novel acridine derivatives," European Journal of Medicinal Chemistry, 45(2):555-563, (2009).
STN-Chemical Database Registry No. 5438-91-5, entry for alpha-[(dipropylamino)methyl]-5,6,7,8-tetrahydro-3-Acridinemethanol, Hydrochloride, Entered STN: Nov. 16, 1984.
Sweis et al., "Discovery and Development of Potent and Selective Inhibitors of Histone Methyltransferase G9a," ACS Med. Chem. Lett., 5(2):205-209, (2014).
Vedadi et al., "A chemical probe selectively inhibits G9a and GLP methyltransferase activity in cells," Nature Chemical Biology, 7(8):566-574, (2011).
Wang et al., "Histone H3K9 methyltransferase G9a represses PPARy expression and adipogenesis," EMBO J., 32(1):45-59, (2013).
Wang et al., "Human Mu Opiate Receptor. cDNA and Genomic Clones, Pharmacologic Characterization and Chromosomal Assignment," FEBS Lett., 338(2):217-222, (1994).
Wang et al., "Synthesis of Improved Lysomotropic Autophagy Inhibitors," Journal of Medicinal Chemistry, 58(7):3025-3035, (2015).
Yang et al., "G9a coordinates with the RPA complex to promote DNA damage repair and cell survival," Proc. Natl. Acad. Sci. USA, 2017:1700694114, 10 pages, (2017).
You et al., "Cancer Genetics and Epigenetics: Two Sides of the Same Coin?," Cancer Cell., 22(1):9-20, (2012).
Zhang et al., "Down-regulation of G9a triggers DNA damage response and inhibits colorectal cancer cells proliferation," Oncotarget, 6(5):2917-2927, (2015).
Zhang et al., "Synthesis and biological evaluation of benzimidazole derivatives as the G9a Histone Methyltransferase inhibitors that induce autophagy and apoptosis of breast cancer cells," Bioorganic Chemistry, 72:168-181, (2017).
WIPO Application No. PCT/US2018/046541, PCT International Search Report and Written Opinion of the International Searching Authority dated Nov. 26, 2018.
WIPO Application No. PCT/US2018/046554, PCT International Search Report and Written Opinion of the International Searching Authority dated Nov. 23, 2018.
Buckley et al., "Antagonist Binding Properties of Five Cloned Muscarinic Receptors Expressed in CHO-K1 Cells," Mol. Pharmacol., 35(4):469-476, (1989).
Nadarajah, B., "The Effect of Pralidoxime Chloride in the Assay of Acetylcholinesterase Using 5,5'-Dithio-bis(2-nitrobenzoic Acid) (Ellman's Reagent)," J. Anal. Toxicol., 16(3):192-193, (1992).
Robin et al., "Spectral Assignments and Reference Data," Magnetic Resonance in Chemistry, 39:225-228, (2001).
Sanchez et al., "Synthesis and biological evaluation of modified acridines: the effect of N- and O-substitutent in the nitrogenated ring on antitumor activity," European Journal of Medicinal Chemistry, 41:340-352, (2006).
European Application No. 18762967.0, Article 94(3) Communication dated Nov. 8, 2021.
Cao et al., "Recent progress in histone methyltransferase (G9a) inhibitors as anticancer agents," Eur J Med Chem., 179:537-546, (2019).
Hargarten et al., "Epigenetic Regulation of Autophagy: A Path to the Control of Autoimmunity," Frontiers in Immunology, 9:1-10, (Aug. 2018).
Database Registry, 2016, RN: 1990535-77-7, 1979782-29-0, 1979780-92-1, 1979015-73-0, 1978661-23-2, 1978660-05-7, 1978168-34-1, 1977637-49-2, 1975374-34-5, 1975374-28-7, 1970702-49-8, 1969464-

(56) References Cited

OTHER PUBLICATIONS 42-3, 1969464-27-4, 1969029-14-8, 1968373-19-4, 1968372-94-2, 1920308-84-4, 1920246-50-9, 1920154-06-8, 1919356-89-0, 1916663-38-1, 1916296-59-7, 1916296-20-2, 1916295-92-5, 1916239-76-3, 1916239-61-6, 1915858-40-0, 1915847-31-2, 1914490-70-2, 1914490-64-4, 1914490-61-1, 1914490-57-5, 1914344-67-4, 1912974-14-1, 1912289-60-1, 1911814-94-2, 1489600-85-2, 1461683-27-1, 1458741-39-3, 1458388-98-1, 1458190-03-8, 1457748-50-3, 1457264-46-8, 1457262-02-0, 1457111-61-3, 1456083-49-0, 1456050-71-7, 1455960-19-6, 1455956-63-4, 1455818-67-3, 1455289-82-3, 1455110-39-0, 1409779-79-8, 1406796-39-1, 1406095-18-8, 1406000-85-8, 1405794-32-2, 1405672-52-7, 1284727-94-1, 1275563-57-9, 1275562-92-9, 746580-27-8, [Retrieved from STN International, Aug. 2, 2022].

Del Giudice et al., "Synthesis and cholinesterase inhibitory activity of 6-,7-methoxy-(and hydroxy-) tacrine derivatives," Farmaco, 51(11):693-698, (1996).

Kshatriya, K.C., et al., "Acridine derivatives as antimalarials. Part VI. 5-dialkyl amino alkyl amino derivatives of 3-7-dimethoxy-8-chloro, 7-methoxy-8-chloro and 7-methoxy-2-8-dichloro acridine," Journal of the University of Bombay Science: Physical Sciences, Mathematics, Biological Sciences and Medicine, 19(28):69-72, (1950).

Saracoglu, Murat et al., "The Investigation of Structure-Activity Relations of Tacrine Analogues: Electronic-Topological Method," The Open Medicinal Chemistry Journal, 2:75-80, (2008).

STN REG database RN : 1979015-73-0, 1978661-23-2, 1978660-05-7, 4 pgs., (2016).

Tang, Jianhong et al., "The Divergent Transformations of Aromatic o-Aminonitrile with Carbonyl Compound," J. Heterocyclic Chem., 49:533-542, (2012).

Zhou, Jinpei et al., "Synthesis of tetrahydroacridines and their biological activities," Chinese Journal of Medicinal Chemistry, 10(3):172-176, (2000).

CN Application No. 201880064130.8, Office Action dated Aug. 12, 2022.

CN Application No. 201880064130.8, Search Report dated Aug. 18, 2022.

JP Application No. 2020-508394, Office Action dated Aug. 23, 2022.

TW Application No. 107128321, Office Action dated Jul. 13, 2022.

* cited by examiner

TRICYCLIC COMPOUNDS AS HISTONE METHYLTRANSFERASE INHIBITORS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/545,936, filed Aug. 15, 2017 U.S. Provisional Application No. 62/712,864, filed Jul. 31, 2018, and International Application No. PCT/US2018/046541 filed Aug. 13, 2018.

FIELD OF THE DISCLOSURE

The present disclosure provides certain tricyclic compounds that are histone methyltransferases G9a and/or GLP inhibitors, and are therefore useful for the treatment of diseases treatable by inhibition of G9a and/or GLP such as cancers and hemoglobinopathies (e.g., beta-thalassemia and sickle cell disease). Also provided are pharmaceutical compositions containing such compounds and processes for preparing such compounds.

BACKGROUND

Chromatin modification plays an essential role in transcriptional regulation. These modifications, including DNA methylation, histone acetylation and histone methylation, are important in a variety of biological processes including protein production and cellular differentiation, and are emerging as attractive drug targets in various human diseases. Two particular enzymes associated with histone methylation are G9a and GLP, also known as EHMT2 and EHMT1 (Euchromatic histone-lysine N-methyltransferase 2 and 1). G9a and GLP are the primary enzymes for mono- and dimethylation at Lys 9 of histone H3 (H3K9me1 and H3K9me2), and exist predominantly as a G9a-GLP heteromeric complex that appears to be a functional H3K9 methyltransferase in vivo. Structurally, either G9a or GLP is composed of a catalytic SET domain, a domain containing ankyrin repeats (involved in protein-protein interactions) and nuclear localization signals on the N-terminal region. The SET domain is responsible for the addition of methyl groups on H3, whereas the ankyrin repeats have been observed to represent mono- and dimethyl lysine binding regions. The G9a-GLP complex is thus not only able to both methylate histone tails but also able to recognize this modification, and can function as a scaffold for the recruitment of other target molecules on the chromatin. See Shinkai et al., *Genes Dev.* 2011; 25(8):781-8 and Shankar et al., Epigenetics. 2013; 8(1): 16-22.

Many studies have reported that G9a and GLP play critical roles in various biological processes. Several reports have highlighted its link to a variety of cancers. See Cascielle et al., *Front. Immunol.* 2015; 6:487. It is upregulated in hepatocellular carcinoma, B cell acute lymphoblastic leukemia and lung cancers. In addition, elevated expression of G9a in aggressive lung cancer correlates with poor prognosis, while its knockdown in highly invasive lung cancer cells suppressed metastasis in an in vivo mouse model. In prostate cancer cells (PC3), G9a knockdown caused significant morphological changes and inhibition of cell growth. See Liu et al., *J. Med. Chem.* 2013; 56(21):8931-42 and Sweis et al., *ACS Med. Chem. Lett.* 2014; 5(2):205-9. Loss of G9a has been demonstrated to impair DNA damage repair and enhance the sensitivity of cancer cells to radiation and chemotherapeutics. See Yang et al., *Proc. Natl. Acad. Sci. USA,* 2017, doi: 10.1073/pnas. 1700694114.

Interestingly, recent studies have also shown that the inhibition of G9a and GLP by either genetic depletion or pharmacological intervention increased fetal hemoglobin (HbF) gene expression in erythroid cells. See Krivega et al., *Blood,* 2015; 126(5):665-72 and Renneville et al., *Blood* 2015; 126(16): 1930-9. Inducing fetal globin gene would be potentially therapeutically beneficial for the disease of hemoglobinopathies, including beta-thalassemia where the production of normal β-globin, a component of adult hemoglobin, is impaired. Similarly, induction of HbF would potentially be beneficial by diluting the concentration of hemoglobin S (HbS) molecules, thereby reducing polymerization of HbS. See Sankaran et al., *Cold Spring Harb. Perspect. Med.* 2013; 3(1):a011643. Moreover, G9a or GLP inhibitions may potentiate other clinically used therapies, such as hydroxyurea or HDAC inhibitors. These agents may act, at least in part, by increasing γ-globin gene expression through different mechanisms. See Charache et al., *Blood,* 1992; 79(10):2555-65. Thus, there is a need for the development of small molecules that are capable of inhibiting the activity of G9a and/or GLP.

The compounds of the present disclosure fulfill this and related needs.

SUMMARY

In one aspect provided is a compound of Formula (I):

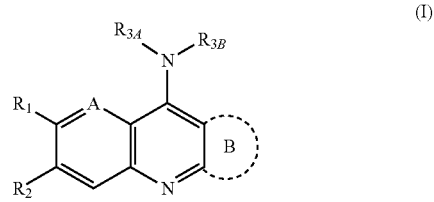

or a pharmaceutically acceptable salt thereof, wherein:
$R_1$ and $R_2$ can be independently hydrogen, halogen, cyano, alkyl, haloalkyl, hydroxy, hydroxyalkyl, aryloxy, heteroaryloxy, cycloalkyl (optionally substituted with one or more hydroxy), cycloalkoxy, cyanoalkoxy, alkoxy (optionally substituted with one or more $R_A$, independently selected from deuterium, hydroxy, alkoxy or (hydroxy)alkoxy), haloalkoxy or aminosulfonyl (optionally substituted with one or more alkyl), provided that $R_1$ and $R_2$ are not each hydrogen; or $R_1$ and $R_2$, together with the atoms to which they are attached, form a monocyclic heterocyclyl group;
A can be CH or N;
$R_{3A}$ can be
(a) heterocyclyl;
(b) heterocyclylalkyl;
(c) spiroheterocycloamino (optionally substituted with one or more $R_B$, independently selected from alkyl, aryl (optionally substituted with one or more $R_D$, independently selected from halogen and alkyl) and alkoxycarbonyl);
(d) cycloalkylalkyl (optionally substituted with one or more $R_C$, independently selected from amino and alkylamino);

(e) heteroaralkyl (optionally substituted with alkyl);
(f) alkyl (optionally substituted with alkylamino); or
(g) hydrogen;

wherein the heterocyclyl rings of (a) and (b) are independently optionally substituted with one or more $R_E$, independently selected from halogen, hydroxy, alkoxy, hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy);

$R_{3B}$ can be hydrogen, alkyl or —(C=O)NH$_2$;
Ring B can be

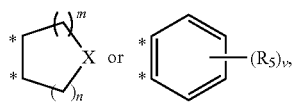

wherein the asterisks indicate the points of attachments to the pyridinyl ring of Formula (I);
m and n are independently 1, 2, 3 or 4, wherein the sum of m+n can be 2, 3, 4 or 5;
X can be $CR_{4A}R_{4B}$, $NR_{4C}$ or O;
$R_{4A}$, $R_{4B}$ and $R_{4C}$ can be independently hydrogen or alkyl;
each $R_5$ can be independently alkyl; and
v can be 0, 1, 2, 3 or 4.

In another aspect provided is a compound of Formula (I):

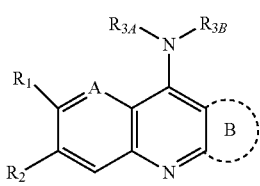

(I)

or a pharmaceutically acceptable salt thereof, wherein:
$R_1$ and $R_2$ can be independently hydrogen, halogen, cyano, alkyl, haloalkyl, hydroxy, hydroxyalkyl, aryloxy, heteroaryloxy, cycloalkyl (optionally substituted with one or more hydroxy), cycloalkoxy, cyanoalkoxy, alkoxy (optionally substituted with one or more $R_A$, independently selected from hydroxy, alkoxy or (hydroxy)alkoxy), haloalkoxy or aminosulfonyl (optionally substituted with one or more alkyl), provided that $R_1$ and $R_2$ are not each hydrogen; or $R_1$ and $R_2$, together with the atoms to which they are attached, form a monocyclic heterocyclyl group;

A can be CH or N;
$R_{3A}$ can be
(a) heterocyclyl;
(b) heterocyclylalkyl;
(c) spiroheterocycloamino (optionally substituted with one or more $R_B$, independently selected from alkyl, aryl (optionally substituted with one or more $R_D$, independently selected from halogen and alkyl) and alkoxycarbonyl);
(d) cycloalkylalkyl (optionally substituted with one or more $R_C$, independently selected from amino and alkylamino);
(e) heteroaralkyl (optionally substituted with alkyl); or
(f) alkyl;

wherein the heterocyclyl rings of (a) and (b) are independently optionally substituted with one or more $R_E$, independently selected from hydroxy, alkoxy, hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy);

$R_{3B}$ can be hydrogen, alkyl or —(C=O)NH$_2$;
Ring B can be

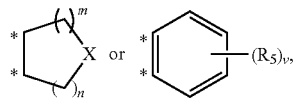

wherein the asterisks indicate the points of attachments to the pyridinyl ring of Formula (I);
m and n are independently 1, 2, 3 or 4, wherein the sum of m+n can be 2, 3, 4 or 5;
X can be $CR_{4A}R_{4B}$, $NR_{4C}$ or O;
$R_{4A}$, $R_{4B}$ and $R_{4C}$ can be independently hydrogen or alkyl;
each $R_5$ can be independently alkyl; and
v can be 0, 1, 2, 3 or 4.

For example, compounds of Formula (I), and pharmaceutically acceptable salts thereof, include compounds of Formula (I-1)

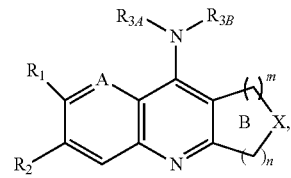

compounds of Formula (I-2)

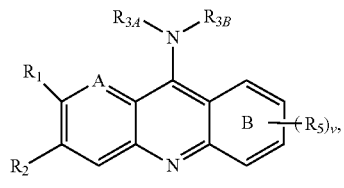

and pharmaceutically acceptable salts of any of the foregoing.

In a second aspect, this disclosure is directed to a pharmaceutical composition comprising a compound of Formula (I) (or any of the embodiments thereof described herein) or a pharmaceutically acceptable salt thereof; and a pharmaceutically acceptable excipient.

In a third aspect, this disclosure is directed to a method of treating a disease treatable by inhibition of G9a and/or GLP in a subject in need of such treatment, can include administering to the subject in need thereof, a compound of Formula (I) (or any of the embodiments thereof described herein) or a pharmaceutically acceptable salt thereof, or a pharmaceutical composition comprising a compound of Formula (I) (or any of the embodiments thereof described herein), or a pharmaceutically acceptable salt thereof, in a therapeutically effective amount, and a pharmaceutically acceptable excipient. In one embodiment, the disease can be a hemoglobinopathy, such as beta-thalassemia and sickle cell disease. See Krivega et al., *Blood* 2015; 126(5):665-72 and Renneville et al., *Blood,* 2015; 126(16): 1930-9. In a second embodiment, the disease can be a cancer or tumor, for example, a cancer or tumor where G9a or GLP can be overexpressed. Examples of such cancers and tumors include, but are not limited to: Colorectal Cancer, Osteosarcoma Cancer, Acute Lymphoblastic Leukemia (ALL); Acute Myeloid Leukemia (AML); Adrenocortical Carcinoma, Kaposi Sarcoma (Soft Tissue Sarcoma); AIDS-Related Lymphoma (Lymphoma); Primary CNS Lymphoma; Anal Cancer; Gastrointestinal Carcinoid Tumors; Astrocytomas; Atypical Teratoid/Rhabdoid Tumor; Basal Cell Carcinoma of the Skin; Bile Duct Cancer; Bladder Cancer; Bone Cancer (includes Ewing Sarcoma and Osteosarcoma and Malignant Librous Histiocytoma); Brain Tumors; Breast Cancer; Bronchial Tumors—Burkitt Lymphoma; Cardiac Tumors; Embryonal Tumors (Brain Cancer); Germ Cell Tumor (Brain Cancer); Primary CNS Lymphoma; Cervical Cancer; Cholangiocarcinoma; Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell Lymphoma; Ductal Carcinoma In Situ (DCIS); Endometrial Cancer (Uterine Cancer); Ependymoma (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Retinoblastoma; Lallopian Tube Cancer; Librous Histiocytoma of Bone; Gallbladder Cancer; Gastric (Stomach) Gastrointestinal Stromal Tumors (GIST) (Soft Tissue Sarcoma); CNS Germ Cell Tumors (Brain Cancer); Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Hepatocellular (Liver) Cancer; Histiocytosis, Langerhans Cell; Hodgkin Lymphoma; Hypopharyngeal Cancer (Head and Neck Cancer); Intraocular Melanoma; Islet Cell Tumors, Pancreatic Neuroendocrine Tumors; Kidney (Renal Cell) Cancer; Langerhans Cell Histiocytosis; Laryngeal Cancer (Head and Neck Cancer); Leukemia; Lip and Oral Cavity Cancer (Head and Neck Cancer); Lung Cancer (Non-Small Cell and Small Cell); Lymphoma; Male Breast Cancer; Melanoma; Merkel Cell Carcinoma (Skin Cancer); Mesothelioma, Malignant Mesothelioma; Metastatic Squamous Neck Cancer with Occult Primary (Head and Neck Cancer); Midline Tract Carcinoma Involving NUT Gene; Mouth Cancer (Head and Neck Cancer); Multiple Endocrine Neoplasia Syndromes; Multiple Myeloma/Plasma Cell Neoplasms; Mycosis Lungoides (Lymphoma); Myelodysplastic Syndromes, Myelodysplastic/Myeloproliferative Neoplasms; Myelogenous Leukemia, Chronic (CML); Myeloproliferative Neoplasms, Chronic; Nasal Cavity and Paranasal Sinus Cancer (Head and Neck Cancer); Nasopharyngeal Cancer (Head and Neck Cancer); Nasopharyngeal Cancer—Neuroblastoma; Non-Hodgkin Lymphoma; Oral Cancer; Lip and Oral Cavity Cancer and Oropharyngeal Cancer (Head and Neck Cancer); Ovarian Cancer; Pancreatic Cancer; Papillomatosis; Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma; Pregnancy and Breast Cancer; Primary CNS Lymphoma; Primary Peritoneal Cancer; Prostate Cancer; Rectal Cancer; Recurrent Cancer; Rhabdomyosarcoma (Soft Tissue Sarcoma); Salivary Gland Cancer (Head and Neck Cancer); Salivary Gland Tumors; Vascular Tumors (Soft Tissue Sarcoma); Uterine Sarcoma; Sezary Syndrome (Lymphoma); Small Intestine Cancer; Soft Tissue Sarcoma; Squamous Cell Carcinoma of the Skin; Skin Cancer; Squamous Neck Cancer with Occult Primary, Metastatic (Head and Neck Cancer); T-Cell Lymphoma, Cutaneous; Lymphoma (Mycosis Fungoides and Sezary Syndrome); Throat Cancer (Head and Neck Cancer); Nasopharyngeal Cancer; Oropharyngeal Cancer; Hypopharyngeal Cancer; Thymoma and Thymic Carcinoma; Thyroid Cancer; Urethral Cancer; Vaginal Cancer; Vascular Tumors (Soft Tissue Sarcoma); Vulvar Cancer; Myelodysplastic syndrome (MDS); and Wilms Tumor. Thus, the terms "cancerous cell," "cancer cell" or "tumor cell" as provided herein, includes a cell afflicted by any one of or related to the above identified conditions. See Cascielle et al., *Front. Immunol.* 2015; 6:487, Agarwal et al., *Cancer Letters* 2016: 467 and Zhang et al., *Oncotarget* 2015, 6(5): 2917. In a second embodiment, treating a cancer and/or tumor comprises increasing tumor free survival and/or reducing tumor mass and/or slowing tumor growth. In a third embodiment, the disease can be a cancer predisposition syndrome, such as Cowden syndrome. See You et al., *Cancer Cell.* 2012; 22(1):9-20. In a fourth embodiment, the disease can be an inflammatory and/or autoimmune disease, such as intestinal inflammation, arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis. See Antignano et al., *J. Clin. Invest.* 2014 4(5): 1945-55. In a fifth embodiment, the disease can be a metabolic disease, such as diabetes and/or obesity. See Wang et al., *EMBO J.* 2013; 32(1):45-59. In a sixth embodiment, the disease can be related to skeletal muscle development and regeneration. See Ling et al., *Proc. Natl. Acad. Sci. USA,* 2012; 109(3):841-6. In a seventh embodiment, the disease can be a viral disease, such as HIV-1 (human immunodeficiency virus 1) and HBV (Hepatitis B Virus). See Imai et al., *J. Biol. Chem.* 2010; 285(22): 16538-45 and Merkling et al., *PLoS Pathog.* 2015; 11(4). The compounds and compositions described herein can be administered with one or more additional therapeutic agents including, but not limited to, anticancer agents and antiviral agents. See, e.g., *Front Immunol.* 2015; 6:487.

In a fourth aspect provided is the use of a compound of Formula (I) (or any of the embodiments thereof described herein) or a pharmaceutically acceptable salt thereof, in the treatment of the diseases provided in the third aspect herein.

In a fifth aspect, this disclosure is directed to a method of inhibiting G9a and/or GLP, that can include contacting a cell that contains G9a with a therapeutically effective amount of a compound of Formula (I) (or any of the embodiments thereof described herein) or a pharmaceutically acceptable salt thereof, thereby inhibiting the activity of G9a. In some embodiments, the cell suffers from one or more of the diseases provided in the third aspect herein.

DETAILED DESCRIPTION

Definitions:

Unless otherwise stated, the following terms used in the specification and claims are defined for the purposes of this Application and have the following meaning:

"Alkyl" means a linear saturated monovalent hydrocarbon radical of one to ten carbon atoms or a branched saturated monovalent hydrocarbon radical of three to ten carbon atoms, e.g., methyl, ethyl, n-propyl, 2-propyl (isopropyl), n-butyl, sec-butyl, iso-butyl, tert-butyl, pentyl (straight-chained or branched), hexyl (straight-chained or branched), heptyl (straight-chained or branched) and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene and the like.

"Alkoxy" means a —OR radical where R is alkyl as defined above, e.g., methoxy, ethoxy, propoxy, or 2-propoxy, n-, iso-, or tert-butoxy and the like.

"Alkoxyalkyl" means alkyl as defined above which is substituted with one or two alkoxy groups as defined above, e.g., methoxyethyl, ethoxyethyl, methoxypropyl and the like.

"Alkylcarbonyl" or "Acyl" means a —COR radical where R is alkyl as defined above, e.g., methylcarbonyl, ethylcarbonyl and the like.

"Alkylsulfonyl" means a —SO$_2$R radical where R is alkyl as defined above, e.g., methylsulfonyl or ethylsulfonyl.

"Alkoxycarbonyl" means a —(C=O)OR radical where R is alkyl as defined above, e.g., tert-butoxycarbonyl and the like.

"Alkoxycarbonylalkyl" means alkyl as defined above which is substituted with one or two alkoxycarbonyl groups as defined above, e.g., methoxycarbonylethyl, ethoxycarbonylethyl, methoxycarbonylpropyl and the like.

"Amino" means a —NH$_2$ group.

"Aminoalkyl" means a -(alkylene)-NR'R" where R' and R" are independently hydrogen or alkyl as defined above.

"Aminosulfonyl" means a "—SO$_2$NH$_2$" group.

"Alkylamino" means a —NR'R" radical where R' and R" are independently hydrogen or alkyl as defined above, and at least one of R' and R" is alkyl.

"Aminocarbonyl" means a —(C=O)—NH$_2$ group, where one or each of the hydrogens in the —NH$_2$ can be independently replaced with an alkyl group, as defined above.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above, e.g., benzyl, phenethyl and the like.

"Aryloxy" means a —OR radical where R is aryl as defined above, e.g., phenoxy, naphthyloxy and the like.

"Cyano" means a —CN group.

"Cyanoalkyl" means an alkyl group as defined above, substituted with one or more cyano groups, e.g., cyanomethyl, cyanoethyl, 2-cyanopropyl, 2,3-dicyanobutyl and the like.

"Cyanoalkoxy" means a —OR radical where R is alkyl as defined above, e.g., methoxy, ethoxy, propoxy, or 2-propoxy, n-, iso-, or tert-butoxy and the like, where R is substituted with a cyano group. For example, cyanomethoxy, 2-cyanoethoxy, 2-cyanopropoxy and the like.

"Cycloalkyl" means a saturated monovalent monocyclic hydrocarbon radical of three to ten carbon atoms, or a saturated monovalent bicyclic hydrocarbon radical of five to ten carbon atoms, unless stated otherwise. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Examples of monocyclic cycloalkyl groups includes, for example, cyclopropyl, cyclobutyl, cyclopentyl, cyclohexyl and the like. Examples of bicyclic cycloalkyl groups include, for example, decalinyl, norbornanyl, decahydronaphthalenyl, dodecahydro-1H-phenalenyl, adamantly, bicyclo[3.3.0]octanyl, spiro[3.3]heptanyl, spiro[3.4]octanyl, spiro[3.4]octanyl, spiro[3.5]nonanyl, spiro[4.4]nonanyl, spiro[3.6]decanyl, spiro[4.5]decanyl and the like.

"Cycloalkoxy" means a —OR radical where R is cycloalkyl as defined above, e.g., forming a cyclopropoxy, cyclobutoxy, cyclopentoxy, cyclohexoxy, cycloheptoxy, cyclooctoxy and the like.

"Cycloalkylalkyl" means a -(alkylene)-R radical where R is cycloalkyl as defined above, e.g., cyclopropylmethyl, cyclohexylmethyl and the like.

"Cycloalkenyl" means a cyclic hydrocarbon radical of three to ten carbon atoms containing a double bond, unless stated otherwise, e.g., cyclopropenyl, cyclobutenyl, cyclopentenyl, cyclohexenyl and the like.

"Carboxyalkyl" means a alkyl radical as defined above that is substituted with a carboxy (—COOH) group.

"Deuterated alkoxy" means an alkoxy radical as defined above, where one or more hydrogen atoms (up to the total number of hydrogen atoms in the alkoxy group) are replaced by deuterium, e.g., —OCHD$_2$, —OCD$_3$, —OCH$_2$CD$_3$, —OCD$_2$CD$_3$ and the like.

"Deuterated alkyl" means an alkyl radical as defined above that is substituted with one, two or three deuterium atoms.

"Halo" or "halogen" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$ and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, —OCH$_2$F and the like. When R is haloalkyl where the alkyl is substituted with only fluoro, it is referred to in this Application as fluoroalkoxy.

"Haloalkoxyalkyl" means alkyl as defined above which is substituted with one or two haloalkoxy groups as defined above, e.g., trifluormethoxyethyl, 3,3,3-trifluoroethoxyethyl and the like.

"Haloalkylcarbonyl" means a —COR radical where R is haloalkyl as defined above, e.g., trifluoromethylcarbonyl, pentafluoroethylcarbonyl and the like.

"Hydroxyalkyl" means alkyl as defined above which is substituted with one or two hydroxy groups as defined above, e.g., hydroxymethyl, hydroxyethyl, 1,3-dihydroxypropyl and the like.

"Halocycloalkyl" means cycloalkyl group as defined above which is substituted with one, two or three halogen as defined above, e.g., 2,2-difluorocyclopropyl and the like.

"Heterocyclyl" means a saturated or unsaturated monovalent group of 3 to 10 ring atoms in which one, two, or three ring atoms are heteroatom independently selected from N, O and $S(O)_n$, where n is an integer from 0 to 2 and the remaining ring atoms are C, unless stated otherwise.

Additionally, one or two ring carbon atoms in the heterocyclyl ring can optionally be replaced by a —C(=O)— group. Heterocyclyl groups can be monocyclic or bicyclic. More specifically the term heterocyclyl includes, but is not limited to, pyrrolidino, piperidino, homopiperidino, 2-oxopyrrolidinyl, 2-oxopiperidinyl, morpholino, piperazino, dihydropyranyl, thiomorpholino, 1,3-dioxinyl, 1,3-dioxanyl, 1,4-dioxanyl, 1,2-dioxolanyl, 1,3-dioxolanyl, 1,4-dioxolanyl, 2H-1,2-oxazinyl, maleimido, succinimido, barbituric acid, thiobarbituric acid, dioxopiperazino, hydantoino, dihydrouracilyl, hexahydro-1,3,5-triazinyl, imidazolino, imidazolidino, isoxazolino, isoxazolidino, oxazolino, oxazolidino, oxazolidinono, thiazolino, thiazolidino, oxiranyl, pyrrolidonyl, pyrrolidionyl, 4-piperidonyl, pyrazolino, pyrazolidino, 2-oxopyrrolidino, tetrahydropyranyl, 4H-pyranyl, tetrahydrothiopyranyl, azepanyl and the like. Heterocyclic groups can be monocyclic, for example, pyrrolidine, piperidine and piperazine, or bicyclic, for example, hexahydro-1H-pyrrolizine. Bicyclic heterocyclyl groups include bridged and fused ring systems, for example, indoline, 7-azabicyclo[2.2.1]heptane, hexahydro-1H-pyrrolizine, 8-azabicyclo[3.2.1]octane and the like. When the heterocyclyl ring is unsaturated it can contain one or two ring double bonds provided that the ring is not aromatic. When the heterocyclyl ring has no double bond, it can be referred to herein as saturated heterocyclyl.

"Heterocyclylalkyl" or "heterocycloalkyl" means a -(alkylene)-R radical where R is heterocyclyl ring as defined above e.g., tetrahydrofuranylmethyl, piperazinylmethyl, morpholinylethyl and the like. When a heterocyclylalkyl group contains a secondary amino group (i.e., —NH—), the alkyl portion of the heterocyclylalkyl may replace the hydrogen on the nitrogen in the heterocyclyl ring, such that the heterocyclyl ring is linked to the alkyl potion of the heterocyclylalkyl group via the nitrogen atom.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl and the like. When the heteroaryl ring contains 5- or 6 ring atoms, it is also referred to herein as 5- or 6-membered heteroaryl.

"Heteroaralkyl" means a -(alkylene)-R radical where R is heteroaryl as defined above, e.g., pyridinylmethyl and the like. The heteroaryl ring in heteroaralkyl can contain from 5- to 10 ring atoms. When the heteroaryl ring in heteroaralkyl contains 5- or 6 ring atoms, it is also referred to herein as 5- or 6-membered heteroaralkyl. When a heteroaralkyl group contains a secondary amino group (i.e., —NH—), the alkyl portion of the heteroaralkyl may replace the hydrogen on the nitrogen in the heteroaryl ring, such that the heteroaryl ring is linked to the alkyl potion of the heteroaralkyl group via the nitrogen atom.

"Heteroaryloxy" means a —OR radical where R is heteroaryl as defined above, e.g., pyridinoxy, pyrazinoxy, pyrimidinoxy, quinolinoxy and the like.

"Hydroxy" means —OH group.

"(Hydroxy)alkoxy" means a —OR radical where R is alkyl as defined above, e.g., methoxy, ethoxy, propoxy, or 2-propoxy, n-, iso-, or tert-butoxy and the like, where R is substituted with one or more hydroxy groups.

"Oxo" means a=(O) radical. As would be readily apparent to one of skill in the art, "carbonyl" refers to an oxo radical attached to a carbon atom, i.e., —C(O)—.

"Spiroheterocycloamino" means a saturated bicyclic ring having 7 to 10 ring atoms in which one, two, or three ring atoms are heteroatom selected from N, N-oxide, O and $S(O)_n$, where n is an integer from 0 to 2, the remaining ring atoms being C, provided that at least one ring atom is N and the rings are connected through only one atom. The connecting atom is also called the spiroatom and is most often a quaternary carbon ("spiro carbon"). Representative examples include, but are not limited to, 2-azaspiro[3.3]heptane, 2-oxaspiro[3.3]heptane, 1-azaspiro[3.3]heptane, 1-oxaspiro[3.3]heptane, 5-oxaspiro[3.4]octane, 5-azaspiro[3.4]octane, 2-oxaspiro[3.4]octane, 2-azaspiro[3.4]octane, 1-oxa-4-azaspiro[4.4]nonane, 1,4-dioxaspiro[4.4]nonane, 2-azaspiro[3.5]nonane, 2-oxaspiro[3.5]nonane, 4-azaspiro[2.5]octane, 4-oxaspiro[2.5]octane, 1,4-dioxaspiro[4.5]decane, 1-thiaspiro[4.5]decane 1,1-dioxide, 2-oxa-1-azaspiro[4.5]decane and the like.

It will be well recognized by a person skilled in the art that when Ring B is cycloalkyl, heterocyclyl, or a spirocycloalkyl, the carbon atoms in these rings that are shared with the adjacent ring (i.e., ring substituted with —NR$^{3A}$R$^{3B}$ in Formula I) are sp$^2$ carbons.

It will also be well recognized by a person skilled in the art that when a group containing carbon atoms and NH groups is substituted, that the possible substituents may differ for the carbon atoms and the NH groups. Specifically, the skilled artisan would recognize that substitutions on an NH group are those that replace the hydrogen of the NH group with a carbon (i.e., forming a nitrogen-carbon bond).

The present disclosure also includes protected derivatives of compounds of the present disclosure. For example, when compounds of the present disclosure contain groups such as hydroxy, carboxy, thiol or any group containing a nitrogen atom(s), these groups can be protected with a suitable protecting group. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of the present disclosure can be prepared by methods well known in the art.

It is to be understood that where compounds disclosed herein have unfilled valencies, then the valencies are to be filled with hydrogen.

The present disclosure also includes deuterated forms of the compound of the present disclosure, or a pharmaceutically acceptable salt thereof. Indeed, also provided herein are isotopologues (isotopically labeled analogues) of the compounds described herein. Substitution with isotopes such as deuterium may afford certain therapeutic advantages resulting from greater metabolic stability, such as, for example, increased in vivo half-life or reduced dosage requirements. In some embodiments, at any position of a compound described herein, or a pharmaceutically acceptable salt thereof, that has a hydrogen, the hydrogen atom can be replaced with hydrogen-2 (deuterium) or hydrogen-3 (tritium). For example, $R^1$, $R^2$, and/or Ring B can include one or more deuteriums (such as 1, 2, 3, 4, 5, or 6 deuteriums), such as when Ring B can be

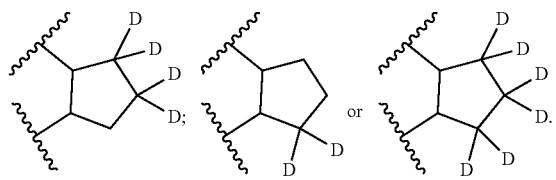

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diastereomeric forms and racemic forms are within the scope of this disclosure, unless the specific stereochemistry or isomeric form is specifically indicated. It will also be well recognized by a person skilled in the art that when a bond is drawn from an optically active center, that a "flat" bond ( ———— ) represents and encompasses both the "wedge" bond ( ▬▬◀ ) and the "dashed" bond ( ⋯⋯⋯⋯ ) each representing the (R) or (S) stereoisomer. It will also be understood by a person of ordinary skill in the art that when a compound is denoted as (R) stereoisomer, it may contain the corresponding (S) stereoisomer as an impurity i.e., the (S) stereoisomer in less than about 5%, preferably 2% by wt. and then it is denoted as a mixture of R and S isomers, the amounts of R or S isomer in the mixture is greater than about 5%, preferably 2% w/w.

Certain compounds of the present disclosure can exist as tautomers and/or geometric isomers. All possible tautomers and cis and tram isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of the present disclosure are within the scope of this disclosure.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

A "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees and apes, and, in particular, humans. In some embodiments, the subject can be human. In some embodiments, the subject can be a human child and/or a human infant, for example, a child or infant with a fever. In other embodiments, the subject can be a human adult.

"Treating" or "treatment" of a disease includes:

(1) preventing the disease, i.e. causing the clinical symptoms of the disease not to develop in a subject that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure or a pharmaceutically acceptable salt thereof that, elicits the biological or medicinal response indicated. For example, when administered to a subject for treating a disease, the therapeutically effective amount of a compound is sufficient to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The "therapeutically effective amount" of the compounds disclosed herein will vary depending on the compound, the disease and its severity and the age, weight, etc., of the subject to be treated.

EMBODIMENTS

In further embodiments 1-235 below, the present disclosure includes:

1. In embodiment 1, the compounds of Formula (I), or a pharmaceutically acceptable salt thereof, are as defined in the Summary.
2. In embodiment 2, the compounds of embodiment 1, or a pharmaceutically acceptable salt thereof, are those wherein A can be CH.
3. In embodiment 3, the compounds of embodiment 1, or a pharmaceutically acceptable salt thereof, are those wherein A can be N.
4. In embodiment 4, the compounds of any one of embodiments 1-3, or a pharmaceutically acceptable salt thereof, are those wherein $R_{3B}$ can be hydrogen.
5. In embodiment 5, the compounds of any one of embodiments 1-3, or a pharmaceutically acceptable salt thereof, are those wherein $R_{3B}$ can be alkyl, for example, a $C_1$-$C_6$ alkyl such as methyl, ethyl, n-propyl, isopropyl, n-butyl, sec-butyl, iso-butyl, tert-butyl, pentyl (straight-chained or branched), or hexyl (straight-chained or branched).
6. In embodiment 6, the compounds of any one of embodiments 1-3, or a pharmaceutically acceptable salt thereof, are those wherein $R_{3B}$ can be —(C=O)NH$_2$.
7. In embodiment 7, the compound of any one of embodiments 1-6, or a pharmaceutically acceptable salt thereof, are those wherein Ring B can be

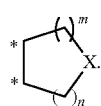

When Ring B is

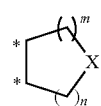

a compound of Formula (I), or a pharmaceutically acceptable salt thereof, can have the structure:

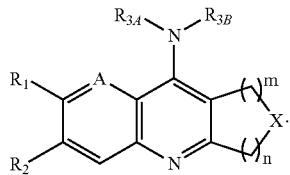

8. In embodiment 8, the compounds of embodiment 7, or a pharmaceutically acceptable salt thereof, are those wherein X can be $CR_{4A}R_{4B}$.
9. In embodiment 9, the compounds of embodiment 8, or a pharmaceutically acceptable salt thereof, are those wherein $R_{4A}$ and $R_{4B}$ can each be hydrogen. For example, in some aspects of embodiment 9, Ring B can be a 5-8 membered monocyclic cycloalkyl group, such as:

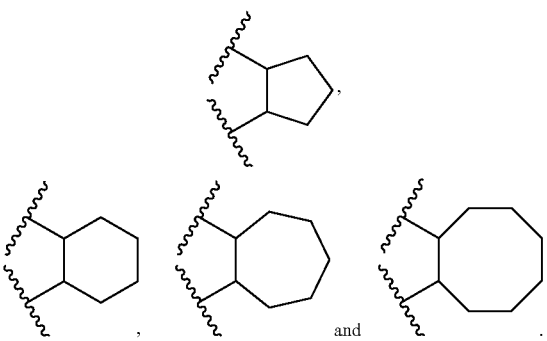

When certain hydrogen atoms of Ring B are replaced with deuterium, Ring B can be, for example, X, D or D.

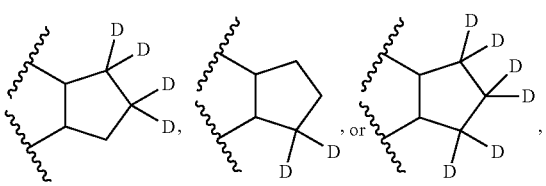

10. In embodiment 10, the compounds of embodiment 8, or a pharmaceutically acceptable salt thereof, are those wherein $R_{4A}$ and $R_{4B}$ can each be alkyl, for example, a $C_1$-$C_6$ alkyl such as methyl, ethyl, n-propyl, isopropyl, n-butyl, tert-butyl, pentyl, or hexyl. In some aspects of embodiment 10, Ring B can be a monocyclic cycloalkyl group selected from:

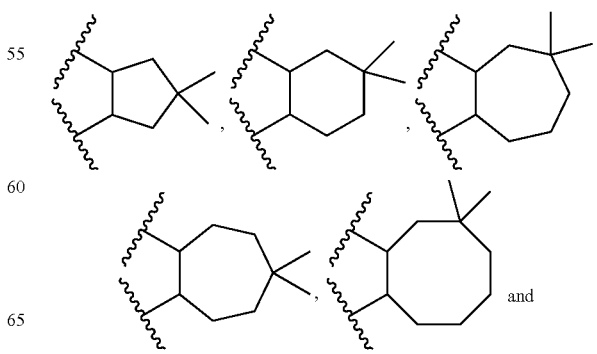

-continued

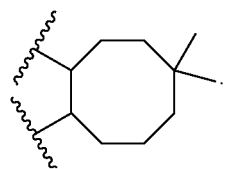

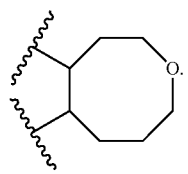

11. In embodiment 11, the compounds of embodiment 8, or a pharmaceutically acceptable salt thereof, are those wherein one of $R_{4A}$ and $R_{4B}$ can be hydrogen and the other of $R_{4A}$ and $R_{4B}$ can be alkyl, for example, a $C_1$-$C_7$ alkyl such as methyl, ethyl, propyl, isopropyl, n-butyl, sec-butyl, iso-butyl, tert-butyl, pentyl (straight-chained or branched), hexyl (straight-chained or branched), or heptyl (straight-chained or branched). In some aspects of embodiment 11, Ring B can be selected from:

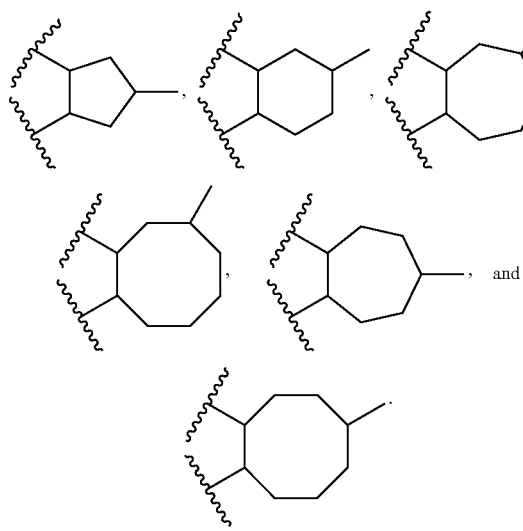

12. In embodiment 12, the compounds of any one of embodiments 10-11, or a pharmaceutically acceptable salt thereof, are those wherein the alkyl can be methyl.

13. In embodiment 13, the compounds of embodiment 7, or a pharmaceutically acceptable salt thereof, are those wherein X can be O (oxygen). For example, in some aspects of embodiment 13, Ring B can be a 5-8 membered monocyclic heterocyclyl group containing one oxygen atom, such as:

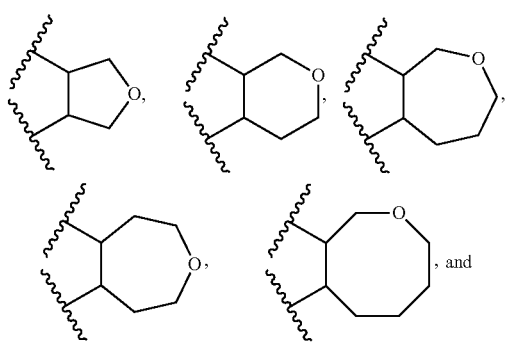

14. In embodiment 14, the compounds of embodiment 7, or a pharmaceutically acceptable salt thereof, are those wherein X can be $NR_{4C}$.

15. In embodiment 15, the compounds of embodiment 14, or a pharmaceutically acceptable salt thereof, are those wherein $R_{4C}$ can be hydrogen. For example, in some aspects of embodiment 15, Ring B can be a 5-8 membered monocyclic heterocyclyl group containing one nitrogen atom, such as:

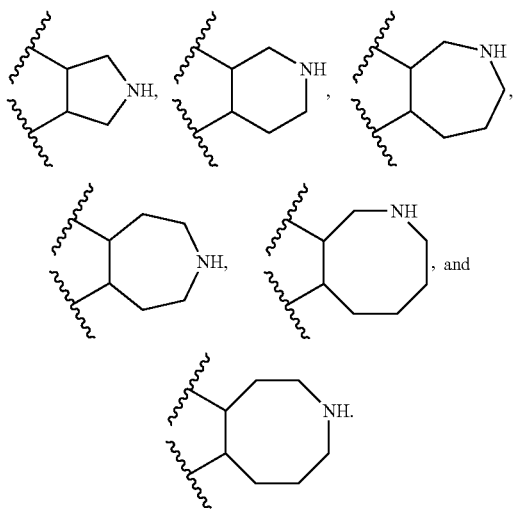

16. In embodiment 16, the compounds of embodiment 14, or a pharmaceutically acceptable salt thereof, are those wherein $R_{4C}$ can be alkyl, for example, a $C_1$-$C_7$ alkyl such as methyl, ethyl, n-propyl, isopropyl, n-butyl, sec-butyl, iso-butyl, tert-butyl, pentyl (straight-chained or branched), hexyl (straight-chained or branched), or heptyl (straight-chained or branched). For example, in some aspects of embodiment 16, Ring B can be a 5-8 membered monocyclic heterocyclyl group selected from:

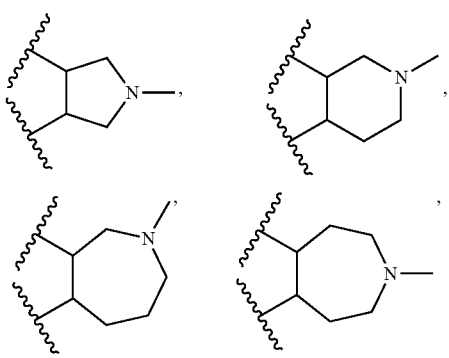

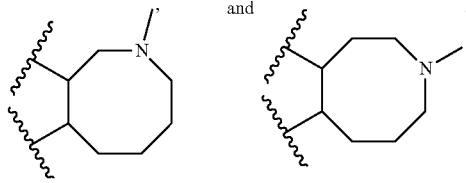

17. In embodiment 17, the compounds of embodiment 16, or a pharmaceutically acceptable salt thereof, are those wherein $R_{4C}$ can be methyl.

18. In embodiment 18, the compounds of any one of embodiments 7-17, or a pharmaceutically acceptable salt thereof, are those wherein m can be 1; and n can be 1.

19. In embodiment 19, the compounds of any one of embodiments 7-17, or a pharmaceutically acceptable salt thereof, are those wherein m can be 2; and n can be 1.

20. In embodiment 20, the compounds of any one of embodiments 7-17, or a pharmaceutically acceptable salt thereof, are those wherein m can be 1; and n can be 2.

21. In embodiment 21, the compounds of any one of embodiments 7-17, or a pharmaceutically acceptable salt thereof, are those wherein m can be 2; and n can be 2.

22. In embodiment 22, the compounds of any one of embodiments 7-17, or a pharmaceutically acceptable salt thereof, are those wherein m can be 3; and n can be 2.

23. In embodiment 23, the compounds of any one of embodiments 7-17, or a pharmaceutically acceptable salt thereof, are those wherein m can be 2; and n can be 3.

24. In embodiment 24, the compounds of any one of embodiments 7-17, or a pharmaceutically acceptable salt thereof, are those wherein m can be 1; and n can be 3.

25. In embodiment 25, the compounds of any one of embodiments 7-17, or a pharmaceutically acceptable salt thereof, are those wherein m can be 3; and n can be 1.

26. In embodiment 26, the compounds of any one of embodiments 7-17, or a pharmaceutically acceptable salt thereof, are those wherein m can be 1; and n can be 4.

27. In embodiment 27, the compounds of any one of embodiments 7-17, or a pharmaceutically acceptable salt thereof, are those wherein m can be 4; and n can be 1.

28. In embodiment 28, the compound of any one of embodiments 1-6, or a pharmaceutically acceptable salt thereof, are those wherein Ring B can be

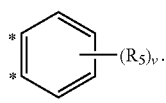

When Ring B is

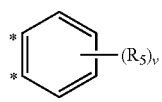

a compound of Formula (I), or a pharmaceutically acceptable salt thereof, can have the structure:

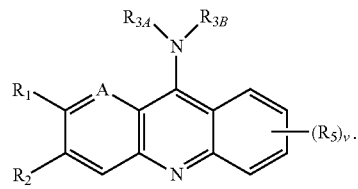

In some aspects of embodiment 28, v can be 0 such that is

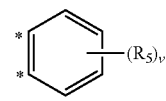

unsubstituted. In other aspects of embodiment 28, v can be 1. When v is 1, the phenyl ring can be substituted at an ortho-, meta- or para-position. In still other aspects of embodiment 28, v can be 2. In yet still other aspects of embodiment 28, v can be 3. In some aspects of embodiment 28, v can be 4.

29. In embodiment 29, the compounds of any one of embodiments 1-6 or 28, or a pharmaceutically acceptable salt thereof, are those wherein each $R_5$ can be independently a $C_1$-$C_4$ alkyl (such as those described herein).

30. In embodiment 30, the compounds of any one of embodiments 28-29, or a pharmaceutically acceptable salt thereof, are those wherein v can be 1, 2, or 3; and each $R_5$ can be independently a $C_1$-$C_4$ alkyl (such as those described herein).

31. In embodiment 31, the compounds of any one of embodiments 1-6 or 28, or a pharmaceutically acceptable salt thereof, are those wherein v can be 0.

32. In embodiment 32, the compounds of any one of embodiments 1-31, or a pharmaceutically acceptable salt thereof, are those wherein $R_1$ can be alkoxy, for example, a $C_1$-$C_4$ alkoxy (optionally substituted with one or more $R_4$, independently selected from deuterium, hydroxy, alkoxy, (hydroxy)alkoxy and cyano), such as methoxy, ethoxy, n-propoxy, iso-propoxy, n-butoxy, sec-butoxy, iso-butoxy or t-butoxy; and $R_2$ can be hydrogen, halogen (for example, fluoro or chloro), cyano, alkyl (for example, a $C_1$-$C_6$ alkyl such as those described herein and including methyl or ethyl), haloalkyl (for example, a $C_1$-$C_6$ haloalkyl such as —$CF_3$ or —$CHF_2$), hydroxyalkyl (for example, a $C_1$-$C_6$ hydroxyalkyl such as those described herein and including hydroxymethyl or hydroxyethyl), aryloxy (for example a $C_6$ aryloxy such as phenoxy), heteroaryloxy (for example a 5- to 6-membered heteroaryloxy such as pyridinoxy or thiazoloxy), cycloalkyl (for example a $C_3$-$C_6$ cycloalkyl such as those described herein and including cyclopropyl)(optionally substituted with one or more hydroxy), cycloalkoxy for example a $C_3$-$C_6$ cycloalkoxy such as those described herein and including cyclopropoxy or cyclobutoxy), cyanoalkoxy (for example, a $C_1$-$C_6$ cyanoalkoxy such as those described herein and including cyanomethoxy or cyanoethoxy), alkoxy (a $C_1$-$C_4$ alkoxy such as methoxy, ethoxy, n-propoxy, iso-propoxy, n-butoxy, sec-butoxy, iso-butoxy or t-butoxy) (optionally substituted with one or more $R_4$, independently selected from deuterium, hydroxy, alkoxy, (hydroxy)alkoxy and cyano), haloalkoxy (for example, a $C_1$-$C_6$ haloalkoxy such as —$OCF_3$ or —$OCHF_2$) or aminosulfonyl (optionally substituted with one or more alkyl).

33. In embodiment 33, the compounds of any one of embodiments 1-32, or a pharmaceutically acceptable salt thereof, are those wherein $R_1$ can be methoxy optionally substituted with one or more deuterium.

34. In embodiment 34, the compounds of any one of embodiments 1-33, or a pharmaceutically acceptable salt thereof, are those wherein $R_1$ can be methoxy.

35. In embodiment 35, the compounds of any one of embodiments 1-33, or a pharmaceutically acceptable salt thereof, are those wherein $R_1$ can be —OCD$_3$.

36. In embodiment 36, the compounds of any one of embodiments 1-33, or a pharmaceutically acceptable salt thereof, are those wherein $R_1$ and $R_2$ can each be methoxy.

37. In embodiment 37, the compounds of any one of embodiments 1-33, or a pharmaceutically acceptable salt thereof, are those wherein $R_1$ and $R_2$ can each be —OCD$_3$.

38. In embodiment 38, the compounds of any one of embodiments 1-33, or a pharmaceutically acceptable salt thereof, are those wherein $R_1$ can be methoxy; and $R_2$ can be haloalkoxy.

39. In embodiment 39, the compounds of any one of embodiments 1-33, or a pharmaceutically acceptable salt thereof, are those wherein $R_1$ can be —OCD$_3$; and $R_2$ can be haloalkoxy.

40. In embodiment 40, the compounds of any one of embodiments 1-33 or 38-39, or a pharmaceutically acceptable salt thereof, are those wherein $R_2$ can be —OCH$_2$F, —OCHF$_2$ or —OCF$_3$.

41. In embodiment 41, the compounds of any one of embodiments 1-33, or a pharmaceutically acceptable salt thereof, are those wherein $R_1$ can be methoxy or —OCD$_3$; and $R_2$ can be alkoxy (for example, a $C_1$-$C_4$ alkoxy such as methoxy, ethoxy, n-propoxy, iso-propoxy, n-butoxy, sec-butoxy, iso-butoxy or t-butoxy) substituted with one or more $R_A$ which can be alkoxy, for example, a $C_1$-$C_4$ alkoxy such as methoxy, ethoxy, n-propoxy, iso-propoxy, n-butoxy, sec-butoxy, iso-butoxy or t-butoxy. In some aspects of embodiment 41, $R_1$ can be methoxy. In some aspects of embodiment 41, $R_1$ can be —OCD$_3$. In some aspects of embodiment 41, $R_2$ can be

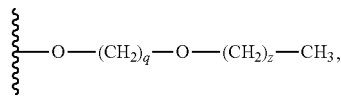

wherein q can be 1, 2, 3 or 4; and z can be 0, 1, 2, 3 or 4. In some aspects of embodiment 41, q can be 1; and z can be 0. In some aspects of embodiment 41, q can be 2; and z can be 0. In some aspects of embodiment 41, q can be 3; and z can be 0. In some aspects of embodiment 41, q can be 4; and z can be 0. In some aspects of embodiment 41, q can be 1; and z can be 1. In some aspects of embodiment 41, q can be 2; and z can be 1. In some aspects of embodiment 41, q can be 3; and z can be 1. In some aspects of embodiment 41, q can be 4; and z can be 1. In some aspects of embodiment 41, q can be 1; and z can be 2. In some aspects of embodiment 41, q can be 2; and z can be 2. In some aspects of embodiment 41, q can be 3; and z can be 2. In some aspects of embodiment 30, q can be 4; and z can be 2. In some aspects of embodiment 41, q can be 1; and z can be 3. In some aspects of embodiment 41, q can be 2; and z can be 3. In some aspects of embodiment 41, q can be 3; and z can be 3. In some aspects of embodiment 41, q can be 4; and z can be 3. In some aspects of embodiment 41, q can be 1; and z can be 4. In some aspects of embodiment 41, q can be 2; and z can be 4. In some aspects of embodiment 41, q can be 3; and z can be 4. In some aspects of embodiment 41, q can be 4; and z can be 4.

42. In embodiment 42, the compounds of embodiment 41, or a pharmaceutically acceptable salt thereof, are those wherein $R_2$ can be

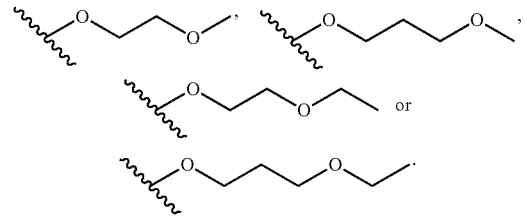

43. In embodiment 43, the compounds of embodiment 41, or a pharmaceutically acceptable salt thereof, are those wherein $R_2$ can be alkoxy (for example, a $C_1$-$C_4$ alkoxy such as methoxy, ethoxy, n-propoxy, iso-propoxy, n-butoxy, sec-butoxy, iso-butoxy or t-butoxy) substituted with one $R_A$. For example, $R_2$ can be alkoxy substituted with a $C_1$-$C_4$ alkoxy such as those described herein and including methoxy and ethoxy.

44. In embodiment 44, the compounds of embodiment 41, or a pharmaceutically acceptable salt thereof, are those wherein $R_2$ can be alkoxy independently substituted with two RA. For example, $R_2$ can be a $C_1$-$C_8$ alkoxy independently substituted with two $C_1$-$C_4$ alkoxys (for example, two methoxy groups or a methoxy and an ethoxy).

45. In embodiment 45, the compounds of embodiment 41, or a pharmaceutically acceptable salt thereof, are those wherein $R_2$ can be alkoxy independently substituted with three $R_A$. For example, $R_2$ can be a $C_1$-$C_8$ alkoxy independently substituted with three $C_1$-$C_4$ alkoxys (for example, three methoxy groups or two methoxy groups and one ethoxy group).

46. In embodiment 46, the compounds of any one of embodiments 1-33, or a pharmaceutically acceptable salt thereof, are those wherein $R_1$ can be methoxy; and $R_2$ can be hydroxyalkyl. Exemplary hydroxyalkyl groups include, but are not limited to $C_1$-$C_4$ hydroxyalkyl groups such as hydroxymethyl, 1-hydroxyethyl, 2-hydroxyethyl, 3-hydroxypropyl, 2-hydroxypropyl, 1-hydroxyisopropyl and 4-hydroxybutyl.

47. In embodiment 47, the compounds of any one of embodiments 1-33, or a pharmaceutically acceptable salt thereof, are those wherein $R_1$ can be —OCD$_3$; and $R_2$ can be hydroxyalkyl. Exemplary hydroxyalkyl groups include, but are not limited to $C_1$-$C_4$ hydroxyalkyl groups such as hydroxymethyl, 1-hydroxyethyl, 2-hydroxyethyl, 3-hydroxypropyl, 2-hydroxypropyl, 1-hydroxyisopropyl and 4-hydroxybutyl.

48. In embodiment 48, the compounds of any one of embodiments 1-33 or 46-47, or a pharmaceutically acceptable salt thereof, are those wherein $R_2$ can be

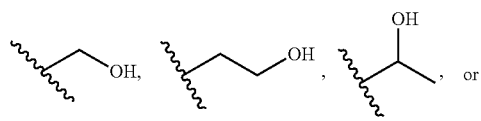

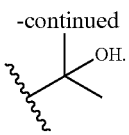

49. In embodiment 49, the compounds of any one of embodiments 1-33, or a pharmaceutically acceptable salt thereof, are those wherein $R_1$ can be methoxy or —$OCD_3$; and $R_2$ can be alkoxy (for example, a $C_1$-$C_{10}$ alkoxy such as methoxy, ethoxy, n-propoxy, iso-propoxy, n-butoxy, sec-butoxy, iso-butoxy, t-butoxy, pentoxy (straight-chained or branched), hexoxy (straight-chained or branched), heptoxy (straight-chained or branched), octoxy (straight-chained or branched), nonoxy (straight-chained or branched) or decoxy (straight-chained or branched)) mono-substituted with $R_A$ which can be hydroxy. For example, in some aspects of embodiment 49, $R_1$ can be methoxy or —$OCD_3$. In other aspects of embodiment 49, $R_1$ can be —$OCD_3$. In some aspects of embodiment 49, $R_2$ can be

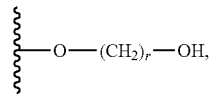

wherein r is 1, 2, 3, 4, 5, 6, 7, 8, 9 or 10. In some aspects of embodiment 49, r can be 1. In some aspects of embodiment 49, r can be 2. In some aspects of embodiment 49, r can be 3. In some aspects of embodiment 49, r can be 4. In some aspects of embodiment 49, r can be 5. In some aspects of embodiment 49, r can be 6. In some aspects of embodiment 49, r can be 7. In some aspects of embodiment 49, r can be 8. In some aspects of embodiment 49, r can be 9. In some aspects of embodiment 49, r can be 10.

50. In embodiment 50, the compounds of any one of embodiments 1-33 or 49, or a pharmaceutically acceptable salt thereof, are those wherein $R_2$ can be

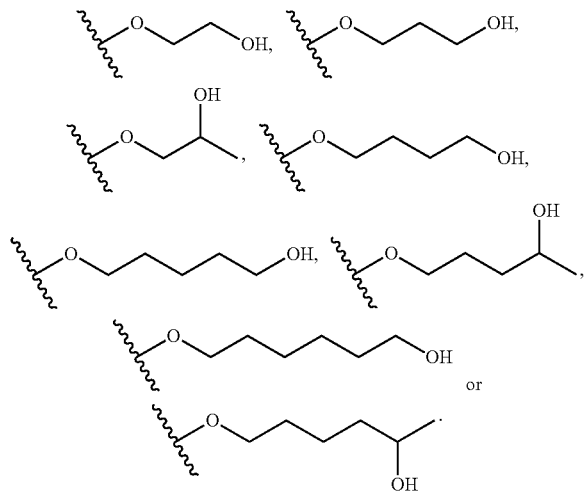

51. In embodiment 51, the compounds of any one of embodiments 1-33, or a pharmaceutically acceptable salt thereof, are those wherein $R_1$ can be methoxy or —$OCD_3$; and $R_2$ can be alkoxy mono-substituted with $R_A$ which can be (hydroxy)alkoxy. In some aspects of embodiment 51, $R_1$ can be methoxy. In other aspects of embodiment 51, $R_1$ can be —$OCD_3$. In some aspects of embodiment 51, $R_2$ can be $C_1$-$C_8$ alkoxy mono-substituted with $R_A$ which can be hydroxy($C_1$-$C_4$)alkoxy. In some aspects of embodiment 51, $R_2$ can be

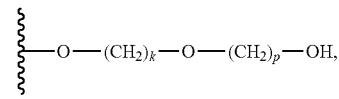

wherein k and p can independently be 1, 2, 3 or 4. In some aspects of embodiment 51, k can be 1; and p can be 1. In some aspects of embodiment 51, k can be 2; and p can be 1. In some aspects of embodiment 51, k can be 3; and p can be 1. In some aspects of embodiment 51, k can be 4; and p can be 1. In some aspects of embodiment 51, k can be 1; and p can be 2. In some aspects of embodiment 51, k can be 2; and p can be 2. In some aspects of embodiment 51, k can be 3; and p can be 2. In some aspects of embodiment 51, k can be 4; and p can be 2. In some aspects of embodiment 51, k can be 1; and p can be 3. In some aspects of embodiment 51, k can be 2; and p can be 3. In some aspects of embodiment 51, k can be 3; and p can be 3. In some aspects of embodiment 51, k can be 4; and p can be 3. In some aspects of embodiment 51, k can be 1; and p can be 4. In some aspects of embodiment 51, k can be 2; and p can be 4. In some aspects of embodiment 51, k can be 3; and p can be 4. In some aspects of embodiment 51, k can be 4; and p can be 4.

52. In embodiment 52, the compounds of embodiment 51, or a pharmaceutically acceptable salt thereof, are those wherein $R_2$ can be

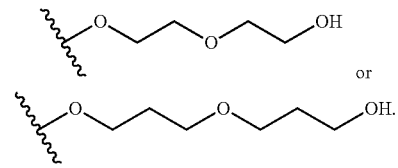

53. In embodiment 53, the compounds of any one of embodiments 1-33, or a pharmaceutically acceptable salt thereof, are those wherein $R_1$ can be methoxy; and $R_2$ can be halogen, for example, fluoro or chloro.

54. In embodiment 54, the compounds of any one of embodiments 1-33, or a pharmaceutically acceptable salt thereof, are those wherein $R_1$ can be —$OCD_3$; and $R_2$ can be halogen, for example, fluoro or chloro.

55. In embodiment 55, the compounds of any one of embodiments 53-54, or a pharmaceutically acceptable salt thereof, are those wherein $R_2$ can be fluoro.

56. In embodiment 56, the compounds of any one of embodiments 53-54, or a pharmaceutically acceptable salt thereof, are those wherein $R_2$ can be chloro.

57. In embodiment 57, the compounds of any one of embodiments 1-33, or a pharmaceutically acceptable salt thereof, are those wherein $R_1$ can be methoxy; and $R_2$ can be cyano.

58. In embodiment 58, the compounds of any one of embodiments 1-33, or a pharmaceutically acceptable salt thereof, are those wherein $R_1$ can be —$OCD_3$; and $R_2$ can be cyano.

59. In embodiment 59, the compounds of any one of embodiments 1-33, or a pharmaceutically acceptable salt thereof, are those wherein R$_1$ can be methoxy or —OCD$_3$; and R$_2$ can be alkyl. In some aspects of embodiment 59, R$_1$ can be methoxy. In other aspects of embodiment 59, R$_1$ can be —OCD$_3$. In some aspects of embodiment 59, R$_2$ can be a C$_1$-C$_7$ alkyl such as methyl, ethyl, n-propyl, isopropyl, n-butyl, sec-butyl, iso-butyl, tert-butyl, pentyl (straight-chained or branched), hexyl (straight-chained or branched) and heptyl (straight-chained or branched).

60. In embodiment 60, the compounds of embodiment 59, or a pharmaceutically acceptable salt thereof, are those wherein R$_2$ can be ethyl.

61. In embodiment 61, the compounds of any one of embodiments 1-33, or a pharmaceutically acceptable salt thereof, are those wherein R$_1$ can be methoxy; and R$_2$ can be hydrogen.

62. In embodiment 62, the compounds of any one of embodiments 1-33, or a pharmaceutically acceptable salt thereof, are those wherein R$_1$ can be —OCD$_3$; and R$_2$ can be hydrogen.

63. In embodiment 63, the compounds of any one of embodiments 1-33, or a pharmaceutically acceptable salt thereof, are those wherein R$_1$ can be methoxy or —OCD$_3$; and R$_2$ can be haloalkyl. In some aspects of embodiment 63, R$_1$ can be methoxy. In other aspects of embodiment 63, R$_1$ can be —OCD$_3$. In some aspects of embodiment 63, R$_2$ can be a C$_1$-C$_6$ haloalkyl group such as —CH$_2$Cl, —CF$_3$, —CHF$_2$, —CH$_2$F, —CH$_2$CF$_3$, —CF$_2$CF$_3$ and —CF(CH$_3$)$_2$.

64. In embodiment 64, the compounds of embodiment 63, or a pharmaceutically acceptable salt thereof, are those wherein R$_2$ can be —CF$_3$.

65. In embodiment 65, the compounds of any one of embodiments 1-33, or a pharmaceutically acceptable salt thereof, are those wherein R$_1$ can be methoxy; and R$_2$ can be aryloxy, for example, a C$_6$ or C$_{10}$ aryloxy such as phenoxy or naphthyloxy.

66. In embodiment 66, the compounds of any one of embodiments 1-33, or a pharmaceutically acceptable salt thereof, are those wherein R$_1$ can be —OCD$_3$; and R$_2$ can be aryloxy, for example, a C$_6$ or C$_{10}$ aryloxy such as phenoxy or naphthyloxy.

67. In embodiment 67, the compounds of any one of embodiments 65-66, or a pharmaceutically acceptable salt thereof, are those wherein R$_2$ can be phenoxy.

68. In embodiment 68, the compounds of any one of embodiments 1-33, or a pharmaceutically acceptable salt thereof, are those wherein R$_1$ can be methoxy or —OCD$_3$; and R$_2$ can be heteroaryloxy. In some aspects of embodiment 68, R$_1$ can be methoxy. In other aspects of embodiment 68, R$_1$ can be —OCD$_3$. In some aspects of embodiment 68, the heteroaryl group in heteroaryloxy can be a 5-membered heteroaryl group, a 6-membered heteroaryl group or a 10-membered heteroaryl group. In some aspects of embodiment 68, the heteroaryl group in heteroaryloxy can be a monocyclic heteroaryl. In some aspects of embodiment 68, the heteroaryl group in heteroaryloxy can be a 5- or 6-membered monocyclic heteroaryl group. In some aspects of embodiment 68, the heteroaryl group in heteroaryloxy can be a nitrogen-containing monocyclic 5- or 6-membered heteroaryl group. In some aspects of embodiment 68, the heteroaryl group in heteroaryloxy can be a 5- or 6-membered heteroaryl group containing nitrogen and oxygen. In some aspects of embodiment 68, the heteroaryl group in heteroaryloxy can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-triazine.

69. In embodiment 69, the compounds of embodiment 68, or a pharmaceutically acceptable salt thereof, are those wherein R$_2$ can be

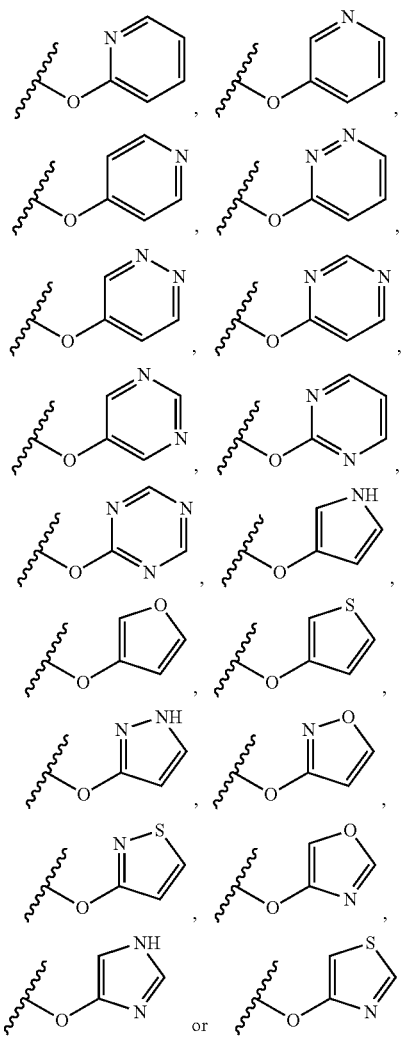

70. In embodiment 70, the compounds of any one of embodiments 1-33, or a pharmaceutically acceptable salt thereof, are those wherein R$_1$ can be methoxy or —OCD$_3$; and R$_2$ can be cyanoalkoxy, for example, a C$_1$-C$_6$ cyanoalkoxy. In some aspects of embodiment 70, R$_1$ can be methoxy. In other aspects of embodiment 70, R$_1$ can be —OCD$_3$. In some aspects of embodiment 70, the cyanoalkoxy group can be:

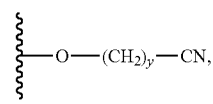

wherein y can be 1, 2, 3, 4, 5 or 6, for example, cyanomethoxy, cyanoethoxy or cyanopropoxy.

71. In embodiment 71, the compounds of embodiment 70, or a pharmaceutically acceptable salt thereof, are those wherein R$_2$ can be

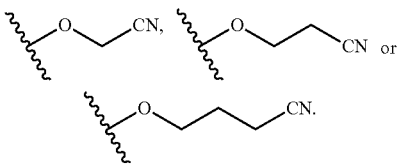 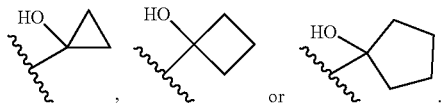 [SMILES: *C1(O)CC1 ; *C1(O)CCC1 ; *C1(O)CCCC1]

72. In embodiment 72, the compounds of any one of embodiments 1-33, or a pharmaceutically acceptable salt thereof, are those wherein $R_1$ can be methoxy or —$OCD_3$; and $R_2$ can be cycloalkoxy. In some aspects of embodiment 72, $R_1$ can be methoxy. In other aspects of embodiment 72, $R_1$ can be $OCD_3$. In some aspects of embodiment 72, the cycloalkoxy group can be a monocyclic $C_3$-$C_8$ cycloalkoxy such as cyclopropoxy, cyclobutoxy, cyclopentoxy, cycloheptoxy or cyclooctoxy. In some aspects of embodiment 72, the cycloalkoxy group can be a $C_6$-$C_{10}$ bicyclic cycloalkoxy, for example, a fused, spiro or bridged cycloalkoxy, for example, octahydropentalenoxy, bicyclo[3.1.1]heptanoxy, or bicyclo[2.2.1]heptanoxy.

73. In embodiment 73, the compounds of embodiment 72 or a pharmaceutically acceptable salt thereof, are those wherein $R_2$ can be cyclopropoxy, cyclobutoxy or cyclopentoxy.

74. In embodiment 74, the compounds of any one of embodiments 1-33, or a pharmaceutically acceptable salt thereof, are those wherein $R_1$ can be methoxy or —$OCD_3$; and $R_2$ can be cycloalkyl. In some aspects of embodiment 74, $R_1$ can be methoxy. In other aspects of embodiment 74, $R_1$ can be $OCD_3$. In some aspects of embodiment 74, the cycloalkyl can be a monocyclic $C_3$-$C_8$ cycloalkyl such as cyclopropyl, cyclobutyl, cyclopentyl, cyclohexyl, or cyclooctyl. In some aspects of embodiment 74, the cycloalkyl can be a $C_6$-$C_{10}$ bicyclic cycloalkyl, for example, a fused, spiro or bridged cycloalkyl, for example, octahydropentalenyl, bicyclo[3.1.1]heptanyl, or bicyclo[2.2.1]heptanyl.

75. In embodiment 75, the compounds of embodiment 74 or a pharmaceutically acceptable salt thereof, are those wherein $R_2$ can be cyclopropyl, cyclobutyl or cyclopentyl.

76. In embodiment 76, the compounds of any one of embodiments 1-33, or a pharmaceutically acceptable salt thereof, are those wherein $R_1$ can be methoxy or —$OCD_3$; and $R_2$ can be cycloalkyl, which can be mono-substituted with hydroxy. In some aspects of embodiment 76, $R_1$ can be methoxy. In other aspects of embodiment 76, $R_1$ can be —$OCD_3$. In some aspects of embodiment 76, the cycloalkyl can be a monocyclic $C_3$-$C_8$ cycloalkyl such as cyclopropyl, cyclobutyl, cyclopentyl, cyclohexyl, or cyclooctyl. In some aspects of embodiment 76, the cycloalkyl can be a $C_6$-$C_{10}$ bicyclic cycloalkyl, for example, a fused, spiro or bridged cycloalkyl, for example, octahydropentalenyl, bicyclo[3.1.1]heptanyl, or bicyclo[2.2.1]heptanyl. Exemplary cycloalkyl groups mono-substituted with hydroxy include, but are not limited to, 1-hydroxycyclopropyl, 2-hydroxycyclopropyl, 1-hydroxycyclobutyl, 2-hydroxycyclobutyl, 3-hydroxycyclobutyl, 1-hydroxycyclopentyl, 2-hydroxycyclopentyl, 3-hydroxycyclopentyl, 1-hydroxycyclohexyl, 2-hydroxycyclohexyl, 3-hydroxycyclohexyl and 4-hydroxycyclohexyl.

77. In embodiment 77, the compounds of embodiment 76 or a pharmaceutically acceptable salt thereof, are those wherein $R_2$ can be 78. In embodiment 78, the compounds of any one of embodiments 1-33, or a pharmaceutically acceptable salt thereof, are those wherein $R_1$ can be methoxy; and $R_2$ can be aminosulfonyl.

79. In embodiment 79, the compounds of any one of embodiments 1-33, or a pharmaceutically acceptable salt thereof, are those wherein $R_1$ can be —$OCD_3$; and $R_2$ can be aminosulfonyl.

80. In embodiment 80, the compounds of any one of embodiments 1-33, or a pharmaceutically acceptable salt thereof, are those wherein $R_1$ can be methoxy or —$OCD_3$; and $R_2$ can be aminosulfonyl, which can be mono-substituted with alkyl, for example, a $C_1$-$C_7$ alkyl such as methyl, ethyl, n-propyl, isopropyl, n-butyl, tert-butyl, sec-butyl, isobutyl, pentyl (straight-chained or branched), hexyl (straight-chained or branched) or heptyl (straight-chained or branched). In some aspects of embodiment 80 $R_1$ can be methoxy. In other aspects of embodiment 80, $R_1$ can be —$OCD_3$.

81. In embodiment 81, the compounds of embodiment 80 or a pharmaceutically acceptable salt thereof, are those wherein $R_2$ can be aminosulfonyl, which can be mono-substituted with methyl.

82. In embodiment 82, the compounds of any one of embodiments 1-33, or a pharmaceutically acceptable salt thereof, are those wherein $R_1$ can be methoxy or —$OCD_3$; and $R_2$ can be hydroxy. In some aspects of embodiment 82, $R_1$ can be methoxy. In other aspects of embodiment 82, $R_1$ can be —$OCD_3$.

83. In embodiment 83, the compounds of any one of embodiments 1-33, or a pharmaceutically acceptable salt thereof, are those wherein $R_1$ and $R_2$, together with the atoms to which they are attached, can form a monocyclic heterocyclyl group. In some aspects of embodiment 83, the heterocyclyl group can be a 5- or 6-membered monocyclic heterocyclyl. In some aspects of embodiment 83, the heterocyclyl group can be a 5- or 6-membered monocyclic heterocyclyl containing one or two oxygen atoms. In some aspects of embodiment 83, the heterocyclyl group can be a 5- or 6-membered monocyclic heterocyclyl containing one or two nitrogen atoms. Exemplary heterocyclyl groups include, but are not limited to: 1,3 dioxole, 2,3-dihydroimidazole, 2,3-dihydrofuran, pyrrolidine, 1,4 dioxine, 3,4-dihydro-1,4-oxazine, piperidine-2-one and tetrahydro-2H-pyranone.

84. In embodiment 84, the compounds of embodiment 83, or a pharmaceutically acceptable salt thereof, are those wherein the heterocyclyl group can be

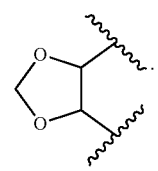 [SMILES: *C1OCOC1*]

85. In embodiment 85, the compounds of any one of embodiments 1-84, or a pharmaceutically acceptable salt thereof, are those wherein $R_{3A}$ can be heteroaralkyl (optionally substituted with alkyl). In some aspects of embodiment 85, the heteroaryl group in heteroaralkyl can be a 5-membered heteroaryl group, a 6-membered heteroaryl group or a 10-membered heteroaryl group. In some aspects of embodiment 85, the heteroaryl group in heteroaralkyl can be a monocyclic heteroaryl. In some aspects of embodiment 85, the heteroaryl group in heteroaralkyl can be a 5- or 6-membered, monocyclic heteroaryl group. In some aspects of embodiment 85, the heteroaryl group in heteroaralkyl can be a nitrogen-containing 5- or 6-membered heteroaryl group. In some aspects of embodiment 85, the heteroaryl group in heteroaralkyl can be a 5- or 6-membered heteroaryl group containing nitrogen and oxygen. In some aspects of embodiment 85, the heteroaryl group in heteroaralkyl can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine or 1,2,4-triazine, 1,3,5-triazine. In some aspects of embodiment 85, the alkylene in heteroaralkyl can be a $C_1$-$C_6$ alkylene, such as —$(CH_2)_{1-6}$—. In some aspects of embodiment 85, the alkylene in heteroaralkyl can be a methylene (—$CH_2$—).

86. In embodiment 86, the compounds of embodiment 85, or a pharmaceutically acceptable salt thereof, are those wherein $R_{3A}$ can be an unsubstituted heteroaralkyl. In some aspects of embodiment 8686, the heteroaryl portion of the heteroaralkyl group can be pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl or tetrazolyl. In some aspects of embodiment 86, the alkylene portion of the heteroaralkyl group can be a $C_1$-$C_4$ alkylene such as —$CH_2$—, —$CH_2CH_2$—, —$CH_2CH_2CH_2$— or —$CH_2CH_2CH_2CH_2$—. Exemplary heteroaralkyl groups include, but are not limited to: pyrrolylmethyl, thienylmethyl, thiazolylmethyl, imidazolylmethyl, furanylmethyl, indolylmethyl, isoindolylmethyl, oxazolylmethyl, isoxazolylmethyl, benzothiazolylmethyl, benzoxazolylmethyl, quinolinylmethyl, isoquinolinylmethyl, pyridinylmethyl, pyrimidinylmethyl, pyrazinylmethyl, pyridazinylmethyl, triazolylmethyl, tetrazolylmethyl, pyrrolylethyl, thienylethyl, thiazolylethyl, imidazolylethyl, furanylethyl, indolylethyl, isoindolylethyl, oxazolylethyl, isoxazolylethyl, benzothiazolylethyl, benzoxazolylethyl, quinolinylethyl, isoquinolinylethyl, pyridinylethyl, pyrimidinylethyl, pyrazinylethyl, pyridazinylethyl, triazolylethyl and tetrazolylethyl.

87. In embodiment 87, the compounds of embodiment 86, or a pharmaceutically acceptable salt thereof, are those wherein $R_{3A}$ can be

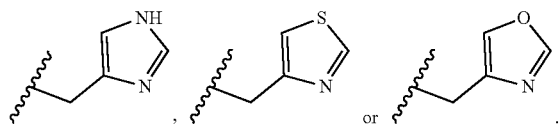

88. In embodiment 88, the compounds of any one of embodiments 1-84, or a pharmaceutically acceptable salt thereof, are those wherein $R_{3A}$ can be heteroaralkyl substituted with alkyl. In some aspects of embodiment 88, the heteroaryl portion of the heteroaralkyl group can be pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl or tetrazolyl. In some aspects of embodiment 88, the alkyl portion of the heteroaralkyl group can be a $C_1$-$C_4$ alkyl such as —$CH_2$—, —$CH_2CH_2$—, —$CH_2CH_2CH_2$— or —$CH_2CH_2CH_2CH_2$—. Exemplary heteroaralkyl groups include, but are not limited to: pyrrolylmethyl, thienylmethyl, thiazolylmethyl, imidazolylmethyl, furanylmethyl, indolylmethyl, isoindolylmethyl, oxazolylmethyl, isoxazolylmethyl, benzothiazolylmethyl, benzoxazolylmethyl, quinolinylmethyl, isoquinolinylmethyl, pyridinylmethyl, pyrimidinylmethyl, pyrazinylmethyl, pyridazinylmethyl, triazolylmethyl, tetrazolylmethyl, pyrrolylethyl, thienylethyl, thiazolylethyl, imidazolylethyl, furanylethyl, indolylethyl, isoindolylethyl, oxazolylethyl, isoxazolylethyl, benzothiazolylethyl, benzoxazolylethyl, quinolinylethyl, isoquinolinylethyl, pyridinylethyl, pyrimidinylethyl, pyrazinylethyl, pyridazinylethyl, triazolylethyl and tetrazolylethyl. In some aspects of embodiment 88, the heteroaralkyl can be substituted with alkyl, for example, a $C_1$-$C_4$ alkyl such as methyl, ethyl, n-propyl, isopropyl, n-butyl, sec-butyl, iso-butyl or t-butyl.

89. In embodiment 89, the compounds of embodiment 88, or a pharmaceutically acceptable salt thereof, are those wherein $R_{3A}$ can be

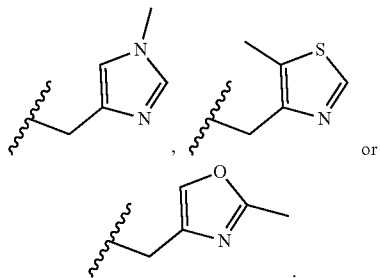

90. In embodiment 90, the compounds of any one of embodiments 1-84, or a pharmaceutically acceptable salt thereof, are those wherein $R_{3A}$ can be cycloalkylalkyl (optionally substituted with one or more $R_C$, independently selected from amino and alkylamino, for example a mono-substituted amino or a di-substituted amino).

91. In embodiment 91, the compounds of embodiment 90, or a pharmaceutically acceptable salt thereof, are those wherein $R_{3A}$ can be an unsubstituted cycloalkylalkyl. In some aspects of embodiment 91, the cycloalkyl can be a monocyclic $C_3$-$C_8$ cycloalkyl such as cyclopropyl, cyclobutyl, cyclopentyl, cyclohexyl or cyclooctyl. In some aspects of embodiment 91, the cycloalkyl can be a $C_6$-$C_{10}$ bicyclic cycloalkyl, for example, a fused, spiro or bridged cycloalkyl, for example, octahydropentalenyl, bicyclo[3.1.1]heptanyl, or bicyclo[2.2.1]heptanyl. In some aspects of embodiment 91, the alkylene in a cycloalkylalkyl group can be a $C_1$-$C_6$ alkylene, for example, —$(CH_2)_{1-6}$—. In some aspects of embodiment 91, the alkylene in a cycloalkylalkyl group can be a methylene (—$CH_2$—).

92. In embodiment 92, the compounds of embodiment 91, or a pharmaceutically acceptable salt thereof, are those wherein $R_{3A}$ can be

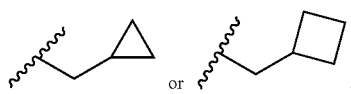

93. In embodiment 93, the compounds of embodiment 90, or a pharmaceutically acceptable salt thereof, are those wherein $R_{3A}$ can be cycloalkylalkyl, which can be substituted with one or more $R_C$, independently selected from amino and alkylamino. In some aspects of embodiment 93, the alkylamino can be, for example, a $C_1$-$C_3$ alkylamino such as methylamino, dimethylamino, ethylamino, diethylamino, isopropylamino, diisopropylamino, n-propylamino or di-n-propylamino.

94. In embodiment 94, the compounds of embodiment 93, or a pharmaceutically acceptable salt thereof, are those wherein $R_{3A}$ can be or

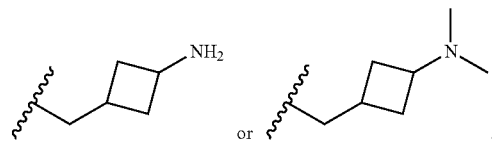

95. In embodiment 95, the compounds of any one of embodiments 1-84, or a pharmaceutically acceptable salt thereof, are those wherein $R_{3A}$ can be spiroheterocycloamino (optionally substituted with one or more $R_B$, independently selected from alkyl, aryl (optionally substituted with one or more $R_D$, independently selected from halogen and alkyl) and alkoxycarbonyl). In some aspects of embodiment 95, the spiroheterocycloamino can be a nitrogen-containing 7-10 membered ring system. In some aspects of embodiment 95, the spiroheterocycloamino can be a 7-10 membered ring system containing nitrogen and oxygen. In some aspects of embodiment 95, the spiroheterocycloamino can be 2-azaspiro[3.3]heptane, 2-oxaspiro[3.3]heptane, 1-azaspiro[3.3]heptane, 1-oxaspiro[3.3]heptane, 5-oxaspiro[3.4]octane, 5-azaspiro[3.4]octane, 2-oxaspiro[3.4]octane, 2-azaspiro[3.4]octane, 1-oxa-4-azaspiro[4.4]nonane, 1,4-dioxaspiro[4.4]nonane, 2-azaspiro[3.5]nonane, 2-oxaspiro[3.5]nonane, 4-azaspiro[2.5]octane, 4-oxaspiro[2.5]octane, 1,4-dioxaspiro[4.5]decane, 1-thiaspiro[4.5]decane 1,1-dioxide or 2-oxa-1-azaspiro[4.5]decane.

96. In embodiment 96, the compounds of embodiment 95, or a pharmaceutically acceptable salt thereof, are those wherein $R_{3A}$ can be an unsubstituted spiroheterocycloamino. In some aspects of embodiment 96, the spiroheterocycloamino can be a nitrogen-containing 7-10 membered ring system. In some aspects of embodiment 96, the spiroheterocycloamino can be a 7-10 membered ring system containing nitrogen and oxygen.

97. In embodiment 97, the compounds of embodiment 96, or a pharmaceutically acceptable salt thereof, are those wherein $R_{3A}$ can be

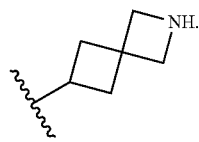

98. In embodiment 98, the compounds of embodiment 95, or a pharmaceutically acceptable salt thereof, are those wherein $R_{3A}$ can be spiroheterocycloamino, which can be substituted with one or more $R_B$, independently selected from alkyl (for example, a $C_1$-$C_4$ alkyl such as methyl, ethyl, n-propyl, isopropyl, n-butyl, isobutyl or t-butyl) and alkoxycarbonyl (for example, a $C_1$-$C_4$ alkoxy such as methoxycarbonyl, ethoxycarbonyl, n-propoxycarbonyl, iso-propoxycarbonyl, n-butoxycarbonyl or t-butoxycarbonyl).

99. In embodiment 99, the compounds of embodiment 98, or a pharmaceutically acceptable salt thereof, are those wherein $R_{3A}$ can be

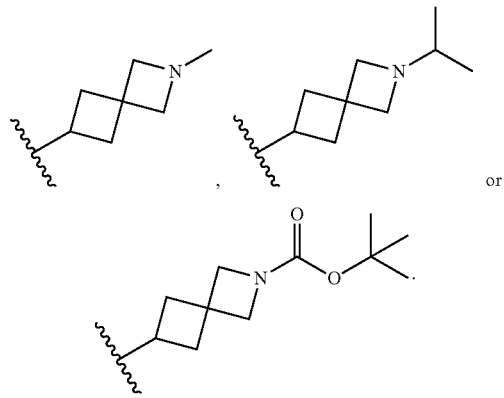

100. In embodiment 100, the compounds of embodiment 95, or a pharmaceutically acceptable salt thereof, are those wherein $R_{3A}$ can be spiroheterocycloamino, which can be substituted with one or more $R_B$, which can be aryl (optionally substituted with one or more $R_D$, independently selected from halogen and alkyl). In some aspects of embodiment 100, the aryl group is an unsubstituted $C_6$ or $C_{10}$ aryl group such as phenyl or naphthyl. In some aspects of embodiment 100, the aryl group is a $C_6$ aryl group substituted with 1, 2, or 3 $R_D$, independently selected from halogen (such as chloro or fluoro) and $C_1$-$C_6$ alkyl (such as those described herein). In some aspects of embodiment 100, the aryl group is a $C_6$ aryl group substituted with one $R_D$, independently selected from halogen (such as chloro or fluoro) and $C_1$-$C_6$ alkyl. In some aspects of embodiment 100, the aryl group is a $C_6$ aryl group substituted with two $R_D$, independently selected from halogen (such as chloro or fluoro) and $C_1$-$C_3$ alkyl (for example, methyl, ethyl, n-propyl or isopropyl).

101. In embodiment 101, the compounds of embodiment 100, or a pharmaceutically acceptable salt thereof, are those wherein $R_{3A}$ can be

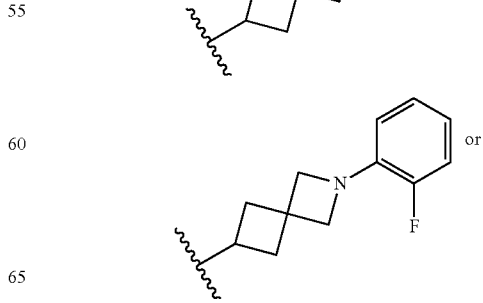

-continued

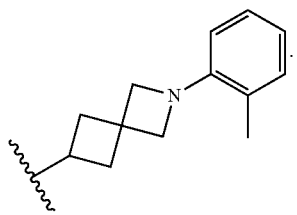

102. In embodiment 102, the compounds of any one of embodiments 1-84, or a pharmaceutically acceptable salt thereof, are those wherein $R_{3A}$ can be heterocyclyl optionally substituted with one or more $R_E$, independently selected from halogen, hydroxy, alkoxy, hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy). In some aspects of embodiment 102, the heterocyclyl of the heterocyclylalkyl can be a monocyclic 5- to 8-membered heterocyclyl. In some aspects of embodiment 102, the heterocyclyl of the heterocyclylalkyl can be a bicyclic 6- to 10-membered heterocyclyl. In some aspects of embodiment 102, the heterocyclyl can contain 1, 2 or 3 heteroatoms, which can be oxygen, nitrogen and/or sulfur. In some aspects of embodiment 102, the heterocyclyl of the heterocyclylalkyl can be a nitrogen-containing heterocyclyl. In some aspects of embodiment 102, the heterocyclyl of the heterocyclylalkyl can be an oxygen-containing heterocyclyl. In some aspects of embodiment 102, the heterocyclyl group of the heterocyclylalkyl can contain oxygen and nitrogen. In some aspects of embodiment 102, the heterocyclyl group of the heterocyclylalkyl can be a monocyclic 5- to 8-membered heterocyclyl containing one nitrogen atom. In some aspects of embodiment 102, when the heterocyclyl group contains one or more —NH— groups in the ring, one or more $R_E$ may be bonded to the nitrogen atom (replacing the hydrogen). In some aspects of embodiment 102, $R_{3A}$ can be heterocyclyl optionally substituted with one or more $R_E$ on one or more NH groups of the heterocyclyl, wherein the one or more $R_E$ independently selected from hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy). In other aspects of embodiment 102, $R_{3A}$ can be heterocyclyl optionally substituted with one or more $R_E$ on one or more carbons atoms of the heterocyclyl, wherein the one or more $R_E$ independently selected from halogen, hydroxy, alkoxy, hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy).

103. In embodiment 103, the compounds of embodiment 102, or a pharmaceutically acceptable salt thereof, are those wherein $R_{3A}$ can be an unsubstituted heterocyclyl. In some aspects of embodiment 103, $R_{3A}$ can be an unsubstituted monocyclic 5 to 8 membered nitrogen-containing heterocyclyl. In some aspects of embodiment 103, $R_{3A}$ can contain one nitrogen. In some aspects of embodiment 103, $R_{3A}$ can contain two nitrogens. In some aspects of embodiment 103, $R_{3A}$ can be selected from: pyrrolidino, piperidino, homopiperidino, 2-oxopyrrolidinyl, 2-oxopiperidinyl, morpholino, piperazino, dihydropyranyl, thiomorpholino, 1,3-dioxinyl, 1,3-dioxanyl, 1,4-dioxanyl, 1,2-dioxolanyl, 1,3-dioxolanyl, 1,4-dioxolanyl, 2H-1,2-oxazinyl, maleimido, succinimido, barbituric acid, thiobarbituric acid, dioxopiperazino, hydantoino, dihydrouracilyl, hexahydro-1,3,5-triazinyl, imidazolino, imidazolidino, isoxazolino, isoxazolidino, oxazolino, oxazolidino, oxazolidinono, thiazolino, thiazolidino, oxiranyl, pyrrolidonyl, pyrrolidionyl, 4-piperidonyl, pyrazolino, pyrazolidino, 2-oxopyrrolidino, tetrahydropyranyl, 4H-pyranyl, tetrahydrothiopyranyl and azepanyl.

104. In embodiment 104, the compounds of embodiment 103, or a pharmaceutically acceptable salt thereof, are those wherein $R_{3A}$ can be

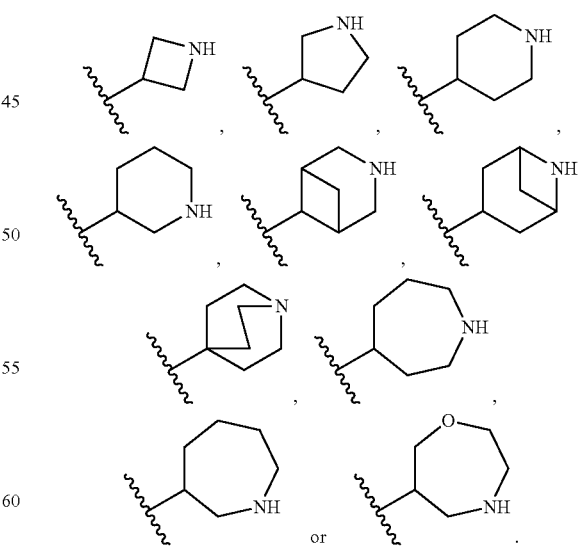

105. In embodiment 105, the compounds of embodiment 102, or a pharmaceutically acceptable salt thereof, are those wherein $R_{3A}$ can be heterocyclyl substituted with one or more $R_E$, independently selected from hydroxy, alkoxy (for example a $C_1$-$C_6$ alkoxy), hydroxyalkyl (for example, hydroxymethyl, hydroxyethyl or hydroxypropyl), cycloalkyl, cyanoalkyl (for example, cyanomethyl, cyanoethyl or cyanopropyl), aralkyl (for example, benzyl), alkoxycarbonyls (for example, a $C_1$-$C_6$ alkoxycarbonyl), aminocarbonyl and cycloalkylalkyl. In some aspects of embodiment 105, the cycloalkyl groups can be monocyclic $C_3$-$C_8$ cycloalkyls. In some aspects of embodiment 105, the cycloalkyl groups can be bicyclic $C_6$-$C_{10}$ cycloalkyls.

106. In embodiment 106, the compounds of embodiment 105, or a pharmaceutically acceptable salt thereof, are those wherein $R_{3A}$ can be heterocyclyl substituted with one or two $R_E$, independently selected from hydroxy, alkoxy (for example a $C_1$-$C_6$ alkoxy), hydroxyalkyl (for example, hydroxymethyl, hydroxyethyl or hydroxypropyl), cycloalkyl (for example a $C_3$-$C_6$ monocyclic cycloalkyl), cyanoalkyl (for example, cyanomethyl, cyanoethyl or cyanopropyl), aralkyl (for example, benzyl), alkoxycarbonyls (for example, a $C_1$-$C_6$ alkoxycarbonyl), aminocarbonyl and cycloalkylalkyl (for example, a $C_3$-$C_6$ monocyclic cycloalkyl($C_1$-$C_3$)alkyl). In some aspects of embodiment 106, the heterocyclyl can be a 5- to 8-membered nitrogen-containing heterocyclyl.

107. In embodiment 107, the compounds of any one of embodiments 105-106, or a pharmaceutically acceptable salt thereof, are those wherein $R_{3A}$ can be

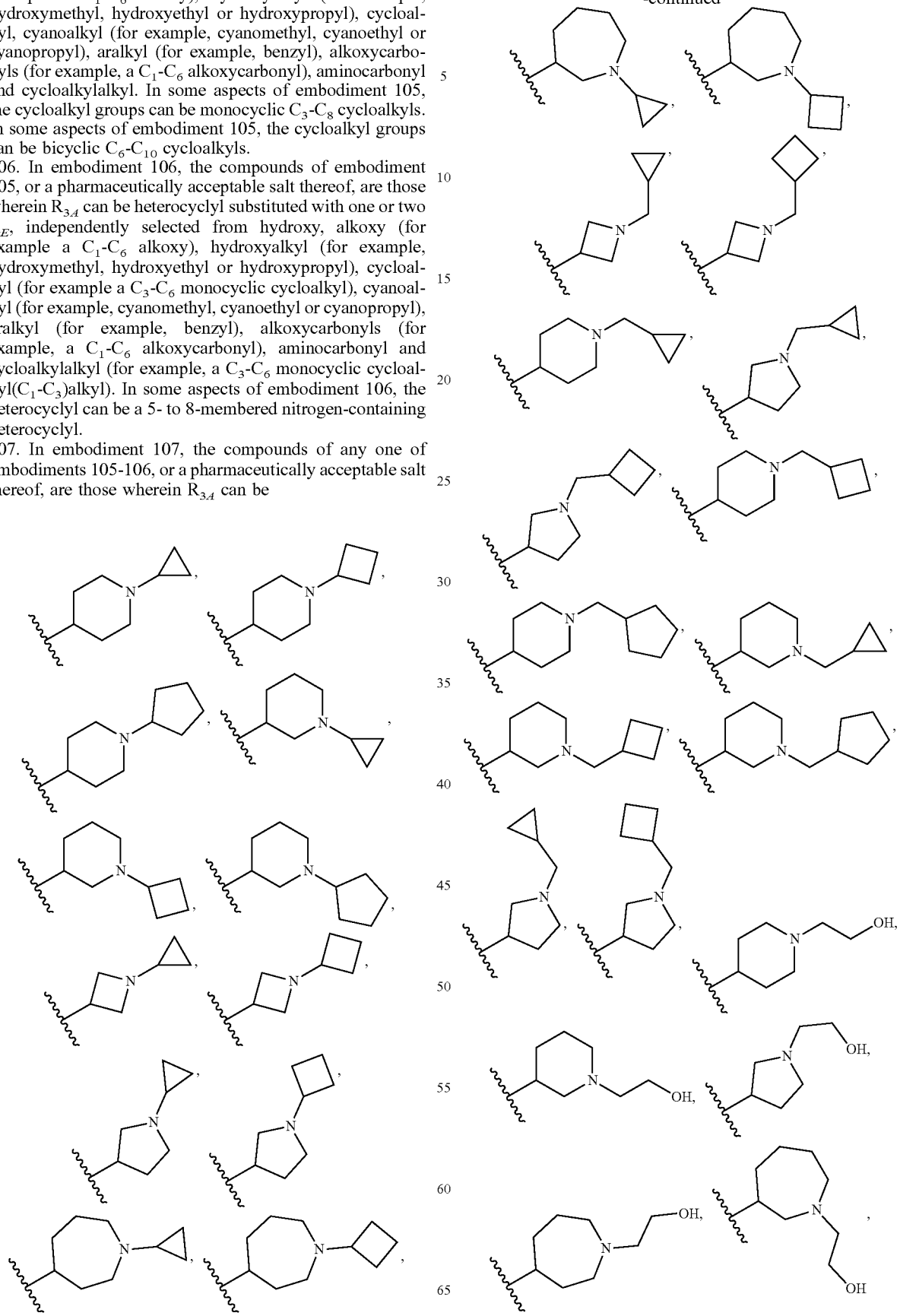

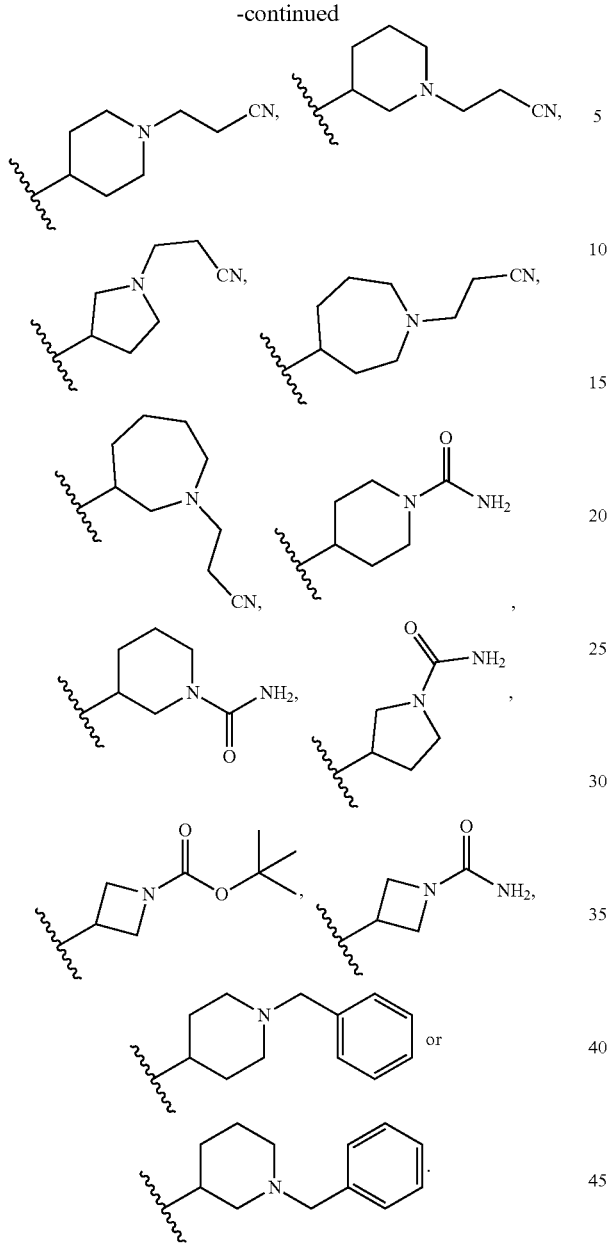

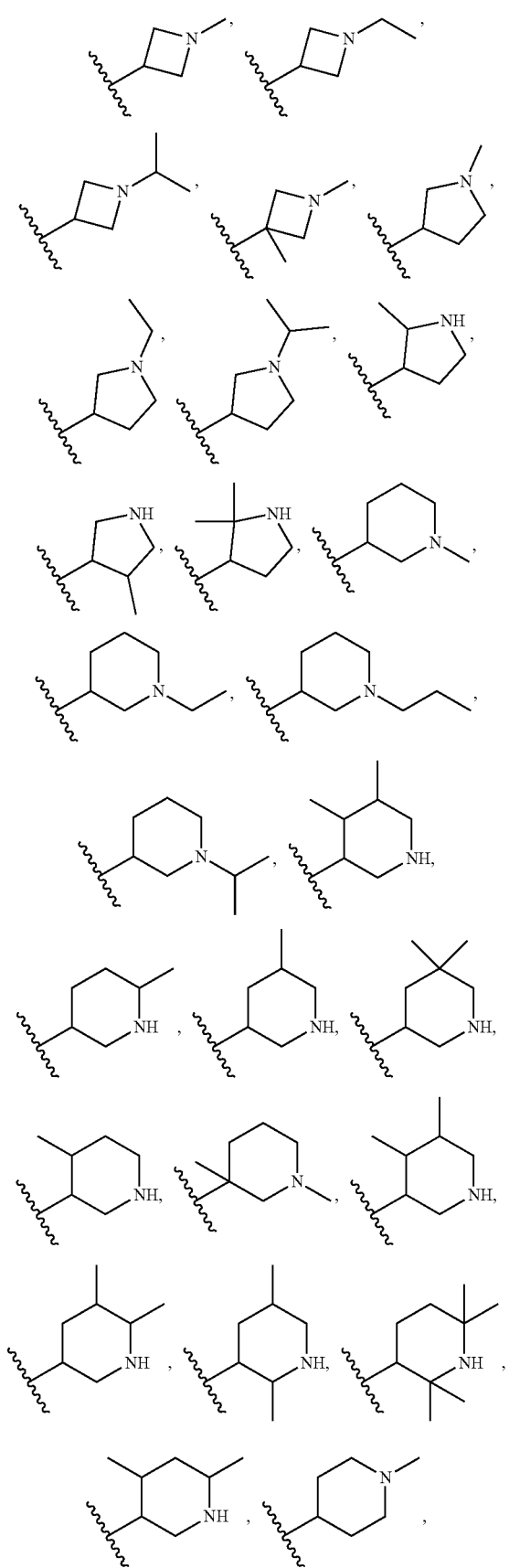

108. In embodiment 108, the compounds of embodiment 102, or a pharmaceutically acceptable salt thereof, are those wherein $R_{3A}$ can be heterocyclyl independently substituted with one or more $R_E$, which can be alkyl (optionally substituted with (i) at least one halogen and at least one hydroxy or with (ii) alkoxy). In some aspects of embodiment 108, the heterocyclyl is a 5- to 8-membered nitrogen-containing heterocyclyl.

109. In embodiment 109, the compounds of embodiment 108, or a pharmaceutically acceptable salt thereof, are those wherein $R_{3A}$ can be heterocyclyl independently substituted with one, two, three or four $R_E$, which can each independently be an unsubstituted alkyl. In some aspects of embodiment 109, the unsubstituted alkyl can be a $C_1$-$C_6$ alkyl group, such as, methyl, ethyl, n-propyl, isopropyl, n-butyl, isobutyl, t-butyl, pentyl (straight-chained or branched) or n-hexyl (straight-chained or branched). 110. In embodiment 110, the compounds of embodiment 109, or a pharmaceutically acceptable salt thereof, are those wherein $R_{3A}$ can be -continued

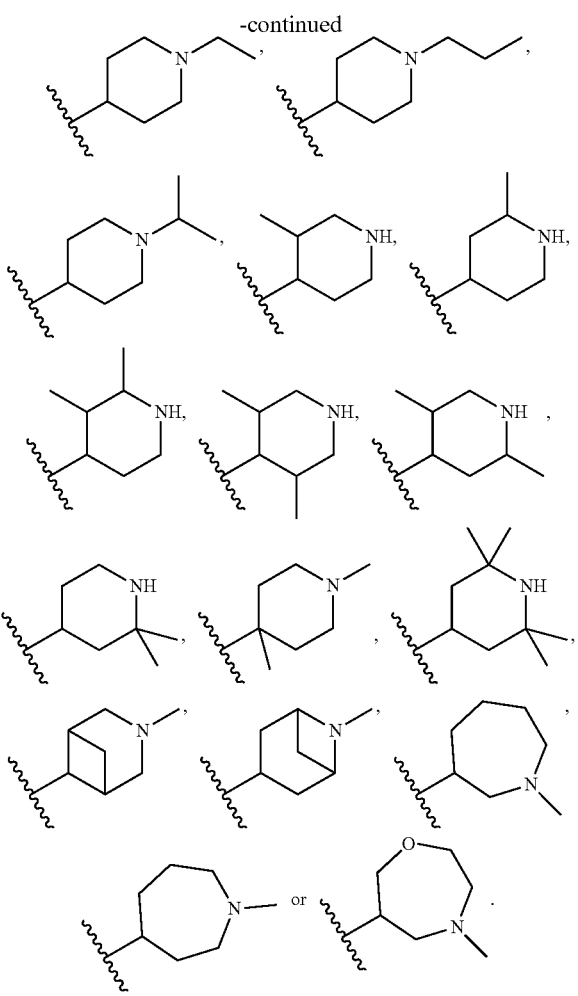

111. In embodiment 111, the compounds of embodiment 108, or a pharmaceutically acceptable salt thereof, are those wherein $R_{3A}$ can be heterocyclyl independently substituted with one or two $R_E$, which can be alkyl independently substituted with at least one halogen (such as chloro or fluoro) and at least one hydroxy.

112. In embodiment 112, the compounds of embodiment 111, or a pharmaceutically acceptable salt thereof, are those wherein $R_{3A}$ can be S or OH.

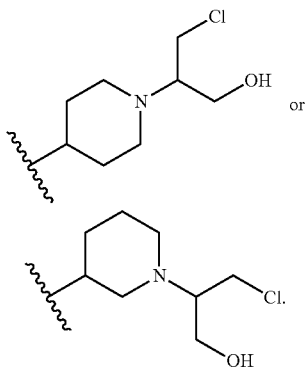

113. In embodiment 113, the compounds of embodiment 108, or a pharmaceutically acceptable salt thereof, are those wherein $R_{3A}$ can be heterocyclyl independently substituted with one or two $R_E$, which can each independently be alkyl substituted with alkoxy. In some aspects of embodiment 116, each $R_E$ can independently be

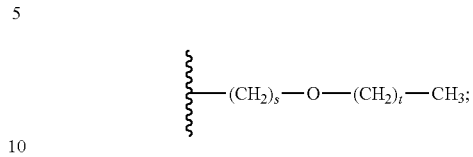

wherein s can be 1, 2, 3, 4, 5, 6, 7, 8, 9 or 10; and t can be 0, 1, 2, 3, 4, 5, 6, 7, 8, 9 or 10. In some aspects of embodiment 116, each $R_E$ can independently be

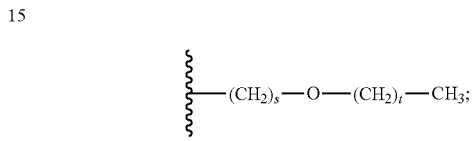

wherein s can be 1, 2 or 3; and t can be 0, 1 or 2. In some aspects of embodiment 116, s can be 1; and t can be 0. In some aspects of embodiment 113, s can be 2; and t can be 0. In some aspects of embodiment 113, s can be 3; and t can be 0. In some aspects of embodiment 113, s can be 1; and t can be 1. In some aspects of embodiment 113, s can be 2; and t can be 1. In some aspects of embodiment 113, s can be 3; and t can be 1. In some aspects of embodiment 113, s can be 1; and t can be 2. In some aspects of embodiment 113, s can be 2; and t can be 2. In some aspects of embodiment 113, s can be 3; and t can be 2.

114. In embodiment 114, the compounds of embodiment 113, or a pharmaceutically acceptable salt thereof, are those wherein $R_{3A}$ can be

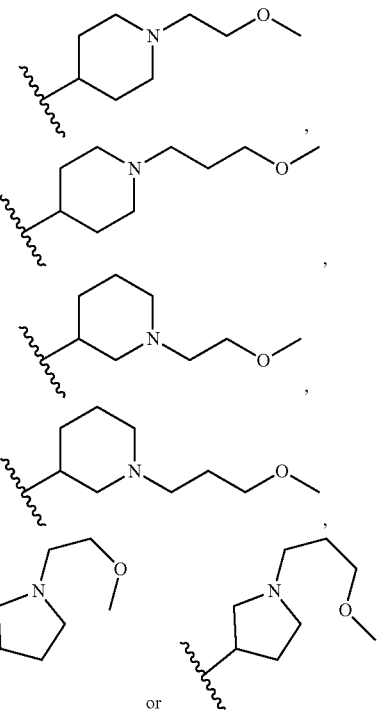

115. In embodiment 115, the compounds of embodiment 108, or a pharmaceutically acceptable salt thereof, are those wherein R$_{3A}$ can be heterocyclyl independently substituted with one or two R$_E$ groups, which can each independently be halogen (for example, fluoro or chloro) or alkylsulfonyl.

116. In embodiment 116, the compounds of any one of embodiments 108 or 115, or a pharmaceutically acceptable salt thereof, are those wherein R$_{3A}$ can be heterocyclyl substituted with one or two R$_E$ groups, which can be independently halogen. In some aspects of embodiment 116, R$_{3A}$ can be substituted with one R$_E$. In other aspects of embodiment 116, R$_{3A}$ can be substituted with two R$_E$ groups. In some aspects of embodiment 116, each R$_E$ can be fluoro. In some aspects of embodiment 116, each R$_E$ can be chloro.

117. In embodiment 117, the compounds of any one of embodiments 108 or 115, or a pharmaceutically acceptable salt thereof, are those wherein R$_{3A}$ can be heterocyclyl independently substituted with one or two R$_E$, which can be (C$_1$-C$_6$ alkyl)sulfonyl, for example, methylsulfonyl, ethylsulfonyl, or isopropylsulfonyl.

118. In embodiment 118, the compounds of any one of embodiments 108 or 115, or a pharmaceutically acceptable salt thereof, are those wherein R$_{3A}$ can be

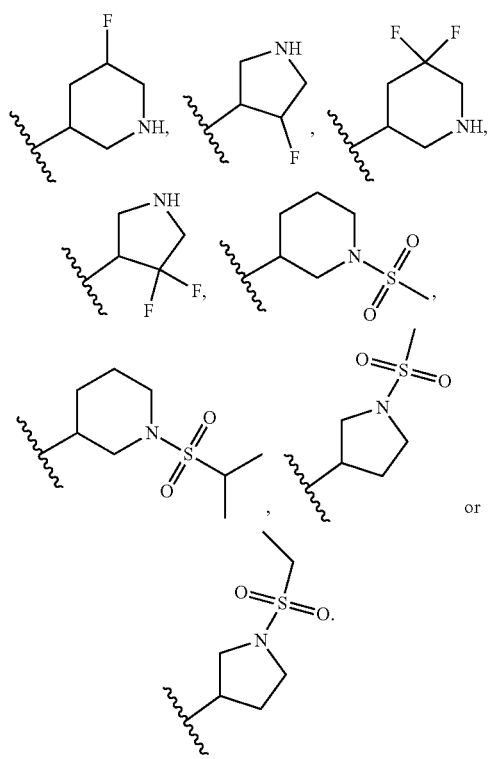

119. In embodiment 119, the compounds of embodiment 102, or a pharmaceutically acceptable salt thereof, are those wherein R$_{3A}$ can be heterocyclyl independently substituted with one or more R$_E$, which can be alkylcarbonyl (optionally substituted with hydroxy or benzyloxy). In some aspects of embodiment 119, the heterocyclyl is a 5- to 8-membered nitrogen-containing heterocyclyl.

120. In embodiment 120, the compounds of embodiment 119, or a pharmaceutically acceptable salt thereof, are those wherein R$_{3A}$ can be heterocyclyl independently substituted with one or more R$_D$, which can be an unsubstituted alkylcarbonyl.

121. In embodiment 121, the compounds of embodiment 120, or a pharmaceutically acceptable salt thereof, are those wherein R$_{3A}$ can be

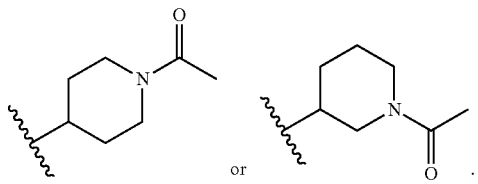

122. In embodiment 122, the compounds of embodiment 119, or a pharmaceutically acceptable salt thereof, are those wherein R$_{3A}$ can be heterocyclyl independently substituted with one or more R$_E$, which can be alkylcarbonyl substituted with hydroxy or benzyloxy.

123. In embodiment 123, the compounds of embodiment 122, or a pharmaceutically acceptable salt thereof, are those wherein R$_{3A}$ can be

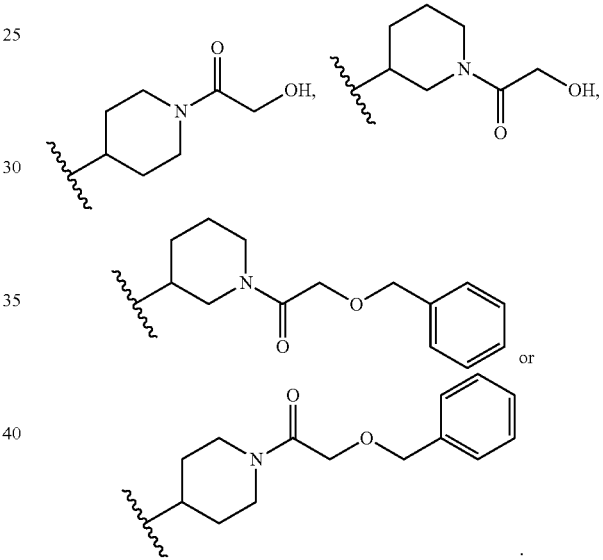

124. In embodiment 124, the compounds of embodiment 108, or a pharmaceutically acceptable salt thereof, are those wherein R$_{3A}$ can be heterocyclyl independently substituted with one or more R$_E$, which can be heteroaryl (optionally substituted with one or more R$_F$ independently selected from halogen, cyano and alkyl).

125. In embodiment 125, the compounds of embodiment 124, or a pharmaceutically acceptable salt thereof, are those wherein R$_{3A}$ can be heterocyclyl independently substituted with one or more R$_E$, which can be an unsubstituted heteroaryl.

126. In embodiment 126, the compounds of embodiment 125, or a pharmaceutically acceptable salt thereof, are those wherein R$_{3A}$ can be heterocyclyl substituted with one R$_E$, which can be an unsubstituted heteroaryl. In some aspects of embodiment 126, the heteroaryl group can be a 5-membered heteroaryl group, a 6-membered heteroaryl group or a 10-membered heteroaryl group. In some aspects of embodiment 126, the heteroaryl group can be a monocyclic 5- or 6-membered heteroaryl. In some aspects of embodiment 126, the heteroaryl group can be a nitrogen-containing 5- or 6-membered monocyclic heteroaryl group. In some aspects of embodiment 126, the heteroaryl group can be a 5- or 6-membered heteroaryl group containing nitrogen and oxygen. In some aspects of embodiment 126, the heteroaryl group can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-triazine. In some aspects of embodiment 126, the heterocyclyl is a 5- to 8-membered nitrogen-containing heterocyclyl.

127. In embodiment 127, the compounds of embodiments 125-126, or a pharmaceutically acceptable salt thereof, are those wherein $R_{3A}$ can be azetidinyl, pyrrolidinyl, piperidinyl, 3-azabicyclo[3.1.1]heptanyl, 6-azabicyclo[3.1.1]heptanyl, quinuclidinyl, azepanyl or 1,4-oxazepanyl, and $R_E$ can be pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl or tetrazolyl.

128. In embodiment 128, the compounds of embodiments 125-127, or a pharmaceutically acceptable salt thereof, are those wherein $R_{3A}$ can be 129. In embodiment 129, the compounds of embodiment 124, or a pharmaceutically acceptable salt thereof, are those wherein $R_{3A}$ can be heterocyclyl independently substituted with one or more $R_E$, which can be heteroaryl substituted with one or more $R_F$ independently selected from halogen (such as fluoro or chloro), alkyl (for example, a $C_1$-$C_6$ alkyl) and cyano. In some aspects of embodiment 132, the $C_1$-$C_6$ alkyl of $R_F$ can be methyl, ethyl, n-propyl or isopropyl.

130. In embodiment 130, the compounds of embodiment 124, or a pharmaceutically acceptable salt thereof, are those wherein $R_{3A}$ can be heterocyclyl substituted with one $R_E$, which can be heteroaryl substituted with one or two $R_F$ independently selected from halogen and alkyl. In some aspects of embodiment 130, the heteroaryl group can be a 5-membered heteroaryl group, a 6-membered heteroaryl group or a 10-membered heteroaryl group. In some aspects of embodiment 130, the heteroaryl group can be a monocyclic 5- or 6-membered heteroaryl. In some aspects of embodiment 130, the heteroaryl group can be a nitrogen-containing 5- or 6-membered monocyclic heteroaryl group.

In some aspects of embodiment 130, the heteroaryl group can be a 5- or 6-membered heteroaryl group containing nitrogen and oxygen. In some aspects of embodiment 130, the heteroaryl group can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-triazine. In some aspects of embodiment 130, the heteroaryl group can be substituted with one or two halogens, for example, fluoro or chloro. In some aspects of embodiment 130, the heteroaryl group can be substituted with one or two alkyl groups, for example, $C_1$-$C_4$ alkyl groups such as methyl, ethyl, propyl, isopropyl, n-butyl, isobutyl and tert-butyl. In some aspects of embodiment 130, the heteroaryl group can be substituted with one halogen and one $C_1$-$C_4$ alkyl group, such as those described herein.

131. In embodiment 131, the compounds of embodiments 129-130, or a pharmaceutically acceptable salt thereof, are those wherein $R_{3A}$ can be

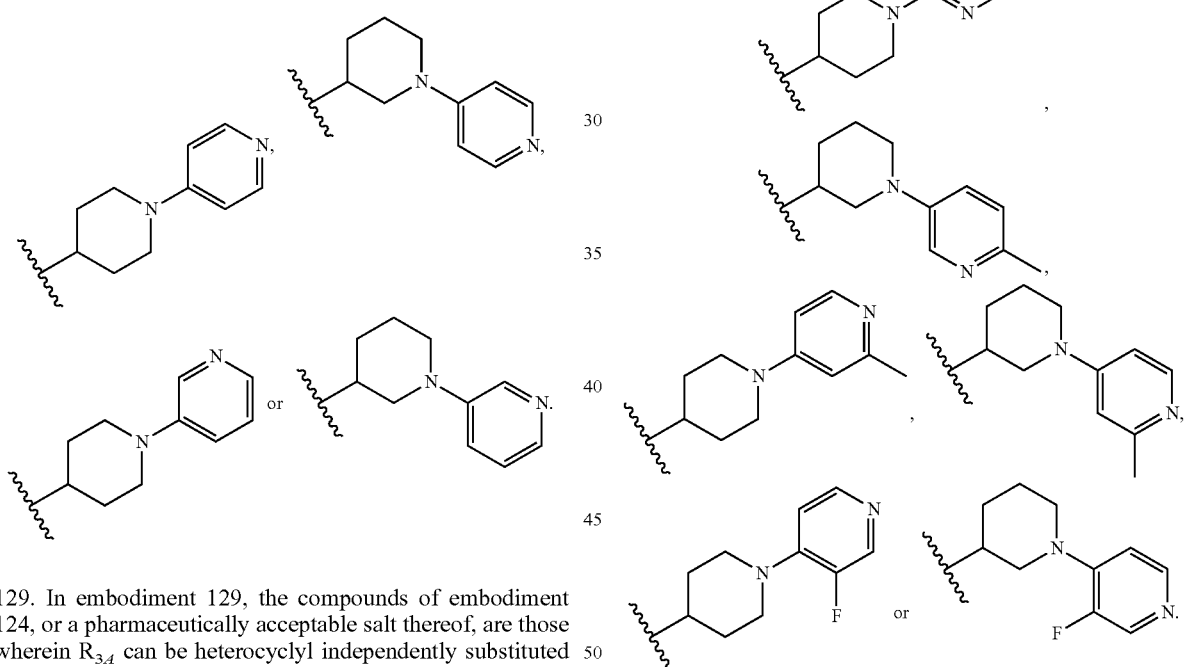

132. In embodiment 132, the compounds of embodiment 108, or a pharmaceutically acceptable salt thereof, are those wherein $R_{3A}$ can be heterocyclyl (optionally substituted with one or more $R_E$, which can be heteroaralkyl (optionally substituted with one or more $R_G$ independently selected from halogen, alkyl, cyano and hydroxy)).

133. In embodiment 133, the compounds of embodiment 132, or a pharmaceutically acceptable salt thereof, are those wherein $R_{3A}$ can be heterocyclyl independently substituted with one or more $R_E$, which can be an unsubstituted heteroaralkyl.

134. In embodiment 134, the compounds of embodiment 132, or a pharmaceutically acceptable salt thereof, are those wherein $R_{3A}$ can be heterocyclyl substituted with one $R_E$, which can be heteroaralkyl substituted with one or two $R_G$ independently selected from halogen, alkyl, cyano and hydroxy. In some aspects of embodiment 134, the heteroaryl group in heteroaralkyl can be a 5-membered heteroaryl group, a 6-membered heteroaryl group or a 10-membered heteroaryl group. In some aspects of embodiment 134, the heteroaryl group in heteroaralkyl can be a monocyclic heteroaryl. In some aspects of embodiment 134, the heteroaryl group in heteroaryloxy can be a 5- or 6-membered heteroaryl group. In some aspects of embodiment 134, the heteroaryl group in heteroaralkyl can be a nitrogen-containing 5- or 6-membered heteroaryl group. In some aspects of embodiment 134, the heteroaryl group in heteroaralkyl can be a 5- or 6-membered heteroaryl group containing nitrogen and oxygen. In some aspects of embodiment 134, the heteroaryl group in heteroaralkyl can be, for example, pyrrole, pyrazole, imidazole, 1,2,4-triazole, furan, thiophene, oxazole, isoxazole, thiazole, isothiazole, 1,2,5-oxadiazole, 1,2,3-oxadiazole, 1,3,4-thiadiazole, pyridine, pyridazine, pyrimidine, pyrazine, 1,2,4-triazine or 1,3,5-triazine. In some aspects of embodiment 137, the alkylene in heteroaralkyl can be a $C_1$-$C_6$ alkylene. In some aspects of embodiment 134, the alkylene in heteroaralkyl can be a methylene (—$CH_2$—).

135. In embodiment 135, the compounds of embodiment 108, or a pharmaceutically acceptable salt thereof, are those wherein $R_{3A}$ can be heterocyclyl independently substituted with one or more $R_E$, which can be heterocyclyl (optionally substituted with one or more $R_H$ independently selected from alkyl, cyano and hydroxy). In some aspects of embodiment 135, $R_{3A}$ and $R_E$ are each independently a 4- to 8-membered nitrogen-containing heterocyclyl.

136. In embodiment 136, the compounds of embodiment 135, or a pharmaceutically acceptable salt thereof, are those wherein $R_{3A}$ can be heterocyclyl substituted with one $R_E$, which can be an unsubstituted heterocyclyl. In some aspects of embodiment 136, the unsubstituted heterocyclyl can be a 5-membered heterocyclyl group, a 6-membered heterocyclyl group, a 7-membered heterocyclyl group or an 8-membered heterocyclyl group. In some aspects of embodiment 136, the heterocyclyl group can be a monocyclic heterocyclyl. In some aspects of embodiment 136, the heterocyclyl group can be a 5- or 6-membered monocyclic heterocyclyl. In some aspects of embodiment 136, the heterocyclyl group can be a bicyclic heterocyclyl. In some aspects of embodiment 136, the heterocyclyl group can be a 7- or 8-membered bicyclic heterocyclyl. In some aspects of embodiment 136, the heterocyclyl group can be a nitrogen-containing heterocyclyl. In some aspects of embodiment 136, the heterocyclyl group can be a nitrogen- and oxygen-containing heterocyclyl. In some aspects of embodiment 136, the heterocyclyl group can be, for example, pyrrolidino, piperidino, morpholino, piperazino, imidazolino, indoline, 7-azabicyclo[2.2.1]heptane, hexahydro-1H-pyrrolizine or 8-azabicyclo[3.2.1]octane. 1,3,5-triazine.

137. In embodiment 137, the compounds of embodiment 136, or a pharmaceutically acceptable salt thereof, are those wherein $R_{3A}$ can be

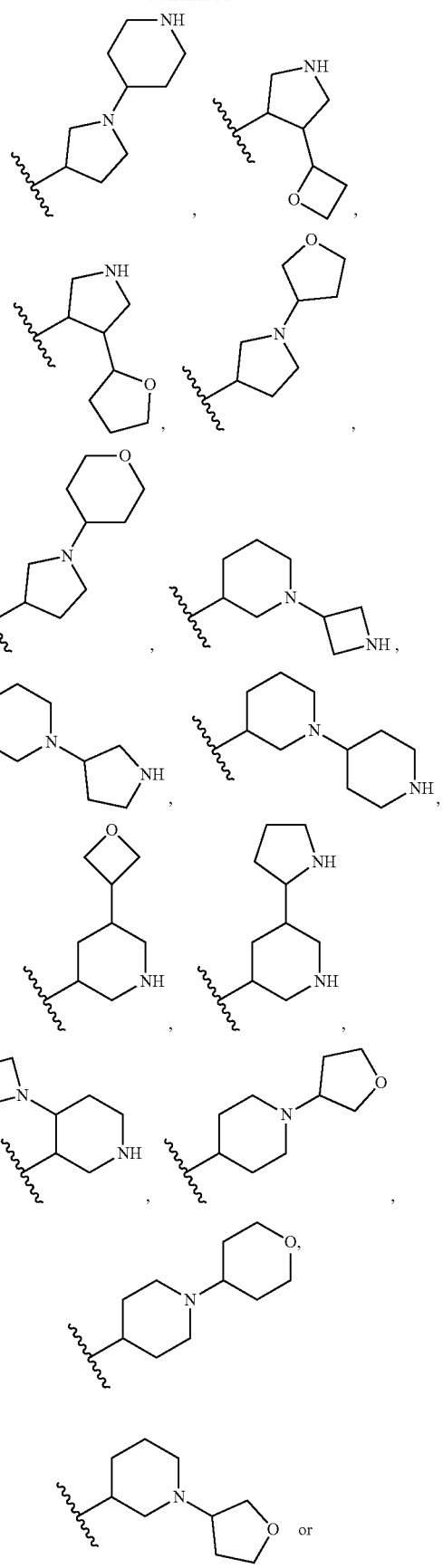

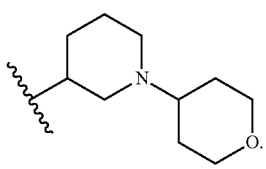

138. In embodiment 138, the compounds of embodiment 135, or a pharmaceutically acceptable salt thereof, are those wherein $R_{3A}$ can be heterocyclyl substituted with one $R_E$, which can be heterocyclyl substituted with one or more $R_H$ independently selected from alkyl (for example, a $C_1$-$C_6$ alkyl), cyano and hydroxy. In some aspects of embodiment 138, the $C_1$-$C_6$ alkyl of $R_E$ can be methyl, ethyl, n-propyl or isopropyl.

139. In embodiment 139, the compounds of embodiment 108, or a pharmaceutically acceptable salt thereof, are those wherein $R_{3A}$ can be heterocyclyl independently substituted with one or more $R_E$, which can be aryl (optionally substituted with one or more $R_1$ independently selected from halogen, alkyl, alkoxy, cyano and hydroxy). In some aspects of embodiment 139, the aryl group can be a $C_6$ or a $C_{10}$ aryl, such as phenyl or naphthyl.

140. In embodiment 140, the compounds of embodiment 139, or a pharmaceutically acceptable salt thereof, are those wherein $R_{3A}$ can be heterocyclyl independently substituted with one or more $R_E$, which can be an unsubstituted aryl. In some aspects of embodiment 140, $R_{3A}$ can be heterocyclyl independently substituted with one or more $R_E$, which can be an unsubstituted phenyl.

141. In embodiment 141, the compounds of embodiment 140, or a pharmaceutically acceptable salt thereof, are those wherein $R_{3A}$ can be

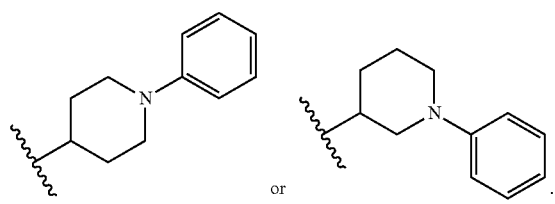 [SMILES: *C1CCN(c2ccccc2)CC1 ; *C1CCCN(c2ccccc2)C1]

or

.

142. In embodiment 142, the compounds of embodiment 139, or a pharmaceutically acceptable salt thereof, are those wherein $R_{3A}$ can be heterocyclyl substituted with one $R_E$, which can be aryl substituted with one or more $R_1$ independently selected from halogen, alkyl, alkoxy, cyano and hydroxy.

143. In embodiment 143, the compounds of embodiment 142, or a pharmaceutically acceptable salt thereof, are those wherein $R_{3A}$ can be heterocyclyl substituted with one $R_E$, which can be aryl substituted with one or more $R_1$ independently selected from halogen, alkyl, alkoxy and cyano.

144. In embodiment 144, the compounds of any one of embodiments 142-143, or a pharmaceutically acceptable salt thereof, are those wherein $R_{3A}$ can be selected from:

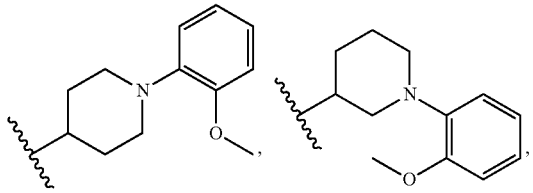

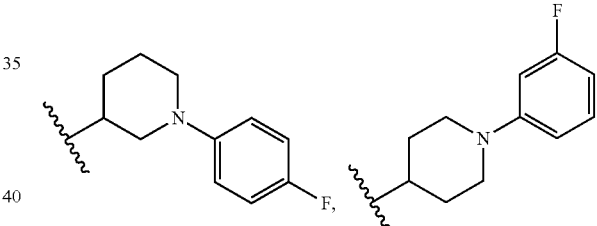

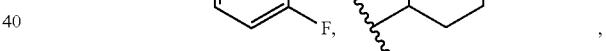

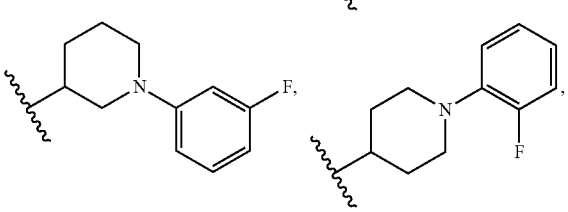

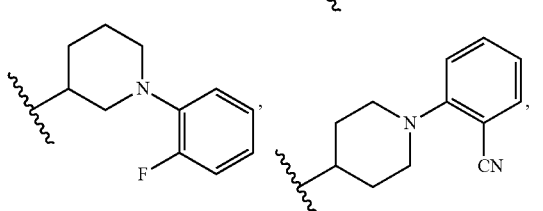

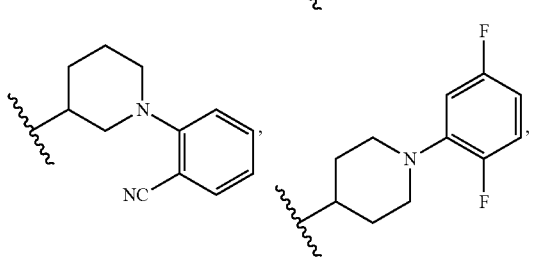

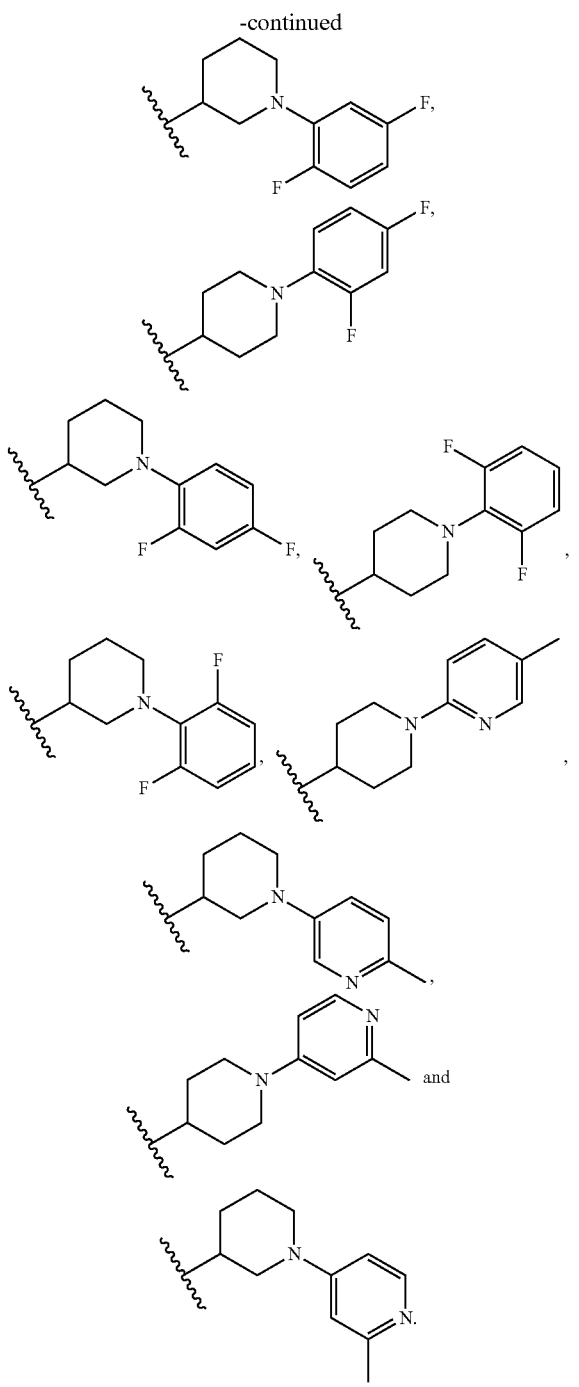

145. In embodiment 145, the compounds of any one of embodiments 1-84, or a pharmaceutically acceptable salt thereof, are those wherein $R_{3A}$ can be heterocyclylalkyl optionally substituted with one or more $R_E$, independently selected from hydroxy, alkoxy, hydroxyalkyl, cycloalkyl, cyanoalkyl, aralkyl, alkoxycarbonyl, aminocarbonyl, cycloalkylalkyl, alkyl, alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy). In some aspects of embodiment 145, the heterocyclyl of the heterocyclylalkyl can be a 5- to 8-membered monocyclic heterocyclyl. In some aspects of embodiment 145, the heterocyclyl of the heterocyclylalkyl can be a 6- to 10-membered bicyclic heterocyclyl. In some aspects of embodiment 145, the heterocyclyl can contain 1, 2 or 3 heteroatoms, which can be oxygen, nitrogen or sulfur. In some aspects of embodiment 145, the heterocyclyl of the heterocyclylalkyl can be a nitrogen-containing heterocyclyl. In some aspects of embodiment 145, the heterocyclyl of the heterocyclylalkyl can be an oxygen-containing heterocyclyl. In some aspects of embodiment 145, the heterocyclyl group of the heterocyclylalkyl can contain oxygen and nitrogen. In some aspects of embodiment 145, the heterocyclyl group of the heterocyclylalkyl can be a 5- to 8-membered monocyclic heterocyclyl containing one nitrogen atom. In some aspects of embodiment 145, the alkylene of the heterocyclylalkyl can be a $C_1$-$C_6$ alkylene, for example, —$(CH_2)_{1-6}$—. In some aspects of embodiment 145, the alkylene of the heterocyclylalkyl can be a methylene (—$CH_2$—). In some aspects of embodiment 145, when the heterocyclylalkyl group contains one or more —NH— groups in the ring, one or more $R_E$ may be bonded to the nitrogen atom (replacing the hydrogen), or, the alkyl group of the heterocyclylalkyl may be bonded to the nitrogen atom of the heterocyclyl (replacing the hydrogen). In some aspects of embodiment 145, $R_{3A}$ can be heterocyclylalkyl optionally substituted with one or more $R_E$ on one or more NH groups of the heterocyclylalkyl, wherein the one or more $R_E$ independently selected from hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy). In other aspects of embodiment 145, $R_{3A}$ can be heterocyclyl optionally substituted with one or more $R_E$ on one or more carbons atoms of the heterocyclyl, wherein the one or more $R_E$ independently selected from halogen, hydroxy, alkoxy, hydroxyalkyl, cycloalkyl, cyanoalkyl, aralkyl, alkoxycarbonyl, aminocarbonyl, cycloalkylalkyl, alkyl (optionally substituted with (i) at least one halogen and at least one hydroxy or with (ii) alkoxy), alkylcarbonyl (optionally substituted with hydroxy or benzyloxy), alkylsulfonyl, heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy) and aryl (optionally substituted with one or more $R_I$ independently selected from halogen, alkyl, alkoxy, cyano and hydroxy).

146. In embodiment 146, the compounds of embodiment 145, or a pharmaceutically acceptable salt thereof, are those wherein $R_{3A}$ can be an unsubstituted heterocyclylalkyl. In some aspects of embodiment 146, the heterocyclyl of the heterocyclylalkyl can be a 5- to 8-membered monocyclic heterocyclyl containing one or two heteroatoms which can be nitrogen or oxygen. In some aspects of embodiment 146, the alkylene of the heterocyclylalkyl can be a methylene (—CH$_2$—).

147. In embodiment 147, the compounds of embodiment 146, or a pharmaceutically acceptable salt thereof, are those wherein R$_{3A}$ can be

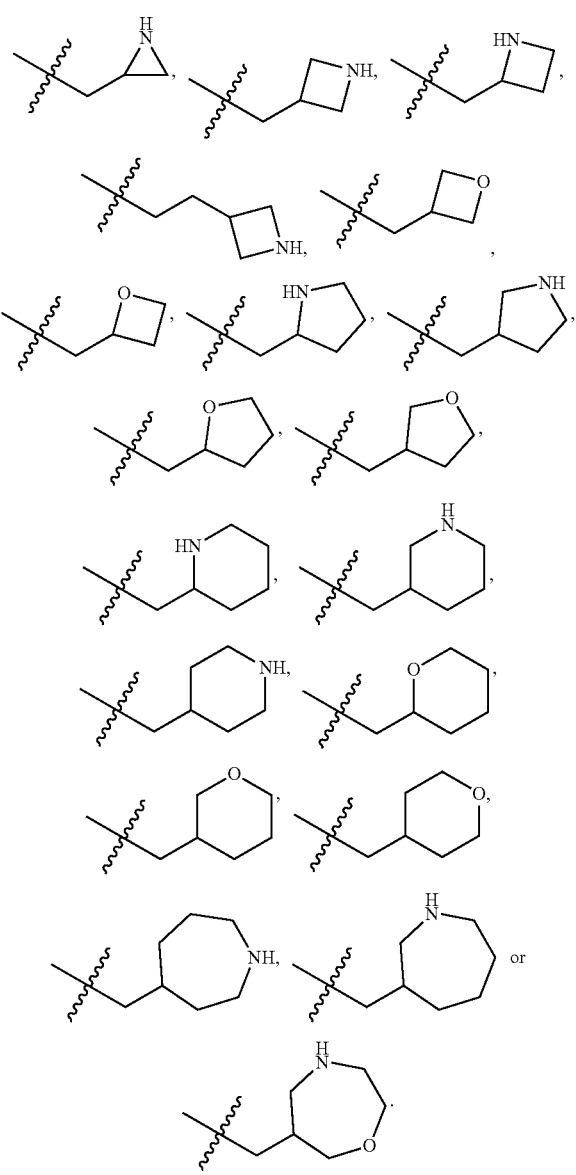

148. In embodiment 148, the compounds of any one of embodiments 145-147, or a pharmaceutically acceptable salt thereof, are those wherein R$_{3A}$ can be

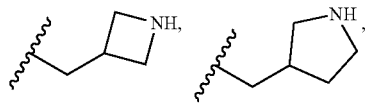

-continued

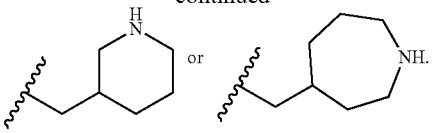

In some aspects of embodiment 148, R$_{3A}$ can be

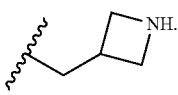

In other aspects of embodiment 148, R$_{3A}$ can be

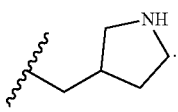 [SMILES: *CC1CCNC1]

In still other aspects of embodiment 148, R$_{3A}$ can be

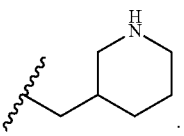

In still other aspects of embodiment 148, R$_{3A}$ can be

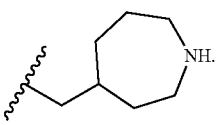 [SMILES: *CC1CCCNCC1]

149. In embodiment 149, the compounds of any one of embodiments 145-147, or a pharmaceutically acceptable salt thereof, are those wherein R$_{3A}$ can be azetidinylmethyl, pyrrolidinylmethyl, piperidinylmethyl, azepanylmethyl or 1,4-oxazepanylmethyl. 150. In embodiment 150, the compounds of embodiment 145, or a pharmaceutically acceptable salt thereof, are those wherein R$_{3A}$ can be heterocyclylalkyl independently substituted with one or more R$_E$, independently selected from alkoxy (for example a C$_1$-C$_6$ alkoxy), hydroxyalkyl (for example, hydroxymethyl, hydroxyethyl or hydroxypropyl), cyanoalkyl (for example, cyanomethyl, cyanoethyl or cyanopropyl), aralkyl (for example, benzyl), alkoxycarbonyl (for example, a C$_1$-C$_6$ alkoxycarbonyl), aminocarbonyl (for example, —(C=O)NH$_2$ or —(C=O)N(Me)$_2$), cycloalkylalkyl, alkylcarbonyl (optionally substituted with hydroxy or benzyloxy), heteroaralkyl (optionally substituted with one or more R$_G$ independently selected from halogen, alkyl, cyano and hydroxy) or heterocyclyl (optionally substituted with one or more R$_H$ independently selected from alkyl, cyano and hydroxy). In some aspects of embodiment 150, the cycloalkyl groups can be monocyclic C$_3$-C$_8$ cycloalkyls. In some aspects of embodiment 150, the cycloalkyl groups can be bicyclic C$_6$-C$_{10}$ cycloalkyls. 151. In embodiment 151, the compounds of embodiment 150, or a pharmaceutically acceptable salt thereof, are those wherein $R_{3A}$ can be heterocyclylalkyl substituted with one $R_E$, which can be selected from hydroxyalkyl, alkoxy, cyanoalkyl, aralkyl, alkoxycarbonyl, aminocarbonyl (for example, —(C═O)NH$_2$ or —(C═O)N(Me)$_2$), cycloalkylalkyl, alkylcarbonyl (optionally substituted with hydroxy or benzyloxy), heteroaralkyl (optionally substituted with one or more $R_G$ independently selected from halogen, alkyl, cyano and hydroxy) or heterocyclyl (optionally substituted with one or more $R_H$ independently selected from alkyl, cyano and hydroxy).

152. In embodiment 152, the compounds of embodiment 145, or a pharmaceutically acceptable salt thereof, are those wherein $R_{3A}$ can be heterocyclylalkyl independently substituted with one or more $R_E$, independently selected from halogen, hydroxy, alkoxy (for example a $C_1$-$C_6$ alkoxy such as methoxy or ethoxy), alkyl (for example a $C_1$-$C_6$ alkyl such as methyl, ethyl, n-propyl or isopropyl), cycloalkyl (for example a monocyclic $C_3$-$C_8$ cycloalkyl), alkylsulfonyl, heteroaryl (for example, a monocyclic 5- or 6-membered nitrogen-containing heteroaryl) (optionally substituted with one or more $R_F$ independently selected from halogen, alkyl, cyano and hydroxy) and aryl (optionally substituted with one or more $R_I$ independently selected from halogen, alkyl, alkoxy, cyano and hydroxy).

153. In embodiment 153, the compounds of any one of embodiments 145 or 152, or a pharmaceutically acceptable salt thereof, are those wherein $R_{3A}$ can be heterocyclylalkyl independently substituted with one or two $R_E$, independently selected from hydroxy, alkoxy, alkyl, cycloalkyl (for example a $C_3$-$C_8$ cycloalkyl), heteroaryl (for example, a 5- or 6-membered nitrogen-containing heteroaryl) (optionally substituted with one or two $R_F$ independently selected from halogen) and aryl (for example a $C_6$ aryl) (optionally substituted with one or more $R_I$ independently selected from halogen).

154. In embodiment 154 the compounds of any one of embodiments 145 or 152-153, or a pharmaceutically acceptable salt thereof, are those wherein $R_{3A}$ can be selected from:

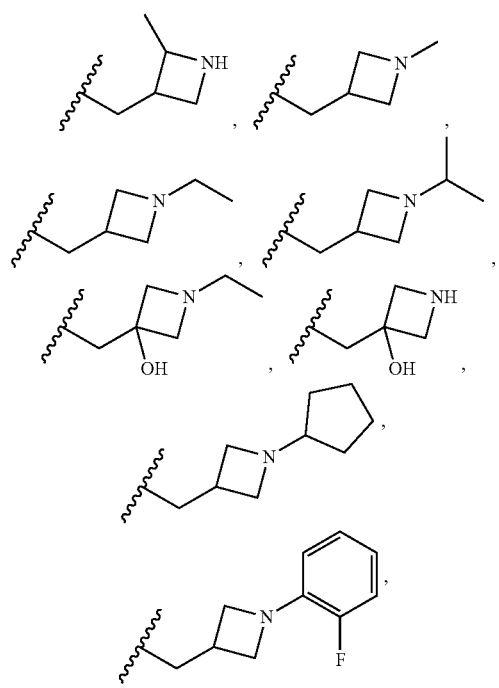

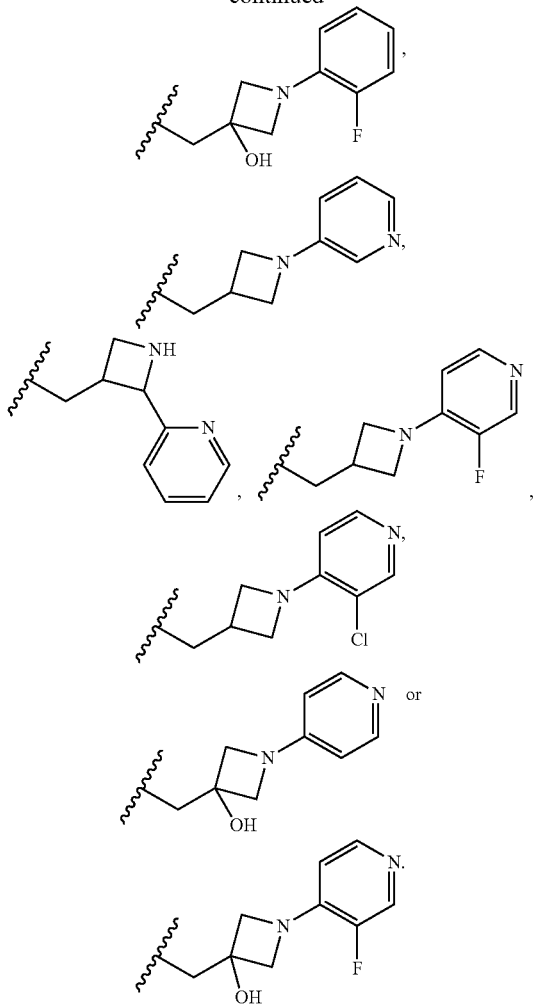

155. In embodiment 155, the compounds of any one of embodiments 145 or 152, or a pharmaceutically acceptable salt thereof, are those wherein $R_{3A}$ can be heterocyclylalkyl independently substituted with one or two $R_E$ groups, which can independently be halogen (for example, fluoro or chloro) or alkylsulfonyl.

156. In embodiment 156, the compounds of any one of embodiments 152 or 155, or a pharmaceutically acceptable salt thereof, are those wherein $R_{3A}$ can be heterocyclylalkyl independently substituted with one or two $R_E$ groups, which can be independently halogen. In some aspects of embodiment 156, $R_{3A}$ can be substituted with one $R_E$. In other aspects of embodiment 156, $R_{3A}$ can be substituted with two $R_E$ groups. In some aspects of embodiment 156, each $R_E$ can be fluoro. In some aspects of embodiment 156, each $R_E$ can be chloro.

157. In embodiment 157, the compounds of any one of embodiments 152 or 155, or a pharmaceutically acceptable salt thereof, are those wherein $R_{3A}$ can be heterocyclylalkyl independently substituted with one or two $R_E$, which can independently be alkylsulfonyl, for example, methylsulfonyl, ethylsulfonyl, or isopropylsulfonyl.

158. In embodiment 158, the compounds of any one of embodiments 152 or 155, or a pharmaceutically acceptable salt thereof, are those wherein $R_{3A}$ can be

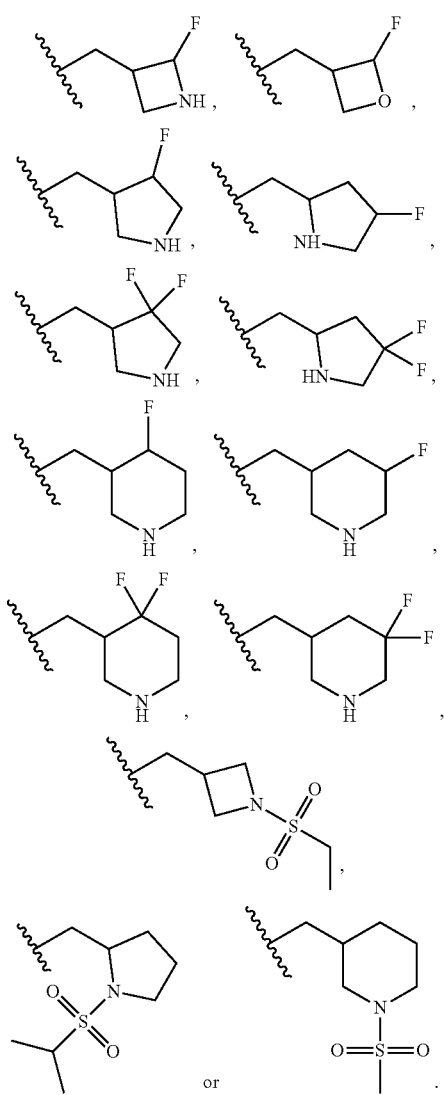

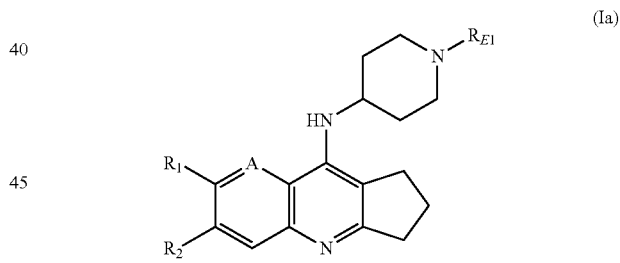

159. In embodiment 159 the compounds of any one of embodiments 1-84, or a pharmaceutically acceptable salt thereof, are those wherein $R_{3A}$ can be alkyl (optionally substituted with alkylamino), for example a $C_1$-$C_8$ alkyl (optionally substituted with alkylamino). In some aspects of embodiment 159, the alkyl can be a $C_1$-$C_8$ alkyl such as methyl, ethyl, n-propyl, isopropyl, n-butyl, isobutyl, t-butyl, pentyl (straight-chained or branched), hexyl (straight-chained or branched), heptyl (straight-chained or branched) or octyl (straight-chained or branched).

160. In embodiment 160, the compounds of embodiment 159, or a pharmaceutically acceptable salt thereof, are those wherein $R_{3A}$ can be methyl or isopropyl.

161. In embodiment 161, the compounds of embodiment 159, or a pharmaceutically acceptable salt thereof, are those wherein $R_{3A}$ can be ethyl, n-propyl, or n-butyl; each can be substituted with alkylamino.

162. In embodiment 162, the compounds of any one of embodiments 159 or 161, or a pharmaceutically acceptable salt thereof, are those wherein $R_{3A}$ can be 163. In embodiment 163, the compounds of any one of embodiments 159-162, or a pharmaceutically acceptable salt thereof, are those wherein $R_{3B}$ can be hydrogen. In some aspects of embodiment 163, $R_{3B}$ can be hydrogen and $R_{3A}$ is not hydrogen.

164. In embodiment 164 the compounds of any one of embodiments 1-84, or a pharmaceutically acceptable salt thereof, are those wherein $R_{3A}$ can be hydrogen.

165. In embodiment 165, the compounds of embodiment 1, or a pharmaceutically acceptable salt thereof, are those having structural formula (Ia), or a pharmaceutically acceptable salt thereof, (Ia)

wherein: A can be CH or N; $R_1$ and $R_2$ are independently selected from —$OCH_3$ and —$OCD_3$; and $R_{E1}$ can be selected from hydrogen, hydroxy, hydroxyalkyl, cycloalkyl, cyanoalkyl, aralkyl, alkoxycarbonyl, aminocarbonyl (for example, —(C=O)$NH_2$ or —(C=O)N(Me)$_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 165, $R_{E1}$ can be hydrogen. In some aspects of embodiment 165, the aforementioned alkyl groups, including $R_{E1}$, can be an unsubstituted $C_1$-$C_6$ alkyl. In some aspects of embodiment 165, $R_{E1}$ can be a $C_1$-$C_3$ alkyl, such as methyl, ethyl, n-propyl and isopropyl. In some aspects of embodiment 165, $R_{E1}$ can be a $C_1$-$C_6$ alkyl substituted with a $C_1$-$C_6$ alkoxy. In some aspects of embodiment 165, the aforementioned alkoxy groups can be $C_1$-$C_6$ alkoxy groups such as those described herein and including methoxy or ethoxy. In some aspects of embodiment 165, $R_{E1}$ can be a $C_1$-$C_3$ alkyl substituted a $C_1$-$C_3$ alkoxy. In some aspects of embodiment 165, $R_{E1}$ can be $C_1$-$C_6$ hydroxyalkyl groups such as those described herein and including hydroxymethyl, hydroxyethyl and 2-hydroxypropyl. In some aspects of embodiment 165, $R_{E1}$ can be $C_1$-$C_6$ cyanoalkyl groups such as those described herein and including cyanomethyl, cyanoethyl and 2-cyanopropyl. In some aspects of embodiment 165, the aforementioned halogens can be fluoro or chloro. In some aspects of embodiment 165, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 165, $R_{E1}$ can be a $C_3$-$C_6$ monocyclic cycloalkyl, such as cyclopropyl, cyclobutyl, cyclopentyl and cyclohexyl. In some aspects of embodiment 165, the aforementioned alkylsulfonyl groups, including $R_{E1}$; can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 165, the aforementioned aryl groups, including $R_{E1}$; can be a $C_6$ aryl such as phenyl. In some aspects of embodiment 165, the aforementioned heteroaryl groups, including $R_{E1}$; can be 5- or 6-membered heteroaryl groups containing one nitrogen atom, two nitrogen atoms, or one nitrogen atom and one heteroatom selected from oxygen and sulfur. In some aspects of embodiment 165, the aforementioned heterocyclyl groups, including $R_{E1}$; can be 5- to 8-membered monocyclic heterocyclyl groups containing one nitrogen atom and one heteroatom selected from oxygen and sulfur. In some aspects of embodiment 165, $R_{E1}$ can be 4- to 6-membered monocyclic heterocyclyl groups containing one or more heteroatoms selected from nitrogen, oxygen and sulfur. In some aspects of embodiment 165, $R_{E1}$ can be a ($C_1$-$C_6$ alkyl)carbonyl. In some aspects of embodiment 165, the structure of formula (Ia) can be

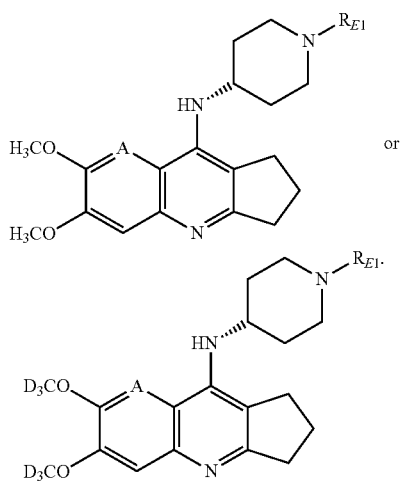

In some aspects of embodiment 165, A can be CH. In other aspects of embodiment 165, A can be N.

166. In embodiment 166, the compounds of embodiment 1, or a pharmaceutically acceptable salt thereof, are those having structural formula (Ib), or a pharmaceutically acceptable salt thereof,

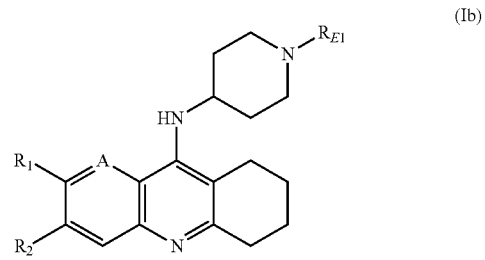

(Ib)

wherein: A can be CH or N; $R_1$ and $R_2$ are independently selected from —$OCH_3$ and —$OCD_3$; and $R_{E1}$ can be selected from hydrogen, hydroxy, hydroxyalkyl, cycloalkyl, cyanoalkyl, aralkyl, alkoxycarbonyl, aminocarbonyl (for example, —(C=O)$NH_2$ or —(C=O)N(Me)$_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 166, $R_{E1}$ can be hydrogen. In some aspects of embodiment 166, the aforementioned alkyl groups, including $R_{E1}$, can be an unsubstituted $C_1$-$C_6$ alkyl. In some aspects of embodiment 166, $R_{E1}$ can be a $C_1$-$C_3$ alkyl, such as methyl, ethyl, n-propyl and isopropyl. In some aspects of embodiment 166, $R_{E1}$ can be a $C_1$-$C_6$ alkyl substituted with a $C_1$-$C_6$ alkoxy. In some aspects of embodiment 166, the aforementioned alkoxy groups can be $C_1$-$C_6$ alkoxy groups such as those described herein and including methoxy and ethoxy. In some aspects of embodiment 166, $R_{E1}$ can be a $C_1$-$C_3$ alkyl substituted a $C_1$-$C_3$ alkoxy. In some aspects of embodiment 166, $R_{E1}$ can be $C_1$-$C_6$ hydroxyalkyl groups such as those described herein and including hydroxymethyl, hydroxyethyl and 2-hydroxypropyl. In some aspects of embodiment 166, $R_{E1}$ can be $C_1$-$C_6$ cyanoalkyl groups such as those described herein and including cyanomethyl, cyanoethyl and 2-cyanopropyl. In some aspects of embodiment 166, the aforementioned halogens can be fluoro or chloro. In some aspects of embodiment 166, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 166, $R_{E1}$ can be a $C_3$-$C_6$ monocyclic cycloalkyl, such as cyclopropyl, cyclobutyl, cyclopentyl and cyclohexyl. In some aspects of embodiment 166, the aforementioned alkylsulfonyl groups, including $R_{E1}$ can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 166, the aforementioned aryl groups, including $R_{E1}$, can be a $C_6$ aryl such as phenyl. In some aspects of embodiment 166, the aforementioned heteroaryl groups, including $R_{E1}$, can be 5- or 6-membered heteroaryl groups containing one nitrogen atom, two nitrogen atoms, or one nitrogen atom and one heteroatom selected from oxygen and sulfur. In some aspects of embodiment 166, the aforementioned heterocyclyl groups, including $R_{E1}$, can be 5- to 8-membered monocyclic heterocyclyl groups containing one nitrogen atom and one heteroatom selected from oxygen and sulfur. In some aspects of embodiment 166, $R_{E1}$ can be 4- to 6-membered monocyclic heterocyclyl groups containing one or more heteroatoms selected from nitrogen, oxygen and sulfur. In some aspects of embodiment 166, $R_{E1}$ can be a ($C_1$-$C_6$ alkyl)carbonyl. In some aspects of embodiment 166, the structure of formula (Ib) can be

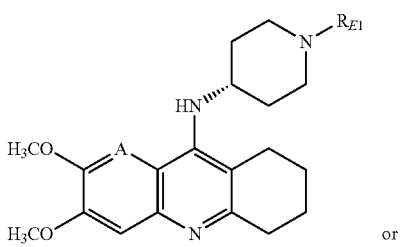

or

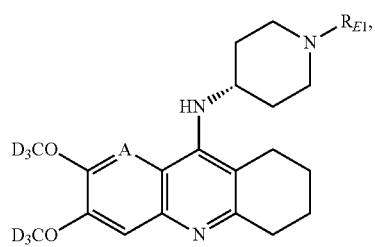

In some aspects of embodiment 166, A can be CH. In other aspects of embodiment 166, A can be N.

167. In embodiment 167, the compounds of embodiment 1, or a pharmaceutically acceptable salt thereof, are those having structural formula (Ic), or a pharmaceutically acceptable salt thereof,

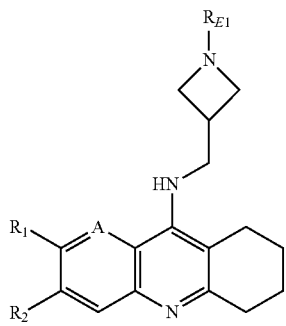

(Ic)

wherein: A can be CH or N; $R_1$ and $R_2$ are independently selected from —$OCH_3$ and —$OCD_3$; and $R_{E1}$ can be selected from hydroxy, hydroxyalkyl, cycloalkyl, cyanoalkyl, aralkyl, alkoxycarbonyl, aminocarbonyl (for example, —(C=O)$NH_2$ or —(C=O)N(Me)$_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 167, $R_{E1}$ can be hydrogen. In some aspects of embodiment 167, the aforementioned alkyl groups, including $R_{E1}$ can be an unsubstituted $C_1$-$C_6$ alkyl. In some aspects of embodiment 167, $R_{E1}$ can be a $C_1$-$C_3$ alkyl, such as methyl, ethyl, n-propyl and isopropyl. In some aspects of embodiment 167, $R_{E1}$ can be a $C_1$-$C_6$ alkyl substituted with a $C_1$-$C_6$ alkoxy. In some aspects of embodiment 167, the aforementioned alkoxy groups can be $C_1$-$C_6$ alkoxy groups such as those described herein and including methoxy and ethoxy. In some aspects of embodiment 167, $R_{E1}$ can be a $C_1$-$C_3$ alkyl substituted a $C_1$-$C_3$ alkoxy. In some aspects of embodiment 167, $R_{E1}$ can be $C_1$-$C_6$ hydroxyalkyl groups such as those described herein and including hydroxymethyl, hydroxyethyl and 2-hydroxypropyl. In some aspects of embodiment 167, $R_{E1}$ can be $C_1$-$C_6$ cyanoalkyl groups such as those described herein and including cyanomethyl, cyanoethyl and 2-cyanopropyl. In some aspects of embodiment 167, the aforementioned halogens can be fluoro or chloro. In some aspects of embodiment 167, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 167, $R_{E1}$ can be a $C_3$-$C_6$ monocyclic cycloalkyl, such as cyclopropyl, cyclobutyl, cyclopentyl and cyclohexyl. In some aspects of embodiment 167, the aforementioned alkylsulfonyl groups, including $R_{E1}$, can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 167, the aforementioned aryl groups, including $R_{E1}$, can be a $C_6$ aryl such as phenyl. In some aspects of embodiment 167, the aforementioned heteroaryl groups, including $R_{E1}$, can be 5- or 6-membered heteroaryl groups containing one nitrogen atom, two nitrogen atoms, or one nitrogen atom and one heteroatom selected from oxygen and sulfur. In some aspects of embodiment 167, the aforementioned heterocyclyl groups, including $R_{E1}$, can be 5- to 8-membered monocyclic heterocyclyl groups containing one nitrogen atom and one heteroatom selected from oxygen and sulfur. In some aspects of embodiment 167, $R_{E1}$ can be 4- to 6-membered monocyclic heterocyclyl groups containing one or more heteroatoms selected from nitrogen, oxygen and sulfur. In some aspects of embodiment 167, $R_{E1}$ can be a ($C_1$-$C_6$ alkyl)carbonyl. In some aspects of embodiment 167, A can be CH. In other aspects of embodiment 167, A can be N.

168. In embodiment 168, the compounds of embodiment 1, or a pharmaceutically acceptable salt thereof, are those having structural formula (Id), or a pharmaceutically acceptable salt thereof,

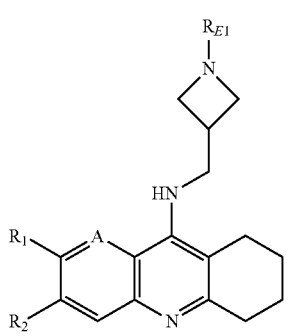

(Id)

wherein: A can be CH or N; $R_1$ and $R_2$ are independently selected from —$OCH_3$ and —$OCD_3$; and $R_{E1}$ can be selected from hydroxy, alkoxy, hydroxyalkyl, cycloalkyl, cyanoalkyl, aralkyl, alkoxycarbonyl, aminocarbonyl (for example, —(C=O)$NH_2$ or —(C=O)N$(Me)_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 168, $R_{E1}$ can be hydrogen. In some aspects of embodiment 168, the aforementioned alkyl groups, including $R_{E1}$, can be an unsubstituted $C_1$-$C_6$ alkyl. In some aspects of embodiment 168, $R_{E1}$ can be a $C_1$-$C_3$ alkyl, such as methyl, ethyl, n-propyl and isopropyl. In some aspects of embodiment 168, $R_{E1}$ can be a $C_1$-$C_6$ alkyl substituted with a $C_1$-$C_6$ alkoxy. In some aspects of embodiment 168, the aforementioned alkoxy groups can be $C_1$-$C_6$ alkoxy groups such as those described herein and including methoxy or ethoxy. In some aspects of embodiment 168, $R_{E1}$ can be a $C_1$-$C_3$ alkyl substituted a $C_1$-$C_3$ alkoxy. In some aspects of embodiment 168, $R_{E1}$ can be $C_1$-$C_6$ hydroxyalkyl groups such as those described herein and including hydroxymethyl, hydroxyethyl and 2-hydroxypropyl. In some aspects of embodiment 168, $R_{E1}$ can be $C_1$-$C_6$ cyanoalkyl groups such as those described herein and including cyanomethyl, cyanoethyl and 2-cyanopropyl. In some aspects of embodiment 168, the aforementioned halogens can be fluoro or chloro. In some aspects of embodiment 168, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 168, $R_{E1}$ can be a $C_3$-$C_6$ monocyclic cycloalkyl, such as cyclopropyl, cyclobutyl, cyclopentyl and cyclohexyl. In some aspects of embodiment 168, the aforementioned alkylsulfonyl groups, including $R_{E1}$, can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 168, the aforementioned aryl groups, including $R_{E1}$, can be a $C_6$ aryl such as phenyl. In some aspects of embodiment 168, the aforementioned heteroaryl groups, including $R_{E1}$, can be 5- or 6-membered heteroaryl groups containing one nitrogen atom, two nitrogen atoms, or one nitrogen atom and one heteroatom selected from oxygen and sulfur. In some aspects of embodiment 168, the aforementioned heterocyclyl groups, including $R_{E1}$, can be 5- to 8-membered monocyclic heterocyclyl groups containing one nitrogen atom and one heteroatom selected from oxygen and sulfur. In some aspects of embodiment 168, $R_{E1}$ can be 4- to 6-membered monocyclic heterocyclyl groups containing one or more heteroatoms selected from nitrogen, oxygen and sulfur. In some aspects of embodiment 168, $R_{E1}$ can be a ($C_1$-$C_6$ alkyl)carbonyl. In some aspects of embodiment 168, A can be CH. In other aspects of embodiment 168, A can be N.

169. In embodiment 169, the compounds of embodiment 1, or a pharmaceutically acceptable salt thereof, are those having structural formula (Ie), or a pharmaceutically acceptable salt thereof,

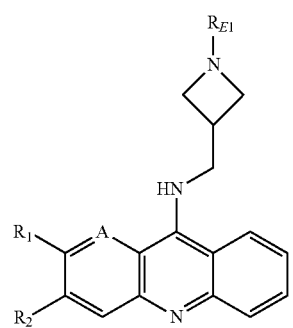

(Ie)

wherein: A can be CH or N; $R_1$ and $R_2$ are independently selected from —$OCH_3$ and —$OCD_3$; and $R_{E1}$ can be selected from hydroxy, hydroxyalkyl, cycloalkyl, cyanoalkyl, aralkyl, alkoxycarbonyl, aminocarbonyl (for example, —(C=O)$NH_2$ or —(C=O)N$(Me)_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 169, $R_{E1}$ can be hydrogen. In some aspects of embodiment 169, the aforementioned alkyl groups, including $R_{E1}$, can be an unsubstituted $C_1$-$C_6$ alkyl. In some aspects of embodiment 169, $R_{E1}$ can be a $C_1$-$C_3$ alkyl, such as methyl, ethyl, n-propyl and isopropyl. In some aspects of embodiment 169, $R_{E1}$ can be a $C_1$-$C_6$ alkyl substituted with a $C_1$-$C_6$ alkoxy. In some aspects of embodiment 169, the aforementioned alkoxy groups can be $C_1$-$C_6$ alkoxy groups such as those described herein and including methoxy and ethoxy. In some aspects of embodiment 169, $R_{E1}$ can be a $C_1$-$C_3$ alkyl substituted a $C_1$-$C_3$ alkoxy. In some aspects of embodiment 169, $R_{E1}$ can be $C_1$-$C_6$ hydroxy alkyl groups such as those described herein and including hydroxymethyl, hydroxyethyl and 2-hydroxypropyl. In some aspects of embodiment 169, REi can be $C_1$-$C_6$ cyanoalkyl groups such as those described herein and including cyanomethyl, cyanoethyl and 2-cyanopropyl. In some aspects of embodiment 169, the aforementioned halogens can be fluoro or chloro. In some aspects of embodiment 169, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 169, $R_{E1}$ can be a $C_3$-$C_6$ monocyclic cycloalkyl, such as cyclopropyl, cyclobutyl, cyclopentyl and cyclohexyl. In some aspects of embodiment 169, the aforementioned alkylsulfonyl groups, including $R_{E1}$, can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 169, the aforementioned aryl groups, including $R_{E1}$, can be a $C_6$ aryl such as phenyl. In some aspects of embodiment 169, the aforementioned heteroaryl groups, including $R_{E1}$, can be 5- or 6-membered heteroaryl groups containing one nitrogen atom, two nitrogen atoms, or one nitrogen atom and one heteroatom selected from oxygen and sulfur. In some aspects of embodiment 169, the aforementioned heterocyclyl groups, including $R_{E1}$, can be 5- to 8-membered monocyclic heterocyclyl groups containing one nitrogen atom and one heteroatom selected from oxygen and sulfur. In some aspects of embodiment 169, $R_{E1}$ can be 4- to 6-membered monocyclic heterocyclyl groups containing one or more heteroatoms selected from nitrogen, oxygen and sulfur. In some aspects of embodiment 169, $R_{E1}$ can be a ($C_1$-$C_6$ alkyl)carbonyl. In some aspects of embodiment 169, A can be CH. In other aspects of embodiment 169, A can be N.

170. In embodiment 170, the compounds of embodiment 1, or a pharmaceutically acceptable salt thereof, are those having structural formula (If), or a pharmaceutically acceptable salt thereof,

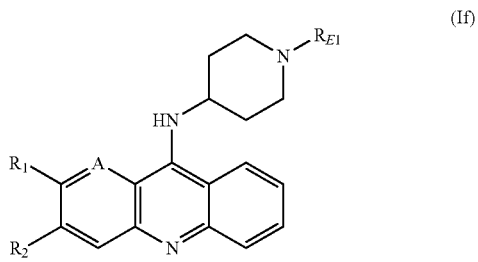

(If)

wherein: A can be CH or N; $R_1$ and $R_2$ are independently selected from —OCH$_3$ and —OCD$_3$; and $R_{E1}$ can be selected from hydroxy, alkoxy, hydroxyalkyl, cycloalkyl, cyanoalkyl, aralkyl, alkoxycarbonyl, aminocarbonyl (for example, —(C=O)NH$_2$ or —(C=O)N(Me)$_2$), cycloalkylalkyl, alkyl (optionally substituted with (i) at least one halogen and at least one hydroxy or with (ii) alkoxy), alkylcarbonyl (optionally substituted with hydroxy or benzyloxy), heteroaryl (optionally substituted with one or more $R_F$ independently selected from halogen, alkyl, cyano and hydroxy), heteroaralkyl (optionally substituted with one or more $R_G$ independently selected from halogen, alkyl, cyano and hydroxy), heterocyclyl (optionally substituted with one or more $R_H$ independently selected from alkyl, cyano and hydroxy), alkylsulfonyl and aryl (optionally substituted with one or more $R_I$ independently selected from halogen, alkyl, alkoxy, cyano and hydroxy). In some aspects of embodiment 170, $R_{E1}$ can be hydrogen. In some aspects of embodiment 170, the aforementioned alkyl groups, including $R_{E1}$, can be an unsubstituted $C_1$-$C_6$ alkyl. In some aspects of embodiment 170, $R_{E1}$ can be a $C_1$-$C_3$ alkyl, such as methyl, ethyl, n-propyl and isopropyl. In some aspects of embodiment 170, $R_{E1}$ can be a $C_1$-$C_6$ alkyl substituted with a $C_1$-$C_6$ alkoxy. In some aspects of embodiment 170, the aforementioned alkoxy groups can be $C_1$-$C_6$ alkoxy groups such as those described herein and including methoxy and ethoxy. In some aspects of embodiment 170, $R_{E1}$ can be a $C_1$-$C_3$ alkyl substituted a $C_1$-$C_3$ alkoxy. In some aspects of embodiment 170, $R_{E1}$ can be $C_1$-$C_6$ hydroxyalkyl groups such as those described herein and including hydroxymethyl, hydroxyethyl and 2-hydroxypropyl. In some aspects of embodiment 170, $R_{E1}$ can be $C_1$-$C_6$ cyanoalkyl groups such as those described herein and including cyanomethyl, cyanoethyl or 2-cyanopropyl. In some aspects of embodiment 170, the aforementioned halogens can be fluoro or chloro. In some aspects of embodiment 170, $R_{E1}$ can be $C_3$-$C_8$ monocyclic cycloalkyl groups such as cyclopropyl, cyclobutyl, cyclopentyl, cyclohexyl, cycloheptyl and cyclooctyl. In some aspects of embodiment 170, $R_{E1}$ can be a $C_3$-$C_6$ monocyclic cycloalkyl, such as cyclopropyl, cyclobutyl, cyclopentyl and cyclohexyl. In some aspects of embodiment 170, the aforementioned alkylsulfonyl groups, including $R_{E1}$, can be a ($C_1$-$C_6$ alkyl)sulfonyl. Examples of ($C_1$-$C_6$ alkyl)sulfonyls include, but are not limited to, methylsulfonyl, ethylsulfonyl and isopropylsulfonyl. In some aspects of embodiment 170, the aforementioned aryl groups, including $R_{E1}$, can be a $C_6$ aryl such as phenyl. In some aspects of embodiment 170, the aforementioned heteroaryl groups, including $R_{E1}$, can be 5- or 6-membered heteroaryl groups containing one nitrogen atom, two nitrogen atoms, or one nitrogen atom and one heteroatom selected from oxygen and sulfur. In some aspects of embodiment 170, the aforementioned heterocyclyl groups, including $R_{E1}$, can be 5- to 8-membered monocyclic heterocyclyl groups containing one nitrogen atom and one heteroatom selected from oxygen and sulfur. In some aspects of embodiment 170, $R_{E1}$ can be 4- to 6-membered monocyclic heterocyclyl groups containing one or more heteroatoms selected from nitrogen, oxygen and sulfur. In some aspects of embodiment 170, $R_{E1}$ can be a ($C_1$-$C_6$ alkyl)carbonyl. In some aspects of embodiment 170, the structure of formula (If) can be

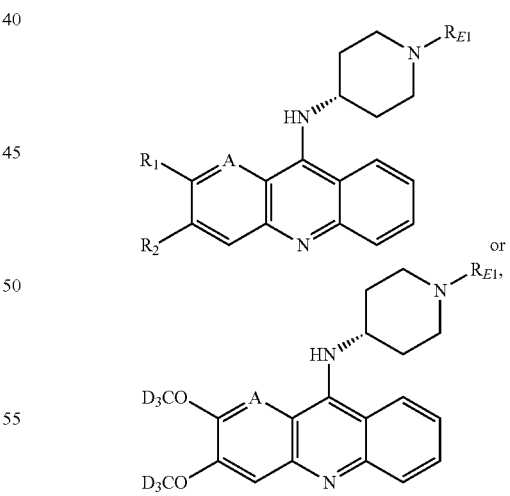

In some aspects of embodiment 170, A can be CH. In other aspects of embodiment 170, A can be N.

171. In embodiment 171 the compounds of any one of embodiments 165-170, or a pharmaceutically acceptable salt thereof, are those wherein $R_{E1}$ can be selected from an unsubstituted $C_1$-$C_3$ alkyl and a $C_1$-$C_3$ alkyl substituted with a $C_1$-$C_3$ alkoxy. In some aspects of embodiment 171, $R_{E1}$ can be methyl, ethyl or n-propyl. In other aspects of embodiment 171, $R_{E1}$ can be methyl, ethyl or n-propyl; each substituted with methoxy or ethoxy.

172. In embodiment 172 the compounds of any one of embodiments 165-170, or a pharmaceutically acceptable salt thereof, are those wherein $R_{E1}$ can be selected from an unsubstituted cyclopropyl, an unsubstituted cyclobutyl, an unsubstituted cyclopentyl, an unsubstituted cyclohexyl and an unsubstituted phenyl.

173. In embodiment 173 the compounds of any one of embodiments 165-170, or a pharmaceutically acceptable salt thereof, are those wherein $R_{E1}$ can be selected from an unsubstituted 4-membered heterocyclyl, an unsubstituted 5-membered heterocyclyl and an unsubstituted 6-membered heterocyclyl.

174. In embodiment 174 the compounds of any one of embodiments 165-170, or a pharmaceutically acceptable salt thereof, are those wherein $R_{E1}$ can be selected from an unsubstituted 5-membered heteroaryl and an unsubstituted 6-membered heteroaryl.

175. In embodiment 175 the compounds of any one of embodiments 165-170, or a pharmaceutically acceptable salt thereof, are those wherein $R_{E1}$ can be methyl, ethyl, n-propyl, isopropyl, cyclopropyl, cyclobutyl, cyclopentyl or phenyl; each of which are unsubstituted.

176. In embodiment 176, the compounds of embodiment 1, or a pharmaceutically acceptable salt thereof, are those having structural formula (Ig), or a pharmaceutically acceptable salt thereof,

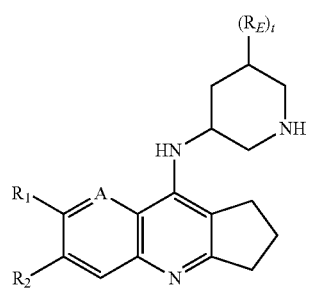

(Ig)

wherein A can be CH or N; $R_1$ and $R_2$ are independently selected from —$OCH_3$ and —$OCD_3$; and each $R_E$ can be independently selected from halogen (such as fluoro or chloro), alkyl (including $C_1$-$C_6$ alkyl) and alkoxy (including $C_1$-$C_6$ alkoxy); and t can be 0, 1 or 2. In some aspects of embodiment 176, A can be CH. In other aspects of embodiment 176, A can be N. In some aspects of embodiment 176, each $R_E$ can be a halogen. In some aspects of embodiment 176, each $R_E$ can be independently selected from fluoro, chloro, $C_1$-$C_3$ alkyl and $C_1$-$C_3$ alkoxy. In some aspects of embodiment 176, t can be 0. In other aspects of embodiment 176, t can be 1. In still other aspects of embodiment 176, t can be 2. In some aspects of embodiment 176, when t is 2, the $R_E$ groups can be the same. In other aspects of embodiment 176, when t is 2, the $R_E$ groups can be the different. In some aspects of embodiment 176, the structure of formula (Ig) can be

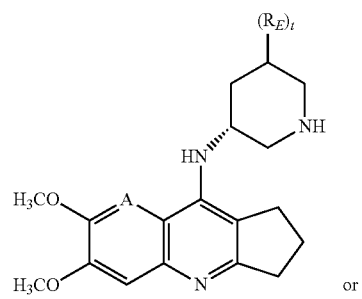

or

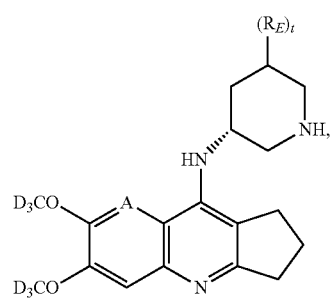

177. In embodiment 177, the compounds of embodiment 1, or a pharmaceutically acceptable salt thereof, are those having structural formula (Ih), or a pharmaceutically acceptable salt thereof, (Ih)

wherein A can be CH or N; $R_1$ and $R_2$ are independently selected from —$OCH_3$ and —$OCD_3$; and each $R_E$ can be independently selected from halogen (such as fluoro or chloro), alkyl (including $C_1$-$C_6$ alkyl) and alkoxy (including $C_1$-$C_6$ alkoxy); and t can be 0, 1 or 2. In some aspects of embodiment 177, A can be CH. In other aspects of embodiment 177, A can be N. In some aspects of embodiment 177, each $R_E$ can be a halogen. In some aspects of embodiment 177, each $R_E$ can be independently selected from fluoro, chloro, $C_1$-$C_3$ alkyl and $C_1$-$C_3$ alkoxy. In some aspects of embodiment 177, t can be 0. In other aspects of embodiment 177, t can be 1. In still other aspects of embodiment 177, t can be 2. In some aspects of embodiment 177, when t is 2, the $R_E$ groups can be the same. In other aspects of embodiment 177, when t is 2, the $R_E$ groups can be the different. In some aspects of embodiment 177, the structure of formula (Ih) can be

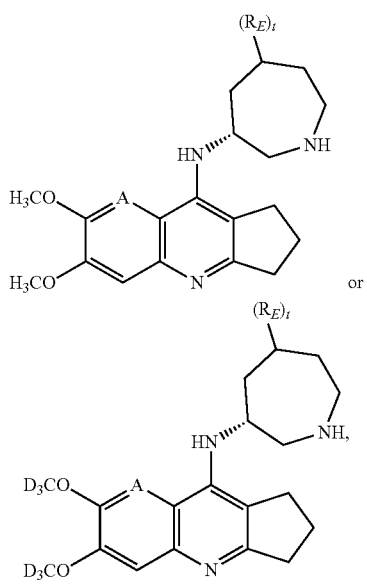

178. In embodiment 178, the compounds of embodiment 1, or a pharmaceutically acceptable salt thereof, are those having structural formula (Ij), or a pharmaceutically acceptable salt thereof,

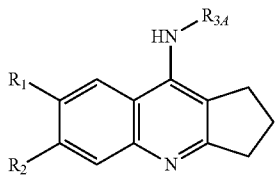

(Ij)

wherein $R_1$ can be alkoxy (optionally substituted with deuterium); $R_2$ can be alkoxy (optionally substituted with deuterium); and $R_{3A}$ can be an optionally substituted heterocyclyl containing 1 or 2 nitrogens. In some aspects of embodiment 178, $R_1$ can be an unsubstituted alkoxy. In some aspects of embodiment 178, $R_1$ can be an unsubstituted $C_1$-$C_3$ alkoxy. In some aspects of embodiment 178, $R_1$ can be methoxy. In some aspects of embodiment 178, $R_1$ can be a deuterated alkoxy. In some aspects of embodiment 178, $R_1$ can be a deuterated $C_1$-$C_3$ alkoxy. In some aspects of embodiment 178, $R_1$ can be —$OCD_3$. In some aspects of embodiment 178, $R_2$ can be an unsubstituted alkoxy. In some aspects of embodiment 178, $R_2$ can be an unsubstituted $C_1$-$C_3$ alkoxy. In some aspects of embodiment 178, $R_2$ can be methoxy. In some aspects of embodiment 178, $R_2$ can be a deuterated alkoxy. In some aspects of embodiment 178, $R_2$ can be a deuterated $C_1$-$C_3$ alkoxy. In some aspects of embodiment 178, $R_2$ can be —$OCD_3$. In some aspects of embodiment 178, $R_{3A}$ can be an optionally substituted monocyclic heterocyclyl containing 1 or 2 nitrogens. In some aspects of embodiment 178, $R_{3A}$ can be an optionally substituted monocyclic 5- to 7-membered heterocyclyl containing 1 or 2 nitrogens. In some aspects of embodiment 178, $R_{3A}$ can be an optionally substituted monocyclic 5- to 7-membered heterocyclyl containing 1 nitrogen. In some aspects of embodiment 178, $R_{3A}$ can be selected from an unsubstituted pyrrolidinyl, an unsubstituted piperidinyl and an unsubstituted azepanyl. In some aspects of embodiment 178, $R_{3A}$ can be selected from a substituted pyrrolidinyl, a substituted piperidinyl and a substituted azepanyl. In some aspects of embodiment 178, $R_{3A}$ can be substituted with one or more of the following groups independently selected from Cu $C_3$ alkyl (optionally substituted with $C_1$-$C_3$ alkoxy), $C_{3-6}$ cycloalkyl, 4- to 6-membered heterocyclyl, phenyl, 5- to 6-membered heteroaryl, ($C_{1-6}$ alkyl)carbonyl and ($C_1$-$C_6$ alkyl)sulfonyl.

179. In embodiment 179, the compounds of embodiment 1, or a pharmaceutically acceptable salt thereof, are those compounds listed in Table 1.

180. In embodiment 180, the compounds of embodiment 1, or a pharmaceutically acceptable salt thereof, are those compounds listed in Table 2.

181. In embodiment 181, the compounds of embodiment 1, are those compounds selected from:

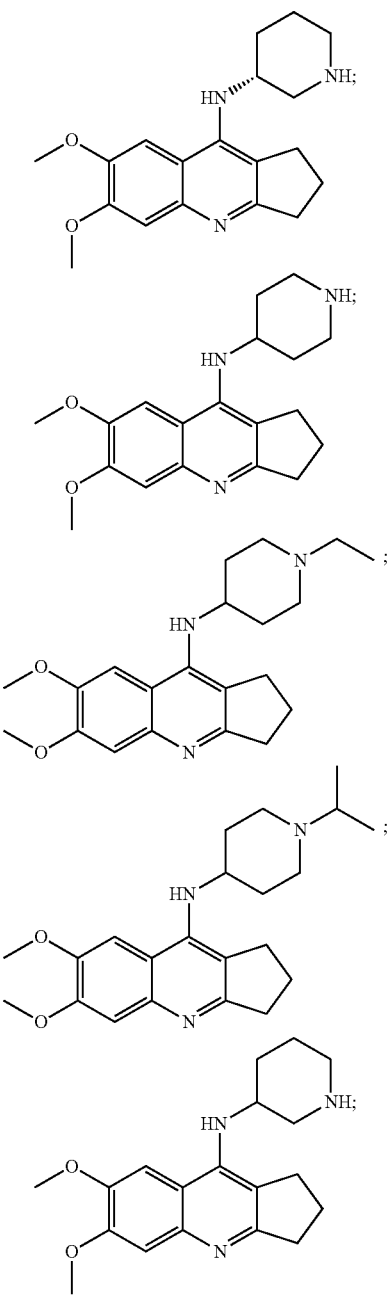

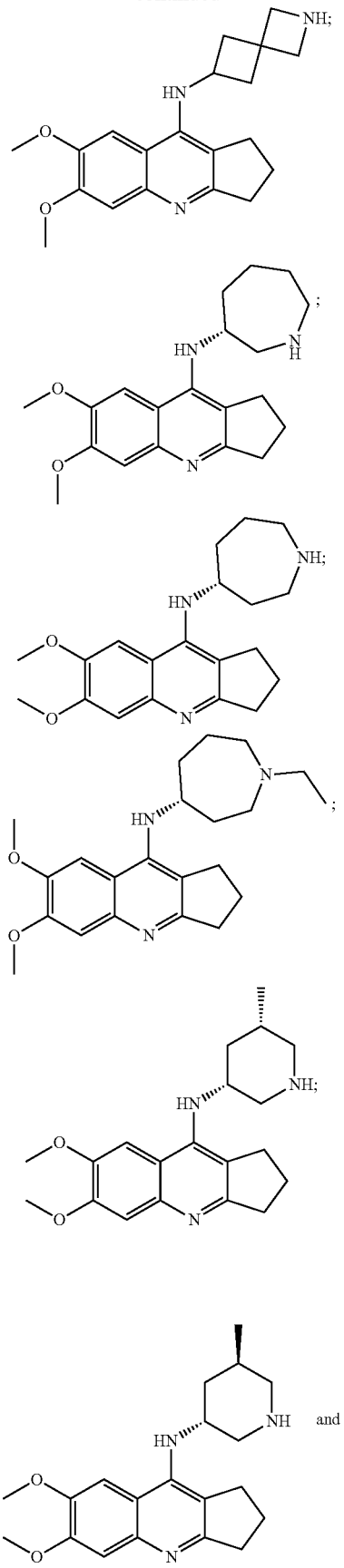

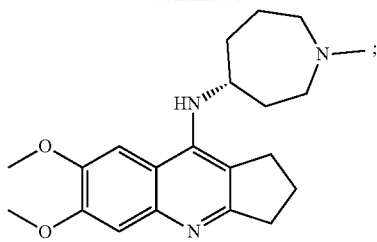

or a pharmaceutically acceptable salt of any of the foregoing.

182. Embodiment 182, provides a pharmaceutical composition comprising a compound of any one of embodiments 1-181, or a pharmaceutically acceptable salt thereof, and a pharmaceutically acceptable excipient.

183. Embodiment 183, provides a method of inhibiting G9a, comprising contacting a cell that contains G9a with a therapeutically effective amount of a compound of any one embodiments 1-181, or a pharmaceutically acceptable salt thereof, thereby inhibiting the activity of G9a.

184. In embodiment 184, the cell of embodiment 183 can be a cancer cell.

185. Embodiment 185, provides a method of ameliorating and/or treating a hemoglobinopathy, comprising administering a therapeutically effective amount of a compound of any one of embodiments 1-181, or a pharmaceutically acceptable salt thereof, or the pharmaceutical composition of embodiment 182 to a subject in need thereof.

186. In embodiment 186, the hemoglobinopathy of embodiment 185 can be sickle cell disease or beta-thalassemia.

187. Embodiment 187, provides a method of ameliorating and/or treating a cancer, comprising administering a therapeutically effective amount of a compound of any one of embodiments 1-181, or a pharmaceutically acceptable salt thereof, or the pharmaceutical composition of embodiment 182 to a subject in need thereof.

188. In embodiment 188, the cancer of embodiment 187 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Librous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Lallopian Tube Cancer; a Librous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sezary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

189. In embodiment 189, the cancer of any one of embodiments 187-188 can be selected from: a Myelodysplastic Syndrome (MDS); an Acute Myeloid Leukemia (AML); an Ovarian Cancer; a Colon Cancer; and a Non-Small Cell Lung Cancer (NSCLC).

190. Embodiment 190, provides a method of ameliorating and/or treating an autoimmune or inflammatory disease, comprising administering a therapeutically effective amount of a compound of any one of embodiments 1-181, or a pharmaceutically acceptable salt thereof, or the pharmaceutical composition of embodiment 182 to a subject in need thereof.

191. In embodiment 191, the autoimmune or inflammatory disease of embodiment 190 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

192. In embodiment 192, the autoimmune or inflammatory disease of any one of embodiments 190-191 can be selected from: Crohn's disease, rheumatoid arthritis, systemic lupus erythematosus, systemic sclerosis, primary biliary cirrhosis and graft-versus-host disease.

193. Embodiment 193, provides for the use of an effective amount of a compound of any one embodiments 1-181, or a pharmaceutically acceptable salt thereof, in the manufacture of a medicament for inhibiting the activity of G9a in a cell.

194. In embodiment 194, the cell of embodiment 193 can be a cancer cell.

195. Embodiment 195, provides an effective amount of a compound of any one embodiments 1-181, or a pharmaceutically acceptable salt thereof, for inhibiting the activity of G9a in a cell.

196. In embodiment 196, the cell of embodiment 195 can be a cancer cell.

197. Embodiment 197, provides for the use of an effective amount of a compound of any one embodiments 1-181, or a pharmaceutically acceptable salt thereof, or the pharmaceutical composition of embodiment 182, in the manufacture of a medicament for ameliorating and/or treating a hemoglobinopathy.

198. In embodiment 198, the hemoglobinopathy of embodiment 197 can be sickle cell disease or beta-thalassemia.

199. Embodiment 199, provides an effective amount of a compound of any one embodiments 1-181, or a pharmaceutically acceptable salt thereof, or the pharmaceutical composition of embodiment 182, for ameliorating and/or treating a hemoglobinopathy.

200. In embodiment 200, the hemoglobinopathy of embodiment 199 can be sickle cell disease or beta-thalassemia.

201. Embodiment 201, provides for the use of an effective amount of a compound of any one embodiments 1-181, or a pharmaceutically acceptable salt thereof, or the pharmaceutical composition of embodiment 182, in the manufacture of a medicament for ameliorating and/or treating a cancer.

202. In embodiment 202, the cancer of embodiment 201 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Librous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Lallopian Tube Cancer; a Librous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sezary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

203. In embodiment 203, the cancer of any one of embodiments 201-202 can be selected from: a Myelodysplastic Syndrome (MDS); an Acute Myeloid Leukemia (AML); an Ovarian Cancer; a Colon Cancer; and a Non-Small Cell Lung Cancer (NSCLC).

204. Embodiment 204, provides an effective amount of a compound of any one embodiments 1-181, or a pharmaceutically acceptable salt thereof, or the pharmaceutical composition of embodiment 182, for ameliorating and/or treating a cancer.

205. In embodiment 205, the cancer of embodiment 204 can be selected from: a Colorectal Cancer; a Osteosarcoma Cancer; an Acute Lymphoblastic Leukemia (ALL); an Acute Myeloid Leukemia (AML); an Adrenocortical Carcinoma; a Kaposi Sarcoma (Soft Tissue Sarcoma); an AIDS-Related Lymphoma (Lymphoma); a Primary CNS Lymphoma; an Anal Cancer; a Gastrointestinal Carcinoid Tumor; an Astrocytoma; an Atypical Teratoid/Rhabdoid Tumor; a Basal Cell Carcinoma of the Skin; a Bile Duct Cancer; a Bladder Cancer; a Bone Cancer (includes Ewing Sarcoma and Osteosarcoma and Malignant Fibrous Histiocytoma); a Brain Tumor; a Breast Cancer; a Bronchial Tumor; a Burkitt Lymphoma; a Cardiac Tumor; an Embryonal Tumor (Brain Cancer); a Germ Cell Tumor (Brain Cancer); a Primary CNS Lymphoma; a Cervical Cancer; a Cholangiocarcinoma; a Chordoma; a Chronic Lymphocytic Leukemia (CLL); a Chronic Myelogenous Leukemia (CML); a Chronic Myeloproliferative Neoplasm; a Craniopharyngioma (Brain Cancer); a Cutaneous T-Cell Lymphoma; a Ductal Carcinoma In Situ (DCIS); an Endometrial Cancer (Uterine Cancer); an Ependymoma (Brain Cancer); an Esophageal Cancer; an Esthesioneuroblastoma; an Ewing Sarcoma (Bone Cancer); Extracranial Germ Cell Tumor; Extragonadal Germ Cell Tumor; Eye Cancer; Intraocular Melanoma; a Retinoblastoma; a Fallopian Tube Cancer; a Fibrous Histiocytoma of Bone; a Gallbladder Cancer; a Gastric (Stomach) Gastrointestinal Stromal Tumor (GIST) (Soft Tissue Sarcoma); a CNS Germ Cell Tumors (Brain Cancer); an Extracranial Germ Cell Tumor; an Extragonadal Germ Cell Tumor; an Ovarian Germ Cell Tumor; a Testicular Cancer; a Gestational Trophoblastic Disease; a Hairy Cell Leukemia; a Head and Neck Cancer; a Hepatocellular (Liver) Cancer; a Histiocytosis, a Langerhans Cell; Hodgkin Lymphoma; a Hypopharyngeal Cancer (Head and Neck Cancer); an Intraocular Melanoma; an Islet Cell Tumor; a Pancreatic Neuroendocrine Tumor; a Kidney (Renal Cell) Cancer; a Langerhans Cell Histiocytosis; a Laryngeal Cancer (Head and Neck Cancer); a Leukemia; a Lip and Oral Cavity Cancer (Head and Neck Cancer); a Lung Cancer (Non-Small Cell and Small Cell); a Lymphoma; a Male Breast Cancer; a Melanoma; a Merkel Cell Carcinoma (Skin Cancer); a Mesothelioma; a Malignant Mesothelioma; a Metastatic Squamous Neck Cancer with Occult Primary (Head and Neck Cancer); a Midline Tract Carcinoma involving NUT Gene; a Mouth Cancer (Head and Neck Cancer); Multiple Endocrine Neoplasia Syndromes; Multiple Myeloma/Plasma Cell Neoplasms; a Mycosis Fungoides (Lymphoma); a Myelodysplastic Syndrome, a Myelodysplastic/Myeloproliferative Neoplasm; a Nasal Cavity and Paranasal Sinus Cancer (Head and Neck Cancer); a Nasopharyngeal Cancer (Head and Neck Cancer); a Nasopharyngeal Cancer—Neuroblastoma; a Non-Hodgkin Lymphoma; an Oral Cancer; Lip and Oral Cavity Cancer and Oropharyngeal Cancer (Head and Neck Cancer); an Ovarian Cancer; a Pancreatic Cancer; a Papillomatosis; a Paraganglioma; a Paranasal Sinus and Nasal Cavity Cancer (Head and Neck Cancer); a Parathyroid Cancer; a Penile Cancer; a Pharyngeal Cancer (Head and Neck Cancer); a Pheochromocytoma; a Pituitary Tumor; a Pleuropulmonary Blastoma; a Primary CNS Lymphoma; a Primary Peritoneal Cancer; a Prostate Cancer; a Rectal Cancer; a Rhabdomyosarcoma (Soft Tissue Sarcoma); a Salivary Gland Cancer (Head and Neck Cancer); a Salivary Gland Tumor; a Vascular Tumor (Soft Tissue Sarcoma); an Uterine Sarcoma; a Sezary Syndrome (Lymphoma); a Small Intestine Cancer; a Squamous Cell Carcinoma; a Skin Cancer; a Squamous Neck Cancer with Occult Primary, Metastatic (Head and Neck Cancer); a Cutaneous T-Cell Lymphoma; a Throat Cancer (Head and Neck Cancer); a Nasopharyngeal Cancer; an Oropharyngeal Cancer; a Hypopharyngeal Cancer; a Thymoma and Thymic Carcinoma; a Thyroid Cancer; an Urethral Cancer; a Vaginal Cancer; a Vascular Tumor (Soft Tissue Sarcoma); a Vulvar Cancer; a Myelodysplastic syndrome (MDS); and a Wilms Tumor.

206. In embodiment 206, the cancer of any one of embodiments 204-205 can be selected from: a Myelodysplastic Syndrome (MDS); an Acute Myeloid Leukemia (AML); an Ovarian Cancer; a Colon Cancer; and a Non-Small Cell Lung Cancer (NSCLC).

207. Embodiment 207, provides for the use of an effective amount of a compound of any one embodiments 1-181, or a pharmaceutically acceptable salt thereof, or the pharmaceutical composition of embodiment 182, in the manufacture of a medicament for ameliorating and/or treating an autoimmune or inflammatory disease.

208. In embodiment 208, the an autoimmune or inflammatory disease of embodiment 207 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

209. In embodiment 209, the an autoimmune or inflammatory disease of any one of embodiments 207-208 can be selected from: Crohn's disease, rheumatoid arthritis, systemic lupus erythematosus, systemic sclerosis, primary biliary cirrhosis and graft-versus-host disease.

210. Embodiment 210, provides an effective amount of a compound of any one embodiments 1-181, or a pharmaceutically acceptable salt thereof, or the pharmaceutical composition of embodiment 182, for ameliorating and/or treating an autoimmune or inflammatory disease.

211. In embodiment 211, the an autoimmune or inflammatory disease of embodiment 210 can be selected from: arthritis, atherosclerosis, multiple sclerosis, myasthenia gravis, Crohn's disease, graft-versus-host disease, psoriasis, granulomatous colitis, lymphocyte colitis, collagenous colitis, ulcerative colitis, Coeliac Disease, subepidermal blistering disorders, systemic lupus erythematosus, discoid lupus erythematosus, cutaneous lupus, dermatomyositis, polymyositis, Sjogren's syndrome, primary biliary cirrhosis, active chronic hepatitis, chronic fatigue syndrome and vasculitis.

212. In embodiment 212, the an autoimmune or inflammatory disease of any one of embodiments 210-211 can be selected from: Crohn's disease, rheumatoid arthritis, systemic lupus erythematosus, systemic sclerosis, primary biliary cirrhosis and graft-versus-host disease.

213. Embodiment 213 provides a method of inhibiting the activity of GLP comprising contacting a cell that contains GLP with an effective amount of a compound of any one of embodiments 1-181, or a pharmaceutically acceptable salt thereof, and thereby inhibiting the activity of GLP.

214. Embodiment 214 provides a method of increasing fetal hemoglobin (HbF) protein levels comprising contacting a cell characterized as having impaired production of β-globin with an effective amount of a compound of any one of embodiments 1-181, or a pharmaceutically acceptable salt thereof, and thereby increasing fetal hemoglobin (HbF) protein levels.

215. Embodiment 215 provides a method of inhibiting the polymerization of hemoglobin S molecules comprising contacting a cell characterized as having a hemoglobin S mutation with an effective amount of a compound of any one of embodiments 1-181, or a pharmaceutically acceptable salt thereof, and thereby inhibiting the polymerization of hemoglobin S molecules.

216. Embodiment 216 provides a method of inhibiting G9a activity in a subject comprising administering to the subject suffering from a disease that is treatable by fetal hemoglobin an effective amount of a compound of any one of embodiments 1-181, or a pharmaceutically acceptable salt thereof.

217. Embodiment 217 provides a method of inhibiting GLP activity in a subject comprising administering to the subject suffering from a disease that is treatable by fetal hemoglobin an effective amount of a compound of any one of embodiments 1-181, or a pharmaceutically acceptable salt thereof.

218. Embodiment 218 provides a method for treating a disease comprising administrating to a subject suffering from a disease treatable by fetal hemoglobin an effective amount of a compound of any one of embodiments 1-181, or a pharmaceutically acceptable salt thereof, or the pharmaceutical composition of embodiment 182.

219. Embodiment 219 provides a method for treating a disease characterized by impaired production of β-globin comprising administrating to a subject suffering from the disease characterized by impaired production of β-globin an effective amount of a compound of any one of embodiments 1-181, or a pharmaceutically acceptable salt thereof, or the pharmaceutical composition of embodiment 182.

220. In embodiment 220, the disease of embodiment 219 can be beta-thalassemia.

221. Embodiment 221 provides a method for treating a disease characterized by increased concentration of polymerized hemoglobin S molecules comprising administrating to a subject suffering from the disease characterized by increased concentration of polymerized hemoglobin S molecules an effective amount of a compound of any one of embodiments 1-181, or a pharmaceutically acceptable salt thereof.

222. In embodiment 222, the disease of embodiment 221 can be sickle cell disease.

223. Embodiment 223 provides for the use of an effective amount of a compound of any one of embodiments 1-181, or a pharmaceutically acceptable salt thereof, in the preparation of a medicament for inhibiting the activity of G9a in a cell that contains G9a.

224. Embodiment 224 provides for the use of an effective amount of a compound of any one of embodiments 1-181, or a pharmaceutically acceptable salt thereof, in the preparation of a medicament for inhibiting the activity of GLP in a cell that contains GLP.

225. Embodiment 225 provides for the use of an effective amount of a compound of any one of embodiments 1-181, or a pharmaceutically acceptable salt thereof, in the preparation of a medicament for increasing fetal hemoglobin (HbF) protein levels in a cell characterized as having impaired production of β-globin.

226. Embodiment 226 provides for the use of an effective amount of a compound of any one of embodiments 1-181, or a pharmaceutically acceptable salt thereof, in the preparation of a medicament for inhibiting the polymerization of hemoglobin S molecules in a cell characterized as having a hemoglobin S mutation.

227. Embodiment 227 provides for the use of an effective amount of a compound of any one of embodiments 1-181, or a pharmaceutically acceptable salt thereof, in the preparation of a medicament for treating a disease treatable by fetal hemoglobin.

228. Embodiment 228 provides for the use of an effective amount of a compound of any one of embodiments 1-181, or a pharmaceutically acceptable salt thereof, in the preparation of a medicament for treating a disease treatable by fetal hemoglobin.

229. Embodiment 229 provides for the use of an effective amount of a compound of any one of embodiments 1-181, or a pharmaceutically acceptable salt thereof, in the preparation of a medicament for treating a disease characterized by impaired production of β-globin.

230. In embodiment 230, the disease of embodiment 229 can be beta-thalassemia.
231. Embodiment 231 provides for the use of an effective amount of a compound of any one of embodiments 1-181, or a pharmaceutically acceptable salt thereof, in the preparation of a medicament for treating a disease characterized by increased concentration of polymerized hemoglobin S molecules.
232. In embodiment 232, the disease of embodiment 231 can be sickle cell disease.
233. Embodiment 233 provides for the use of an effective amount of a compound of any one of embodiments 1-181, or a pharmaceutically acceptable salt thereof, in the preparation of a medicament for ameliorating or treating a hemoglobinopathy.
234. In embodiment 234, the hemoglobinopathy of embodiment 233 can be sickle cell disease.
235. In embodiment 235, the hemoglobinopathy of embodiment 233 can be beta-thalassemia. Representative compounds of Formula (I), or pharmaceutically acceptable salts thereof, are disclosed in Tables 1 and 2 below. Compounds in Table 1 were prepared either as a free base, or in salt form, for example, with formic acid, HCl or trifluoroacetic acid.

TABLE 1

| No | Structure | IUPAC Name | MS found |
|---|---|---|---|
| 1 | 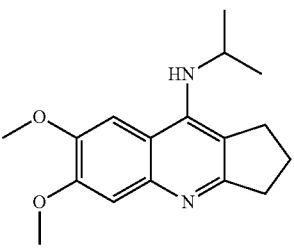 [SMILES: COc1cc2nc3c(c(NC(C)C)c2cc1OC)CCC3] | 6,7-dimethoxy-N-(propan-2-yl)-1H,2H,3H-cyclopenta[b]quinolin-9-amine | 287 |
| 2 | 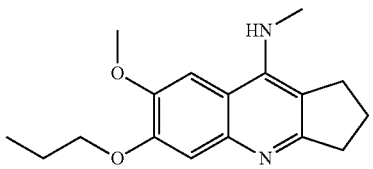 [SMILES: CCCOc1cc2nc3c(c(NC)c2cc1OC)CCC3] | 7-methoxy-N-methyl-6-propoxy-1H,2H,3H-cyclopenta[b]quinolin-9-amine | 287.2 |
| 3 | 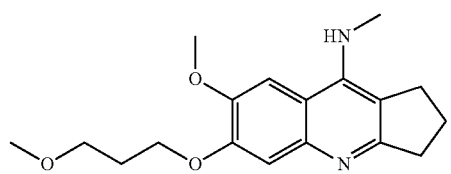 [SMILES: CNc1c2c(nc3cc(OCCCOC)c(OC)cc13)CCC2] | 7-methoxy-6-(3-methoxypropoxy)-N-methyl-1H,2H,3H-cyclopenta[b]quinolin-9-amine | 317.3 |
| 4 | 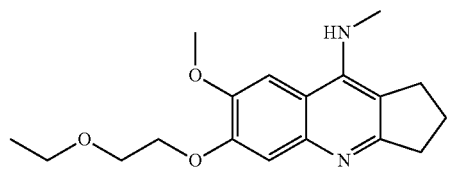 [SMILES: CCOCCOc1cc2nc3c(c(NC)c2cc1OC)CCC3] | 6-(2-ethoxyethoxy)-7-methoxy-N-methyl-1H,2H,3H-cyclopenta[b]quinolin-9-amine | 317.2 |
| 5 | 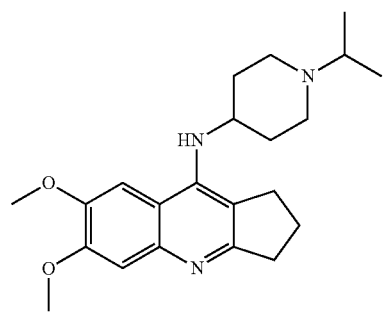 [SMILES: COc1cc2nc3c(c(NC4CCN(C(C)C)CC4)c2cc1OC)CCC3] | N-{6,7-dimethoxy-1H,2H,3H-cyclopenta[b]quinolin-9-yl}-1-(propan-2-yl)piperidin-4-amine | 370.4 |

TABLE 1-continued

| No | Structure | IUPAC Name | MS found |
|---|---|---|---|
| 6 | 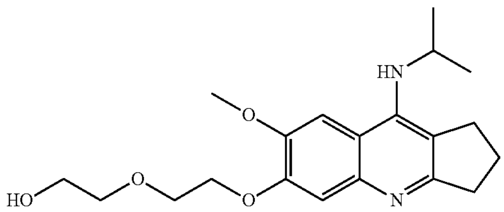 [SMILES: COc1cc2c(NC(C)C)c3c(nc2cc1OCCOCCO)CCC3] | 2-[2-({7-methoxy-9-[(propan-2-yl)amino]-1H,2H,3H-cyclopenta[b]quinolin-6-yl}oxy)ethoxy]ethan-1-ol | 361.2 |
| 7 | 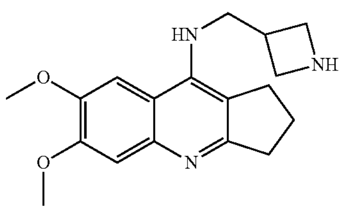 [SMILES: COc1cc2nc3c(c(NCC4CNC4)c2cc1OC)CCC3] | N-[(azetidin-3-yl)methyl]-6,7-dimethoxy-1H,2H,3H-cyclopenta[b]quinolin-9-amine | 314.2 |
| 8 | 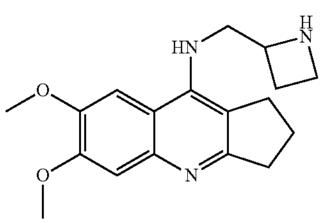 [SMILES: COc1cc2nc3c(c(NCC4CCN4)c2cc1OC)CCC3] | N-[(azetidin-2-yl)methyl]-6,7-dimethoxy-1H,2H,3H-cyclopenta[b]quinolin-9-amine | 314.2 |
| 9 | 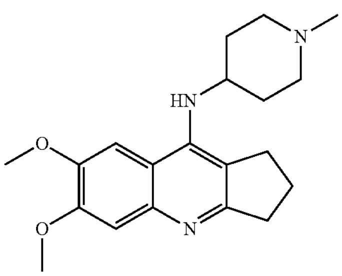 | N-{6,7-dimethoxy-1H,2H,3H-cyclopenta[b]quinolin-9-yl}-1-methylpiperidin-4-amine | 342.3 |
| 10 | 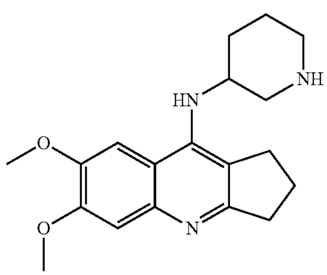 [SMILES: COc1cc2nc3c(c(NC4CCCNC4)c2cc1OC)CCC3] | N-{6,7-dimethoxy-1H,2H,3H-cyclopenta[b]quinolin-9-yl}piperidin-3-amine | 328.3 |
| 11 | 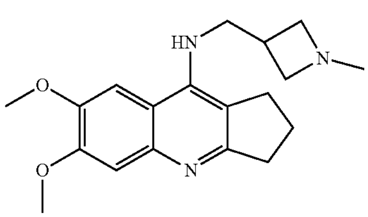 | 6,7-dimethoxy-N-[(1-methylazetidin-3-yl)methyl]-1H,2H,3H-cyclopenta[b]quinolin-9-amine | 328.3 |

TABLE 1-continued

| No | Structure | IUPAC Name | MS found |
|---|---|---|---|
| 12 | 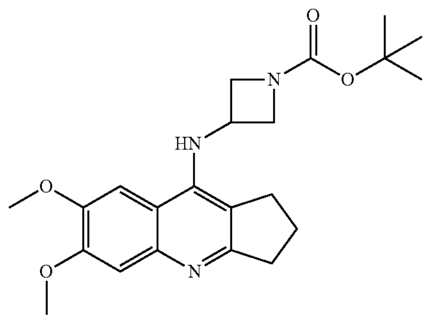 [SMILES: COc1cc2nc3c(c(NC4CN(C(=O)OC(C)(C)C)C4)c2cc1OC)CCC3] | tert-butyl 3-({6,7-dimethoxy-1H,2H,3H-cyclopenta[b]quinolin-9-yl}amino)azetidine-1-carboxylate | 400.5 |
| 13 | 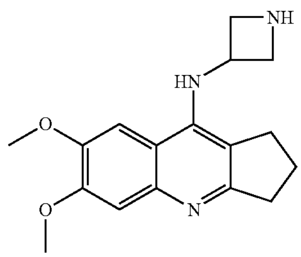 [SMILES: COc1cc2nc3c(c(NC4CNC4)c2cc1OC)CCC3] | N-{6,7-dimethoxy-1H,2H,3H-cyclopenta[b]quinolin-9-yl}azetidin-3-amine | 300.2 |
| 14 | 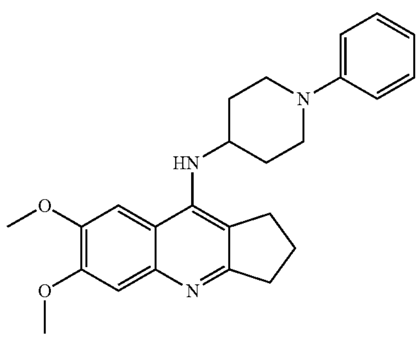 [SMILES: COc1cc2nc3c(c(NC4CCN(c5ccccc5)CC4)c2cc1OC)CCC3] | N-{6,7-dimethoxy-1H,2H,3H-cyclopenta[b]quinolin-9-yl}-1-phenylpiperidin-4-amine | 404.4 |
| 15 | 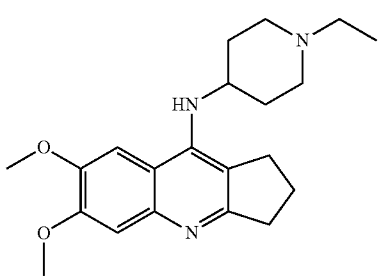 [SMILES: CCN1CCC(Nc2c3c(nc4cc(OC)c(OC)cc24)CCC3)CC1] | N-{6,7-dimethoxy-1H,2H,3H-cyclopenta[b]quinolin-9-yl}-1-ethylpiperidin-4-amine | 356.4 |
| 16 | 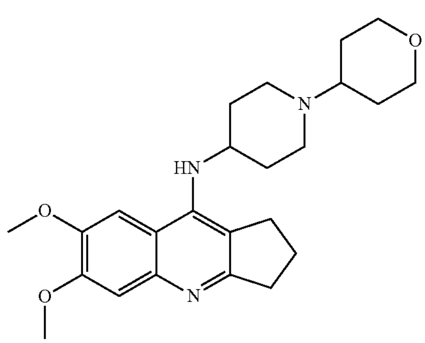 [SMILES: COc1cc2nc3c(c(NC4CCN(C5CCOCC5)CC4)c2cc1OC)CCC3] | N-{6,7-dimethoxy-1H,2H,3H-cyclopenta[b]quinolin-9-yl}-1-(oxan-4-yl)piperidin-4-amine | 412.5 |

TABLE 1-continued

| No | Structure | IUPAC Name | MS found |
|----|-----------|------------|----------|
| 17 | 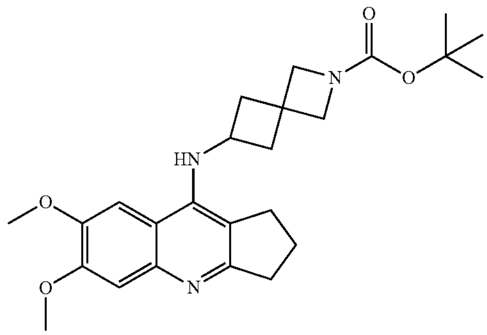 [SMILES: COc1cc2nc3c(c(NC4CC5(C4)CN(C(=O)OC(C)(C)C)C5)c2cc1OC)CCC3] | tert-butyl 6-({6,7-dimethoxy-1H,2H,3H-cyclopenta[b]quinolin-9-yl}amino)-2-azaspiro[3.3]heptane-2-carboxylate | 440.2 |
| 18 | 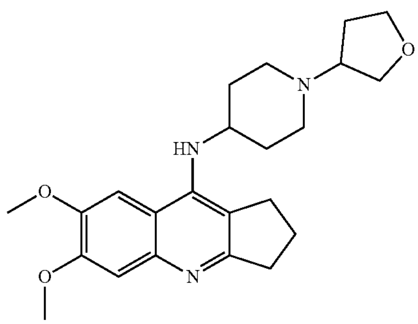 [SMILES: COc1cc2nc3c(c(NC4CCN(C5CCOC5)CC4)c2cc1OC)CCC3] | N-{6,7-dimethoxy-1H,2H,3H-cyclopenta[b]quinolin-9-yl}-1-(oxolan-3-yl)piperidin-4-amine | 398.4 |
| 19 | 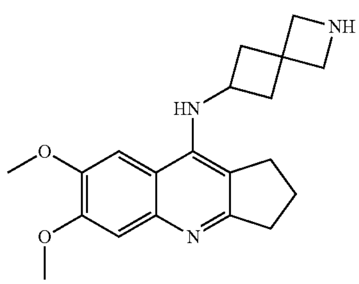 [SMILES: COc1cc2nc3c(c(NC4CC5(CNC5)C4)c2cc1OC)CCC3] | N-{6,7-dimethoxy-1H,2H,3H-cyclopenta[b]quinolin-9-yl}-2-azaspiro[3.3]heptan-6-amine | 340.2 |
| 20 | 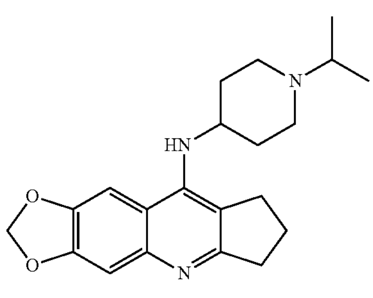 [SMILES: CC(C)N1CCC(Nc2c3c(nc4cc5c(cc24)OCO5)CCC3)CC1] | N-[1-(propan-2-yl)piperidin-4-yl]-12,14-dioxa-2-azatetracyclo[7.7.0.0$^{3,7}$.0$^{11,15}$]hexadeca-1(9),2,7,10,15-pentaen-8-amine | 354.3 |
| 21 | 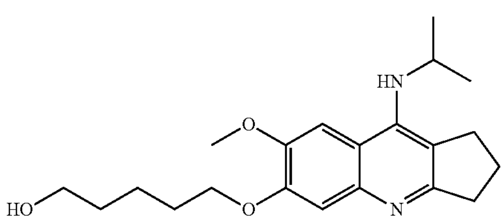 [SMILES: COc1cc2c(NC(C)C)c3c(nc2cc1OCCCCCO)CCC3] | 5-({7-methoxy-9-[(propan-2-yl)amino]-1H,2H,3H-cyclopenta[b]quinolin-6-yl}oxy)pentan-1-ol | 359.2 |

TABLE 1-continued

| No | Structure | IUPAC Name | MS found |
|---|---|---|---|
| 22 | 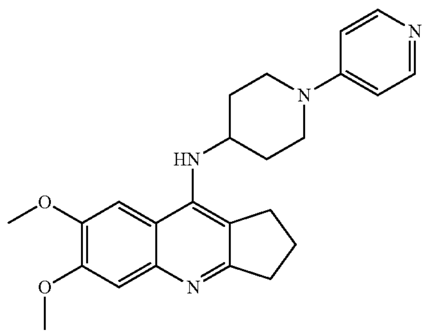 [SMILES: COc1cc2nc3c(c(NC4CCN(c5ccncc5)CC4)c2cc1OC)CCC3] | N-{6,7-dimethoxy-1H,2H,3H-cyclopenta[b]quinolin-9-yl}-1-(pyridin-4-yl)piperidin-4-amine | 405.3 |
| 23 | 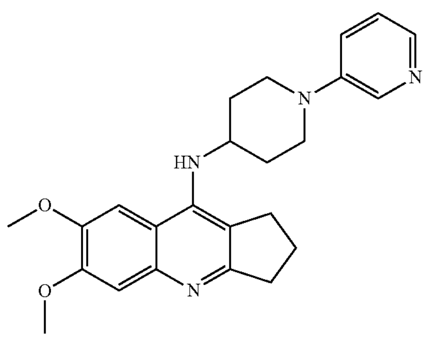 [SMILES: COc1cc2nc3c(c(NC4CCN(c5cccnc5)CC4)c2cc1OC)CCC3] | N-{6,7-dimethoxy-1H,2H,3H-cyclopenta[b]quinolin-9-yl}-1-(pyridin-3-yl)piperidin-4-amine | 405.3 |
| 24 | 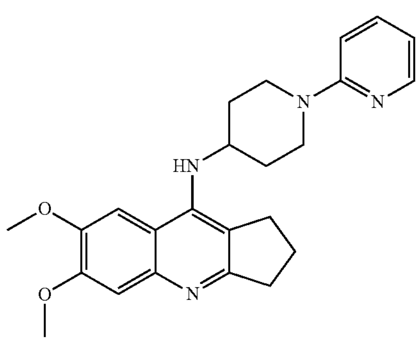 [SMILES: COc1cc2nc3c(c(NC4CCN(c5ccccn5)CC4)c2cc1OC)CCC3] | N-{6,7-dimethoxy-1H,2H,3H-cyclopenta[b]quinolin-9-yl}-1-(pyridin-2-yl)piperidin-4-amine | 405.2 |
| 25 | 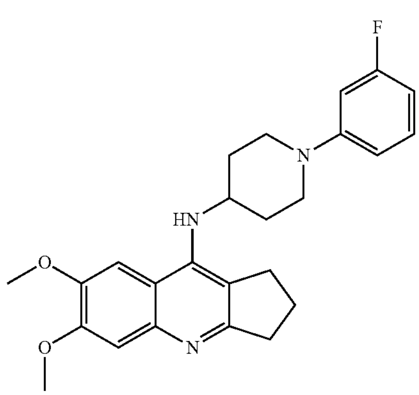 [SMILES: COc1cc2nc3c(c(NC4CCN(c5cccc(F)c5)CC4)c2cc1OC)CCC3] | N-{6,7-dimethoxy-1H,2H,3H-cyclopenta[b]quinolin-9-yl}-1-(3-fluorophenyl)piperidin-4-amine | 422.2 |

TABLE 1-continued

| No | Structure | IUPAC Name | MS found |
|---|---|---|---|
| 26 | 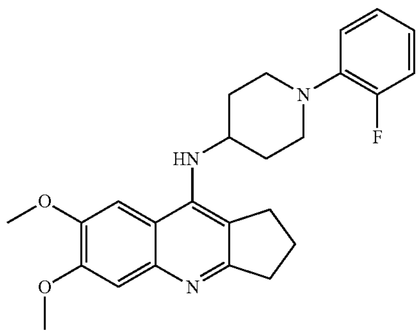 [SMILES: COc1cc2nc3c(c(NC4CCN(c5ccccc5F)CC4)c2cc1OC)CCC3] | N-{6,7-dimethoxy-1H,2H,3H-cyclopenta[b]quinolin-9-yl}-1-(2-fluorophenyl)piperidin-4-amine | 422.4 |
| 27 | 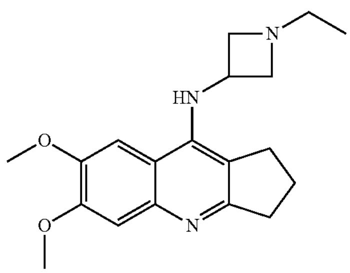 [SMILES: CCN1CC(Nc2c3c(nc4cc(OC)c(OC)cc24)CCC3)C1] | N-{6,7-dimethoxy-1H,2H,3H-cyclopenta[b]quinolin-9-yl}-1-ethylazetidin-3-amine | 328.4 |
| 28 | 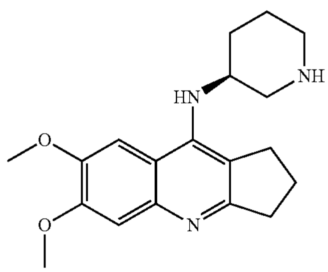 [SMILES: COc1cc2nc3c(c(N[C@H]4CCCNC4)c2cc1OC)CCC3] | (3S)-N-{6,7-dimethoxy-1H,2H,3H-cyclopenta[b]quinolin-9-yl}piperidin-3-amine | 328.3 |
| 29 | 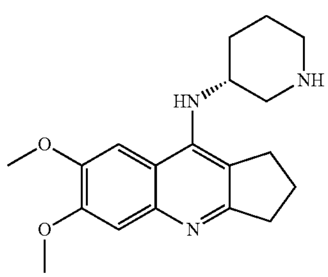 [SMILES: COc1cc2nc3c(c(N[C@@H]4CCCNC4)c2cc1OC)CCC3] | (3R)-N-{6,7-dimethoxy-1H,2H,3H-cyclopenta[b]quinolin-9-yl}piperidin-3-amine | 328.3 |
| 30 | 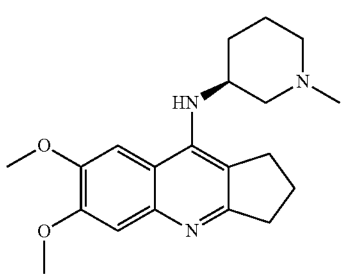 | (3S)-N-{6,7-dimethoxy-1H,2H,3H-cyclopenta[b]quinolin-9-yl}-1-methylpiperidin-3-amine | 342.4 |

TABLE 1-continued

| No | Structure | IUPAC Name | MS found |
|---|---|---|---|
| 31 | 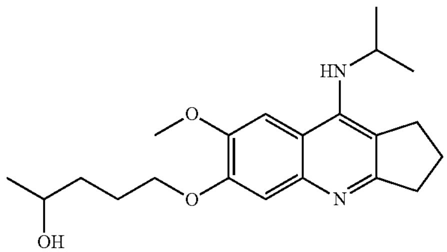 [SMILES: COc1cc2c(NC(C)C)c3c(nc2cc1OCCCC(C)O)CCC3] | 5-({7-methoxy-9-[(propan-2-yl)amino]-1H,2H,3H-cyclopenta[b]quinolin-6-yl}oxy)pentan-2-ol | 359.2 |
| 32 | 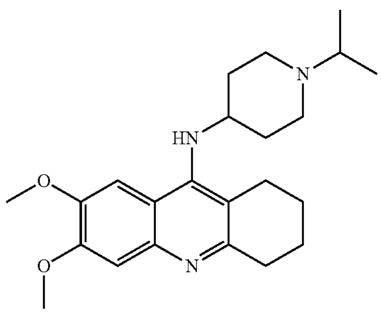 [SMILES: COc1cc2nc3c(c(NC4CCN(C(C)C)CC4)c2cc1OC)CCCC3] | 6,7-dimethoxy-N-[1-(propan-2-yl)piperidin-4-yl]-1,2,3,4-tetrahydroacridin-9-amine | 384.3 |
| 33 | 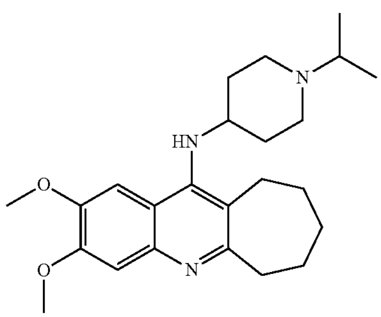 [SMILES: COc1cc2nc3c(c(NC4CCN(C(C)C)CC4)c2cc1OC)CCCCC3] | N-{2,3-dimethoxy-6H,7H,8H,9H,10H-cyclohepta[b]quinolin-11-yl}-1-(propan-2-yl)piperidin-4-amine | 398.2 |
| 34 | 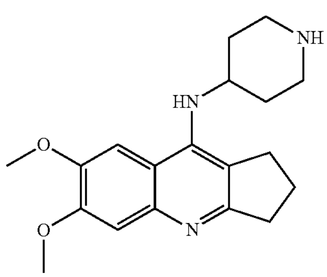 [SMILES: COc1cc2nc3c(c(NC4CCNCC4)c2cc1OC)CCC3] | N-{6,7-dimethoxy-1H,2H,3H-cyclopenta[b]quinolin-9-yl}piperidin-4-amine | 328.2 |
| 35 | 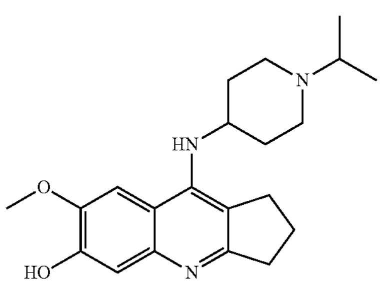 [SMILES: COc1cc2c(NC3CCN(C(C)C)CC3)c3c(nc2cc1O)CCC3] | 7-methoxy-9-{[1-(propan-2-yl)piperidin-4-yl]amino}-1H,2H,3H-cyclopenta[b]quinolin-6-ol | 356.4 |

TABLE 1-continued

| No | Structure | IUPAC Name | MS found |
|---|---|---|---|
| 36 | 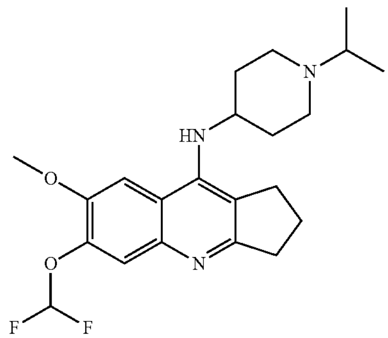 [SMILES: COc1cc2c(NC3CCN(C(C)C)CC3)c3c(nc2cc1OC(F)F)CCC3] | N-[6-(difluoromethoxy)-7-methoxy-1H,2H,3H-cyclopenta[b]quinolin-9-yl]-1-(propan-2-yl)piperidin-4-amine | 406.3 |
| 37 | 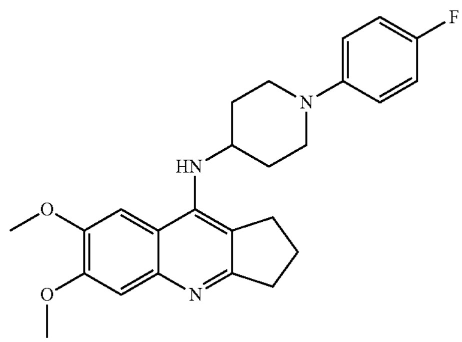 [SMILES: COc1cc2nc3c(c(NC4CCN(c5ccc(F)cc5)CC4)c2cc1OC)CCC3] | N-{6,7-dimethoxy-1H,2H,3H-cyclopenta[b]quinolin-9-yl}-1-(4-fluorophenyl)piperidin-4-amine | 422.4 |
| 38 | 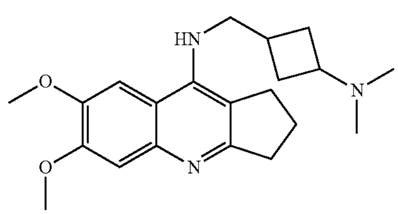 | N-{[3-(dimethylamino)cyclobutyl]methyl}-6,7-dimethoxy-1H,2H,3H-cyclopenta[b]quinolin-9-amine | 356.2 |
| 39 | 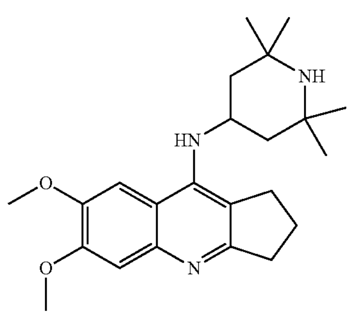 | N-{6,7-dimethoxy-1H,2H,3H-cyclopenta[b]quinolin-9-yl}-2,2,6,6-tetramethylpiperidin-4-amine | 384.1 |

TABLE 1-continued

| No | Structure | IUPAC Name | MS found |
|---|---|---|---|
| 40 | 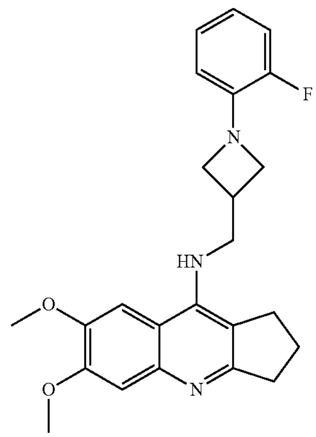 [SMILES: COc1cc2nc3c(c(NCC4CN(c5ccccc5F)C4)c2cc1OC)CCC3] | N-{[1-(2-fluorophenyl)azetidin-3-yl]methyl}-6,7-dimethoxy-1H,2H,3H-cyclopenta[b]quinolin-9-amine | 408.2 |
| 41 | 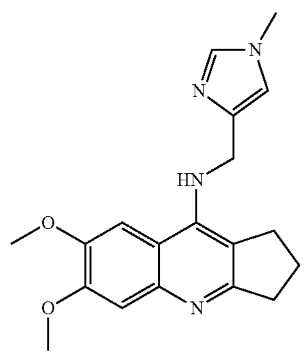 [SMILES: COc1cc2nc3c(c(NCc4cn(C)cn4)c2cc1OC)CCC3] | N-{[1-(2-fluorophenyl)azetidin-3-yl]methyl}-6,7-dimethoxy-1H,2H,3H-cyclopenta[b]quinolin-9-amine | 339.1 |
| 42 | 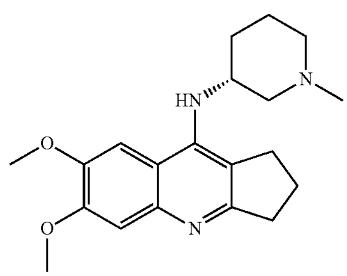 | (3R)-N-{6,7-dimethoxy-1H,2H,3H-cyclopenta[b]quinolin-9-yl}-1-methylpiperidin-3-amine | 342.2 |
| 43 | 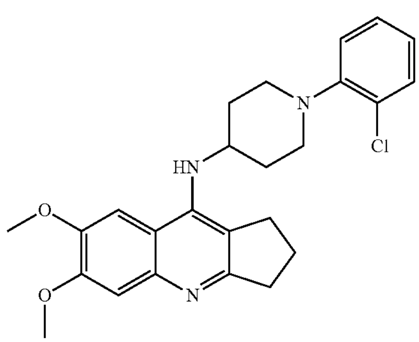 | 1-(2-chlorophenyl)-N-{6,7-dimethoxy-1H,2H,3H-cyclopenta[b]quinolin-9-yl}piperidin-4-amine | 438.2 |

TABLE 1-continued

| No | Structure | IUPAC Name | MS found |
|---|---|---|---|
| 44 | 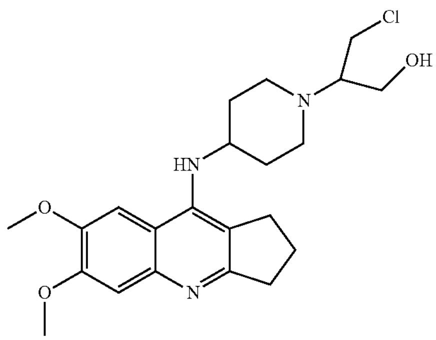 [SMILES: COc1cc2nc3c(c(NC4CCN(C(CO)CCl)CC4)c2cc1OC)CCC3] | 3-chloro-2-[4-({6,7-dimethoxy-1H,2H,3H-cyclopenta[b]quinolin-9-yl}amino)piperidin-1-yl]propan-1-ol | 420.3 |
| 45 | 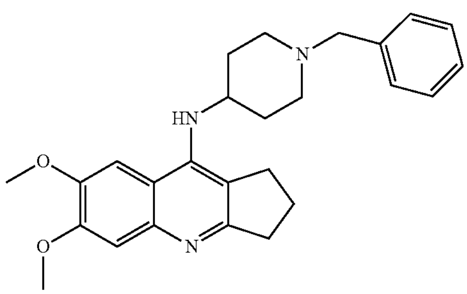 [SMILES: COc1cc2nc3c(c(NC4CCN(Cc5ccccc5)CC4)c2cc1OC)CCC3] | 1-benzyl-N-{6,7-dimethoxy-1H,2H,3H-cyclopenta[b]quinolin-9-yl}piperidin-4-amine | 418.4 |
| 46 | 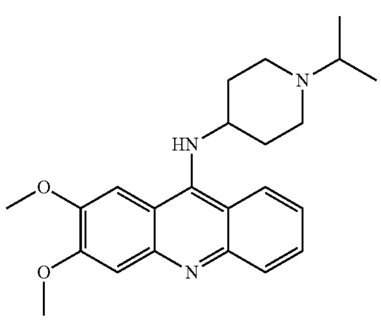 [SMILES: COc1cc2nc3ccccc3c(NC3CCN(C(C)C)CC3)c2cc1OC] | 2,3-dimethoxy-N-[1-(propan-2-yl)piperidin-4-yl]acridin-9-amine | 380.2 |
| 47 | 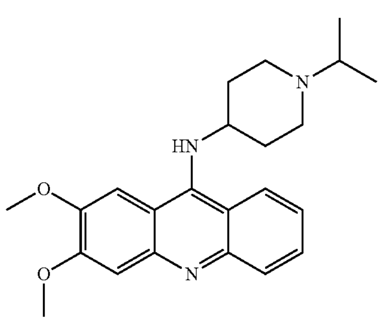 [SMILES: COc1cc2nc3ccccc3c(NC3CCN(C(C)C)CC3)c2cc1OC] | 2,3-dimethoxy-N-[1-(propan-2-yl)piperidin-4-yl]acridin-9-amine | 380.2 |
| 48 | 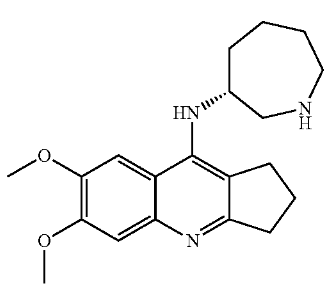 [SMILES: COc1cc2nc3c(c(N[C@@H]4CCCCNC4)c2cc1OC)CCC3] | (3R)-N-{6,7-dimethoxy-1H,2H,3H-cyclopenta[b]quinolin-9-yl}azepan-3-amine | 342.3 |

TABLE 1-continued

| No | Structure | IUPAC Name | MS found |
|---|---|---|---|
| 49 | 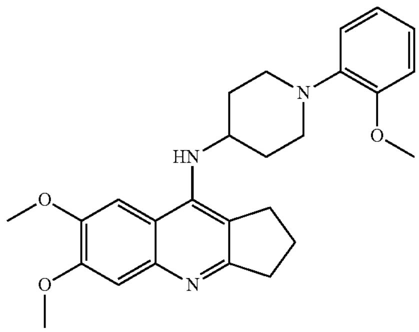 | N-{6,7-dimethoxy-1H,2H,3H-cyclopenta[b]quinolin-9-yl}-1-(2-methoxyphenyl)piperidin-4-amine | 434.3 |
| 50 | 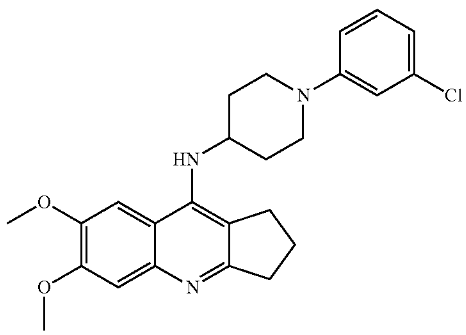 [SMILES: COc1cc2nc3c(c(NC4CCN(c5cccc(Cl)c5)CC4)c2cc1OC)CCC3] | 1-(3-chlorophenyl)-N-{6,7-dimethoxy-1H,2H,3H-cyclopenta[b]quinolin-9-yl}piperidin-4-amine | 438.2, 440.3 |
| 51 | 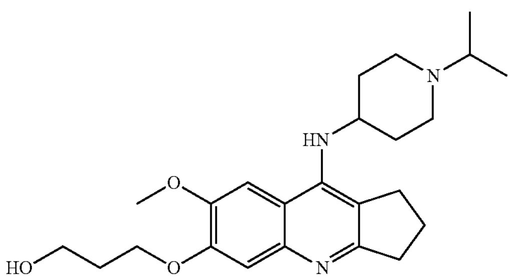 [SMILES: COc1cc2c(NC3CCN(C(C)C)CC3)c3c(nc2cc1OCCCO)CCC3] | 3-[(7-methoxy-9-{[1-(propan-2-yl)piperidin-4-yl]amino}-1H,2H,3H-cyclopenta[b]quinolin-6-yl)oxy]propan-1-ol | 414.2 |
| 52 | 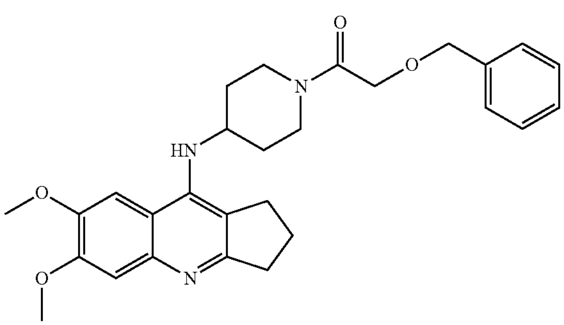 [SMILES: COc1cc2nc3c(c(NC4CCN(C(=O)COCc5ccccc5)CC4)c2cc1OC)CCC3] | 2-(benzyloxy)-1-[4-({6,7-dimethoxy-1H,2H,3H-cyclopenta[b]quinolin-9-yl}amino)piperidin-1-yl]ethan-1-one | 476.9 |
| 53 | 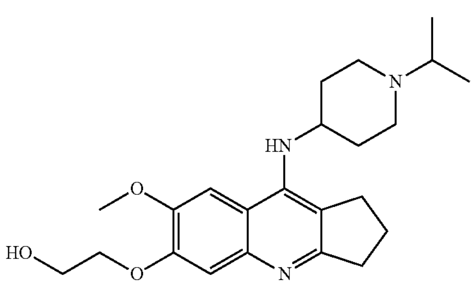 [SMILES: COc1cc2c(NC3CCN(C(C)C)CC3)c3c(nc2cc1OCCO)CCC3] | 2-[(7-methoxy-9-{[1-(propan-2-yl)piperidin-4-yl]amino}-1H,2H,3H-cyclopenta[b]quinolin-6-yl)oxy]ethan-1-ol | 400.2 |

TABLE 1-continued

| No | Structure | IUPAC Name | MS found |
|---|---|---|---|
| 54 | 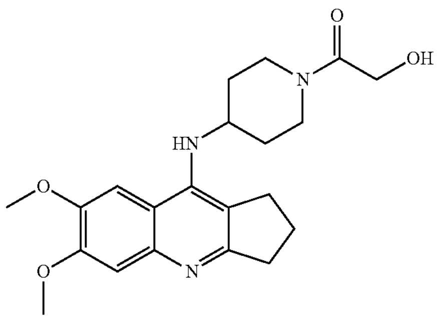 [SMILES: COc1cc2nc3c(c(NC4CCN(C(=O)CO)CC4)c2cc1OC)CCC3] | 1-[4-({6,7-dimethoxy-1H,2H,3H-cyclopenta[b]quinolin-9-yl}amino)piperidin-1-yl]-2-hydroxyethan-1-one | 386.1 |
| 55 | 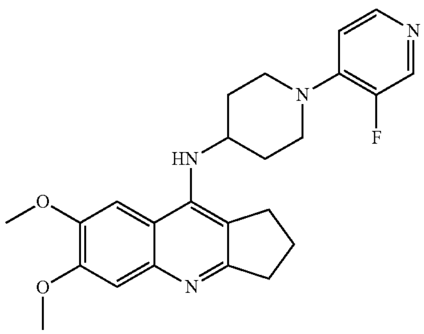 [SMILES: COc1cc2nc3c(c(NC4CCN(c5ccncc5F)CC4)c2cc1OC)CCC3] | N-{6,7-dimethoxy-1H,2H,3H-cyclopenta[b]quinolin-9-yl}-1-(3-fluoropyridin-4-yl)piperidin-4-amine | 423.2 |
| 56 | 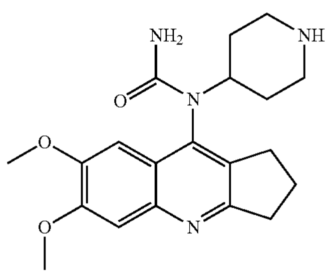 [SMILES: COc1cc2nc3c(c(N(C(N)=O)C4CCNCC4)c2cc1OC)CCC3] | 1-{6,7-dimethoxy-1H,2H,3H-cyclopenta[b]quinolin-9-yl}-1-(piperidin-4-yl)urea | 370.8 |
| 57 | 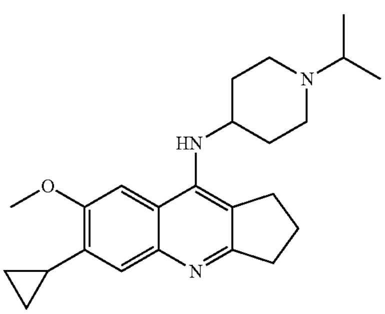 [SMILES: COc1cc2c(NC3CCN(C(C)C)CC3)c3c(nc2cc1C1CC1)CCC3] | N-{6-cyclopropyl-7-methoxy-1H,2H,3H-cyclopenta[b]quinolin-9-yl}-1-(propan-2-yl)piperidin-4-amine | 380.2 |
| 58 | 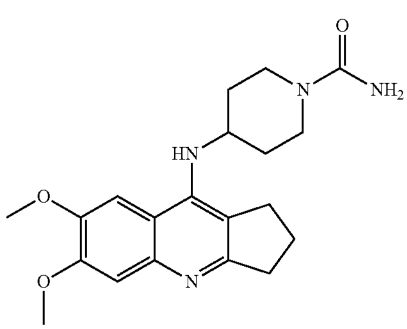 [SMILES: COc1cc2nc3c(c(NC4CCN(C(N)=O)CC4)c2cc1OC)CCC3] | 4-({6,7-dimethoxy-1H,2H,3H-cyclopenta[b]quinolin-9-yl}amino)piperidine-1-carboxamide | 370.9 |

TABLE 1-continued

| No | Structure | IUPAC Name | MS found |
|----|-----------|------------|----------|
| 59 | 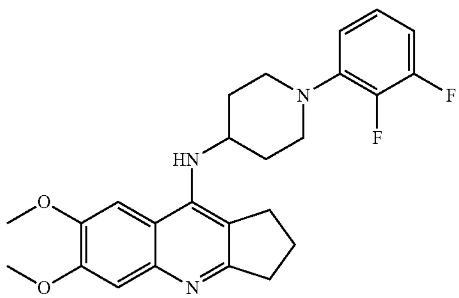 [SMILES: COc1cc2nc3c(c(NC4CCN(c5cccc(F)c5F)CC4)c2cc1OC)CCC3] | 1-(2,3-difluorophenyl)-N-{6,7-dimethoxy-1H,2H,3H-cyclopenta[b]quinolin-9-yl}piperidin-4-amine | 440.3 |
| 60 | 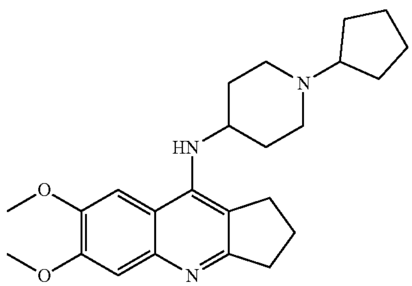 [SMILES: COc1cc2nc3c(c(NC4CCN(C5CCCC5)CC4)c2cc1OC)CCC3] | 1-cyclopentyl-N-{6,7-dimethoxy-1H,2H,3H-cyclopenta[b]quinolin-9-yl}piperidin-4-amine | 396.2 |
| 61 | 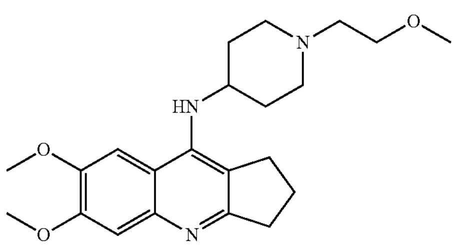 | N-{6,7-dimethoxy-1H,2H,3H-cyclopenta[b]quinolin-9-yl}-1-(2-methoxyethyl)piperidin-4-amine | 386.1 |
| 62 | 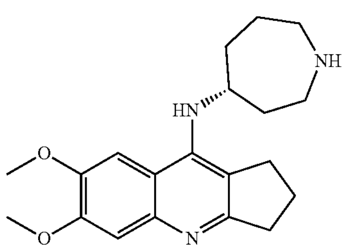 [SMILES: COc1cc2nc3c(c(N[C@@H]4CCCNCC4)c2cc1OC)CCC3] | (4R)-N-{6,7-dimethoxy-1H,2H,3H-cyclopenta[b]quinolin-9-yl}azepan-4-amine | 342.2 |
| 63 | 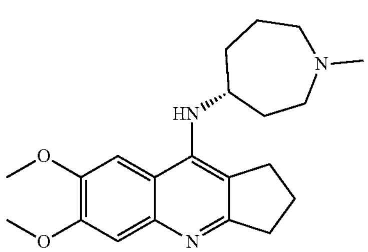 | (4R)-N-{6,7-dimethoxy-1H,2H,3H-cyclopenta[b]quinolin-9-yl}-1-methylazepan-4-amine | 356.1 |

TABLE 1-continued

| No | Structure | IUPAC Name | MS found |
|---|---|---|---|
| 64 | 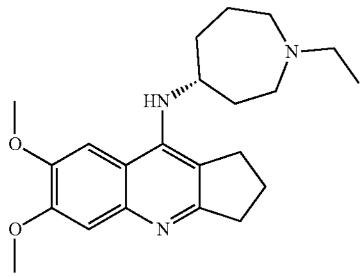 [SMILES: CCN1CCC[C@@H](Nc2c3c(nc4cc(OC)c(OC)cc24)CCC3)CC1] | (4R)-N-{6,7-dimethoxy-1H,2H,3H-cyclopenta[b]quinolin-9-yl}-1-ethylazepan-4-amine | 370.3 |
| 65 | 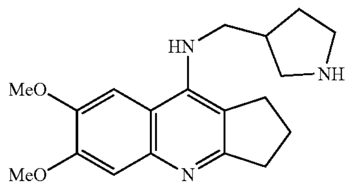 [SMILES: COc1cc2nc3c(c(NCC4CCNC4)c2cc1OC)CCC3] | 6,7-dimethoxy-N-[(pyrrolidin-3-yl)methyl]-1H,2H,3H-cyclopenta[b]quinolin-9-amine | 328.1 |
| 66 | 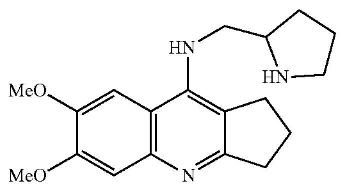 [SMILES: COc1cc2nc3c(c(NCC4CCCN4)c2cc1OC)CCC3] | 6,7-dimethoxy-N-[(pyrrolidin-2-yl)methyl]-1H,2H,3H-cyclopenta[b]quinolin-9-amine | 328.1 |
| 67 | 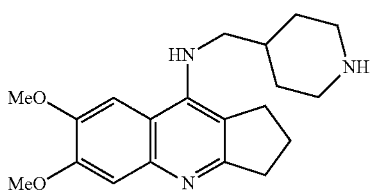 [SMILES: COc1cc2nc3c(c(NCC4CCNCC4)c2cc1OC)CCC3] | 6,7-dimethoxy-N-[(piperidin-4-yl)methyl]-1H,2H,3H-cyclopenta[b]quinolin-9-amine | 342.1 |
| 68 | 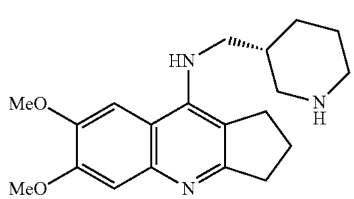 [SMILES: COc1cc2nc3c(c(NC[C@@H]4CCCNC4)c2cc1OC)CCC3] | 6,7-dimethoxy-N-{[(3R)-piperidin-3-yl]methyl}-1H,2H,3H-cyclopenta[b]quinolin-9-amine | 342.0 |
| 69 | 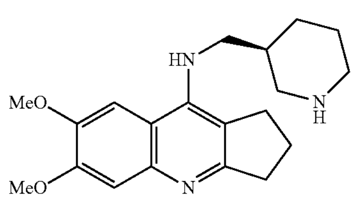 [SMILES: COc1cc2nc3c(c(NC[C@H]4CCCNC4)c2cc1OC)CCC3] | 6,7-dimethoxy-N-{(3S)-piperidin-3-yl]methyl}-1H,2H,3H-cyclopenta[b]quinolin-9-amine | 342.0 |
| 134 | 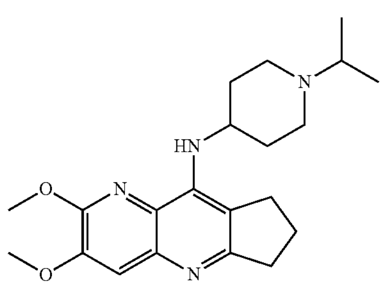 [SMILES: COc1cc2nc3c(c(NC4CCN(C(C)C)CC4)c2nc1OC)CCC3] | N-[2,3-dimethoxy-6H,7H,8H-cyclopenta[b]1,5-naphthyridin-9-yl]-1-(propan-2-yl)piperidin-4-amine | 371.2 |

TABLE 1-continued

| No | Structure | IUPAC Name | MS found |
|---|---|---|---|
| 149 | 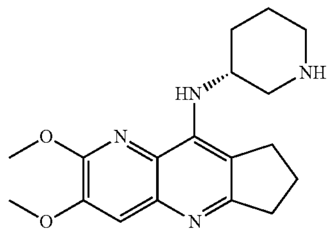 [SMILES: COc1cc2nc3c(c(N[C@@H]4CCCNC4)c2nc1OC)CCC3] | (3R)-N-[2,3-dimethoxy-6H,7H,8Hcyclopenta[b]1,5naphthyridin-9-yl]piperidin-3-amine | 329.2 |
| 163 | 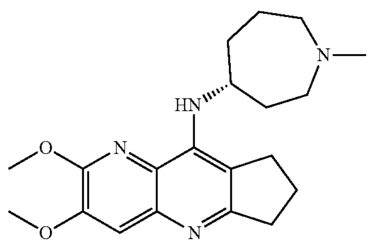 | (4R)-N-[2,3-dimethoxy-6H,7H,8H-cyclopenta[b]1,5-naphthyridin-9-yl]azepan-4-amine | 343.2 |
| 164 | 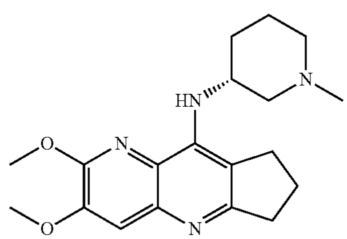 | (3R)-N-[2,3-dimethoxy-6H,7H,8H-cyclopenta[b]1,5-naphthyridin-9-yl]-1-methylpiperidin-3-amine | 343.2 |
| 165 | 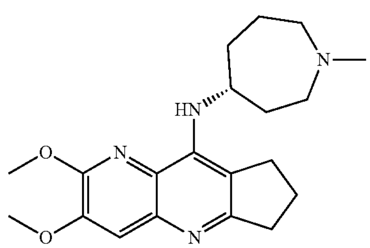 | (4R)-N-{2,3-dimethoxy-6H,7H,8H-cyclopenta[b]1,5-naphthyridin-9-yl}-1-methylazepan-4-amine | 357.2 |
| 286 | 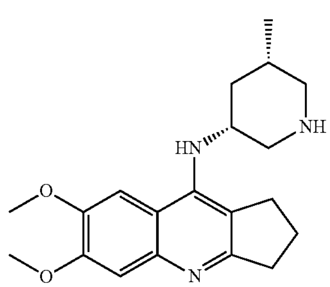 [SMILES: COc1cc2nc3c(c(N[C@H]4CNC[C@@H](C)C4)c2cc1OC)CCC3] | (3R,5S)-N-{6,7-dimethoxy-1H,2H,3H-cyclopenta[b]quinolin-9-yl}-5-methylpiperidin-3-amine | 342.2 |
| 402 | 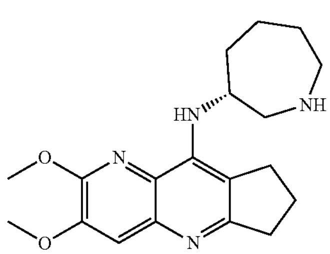 [SMILES: COc1cc2nc3c(c(N[C@@H]4CCCCNC4)c2nc1OC)CCC3] | (3R)-N-[2,3-dimethoxy-6H,7H,8H-cyclopenta[b]1,5-naphthyridin-9-yl azepan-3-amine | 343.2 |

TABLE 1-continued

| No | Structure | IUPAC Name | MS found |
|---|---|---|---|
| 403 | 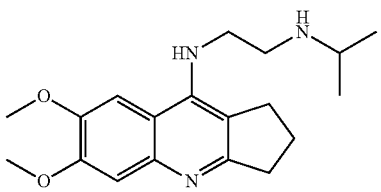 [SMILES: COc1cc2nc3c(c(NCCNC(C)C)c2cc1OC)CCC3] | 6,7-dimethoxy-N-{2-[(propan-2-yl)amino]ethyl}-1H,2H,3H-cyclopenta[b]quinolin-9-amine | 330.1 |
| 404 | 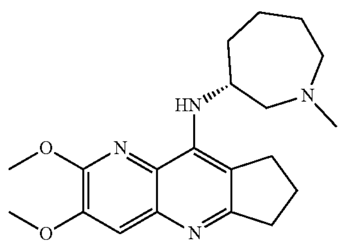 | (3R)-N-[2,3-dimethoxy-6H,7H,8H-cyclopenta[b]1,5-naphthyridin-9-yl]-1-methylazepan-3-amine | 357.5 |
| 405 | 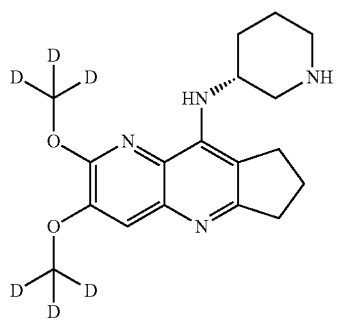 | (3R)-N-[6,7-di(2H3)methoxy-1H,2H,3H-cyclopenta[b]quinolin-9-yl]piperidin-3-amine | 334 |
| 406 | 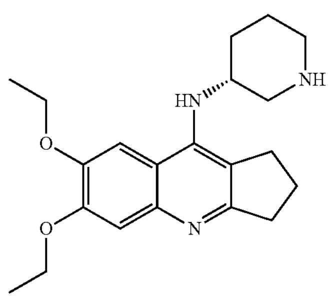 [SMILES: CCOc1cc2nc3c(c(N[C@@H]4CCCNC4)c2cc1OCC)CCC3] | (3R)-N-[6,7-di(2H3)ethoxy-1H,2H,3H-cyclopenta[b]quinolin-9-yl]piperidin-3-amine | 356.1 |
| 407 | 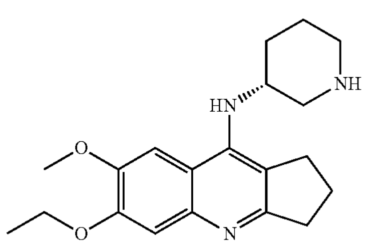 [SMILES: CCOc1cc2nc3c(c(N[C@@H]4CCCNC4)c2cc1OC)CCC3] | (3R)-N-{6-ethoxy-7-methoxy-1H,2H,3H-cyclopenta[b]quinolin-9-yl}piperidin-3-amine | 341.9 |
| 408 | 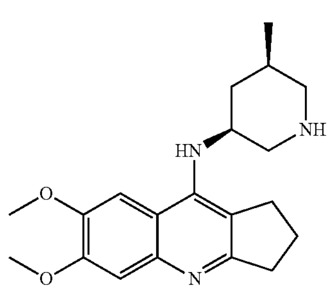 [SMILES: COc1cc2nc3c(c(N[C@@H]4CNC[C@H](C)C4)c2cc1OC)CCC3] | (3S,5R)-N-{6,7-dimethoxy-1H,2H,3H-cyclopenta[b]quinolin-9-yl}-5-methylpiperidin-3-amine | 342.2 |

TABLE 1-continued

| No | Structure | IUPAC Name | MS found |
|---|---|---|---|
| 409 | 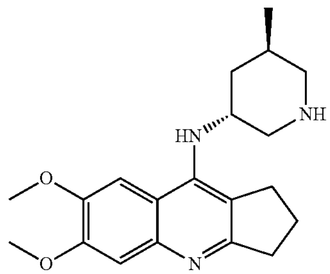 [SMILES: COc1cc2nc3c(c(N[C@H]4CNC[C@H](C)C4)c2cc1OC)CCC3] | (3R,5R)-N-{6,7-dimethoxy-1H,2H,3H-cyclopenta[b]quinolin-9-yl}-5-methylpiperidin-3-amine | 342.2 |
| 410 | 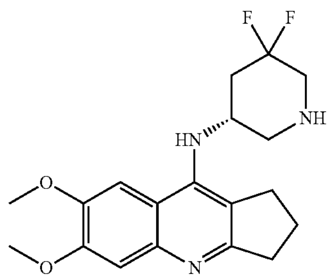 [SMILES: COc1cc2nc3c(c(N[C@H]4CNCC(F)(F)C4)c2cc1OC)CCC3] | (3R)-N-{6,7-dimethoxy-1H,2H,3H-cyclopenta[b]quinolin-9-yl}-5,5-difluoropiperidin-3-amine | 364.2 |
| 411 | 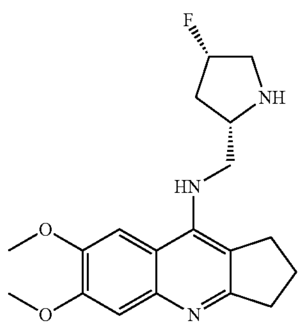 [SMILES: COc1cc2nc3c(c(NC[C@@H]4C[C@H](F)CN4)c2cc1OC)CCC3] | N-{[(2S,4S)-4-fluoropyrrolidin-2-yl]methyl}-6,7-dimethoxy-1H,2H,3H-cyclopenta[b]quinolin-9-amine | 346.1 |
| 412 | 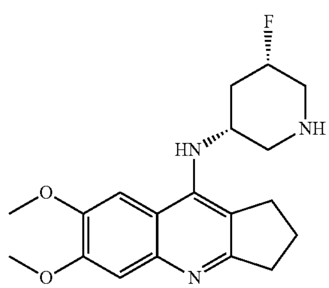 [SMILES: COc1cc2nc3c(c(N[C@H]4CNC[C@@H](F)C4)c2cc1OC)CCC3] | (3R,5S)-N-{6,7-dimethoxy-1H,2H,3H-cyclopenta[b]quinolin-9-yl}-5-fluoropiperidin-3-amine | 346.1 |
| 413 | 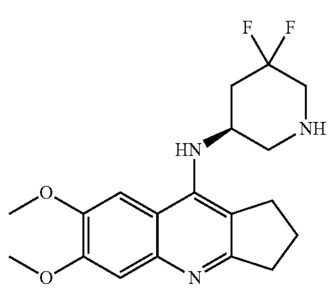 [SMILES: COc1cc2nc3c(c(N[C@@H]4CNCC(F)(F)C4)c2cc1OC)CCC3] | (3S)-N-{6,7-dimethoxy-1H,2H,3H-cyclopenta[b]quinolin-9-yl}-5,5-difluoropiperidin-3-amine | 364.1 |

TABLE 1-continued

| No | Structure | IUPAC Name | MS found |
|---|---|---|---|
| 414 | 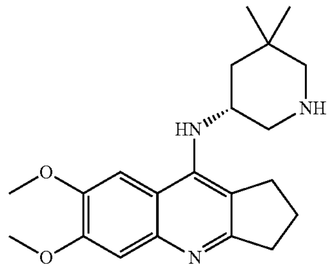 [SMILES: COc1cc2nc3c(c(N[C@H]4CNCC(C)(C)C4)c2cc1OC)CCC3] | (3R)-N-{6,7-dimethoxy-1H,2H,3H-cyclopenta[b]quinolin-9-yl}-5,5-dimethylpiperidin-3-amine | 356.2 |
| 415 | 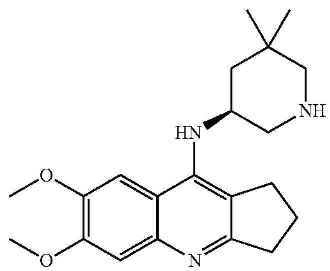 [SMILES: COc1cc2nc3c(c(N[C@@H]4CNCC(C)(C)C4)c2cc1OC)CCC3] | (3S)-N-{6,7-dimethoxy-1H,2H,3H-cyclopenta[b]quinolin-9-yl}-5,5-dimethylpiperidin-3-amine | 356.3 |
| 416 | 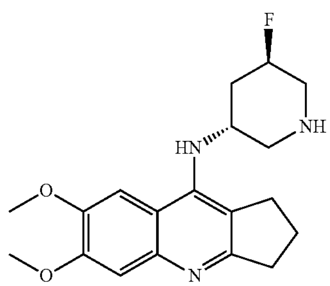 [SMILES: COc1cc2nc3c(c(N[C@H]4CNC[C@H](F)C4)c2cc1OC)CCC3] | (3R,5R)-N-{6,7-dimethoxy-1H,2H,3H-cyclopenta[b]quinolin-9-yl}-5-fluoropiperidin-3-amine | 346.3 |

TABLE 2

| No. | Structure | IUPAC Name |
|---|---|---|
| 70 | 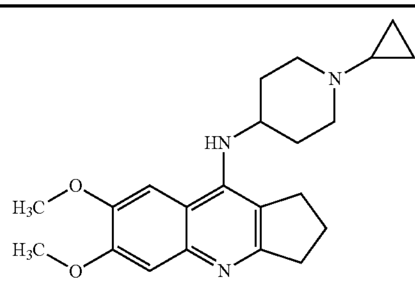 | 1-cyclopropyl-N-{6,7-dimethoxy-1H,2H,3H-cyclopenta[b]quinolin-9-yl}piperidin-4-amine |
| 71 | 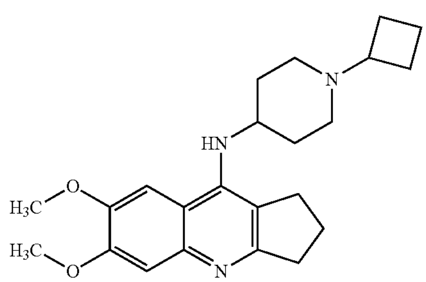 [SMILES: COc1cc2nc3c(c(NC4CCN(C5CCC5)CC4)c2cc1OC)CCC3] | 1-cyclobutyl-N-{6,7-dimethoxy-1H,2H,3H-cyclopenta[b]quinolin-9-yl}piperidin-4-amine |

TABLE 2-continued

| No. | Structure | IUPAC Name |
|---|---|---|
| 72 | 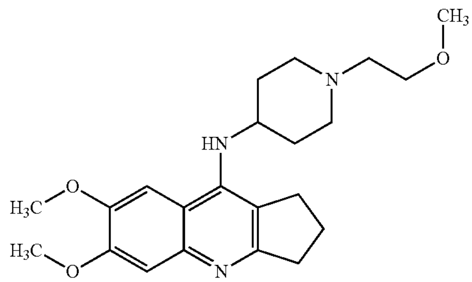 | N-{6,7-dimethoxy-1H,2H,3H-cyclopenta[b]quinolin-9-yl}-1-(2-methoxyethyl)piperidin-4-amine |
| 73 | 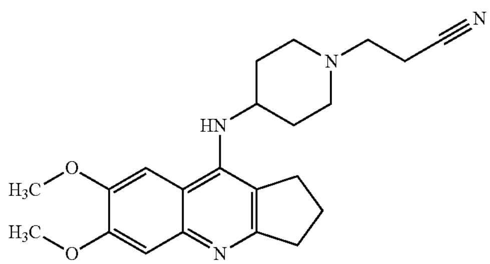 [SMILES: COc1cc2nc3c(c(NC4CCN(CCC#N)CC4)c2cc1OC)CCC3] | 3-[4-({6,7-dimethoxy-1H,2H,3H-cyclopenta[b]quinolin-9-yl}amino)piperidin-1-yl]propanenitrile |
| 74 | 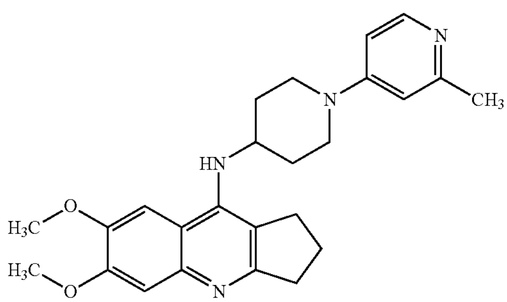 | N-{6,7-dimethoxy-1H,2H,3H-cyclopenta[b]quinolin-9-yl}-1-(2-methylpyridin-4-yl)piperidin-4-amine |
| 75 | 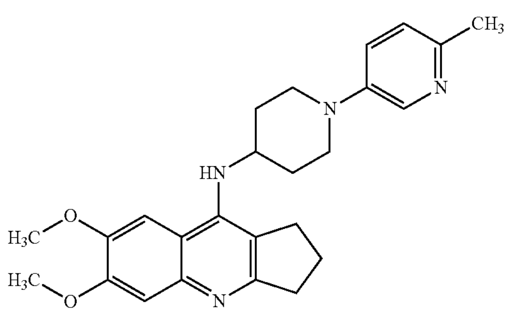 | N-{6,7-dimethoxy-1H,2H,3H-cyclopenta[b]quinolin-9-yl}-1-(6-methylpyridin-3-yl)piperidin-4-amine |
| 76 | 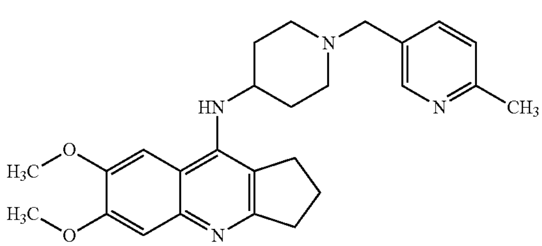 | N-{6,7-dimethoxy-1H,2H,3H-cyclopenta[b]quinolin-9-yl}-1-[(6-methylpyridin-3-yl)methyl]piperidin-4-amine |

TABLE 2-continued

| No. | Structure | IUPAC Name |
|---|---|---|
| 77 | 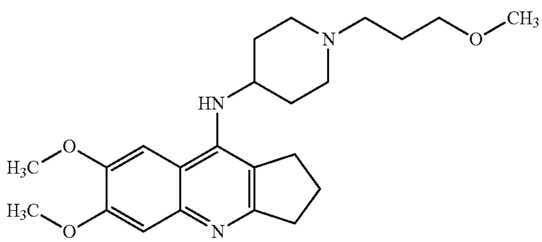 | N-{6,7-dimethoxy-1H,2H,3H-cyclopenta[b]quinolin-9-yl}-1-(3-methoxypropyl)piperidin-4-amine |
| 78 | 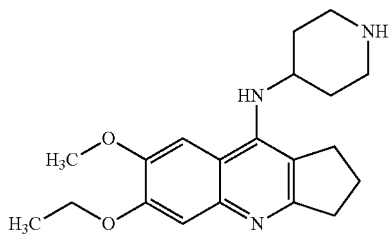 [SMILES: CCOc1cc2nc3c(c(NC4CCNCC4)c2cc1OC)CCC3] | N-{6-ethoxy-7-methoxy-1H,2H,3H-cyclopenta[b]quinolin-9-yl}piperidin-4-amine |
| 79 | 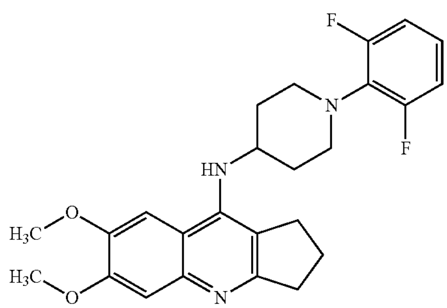 [SMILES: COc1cc2nc3c(c(NC4CCN(c5c(F)cccc5F)CC4)c2cc1OC)CCC3] | 1-(2,6-difluorophenyl)-N-{6,7-dimethoxy-1H,2H,3H-cyclopenta[b]quinolin-9-yl}piperidin-4-amine |
| 80 | 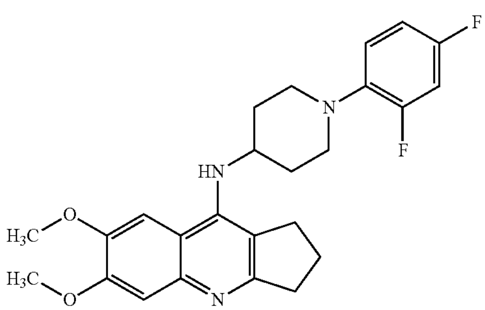 [SMILES: COc1cc2nc3c(c(NC4CCN(c5ccc(F)cc5F)CC4)c2cc1OC)CCC3] | 1-(2,4-difluorophenyl)-N-{6,7-dimethoxy-1H,2H,3H-cyclopenta[b]quinolin-9-yl}piperidin-4-amine |
| 81 | 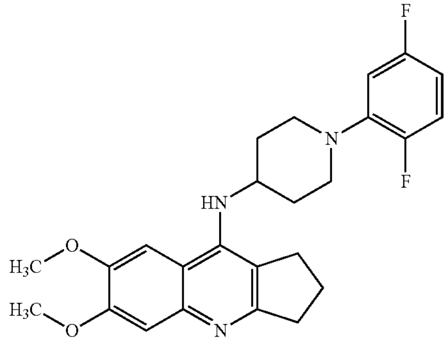 [SMILES: COc1cc2nc3c(c(NC4CCN(c5cc(F)ccc5F)CC4)c2cc1OC)CCC3] | 1-(2,5-difluorophenyl)-N-{6,7-dimethoxy-1H,2H,3H-cyclopenta[b]quinolin-9-yl}piperidin-4-amine |

TABLE 2-continued

| No. | Structure | IUPAC Name |
|---|---|---|
| 82 | 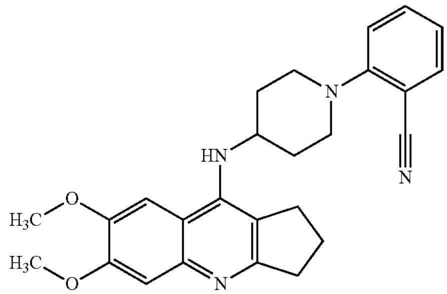 [SMILES: COc1cc2nc3c(c(NC4CCN(c5ccccc5C#N)CC4)c2cc1OC)CCC3] | 2-[4-({6,7-dimethoxy-1H,2H,3H-cyclopenta[b]quinolin-9-yl}amino)piperidin-1-yl]benzonitrile |
| 83 | 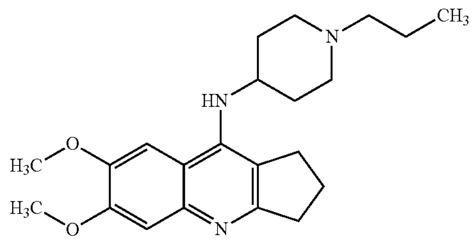 [SMILES: CCCN1CCC(Nc2c3c(nc4cc(OC)c(OC)cc24)CCC3)CC1] | N-{6,7-dimethoxy-1H,2H,3H-cyclopenta[b]quinolin-9-yl}-1-propylpiperidin-4-amine |
| 84 | 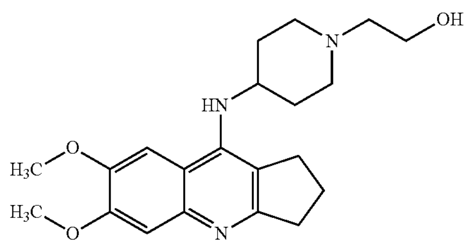 [SMILES: COc1cc2nc3c(c(NC4CCN(CCO)CC4)c2cc1OC)CCC3] | 2-[4-({6,7-dimethoxy-1H,2H,3H-cyclopenta[b]quinolin-9-yl}amino)piperidin-1-yl]ethan-1-ol |
| 85 | 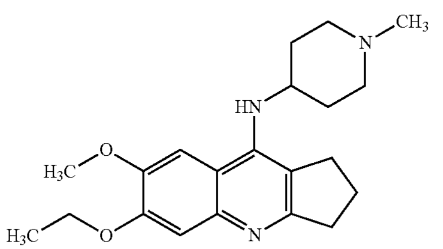 [SMILES: CCOc1cc2nc3c(c(NC4CCN(C)CC4)c2cc1OC)CCC3] | N-{6-ethoxy-7-methoxy-1H,2H,3H-cyclopenta[b]quinolin-9-yl}-1-methylpiperidin-4-amine |
| 86 | 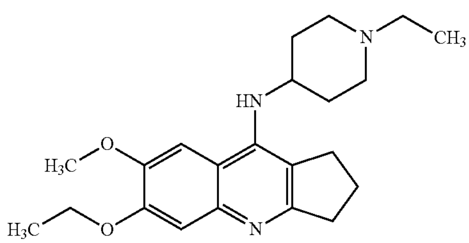 [SMILES: CCOc1cc2nc3c(c(NC4CCN(CC)CC4)c2cc1OC)CCC3] | N-{6-ethoxy-7-methoxy-1H,2H,3H-cyclopenta[b]quinolin-9-yl}-1-ethylpiperidin-4-amine |
| 87 | 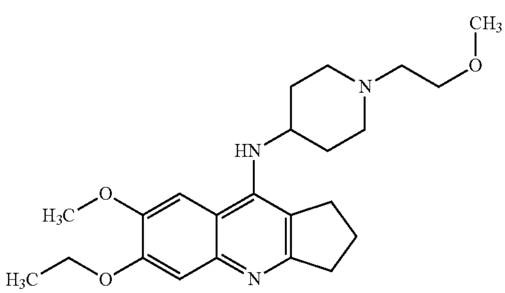 [SMILES: CCOc1cc2nc3c(c(NC4CCN(CCOC)CC4)c2cc1OC)CCC3] | N-{6-ethoxy-7-methoxy-1H,2H,3H-cyclopenta[b]quinolin-9-yl}-1-(2-methoxyethyl)piperidin-4-amine |

TABLE 2-continued

| No. | Structure | IUPAC Name |
|---|---|---|
| 88 | 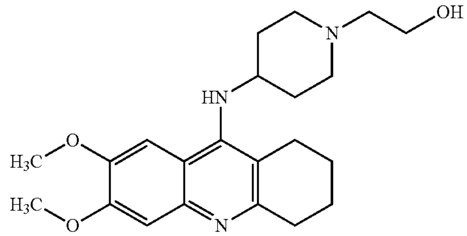 [SMILES: COc1cc2nc3c(c(NC4CCN(CCO)CC4)c2cc1OC)CCCC3] | 2-{4-[(6,7-dimethoxy-1,2,3,4-tetrahydroacridin-9-yl)amino]piperidin-1-yl}ethan-1-ol |
| 89 | 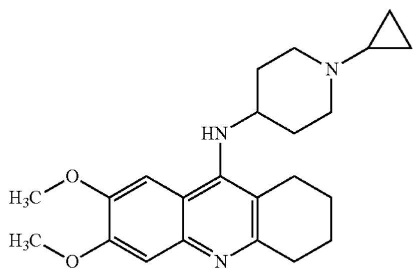 [SMILES: COc1cc2nc3c(c(NC4CCN(C5CC5)CC4)c2cc1OC)CCCC3] | N-(1-cyclopropylpiperidin-4-yl)-6,7-dimethoxy-1,2,3,4-tetrahydroacridin-9-amine |
| 90 | 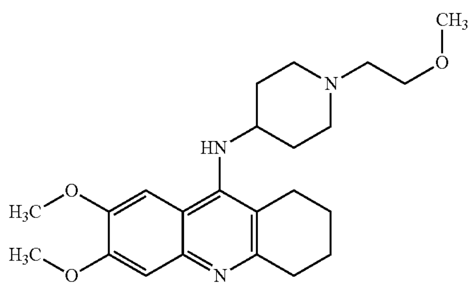 | 6,7-dimethoxy-N-[1-(2-methoxyethyl)piperidin-4-yl]-1,2,3,4-tetrahydroacridin-9-amine |
| 91 | 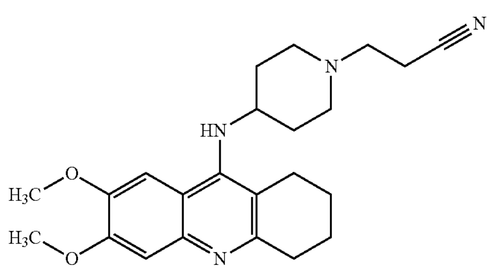 [SMILES: COc1cc2nc3c(c(NC4CCN(CCC#N)CC4)c2cc1OC)CCCC3] | 3-{4-[(6,7-dimethoxy-1,2,3,4-tetrahydroacridin-9-yl)amino]piperidin-1-yl}propanenitrile |
| 92 | 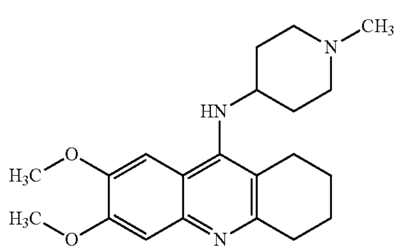 | 6,7-dimethoxy-N-(1-methylpiperidin-4-yl)-1,2,3,4-tetrahydroacridin-9-amine |
| 93 | 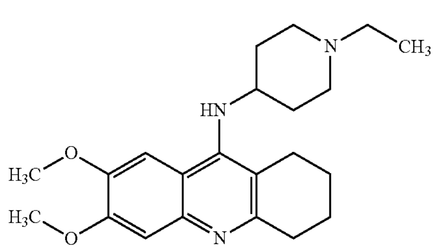 | N-(1-ethylpiperidin-4-yl)-6,7-dimethoxy-1,2,3,4-tetrahydroacridin-9-amine |

TABLE 2-continued

| No. | Structure | IUPAC Name |
|---|---|---|
| 94 | 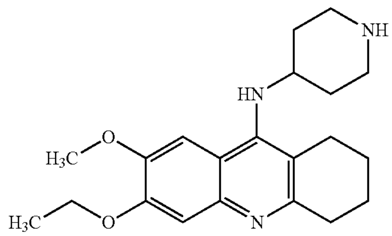 [SMILES: CCOc1cc2nc3c(c(NC4CCNCC4)c2cc1OC)CCCC3] | 6-ethoxy-7-methoxy-N-(piperidin-4-yl)-1,2,3,4-tetrahydroacridin-9-amine |
| 95 | 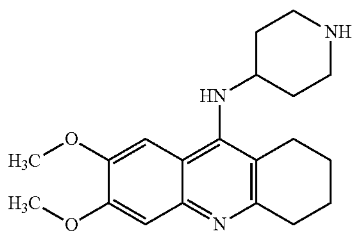 [SMILES: COc1cc2nc3c(c(NC4CCNCC4)c2cc1OC)CCCC3] | 6,7-dimethoxy-N-(piperidin-4-yl)-1,2,3,4-tetrahydroacridin-9-amine |
| 96 | 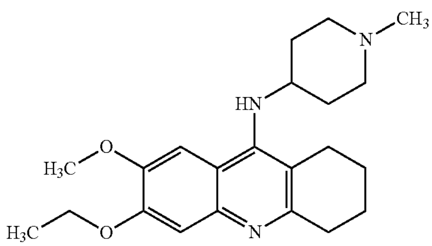 [SMILES: CCOc1cc2nc3c(c(NC4CCN(C)CC4)c2cc1OC)CCCC3] | 6-ethoxy-7-methoxy-N-(1-methylpiperidin-4-yl)-1,2,3,4-tetrahydroacridin-9-amine |
| 97 | 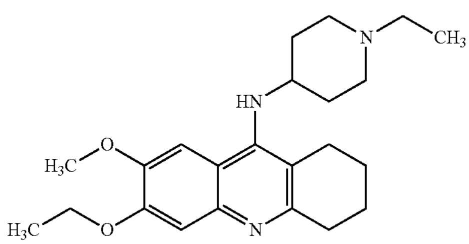 [SMILES: CCOc1cc2nc3c(c(NC4CCN(CC)CC4)c2cc1OC)CCCC3] | 6-ethoxy-N-(1-ethylpiperidin-4-yl)-7-methoxy-1,2,3,4-tetrahydroacridin-9-amine |
| 98 | 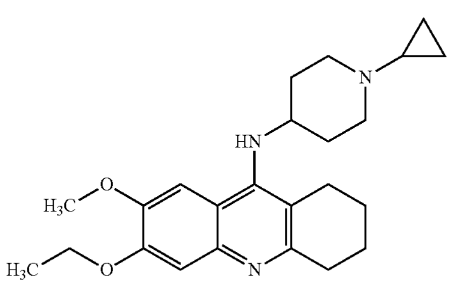 [SMILES: CCOc1cc2nc3c(c(NC4CCN(C5CC5)CC4)c2cc1OC)CCCC3] | N-(1-cyclopropylpiperidin-4-yl)-6-ethoxy-7-methoxy-1,2,3,4-tetrahydroacridin-9-amine |
| 99 | 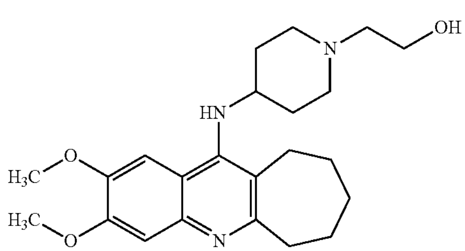 [SMILES: COc1cc2nc3c(c(NC4CCN(CCO)CC4)c2cc1OC)CCCCC3] | 2-[4-({2,3-dimethoxy-6H,7H,8H,9H,10H-cyclohepta[b]quinolin-11-yl}amino)piperidin-1-yl]ethan-1-ol |

| No. | Structure | IUPAC Name |
|---|---|---|
| 100 | 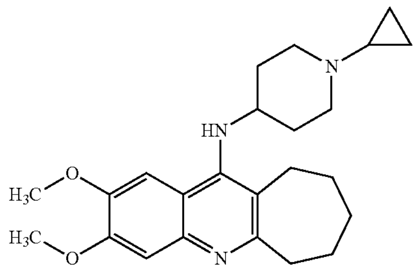 [SMILES: COc1cc2nc3c(c(NC4CCN(C5CC5)CC4)c2cc1OC)CCCCC3] | 1-cyclopropyl-N-{2,3-dimethoxy-6H,7H,8H,9H,10H-cyclohepta[b]quinolin-11-yl}piperidin-4-amine |
| 101 | 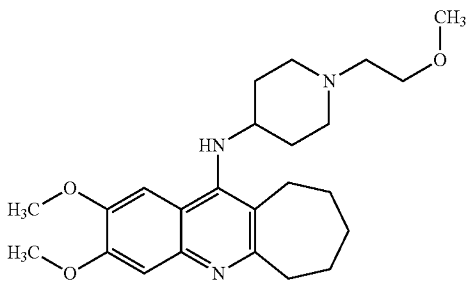 | N-{2,3-dimethoxy-6H,7H,8H,9H,10H-cyclohepta[b]quinolin-11-yl}-1-(2-methoxyethyl)piperidin-4-amine |
| 102 | 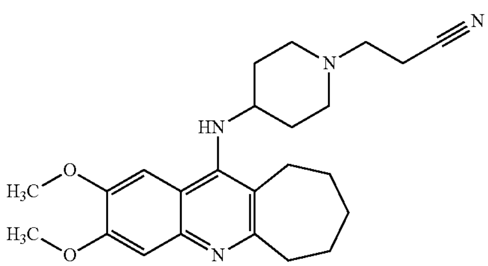 [SMILES: COc1cc2nc3c(c(NC4CCN(CCC#N)CC4)c2cc1OC)CCCCC3] | 3-[4-({2,3-dimethoxy-6H,7H,8H,9H,10H-cyclohepta[b]quinolin-11-yl}amino)piperidin-1-yl]propanenitrile |
| 103 | 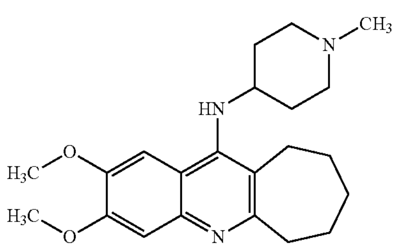 | N-{2,3-dimethoxy-6H,7H,8H,9H,10H-cyclohepta[b]quinolin-11-yl}-1-methylpiperidin-4-amine |
| 104 | 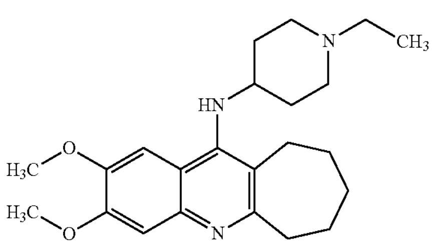 [SMILES: CCN1CCC(Nc2c3c(nc4cc(OC)c(OC)cc24)CCCCC3)CC1] | N-{2,3-dimethoxy-6H,7H,8H,9H,10H-cyclohepta[b]quinolin-11-yl}-1-ethylpiperidin-4-amine |
| 105 | 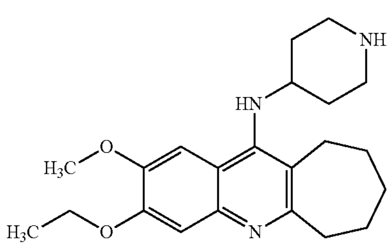 [SMILES: CCOc1cc2nc3c(c(NC4CCNCC4)c2cc1OC)CCCCC3] | N-{3-ethoxy-2-methoxy-6H,7H,8H,9H,10H-cyclohepta[b]quinolin-11-yl}piperidin-4-amine |

TABLE 2-continued

| No. | Structure | IUPAC Name |
|---|---|---|
| 106 | 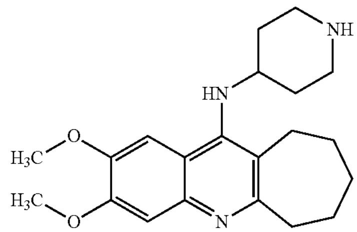 | N-{2,3-dimethoxy-6H,7H,8H,9H,10H-cyclohepta[b]quinolin-11-yl}piperidin-4-amine |
| 107 | 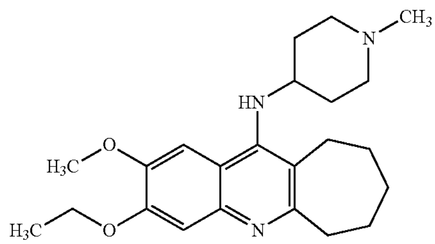 [SMILES: CCOc1cc2nc3c(c(NC4CCN(C)CC4)c2cc1OC)CCCCC3] | N-{3-ethoxy-2-methoxy-6H,7H,8H,9H,10H-cyclohepta[b]quinolin-11-yl}-1-methylpiperidin-4-amine |
| 108 | 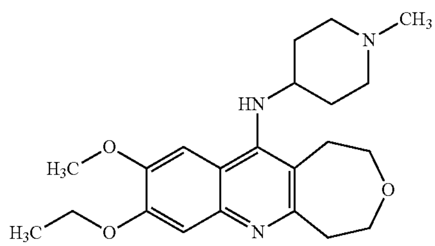 | N-{8-ethoxy-9-methoxy-1H,2H,4H,5H-oxepino[4,5-b]quinolin-11-yl}-1-methylpiperidin-4-amine |
| 109 | 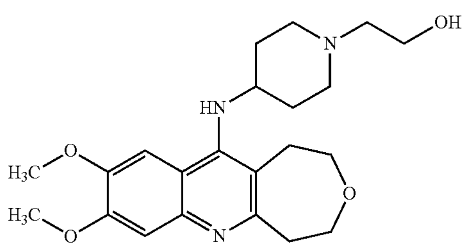 | 2-[4-({8,9-dimethoxy-1H,2H,4H,5H-oxepino[4,5-b]quinolin-11-yl}amino)piperidin-1-yl]ethan-1-ol |
| 110 | 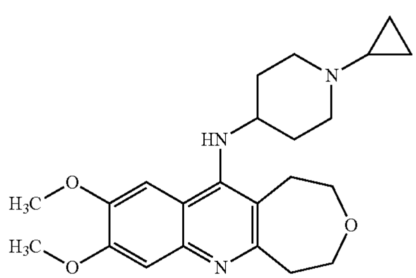 | 1-cyclopropyl-N-{8,9-dimethoxy-1H,2H,4H,5H-oxepino[4,5-b]quinolin-11-yl}piperidin-4-amine |
| 111 | 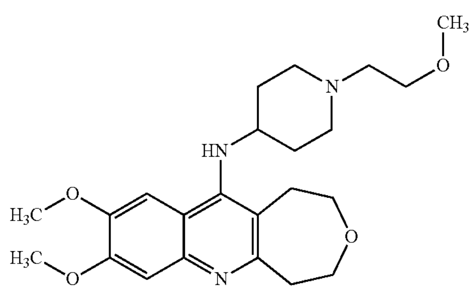 | N-{8,9-dimethoxy-1H,2H,4H,5H-oxepino[4,5-b]quinolin-11-yl}-1-(2-methoxyethyl)piperidin-4-amine |

TABLE 2-continued

| No. | Structure | IUPAC Name |
| --- | --- | --- |
| 112 | 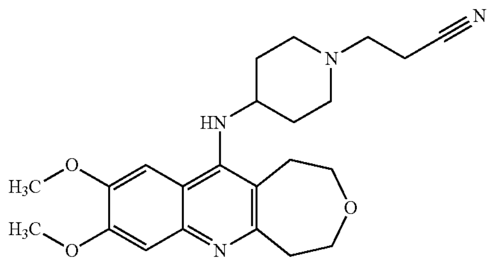 | 3-[4-({8,9-dimethoxy-1H,2H,4H,5H-oxepino[4,5-b]quinolin-11-yl}amino)piperidin-1-yl]propanenitrile |
| 113 | 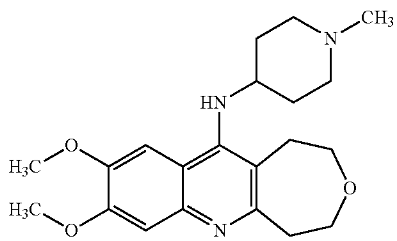 | N-{8,9-dimethoxy-1H,2H,4H,5H-oxepino[4,5-b]quinolin-11-yl}-1-methylpiperidin-4-amine |
| 114 | 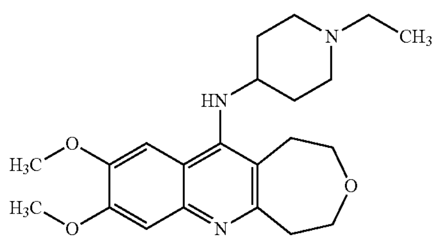 | N-{8,9-dimethoxy-1H,2H,4H,5H-oxepino[4,5-b]quinolin-11-yl}-1-ethylpiperidin-4-amine |
| 115 | 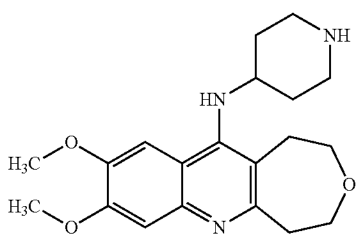 [SMILES: COc1cc2nc3c(c(NC4CCNCC4)c2cc1OC)CCOCC3] | N-{8,9-dimethoxy-1H,2H,4H,5H-oxepino[4,5-b]quinolin-11-yl}piperidin-4-amine |
| 116 | 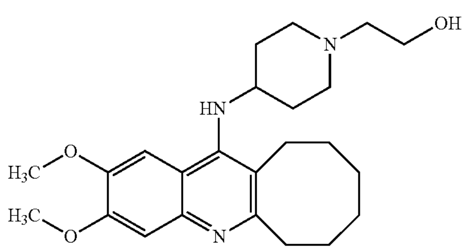 [SMILES: COc1cc2nc3c(c(NC4CCN(CCO)CC4)c2cc1OC)CCCCCC3] | 2-[4-({2,3-dimethoxy-6H,7H,8H,9H,10H,11H-cycloocta[b]quinolin-12-yl}amino)piperidin-1-yl]ethan-1-ol |
| 117 | 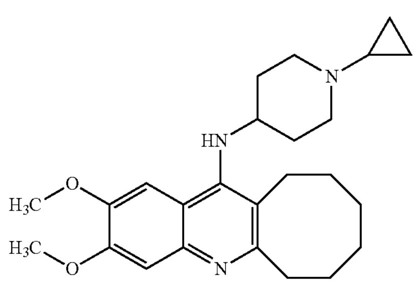 [SMILES: COc1cc2nc3c(c(NC4CCN(C5CC5)CC4)c2cc1OC)CCCCCC3] | 1-cyclopropyl-N-{2,3-dimethoxy-6H,7H,8H,9H,10H,11H-cycloocta[b]quinolin-12-yl}piperidin-4-amine |

TABLE 2-continued

| No. | Structure | IUPAC Name |
|---|---|---|
| 118 | 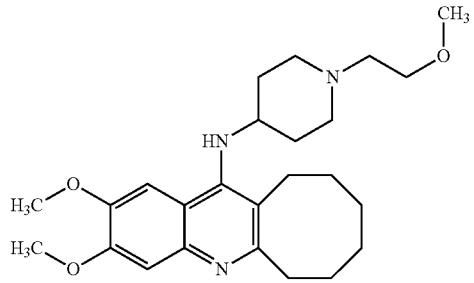 | N-{2,3-dimethoxy-6H,7H,8H,9H,10H,11H-cycloocta[b]quinolin-12-yl}-1-(2-methoxyethyl)piperidin-4-amine |
| 119 | 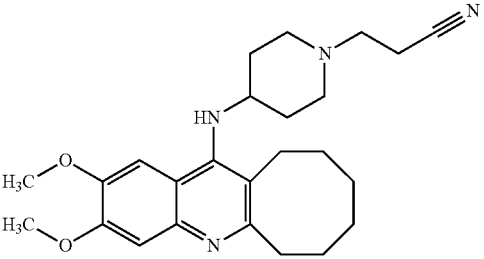 [SMILES: COc1cc2nc3c(c(NC4CCN(CCC#N)CC4)c2cc1OC)CCCCCC3] | 3-[4-({2,3-dimethoxy-6H,7H,8H,9H,10H,11H-cycloocta[b]quinolin-12-yl}amino)piperidin-1-yl]propanenitrile |
| 120 | 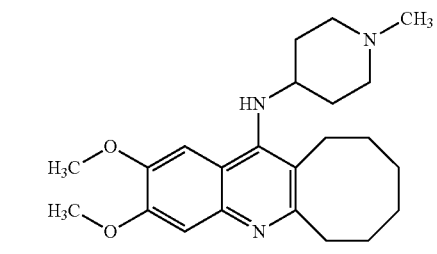 | N-{2,3-dimethoxy-6H,7H,8H,9H,10H,11H-cycloocta[b]quinolin-12-yl}-1-methylpiperidin-4-amine |
| 121 | 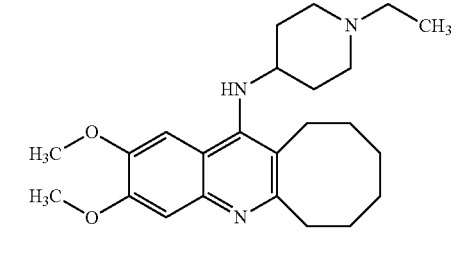 [SMILES: CCN1CCC(Nc2c3c(nc4cc(OC)c(OC)cc24)CCCCCC3)CC1] | N-{2,3-dimethoxy-6H,7H,8H,9H,10H,11H-cycloocta[b]quinolin-12-yl}-1-ethylpiperidin-4-amine |
| 122 | 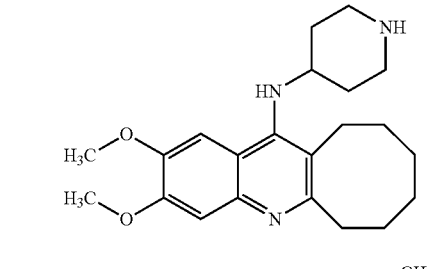 | N-{2,3-dimethoxy-6H,7H,8H,9H,10H,11H-cycloocta[b]quinolin-12-yl}piperidin-4-amine |
| 123 | 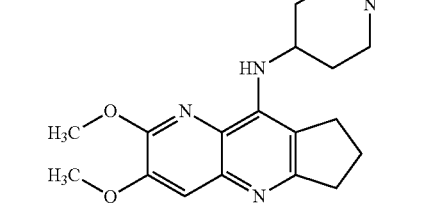 | N-{2,3-dimethoxy-6H,7H,8H-cyclopenta[b]1,5-naphthyridin-9-yl}-1-methylpiperidin-4-amine |

TABLE 2-continued

| No. | Structure | IUPAC Name |
|---|---|---|
| 124 | 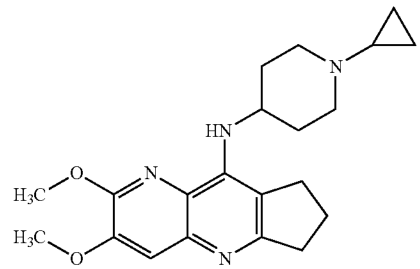 [SMILES: COc1cc2nc3c(c(NC4CCN(C5CC5)CC4)c2nc1OC)CCC3] | 1-cyclopropyl-N-{2,3-dimethoxy-6H,7H,8H-cyclopenta[b]1,5-naphthyridin-9-yl}piperidin-4-amine |
| 125 | 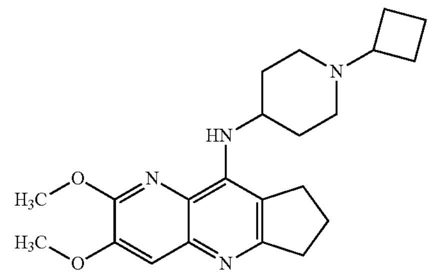 [SMILES: COc1cc2nc3c(c(NC4CCN(C5CCC5)CC4)c2nc1OC)CCC3] | 1-cyclobutyl-N-{2,3-dimethoxy-6H,7H,8H-cyclopenta[b]1,5-naphthyridin-9-yl}piperidin-4-amine |
| 126 | 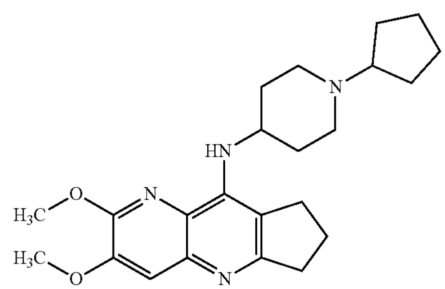 [SMILES: COc1cc2nc3c(c(NC4CCN(C5CCCC5)CC4)c2nc1OC)CCC3] | 1-cyclopentyl-N-{2,3-dimethoxy-6H,7H,8H-cyclopenta[b]1,5-naphthyridin-9-yl}piperidin-4-amine |
| 127 | 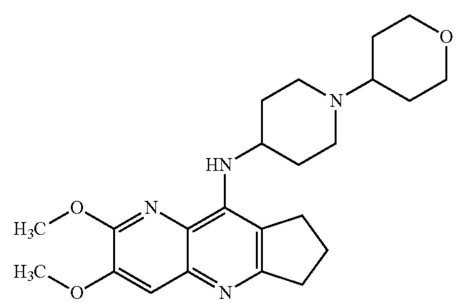 [SMILES: COc1cc2nc3c(c(NC4CCN(C5CCOCC5)CC4)c2nc1OC)CCC3] | N-{2,3-dimethoxy-6H,7H,8H-cyclopenta[b]1,5-naphthyridin-9-yl}-1-(oxan-4-yl)piperidin-4-amine |
| 128 | 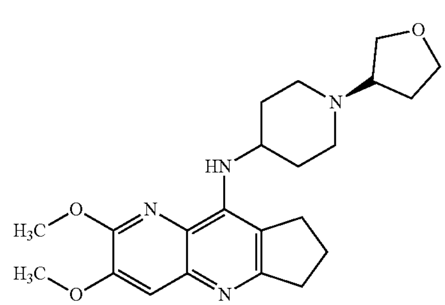 | N-{2,3-dimethoxy-6H,7H,8H-cyclopenta[b]1,5-naphthyridin-9-yl}-1-(oxolan-3-yl)piperidin-4-amine |

TABLE 2-continued

| No. | Structure | IUPAC Name |
| --- | --- | --- |
| 129 | 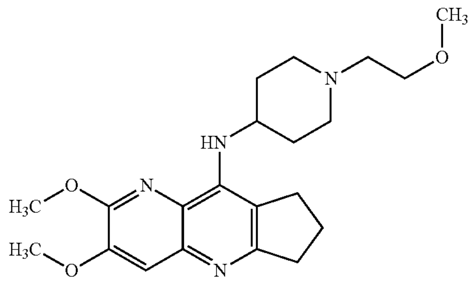 | N-{2,3-dimethoxy-6H,7H,8H-cyclopenta[b]1,5-naphthyridin-9-yl}-1-(2-methoxyethyl)piperidin-4-amine |
| 130 | 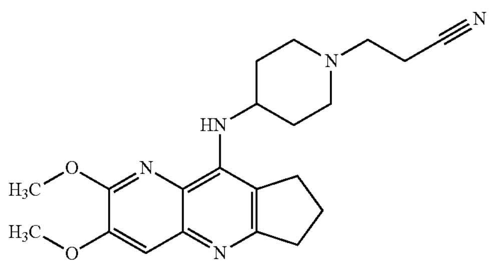 | 3-[4-({2,3-dimethoxy-6H,7H,8H-cyclopenta[b]1,5-naphthyridin-9-yl}amino)piperidin-1-yl]propanenitrile |
| 131 | 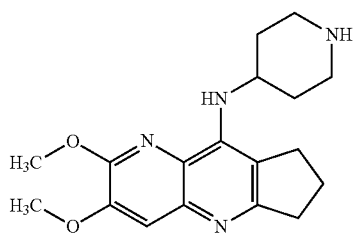 [SMILES: COc1cc2nc3c(c(NC4CCNCC4)c2nc1OC)CCC3] | N-{2,3-dimethoxy-6H,7H,8H-cyclopenta[b]1,5-naphthyridin-9-yl}piperidin-4-amine |
| 132 | 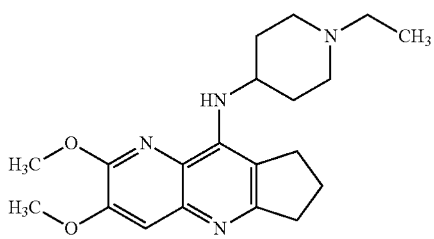 [SMILES: CCN1CCC(Nc2c3c(nc4cc(OC)c(OC)nc24)CCC3)CC1] | N-{2,3-dimethoxy-6H,7H,8H-cyclopenta[b]1,5-naphthyridin-9-yl}-1-ethylpiperidin-4-amine |
| 133 | 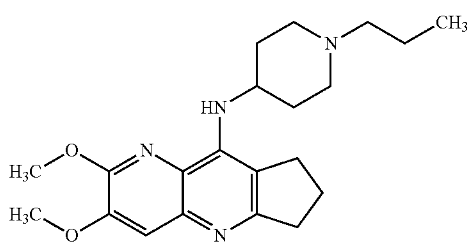 [SMILES: CCCN1CCC(Nc2c3c(nc4cc(OC)c(OC)nc24)CCC3)CC1] | N-{2,3-dimethoxy-6H,7H,8H-cyclopenta[b]1,5-naphthyridin-9-yl}-1-propylpiperidin-4-amine |
| 135 | 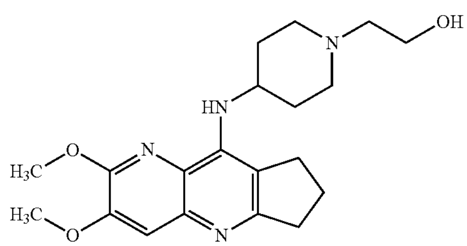 [SMILES: COc1cc2nc3c(c(NC4CCN(CCO)CC4)c2nc1OC)CCC3] | 2-[4-({2,3-dimethoxy-6H,7H,8H-cyclopenta[b]1,5-naphthyridin-9-yl}amino)piperidin-1-yl]ethan-1-ol |

TABLE 2-continued

| No. | Structure | IUPAC Name |
|---|---|---|
| 136 | 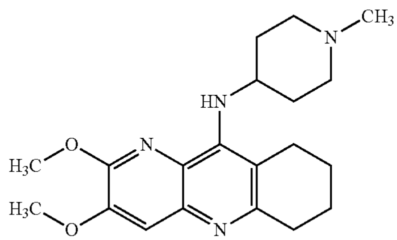 | N-{2,3-dimethoxy-6H,7H,8H,9H-cyclohexa[b]1,5-naphthyridin-10-yl}-1-methylpiperidin-4-amine |
| 137 | 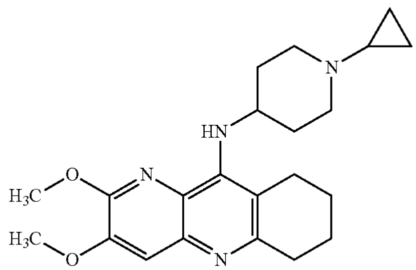 [SMILES: COc1cc2nc3c(c(NC4CCN(C5CC5)CC4)c2nc1OC)CCCC3] | 1-cyclopropyl-N-{2,3-dimethoxy-6H,7H,8H,9H-cyclohexa[b]1,5-naphthyridin-10-yl}piperidin-4-amine |
| 138 | 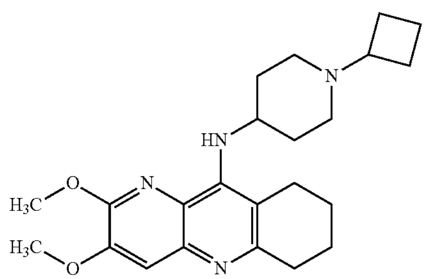 [SMILES: COc1cc2nc3c(c(NC4CCN(C5CCC5)CC4)c2nc1OC)CCCC3] | 1-cyclobutyl-N-{2,3-dimethoxy-6H,7H,8H,9H-cyclohexa[b]1,5-naphthyridin-10-yl}piperidin-4-amine |
| 139 | 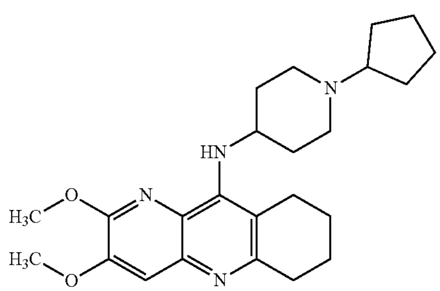 [SMILES: COc1cc2nc3c(c(NC4CCN(C5CCCC5)CC4)c2nc1OC)CCCC3] | 1-cyclopentyl-N-{2,3-dimethoxy-6H,7H,8H,9H-cyclohexa[b]1,5-naphthyridin-10-yl}piperidin-4-amine |
| 140 | 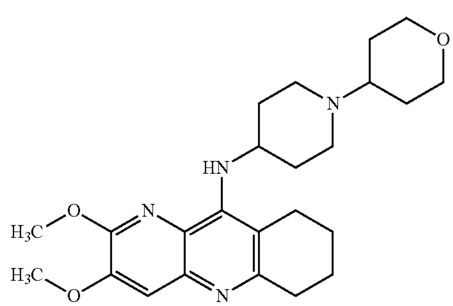 [SMILES: COc1cc2nc3c(c(NC4CCN(C5CCOCC5)CC4)c2nc1OC)CCCC3] | N-{2,3-dimethoxy-6H,7H,8H,9H-cyclohexa[b]1,5-naphthyridin-10-yl}-1-(oxan-4-yl)piperidin-4-amine |

TABLE 2-continued

| No. | Structure | IUPAC Name |
|-----|-----------|------------|
| 141 | 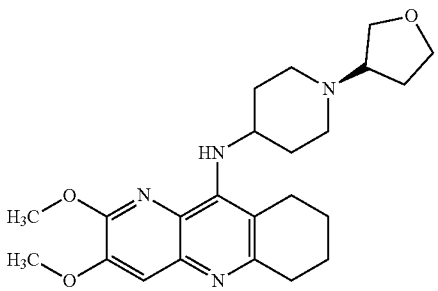 | N-{2,3-dimethoxy-6H,7H,8H,9H-cyclohexa[b]1,5-naphthyridin-10-yl}-1-(oxolan-3-yl)piperidin-4-amine |
| 142 | 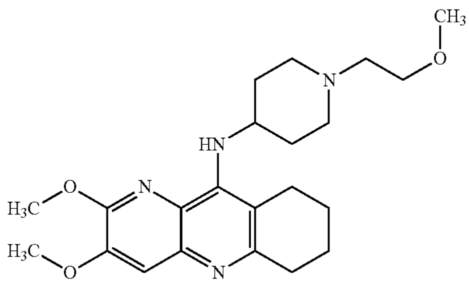 | N-{2,3-dimethoxy-6H,7H,8H,9H-cyclohexa[b]1,5-naphthyridin-10-yl}-1-(2-methoxyethyl)piperidin-4-amine |
| 143 | 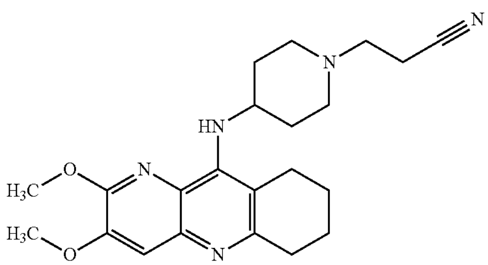 | 3-[4-({2,3-dimethoxy-6H,7H,8H,9H-cyclohexa[b]1,5-naphthyridin-10-yl}amino)piperidin-1-yl]propanenitrile |
| 144 | 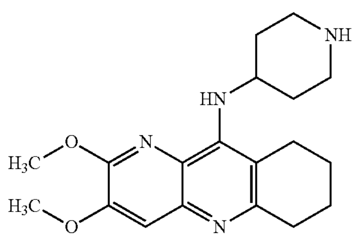 [SMILES: COc1cc2nc3c(c(NC4CCNCC4)c2nc1OC)CCCC3] | N-{2,3-dimethoxy-6H,7H,8H,9H-cyclohexa[b]1,5-naphthyridin-10-yl}piperidin-4-amine |
| 145 | 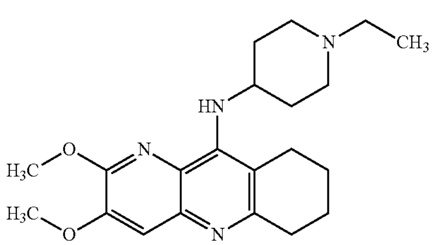 [SMILES: CCN1CCC(Nc2c3c(nc4cc(OC)c(OC)nc24)CCCC3)CC1] | N-{2,3-dimethoxy-6H,7H,8H,9H-cyclohexa[b]1,5-naphthyridin-10-yl}-1-ethylpiperidin-4-amine |
| 146 | 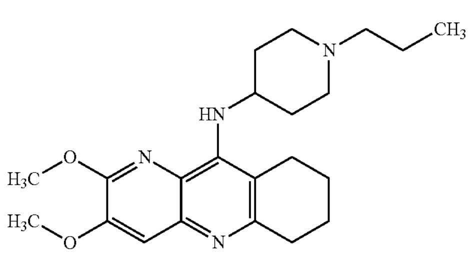 [SMILES: CCCN1CCC(Nc2c3c(nc4cc(OC)c(OC)nc24)CCCC3)CC1] | N-{2,3-dimethoxy-6H,7H,8H,9H-cyclohexa[b]1,5-naphthyridin-10-yl}-1-propylpiperidin-4-amine |

TABLE 2-continued

| No. | Structure | IUPAC Name |
|---|---|---|
| 147 | 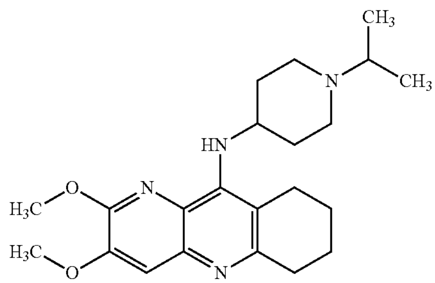 [SMILES: COc1cc2nc3c(c(NC4CCN(C(C)C)CC4)c2nc1OC)CCCC3] | N-{2,3-dimethoxy-6H,7H,8H,9H-cyclohexa[b]1,5-naphthyridin-10-yl}-1-(propan-2-yl)piperidin-4-amine |
| 148 | 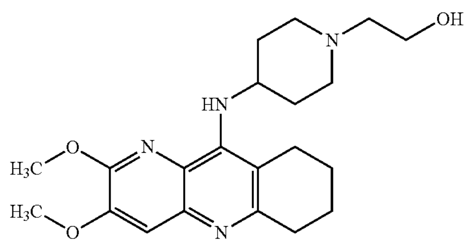 [SMILES: COc1cc2nc3c(c(NC4CCN(CCO)CC4)c2nc1OC)CCCC3] | 2-[4-({2,3-dimethoxy-6H,8H,9H-cyclohexa[b]1,5-naphthyridin-10-yl}amino)piperidin-1-yl]ethan-1-ol |
| 150 | 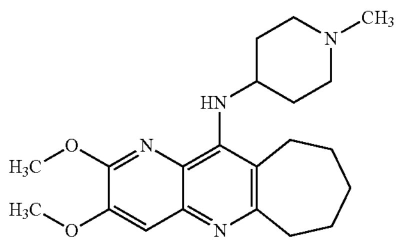 | N-{2,3-dimethoxy-6H,7H,8H,9H,10H-cyclohepta[b]1,5-naphthyridin-11-yl}-1-methylpiperidin-4-amine |
| 151 | 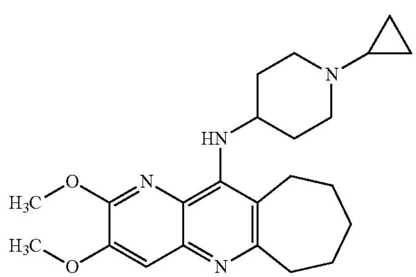 [SMILES: COc1cc2nc3c(c(NC4CCN(C5CC5)CC4)c2nc1OC)CCCCC3] | 1-cyclopropyl-N-{2,3-dimethoxy-6H,7H,8H,9H,10H-cyclohepta[b]1,5-naphthyridin-11-yl}piperidin-4-amine |
| 152 | 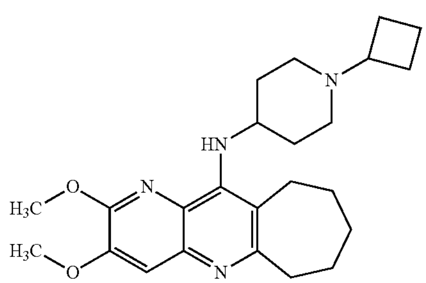 [SMILES: COc1cc2nc3c(c(NC4CCN(C5CCC5)CC4)c2nc1OC)CCCCC3] | 1-cyclobutyl-N-{2,3-dimethoxy-6H,7H,8H,9H,10H-cyclohepta[b]1,5-naphthyridin-11-yl}piperidin-4-amine |

TABLE 2-continued

| No. | Structure | IUPAC Name |
|---|---|---|
| 153 | 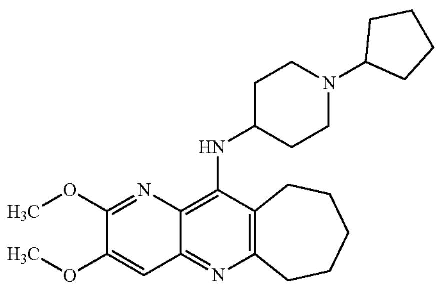 [SMILES: COc1cc2nc3c(c(NC4CCN(C5CCCC5)CC4)c2nc1OC)CCCCC3] | 1-cyclopentyl-N-{2,3-dimethoxy-6H,7H,8H,9H,10H-cyclohepta[b]1,5-naphthyridin-11-yl}piperidin-4-amine |
| 154 | 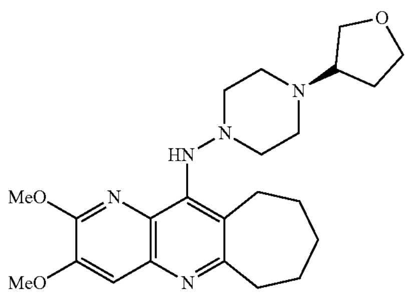 | N-{2,3-dimethoxy-6H,7H,8H,9H,10H-cyclohepta[b]1,5-naphthyridin-11-yl}-4-(oxolan-3-yl)piperazin-1-amine |
| 155 | 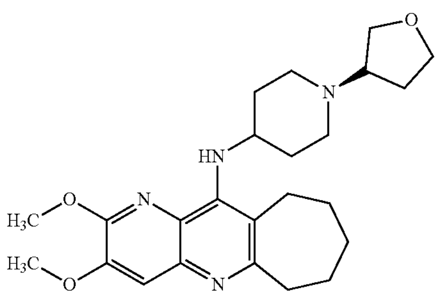 | N-{2,3-dimethoxy-6H,7H,8H,9H,10H-cyclohepta[b]1,5-naphthyridin-11-yl}-1-(oxolan-3-yl)piperidin-4-amine |
| 156 | 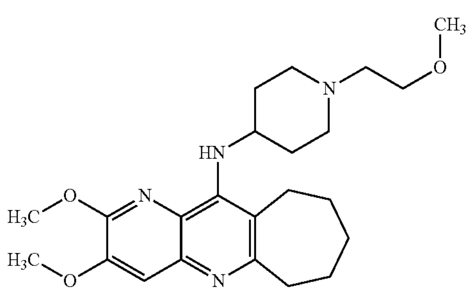 | N-{2,3-dimethoxy-6H,7H,8H,9H,10H-cyclohepta[b]1,5-naphthyridin-11-yl}-1-(2-methoxyethyl)piperidin-4-amine |
| 157 | 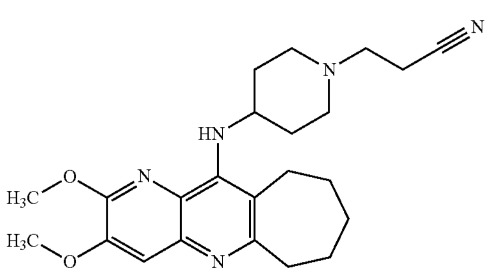 [SMILES: COc1cc2nc3c(c(NC4CCN(CCC#N)CC4)c2nc1OC)CCCCC3] | 3-[4-({2,3-dimethoxy-6H,7H,8H,9H,10H-cyclohepta[b]1,5-naphthyridin-11-yl}amino)piperidin-1-yl]propanenitrile |

TABLE 2-continued

| No. | Structure | IUPAC Name |
| --- | --- | --- |
| 158 | 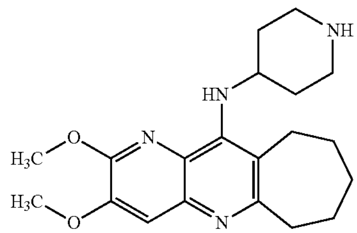 [SMILES: COc1cc2nc3c(c(NC4CCNCC4)c2nc1OC)CCCCC3] | N-{2,3-dimethoxy-6H,7H,8H,9H,10H-cyclohepta[b]1,5-naphthyridin-11-yl}piperidin-4-amine |
| 159 | 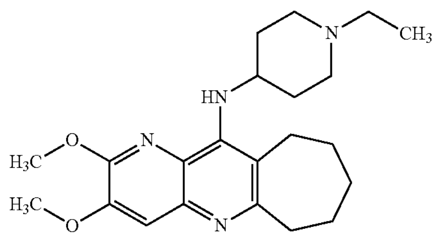 [SMILES: CCN1CCC(Nc2c3c(nc4cc(OC)c(OC)nc24)CCCCC3)CC1] | N-{2,3-dimethoxy-6H,7H,8H,9H,10H-cyclohepta[b]1,5-naphthyridin-11-yl}-1-ethylpiperidin-4-amine |
| 160 | 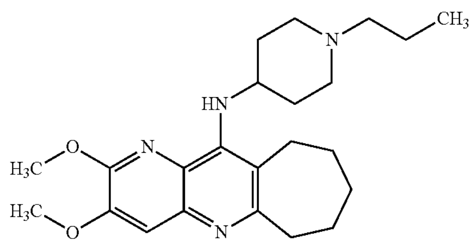 [SMILES: CCCN1CCC(Nc2c3c(nc4cc(OC)c(OC)nc24)CCCCC3)CC1] | N-{2,3-dimethoxy-6H,7H,8H,9H,10H-cyclohepta[b]1,5-naphthyridin-11-yl}-1-propylpiperidin-4-amine |
| 161 | 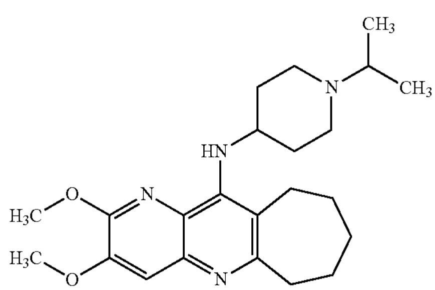 [SMILES: COc1cc2nc3c(c(NC4CCN(C(C)C)CC4)c2nc1OC)CCCCC3] | N-{2,3-dimethoxy-6H,7H,8H,9H,10H-cyclohepta[b]1,5-naphthyridin-11-yl}-1-(propan-2-yl)piperidin-4-amine |
| 162 | 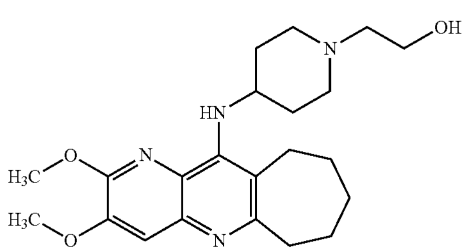 | 2-[4-({2,3-dimethoxy-6H,7H,8H,9H,10H-cyclohepta[b]1,5-naphthyridin-11-yl}amino)piperidin-1-yl]ethan-1-ol |
| 166 | 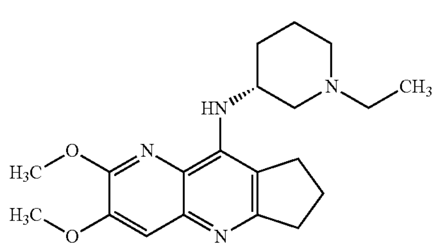 [SMILES: CCN1CCC[C@@H](Nc2c3c(nc4cc(OC)c(OC)nc24)CCC3)C1] | (3R)-N-{2,3-dimethoxy-6H,7H,8H-cyclopenta[b]1,5-naphthyridin-9-yl}-1-ethylpiperidin-3-amine |

TABLE 2-continued

| No. | Structure | IUPAC Name |
|---|---|---|
| 167 | 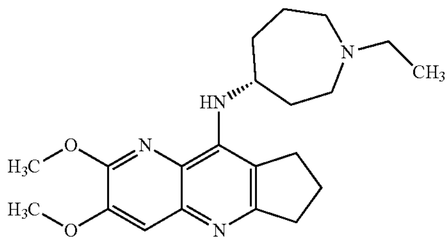 [SMILES: CCN1CCC[C@@H](Nc2c3c(nc4cc(OC)c(OC)nc24)CCC3)CC1] | (4R)-N-{2,3-dimethoxy-6H,7H,8H-cyclopenta[b]1,5-naphthyridin-9-yl}-1-ethylazepan-4-amine |
| 168 | 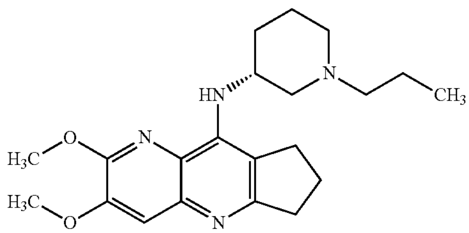 [SMILES: CCCN1CCC[C@@H](Nc2c3c(nc4cc(OC)c(OC)nc24)CCC3)C1] | (3R)-N-{2,3-dimethoxy-6H,7H,8H-cyclopenta[b]1,5-naphthyridin-9-yl}-1-propylpiperidin-3-amine |
| 169 | 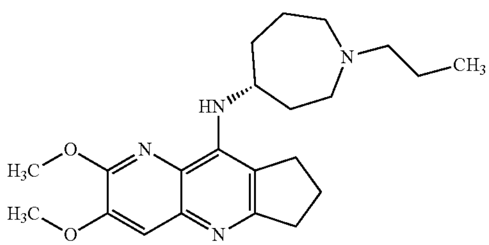 [SMILES: CCCN1CCC[C@@H](Nc2c3c(nc4cc(OC)c(OC)nc24)CCC3)CC1] | (4R)-N-{2,3-dimethoxy-6H,7H,8H-cyclopenta[b]1,5-naphthyridin-9-yl}-1-propylazepan-4-amine |
| 170 | 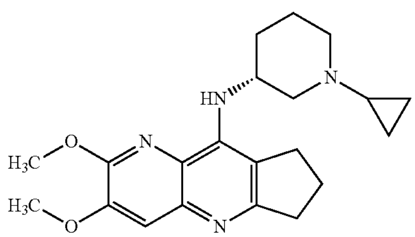 [SMILES: COc1cc2nc3c(c(N[C@@H]4CCCN(C5CC5)C4)c2nc1OC)CCC3] | (3R)-1-cyclopropyl-N-{2,3-dimethoxy-6H,7H,8H-cyclopenta[b]1,5-naphthyridin-9-yl}piperidin-3-amine |
| 171 | 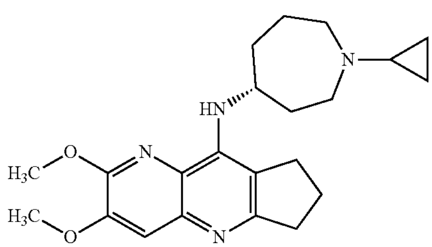 [SMILES: COc1cc2nc3c(c(N[C@@H]4CCCN(C5CC5)CC4)c2nc1OC)CCC3] | (4R)-1-cyclopropyl-N-{2,3-dimethoxy-6H,7H,8H-cyclopenta[b]1,5-naphthyridin-9-yl}azepan-4-amine |
| 172 | 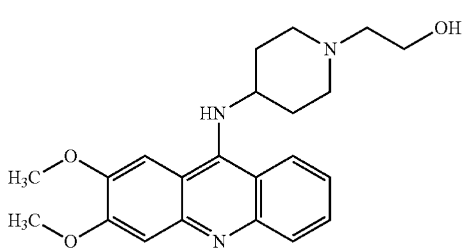 [SMILES: COc1cc2nc3ccccc3c(NC3CCN(CCO)CC3)c2cc1OC] | 2-{4-[(2,3-dimethoxyacridin-9-yl)amino]piperidin-1-yl}ethan-1-ol |

TABLE 2-continued
| No. | Structure | IUPAC Name |
|---|---|---|
| 173 | 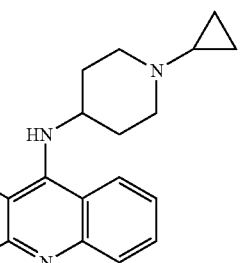 | N-(1-cyclopropylpiperidin-4-yl)-2,3-dimethoxyacridin-9-amine |
| 174 | 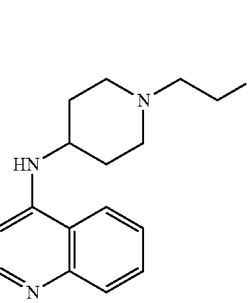 | 2,3-dimethoxy-N-[1-(2-methoxyethyl)piperidin-4-yl]acridin-9-amine |
| 175 | 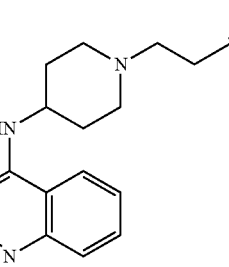 | 3-{4-[(2,3-dimethoxyacridin-9-yl)amino]piperidin-1-yl}propanenitrile |
| 176 | 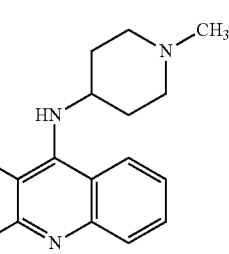 | 2,3-dimethoxy-N-(1-methylpiperidin-4-yl)acridin-9-amine |
| 177 | 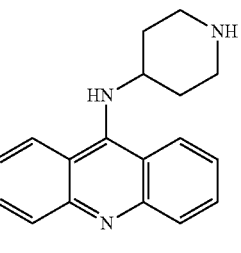 | 3-ethoxy-2-methoxy-N-(piperidin-4-yl)acridin-9-amine |
| 178 | 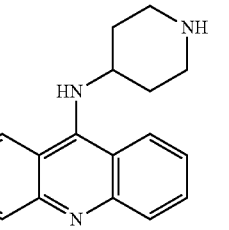 | 2,3-dimethoxy-N-(piperidin-4-yl)acridin-9-amine |

TABLE 2-continued

| No. | Structure | IUPAC Name |
|---|---|---|
| 179 | 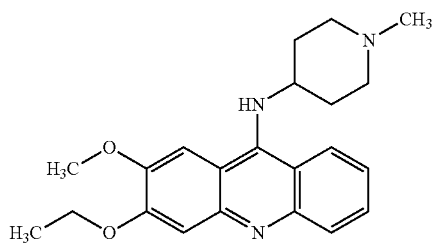 [SMILES: CCOc1cc2nc3ccccc3c(NC3CCN(C)CC3)c2cc1OC] | 3-ethoxy-2-methoxy-N-(1-methylpiperidin-4-yl)acridin-9-amine |
| 180 | 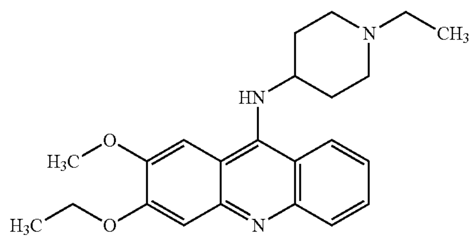 [SMILES: CCOc1cc2nc3ccccc3c(NC3CCN(CC)CC3)c2cc1OC] | 3-ethoxy-N-(1-ethylpiperidin-4-yl)-2-methoxyacridin-9-amine |
| 181 | 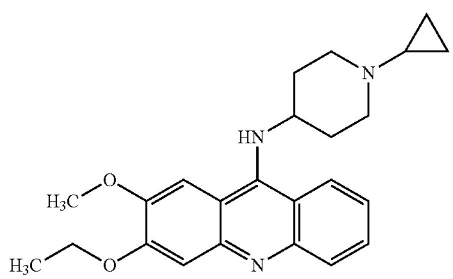 [SMILES: CCOc1cc2nc3ccccc3c(NC3CCN(C4CC4)CC3)c2cc1OC] | N-(1-cyclopropylpiperidin-4-yl)-3-ethoxy-2-methoxyacridin-9-amine |
| 182 | 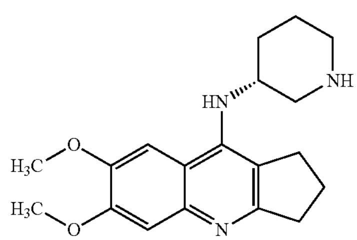 [SMILES: COc1cc2nc3c(c(N[C@@H]4CCCNC4)c2cc1OC)CCC3] | (3R)-N-{6,7-dimethoxy-1H,2H,3H-cyclopenta[b]quinolin-9-yl}piperidin-3-amine |
| 183 | 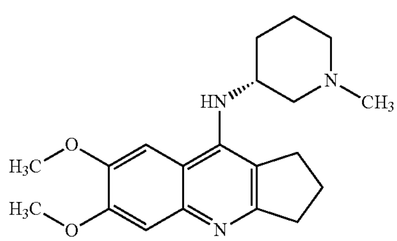 | (3R)-N-{6,7-dimethoxy-1H,2H,3H-cyclopenta[b]quinolin-9-yl}-1-methylpiperidin-3-amine |
| 184 | 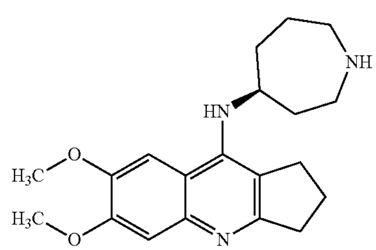 [SMILES: COc1cc2nc3c(c(N[C@H]4CCCNCC4)c2cc1OC)CCC3] | (4S)-N-{6,7-dimethoxy-1H,2H,3H-cyclopenta[b]quinolin-9-yl}azepan-4-amine |

TABLE 2-continued

| No. | Structure | IUPAC Name |
|---|---|---|
| 185 | 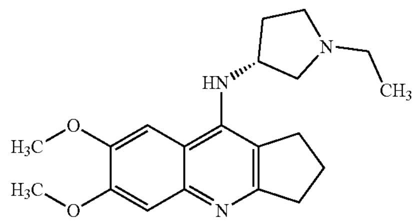 [SMILES: CCN1CC[C@@H](Nc2c3c(nc4cc(OC)c(OC)cc24)CCC3)C1] | (3R)-N-{6,7-dimethoxy-1H,2H,3H-cyclopenta[b]quinolin-9-yl}-1-ethylpyrrolidin-3-amine |
| 186 | 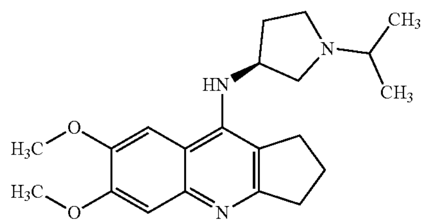 [SMILES: COc1cc2nc3c(c(N[C@H]4CCN(C(C)C)C4)c2cc1OC)CCC3] | (3S)-N-{6,7-dimethoxy-1H,2H,3H-cyclopenta[b]quinolin-9-yl}-1-(propan-2-yl)pyrrolidin-3-amine |
| 187 | 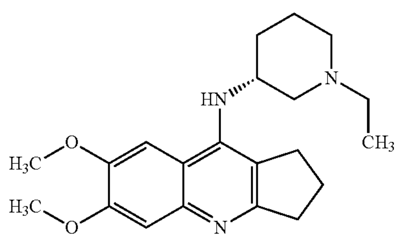 [SMILES: CCN1CCC[C@@H](Nc2c3c(nc4cc(OC)c(OC)cc24)CCC3)C1] | (3R)-N-{6,7-dimethoxy-1H,2H,3H-cyclopenta[b]quinolin-9-yl}-1-ethylpiperidin-3-amine |
| 188 | 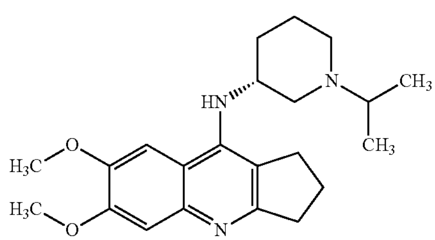 [SMILES: COc1cc2nc3c(c(N[C@@H]4CCCN(C(C)C)C4)c2cc1OC)CCC3] | (3R)-N-{6,7-dimethoxy-1H,2H,3H-cyclopenta[b]quinolin-9-yl}-1-(propan-2-yl)piperidin-3-amine |
| 189 | 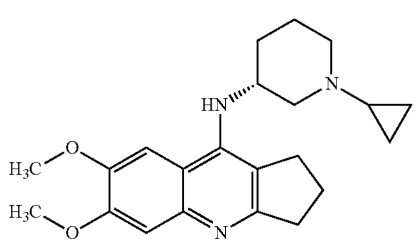 [SMILES: COc1cc2nc3c(c(N[C@@H]4CCCN(C5CC5)C4)c2cc1OC)CCC3] | (3R)-1-cyclopropyl-N-{6,7-dimethoxy-1H,2H,3H-cyclopenta[b]quinolin-9-yl}piperidin-3-amine |
| 190 | 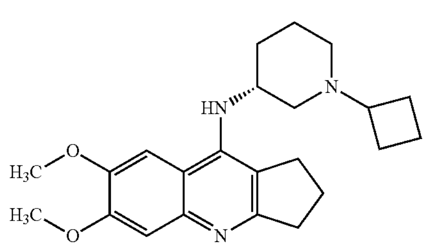 [SMILES: COc1cc2nc3c(c(N[C@@H]4CCCN(C5CCC5)C4)c2cc1OC)CCC3] | (3R)-1-cyclobutyl-N-{6,7-dimethoxy-1H,2H,3H-cyclopenta[b]quinolin-9-yl}piperidin-3-amine |

TABLE 2-continued

| No. | Structure | IUPAC Name |
|---|---|---|
| 191 | 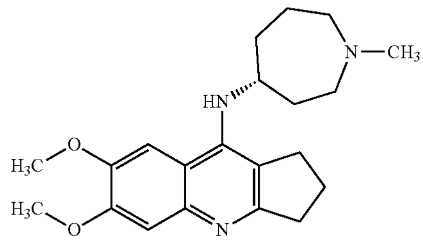 | (4R)-N-{6,7-dimethoxy-1H,2H,3H-cyclopenta[b]quinolin-9-yl}-1-methylazepan-4-amine |
| 192 | 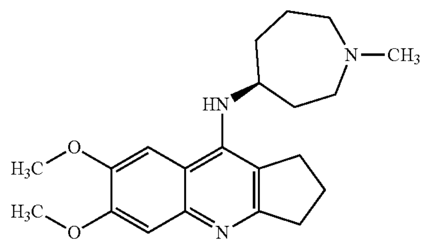 | (4S)-N-{6,7-dimethoxy-1H,2H,3H-cyclopenta[b]quinolin-9-yl}-1-methylazepan-4-amine |
| 193 | 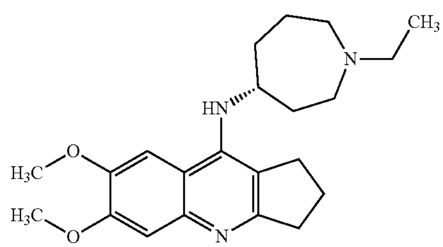 [SMILES: CCN1CCC[C@@H](Nc2c3c(nc4cc(OC)c(OC)cc24)CCC3)CC1] | (4R)-N-{6,7-dimethoxy-1H,2H,3H-cyclopenta[b]quinolin-9-yl}-1-ethylazepan-4-amine |
| 194 | 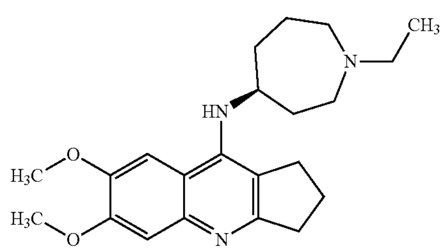 [SMILES: CCN1CCC[C@H](Nc2c3c(nc4cc(OC)c(OC)cc24)CCC3)CC1] | (4S)-N-{6,7-dimethoxy-1H,2H,3H-cyclopenta[b]quinolin-9-yl}-1-ethylazepan-4-amine |
| 195 | 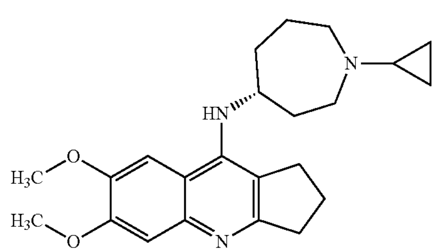 [SMILES: COc1cc2nc3c(c(N[C@@H]4CCCN(C5CC5)CC4)c2cc1OC)CCC3] | (4R)-1-cyclopropyl-N-{6,7-dimethoxy-1H,2H,3H-cyclopenta[b]quinolin-9-yl}azepan-4-amine |
| 196 | 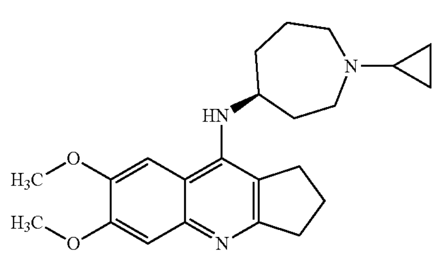 [SMILES: COc1cc2nc3c(c(N[C@H]4CCCN(C5CC5)CC4)c2cc1OC)CCC3] | (4S)-1-cyclopropyl-N-{6,7-dimethoxy-1H,2H,3H-cyclopenta[b]quinolin-9-yl}azepan-4-amine |

TABLE 2-continued

| No. | Structure | IUPAC Name |
| --- | --- | --- |
| 197 | 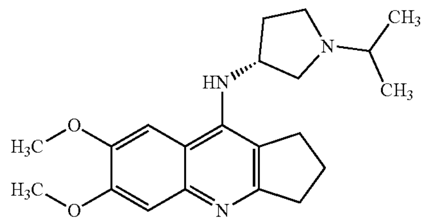 [SMILES: COc1cc2nc3c(c(N[C@@H]4CCN(C(C)C)C4)c2cc1OC)CCC3] | (3R)-N-{6,7-dimethoxy-1H,2H,3H-cyclopenta[b]quinolin-9-yl}-1-(propan-2-yl)pyrrolidin-3-amine |
| 198 | 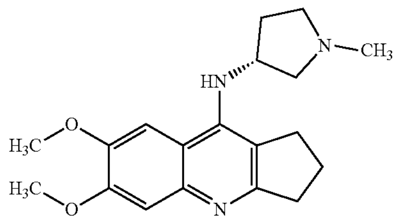 | (3R)-N-{6,7-dimethoxy-1H,2H,3H-cyclopenta[b]quinolin-9-yl}-1-methylpyrrolidin-3-amine |
| 199 | 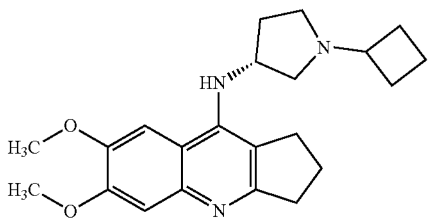 [SMILES: COc1cc2nc3c(c(N[C@@H]4CCN(C5CCC5)C4)c2cc1OC)CCC3] | (3R)-1-cyclobutyl-N-{6,7-dimethoxy-1H,2H,3H-cyclopenta[b]quinolin-9-yl}pyrrolidin-3-amine |
| 200 | 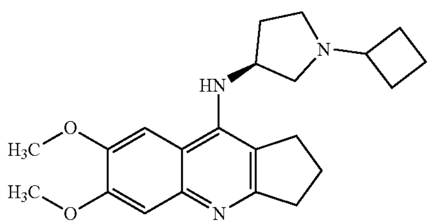 [SMILES: COc1cc2nc3c(c(N[C@H]4CCN(C5CCC5)C4)c2cc1OC)CCC3] | (3S)-1-cyclobutyl-N-{6,7-dimethoxy-1H,2H,3H-cyclopenta[b]quinolin-9-yl}pyrrolidin-3-amine |
| 201 | 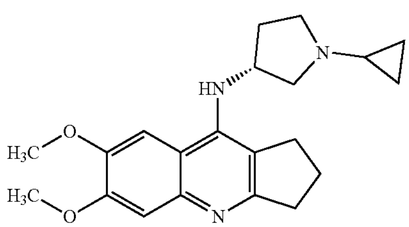 [SMILES: COc1cc2nc3c(c(N[C@@H]4CCN(C5CC5)C4)c2cc1OC)CCC3] | (3R)-1-cyclopropyl-N-{6,7-dimethoxy-1H,2H,3H-cyclopenta[b]quinolin-9-yl}pyrrolidin-3-amine |
| 202 | 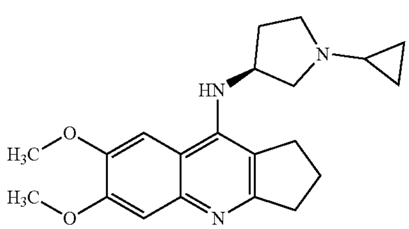 [SMILES: COc1cc2nc3c(c(N[C@H]4CCN(C5CC5)C4)c2cc1OC)CCC3] | (3S)-1-cyclopropyl-N-{6,7-dimethoxy-1H,2H,3H-cyclopenta[b]quinolin-9-yl}pyrrolidin-3-amine |
| 203 | 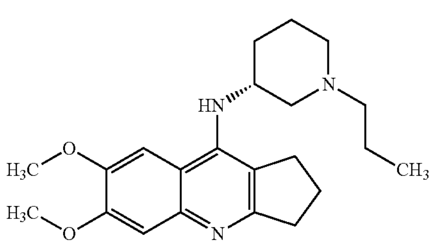 [SMILES: CCCN1CCC[C@@H](Nc2c3c(nc4cc(OC)c(OC)cc24)CCC3)C1] | (3R)-N-{6,7-dimethoxy-1H,2H,3H-cyclopenta[b]quinolin-9-yl}-1-propylpiperidin-3-amine |

TABLE 2-continued

| No. | Structure | IUPAC Name |
|---|---|---|
| 204 | 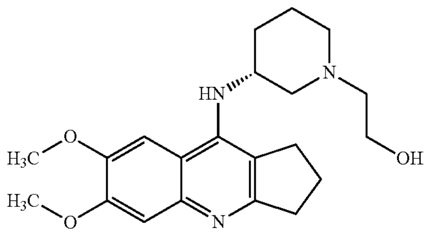 [SMILES: COc1cc2nc3c(c(N[C@@H]4CCCN(CCO)C4)c2cc1OC)CCC3] | 2-[(3R)-3-({6,7-dimethoxy-1H,2H,3H-cyclopenta[b]quinolin-9-yl}amino)piperidin-1-yl]ethan-1-ol |
| 205 | 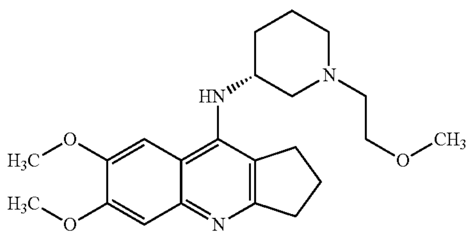 | (3R)-N-{6,7-dimethoxy-1H,2H,3H-cyclopenta[b]quinolin-9-yl}-1-(2-methoxyethyl)piperidin-3-amine |
| 206 | 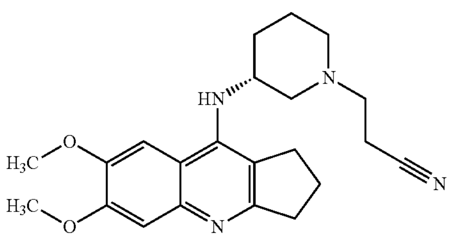 [SMILES: COc1cc2nc3c(c(N[C@@H]4CCCN(CCC#N)C4)c2cc1OC)CCC3] | 3-[(3R)-3-({6,7-dimethoxy-1H,2H,3H-cyclopenta[b]quinolin-9-yl}amino)piperidin-1-yl]propanenitrile |
| 207 | 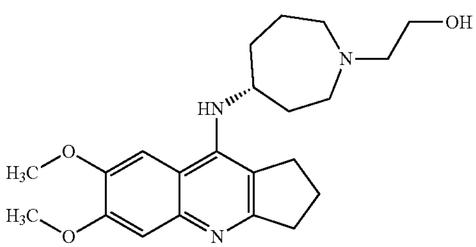 [SMILES: COc1cc2nc3c(c(N[C@@H]4CCCN(CCO)CC4)c2cc1OC)CCC3] | 2-[(4R)-4-({6,7-dimethoxy-1H,2H,3H-cyclopenta[b]quinolin-9-yl}amino)azepan-1-yl]ethan-1-ol |
| 208 | 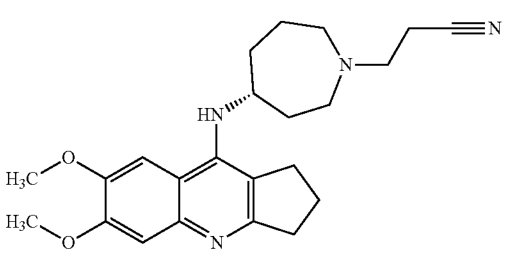 [SMILES: COc1cc2nc3c(c(N[C@@H]4CCCN(CCC#N)CC4)c2cc1OC)CCC3] | 3-[(4R)-4-({6,7-dimethoxy-1H,2H,3H-cyclopenta[b]quinolin-9-yl}amino)azepan-1-yl]propanenitrile |
| 209 | 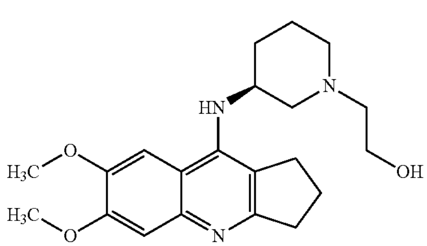 [SMILES: COc1cc2nc3c(c(N[C@H]4CCCN(CCO)C4)c2cc1OC)CCC3] | 2-[(3S)-3-({6,7-dimethoxy-1H,2H,3H-cyclopenta[b]quinolin-9-yl}amino)piperidin-1-yl]ethan-1-ol |

TABLE 2-continued

| No. | Structure | IUPAC Name |
|---|---|---|
| 210 | 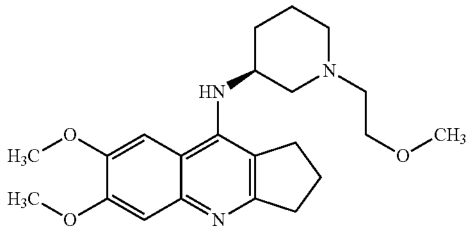 | (3S)-N-{6,7-dimethoxy-1H,2H,3H-cyclopenta[b]quinolin-9-yl}-1-(2-methoxyethyl)piperidin-3-amine |
| 211 | 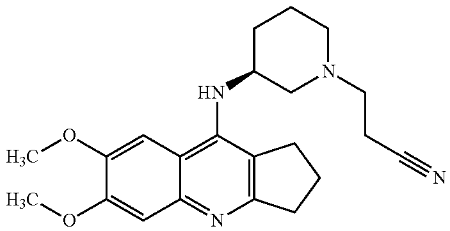 [SMILES: COc1cc2nc3c(c(N[C@H]4CCCN(CCC#N)C4)c2cc1OC)CCC3] | 3-[(3S)-3-({6,7-dimethoxy-1H,2H,3H-cyclopenta[b]quinolin-9-yl}amino)piperidin-1-yl]propanenitrile |
| 212 | 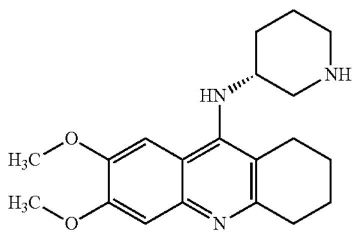 [SMILES: COc1cc2nc3c(c(N[C@@H]4CCCNC4)c2cc1OC)CCCC3] | 6,7-dimethoxy-N-[(3R)-piperidin-3-yl]-1,2,3,4-tetrahydroacridin-9-amine |
| 213 | 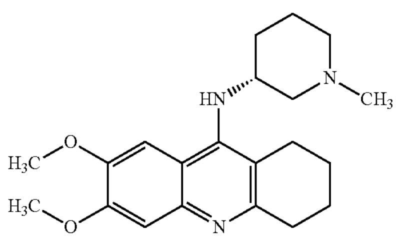 | 6,7-dimethoxy-N-[(3R)-1-methylpiperidin-3-yl]-1,2,3,4-tetrahydroacridin-9-amine |
| 214 | 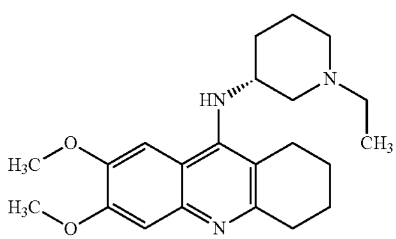 [SMILES: CCN1CCC[C@@H](Nc2c3c(nc4cc(OC)c(OC)cc24)CCCC3)C1] | N-[(3R)-1-ethylpiperidin-3-yl]-6,7-dimethoxy-1,2,3,4-tetrahydroacridin-9-amine |
| 215 | 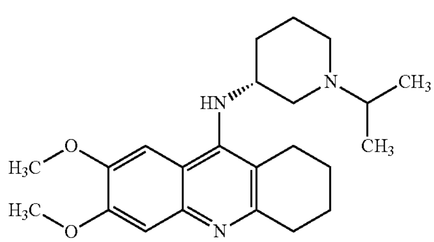 [SMILES: COc1cc2nc3c(c(N[C@@H]4CCCN(C(C)C)C4)c2cc1OC)CCCC3] | 6,7-dimethoxy-N-[(3R)-1-(propan-2-yl)piperidin-3-yl]-1,2,3,4-tetrahydroacridin-9-amine |

TABLE 2-continued

| No. | Structure | IUPAC Name |
| --- | --- | --- |
| 216 | 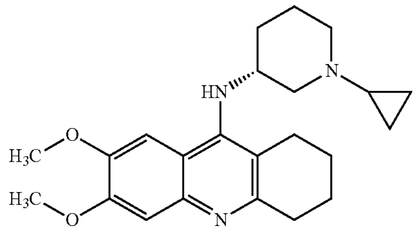 [SMILES: COc1cc2nc3c(c(N[C@@H]4CCCN(C5CC5)C4)c2cc1OC)CCCC3] | N-[(3R)-1-cyclopropylpiperidin-3-yl]-6,7-dimethoxy-1,2,3,4-tetrahydroacridin-9-amine |
| 217 | 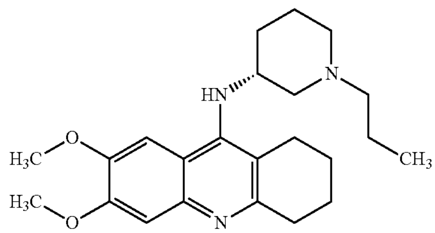 [SMILES: CCCN1CCC[C@@H](Nc2c3c(nc4cc(OC)c(OC)cc24)CCCC3)C1] | 6,7-dimethoxy-N-[(3R)-1-propylpiperidin-3-yl]-1,2,3,4-tetrahydroacridin-9-amine |
| 218 | 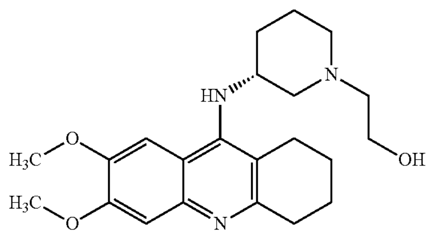 [SMILES: COc1cc2nc3c(c(N[C@@H]4CCCN(CCO)C4)c2cc1OC)CCCC3] | 2-[(3R)-3-[(6,7-dimethoxy-1,2,3,4-tetrahydroacridin-9-yl)amino]piperidin-1-yl]ethan-1-ol |
| 219 | 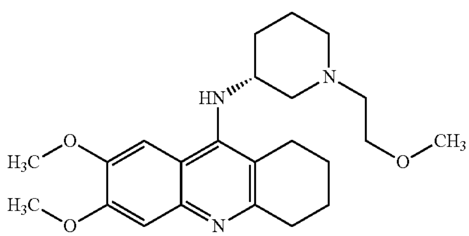 | 6,7-dimethoxy-N-[(3R)-1-(2-methoxyethyl)piperidin-3-yl]-1,2,3,4-tetrahydroacridin-9-amine |
| 220 | 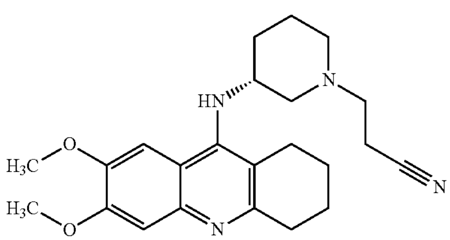 [SMILES: COc1cc2nc3c(c(N[C@@H]4CCCN(CCC#N)C4)c2cc1OC)CCCC3] | 3-[(3R)-3-[(6,7-dimethoxy-1,2,3,4-tetrahydroacridin-9-yl)amino]piperidin-1-yl]propanenitrile |
| 221 | 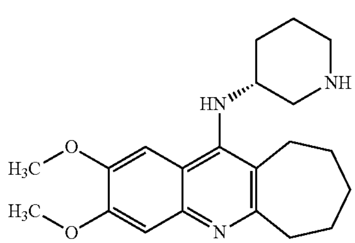 [SMILES: COc1cc2nc3c(c(N[C@@H]4CCCNC4)c2cc1OC)CCCCC3] | (3R)-N-{2,3-dimethoxy-6H,7H,8H,9H,10H-cyclohepta[b]quinolin-11-yl}piperidin-3-amine |

TABLE 2-continued

| No. | Structure | IUPAC Name |
|-----|-----------|------------|
| 222 | 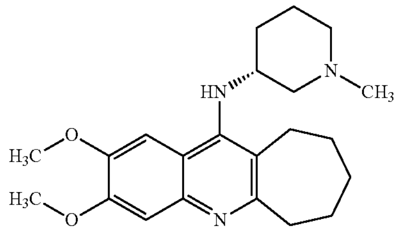 | (3R)-N-{2,3-dimethoxy-6H,7H,8H,9H,10H-cyclohepta[b]quinolin-11-yl}-1-methylpiperidin-3-amine |
| 223 | 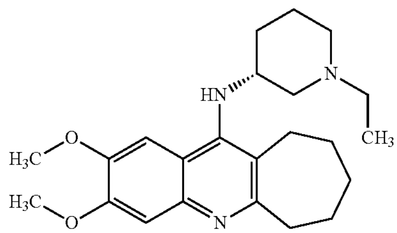 [SMILES: CCN1CCC[C@@H](Nc2c3c(nc4cc(OC)c(OC)cc24)CCCCC3)C1] | (3R)-N-{2,3-dimethoxy-6H,7H,8H,9H,10H-cyclohepta[b]quinolin-11-yl}-1-ethylpiperidin-3-amine |
| 224 | 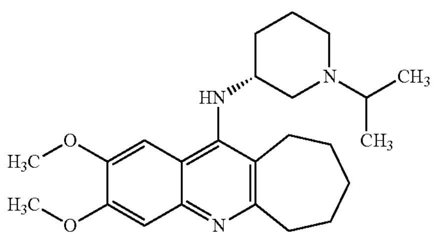 [SMILES: COc1cc2nc3c(c(N[C@@H]4CCCN(C(C)C)C4)c2cc1OC)CCCCC3] | (3R)-N-{2,3-dimethoxy-6H,7H,8H,9H,10H-cyclohepta[b]quinolin-11-yl}-1-(propan-2-yl)piperidin-3-amine |
| 225 | 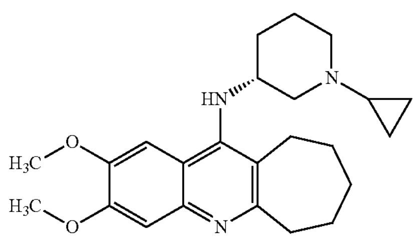 [SMILES: COc1cc2nc3c(c(N[C@@H]4CCCN(C5CC5)C4)c2cc1OC)CCCCC3] | (3R)-1-cyclopropyl-N-{2,3-dimethoxy-6H,7H,8H,9H,10H-cyclohepta[b]quinolin-11-yl}piperidin-3-amine |
| 226 | 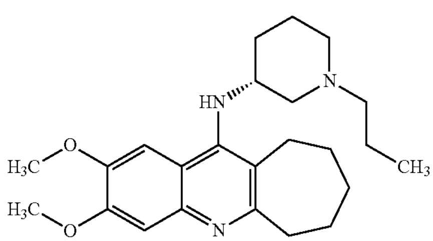 [SMILES: CCCN1CCC[C@@H](Nc2c3c(nc4cc(OC)c(OC)cc24)CCCCC3)C1] | (3R)-N-{2,3-dimethoxy-6H,7H,8H,9H,10H-cyclohepta[b]quinolin-11-yl}-1-propylpiperidin-3-amine |
| 228 | 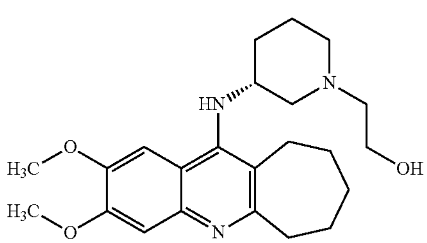 [SMILES: COc1cc2nc3c(c(N[C@@H]4CCCN(CCO)C4)c2cc1OC)CCCCC3] | 2-[(3R)-3-({2,3-dimethoxy-6H,7H,8H,9H,10H-cyclohepta[b]quinolin-11-yl}amino)piperidin-1-yl]ethan-1-ol |

| No. | Structure | IUPAC Name |
|---|---|---|
| 229 | 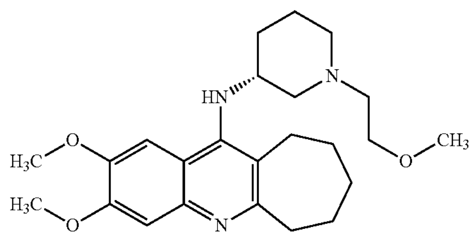 | (3R)-N-{2,3-dimethoxy-6H,7H,8H,9H,10H-cyclohepta[b]quinolin-11-yl}-1-(2-methoxyethyl)piperidin-3-amine |
| 230 | 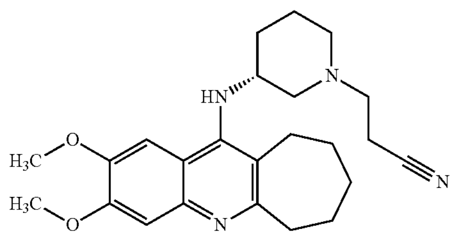 [SMILES: COc1cc2nc3c(c(N[C@@H]4CCCN(CCC#N)C4)c2cc1OC)CCCCC3] | 3-[(3R)-3-({2,3-dimethoxy-6H,7H,8H,9H,10H-cyclohepta[b]quinolin-11-yl}amino)piperidin-1-yl]propanenitrile |
| 231 | 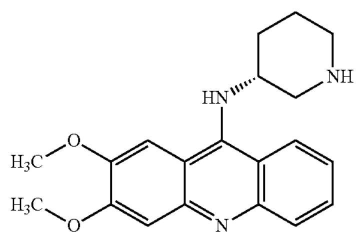 [SMILES: COc1cc2nc3ccccc3c(N[C@@H]3CCCNC3)c2cc1OC] | 2,3-dimethoxy-N-[(3R)-piperidin-3-yl]acridin-9-amine |
| 232 | 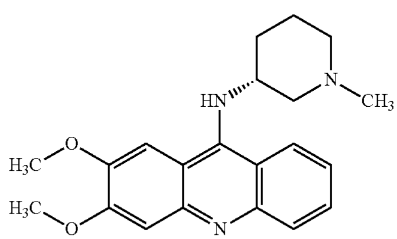 | 2,3-dimethoxy-N-[(3R)-1-methylpiperidin-3-yl]acridin-9-amine |
| 233 | 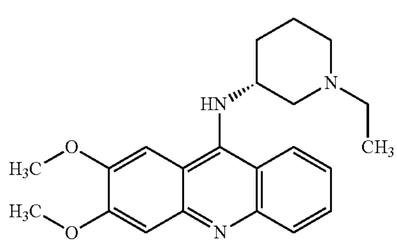 [SMILES: CCN1CCC[C@@H](Nc2c3ccccc3nc3cc(OC)c(OC)cc23)C1] | N-[(3R)-1-ethylpiperidin-3-yl]-2,3-dimethoxyacridin-9-amine |
| 234 | 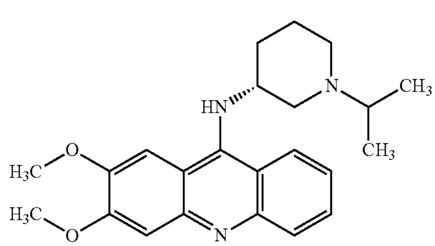 [SMILES: COc1cc2nc3ccccc3c(N[C@@H]3CCCN(C(C)C)C3)c2cc1OC] | 2,3-dimethoxy-N-[(3R)-1-(propan-2-yl)piperidin-3-yl]acridin-9-amine |

TABLE 2-continued

| No. | Structure | IUPAC Name |
| --- | --- | --- |
| 235 | 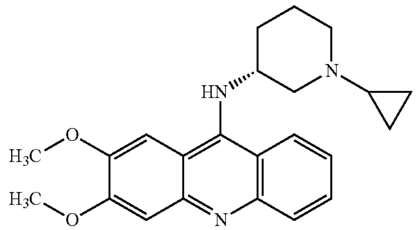 [SMILES: COc1cc2nc3ccccc3c(N[C@@H]3CCCN(C4CC4)C3)c2cc1OC] | N-[(3R)-1-cyclopropylpiperidin-3-yl]-2,3-dimethoxyacridin-9-amine |
| 236 | 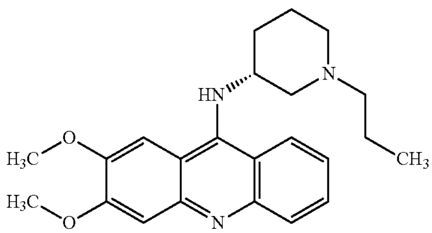 [SMILES: CCCN1CCC[C@@H](Nc2c3ccccc3nc3cc(OC)c(OC)cc23)C1] | 2,3-dimethoxy-N-[(3R)-1-propylpiperidin-3-yl]acridin-9-amine |
| 237 | 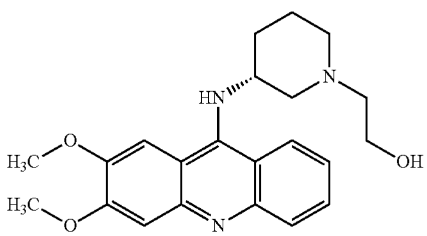 [SMILES: COc1cc2nc3ccccc3c(N[C@@H]3CCCN(CCO)C3)c2cc1OC] | 2-[(3R)-3-[(2,3-dimethoxyacridin-9-yl)amino]piperidin-1-yl]ethan-1-ol |
| 238 | 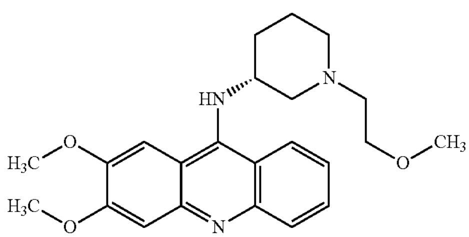 | 2,3-dimethoxy-N-[(3R)-1-(2-methoxyethyl)piperidin-3-yl]acridin-9-amine |
| 239 | 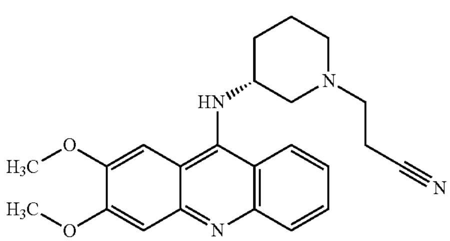 [SMILES: COc1cc2nc3ccccc3c(N[C@@H]3CCCN(CCC#N)C3)c2cc1OC] | 3-[(3R)-3-[(2,3-dimethoxyacridin-9-yl)amino]piperidin-1-yl]propanenitrile |
| 240 | 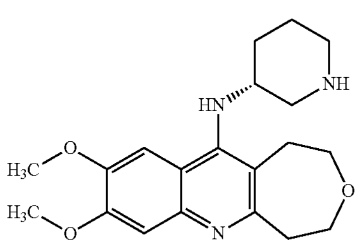 [SMILES: COc1cc2nc3c(c(N[C@@H]4CCCNC4)c2cc1OC)CCOCC3] | (3R)-N-{8,9-dimethoxy-1H,2H,4H,5H-oxepino[4,5-b]quinolin-11-yl}piperidin-3-amine |

TABLE 2-continued

| No. | Structure | IUPAC Name |
|---|---|---|
| 241 | 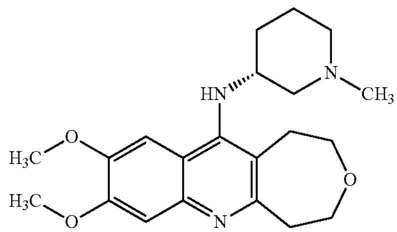 | (3R)-N-{8,9-dimethoxy-1H,2H,4H,5H-oxepino[4,5-b]quinolin-11-yl}-1-methylpiperidin-3-amine |
| 242 | 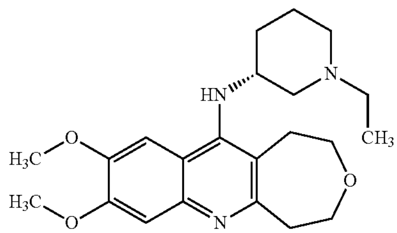 [SMILES: CCN1CCC[C@@H](Nc2c3c(nc4cc(OC)c(OC)cc24)CCOCC3)C1] | (3R)-N-{8,9-dimethoxy-1H,2H,4H,5H-oxepino[4,5-b]quinolin-11-yl}-1-ethylpiperidin-3-amine |
| 243 | 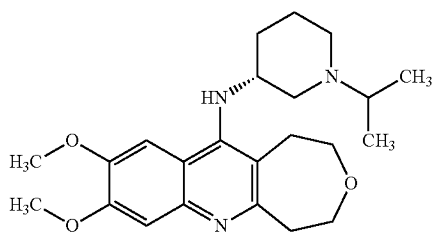 [SMILES: COc1cc2nc3c(c(N[C@@H]4CCCN(C(C)C)C4)c2cc1OC)CCOCC3] | (3R)-N-{8,9-dimethoxy-1H,2H,4H,5H-oxepino[4,5-b]quinolin-11-yl}-1-(propan-2-yl)piperidin-3-amine |
| 244 | 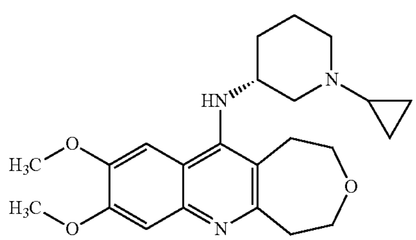 [SMILES: COc1cc2nc3c(c(N[C@@H]4CCCN(C5CC5)C4)c2cc1OC)CCOCC3] | (3R)-1-cyclopropyl-N-{8,9-dimethoxy-1H,2H,4H,5H-oxepino[4,5-b]quinolin-11-yl}piperidin-3-amine |
| 245 | 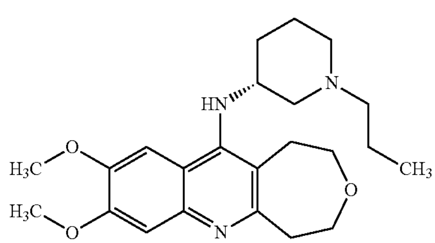 [SMILES: CCCN1CCC[C@@H](Nc2c3c(nc4cc(OC)c(OC)cc24)CCOCC3)C1] | (3R)-N-{8,9-dimethoxy-1H,2H,4H,5H-oxepino[4,5-b]quinolin-11-yl}-1-propylpiperidin-3-amine |
| 246 | 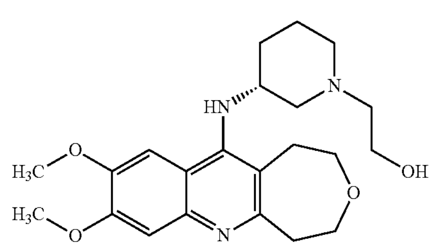 [SMILES: COc1cc2nc3c(c(N[C@@H]4CCCN(CCO)C4)c2cc1OC)CCOCC3] | 2-[(3R)-3-({8,9-dimethoxy-1H,2H,4H,5H-oxepino[4,5-b]quinolin-11-yl}amino)piperidin-1-yl]ethan-1-ol |

TABLE 2-continued

| No. | Structure | IUPAC Name |
|---|---|---|
| 247 | 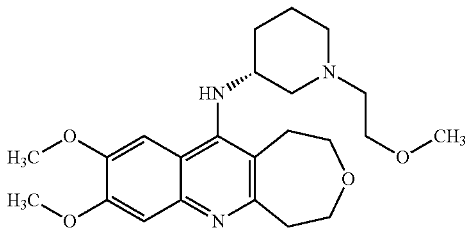 | (3R)-N-{8,9-dimethoxy-1H,2H,4H,5H-oxepino[4,5-b]quinolin-11-yl}-1-(2-methoxyethyl)piperidin-3-amine |
| 248 | 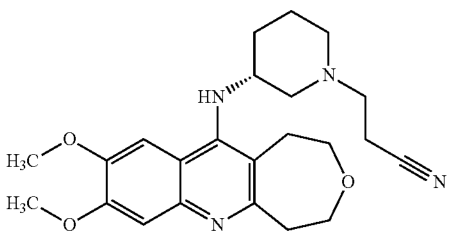 [SMILES: COc1cc2nc3c(c(N[C@@H]4CCCN(CCC#N)C4)c2cc1OC)CCOCC3] | 3-[(3R)-3-({8,9-dimethoxy-1H,2H,4H,5H-oxepino[4,5-b]quinolin-11-yl}amino)piperidin-1-yl]propanenitrile |
| 249 | 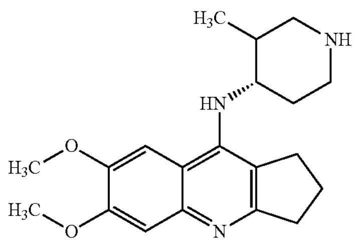 [SMILES: COc1cc2nc3c(c(N[C@H]4CCNCC4C)c2cc1OC)CCC3] | N-{6,7-dimethoxy-1H,2H,3H-cyclopenta[b]quinolin-9-yl}-3-methylpiperidin-4-amine |
| 250 | 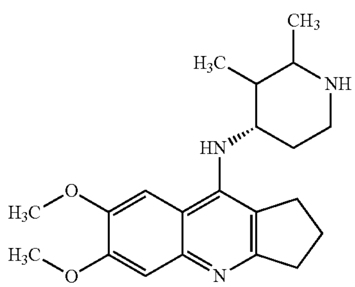 [SMILES: COc1cc2nc3c(c(N[C@H]4CCNC(C)C4C)c2cc1OC)CCC3] | N-{6,7-dimethoxy-1H,2H,3H-cyclopenta[b]quinolin-9-yl}-2,3-dimethylpiperidin-4-amine |
| 251 | 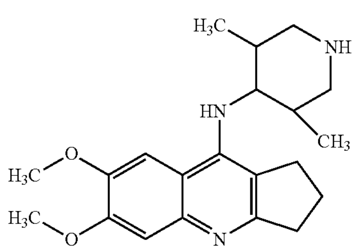 [SMILES: COc1cc2nc3c(c(NC4C(C)CNCC4C)c2cc1OC)CCC3] | N-{6,7-dimethoxy-1H,2H,3H-cyclopenta[b]quinolin-9-yl}-3,5-dimethylpiperidin-4-amine |
| 252 | 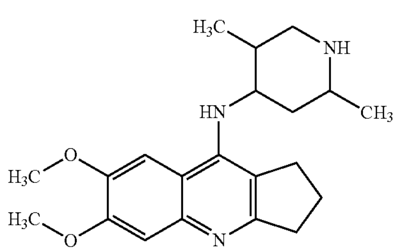 | N-{6,7-dimethoxy-1H,2H,3H-cyclopenta[b]quinolin-9-yl}-2,5-dimethylpiperidin-4-amine |

TABLE 2-continued

| No. | Structure | IUPAC Name |
|---|---|---|
| 253 | 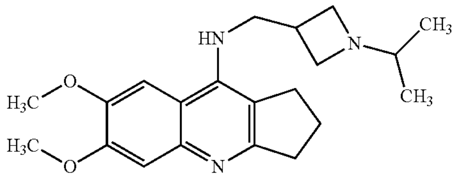 [SMILES: COc1cc2nc3c(c(NCC4CN(C(C)C)C4)c2cc1OC)CCC3] | 6,7-dimethoxy-N-{[1-(propan-2-yl)azetidin-3-yl]methyl}-1H,2H,3H-cyclopenta[b]quinolin-9-amine |
| 254 | 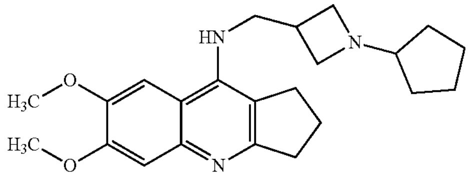 [SMILES: COc1cc2nc3c(c(NCC4CN(C5CCCC5)C4)c2cc1OC)CCC3] | N-[(1-cyclopentylazetidin-3-yl)methyl]-6,7-dimethoxy-1H,2H,3H-cyclopenta[b]quinolin-9-amine |
| 255 | 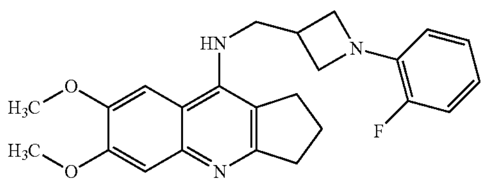 [SMILES: COc1cc2nc3c(c(NCC4CN(c5ccccc5F)C4)c2cc1OC)CCC3] | N-{[1-(2-fluorophenyl)azetidin-3-yl]methyl}-6,7-dimethoxy-1H,2H,3H-cyclopenta[b]quinolin-9-amine |
| 256 | 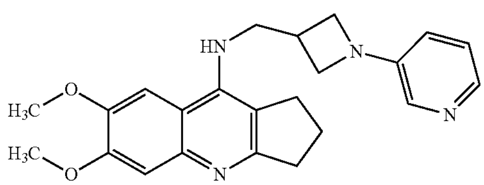 [SMILES: COc1cc2nc3c(c(NCC4CN(c5cccnc5)C4)c2cc1OC)CCC3] | 6,7-dimethoxy-N-{[1-(pyridin-3-yl)azetidin-3-yl]methyl}-1H,2H,3H-cyclopenta[b]quinolin-9-amine |
| 257 | 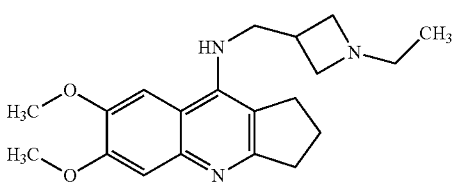 [SMILES: CCN1CC(CNc2c3c(nc4cc(OC)c(OC)cc24)CCC3)C1] | N-[(1-ethylazetidin-3-yl)methyl]-6,7-dimethoxy-1H,2H,3H-cyclopenta[b]quinolin-9-amine |
| 258 | 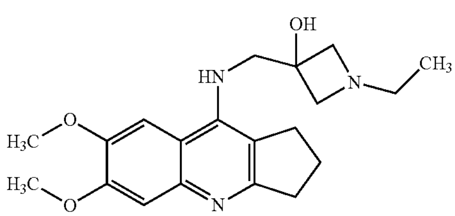 [SMILES: CCN1CC(O)(CNc2c3c(nc4cc(OC)c(OC)cc24)CCC3)C1] | 3-[({6,7-dimethoxy-1H,2H,3H-cyclopenta[b]quinolin-9-yl}amino)methyl]-1-ethylazetidin-3-ol |
| 259 | 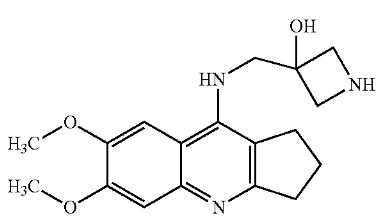 [SMILES: COc1cc2nc3c(c(NCC4(O)CNC4)c2cc1OC)CCC3] | 3-[({6,7-dimethoxy-1H,2H,3H-cyclopenta[b]quinolin-9-yl}amino)methyl]azetidin-3-ol |
| 260 | 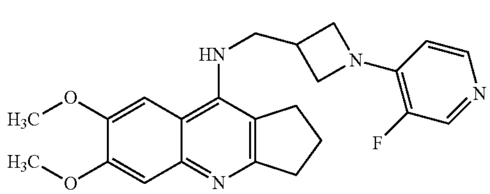 [SMILES: COc1cc2nc3c(c(NCC4CN(c5ccncc5F)C4)c2cc1OC)CCC3] | N-{[1-(3-fluoropyridin-4-yl)azetidin-3-yl]methyl}-6,7-dimethoxy-1H,2H,3H-cyclopenta[b]quinolin-9-amine |

TABLE 2-continued

| No. | Structure | IUPAC Name |
|---|---|---|
| 261 | 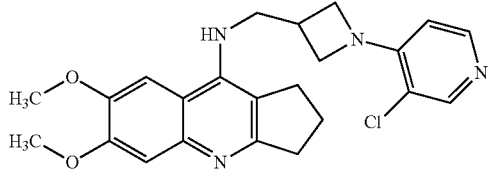 | N-{[1-(3-chloropyridin-4-yl)azetidin-3-yl]methyl}-6,7-dimethoxy-1H,2H,3H-cyclopenta[b]quinolin-9-amine |
| 262 | 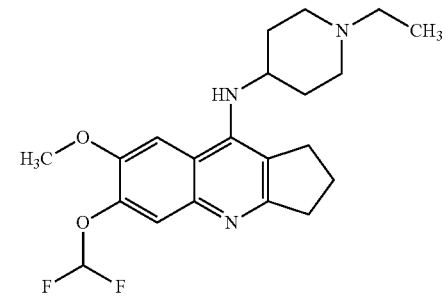 [SMILES: CCN1CCC(Nc2c3c(nc4cc(OC(F)F)c(OC)cc24)CCC3)CC1] | N-[6-(difluoromethoxy)-7-methoxy-1H,2H,3H-cyclopenta[b]quinolin-9-yl]-1-ethylpiperidin-4-amine |
| 263 | 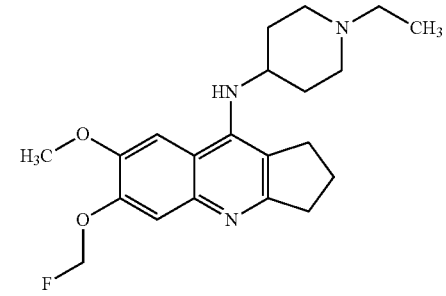 [SMILES: CCN1CCC(Nc2c3c(nc4cc(OCF)c(OC)cc24)CCC3)CC1] | 1-ethyl-N-[6-(fluoromethoxy)-7-methoxy-1H,2H,3H-cyclopenta[b]quinolin-9-yl]piperidin-4-amine |
| 264 | 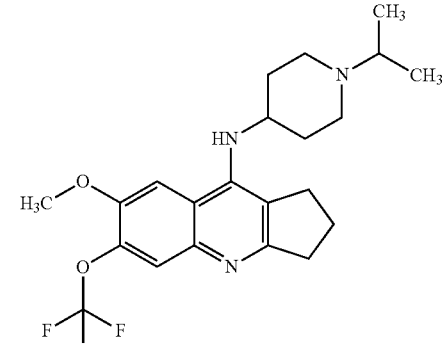 | N-[7-methoxy-6-(trifluoromethoxy)-1H,2H,3H-cyclopenta[b]quinolin-9-yl]-1-(propan-2-yl)piperidin-4-amine |
| 265 | 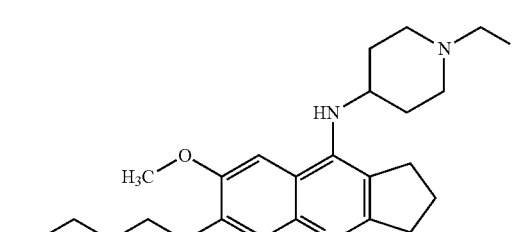 | 3-({9-[(1-ethylpiperidin-4-yl)amino]-7-methoxy-1H,2H,3H-cyclopenta[b]quinolin-6-yl}oxy)propan-1-ol |
| 266 | 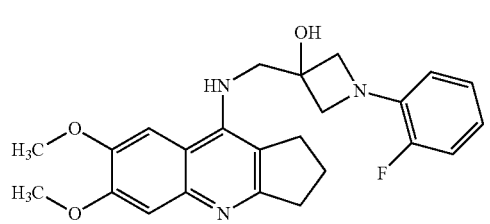 [SMILES: COc1cc2nc3c(c(NCC4(O)CN(c5ccccc5F)C4)c2cc1OC)CCC3] | 3-[({6,7-dimethoxy-1H,2H,3H-cyclopenta[b]quinolin-9-yl}amino)methyl]-1-(2-fluorophenyl)azetidin-3-ol |

TABLE 2-continued

| No. | Structure | IUPAC Name |
|---|---|---|
| 267 | 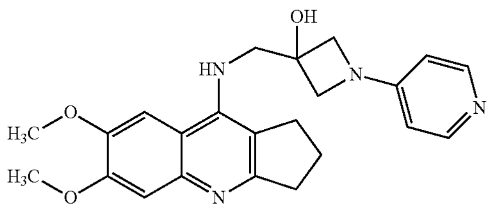 [SMILES: COc1cc2nc3c(c(NCC4(O)CN(c5ccncc5)C4)c2cc1OC)CCC3] | 3-[({6,7-dimethoxy-1H,2H,3H-cyclopenta[b]quinolin-9-yl}amino)methyl]-1-(pyridin-4-yl)azetidin-3-ol |
| 268 | 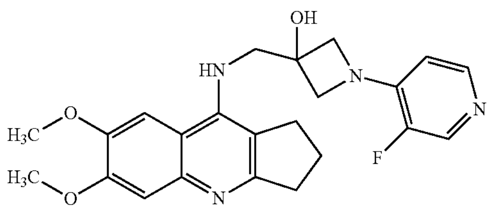 [SMILES: COc1cc2nc3c(c(NCC4(O)CN(c5ccncc5F)C4)c2cc1OC)CCC3] | 3-[({6,7-dimethoxy-1H,2H,3H-cyclopenta[b]quinolin-9-yl}amino)methyl]-1-(3-fluoropyridin-4-yl)azetidin-3-ol |
| 269 | 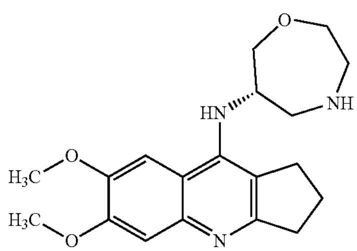 [SMILES: COc1cc2nc3c(c(N[C@H]4CNCCOC4)c2cc1OC)CCC3] | (6S)-N-{6,7-dimethoxy-1H,2H,3H-cyclopenta[b]quinolin-9-yl}-1,4-oxazepan-6-amine |
| 270 | 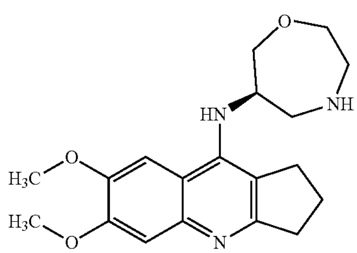 [SMILES: COc1cc2nc3c(c(N[C@@H]4CNCCOC4)c2cc1OC)CCC3] | (6R)-N-{6,7-dimethoxy-1H,2H,3H-cyclopenta[b]quinolin-9-yl}-1,4-oxazepan-6-amine |
| 271 | 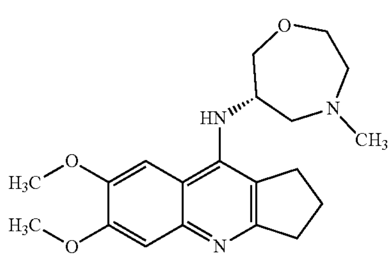 | (6S)-N-{6,7-dimethoxy-1H,2H,3H-cyclopenta[b]quinolin-9-yl}-4-methyl-1,4-oxazepan-6-amine |
| 272 | 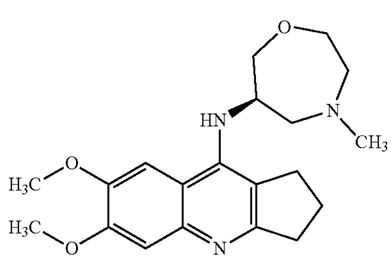 | (6R)-N-{6,7-dimethoxy-1H,2H,3H-cyclopenta[b]quinolin-9-yl}-4-methyl-1,4-oxazepan-6-amine |

TABLE 2-continued

| No. | Structure | IUPAC Name |
|---|---|---|
| 273 | 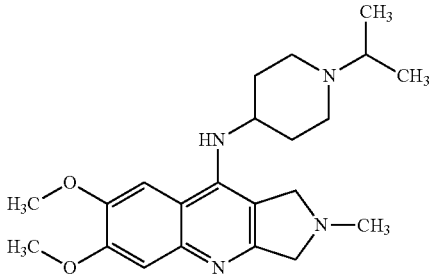 [SMILES: COc1cc2nc3c(c(NC4CCN(C(C)C)CC4)c2cc1OC)CN(C)C3] | 7-methoxy-N-methyl-9-[(1-methylpiperidin-4-yl)amino]-1H,2H,3H-cyclopenta[b]quinoline-6-sulfonamide |
| 274 | 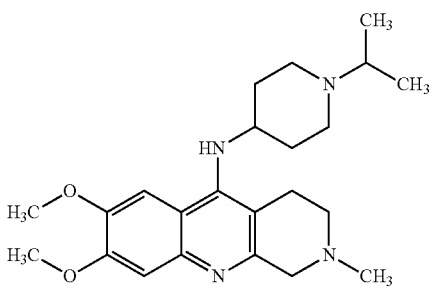 [SMILES: COc1cc2nc3c(c(NC4CCN(C(C)C)CC4)c2cc1OC)CCN(C)C3] | N-{6,7-dimethoxy-2-methyl-1H,2H,3H-pyrrolo[3,4-b]quinolin-9-yl}-1-(propan-2-yl)piperidin-4-amine |
| 275 | 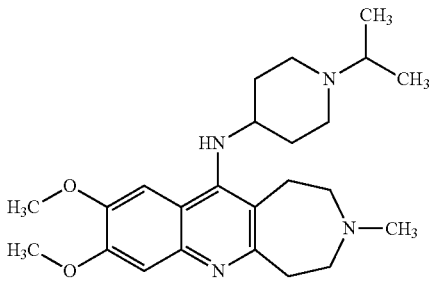 [SMILES: COc1cc2nc3c(c(NC4CCN(C(C)C)CC4)c2cc1OC)CCN(C)CC3] | N-{7,8-dimethoxy-2-methyl-1H,2H,3H,4H-benzo[b]1,7-naphthyridin-5-yl}-1-(propan-2-yl)piperidin-4-amine |
| 276 | 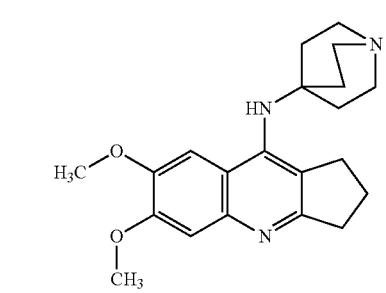 [SMILES: COc1cc2nc3c(c(NC45CCN(CC4)CC5)c2cc1OC)CCC3] | N-{6,7-dimethoxy-1H,2H,3H-cyclopenta[b]quinolin-9-yl}-1-azabicyclo[2.2.2]octan-4-amine |
| 277 | 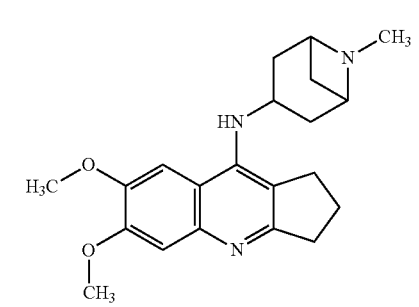 | N-{6,7-dimethoxy-1H,2H,3H-cyclopenta[b]quinolin-9-yl}-6-methyl-6-azabicyclo[3.1.1]heptan-3-amine |

TABLE 2-continued

| No. | Structure | IUPAC Name |
|---|---|---|
| 278 | 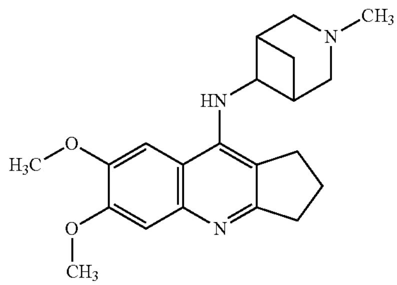 | N-{6,7-dimethoxy-1H,2H,3H-cyclopenta[b]quinolin-9-yl}-3-methyl-3-azabicyclo[3.1.1]heptan-6-amine |
| 279 | 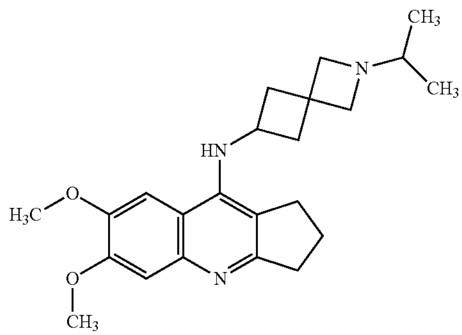 [SMILES: COc1cc2nc3c(c(NC4CC5(C4)CN(C(C)C)C5)c2cc1OC)CCC3] | N-{6,7-dimethoxy-1H,2H,3H-cyclopenta[b]quinolin-9-yl}-2-(propan-2-yl)-2-azaspiro[3.3]heptan-6-amine |
| 280 | 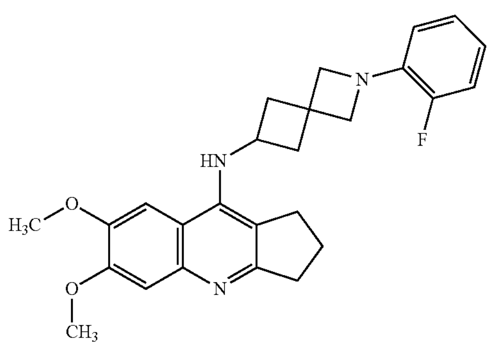 [SMILES: COc1cc2nc3c(c(NC4CC5(C4)CN(c4ccccc4F)C5)c2cc1OC)CCC3] | N-{6,7-dimethoxy-1H,2H,3H-cyclopenta[b]quinolin-9-yl}-2-(2-fluorophenyl)-2-azaspiro[3.3]heptan-6-amine |
| 281 | 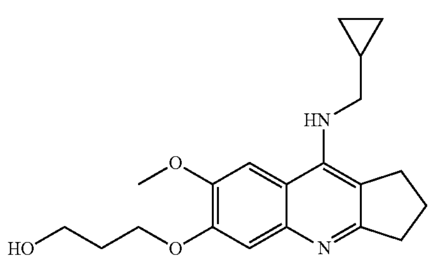 [SMILES: COc1cc2c(NCC3CC3)c3c(nc2cc1OCCCO)CCC3] | 3-({9-[(cyclopropylmethyl)amino]-7-methoxy-1H,2H,3H-cyclopenta[b]quinolin-6-yl}oxy)propan-1-ol |
| 282 | 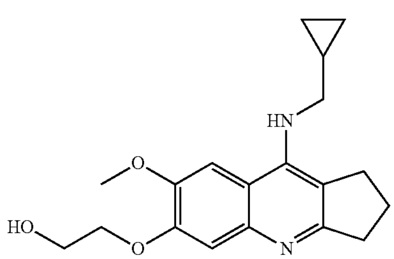 [SMILES: COc1cc2c(NCC3CC3)c3c(nc2cc1OCCO)CCC3] | 2-({9-[(cyclopropylmethyl)amino]-7-methoxy-1H,2H,3H-cyclopenta[b]quinolin-6-yl}oxy)ethan-1-ol |

TABLE 2-continued

| No. | Structure | IUPAC Name |
|---|---|---|
| 283 | 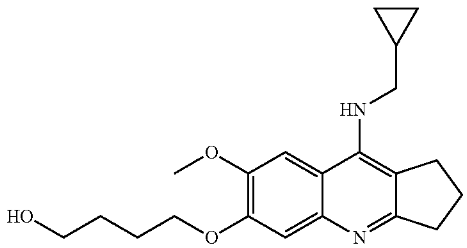 [SMILES: COc1cc2c(NCC3CC3)c3c(nc2cc1OCCCCO)CCC3] | 4-({9-[(cyclopropylmethyl)amino]-7-methoxy-1H,2H,3H-cyclopenta[b]quinolin-6-yl}oxy)butan-1-ol |
| 284 | 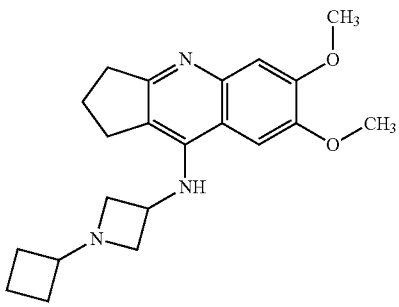 [SMILES: COc1cc2nc3c(c(NC4CN(C5CCC5)C4)c2cc1OC)CCC3] | 1-cyclobutyl-N-{6,7-dimethoxy-1H,2H,3H-cyclopenta[b]quinolin-9-yl}azetidin-3-amine |
| 285 | 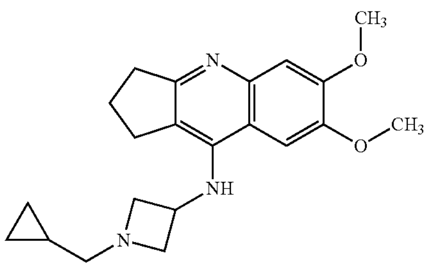 [SMILES: COc1cc2nc3c(c(NC4CN(CC5CC5)C4)c2cc1OC)CCC3] | 1-(cyclopropylmethyl)-N-{6,7-dimethoxy-1H,2H,3H-cyclopenta[b]quinolin-9-yl}azetidin-3-amine |
| 287 | 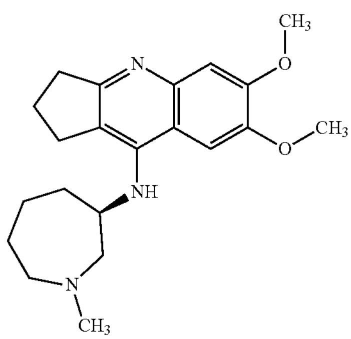 [SMILES: COc1cc2nc3c(c(N[C@@H]4CCCCN(C)C4)c2cc1OC)CCC3] | (3R)-N-{6,7-dimethoxy-1H,2H,3H-cyclopenta[b]quinolin-9-yl}-1-methylazepan-3-amine |
| 288 | 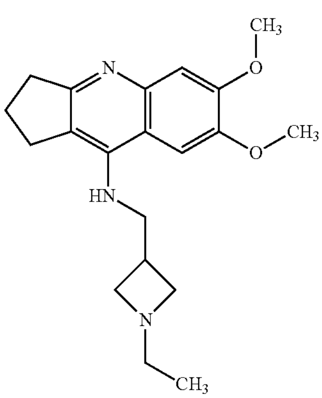 [SMILES: CCN1CC(CNc2c3c(nc4cc(OC)c(OC)cc24)CCC3)C1] | N-[(1-ethylazetidin-3-yl)methyl]-6,7-dimethoxy-1H,2H,3H-cyclopenta[b]quinolin-9-amine |

TABLE 2-continued

| No. | Structure | IUPAC Name |
|---|---|---|
| 289 | 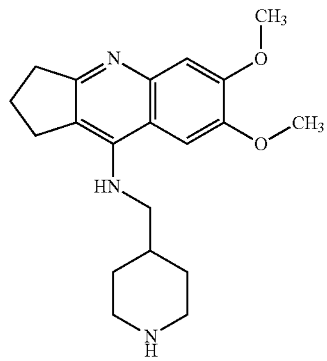 [SMILES: COc1cc2nc3c(c(NCC4CCNCC4)c2cc1OC)CCC3] | 6,7-dimethoxy-N-[(piperidin-4-yl)methyl]-1H,2H,3H-cyclopenta[b]quinolin-9-amine |
| 290 | 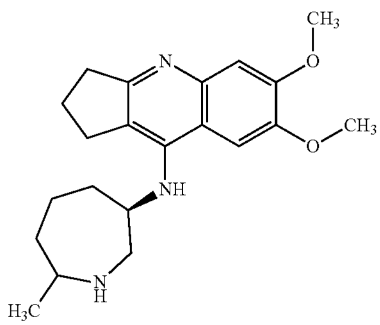 | (3R)-N-{6,7-dimethoxy-1H,2H,3H-cyclopenta[b]quinolin-9-yl}-7-methylazepan-3-amine |
| 291 | 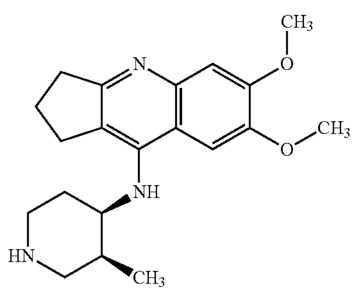 [SMILES: COc1cc2nc3c(c(N[C@@H]4CCNC[C@@H]4C)c2cc1OC)CCC3] | (3S,4R)-N-{6,7-dimethoxy-1H,2H,3H-cyclopenta[b]quinolin-9-yl}-3-methylpiperidin-4-amine |
| 292 | 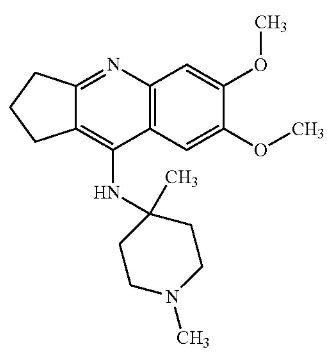 [SMILES: COc1cc2nc3c(c(NC4(C)CCN(C)CC4)c2cc1OC)CCC3] | N-{6,7-dimethoxy-1H,2H,3H-cyclopenta[b]quinolin-9-yl}-1,4-dimethylpiperidin-4-amine |
| 293 | 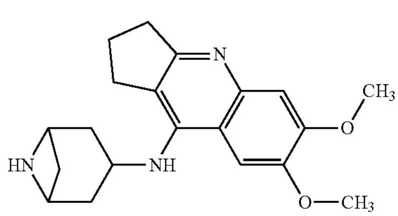 [SMILES: COc1cc2nc3c(c(NC4CC5CC(C4)N5)c2cc1OC)CCC3] | N-{6,7-dimethoxy-1H,2H,3H-cyclopenta[b]quinolin-9-yl}-6-azabicyclo[3.1.1]heptan-3-amine |

TABLE 2-continued

| No. | Structure | IUPAC Name |
|---|---|---|
| 294 | 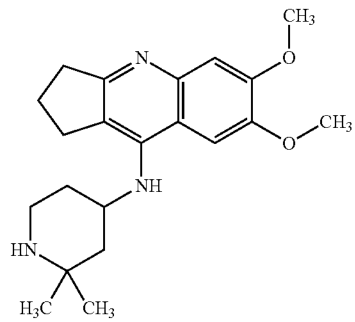 [SMILES: COc1cc2nc3c(c(NC4CCNC(C)(C)C4)c2cc1OC)CCC3] | N-{6,7-dimethoxy-1H,2H,3H-cyclopenta[b]quinolin-9-yl}-2,2-dimethylpiperidin-4-amine |
| 295 | 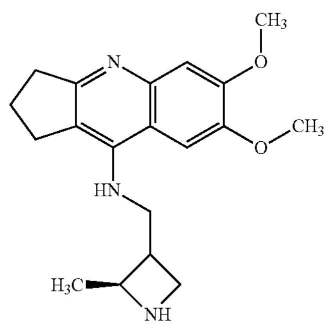 [SMILES: COc1cc2nc3c(c(NCC4CN[C@H]4C)c2cc1OC)CCC3] | 6,7-dimethoxy-N-{[(2S)-2-methylazetidin-3-yl]methyl}-1H,2H,3H-cyclopenta[b]quinolin-9-amine |
| 296 | 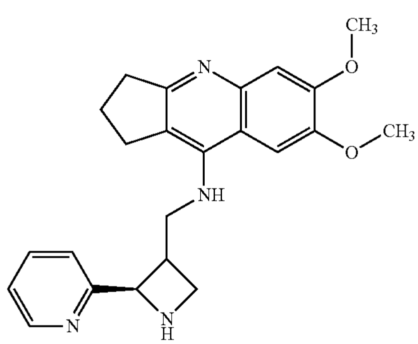 [SMILES: COc1cc2nc3c(c(NCC4CN[C@H]4c4ccccn4)c2cc1OC)CCC3] | 6,7-dimethoxy-N-{[(2R)-2-(pyridin-2-yl)azetidin-3-yl]methyl}-1H,2H,3H-cyclopenta[b]quinolin-9-amine |
| 297 | 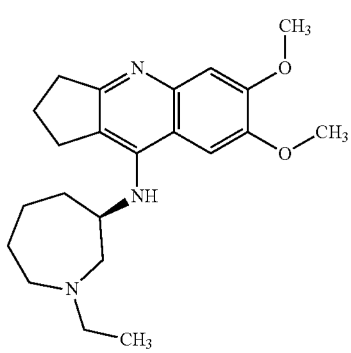 [SMILES: CCN1CCCC[C@@H](Nc2c3c(nc4cc(OC)c(OC)cc24)CCC3)C1] | (3R)-N-{6,7-dimethoxy-1H,2H,3H-cyclopenta[b]quinolin-9-yl}-1-ethylazepan-3-amine |

TABLE 2-continued
| No. | Structure | IUPAC Name |
|---|---|---|
| 298 | 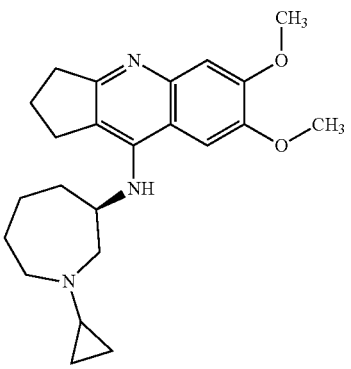 [SMILES: COc1cc2nc3c(c(N[C@@H]4CCCCN(C5CC5)C4)c2cc1OC)CCC3] | (3R)-1-cyclopropyl-N-{6,7-dimethoxy-1H,2H,3H-cyclopenta[b]quinolin-9-yl}azepan-3-amine |
| 299 | 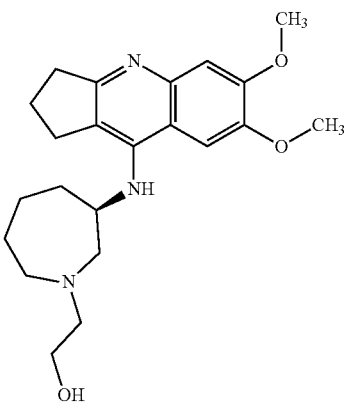 [SMILES: COc1cc2nc3c(c(N[C@@H]4CCCCN(CCO)C4)c2cc1OC)CCC3] | 2-[(3R)-3-({6,7-dimethoxy-1H,2H,3H-cyclopenta[b]quinolin-9-yl}amino)azepan-1-yl]ethan-1-ol |
| 300 | 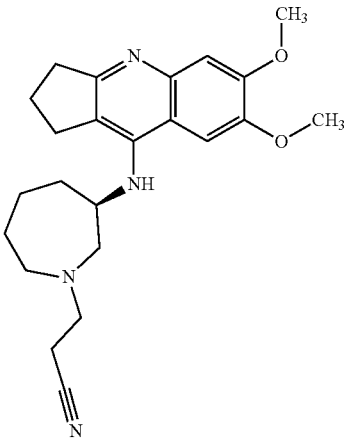 [SMILES: COc1cc2nc3c(c(N[C@@H]4CCCCN(CCC#N)C4)c2cc1OC)CCC3] | 3-[(3R)-3-({6,7-dimethoxy-1H,2H,3H-cyclopenta[b]quinolin-9-yl}amino)azepan-1-yl]propanenitrile |
| 301 | 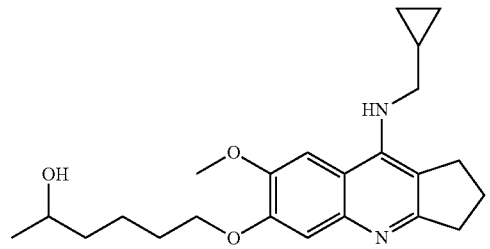 | 6-((9-((cyclopropylmethyl)amino)-7-methoxy-2,3-dihydro-1H-cyclopenta[b]quinolin-6-yl)oxy)hexan-2-ol |

TABLE 2-continued

| No. | Structure | IUPAC Name |
|---|---|---|
| 302 | 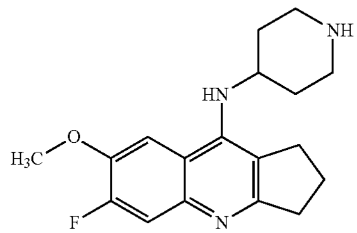 [SMILES: COc1cc2c(NC3CCNCC3)c3c(nc2cc1F)CCC3] | N-{6-fluoro-7-methoxy-1H,2H,3H-cyclopenta[b]quinolin-9-yl}piperidin-4-amine |
| 303 | 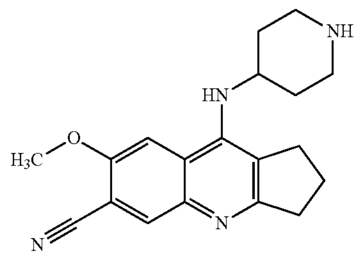 [SMILES: COc1cc2c(NC3CCNCC3)c3c(nc2cc1C#N)CCC3] | 7-methoxy-9-[(piperidin-4-yl)amino]-1H,2H,3H-cyclopenta[b]quinoline-6-carbonitrile |
| 304 | 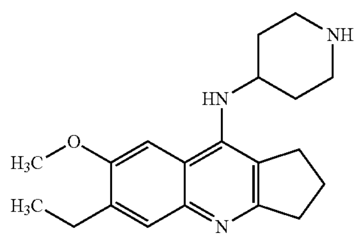 [SMILES: CCc1cc2nc3c(c(NC4CCNCC4)c2cc1OC)CCC3] | N-{6-ethyl-7-methoxy-1H,2H,3H-cyclopenta[b]quinolin-9-yl}piperidin-4-amine |
| 305 | 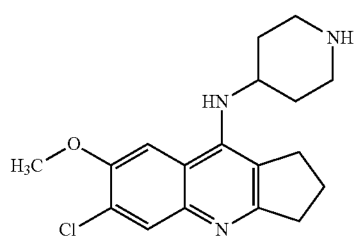 [SMILES: COc1cc2c(NC3CCNCC3)c3c(nc2cc1Cl)CCC3] | N-{6-chloro-7-methoxy-1H,2H,3H-cyclopenta[b]quinolin-9-yl}piperidin-4-amine |
| 306 | 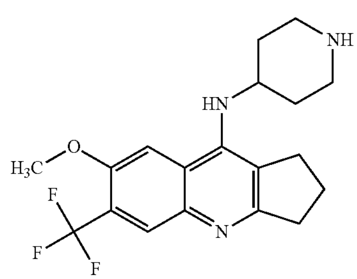 [SMILES: COc1cc2c(NC3CCNCC3)c3c(nc2cc1C(F)(F)F)CCC3] | N-[7-methoxy-6-(trifluoromethyl)-1H,2H,3H-cyclopenta[b]quinolin-9-yl]piperidin-4-amine |
| 307 | 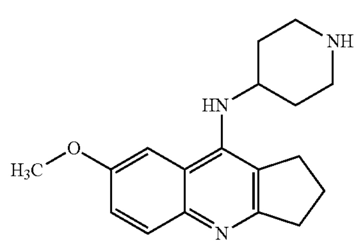 [SMILES: COc1ccc2nc3c(c(NC4CCNCC4)c2c1)CCC3] | N-{7-methoxy-1H,2H,3H-cyclopenta[b]quinolin-9-yl}piperidin-4-amine |

| No. | Structure | IUPAC Name |
|---|---|---|
| 308 | 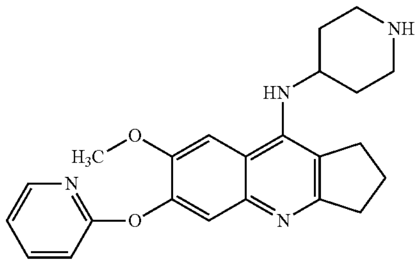 [SMILES: COc1cc2c(NC3CCNCC3)c3c(nc2cc1Oc1ccccn1)CCC3] | N-[7-methoxy-6-(pyridin-2-yloxy)-1H,2H,3H-cyclopenta[b]quinolin-9-yl]piperidin-4-amine |
| 309 | 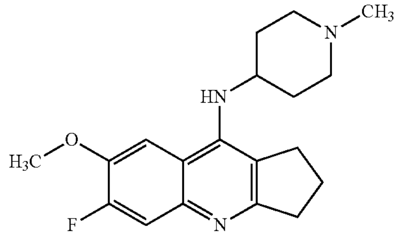 | N-{6-fluoro-7-methoxy-1H,2H,3H-cyclopenta[b]quinolin-9-yl}-1-methylpiperidin-4-amine |
| 310 | 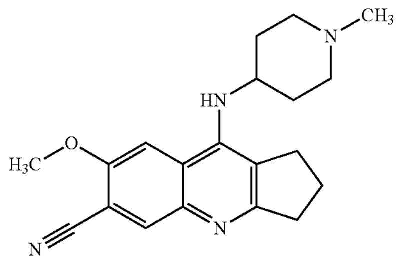 | 7-methoxy-9-[(1-methylpiperidin-4-yl)amino]-1H,2H,3H-cyclopenta[b]quinoline-6-carbonitrile |
| 311 | 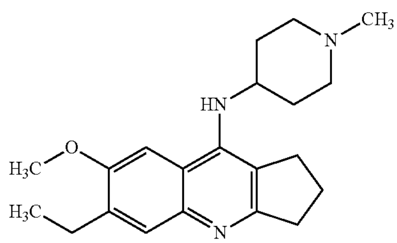 | N-{6-ethyl-7-methoxy-1H,2H,3H-cyclopenta[b]quinolin-9-yl}-1-methylpiperidin-4-amine |
| 312 | 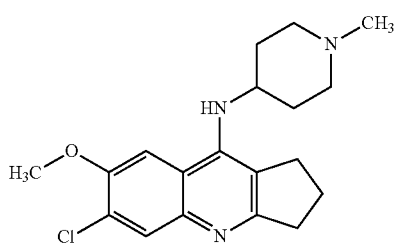 | N-{6-chloro-7-methoxy-1H,2H,3H-cyclopenta[b]quinolin-9-yl}-1-methylpiperidin-4-amine |
| 313 | 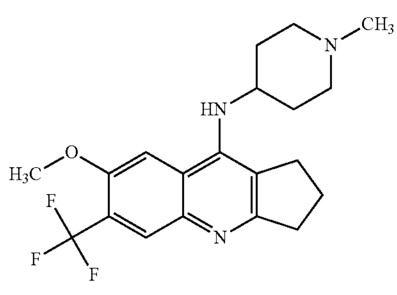 | N-[7-methoxy-6-(trifluoromethyl)-1H,2H,3H-cyclopenta[b]quinolin-9-yl]-1-methylpiperidin-4-amine |

TABLE 2-continued

| No. | Structure | IUPAC Name |
| --- | --- | --- |
| 314 | 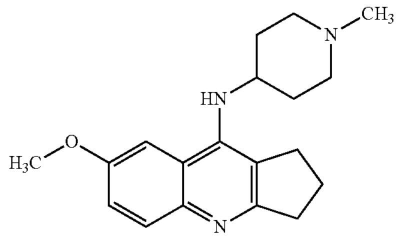 | N-{7-methoxy-1H,2H,3H-cyclopenta[b]quinolin-9-yl}-1-methylpiperidin-4-amine |
| 315 | 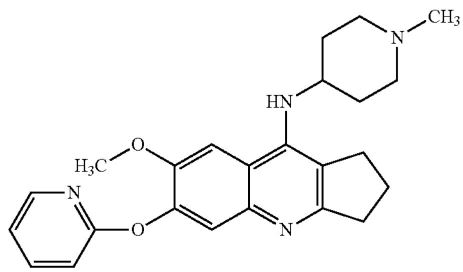 [SMILES: COc1cc2c(NC3CCN(C)CC3)c3c(nc2cc1Oc1ccccn1)CCC3] | N-[7-methoxy-6-(pyridin-2-yloxy)-1H,2H,3H-cyclopenta[b]quinolin-9-yl]-1-methylpiperidin-4-amine |
| 316 | 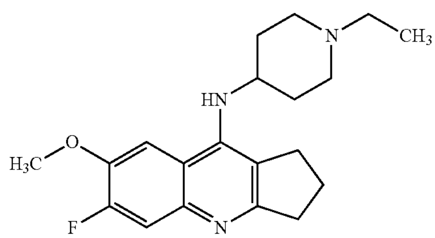 [SMILES: CCN1CCC(Nc2c3c(nc4cc(F)c(OC)cc24)CCC3)CC1] | 1-ethyl-N-{6-fluoro-7-methoxy-1H,2H,3H-cyclopenta[b]quinolin-9-yl}piperidin-4-amine |
| 317 | 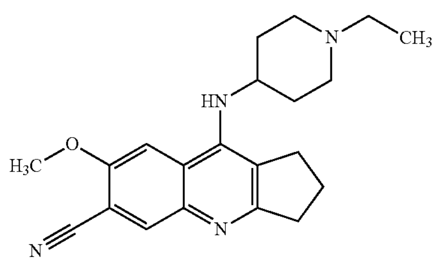 [SMILES: CCN1CCC(Nc2c3c(nc4cc(C#N)c(OC)cc24)CCC3)CC1] | 9-[(1-ethylpiperidin-4-yl)amino]-7-methoxy-1H,2H,3H-cyclopenta[b]quinoline-6-carbonitrile |
| 318 | 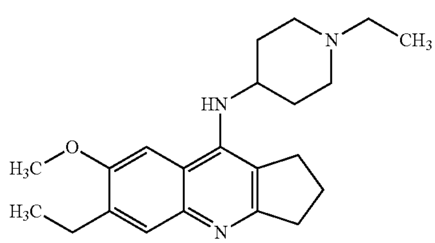 [SMILES: CCc1cc2nc3c(c(NC4CCN(CC)CC4)c2cc1OC)CCC3] | 1-ethyl-N-{6-ethyl-7-methoxy-1H,2H,3H-cyclopenta[b]quinolin-9-yl}piperidin-4-amine |
| 319 | 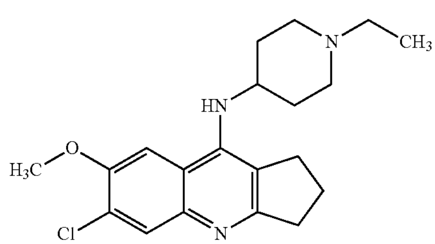 [SMILES: CCN1CCC(Nc2c3c(nc4cc(Cl)c(OC)cc24)CCC3)CC1] | N-{6-chloro-7-methoxy-1H,2H,3H-cyclopenta[b]quinolin-9-yl}-1-ethylpiperidin-4-amine |

TABLE 2-continued

| No. | Structure | IUPAC Name |
|---|---|---|
| 320 | 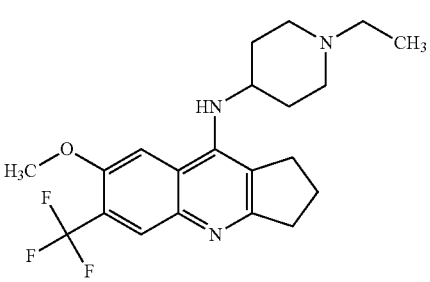 [SMILES: CCN1CCC(Nc2c3c(nc4cc(C(F)(F)F)c(OC)cc24)CCC3)CC1] | 1-ethyl-N-[7-methoxy-6-(trifluoromethyl)-1H,2H,3H-cyclopenta[b]quinolin-9-yl]piperidin-4-amine |
| 321 | 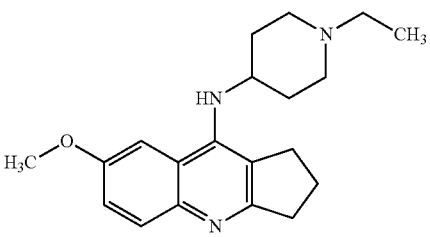 [SMILES: CCN1CCC(Nc2c3c(nc4ccc(OC)cc24)CCC3)CC1] | 1-ethyl-N-{7-methoxy-1H,2H,3H-cyclopenta[b]quinolin-9-yl}piperidin-4-amine |
| 322 | 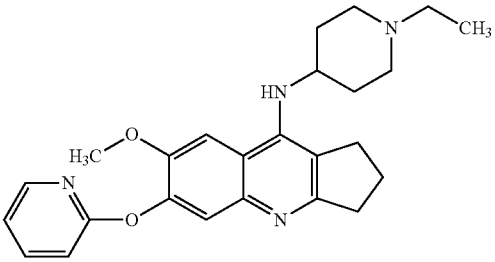 [SMILES: CCN1CCC(Nc2c3c(nc4cc(Oc5ccccn5)c(OC)cc24)CCC3)CC1] | 1-ethyl-N-[7-methoxy-6-(pyridin-2-yloxy)-1H,2H,3H-cyclopenta[b]quinolin-9-yl]piperidin-4-amine |
| 323 | 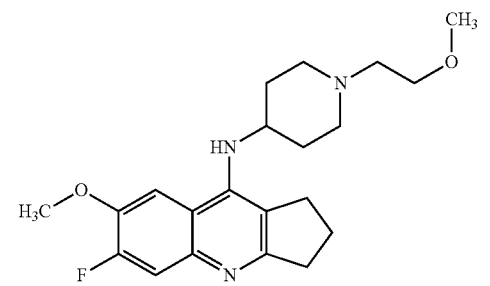 | N-{6-fluoro-7-methoxy-1H,2H,3H-cyclopenta[b]quinolin-9-yl}-1-(2-methoxyethyl)piperidin-4-amine |
| 324 | 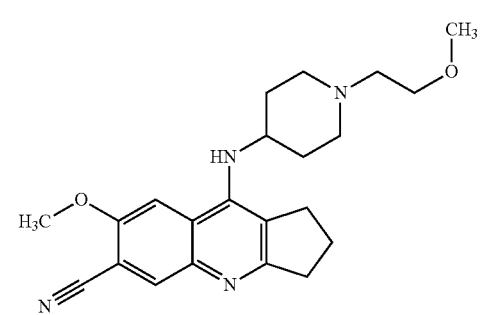 | 7-methoxy-9-{[1-(2-methoxyethyl)piperidin-4-yl]amino}-1H,2H,3H-cyclopenta[b]quinoline-6-carbonitrile |

TABLE 2-continued

| No. | Structure | IUPAC Name |
|---|---|---|
| 325 | 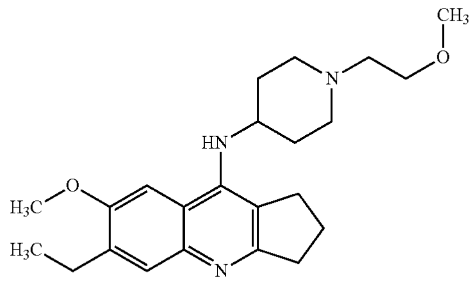 | N-{6-ethyl-7-methoxy-1H,2H,3H-cyclopenta[b]quinolin-9-yl}-1-(2-methoxyethyl)piperidin-4-amine |
| 326 | 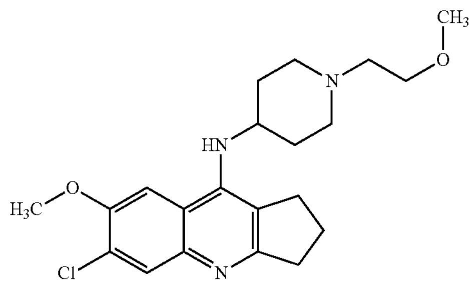 | N-{6-chloro-7-methoxy-1H,2H,3H-cyclopenta[b]quinolin-9-yl}-1-(2-methoxyethyl)piperidin-4-amine |
| 327 | 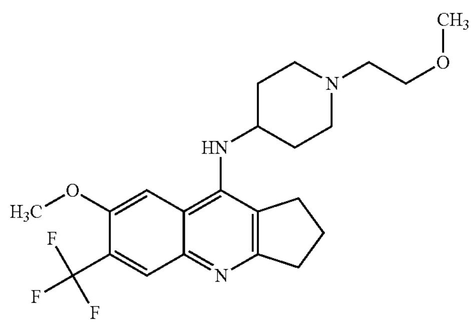 | N-[7-methoxy-6-(trifluoromethyl)-1H,2H,3H-cyclopenta[b]quinolin-9-yl]-1-(2-methoxyethyl)piperidin-4-amine |
| 328 | 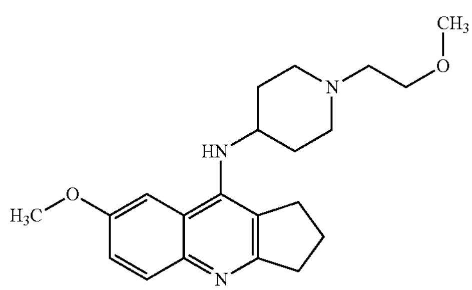 | N-{7-methoxy-1H,2H,3H-cyclopenta[b]quinolin-9-yl}-1-(2-methoxyethyl)piperidin-4-amine |
| 329 | 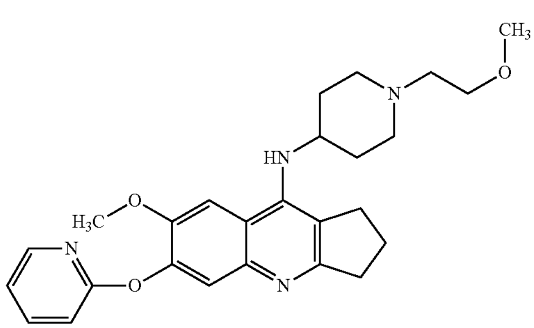 [SMILES: COCCN1CCC(Nc2c3c(nc4cc(Oc5ccccn5)c(OC)cc24)CCC3)CC1] | N-[7-methoxy-6-(pyridin-2-yloxy)-1H,2H,3H-cyclopenta[b]quinolin-9-yl]-1-(2-methoxyethyl)piperidin-4-amine |

TABLE 2-continued

| No. | Structure | IUPAC Name |
|---|---|---|
| 330 | 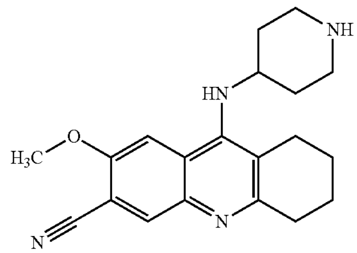 [SMILES: COc1cc2c(NC3CCNCC3)c3c(nc2cc1C#N)CCCC3] | 2-methoxy-9-[(piperidin-4-yl)amino]-5,6,7,8-tetrahydroacridine-3-carbonitrile |
| 331 | 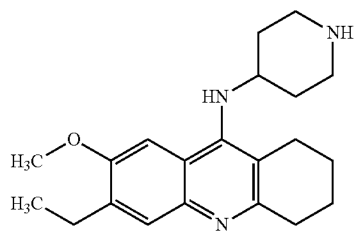 [SMILES: CCc1cc2nc3c(c(NC4CCNCC4)c2cc1OC)CCCC3] | 6-ethyl-7-methoxy-N-(piperidin-4-yl)-1,2,3,4-tetrahydroacridin-9-amine |
| 332 | 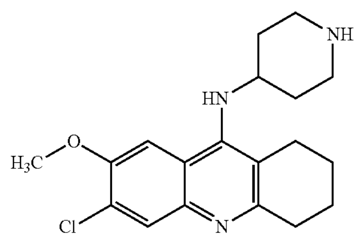 [SMILES: COc1cc2c(NC3CCNCC3)c3c(nc2cc1Cl)CCCC3] | 6-chloro-7-methoxy-N-(piperidin-4-yl)-1,2,3,4-tetrahydroacridin-9-amine |
| 333 | 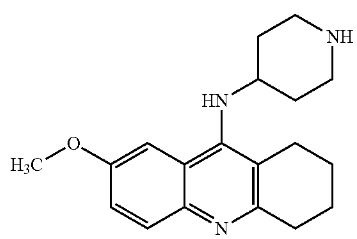 [SMILES: COc1ccc2nc3c(c(NC4CCNCC4)c2c1)CCCC3] | 7-methoxy-N-(piperidin-4-yl)-1,2,3,4-tetrahydroacridin-9-amine |
| 334 | 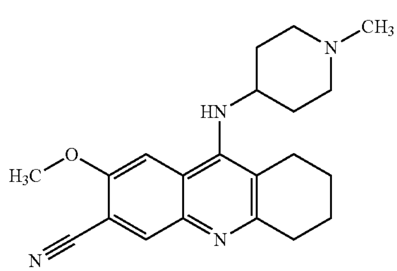 | 2-methoxy-9-[(1-methylpiperidin-4-yl)amino]-5,6,7,8-tetrahydroacridine-3-carbonitrile |
| 335 | 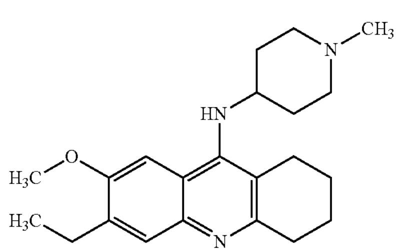 | 6-ethyl-7-methoxy-N-(1-methylpiperidin-4-yl)-1,2,3,4-tetrahydroacridin-9-amine |

TABLE 2-continued

| No. | Structure | IUPAC Name |
|---|---|---|
| 336 | 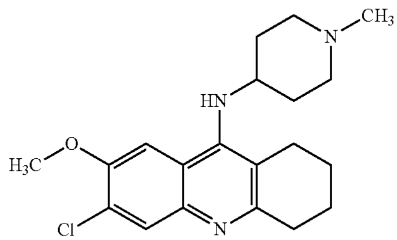 | 6-chloro-7-methoxy-N-(1-methylpiperidin-4-yl)-1,2,3,4-tetrahydroacridin-9-amine |
| 337 | 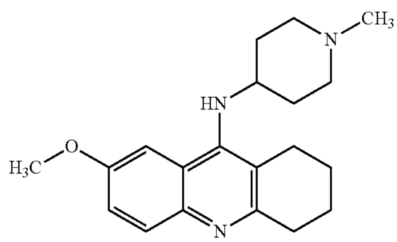 | 7-methoxy-N-(1-methylpiperidin-4-yl)-1,2,3,4-tetrahydroacridin-9-amine |
| 338 | 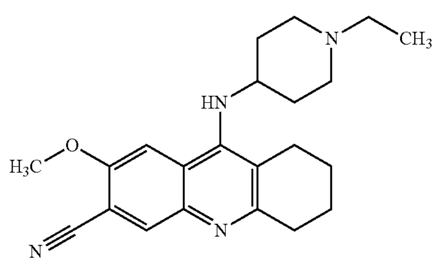 [SMILES: CCN1CCC(Nc2c3c(nc4cc(C#N)c(OC)cc24)CCCC3)CC1] | 9-[(1-ethylpiperidin-4-yl)amino]-2-methoxy-5,6,7,8-tetrahydroacridine-3-carbonitrile |
| 339 | 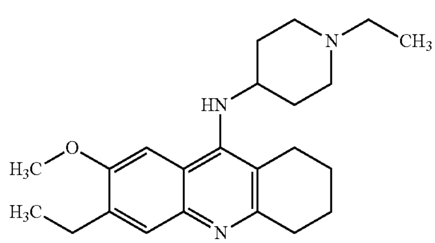 [SMILES: CCc1cc2nc3c(c(NC4CCN(CC)CC4)c2cc1OC)CCCC3] | 6-ethyl-N-(1-ethylpiperidin-4-yl)-7-methoxy-1,2,3,4-tetrahydroacridin-9-amine |
| 340 | 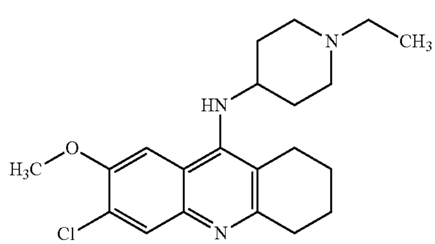 [SMILES: CCN1CCC(Nc2c3c(nc4cc(Cl)c(OC)cc24)CCCC3)CC1] | 6-chloro-N-(1-ethylpiperidin-4-yl)-7-methoxy-1,2,3,4-tetrahydroacridin-9-amine |
| 341 | 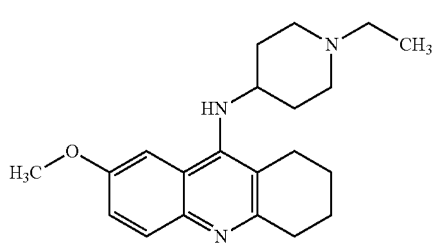 [SMILES: CCN1CCC(Nc2c3c(nc4ccc(OC)cc24)CCCC3)CC1] | N-(1-ethylpiperidin-4-yl)-7-methoxy-1,2,3,4-tetrahydroacridin-9-amine |

TABLE 2-continued

| No. | Structure | IUPAC Name |
|---|---|---|
| 342 | 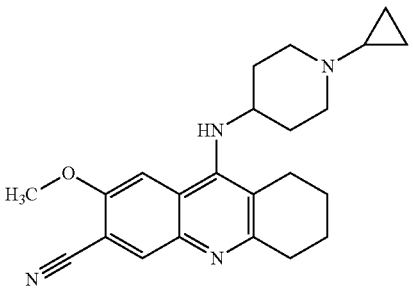 [SMILES: COc1cc2c(NC3CCN(C4CC4)CC3)c3c(nc2cc1C#N)CCCC3] | 9-[(1-cyclopropylpiperidin-4-yl)amino]-2-methoxy-5,6,7,8-tetrahydroacridine-3-carbonitrile |
| 343 | 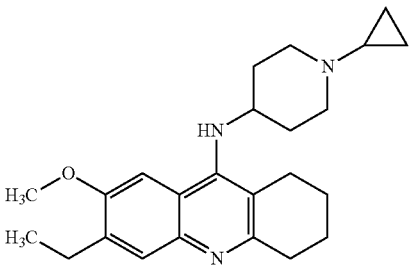 | N-(1-cyclopropylpiperidin-4-yl)-6-ethyl-7-methoxy-1,2,3,4-tetrahydroacridin-9-amine |
| 344 | 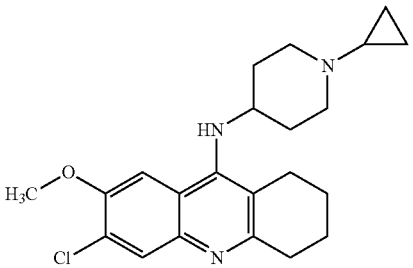 [SMILES: COc1cc2c(NC3CCN(C4CC4)CC3)c3c(nc2cc1Cl)CCCC3] | 6-chloro-N-(1-cyclopropylpiperidin-4-yl)-7-methoxy-1,2,3,4-tetrahydroacridin-9-amine |
| 345 | 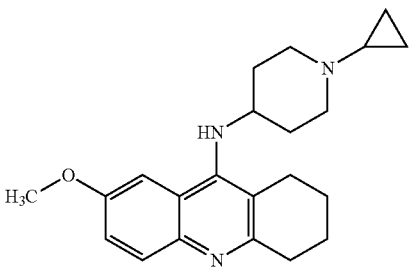 [SMILES: COc1ccc2nc3c(c(NC4CCN(C5CC5)CC4)c2c1)CCCC3] | N-(1-cyclopropylpiperidin-4-yl)-7-methoxy-1,2,3,4-tetrahydroacridin-9-amine |
| 346 | 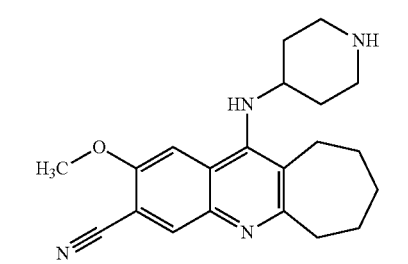 [SMILES: COc1cc2c(NC3CCNCC3)c3c(nc2cc1C#N)CCCCC3] | 2-methoxy-11-[(piperidin-4-yl)amino]-6H,7H,8H,9H,10H-cyclohepta[b]quinoline-3-carbonitrile |

TABLE 2-continued

| No. | Structure | IUPAC Name |
|---|---|---|
| 347 | 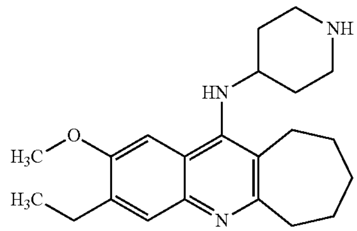 [SMILES: CCc1cc2nc3c(c(NC4CCNCC4)c2cc1OC)CCCCC3] | N-{3-ethyl-2-methoxy-6H,7H,8H,9H,10H-cyclohepta[b]quinolin-11-yl}piperidin-4-amine |
| 348 | 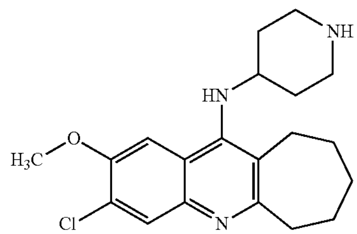 [SMILES: COc1cc2c(NC3CCNCC3)c3c(nc2cc1Cl)CCCCC3] | N-{3-chloro-2-methoxy-6H,7H,8H,9H,10H-cyclohepta[b]quinolin-11-yl}piperidin-4-amine |
| 349 | 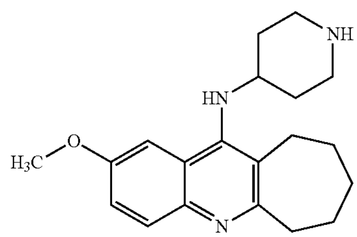 [SMILES: COc1ccc2nc3c(c(NC4CCNCC4)c2c1)CCCCC3] | N-{2-methoxy-6H,7H,8H,9H,10H-cyclohepta[b]quinolin-11-yl}piperidin-4-amine |
| 350 | 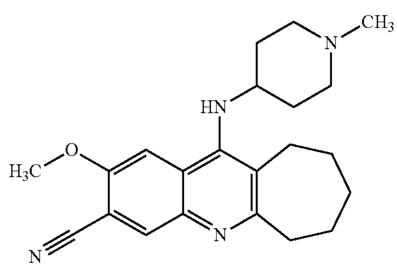 | 2-methoxy-11-[(1-methylpiperidin-4-yl)amino]-6H,7H,8H,9H,10H-cyclohepta[b]quinoline-3-carbonitrile |
| 351 | 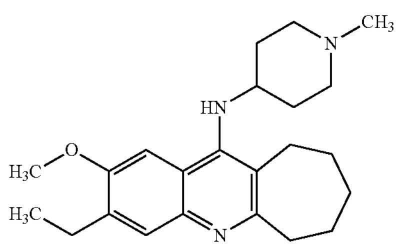 | N-{3-ethyl-2-methoxy-6H,7H,8H,9H,10H-cyclohepta[b]quinolin-11-yl}-1-methylpiperidin-4-amine |
| 352 | 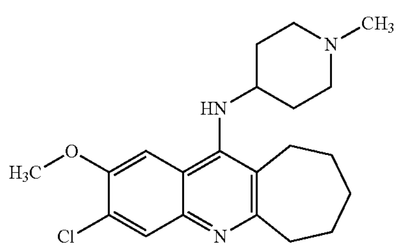 | N-{3-chloro-2-methoxy-6H,7H,8H,9H,10H-cyclohepta[b]quinolin-11-yl}-1-methylpiperidin-4-amine |

| No. | Structure | IUPAC Name |
|---|---|---|
| 353 | 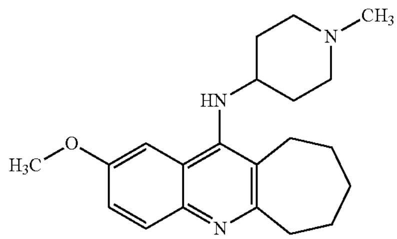 | N-{2-methoxy-6H,7H,8H,9H,10H-cyclohepta[b]quinolin-11-yl}-1-methylpiperidin-4-amine |
| 354 | 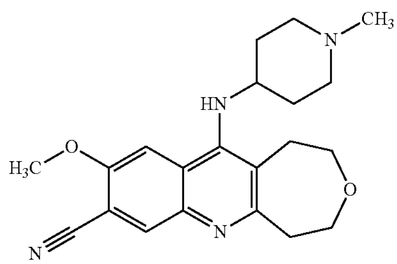 | 9-methoxy-11-[(1-methylpiperidin-4-yl)amino]-1H,2H,4H,5H-oxepino[4,5-b]quinoline-8-carbonitrile |
| 355 | 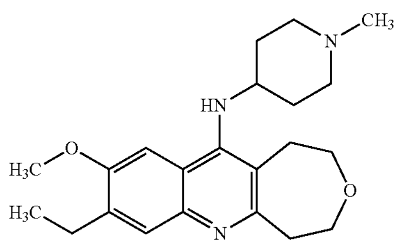 | N-{8-ethyl-9-methoxy-1H,2H,4H,5H-oxepino[4,5-b]quinolin-11-yl}-1-methylpiperidin-4-amine |
| 356 | 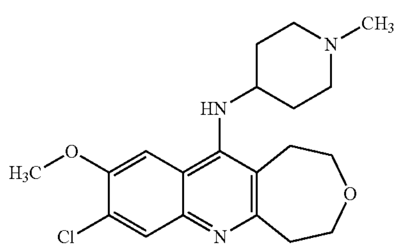 | N-{8-chloro-9-methoxy-1H,2H,4H,5H-oxepino[4,5-b]quinolin-11-yl}-1-methylpiperidin-4-amine |
| 357 | 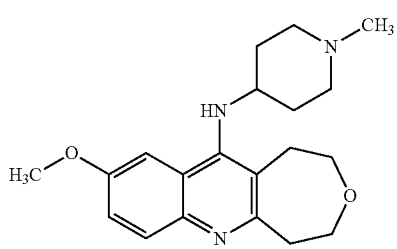 | N-{9-methoxy-1H,2H,4H,5H-oxepino[4,5-b]quinolin-11-yl}-1-methylpiperidin-4-amine |
| 358 | 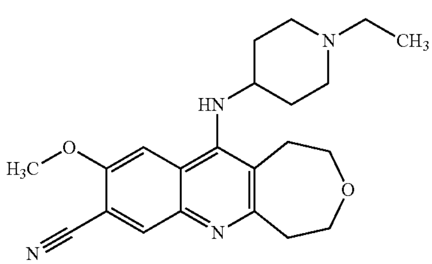 [SMILES: CCN1CCC(Nc2c3c(nc4cc(C#N)c(OC)cc24)CCOCC3)CC1] | 11-[(1-ethylpiperidin-4-yl)amino]-9-methoxy-1H,2H,4H,5H-oxepino[4,5-b]quinoline-8-carbonitrile |

| No. | Structure | IUPAC Name |
|---|---|---|
| 359 | 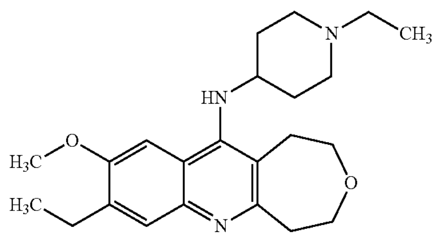 [SMILES: CCc1cc2nc3c(c(NC4CCN(CC)CC4)c2cc1OC)CCOCC3] | 1-ethyl-N-{8-ethyl-9-methoxy-1H,2H,4H,5H-oxepino[4,5-b]quinolin-11-yl}piperidin-4-amine |
| 360 | 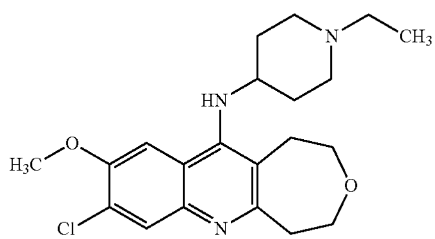 [SMILES: CCN1CCC(Nc2c3c(nc4cc(Cl)c(OC)cc24)CCOCC3)CC1] | N-{8-chloro-9-methoxy-1H,2H,4H,5H-oxepino[4,5-b]quinolin-11-yl}-1-ethylpiperidin-4-amine |
| 361 | 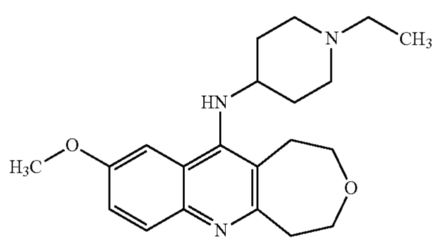 [SMILES: CCN1CCC(Nc2c3c(nc4ccc(OC)cc24)CCOCC3)CC1] | 1-ethyl-N-{9-methoxy-1H,2H,4H,5H-oxepino[4,5-b]quinolin-11-yl}piperidin-4-amine |
| 362 | 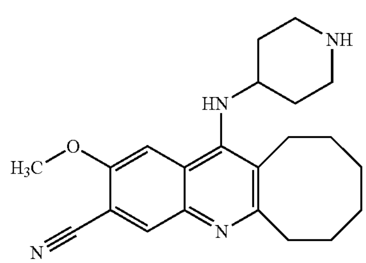 [SMILES: COc1cc2c(NC3CCNCC3)c3c(nc2cc1C#N)CCCCCC3] | 2-methoxy-12-[(piperidin-4-yl)amino]-6H,7H,8H,9H,10H,11H-cycloocta[b]quinoline-3-carbonitrile |
| 363 | 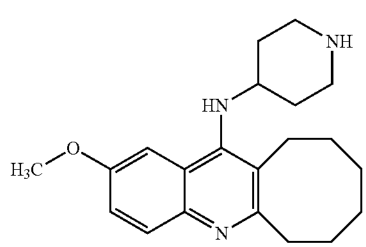 [SMILES: COc1ccc2nc3c(c(NC4CCNCC4)c2c1)CCCCCC3] | N-{2-methoxy-6H,7H,8H,9H,10H,11H-cycloocta[b]quinolin-12-yl}piperidin-4-amine |
| 364 | 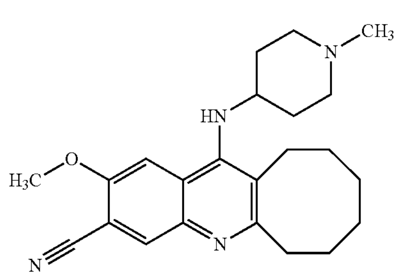 | 2-methoxy-12-[(1-methylpiperidin-4-yl)amino]-6H,7H,8H,9H,10H,11H-cycloocta[b]quinoline-3-carbonitrile |

TABLE 2-continued
| No. | Structure | IUPAC Name |
|---|---|---|
| 365 | 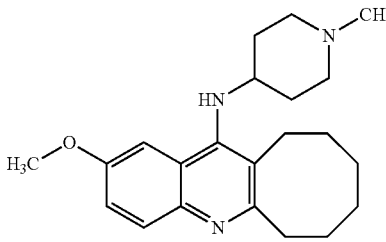 | N-{2-methoxy-6H,7H,8H,9H,10H,11H-cycloocta[b]quinolin-12-yl}-1-methylpiperidin-4-amine |
| 366 | 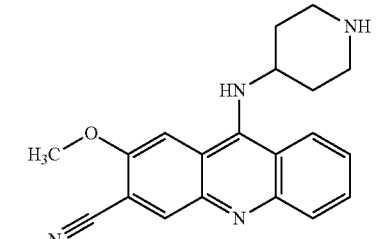 | 2-methoxy-9-[(piperidin-4-yl)amino]acridine-3-carbonitrile |
| 367 | 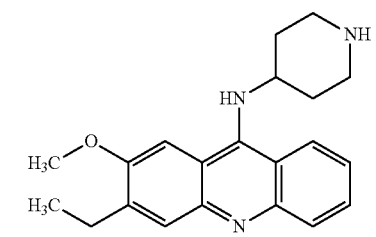 [SMILES: CCc1cc2nc3ccccc3c(NC3CCNCC3)c2cc1OC] | 3-ethyl-2-methoxy-N-(piperidin-4-yl)acridin-9-amine |
| 368 | 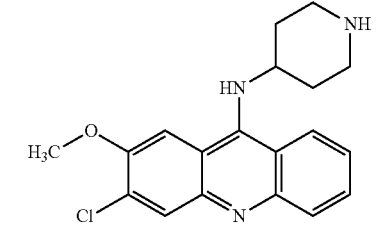 [SMILES: COc1cc2c(NC3CCNCC3)c3ccccc3nc2cc1Cl] | 3-chloro-2-methoxy-N-(piperidin-4-yl)acridin-9-amine |
| 369 | 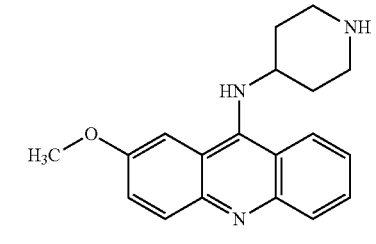 [SMILES: COc1ccc2nc3ccccc3c(NC3CCNCC3)c2c1] | 2-methoxy-N-(piperidin-4-yl)acridin-9-amine |
| 370 | 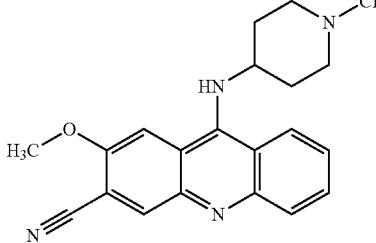 | 2-methoxy-9-[(1-methylpiperidin-4-yl)amino]acridine-3-carbonitrile |

TABLE 2-continued
| No. | Structure | IUPAC Name |
|---|---|---|
| 371 | 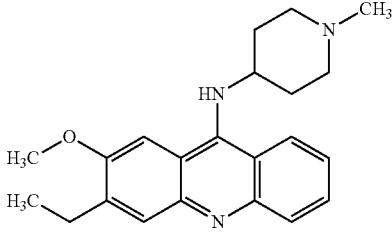 | 3-ethyl-2-methoxy-N-(1-methylpiperidin-4-yl)acridin-9-amine |
| 372 | 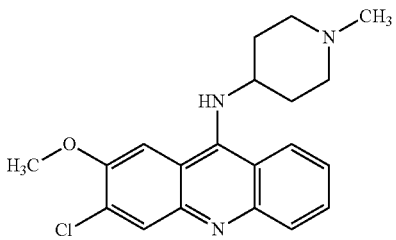 | 3-chloro-2-methoxy-N-(1-methylpiperidin-4-yl)acridin-9-amine |
| 373 | 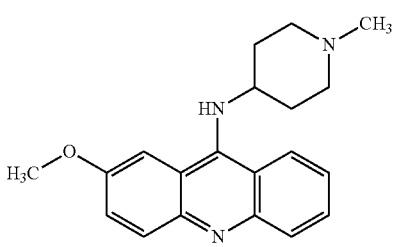 | 2-methoxy-N-(1-methylpiperidin-4-yl)acridin-9-amine |
| 374 | 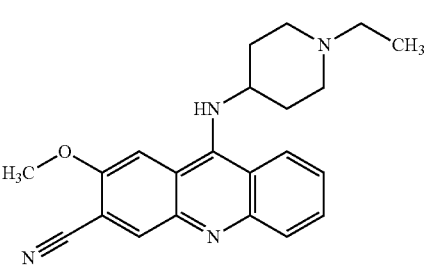 [SMILES: CCN1CCC(Nc2c3ccccc3nc3cc(C#N)c(OC)cc23)CC1] | 9-[(1-ethylpiperidin-4-yl)amino]-2-methoxyacridine-3-carbonitrile |
| 375 | 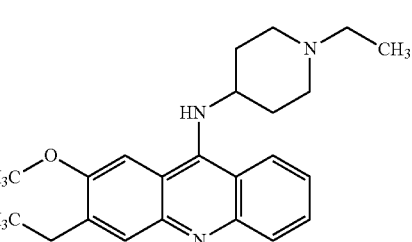 | 3-ethyl-N-(1-ethylpiperidin-4-yl)-2-methoxyacridin-9-amine |
| 376 | 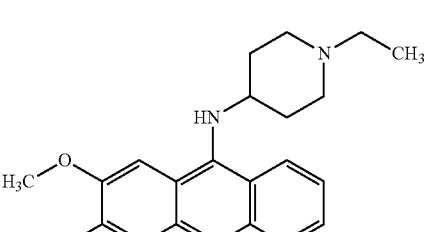 | 3-chloro-N-(1-ethylpiperidin-4-yl)-2-methoxyacridin-9-amine |

TABLE 2-continued

| No. | Structure | IUPAC Name |
|---|---|---|
| 377 | 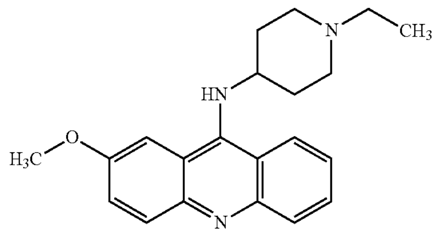 [SMILES: CCN1CCC(Nc2c3ccccc3nc3ccc(OC)cc23)CC1] | N-(1-ethylpiperidin-4-yl)-2-methoxyacridin-9-amine |
| 378 | 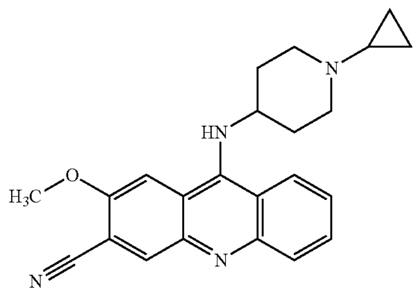 [SMILES: COc1cc2c(NC3CCN(C4CC4)CC3)c3ccccc3nc2cc1C#N] | 9-[(1-cyclopropylpiperidin-4-yl)amino]-2-methoxyacridine-3-carbonitrile |
| 379 | 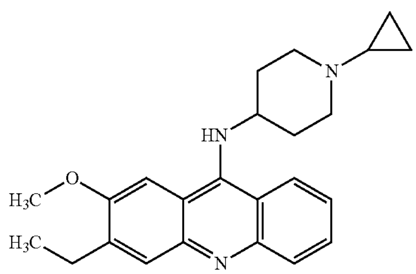 [SMILES: CCc1cc2nc3ccccc3c(NC3CCN(C4CC4)CC3)c2cc1OC] | N-(1-cyclopropylpiperidin-4-yl)-3-ethyl-2-methoxyacridin-9-amine |
| 380 | 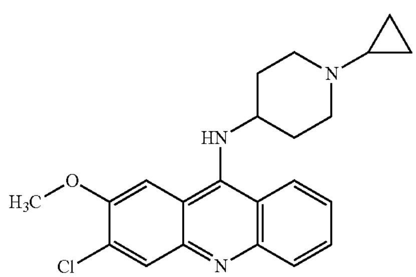 [SMILES: COc1cc2c(NC3CCN(C4CC4)CC3)c3ccccc3nc2cc1Cl] | 3-chloro-N-(1-cyclopropylpiperidin-4-yl)-2-methoxyacridin-9-amine |
| 381 | 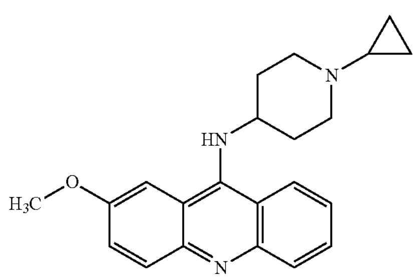 [SMILES: COc1ccc2nc3ccccc3c(NC3CCN(C4CC4)CC3)c2c1] | N-(1-cyclopropylpiperidin-4-yl)-2-methoxyacridin-9-amine |
| 382 | 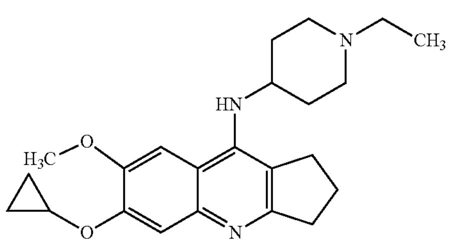 [SMILES: CCN1CCC(Nc2c3c(nc4cc(OC5CC5)c(OC)cc24)CCC3)CC1] | N-{6-cyclopropoxy-7-methoxy-1H,2H,3H-cyclopenta[b]quinolin-9-yl}-1-ethylpiperidin-4-amine |

TABLE 2-continued

| No. | Structure | IUPAC Name |
|---|---|---|
| 383 | 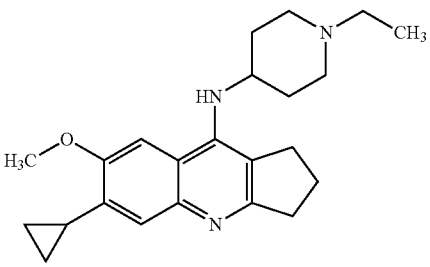 [SMILES: CCN1CCC(Nc2c3c(nc4cc(C5CC5)c(OC)cc24)CCC3)CC1] | N-{6-cyclopropyl-7-methoxy-1H,2H,3H-cyclopenta[b]quinolin-9-yl}-1-ethylpiperidin-4-amine |
| 384 | 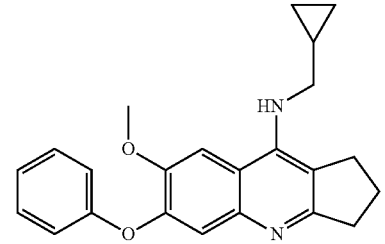 [SMILES: COc1cc2c(NCC3CC3)c3c(nc2cc1Oc1ccccc1)CCC3] | N-(cyclopropylmethyl)-7-methoxy-6-phenoxy-1H,2H,3H-cyclopenta[b]quinolin-9-amine |
| 385 | 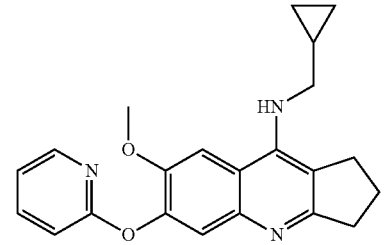 [SMILES: COc1cc2c(NCC3CC3)c3c(nc2cc1Oc1ccccn1)CCC3] | N-(cyclopropylmethyl)-7-methoxy-6-(pyridin-2-yloxy)-1H,2H,3H-cyclopenta[b]quinolin-9-amine |
| 386 | 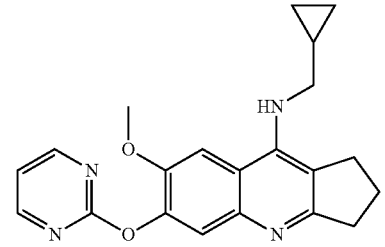 [SMILES: COc1cc2c(NCC3CC3)c3c(nc2cc1Oc1ncccn1)CCC3] | N-(cyclopropylmethyl)-7-methoxy-6-(pyrimidin-2-yloxy)-1H,2H,3H-cyclopenta[b]quinolin-9-amine |
| 387 | 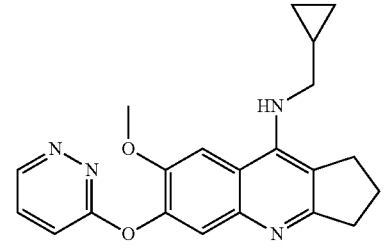 [SMILES: COc1cc2c(NCC3CC3)c3c(nc2cc1Oc1cccnn1)CCC3] | N-(cyclopropylmethyl)-7-methoxy-6-(pyridazin-3-yloxy)-1H,2H,3H-cyclopenta[b]quinolin-9-amine |
| 388 | 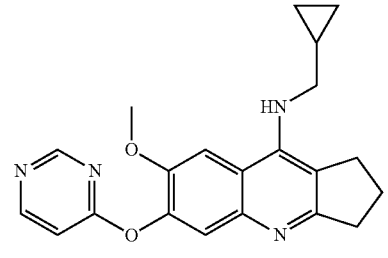 [SMILES: COc1cc2c(NCC3CC3)c3c(nc2cc1Oc1ccncn1)CCC3] | N-(cyclopropylmethyl)-7-methoxy-6-(pyrimidin-4-yloxy)-1H,2H,3H-cyclopenta[b]quinolin-9-amine |

TABLE 2-continued

| No. | Structure | IUPAC Name |
|---|---|---|
| 389 | 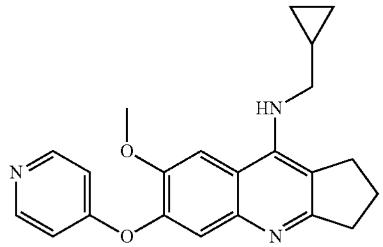 [SMILES: COc1cc2c(NCC3CC3)c3c(nc2cc1Oc1ccncc1)CCC3] | N-(cyclopropylmethyl)-7-methoxy-6-(pyridin-4-yloxy)-1H,2H,3H-cyclopenta[b]quinolin-9-amine |
| 390 | 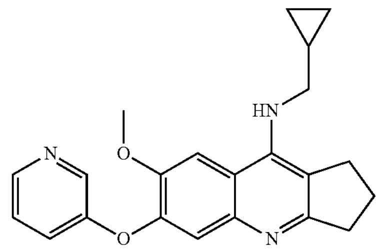 [SMILES: COc1cc2c(NCC3CC3)c3c(nc2cc1Oc1cccnc1)CCC3] | N-(cyclopropylmethyl)-7-methoxy-6-(pyridin-3-yloxy)-1H,2H,3H-cyclopenta[b]quinolin-9-amine |
| 391 | 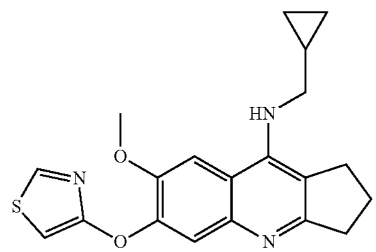 [SMILES: COc1cc2c(NCC3CC3)c3c(nc2cc1Oc1cscn1)CCC3] | N-(cyclopropylmethyl)-7-methoxy-6-(1,3-thiazol-4-yloxy)-1H,2H,3H-cyclopenta[b]quinolin-9-amine |
| 392 | 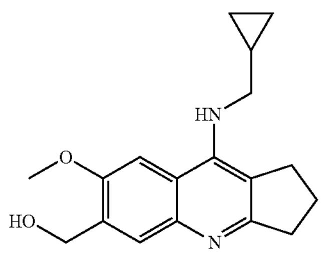 [SMILES: COc1cc2c(NCC3CC3)c3c(nc2cc1CO)CCC3] | {9-[(cyclopropylmethyl)amino]-7-methoxy-1H,2H,3H-cyclopenta[b]quinolin-6-yl}methanol |
| 393 | 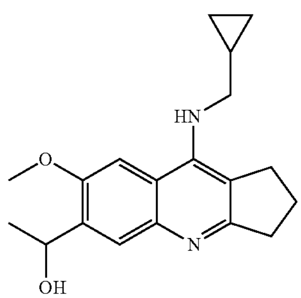 [SMILES: COc1cc2c(NCC3CC3)c3c(nc2cc1C(C)O)CCC3] | 1-{9-[(cyclopropylmethyl)amino]-7-methoxy-1H,2H,3H-cyclopenta[b]quinolin-6-yl}ethan-1-ol |
| 394 | 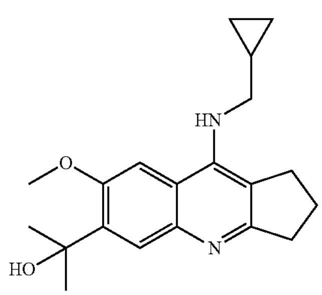 [SMILES: COc1cc2c(NCC3CC3)c3c(nc2cc1C(C)(C)O)CCC3] | 2-{9-[(cyclopropylmethyl)amino]-7-methoxy-1H,2H,3H-cyclopenta[b]quinolin-6-yl}propan-2-ol |

TABLE 2-continued

| No. | Structure | IUPAC Name |
|---|---|---|
| 395 | 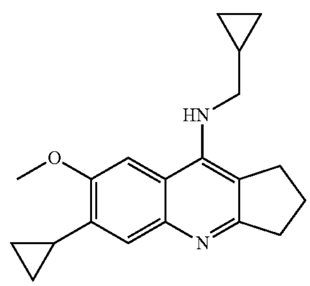 [SMILES: COc1cc2c(NCC3CC3)c3c(nc2cc1C1CC1)CCC3] | 6-cyclopropyl-N-(cyclopropylmethyl)-7-methoxy-1H,2H,3H-cyclopenta[b]quinolin-9-amine |
| 396 | 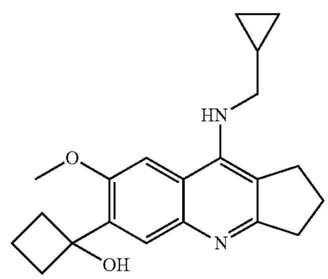 [SMILES: COc1cc2c(NCC3CC3)c3c(nc2cc1C1(O)CCC1)CCC3] | 1-{9-[(cyclopropylmethyl)amino]-7-methoxy-1H,2H,3H-cyclopenta[b]quinolin-6-yl}cyclobutan-1-ol |
| 397 | 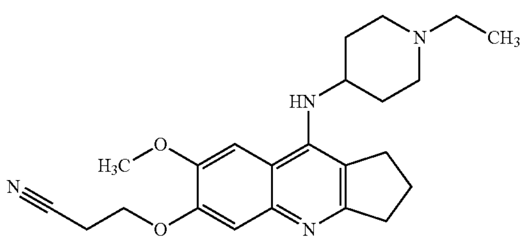 [SMILES: CCN1CCC(Nc2c3c(nc4cc(OCCC#N)c(OC)cc24)CCC3)CC1] | 3-({9-[(1-ethylpiperidin-4-yl)amino]-7-methoxy-1H,2H,3H-cyclopenta[b]quinolin-6-yl}oxy)propanenitrile |
| 398 | 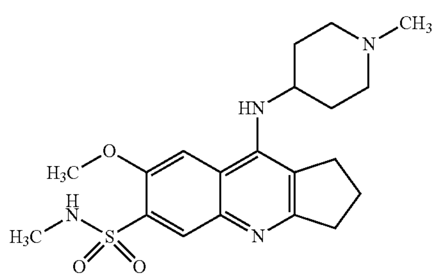 | 9-((cyclopropylmethyl)amino)-7-methoxy-N-methyl-2,3-dihydro-1H-cyclopenta[b]quinoline-6-sulfonamide |
| 399 | 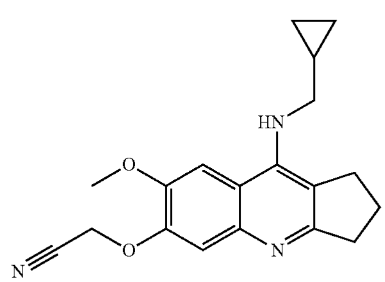 [SMILES: COc1cc2c(NCC3CC3)c3c(nc2cc1OCC#N)CCC3] | 2-({9-[(cyclopropylmethyl)amino]-7-methoxy-1H,2H,3H-cyclopenta[b]quinolin-6-yl}oxy)acetonitrile |
| 400 | 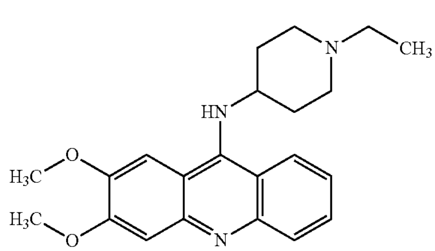 | N-(1-ethylpiperidin-4-yl)-2,3-dimethoxyacridin-9-amine |

TABLE 2-continued

| No. | Structure | IUPAC Name |
|---|---|---|
| 401 | 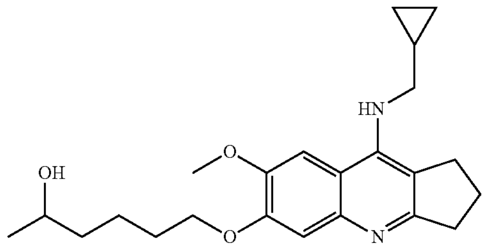 [SMILES: COc1cc2c(NCC3CC3)c3c(nc2cc1OCCCCC(C)O)CCC3] | 6-({9-[(cyclopropylmethyl)amino]-7-methoxy-1H,2H,3H-cyclopenta[b]quinolin-6-yl}oxy)hexan-2-ol |

General Synthetic Schemes

Compounds of this disclosure can be made by the methods depicted in the reaction schemes shown below.

The starting materials and reagents used in preparing these compounds are either available from commercial suppliers such as Sigma-Aldrich Chemical Co., (Milwaukee, Wis.), Acros Organics, Oakwood Chemicals, Matrix Chemicals, and Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). Generic schemes 1-6 are merely illustrative of some methods by which the compounds of this disclosure, and pharmaceutically acceptable salts thereof, can be synthesized, and various modifications to these schemes can be made and will be suggested to one skilled in the art reading this disclosure. The starting materials, the intermediates, and the final products of the reaction(s) may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 200° C., such as from about 0° C. to about 125° C. and further such as at about room (or ambient) temperature, e.g., about 20° C. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of described herein such as compounds of Formula (I-1), and pharmaceutically acceptable salts thereof, are defined herein, and can be prepared as illustrated and described in Scheme 1 below.

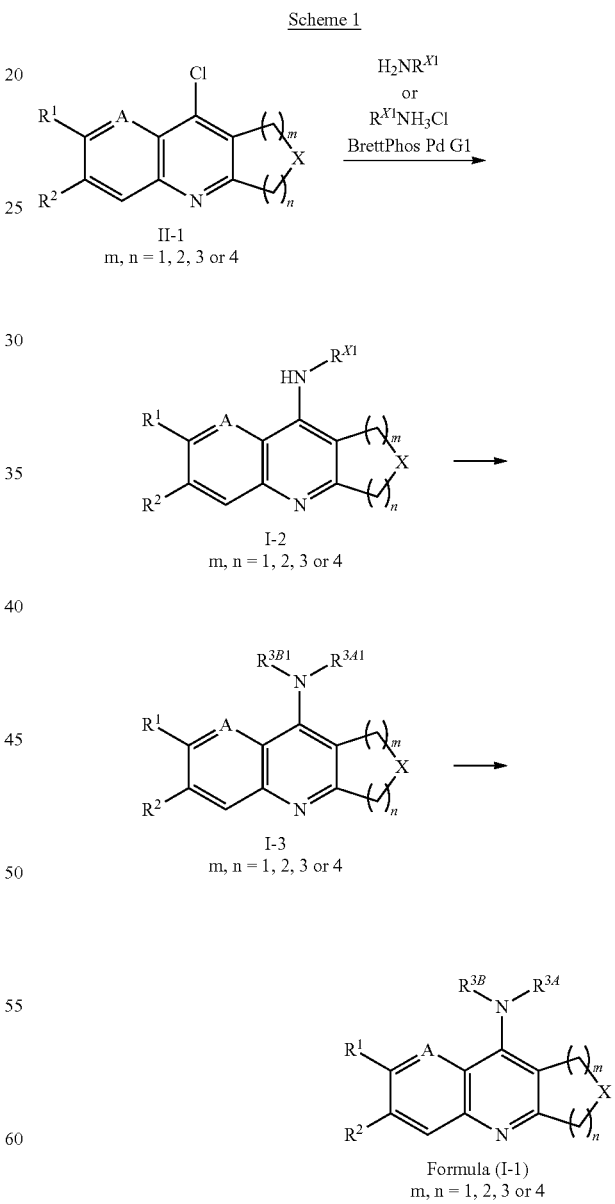

Reacting compounds of formula II-1 wherein A can be N or CH; X can be $CH_2$ or O; and m, n can independently be 1, 2, 3 or 4; $R^1$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), haloalkoxy (for example, —OCH$_2$F, —OCHF$_2$, —OCF$_3$, or —OCH$_2$CF$_3$), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); R$^2$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), cycloalkoxy (for example, cyclopropoxy or cyclobutoxy), alkylamino (for example, —NHMe, —NMe$_2$, or —NHEt), haloalkyl (for example, —CHF$_2$ or —CF$_3$), or haloalkoxy (for example, —OCHF$_2$ or —OCF$_3$), with appropriate commercially available amines H$_2$NR$^{X1}$, or the corresponding HCl salts, under Buchwald coupling conditions using catalysts such as BrettPhos Pd G1, methyl t-butyl ether adduct, provides compounds of formula I-2. Some compounds of formula I-2 are compounds of Formula (I-1). Some compounds of formula I-2 are further converted into compounds of formula I-3 by methods well known in the art, such as TFA mediated removal of the Boc group from nitrogen atom(s) within NR$^{X1}$, or palladium catalyzed hydrogenative cleavage of benzyl group from nitrogen atom(s) within NR$^{X1}$. Some compounds of formula I-3 are compounds of Formula (I-1). Some compounds of formula I-3 are converted to compounds of Formula (I-1) by methods well known in the art, such as N-acylations with appropriate acyl chlorides or acyl anhydride followed with chemical reactions well known in the art, or N-alkylation with appropriate halides or tosylate, reductive aminations with appropriate aldehydes or ketones, or Buchwald coupling with appropriate aryl halides or triflates. This conversion may be carried out once (i.e., wherein R$^{3B}$ can be hydrogen), or twice (i.e., where R$^{3B}$ can be alkyl or —(C=O)—NH$_2$). The acyl chlorides, halides, tosylates, aldehydes, ketones, aryl halides or aryl triflates are available from commercial resources, or easily accessible by synthetic methods well known in the art.

Some of compounds of formula II-1 where A can be CH; X can be CH$_2$ or O; and m, n can independently be 1, 2, 3 or 4; R$^1$ can be alkoxy (for example, methoxy), deuterated alkoxy (for example, —OCD$_3$), haloalkoxy (for example, —OCH$_2$F, —OCHF$_2$, —OCF$_3$, or —OCH$_2$CF$_3$), hydrogen, halogen (for example fluoro or chloro), haloalkyl (for example, —CHF$_2$ or —CF$_3$), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); R$^2$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), cycloalkoxy (for example, cyclopropoxy or cyclobutoxy), alkylamino (for example, —NHMe, —NMe$_2$, or —NHEt), haloalkyl (for example, —CHF$_2$ or —CF$_3$), or haloalkoxy (for example, —OCH$_2$F, —OCHF$_2$, —OCF$_3$, or —OCH$_2$CF$_3$), as defined in the summary can be prepared as illustrated and described in Scheme 2 below.

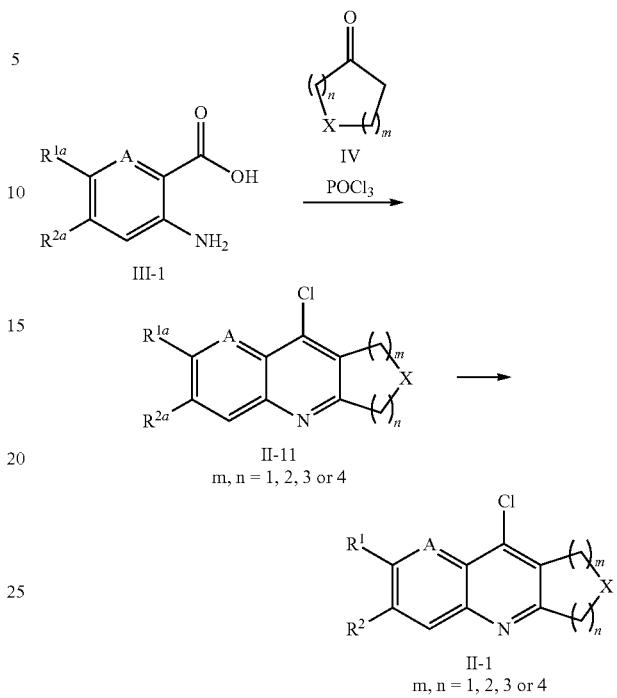

Scheme 2

Reaction of amino carboxylate compounds of formula III-1 where A can be CH; R$^{1a}$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), haloalkoxy (for example, —OCH$_2$F, —OCHF$_2$, —OCF$_3$, or —OCH$_2$CF$_3$), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); R$^{2a}$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), cycloalkoxy (for example, cyclopropoxy or cyclobutoxy), alkylamino (for example, —NHMe, —NMe$_2$, or —NHEt$_2$), haloalkyl (for example, —CHF$_2$ or —CF$_3$), or haloalkoxy (for example, —OCHF$_2$ or —OCF$_3$), with an appropriate cyclic ketones IV where X can be CH$_2$ or O; and m, n can independently be 1, 2, 3 or 4, in the presence of POCl$_3$ provides compounds of formula II-11. Some compounds of formula II-11 are compounds of Formula (I-1). Some compounds of formula II-11 are converted to compounds of formula II-1 by methods well known in the art. Some compounds of formula III-1 are commercially available. Some compounds of formula III-1 can be prepared by methods well known in the art. Compounds of formula IV such as cyclopentanone, cyclohexanone, and cycloheptanone are commercially available.

Some of compounds of formula of II-1 where A can be CH or N; X can be CH$_2$ or O; m, n can independently be 1, 2, 3 or 4; R$^1$ can be alkoxy (for example, methoxy), deuterated alkoxy (for example, —OCD$_3$), haloalkoxy (for example, —OCH$_2$F, —OCHF$_2$, —OCF$_3$, or —OCH$_2$CF$_3$), hydrogen, halogen (for example fluoro or chloro), haloalkyl (for example, —CHF$_2$ or —CF$_3$), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); and R$^2$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), cycloalkoxy (for example, cyclopropoxy or cyclobutoxy), alkylamino (for example, —NHMe, —NMe$_2$, or —NHEt), haloalkyl (for example, —CHF$_2$ or —CF$_3$), or haloalkoxy (for example, —OCHF$_2$ or —OCF$_3$), can be prepared as illustrated and described in Scheme 3 below.

tion with Tf$_2$O in the presence of a base, for example, trimethylamine. Some compounds of formula II-4 are compounds in formula II-1. Some compounds of formula II-4 (for example L=Br or OTf) can be converted to compounds of formula II-1 via chemical transformations well known in the art, including, for example, metal catalyzed hydrogenation or, via Suzuki, Stille, Nigishi or Buchwald coupling reactions with appropriate commercially available reagents. Compounds of formula II-2 can be made from commercially available materials via well-known methods well known in the art as illustrated in scheme 2.

Some compounds of formula II-1 where A can be CH or N; X can be CH$_2$ or O; m, n can independently be 1, 2, 3 or 4; R$^1$ can be hydrogen, cyano, halogen (for example fluoro Scheme 3

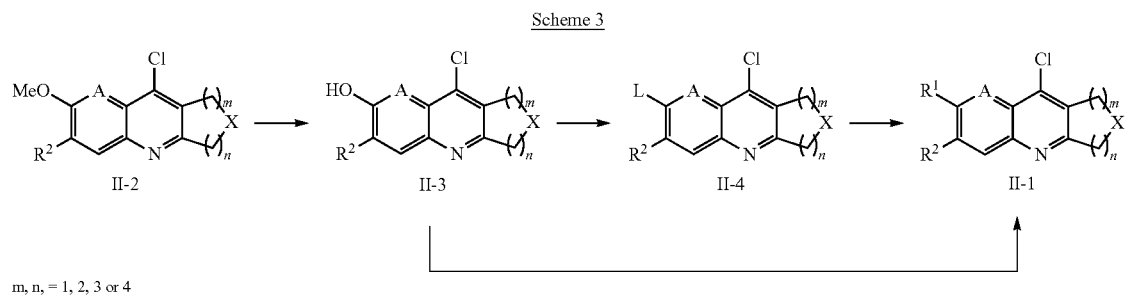

m, n, = 1, 2, 3 or 4

De-methylation of compounds of formula II-2 under conditions well known in the art, such as reacting II-2 with AlCl$_3$, provides hydroxy compounds of formula II-3. Compounds of formula II-3 can also be converted to compounds of formula II-1 (R$^1$=aryloxy (for example, phenoxy) or heteroaryloxy (for example, pyridinoxy, pyrimidinoxy, thiazoloxy, or pyrroloxy)) by reaction with appropriate commercially available aryl halides or heteroaryl halides under conditions well known in the art. Compounds of formula II-3 can be converted to compounds of formula II-4 (L=OCHF$_2$) by reaction with diethyl bromo(difluoro) methyl-phosphonate in the presence of a base, for example, KOH. Compounds of formula II-3 can also be converted to compounds of formula II-4 (L=alkoxy, for example, methoxy, ethoxy, n-propoxy, or iso-propoxy) by either alkylation with appropriate commercially available alkyl halides or Mitsunobu reaction with appropriate commercially available alcohols under conditions well known in the art. Compounds of formula II-3 can also be converted to compounds of formula II-4 (L=Cl or Br) by reaction with POCl$_3$, or POBr$_3$, or to compounds of formula II-4 (L=OTf) by reacor chloro), alkyl (for example, methyl, ethyl, n-propyl, or isopropyl), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); and R$^2$ can be hydrogen, cyano, alkyl (for example, methyl, ethyl, n-propyl, or isopropyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), cycloalkoxy (for example, cyclopropoxy or cyclobutoxy), alkylamino (for example, —NHMe, —NMe$_2$, or —NHEt), haloalkyl (for example, —CHF$_2$ or —CF$_3$), or haloalkoxy (for example, —OCHF$_2$ or —OCF$_3$) can be prepared as illustrated and described in Scheme 4 below.

Scheme 4

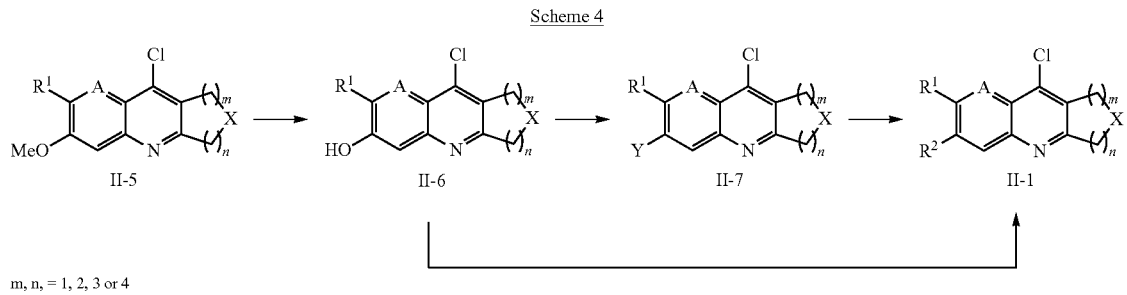

m, n, = 1, 2, 3 or 4

De-methylation of compounds of formula II-5 under reaction conditions well known in the art, such as reacting compounds of formula II-5 with AlCl$_3$, provides hydroxy compounds of formula II-6. Compounds of formula II-6 can be converted to compounds of formula II-1 (R$^2$=aryloxy (for example, phenoxy) or heteroaryloxy (for example, pyridinoxy, pyrimidinoxy, thiazoloxy, or pyrroloxy)) by reaction with appropriate commercially available aryl halides or heteroaryl halides. Compounds of formula II-6 can also be converted to compounds of formula II-1 ($R^2$=OCHF$_2$) by reaction with diethyl bromo(difluoro)methyl-phosphonate in the presence of a base, such as KOH. Compounds of formula II-6 can also be converted to compounds of formula II-1 ($R^2$=alkoxy (for example, methoxy, ethoxy, n-propoxy, or iso-propoxy) or cycloalkoxy (for example, cyclopropoxy or cyclobutoxy)) by alkylation with appropriate commercially available alkyl halides. Some compounds of formula II-6 can also be converted to compounds of formula II-7 ($R^2$=alkoxy (for example, methoxy, ethoxy, n-propoxy, or iso-propoxy), deuterated alkoxy (for example, —OCD$_3$, —OCH$_2$CD$_3$, or —OCD$_2$CD$_3$), or cycloalkoxy (for example, cyclopropoxy or cyclobutoxy)) either by alkylation with appropriate commercially available alkyl halides or by Mitsunobu reactions with appropriate commercially available alcohols under conditions well known in the art. Compounds of formula II-6 can also be converted to compounds of formula II-7 (Y=Cl or Br) by reaction with POCl$_3$, or POBr$_3$, or to compounds of formula II-7 (Y=OTf) by reaction with Tf$_2$O in the presence of a base, such as trimethylamine. Some compounds of formula II-7 are compounds of formula II-1. Some compounds of formula II-7 can be converted to compounds of formula II-1 by appropriate chemical transformation of the Y group via methods well known in the art including, for example, desilyation, alkylation, acylation, and sulfonylation. Some compounds of formula II-7 (for examples Y=Br or OTf) can be converted to compounds of formula II-1 by appropriate chemical transformation of Y group via methods well known in the art, for example, via metal catalyzed hydrogenation, or via metal-catalyzed coupling reactions such as Suzuki, Stille, Nigishi or Buchwald reactions with appropriate commercially available reagents. Compounds of formula II-5 can be made from commercially available materials via well-known methods as illustrated in scheme 2.

Some compounds of formula II-1 where A can be N; X can be CH$_2$ or O; m, n can independently be 1, 2, 3 or 4; $R^1$ can be hydrogen, cyano, halogen (for example fluoro or chloro), alkyl (for example, methyl, ethyl, n-propyl, or isopropyl), alkylamino (for example, —NHMe, —NMe$_2$, or —NHEt), cycloalkyl (for example, cyclopropyl or cyclobutyl), aryloxy (for example, phenoxy), heteroaryloxy (for example, pyridinoxy, pyrimidinoxy, thiazoloxy, or pyrroloxy), haloalkoxy (for example, —OCHF$_2$ or —OCF$_3$), alkoxy (for example, methoxy, ethoxy, n-propoxy, or iso-propoxy), or deuterated alkoxy (for example, —OCD$_3$, —OCH$_2$CD$_3$, or —OCD$_2$CD$_3$); and $R^2$ can be hydrogen, cyano, halogen (for example fluoro or chloro), alkyl (for example, methyl, ethyl, n-propyl, or isopropyl), alkoxy (for example, methoxy, ethoxy, n-propoxy, or iso-propoxy), cycloalkoxy (for example, cyclopropoxy or cyclobutoxy), alkylamino (for example, —NHMe, —NMe$_2$, or —NHEt), haloalkoxy (for example, —OCHF$_2$ or —OCF$_3$), haloalkoxy (for example, —OCHF$_2$ or —OCF$_3$); can be prepared as illustrated and described in Scheme 5 below.

Scheme 5

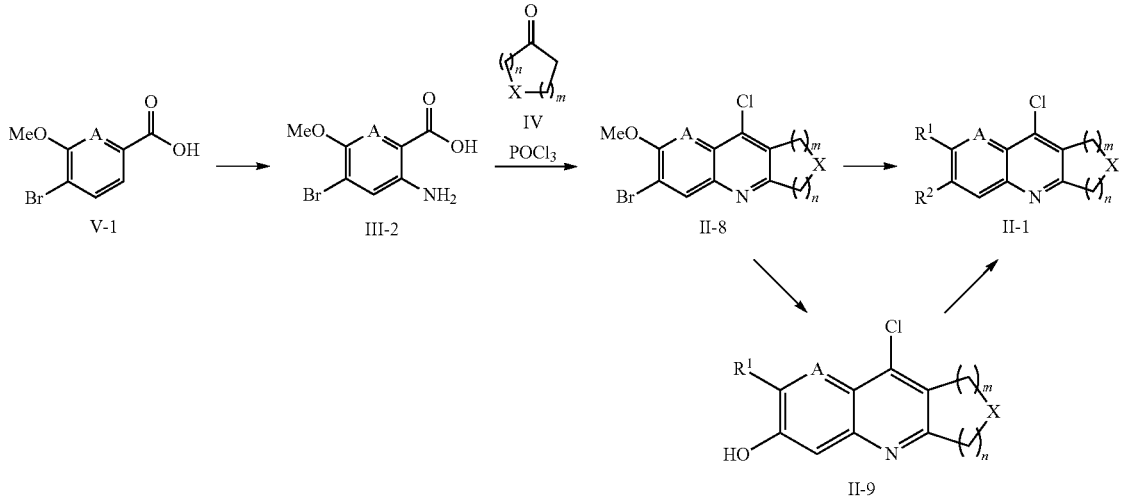

m, n, = 1, 2, 3 or 4

Nitration of compounds of formula V-1 followed by reduction of the resulting product by methods well known in the art, including treatment with SnCl$_2$, or treatment with iron in the presence of NH$_4$Cl, provides the amino-carboxylate compounds of formula III-2. Compounds of formula III-2 are converted to compounds of formula II-8 upon reaction with appropriate cyclic ketone compounds of formula IV in the presence of POCl$_3$. Some compounds of formula II-8 are compounds of formula II-1. Reacting some compounds of formula II-8 with 4,4,5,5-tetramethyl-2-(propan-2-yloxy)-1,3,2-dioxaborolane in the presence of "BuLi, followed by reaction of the resulting product with hydrogen peroxide provides compounds of formula II-9, which after chemical transformations well known in the art, including, for example, O-alkylation, or Mitsunobu reactions with appropriate reagents, lead to compounds of formula II-1 ($R^1$=MeO; $R^2$=alkoxy, for example, methoxy, ethoxy, n-propoxy, or isopropoxy). Some compounds of formula II-8 can also be converted to compounds of formula II-1 via metal catalyzed coupling reactions well known in the arts, including, for example, Suzuki, Stille, Nigishi and Buchwald reactions.

Some compounds of formula II-1 where A can be CH; X can be CH$_2$ or O; m, n can independently be 1, 2, 3 or 4; $R^1$ and $R^2$ together form —OCH$_2$O— linkage, can be prepared as illustrated and described in Scheme 6 below.

Scheme 6

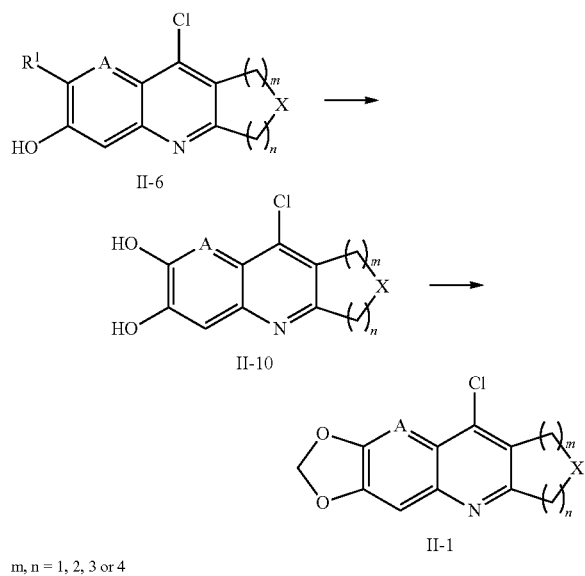

m, n = 1, 2, 3 or 4

De-methylation of compounds of formula II-6 ($R^1$=OMe) with BBr$_3$ provides the dihydroxy compounds of formula II-10, which upon treatment with dibromoethane in the presence of CsF leads to compounds of formula II-1 (A can be CH; X can be CH$_2$ or O; m, n can be 1, 2, 3 or 4; $R^1$ and $R^2$ together form a —OCH$_2$O— linkage.

Compounds of described herein such as compounds of Formula (I-2), and pharmaceutically acceptable salts thereof, are defined herein, and can be prepared as illustrated and described in Scheme 7 below.

cyano, alkyl (for example, methyl, ethyl, n-propyl, or iso-propyl), alkoxy (for example, methoxy, ethoxy, n-propoxy, or iso-propoxy), deuterated alkoxy (for example, —OCD$_3$, —OCH$_2$CD$_3$, or —OCD$_2$CD$_3$), alkylamino (for example, —NHMe, —NMe$_2$, or —NHEt), cycloalkyl (for example, cyclopropyl or cyclobutyl), aryloxy (for example, phenoxy), or heteroaryloxy (for example, pyridinoxy, pyrimidinoxy, thiazoloxy, or pyrroloxy); $R^{2b}$ can be hydrogen, halogen (for example, fluoro or chloro), cyano, alkyl (for example, methyl, ethyl, n-propyl, or isopropyl), alkoxy (for example, methoxy, ethoxy, n-propoxy, or iso-propoxy), cycloalkoxy (for example, cyclopropoxy or cyclobutoxy), alkylamino (for example, —NHMe, —NMe$_2$, or —NHEt), haloalkyl (for example, —CHF$_2$ or —CF$_3$), or haloalkoxy (for example, —OCHF$_2$ or —OCF$_3$), with appropriate aryl or heteroaryl halides (for example, phenyl or naphthyl halides, or 5 to 10 membered nitrogen containing heteroaryl halides) compounds of formula VI-1 (D=Cl, Br or I), or an aryl or heteroaryl trifluoromethanesulfonate (for example, phenyl or naphthyl triflates, or 5 to 10 membered nitrogen containing heteroaryl triflates) compounds of formula VI-1 (D=OTf), under appropriate conditions, for example, Buchwald coupling condition using catalysts such as BrettPhos Pd G1, methyl t-butyl ether adduct, provides compounds of formula VII-1. Some compounds of formula VII-1 ($R^{1bb}$=H) are further converted into compounds of formula VIII-1 by methods well known in the art, such as reaction with POCl$_3$. Some compounds of formula VII-1 (for example, $R^{1bb}$=C$_1$-C$_6$ alkyl as described herein, such as methyl or ethyl) are further converted into compounds of formula VIII-1 through saponification followed by treatment with POCl$_3$. Some compounds of formula VIII-1 can further react with appropriate commercially available amines HNR$^{3B1}$R$^{3A1}$, or the corresponding HCl salts, under Buchwald coupling condition using catalysts such as BrettPhos Pd G1, methyl t-butyl ether adduct, to provide compounds of formula IX-1. Some compounds of IX-1 are compounds in formula of I-2. Some compounds of formula IX-1 are converted to compounds of Formula (I-2) via appropriate chemical modifications of the

Scheme 7

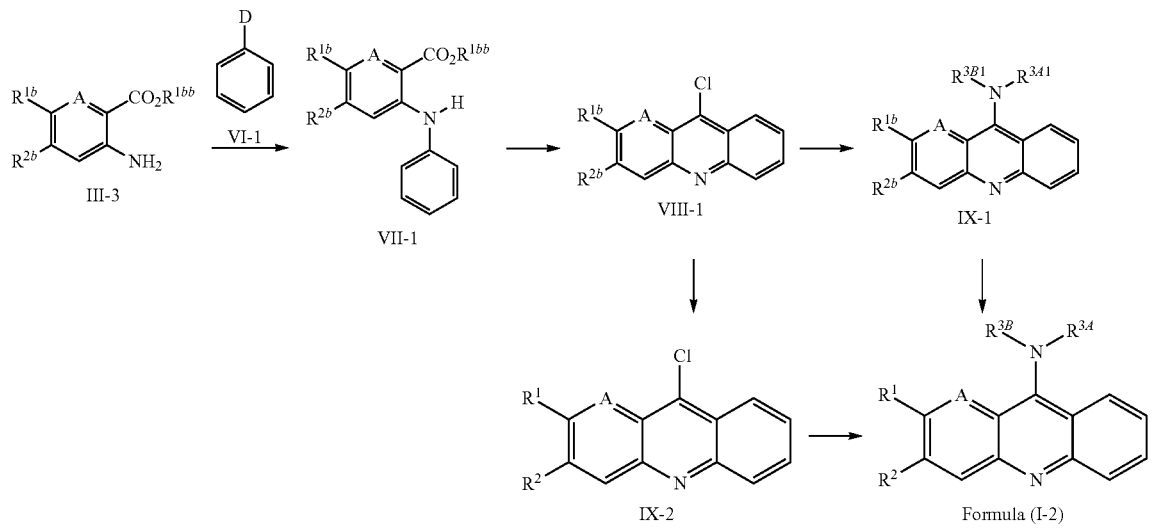

Reacting compounds of formula III-3 wherein A can be N or CH; $R^{1bb}$ can be H, alky, for example, methyl, ethyl; $R^{1b}$ can be hydrogen, halogen (for example, fluoro or chloro), $R^{1b}$, and/or the $R^{2b}$, and/or $R^{3B1}$, and/or $R^{3A1}$ group(s) under conditions well known in the art. Some compounds of formula VIII-1 can also be converted to compounds of formula IX-2 under appropriate conditions well known in the art. Compounds of formula IX-2 can be further converted to compounds of Formula (I-2) by reaction with appropriate commercially available amines $HNR^{3B1}R^{3A1}$, or the corresponding HCl salts, under conditions well known in the art, for example, Buchwald coupling conditions using catalysts such as BrettPhos Pd G1, methyl t-butyl ether adduct, optionally followed by further chemical transformations of the $R^{3B1}$ and or $R^{3A1}$ groups under conditions well known in the art. Some compounds of formula III-3, for example, 2-amino-4,5-dimethoxybenzoic acid, are commercially available. Some compounds of formula III-3 can be readily accessible from commercially available material (for example, methyl 3,4-dimethoxybenzoate, ethyl 3,4-dimethoxybenzoate) through conditions well known in the art.

Testing

The G9a inhibitory activity of the compounds of the present disclosure can be tested using the in vitro assay described in Biological Examples 1 below.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg subject body weight per day, which can be administered in single or multiple doses. A suitable dosage level may be from about 0.1 to about 250 mg/kg per day or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, or 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents and/or anti-cancer therapies. In some embodiments, the anti-cancer therapies can be surgery and/or radiation therapy. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation and analogs of paclitaxel (Taxol™), such as docetaxel (Taxotere™). Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, or axitinib; EGFR inhibitor such as afatinib, brivanib, carbozantinib, erlotinib, gefitinib, neratinib, or lapatinib; PI3K inhibitor such as XL147, XL765, BKM120 (buparlisib), GDC-0941, BYL719, IPI145, BAY80-6946. BEX235 (dactolisib), CAL101 (idelalisib), GSK2636771, or TG100-115; MTOR inhibitor such as rapamycin (sirolimus), temsirolimus, everolimus, XL388, XL765, AZD2013, PF04691502, PKI-587, BEZ235, or GDC0349; MEK inhibitor such as AZD6244, trametinib, PD184352, pimasertinib, GDC-0973, or AZD8330; and proteasome inhibitor such as carfilzomib, MLN9708, delanzomib, or bortezomib.

Other anti-cancer agents that can be employed in combination with a compound of this disclosure include adriamycin; dactinomycin; bleomycin; vinblastine; cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or RiI2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a compound of the disclosure including 20-epi-analogues of 1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+, diethylstibestrol; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; Rn retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan, etc.), nitrosoureas (e.g., carmustine, lomusitne, etc.), or triazenes (decarbazine, etc.). Examples of antimetabolites include but are not limited to folic acid analog (e.g., methotrexate), pyrimidine analogs (e.g., cytarabine, etc.), or purine analogs (e.g., mercaptopurine, thioguanine, pentostatin, etc.).

Examples of natural products useful in combination with a compound of this disclosure include but are not limited to vinca alkaloids (e.g., vincristine, etc.), epipodophyllotoxins (e.g., etoposide, etc.), antibiotics (e.g., daunorubicin, doxorubicin, bleomycin, etc.), enzymes (e.g., L-asparaginase, etc.), or biological response modifiers (e.g., interferon alpha, etc.).

Examples of alkylating agents that can be employed in combination a compound of this disclosure include, but are not limited to, nitrogen mustards (e.g., mechloroethamine, cyclophosphamide, chlorambucil, melphalan, etc.), ethylenimine and methylmelamines (e.g., hexamethlymelamine, thiotepa, etc.), alkyl sulfonates (e.g., busulfan, etc.), nitrosoureas (e.g., carmustine, lomusitne, semustine, streptozocin, etc.), or triazenes (decarbazine, etc.). Examples of antimetabolites include, but are not limited to folic acid analog (e.g., methotrexate, etc.), pyrimidine analogs (e.g., fluorouracil, floxuridine, cytarabine, etc.), or purine analogs (e.g., mercaptopurine, thioguanine, pentostatin, etc.).

Examples of hormones and antagonists useful in combination a compound of this disclosure include, but are not limited to, adrenocorticosteroids (e.g., prednisone, etc.), progestins (e.g., hydroxyprogesterone caproate, megestrol acetate and medroxyprogesterone acetate, etc.), estrogens (e.g., diethylstilbestrol and ethinyl estradiol, etc.), antiestrogen (e.g., tamoxifen, etc.), androgens (e.g., testosterone propionate, fluoxymesterone, etc.), antiandrogen (e.g., flutamide, etc.) and gonadotropin releasing hormone analog (e.g., leuprolide, etc.). Other agents that can be used in the methods and compositions described herein for the treatment or prevention of cancer include platinum coordination complexes (e.g., cisplatin, carboplatin, etc.), anthracenedione (e.g., mitoxantrone, etc.), substituted urea (e.g., hydroxyurea, etc.), methyl hydrazine derivative (e.g., procarbazine, etc.) and adrenocortical suppressant (e.g., mitotane, aminoglutethimide, etc.).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8 and Spongistatin 9), Cemadotin hydrochloride (also known as LU-103793 and NSC-D-669356), Epothilones (such as Epothilone A, Epothilone B, Epothilone C (also known as desoxyepothilone A or dEpoA)), Epothilone D (also referred to as KOS-862, dEpoB and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone, Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as TEX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (*Asta Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A and Z-Eleutherobin), Caribaeoside, Caribaeolin, Halichondrin B, D-64131 (*Asta Medica*), D-68144 (*Asta Medica*), Diazonamide A, A-293620 (Abbott), NPI-2350 (Nereus), Taccalonolide A, TUB-245 (Aventis), A-259754 (Abbott), Diozostatin, (—)-Phenylahistin (also known as NSCL-96F037), D-68838 (*Asta Medica*), D-68836 (*Asta Medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes) and SSR-250411 (Sanofi).

EXAMPLES

The following preparations of compounds of Formula (I) (Examples) and intermediates (References) are given to enable those skilled in the art to more clearly understand and to practice the present disclosure. They should not be considered as limiting the scope of the disclosure, but merely as being illustrative and representative thereof.

Common intermediates that had been made for the syntheses of the described examples are listed in Table A below:

TABLE A

| Intermediate No. | Structure |
|---|---|
| 1 | (cyclopenta-fused dimethoxyquinoline with Cl) |
| 2 | (tetrahydro dimethoxyacridine with Cl) |
| 3 | (dimethoxyacridine with Cl) |

TABLE A-continued

| Intermediate No. | Structure |
|---|---|
| 4 | 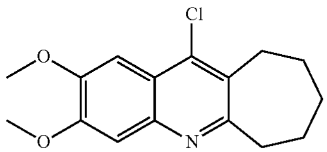 [SMILES: COc1cc2nc3c(c(Cl)c2cc1OC)CCCCC3] |
| 5 | 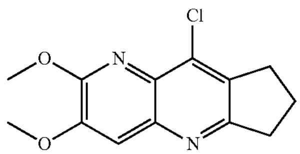 [SMILES: COc1cc2nc3c(c(Cl)c2nc1OC)CCC3] |
| 1-a | 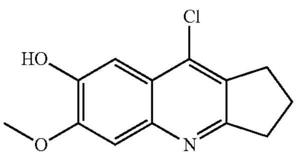 [SMILES: COc1cc2nc3c(c(Cl)c2cc1O)CCC3] |
| 1-b | 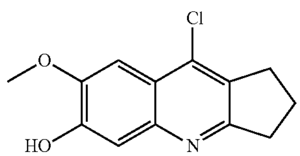 [SMILES: COc1cc2c(Cl)c3c(nc2cc1O)CCC3] |
| 6 | 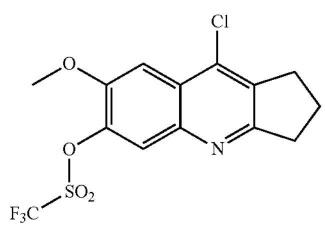 [SMILES: COc1cc2c(Cl)c3c(nc2cc1OS(=O)(=O)C(F)(F)F)CCC3] |
| 7 | 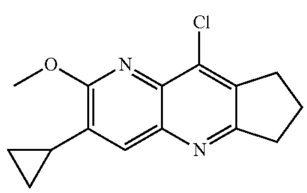 [SMILES: COc1nc2c(Cl)c3c(nc2cc1C1CC1)CCC3] |
| 8 | 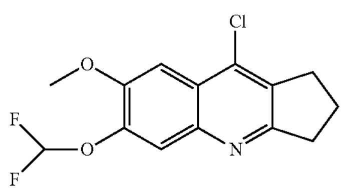 [SMILES: COc1cc2c(Cl)c3c(nc2cc1OC(F)F)CCC3] |
| 9 | 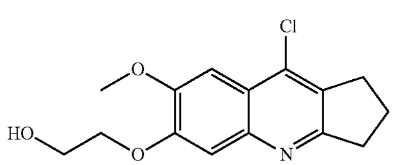 [SMILES: COc1cc2c(Cl)c3c(nc2cc1OCCO)CCC3] |

Reference 1

9-chloro-6,7-dimethoxy-1H,2H,3H-cyclopenta[b]quinolone (Intermediate 1)

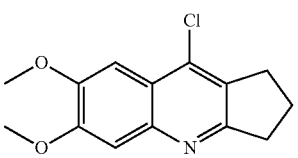 [SMILES: COc1cc2nc3c(c(Cl)c2cc1OC)CCC3]

Into a 3-L 4-necked round-bottom flask, was placed 2-amino-4,5-dimethoxybenzoic acid (80 g, 405.70 mmol, 1 eq), POCl$_3$ (2.5 L) and cyclopentanone (37.8 g, 449.38 mmol, 1.10 eq). The solution was stirred at 110° C. for 16 h. After removal of the volatiles under reduced pressure, the remaining residue was treated with ice/water (1.0 L), basified with 1 N NaOH (aq) to pH=7~8 and extracted with a mixed solution of CH$_2$Cl$_2$/methanol (MeOH) (V/V-10/1, 5×1.0 L). The organic layers were dried over anhydrous Na$_2$SO$_4$ and concentrated under reduced pressure. The residue was purified by chromatography on silica gel column with ethyl acetate (EtOAc)/petroleum ether (1:1) to provide the title compound as a white solid (25.7 g, 24%). LCMS (ES) [M+1]$^+$ m/z 264.0.

Reference 2

9-chloro-6,7-dimethoxy-1,2,3,4-tetrahydroacridine (Intermediate 2)

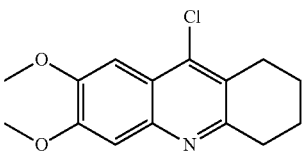 [SMILES: COc1cc2nc3c(c(Cl)c2cc1OC)CCCC3]

The title compound was made from 2-amino-4, 5-dimethoxybenzoic acid and cyclohexanone following a synthetic method similar as described for Intermediate 1 (reference 1). LCMS (ES) [M+1]$^+$ m/z 278.1.

Reference 3

9-chloro-2,3-dimethoxyacridine (Intermediate 3)

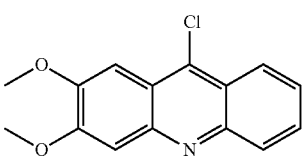 [SMILES: COc1cc2nc3ccccc3c(Cl)c2cc1OC]

Step 1

To a solution of methyl 4,5-dimethoxy-2-nitrobenzoate (10.0 g, 41.46 mmol, 1 eq) in MeOH (200 mL) was added 10% Pd/C (50% water moistened, 2.0 g). The mixture was degassed and purged with hydrogen gas three times. The mixture was stirred under H$_2$ atmosphere at room temperature (rt) for 16 h. The solids were filtered off through a pad of celite. The filtrate was concentrated under reduced pressure to provide methyl 2-amino-4,5-dimethoxybenzoate as a yellow solid (7.6 g, 87%). LCMS (ES) [M+1]$^+$ m/z 212.2.

Step 2

Into a 500-mL round-bottom flask, was placed methyl 2-amino-4,5-dimethoxybenzoate (7.5 g, 35.51 mmol, 1 eq), iodobenzene (8.7 g, 42.65 mmol, 1.20 eq), 1,4-dioxane (150 mL), Cs$_2$CO$_3$ (23.2 g, 71.20 mmol, 2 eq), XantPhos (2.1 g, 3.63 mmol, 0.10 eq) and Pd$_2$(dba)$_3$ (1.8 g, 1.97 mmol, 0.05 eq). The mixture was stirred for 16 h at 100° C. under N$_2$. The mixture was filtered and the filter cake was washed with EtOAc (2×100 mL). The filtrate was concentrated under reduced pressure and the residue was purified by chromatography on silica gel column with EtOAc/Hexanes troleum (1:2) to provide methyl 4,5-dimethoxy-2-(phenylamino) benzoate as a light yellow solid (4.55 g, 45%). LCMS (ES) [M+1]$^+$ m/z 288.1.

Step 3

Into a 100-mL round-bottom flask, was placed methyl 4,5-dimethoxy-2-(phenylamino)benzoate (4.5 g, 15.66 mmol, 1 eq), MeOH (40 mL), water (10 mL) NaOH (1.3 g, 31.32 mmol, 2 eq). The solution was stirred for 4 h at 80° C. The solution was concentrated under reduced pressure. To the residue was added water (20 mL) and acidified with HCl (1 mol/L) (pH ~4). The mixture was extracted with EtOAc (3×30 mL). The combined organic layer was washed with brine (30 mL), dried over anhydrous Na$_2$SO$_4$ and concentrated under reduced pressure to provide 4,5-dimethoxy-2-(phenylamino)benzoic acid as a light yellow solid (3.58 g, 84%). LCMS (ES) [M+1]$^+$ m/z 274.2.

Step 4

Into a 100-mL round-bottom flask, was placed a solution of 4,5-dimethoxy-2-(phenylamino)benzoic acid (2.0 g, 7.32 mmol, 1 eq) and POCl$_3$ (40 mL). The solution was stirred for 16 h at 110° C. The mixture was concentrated under reduced pressure and ice water (50 mL) was added, basified with 10% NaHCO$_3$ (aq) to pH 7~8 and extracted with EtOAc (200 mL). The organic layer was dried over anhydrous Na$_2$SO$_4$ and concentrated under reduced pressure, and the residue was purified by flash chromatography on silica gel with EtOAc/Hexanes (1:1) as eluents to provide the title compound as a light yellow solid (1.54 g, 77%). LCMS (ES) [M+1]$^+$ m/z 274.1.

Reference 4

11-chloro-2,3-dimethoxy-6H,7H,8H,9H, 10H-cyclohepta[b]quinolone (Intermediate 4)

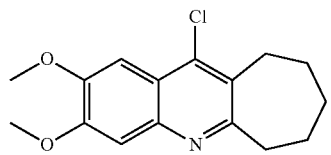

The title compound was made from 2-amino-4, 5-dimethoxybenzoic acid and cycloheptanone following a synthetic method similar as described for Intermediate 1 (reference 1), except that the final crude product was purified by flash chromatography on silica gel with EtOAc/Hexanes (1:1) as eluents to provide the title compound as a yellow solid 1.7 g (21%). LCMS (ES) [M+1]$^+$ m/z 292.0.

Reference 5

9-chloro-2,3-dimethoxy-6H,7H,8H-cyclopenta[b]1, 5-naphthyridine (Intermediate 5)

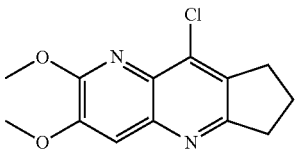

Step 1

To a solution of 5-bromo-6-methoxypyridine-2-carboxylic acid (500 mg, 2.15 mmol, 1 eq) in sulfuric acid (10 mL) in ice bath was added HNO$_3$ (5 mL) dropwise. The solution was stirred at 60° C. for 16 h. After cooling to rt, the solution was poured into ice/water (20 mL). The solids were collected by filtration to provide 3-amino-5-bromo-6-methoxypyridine-2-carboxylic acid as a light yellow solid (260 mg, 44%). LCMS (ES) [M−1]$^-$ m/z 275.0.

Step 2

To 5-bromo-6-methoxy-3-nitropyridine-2-carboxylic acid (2.6 g, 9.39 mmol, 1 eq) in EtOH (25 mL) and water (25 mL) was added NH$_4$Cl (1.49 g, 28.17 mmol, 3 eq) and Fe (dust) (2.63 g, 46.95 mmol, 5 eq). The mixture was stirred at 70° C. for 3 h. The mixture was basified with 2.0 N NaOH (aq) to pH ~10. The precipitate was filtered. The filter cake was washed with MeOH/H$_2$O (V/V=1/1, 2×50 mL). The filtrate was concentrated under reduced pressure. The residue was redissolved in DMF (20 mL), filtered and subjected to reverse phase preparative HPLC (Prep-C18, 20-45 μM, 120 g, Tianjin Bonna-Agela Technologies; gradient elution of 0% MeCN in water to 5% MeCN in water over a 7 min period, 100% MeCN to 100% MeCN over a 4 min period, where both solvents contain 0.05% FA) to provide 3-amino-5-bromo-6-methoxypyridine-2-carboxylic acid as a light yellow solid (1.0 g, 43%). LCMS (ES) [M−1]$^-$ m/z 245.0.

Step 3

To a solution of 3-amino-5-bromo-6-methoxypyridine-2-carboxylic acid (1.0 g, 4.05 mmol, 1 eq) in POCl$_3$ (30 mL) was added cyclopentanone (680 mg, 8.10 mmol, 2 eq). The solution was stirred at 90° C. for 16 h. The mixture was concentrated under reduced pressure. To the residue was added CH$_2$Cl$_2$ (25 mL) and the mixture was slowly added into ice/water (100 mL) dropwise. The mixture was then basified with 2.0 N NaOH (aq.) to pH=10 and extracted with EtOAc thrice. The combined organic layers were dried over anhydrous Na$_2$SO$_4$ and concentrated under reduced pressure. The residue was purified by chromatography on silica gel column with EtOAc/Hexanes (1/2) as eluents to provide 3-bromo-9-chloro-2-methoxy-6H, 7H, 8H-cyclopenta[b] 1, 5-naphthyridine as a light yellow solid (700 mg, 55%). LCMS (ES) [M+1]$^+$ m/z 315.1.

Step 4

To a solution of 3-bromo-9-chloro-2-methoxy-6H,7H,8H-cyclopenta[b]1,5-naphthyridine (700 mg, 2.23 mmol, 1 eq) and 4,4,5,5-tetramethyl-2-(propan-2-yloxy)-1,3,2-dioxaborolane (1.24 g, 6.69 mmol, 3 eq) in dry THF (15 mL) at −78° C. under N$_2$ atmosphere was added $^n$BuLi (2.7 mL, 2.5 M in hexane, 6.69 mmol, 3 eq) dropwise. The solution was stirred at −78° C. for 1 h before being quenched with H$_2$O (2 mL) followed with H$_2$O$_2$ (30% aq., 2 mL). The mixture was stirred at rt for additional 1 h. To the solution was added saturated aq.Na$_2$SO$_3$ (30 mL) and the mixture was stirred at rt for 30 min. The crude mixture was extracted with EtOAc (5×50 mL). The organic layers were combined, dried over anhydrous Na$_2$SO$_4$ and concentrated under reduced pressure. The residue was purified by chromatography on silica gel column with EtOAc/Hexanes (2/1) as eluents to provide 9-chloro-2-methoxy-6H, 7H, 8H-cyclopenta[b] 1, 5-naphthyridin-3-ol as a light yellow solid (301 mg, 54%). LCMS (ES) [M+1]$^+$ m/z 251.2.

Step 5

To a solution of 9-chloro-2-methoxy-6H,7H,8H-cyclopenta[b]1,5-naphthyridin-3-ol (301 mg, 3.99 mmol, 1.2 eq) in MeCN (10 mL) was added K$_2$CO$_3$ (490 mg g, 3.02 mmol, 3 eq) and MeI (256 mg, 1.8 mmol, 1.50 eq). The mixture was stirred for 1 h at rt. The mixture was concentrated under reduced pressure. The residue was purified by chromatography on silica gel column with EtOAc/Hexanes (2:1) as eluents to provide 204 mg (65%) of the title compound as an off-white solid. LCMS (ES) [M+1]$^+$ m/z 265.0.

Reference 6

9-chloro-7-methoxy-1H,2H,3H-cyclopenta[b]quinolin-6-ol (Intermediate 1-b)

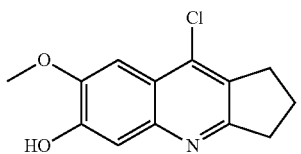

Step 1

Into a 2-L 4-necked round-bottom flask was placed 9-chloro-6,7-dimethoxy-1H,2H,3H-cyclopenta[b]quinolone (Intermediate 1) (31.6 g, 0.12 mol, 1 eq), CH$_2$Cl$_2$ (1.0 L) followed by AlCl$_3$ (47.88 g, 0.36 mol 3 eq). The solution was stirred at 40° C. for 16 h. This reaction was repeated in this same scale for 4 batches. The reaction mixtures were combined, treated with ice/water (2.0 L) and basified with aq. NaOH (1.0 N) to pH 7~8. The mixture were combined and directly used in the next step without purification.

Step 2

To the above mixture was added CH$_2$Cl$_2$ (2.0 L), BoC$_2$O (314 g, 1.44 mol, 3 eq) and 4-dimethylaminopyridine (6.1 g, 0.05 mol, 0.10 eq). The mixture was stirred at rt for 16 h. The organic layer was separated. The water layer was back extracted with a mixed solution of CH$_2$Cl$_2$/MeOH (V/V=10/1, 3.0 L) thrice. All the organic layers were combined and dried over anhydrous Na$_2$SO$_4$. After removal of the organic solvents under reduced pressure, the residue was purified by chromatography on silica gel column with EtOAc/Hexanes (5:1 to 1:1) as eluents to provide tert-butyl 9-chloro-7-methoxy-2,3-dihydro-1H-cyclopenta[b]quinolin-6-yl carbonate as white solid (48 g, 20%), LCMS (ES) [M+1]$^+$ m/z 350.1; and tert-butyl 9-chloro-6-methoxy-2,3-dihydro-1H-cyclopenta [b]quinolin-7-yl carbonate as a white solid (50 g, 21%), LCMS (ES) [M+1]$^+$ m/z 350.1.

Step 3

Into a rt solution of tert-butyl 9-chloro-7-methoxy-2,3-dihydro-1H-cyclopenta[b]quinolin-6-yl carbonate (48.0 g, 0.14 mol, 1 eq) in CH$_2$Cl$_2$ (500 mL) was added a sat. HCl solution in 1,4-dioxane (175 mL) dropwise. The solution was stirred at rt for 16 h. After removal of volatiles under reduced pressure, the residue was triturated with EtOAc (2×200 mL) to provide of the title compound as a light brown solid (25.26 g, 74%). LCMS (ES) [M+1]$^+$ m/z 250.0.

Reference 7

9-chloro-6-methoxy-1H,2H,3H-cyclopenta[b]quinolin-7-ol (Intermediate 1-a)

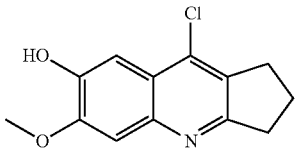 [SMILES: COc1cc2nc3c(c(Cl)c2cc1O)CCC3]

To a solution of tert-butyl 9-chloro-6-methoxy-2,3-dihydro-1H-cyclopenta[b]quinolin-7-yl carbonate (Reference 6, step 2) (1.2 g, 3.43 mmol, 1 eq) in CH$_2$Cl$_2$ (20 mL) was added a sat. HCl solution in 1,4-dioxane (10 mL) sat. HCl (gas) dropwise. The solution was stirred at rt for 16 h. After removal of organic volatiles under reduced pressure, the remaining residue was triturated with EtOAc (2×10 mL) to provide the title compound as an off-white solid (769.1 mg, 90%). LCMS (ES) [M+1]$^+$ m/z 250.0.

Reference 8

9-chloro-7-methoxy-1H,2H,3H-cyclopenta[b]quinolin-6-yl trifluoromethanesulfonate (Intermediate 6)

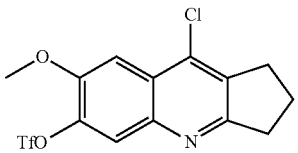

To 9-chloro-7-methoxy-1H,2H,3H-cyclopenta[b]quinolin-6-ol (Intermediate 1-b, reference 6) (450 mg; 1.80 mmol; 1 eq.) in CH$_2$Cl$_2$ (7 mL) and Et$_3$N (3 mL) in ice bath under N$_2$ atmosphere was added trifluoromethanesulfonyl trifluoromethanesulfonate (762.71 mg; 2.70 mmol; 1.50 eq.) dropwise. The mixture was allowed to warm with the ice bath to rt and stir at rt for 6 hr. The mixture was concentrated under reduced pressure and the remaining residue was purified by flash chromatography on silica gel column with 0-5% MeOH/CH$_2$Cl$_2$ as eluent to provide the title compounds as an off-white solid (350 mg, 51%), LCMS (ES) [M+1]$^+$ m/z 382.1.

Reference 9

9-chloro-3-cyclopropyl-2-methoxy-6H,7H,8H-cyclopenta[b]1,5-naphthyridine (Intermediate 7)

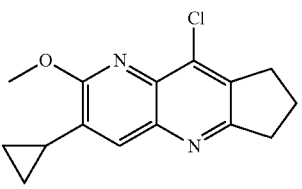 [SMILES: COc1nc2c(Cl)c3c(nc2cc1C1CC1)CCC3]

A mixture of 9-chloro-7-methoxy-1H,2H,3H-cyclopenta[b]quinolin-6-yl trifluoromethane sulfonate (Intermediate 6) (50 mg; 0.13 mmol; 1 eq.), cyclopropylboronic acid (13.50 mg; 0.16 mmol; 1.20 eq.), Pd(dppf)$_2$Cl$_2$—CH$_2$Cl$_2$ (10.70 mg; 0.01 mmol; 0.10 eq.) and K$_2$CO$_3$ (54.22 mg; 0.39 mmol; 3 eq.) in toluene (1.5 mL) and water (0.2 mL) was purged with N$_2$ for 2 min. The reaction vessel was sealed and the mixture was stirred at 80° C. for 90 min. The mixture was cooled to rt, diluted with water and extracted with EtOAc thrice. The combined organic layers were concentrated under reduced pressure. The remaining residue was purified by flash chromatography on silica gel column with 0-100% EtOAc/Hexanes as eluent to provide the title compound as a white solid (22 mg, 62%). LCMS (ES) [M+1]$^+$ m/z 274.0.

Reference 10

9-chloro-6-(difluoromethoxy)-7-methoxy-1H,2H,3H-cyclopenta[b]quinolone (Intermediate 8)

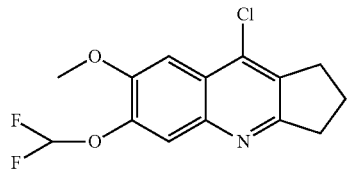 [SMILES: COc1cc2c(Cl)c3c(nc2cc1OC(F)F)CCC3]

Into 9-chloro-7-methoxy-1H,2H,3H-cyclopenta[b]quinolin-6-ol (Intermediate 1-b) (491 mg; 1.97 mmol; 1 eq.) and KOH (3309.81 mg; 58.99 mmol; 30 eq.) in MeCN (2 mL) and water (2 mL) in an ice bath was added diethyl bromo(difluoro)methylphosphonate (2*100.2 mg; 7.87 mmol; 4 eq.). After 5 min, the mixture was removed from ice bath and was stirred at rt for 60 min and then at 50° C. for 60 min subsequently. The mixture was cooled to rt, diluted with water and extracted with EtOAc thrice. The organic layers were combined. After removal of the organic volatiles under reduced pressure, the remaining residue was purified by chromatography on silica gel column with 0-50% EtOAc/Hexanes to provide the title compound as an off white solid (385 mg, 65%). LCMS (ES) [M+1]$^+$ m/z 300.1.

Reference 11

2-({9-chloro-7-methoxy-1H,2H, 3H-cyclopenta[b]quinolin-6-yl}oxy)ethan-1-ol (Intermediate 9)

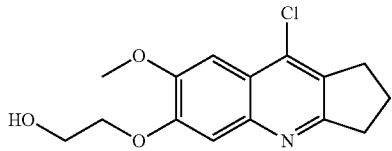 [SMILES: COc1cc2c(Cl)c3c(nc2cc1OCCO)CCC3]

To a vial charged with a solution of 9-chloro-7-methoxy-1H,2H,3H-cyclopenta[b]quinolin-6-ol (Intermediate 1-b) (315 mg; 1.26 mmol; 1 eq.) in toluene (1.0 mL) was added a solution of (tributylphosphoranylidene)acetonitrile (761.20 mg; 3.15 mmol; 2.50 eq.) in toluene (0.4 mL). The mixture was stirred at 130° C. for 15 min while N$_2$ was used to blow off most solvent. To the reside was added ethane-1,2-diol (1 174.53 mg; 18.92 mmol; 15 eq.) in toluene (0.8 mL). The mixture was stirred at 130° C. for 30 min while N$_2$ was used to blow off most of the solvents. The vial was cooled to rt and the residue was subjected to purification by chromatography silica gel column with 0-100% EtOAc/Hexanes as eluents to provide 2-({9-chloro-7-methoxy-1H,2H,3H-cyclopenta[b]quinolin-6-yl}oxy)ethan-1-ol (354 mg, 96%). LCMS (ES) [M+1]$^+$ m/z m/z 294.2.

Example 1

6,7-dimethoxy-N-(propan-2-yl)-1H,2H,3H-cyclopenta[b]quinolin-9-amine formate

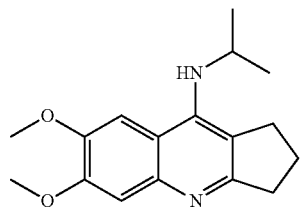 [SMILES: COc1cc2nc3c(c(NC(C)C)c2cc1OC)CCC3]

To Intermediate 1 (200 mg, 0.76 mmol, 1 eq), toluene (5 mL), propan-2-amine (448 mg, 7.60 mmol, 10 eq), t-BuONa (146 mg, 1.52 mmol, 2 eq) was added chloro[2-(dicyclohexylphosphino)-3,6-dimethoxy-2',4', 6'-triisopropyl-1,1'-biphenyl][2-(2-aminoethyl)phenyl]palladium(II) (BrettPhos Pd G1, Methyl t-Butyl Ether Adduct) (34 mg, 0.04 mmol, 0.05 eq). The mixture was purged with N$_2$ for 5 min, and stirred at 90° C. under N$_2$ for 2 h cooled to rt and concentrated under reduced pressure. The residue was dissolved in DMF (5 mL) and the solution was filtered and subjected to reverse phase preparative HPLC (Prep-C18, 5 μM SunFire column, 19×150 mm, Waters; gradient elution of 21% MeCN in water to 36% MeCN in water over a 6 min period, where both solvents contain 0.1% FA) to provide the title compound as a white solid (71.8 mg, 28%). LCMS (ES) [M-FA+1]$^+$ m/z 287.2.

Example 2

N-{6,7-dimethoxy-1H,2H,3H-cyclopenta[b]quinolin-9-yl}-1-(propan-2-yl)piperidin-4-amine; bis(formic acid)

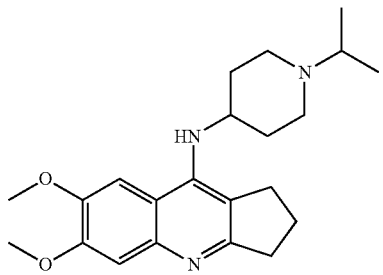

A mixture of Intermediate 1 (200 mg, 0.75 mmol) in 1,4-dioxane (6 ml) in a 20 mL microwave reaction vial was purged with Ar gas for 5 min. To the mixture was added 1-isopropylpiperidin-4-amine (130 mg, 1.15 mmol), chloro[2-(dicyclohexylphosphino)-3,6-dimethoxy-2',4', 6'-triisopropyl-1,1'-biphenyl][2-(2-aminoethyl)phenyl]palladium (II) (BrettPhos Pd G1, Methyl t-Butyl Ether Adduct, 60 mg) followed by 'BuONa (293 mg, 3.03 mmol). The reaction vial was sealed and subjected to a microwave reactor at 115° C. for 45 min. The mixture was cooled to rt, treated with water and extracted with 10% MeOH/CH₂Cl₂ thrice. The combined organic layers were concentrated under reduced pressure. The remaining residue was redissolved in DMSO, filtered and subjected to purification on reverse phase preparative HPLC (Prep-C18, 5 μM SunFire column, 19×150 mm, Waters; gradient elution of 5% MeCN in water to 25% MeCN in water over a 6 min period, where both solvents contain 0.1% FA) to provide the title compound as an off-white solid. LCMS (ES) [M-2FA+1]⁺ m/z 370.4.

Example 3

N-{6,7-dimethoxy-1H,2H,3H-cyclopenta[b]quinolin-9-yl}-1-methylpiperidin-4-amine—2HCl

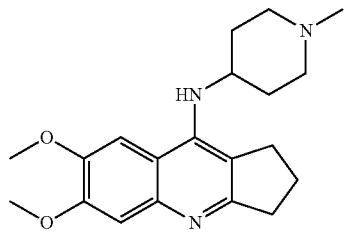

A mixture of Intermediate 1 (80 mg, 0.3 mmol) in 1,4-dioxane (2 ml) in a 10 mF microwave reaction vial was purged with Ar gas for 5 min. To the mixture was added 1-methyl-4-piperidine (52 mg, 0.46 mmol), chloro[2-(dicyclohexylphosphino)-3,6-dimethoxy-2',4', 6'-triisopropyl-1,1'-biphenyl][2-(2-aminoethyl)phenyl] palladium(II) (BrettPhos Pd G1, Methyl t-Butyl Ether Adduct, 24 mg) followed by 'BuONa (117 mg, 1.21 mmol). The reaction vial was sealed and subjected to a microwave reactor at 115° C. for 45 min. The mixture was cooled to rt, diluted with water and acetonitrile and filtered through a small pad of celite. The solution was subjected to purification on reverse phase preparative HPLC (Waters XSelect CSH C18 column, gradient elution of 10% MeCN in water to 40% MeCN in water over 13 min, where both solvents contain 0.1% HCl) to provide the title compound as an off-white solid (95 mg, 75%). LCMS (ES) [M-2HCl+1]⁺ m/z 342.4.

Example 4

N-{6,7-dimethoxy-1H,2H,3H-cyclopenta[b]quinolin-9-yl}piperidin-4-amine; bis(formic acid)

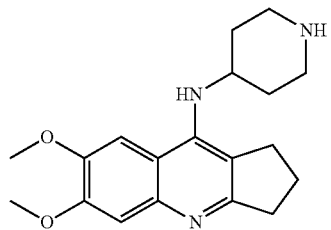 [SMILES: COc1cc2nc3c(c(NC4CCNCC4)c2cc1OC)CCC3]

Step 1

A mixture of Intermediate 1 (320 mg, 1.2 mmol) in 1,4-dioxane (6 ml) in a microwave reaction vial was purged with Ar gas for 5 min. To the mixture was added tert-butyl 4-aminopiperidine-1-carboxylate (320 mg, 1.6 mmol), chloro[2-(dicyclohexylphosphino)-3,6-dimethoxy-2',4', 6'-triisopropyl-1,1'-biphenyl][2-(2-aminoethyl)phenyl]palladium(II) (BrettPhos Pd G1, Methyl t-Butyl Ether Adduct, 96 mg) followed by 'BuONa (468 mg, 4.85 mmol). The reaction vial was sealed and subjected to a microwave reactor at 115° C. for 45 min. The mixture was cooled to rt, diluted with water and extracted with 10% MeOH/CH₂Cl₂ thrice. The organic layers were combined. After removal of the organic solvents under reduced pressure, the residue purified by chromatography on silica gel column with 0-10% MeOH/CH₂Cl₂ as eluents to provide tert-butyl 4-({6, 7-dimethoxy-1H,2H,3H-cyclopenta[b]quinolin-9-yl}amino)piperidine-1-carboxylate as white solid (390 mg, 77%).

Step 2

To a rt solution of tert-butyl 4-({6,7-dimethoxy-1H,2H, 3H-cyclopenta[b]quinolin-9-yl}amino)piperidine-1-carboxylate as white solid (190 mg, 0.44 mmol) in CH₂Cl₂ (5 mL) was added trifluoroacetic acid (TFA, 2 mL). The mixture was stirred at 45° C. for 30 min. After removal of the organic volatiles under reduced pressure, the remaining residue was redissolved in DMF and subjected to purification on reverse phase preparative HPLC (Prep-C18, 5 μM XBridge column, 19×150 mm, Waters; gradient elution of 11 MeCN in water to 39% MeCN in water over a 6 min period, where both solvents contain 0.1% FA) to provide the title compound as an off-white solid as a white solid (120.8, 75%). LCMS (ES) [M-2FA+1]⁺ m/z 328.2.

Example 5

(3R)—N-{6,7-dimethoxy-1H,2H,3H-cyclopenta[b] quinolin-9-yl}piperidin-3-amine-2HCl

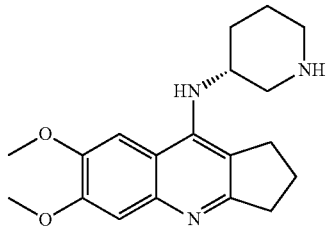

Step 1

To a rt solution of Intermediate 1 (300 mg; 1.14 mmol; 1 eq.) in 1,4-dioxane (4 mL) was added tert-butyl (3R)-3-aminopiperidine-1-carboxylate (341.75 mg; 1.71 mmol; 1.50 eq.) and chloro[2-(dicyclohexylphosphino)-3,6-dimethoxy-2',4', 6'-triisopropyl-1,1'-biphenyl][2-(2-aminoethyl)phenyl]palladium(II) (BrettPhos Pd G1, Methyl t-Butyl Ether Adduct, 45.44 mg) followed by 'BuONa (218.65 mg; 2.28 mmol; 2 eq.). The mixture was purged with N₂ for 5 min and was stirred at 125° C. for 25 min. The mixture was cooled to rt, diluted with MeCN and the insoluble components were filtered off. The filtrate was concentrated under reduced pressure and the remaining residue was subjected to purification by preparative HPLC (Waters XSelect CSH C18 column, gradient elution of 5% MeCN in water to 95% MeCN in water over a 13 min period, where both solvents contain 0.1% HCl) to give tert-butyl (R)-3-((6,7-dimethoxy- 2,3-dihydro-1H-cyclopenta[b]quinolin-9-yl)amino)piperidine-1-carboxylate in HCl salt form as off-white solid.

Step 2

To a solution of the above tert-butyl (R)-3-((6,7-dimethoxy-2,3-dihydro-1H-cyclopenta[b]quinolin-9-yl)amino)piperidine-1-carboxylate HCl salt in CH$_2$Cl$_2$ (2 mL) was added TFA (2 mL). The mixture was stirred at rt for 1 h. The mixture was concentrated under reduced pressure and the remaining residue was subjected to purification by preparative HPLC (Waters XSelect CSH C18 column, gradient elution of 5% MeCN in water to 40% MeCN in water over a 13 min period), where both solvents contain 0.1% HCl) to give the title compounds as a white solid. (344 mg, 75%). LCMS (ES) [M-2HCl+1]$^+$ m/z 328.3.

Example 6

(3R)—N-{6,7-dimethoxy-1H,2H,3H-cyclopenta[b]quinolin-9-yl}-1-methylpiperidin-3-amine—2HCl

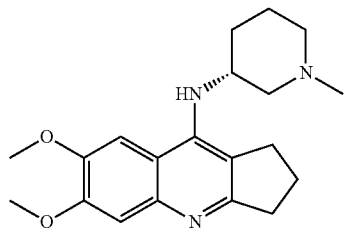

A rt solution of (3R)—N-{6,7-dimethoxy-1H,2H,3H-cyclopenta[b]quinolin-9-yl}piperidin-3-amine—2HCl (Example 5) (0.20 g; 0.61 mmol; 1 eq.) and formaldehyde (0.18 mL; 2.44 mmol; 4 eq.) in MeOH (2 mL) was stirred at rt for 10 min followed by sodium cyanoborohydride (0.12 g; 1.83 mmol; 3 eq.). The mixture was stirred at rt for 15 h, after which the crude solution was concentrated under reduced pressure. The remaining residue was diluted with water and MeCN and subjected to purification preparative HPLC (Waters XSelect CSH C18 column, gradient elution of 5% MeCN in water to 95% MeCN in water over a 13 min period, where both solvents contain 0.1% HCl) to give the title compound as white solid (93 mg, 45%). LCMS (ES) [M-2HCl+1]$^+$ m/z 342.2.

Example 7

N-{6,7-dimethoxy-1H,2H,3H-cyclopenta[b]quinolin-9-yl}-1-ethylpiperidin-4-amine—2HCl

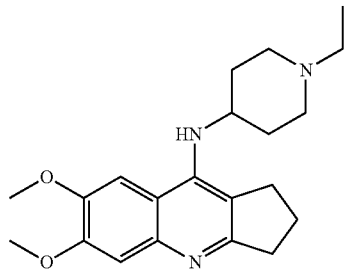 [SMILES: CCN1CCC(Nc2c3c(nc4cc(OC)c(OC)cc24)CCC3)CC1]

The title compound was made from Intermediate 1 following a synthetic method similar as described for Example 3, except that 1-ethyl-4-piperidine was used in the place of 1-methyl-4-piperidine. The title compound was obtained as an off-white solid. LCMS (ES) [M-2HCl+1]$^+$ m/z 356.3.

Example 8

N-[(azetidin-3-yl)methyl]-6,7-dimethoxy-1H,2H,3H-cyclopenta[b]quinolin-9-amine—2HCl

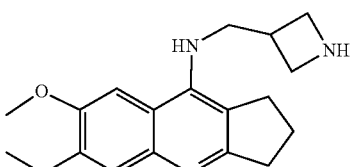

The title compound was made from Intermediate 1 and following a 2-step synthetic method similar as described for Example 5, except that tert-butyl 3-(aminomethyl)azetidine-1-carboxylate was used in the place of tert-butyl 3-aminopiperidine-1-carboxylate. The title compounds was obtained as an off-white solid. LCMS (ES) [M-2HCl+1]$^+$ m/z 314.2.

Example 9

N-{6,7-dimethoxy-1H,2H,3H-cyclopenta[b]quinolin-9-yl}azetidin-3-amine—2HCl

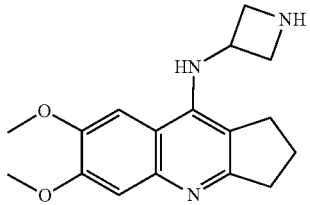 [SMILES: COc1cc2nc3c(c(NC4CNC4)c2cc1OC)CCC3]

The title compound was made from Intermediate 1 and following a 2-step synthetic method similar as described for Example 5, except that tert-butyl 3-amino-1-azetidinecarboxylate was used in the place of tert-butyl 3-aminopiperidine-1-carboxylate. The title compounds was obtained as an off-white solid. LCMS (ES) [M-2HCl+1]$^+$ m/z 300.4.

Example 10

N-{6,7-dimethoxy-1H,2H,3H-cyclopenta[b]quinolin-9-yl}-1-(oxan-4-yl)piperidin-4-amine—2HCl

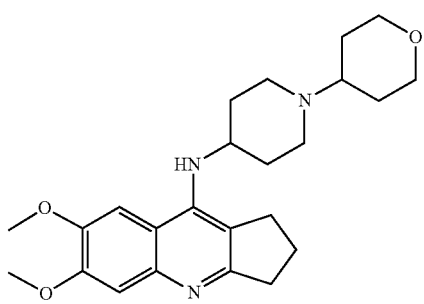 [SMILES: COc1cc2nc3c(c(NC4CCN(C5CCOCC5)CC4)c2cc1OC)CCC3]

The title compound was made from Intermediate 1 following a synthetic method similar as described for Example 3, except that 1-tetrahydro-2H-pyran-4-yl-4-piperidinamine-2HCl was used in place of 1-methyl-4-piperidine. The title compounds was obtained as an off-white solid. LCMS (ES) [M-2HCl+1]$^+$ m/z 412.5.

Example 11

N-{6,7-dimethoxy-1H,2H,3H-cyclopenta[b]quinolin-9-yl}-1-(oxolan-3-yl)piperidin-4-amine—2HCl

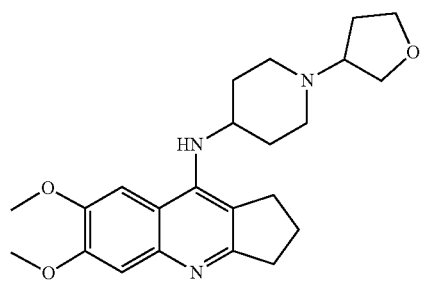 [SMILES: COc1cc2nc3c(c(NC4CCN(C5CCOC5)CC4)c2cc1OC)CCC3]

The title compound was made from Intermediate 1 following a synthetic method similar as described for Example 3, except that 1-(tetrahydrofuran-3-yl)piperidin-4-amine was used in place of 1-methyl-4-piperidine. The title compounds was obtained as an off-white solid. LCMS (ES) [M-2HCl+1]$^+$ m/z 398.4.

Example 12

N-{6,7-dimethoxy-1H,2H,3H-cyclopenta[b]quinolin-9-yl}-2-azaspiro[3.3]heptan-6-amine—2HCl

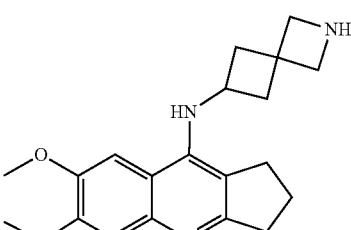

The title compound was made from Intermediate 1 following a 2-step synthetic method similar as described for Example 5, except that tert-butyl 6-amino-2-azaspiro[3.3]heptane-2-carboxylate was used in place of tert-butyl (3R)-3-aminopiperidine-1-carboxylate. The title compounds was obtained as a colorless solid. LCMS (ES) [M-2HCl+1]$^+$ m/z 340.2.

Example 13

N-{6,7-dimethoxy-1H,2H,3H-cyclopenta[b]quinolin-9-yl}-1-(pyridin-4-yl)piperidin-4-amine—2HCl

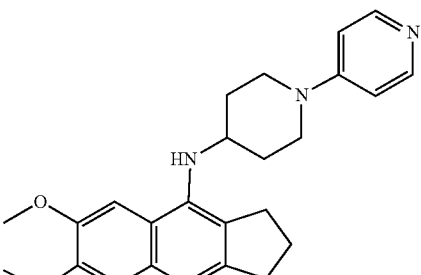

The title compound was made from Intermediate 1 following a synthetic method similar as described for Example 3, except that 1-(4-pyridinyl)-4-piperidinamine—2HCl was used in place of 1-methyl-4-piperidine. The title compounds was obtained as a white solid. LCMS (ES) [M-2HCl+1]$^+$ m/z 405.3.

Example 14

N-{6,7-dimethoxy-1H,2H,3H-cyclopenta[b]quino-lin-9-yl}-1-(pyridin-3-yl)piperidin-4-amine—2HCl

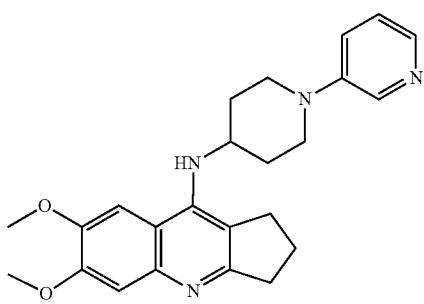 [SMILES: COc1cc2nc3c(c(NC4CCN(c5cccnc5)CC4)c2cc1OC)CCC3]

The title compound was made from Intermediate 1 following a synthetic method similar as described for Example 3, except that 1-(Pyridin-3-yl)piperidin-4-amine was used in place of 1-methyl-4-piperidine. The title compounds was obtained as a white solid. LCMS (ES) [M-2HCl+1]$^+$ m/z 405.2.

Example 15

N-{6,7-dimethoxy-1H,2H,3H-cyclopenta[b]quino-lin-9-yl}-1-(pyridin-2-yl)piperidin-4-amine—2HCl

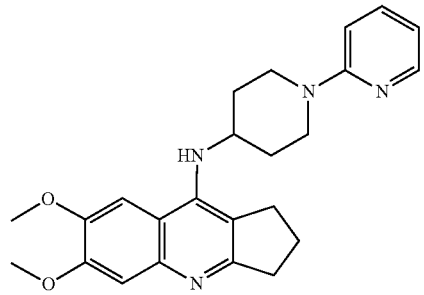 [SMILES: COc1cc2nc3c(c(NC4CCN(c5ccccn5)CC4)c2cc1OC)CCC3]

The title compound was made from Intermediate 1 following a synthetic method similar as described for Example 3, except that 1-(2-Pyridinyl)-4-piperidinylamine was used in place of 1-methyl-4-piperidine. The title compounds was obtained as a white solid. LCMS (ES) [M-2HCl+1]$^+$ m/z 405.2.

Example 16

N-{6,7-dimethoxy-1H,2H,3H-cyclopenta[b]quino-lin-9-yl}-1-(2-fluorophenyl)piperidin-4-amine hydrochloride

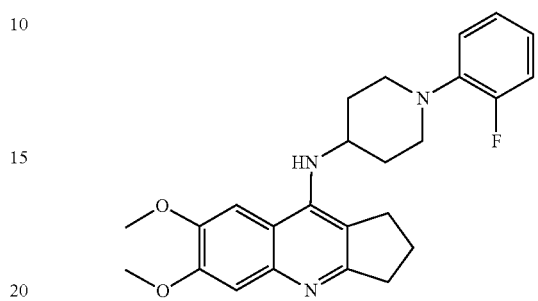

The title compound was made from Intermediate 1 following a synthetic method similar as described for Example 3, except that 1-(2-fluorophenyl)piperidin-4-amine was used in place of 1-methyl-4-piperidine. The final crude product was purified by reverse phase preparative HPLC (Phenomenex Luna C18 column, gradient elution of 10% MeCN in water to 40% MeCN in water over a 13 min period, where both solvents contain 0.1% HCl) to give the title compound as white a yellow solid. LCMS (ES) [M-2HCl+1]$^+$ m/z 422.3.

Example 17

N-{6,7-dimethoxy-1H,2H,3H-cyclopenta[b]quino-lin-9-yl}-1-ethylazetidin-3-amine—2HCl

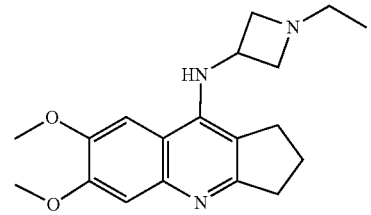 [SMILES: CCN1CC(Nc2c3c(nc4cc(OC)c(OC)cc24)CCC3)C1]

To N-{6,7-dimethoxy-1H,2H,3H-cyclopenta[b]quinolin-9-yl}azetidin-3-amine (HCl)$_2$ (Example 9; 40 mg; 0.13 mmol; 1 eq.) and Hunig's base (0.23 mL; 1.34 mmol; 10 eq.) in N,N-dimethylformamide (1.34 mL) at ambient temperature was added iodoethane (0.01 mL; 0.13 mmol; 1 eq.) drop-wise. The mixture was stirred at ambient temperature overnight (17 h) then it was diluted with 1:1 PhMe/EtOAc, washed with brine, dried over MgSO4, filtered and concentrated. The residue was taken up in 1.0 N HCl (1.5 mL) and subjected to purification by reverse phase preparative HPLC (Waters XSelect CSH C18 column, gradient elution of 0% MeCN in water to 70% MeCN in water over a 13 min period, where both solvents contain 0.1% HCl) to provide the title product as a colorless powder (4.6 mg; 11%). LCMS (ES) [M-2HCl+1]$^+$ m/z 328.4.

Example 18

6,7-dimethoxy-N-[1-(propan-2-yl)piperidin-4-yl]-1,2,3,4-tetrahydroacridin-9-amine; bis (formic acid)

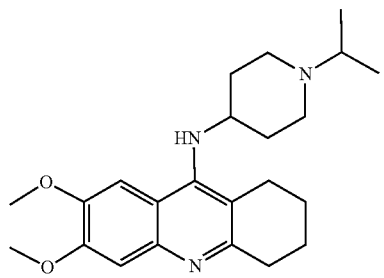 [SMILES: COc1cc2nc3c(c(NC4CCN(C(C)C)CC4)c2cc1OC)CCCC3]

The title compound was made from Intermediate 2 and 1-isopropylpiperidin-4-amine following a synthetic method similar as described for Example 2. The crude final compound was purified by reverse phase preparative HPLC (Prep-C18, 5 μM SunFire column, 19×150 mm, Waters; gradient elution of 2% MeCN in water to 11% MeCN in water over a 6 min period, where both solvents contain 0.1% FA) to provide the title compound as a white solid (71.8 mg, 21%). LCMS (ES) [M-2FA+1]$^+$ m/z 384.3.

Example 19

N-{2,3-dimethoxy-6H,7H,8H,9H,10H-cyclohepta[b]quinolin-11-yl}-1-(propan-2-yl)piperidin-4-amine; bis(formic acid)

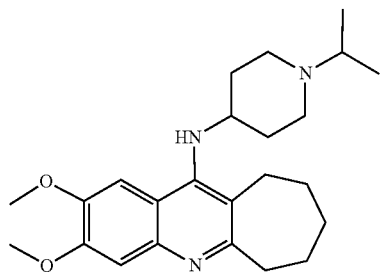 [SMILES: COc1cc2nc3c(c(NC4CCN(C(C)C)CC4)c2cc1OC)CCCCC3]

Into a 40-mL vial was placed Intermediate 4 (300 mg, 1.03 mmol, 1 eq), 1,4-dioxane (20 mL), 1-(propan-2-yl)piperidin-4-amine (438.8 mg, 3.09 mmol, 3 eq), $^t$BuONa (296.6 mg, 3.09 mmol, 3 eq) and 3rd BrettPhos precatalyst (45 mg, 0.05 mmol, 0.05 eq). The mixture was purged with N$_2$ for 5 min and then stirred 90° C. under N$_2$ for 2 h. The mixture was filtered and subjected to reverse phase preparative HPLC (Prep-C18, 5 μM XBridge column, 19×150 mm, Waters; gradient elution of 2% MeCN in water to 17% MeCN in water over a 6 min period, where both solvents contain 0.1% FA) to provide the title compound as an off-white solid (216.4 mg, 47%). LCMS (ES) [M-2FA+1]$^+$ m/z 398.2.

Example 20

6,7-dimethoxy-N-{[1-(propan-2-yl)azetidin-3-yl]methyl}-1H,2H,3H-cyclopenta[b]quinolin-9-amine—2HCl

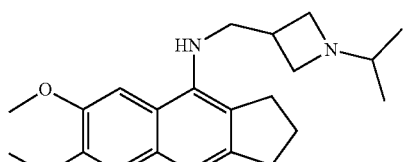

The title compound was made from Intermediate 1 following a synthetic method similar as described for Example 3, except that (1-isopropylazetidin-3-yl)methanamine was used in place of 1-methyl-4-piperidine. The title compounds was obtained as an off white solid. LCMS (ES) [M-2HCl+1]$^+$ m/z 356.2

Example 21

6,7-dimethoxy-N-[(1-methyl-1H-imidazol-4-yl)methyl]-1H,2H,3H-cyclopenta[b]quinolin-9-amine—2HCl

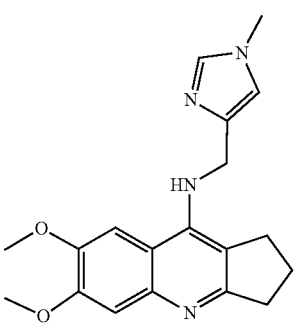 [SMILES: COc1cc2nc3c(c(NCc4cn(C)cn4)c2cc1OC)CCC3]

The title compound was made from Intermediate 1 following a synthetic method similar as described for Example 3, except that 1-(4-pyridinyl)-4-piperidinamine—2HCl was used in place of 1-methyl-4-piperidine. The title compound was obtained as a white solid. LCMS (ES) [M-2HCl+1]$^+$ m/z 339.1.

Example 22

3-chloro-2-[4-({6,7-dimethoxy-1H,2H,3H-cyclopenta[b]quinolin-9-yl}amino)piperidin-1-yl]propan-1-ol 2HCl

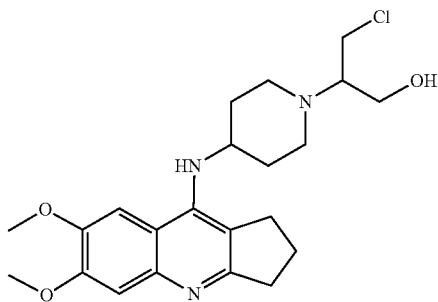 [SMILES: COc1cc2nc3c(c(NC4CCN(C(CO)CCl)CC4)c2cc1OC)CCC3]

The title compound was made from Intermediate 1 following a synthetic method similar as described for Example 3, except that 1-(oxetan-3-yl)piperidin-4-amine oxalate was used in place of 1-methyl-4-piperidine. The title compounds was obtained as a tan solid. LCMS (ES) [M-2HCl+1]⁺ m/z 420.3.

Example 23

1-benzyl-N-{6,7-dimethoxy-1H,2H,3H-cyclopenta[b]quinolin-9-yl}piperidin-4-amine—2HCl

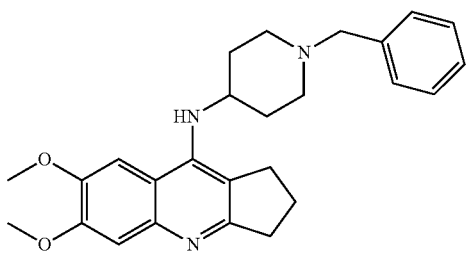 [SMILES: COc1cc2nc3c(c(NC4CCN(Cc5ccccc5)CC4)c2cc1OC)CCC3]

The title compound was made from Intermediate 1 following a synthetic method similar as described for Example 3, except that 1-benzyl-4-piperidinamine was used in place of 1-methyl-4-piperidine. The title compounds was obtained as an off white solid. LCMS (ES) [M-2HCl+1]⁺ m/z 418.4.

Example 24

(3R)—N-{6,7-dimethoxy-1H,2H,3H-cyclopenta[b]quinolin-9-yl}azepan-3-amine—2HCl

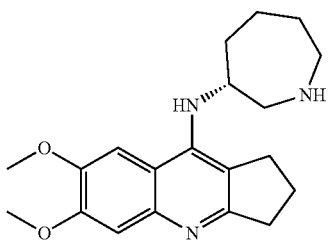

The title compound was made from Intermediate 1 following a 2-step synthetic method similar as described for Example 5, except that tert-butyl (R)-3-aminoazepane-1-carboxylate was used in place of tert-butyl (3R)-3-aminopiperidine-1-carboxylate. The title compounds was obtained as a white solid. LCMS (ES) [M-2HCl+1]⁺ m/z 342.1.

Example 25

2-[(7-methoxy-9-{[1-(propan-2-yl)piperidin-4-yl]amino}-1H,2H,3H-cyclopenta[b]quinolin-6-yl)oxy]ethan-1-ol 2HCl

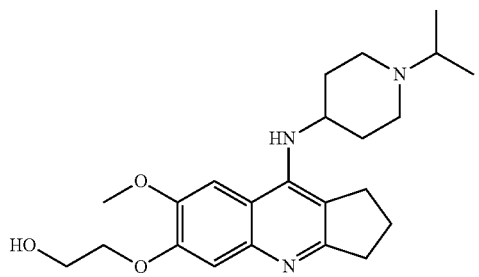 [SMILES: COc1cc2c(NC3CCN(C(C)C)CC3)c3c(nc2cc1OCCO)CCC3]

Step 1

To a solution of Intermediate 9 (354 mg; 1.21 mmol; 1 eq) and diisopropylethyl amine (1.0 mL) in CH₂Cl₂ (3 mL) and DMF (1.5 mL) under N₂ atmosphere in ice bath was added tert-butyl(chloro)dimethylsilane (272.46 mg; 1.81 mmol; 1.50 eq.). The mixture was allowed to warm with ice bath to rt and stir at rt for 1.5 h. The mixture was concentrated under reduced pressure and the remaining residue was dissolved in EtOAc, washed with water and brine. After removal of the organic volatiles under reduced pressure, the residue was purified by chromatography on silica gel column with 0-30% EtOAc/Hexanes as eluents to provide 6-{2-[(tert-butyldimethylsilyl)oxy]ethoxy}-9-chloro-7-methoxy-1H,2H,3H-cyclopenta[b]quinoline as white solid (360 mg, 73%) LCMS (ES) [M+1]⁺ m/z 408.8.

Step 2

A mixture of 6-{2-[(tert-butyldimethylsilyl)oxy]ethoxy}-9-chloro-7-methoxy-1H,2H,3H-cyclopenta[b]quinoline (90 mg, 0.22 mmol) in 1,4-dioxane (2 ml) in a 10 ml, microwave reaction vial was purged with Ar gas for 5 min. To the mixture was added 1-methyl-4-piperidine (52 mg, 0.46 mmol), chloro[2-(dicyclohexylphosphino)-3,6-dimethoxy-2',4',6'-triisopropyl-1,1'-biphenyl][2-(2-aminoethyl)phenyl]palladium(II) (BrettPhos Pd G1, Methyl t-Butyl Ether Adduct, 18 mg; 0.023 mol; 0.10 eq) followed by ᵗBuONa (99 mg, 0.88 mmol, 4.0 eq). The reaction vial was sealed and subjected to a microwave reactor at 120° C. for 30 min. The mixture was cooled to rt, diluted with water and extracted with EtOAc thrice. After removal of organic solvents under reduced pressure, the residue was purified by chromatography on silica gel column with 0-100% EtOAc/Hexanes as eluents to provide N-(6-{2-[(tert-butyldimethylsilyl)oxy]ethoxy}-7-methoxy-1H,2H,3H-cyclopenta[b]quinolin-9-yl)-1-(propan-2-yl)piperidin-4-amine as a white solid (75 mg, 66%). LCMS (ES) [M+1]⁻ m/z 513.8.

Step 3

To a solution N-(6-{2-[(tert-butyldimethylsilyl)oxy]ethoxy}-7-methoxy-1H,2H,3H-cyclopenta[b]quinolin-9-yl)-1-(propan-2-yl)piperidin-4-amine (75 mg, 0.15 mmol) in CH₂Cl₂ (0.5 mL) was added tetrabutylammonium fluoride (1.5 mL, 1.0 N in THF) and water (0.4 mL). The mixture was stirred 50° C. for 25 min. The organic solvents were removed under reduced pressure, the remaining mixture was treated with water and extracted with 25% ⁱPrOH/chloroform thrice. After removal of organic volatiles under reduced pressure, the residue was redissolved in DMSO, filtered and subjected to purification on reverse phase preparative HPLC (Waters XSelect CSH C18 column, gradient elution of 0% MeCN in water to 20% MeCN in water over a 20 min period, where both solvents contain 0.1% HCl) to provide the title compound as an off-white solid. LCMS (ES) [M-2HCl+1]⁻ m/z 400.2

Example 26

N-{6-cyclopropyl-7-methoxy-1H,2H,3H-cyclopenta[b]quinolin-9-yl}-1-(propan-2-yl)piperidin-4-amine—2HCl

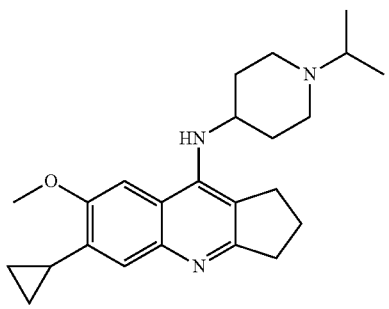 [SMILES: COc1cc2c(NC3CCN(C(C)C)CC3)c3c(nc2cc1C1CC1)CCC3]

The title compound was made from Intermediate 7 following a synthetic method similar as described for Example 3, except that 1-isopropylpiperidin-4-amine was used in place of 1-methyl-4-piperidine. The title compounds was obtained as a white solid. LCMS (ES) [M-2HCl+1]⁺ m/z 380.2.

Example 27

1-cyclopentyl-N-{6,7-dimethoxy-1H,2H,3H-cyclopenta[b]quinolin-9-yl}piperidin-4-amine—2HCl

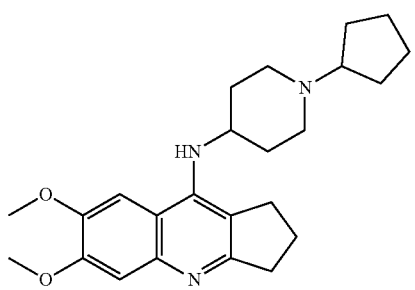 [SMILES: COc1cc2nc3c(c(NC4CCN(C5CCCC5)CC4)c2cc1OC)CCC3]

The title compound was made from Intermediate 1 following a synthetic method similar as described for Example 3, except that 1-Cyclopentyl-4-piperidinylamine was used in place of 1-methyl-4-piperidine and N-Methyl-2-pyrrolidinone was used as solvent. The title compounds was obtained as a white solid. LCMS (ES) [M-2HCl+1]⁺ m/z 396.2.

Example 28

(4R)—N-{6,7-dimethoxy-1H,2H,3H-cyclopenta[b]quinolin-9-yl}azepan-4-amine—2HCl

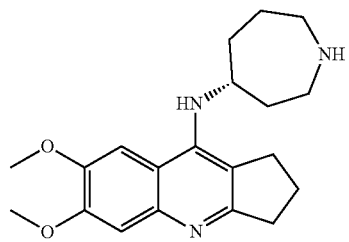 [SMILES: COc1cc2nc3c(c(N[C@@H]4CCCNCC4)c2cc1OC)CCC3]

The title compound was made from Intermediate 1 following a 2-step synthetic method similar as described for Example 5, except that tert-butyl (R)-4-aminoazepane-1-carboxylate was used in place of tert-butyl (3R)-3-aminopiperidine-1-carboxylate. The title compounds was obtained as a white solid. LCMS (ES) [M-2HCl+1]⁺ m/z 342.2.

Example 29

(4R)—N-{6,7-dimethoxy-1H,2H, 3H-cyclopenta[b]quinolin-9-yl}-1-methylazepan-4-amine—2HCl

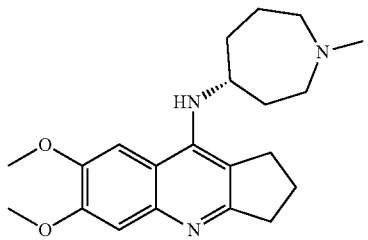

The title compound was made from (4R)—N-{6,7-dimethoxy-1H,2H,3H-cyclopenta[b]quinolin-9-yl}azepan-4-amine—2HCl (Example 28) following a synthetic method similar as described for Example 6. The title compounds was obtained as a white solid. LCMS (ES) [M-2HCl+1]⁺ m/z 356.1. Example 30 N-{6,7-dimethoxy-1H,2H,3H-cyclopenta[b]quinolin-9-yl}-1-(propan-2-yl)azetidin-3-amine—2HCl

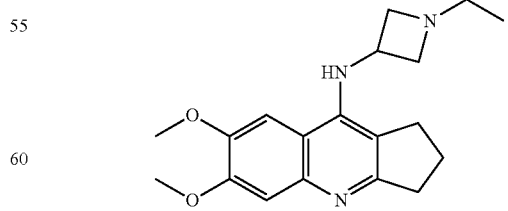

The title compound was made from N-{6,7-dimethoxy-1H,2H,3H-cyclopenta[b]quinolin-9-yl}azetidin-3-amine—2HCl (Example 9) (50 mg; 0.17 mmol; 1 eq.), following a synthetic method similar as described for Example 6, except that propan-2-one was used in place of formaldehyde. The title compounds was obtained as colorless powder. LCMS (ES) [M-2HCl+1]⁺ m/z 342.4

Example 31

(3R)—N-{6,7-dimethoxy-1H,2H, 3H-cyclopenta[b]quinolin-9-yl}-1-methylazepan-3-amine—2HCl

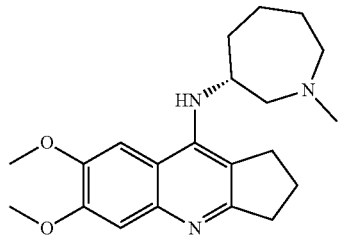

The title compound was made from (3R)—N-{6,7-dimethoxy-1H,2H,3H-cyclopenta[b]quinolin-9-yl}azepan-3-amine—2HCl (Example 24) following a synthetic method similar as described for Example 6. The title compounds was obtained as a white solid. LCMS (ES) [M-2HCl+1]⁺ m/z 356.3.

Example 32

N-[2,3-dimethoxy-6H,7H,8H-cyclopenta[b]1,5-naphthyridin-9-yl]-1-(propan-2-yl)piperidin-4-amine (bis formic acid salt)

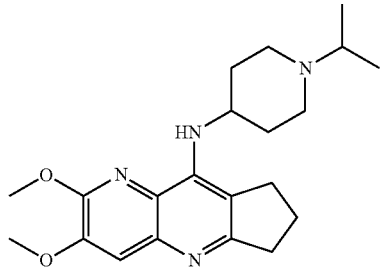 [SMILES: COc1cc2nc3c(c(NC4CCN(C(C)C)CC4)c2nc1OC)CCC3]

Into a 40-mL vial, was placed Intermediate 5 (150 mg, 0.57 mmol, 1 eq.), dioxane (10 mL), 1-(propan-2-yl)piperidin-4-amine (243 mg, 1.71 mmol, 3 eq.), t-BuONa (164 mg, 1.71 mmol, 3 eq.) and 3rd BrettPhos precatalyst (27 mg, 0.03 mmol, 0.05 eq.). The mixture was stirred for 2 h at 90° C. under N₂ and concentrated under vacuum. The residue was diluted with DMF (5 mL), filtered and subjected to reverse phase preparative HPLC (Prep-C18, 5 µM XBridge column, 19×150 mm, Waters; gradient elution of 2% MeCN in water to 20% MeCN in water over a 6-min period, where both solvents contain 0.1% FA) to provide the title compound as a white solid (82.9 mg, 32%). NMR (300 MHz, DMSO-de) δ 10.53 (br, 1H), 7.54 (s, 1H), 7.20 (br, 1H), 4.63-4.43 (m, 1H), 4.15 (s, 3H), 3.97 (s, 3H), 3.60-3.32 (m, 3H), 3.19-3.08 (m, 6H), 2.27-2.03 (m, 6H), 1.32 (d, J=7.2 Hz, 6H). LCMS (ES) [M+1]⁺ m/z 371.2.

Example 33

(3R)—N-[2, 3-dimethoxy-6H, 7H, 8Hcyclopenta[b]1,5 naphthyridin-9-yl] piperidin-3-amine—HCl

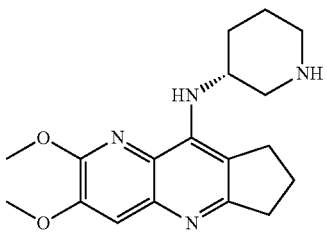 [SMILES: COc1cc2nc3c(c(N[C@@H]4CCCNC4)c2nc1OC)CCC3]

Into a 40-mL vial, was placed a mixture of Intermediate 5 (120 mg, 0.45 mmol, 1 eq.), dioxane (10 mL), tert-butyl (3R)-3-aminopiperidine-1-carboxylate (270 mg, 1.35 mmol, 3 eq.), 3rd BrettPhos precatalyst (18 mg, 0.02 mmol, 0.05 eq.) and t-BuONa (130 mg, 1.35 mmol, 3 eq.). The mixture was stirred for 2 h at 90° C. under N₂ and then concentrated under vacuum. The residue was purified by a silica gel column eluted with dichloromethane (CH₂Cl₂)/MeOH (10/1) to provide (7R)-1-tert-butyl-7-([2,3-dimethoxy-6H,7H,8H-cyclopenta[b]1,5-naphthyridin-9-yl]amino)-1´[3],3-oxazocan-2-one an off-white solid (132 mg, 68%). LCMS (ES) [M+1]⁺ m/z 429.2.

To a solution of tert-butyl (R)-3-((2,3-dimethoxy-7,8-dihydro-6H-cyclopenta[b][1,5]naphthyridin-9-yl)amino)piperidine-1-carboxylate (132 mg, 0.31 mmol, 1 eq.) in CH₂Cl₂ (5 mL) was added HCl/dioxane (0.4 mL, 4M in dioxane, 1.55 mmol, 5 eq.). The solution was stirred for 2 h at rt. The mixture was concentrated under vacuum, diluted ±with DMF (5 mL), filtered and subjected to reverse phase preparative HPLC (Prep-C18, 5 µM XBridge column, 19×150 mm, Waters; gradient elution of 2% MeCN in water to 12% MeCN in water over a 6 min period, where both solvents contain 0.1% PA). To the eluent was added 1 M HCl (aq., 10 mL) and the solution was lyophilized to provide the title compound as brown solid (81.1 mg, 66%). ¹H NMR (300 MHz, DMSO-d₆) δ 14.62 (br, 1H), 9.50 (br, 2H), 7.57 (br, 1H), 4.15 (s, 3H), 4.07 (s, 3H), 3.48-3.14 (m, 8H), 2.80-2.74 (m, 1H), 2.28-2.20 (m, 2H), 2.17-2.02 (m, 1H), 2.00-1.83 (m, 3H). LCMS (ES) [M+1]⁺ m/z 329.2.

Example 34

(3R)—N-[2, 3-dimethoxy-6H, 7H, 8H-cyclopenta[b] 1, 5-naphthyridin-9-yl]-1-methylpiperidin-3-amine—HCl

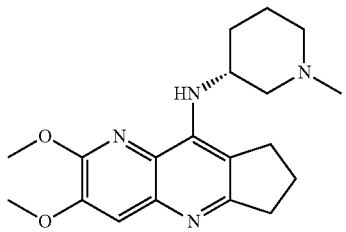

The title compound was made from Intermediate 5 following a synthetic method similar as described for Example 32, except that (3R)-1-methylpiperidin-3-amine was used in place of 1-(propan-2-yl)piperidin-4-amine. The title compound was obtained as a lyophilized off-white solid (44.2 mg, 23%). $^1$H NMR (300 MHz, DMSO-d6) δ 14.57 (br, 1H), 11.30 (br, 1H), 7.55 (s, 1H), 7.50 (br, 1H), 4.15 (s, 3H), 4.10 (s, 3H), 3.57-3.43 (m, 4H), 3.33-3.12 (m, 4H), 2.85-2.78 (m, 4H), 2.28-2.20 (m, 2H), 2.18-2.10 (m, 1H), 2.06-1.80 (m, 3H). LCMS (ES) [M+1]$^+$ m/z 343.2.

Example 35

(3R)—N-[2, 3-dimethoxy-6H, 7H, 8H-cyclopenta[b] 1, 5-naphthyridin-9-yl] azepan-3-amine—HCl

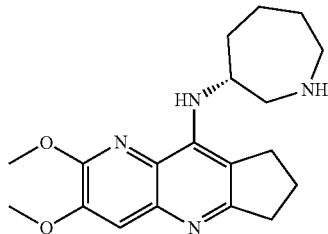 [SMILES: COc1cc2nc3c(c(N[C@@H]4CCCCNC4)c2nc1OC)CCC3]

The title compound was made from Intermediate 5 following a synthetic method similar as described for Example 33, except that tert-butyl (3R)-3-aminoazepane-1-carboxylate was used in place of tert-butyl (3R)-3-aminopiperidine-1-carboxylate. The title compound was obtained as a lyophilized light brown solid (42.8 mg, 31%). $^1$H NMR (300 MHz, MeOD) δ 7.38 (s, 1H), 4.21 (s, 3H), 4.06 (s, 3H), 3.75-3.60 (m, 4H), 3.56-3.40 (m, 3H), 3.28-3.20 (m, 2H), 2.44-2.33 (m, 3H), 2.11-2.00 (m, 4H), 1.85-1.76 (m, 1H). LCMS (ES) [M+1]+m/z 343.2.

Example 36

(4R)—N-[2, 3-dimethoxy-6H, 7H, 8H-cyclopenta[b] 1, 5-naphthyridin-9-yl] azepan-4-amine—HCl

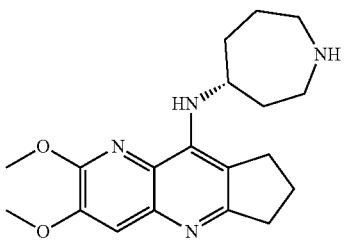

The title compound was made from Intermediate 5 following a synthetic method similar as described for Example 33, except that tert-butyl (4R)-4-aminoazepane-1-carboxylate was used in place of tert-butyl (3R)-3-aminopiperidine-1-carboxylate. The title compound was obtained as a lyophilized light yellow solid (36 mg, 43%). $^1$H NMR (300 MHz, CD$_3$OD) δ 7.36 (s, 1H), 4.18 (s, 3H), 4.05 (s, 3H), 3.69-3.65 (m, 2H), 3.61-3.57 (m, 3H), 3.40-3.34 (m, 2H) 3.24-3.21 (m, 2H), 2.39-1.95 (m, 8H). LCMS (ES) [M+1]$^+$ m/z 343.2.

Example 37

(3R,5S)—N-{6,7-dimethoxy-1H,2H,3H-cyclopenta[b]quinolin-9-yl}-5-methylpiperidin-3-amine

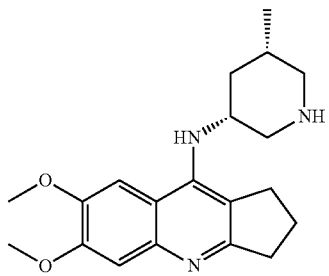 [SMILES: COc1cc2nc3c(c(N[C@H]4CNC[C@@H](C)C4)c2cc1OC)CCC3]

Tert-butyl N-[(3R,5S)-5-methylpiperidin-3-yl]carbamate (0.14 g; 0.64 mmol; 1 eq.) (Synthonix) was dissolved in CH$_2$Cl$_2$ (dry, 2 ml). Triethylamine (0.11 mL; 0.77 mmol; 1.20 eq.) was added and the reaction was cooled in an ice bath. Benzyl chloroformate (0.10 mL; 0.74 mmol; 1.15 eq.) dissolved in 0.5 ml of CH$_2$Cl$_2$ was then added dropwise. After 1.3 h, the reaction was quenched with 1 M HCl solution (2 ml) and partitioned into CH$_2$Cl$_2$ (25 ml) and water (10 ml). The phases were separated and the aqueous phase was extracted once more with CH$_2$Cl$_2$ (20 ml) The combined organics were dried over Na$_2$SO$_4$, evaporated and purified by silica gel chromatography (0-40% EtOAc/CH$_2$Cl$_2$) to give a film of benzyl (3R,5S)-3-{[(tert-butoxy)carbonyl]amino}-5-methylpiperidine-1-carboxylate (0.114 g, 51%). $^1$H NMR (400 MHz, Chloroform-d) δ 7.40-7.28 (m, 5H), 5.11 (s, 2H), 4.45-3.98 (m, 4H), 3.61-3.41 (m, 1H), 2.39-2.16 (m, 2H), 1.76-1.61 (m, 1H), 1.43 (s, 12H), 0.90 (d, J=6.6 Hz, 3H). MS (ES): (M+Na)$^+$=371.3.

Benzyl (3R,5S)-3-{[(tert-butoxy)carbonyl]amino}-5-methylpiperidine-1-carboxylate (114 mg; 0.33 mmol; 1 eq.) was dissolved in CH$_2$Cl$_2$ (dry, 3 ml). The solution was cooled in an ice bath and trifluoracetic acid (1.10 mL; 0.30 mol/L; 0.33 mmol; 1.01 eq.) was added. The reaction was stirred at 25° C. for 2 h and then evaporated. The residue was suspended with toluene (20 ml) and evaporated again to a residue which was used as-is in the next step.

Benzyl (3R,5S)-3-amino-5-methylpiperidine-1-carboxylate; trifluoroacetic acid (118.7 mg; 0.33 mmol; 1.20 eq.) and 9-chloro-6,7-dimethoxy-1H,2H,3H-cyclopenta[b]quinoline (72 mg; 0.27 mmol; 1 eq.) were suspended in 1,4-dioxane (dry, 3 ml). The mixture was purged with Ar. BrettPhos Pd G1 (21.8 mg; 0.03 mmol; 0.10 eq.) (Aldrich) and NaO$^t$Bu (157.4 mg; 1.64 mmol; 6 eq.) were added, the reaction vessel sealed and heated in a microwave reactor at 110° C. for 50 m. After cooling, the mixture was filtered through Celite, and then rinsed through with EtOAc and 5-10% MeOH/CH$_2$Cl$_2$. The filtrate was evaporated and purified by silica gel chromatography (0-10% MeOH/CH$_2$Cl$_2$) to give benzyl (3R,5S)-3-({6,7-dimethoxy-1H,2H,3H-cyclopenta[b]quinolin-9-yl}amino)-5-methylpiperidine-1-carboxylate (76 mg, 58% for Cbz-protected product). MS (ES): (M+H)$^+$=476.4.

Benzyl (3R,5S)-3-({6,7-dimethoxy-1H,2H,3H-cyclopenta[b]quinolin-9-yl}amino)-5-methyl piperidine-1-carboxylate (76 mg; 0.16 mmol; 1 eq.) was dissolved in warm ethanol (absolute, 4 ml). 10% palladium on carbon (Aldrich, wet, ~90 mg) in ethanol (~ 1 ml) was then added and the reaction vessel was charged with an H$_2$-filled balloon. After 3 h, the mixture was purged with nitrogen gas, filtered through celite and rinsed through with MeOH. After evaporation the crude residue was combined with deprotected product collected from the preceding step and purified by reverse phase chromatography (Waters XSelect CSH C18 column, 0.1% aqueous HCl/acetonitrile gradient). Lyophilization gave a white solid of (3R,5S)—N-{6,7-dimethoxy-1H,2H,3H-cyclopenta[b]quinolin-9-yl}-5-methylpiperidin-3-amine—2HCl (66 mg, 64% (two steps). $^1$H NMR (400 MHz, DMSO-d6) δ 14.36 (s, 1H), 9.82-9.32 (m, 2H), 8.29 (d, J=9.3 Hz, 1H), 8.01 (s, 1H), 7.30 (s, 1H), 4.66 (s, 1H), 4.05-3.85 (m, 6H), 3.31-3.03 (m, 8H), 2.43-2.29 (m, 1H), 2.18-2.03 (m, 3H), 1.81-1.62 (m, 1H), 0.96 (d, J=6.5 Hz, 3H). MS (ES): (M+H)$^+$=342.2.

Example 38

6,7-dimethoxy-N-{2-[(propan-2-yl)amino]ethyl}-1H,2H,3H-cyclopenta[b]quinolin-9-amine

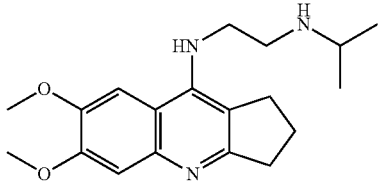 [SMILES: COc1cc2nc3c(c(NCCNC(C)C)c2cc1OC)CCC3]

The title compound was made from Intermediate 1 following a 2-step synthetic method similar as described for Example 5, except that tert-butyl N-(2-aminoethyl)-N-(propan-2-yl)carbamate was used in place of tert-butyl (3R)-3-aminopiperidine-1-carboxylate. LCMS (ES) [M+H]$^+$ m/z 330.1. $^1$H NMR (400 MHz, Methanol-d$_4$) δ 7.78 (s, 1H), 7.09 (s, 1H), 4.17 (t, J=6.5 Hz, 2H), 4.01 (d, J=19.8 Hz, 6H), 3.46 (p, J=6.6 Hz, 1H), 3.40 (dt, J=11.1, 7.0 Hz, 4H), 3.16 (t, J=7.9 Hz, 2H), 2.36-2.24 (m, 2H), 1.39 (d, J=6.5 Hz, 6H).

Example 39

(3R)—N-[2, 3-dimethoxy-6H, 7H, 8H-cyclopenta[b]1, 5-naphthyridin-9-yl]-1-methylazepan-3-amine-HCl

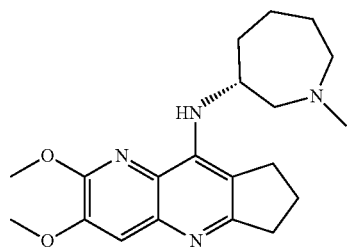

Into a 8-mL vial, was placed a solution of (3R)—N-[2, 3-dimethoxy-6H,7H,8H-cyclopenta[b]1,5-naphthyridin-9-yl]azepan-3-amine hydrogen chloride (80 mg, 0.23 mmol, 1 eq.), MeOH (5 mL), CH$_2$O (aq.) (1 mL), TEA (70 mg, 0.69 mmol, 3 eq.) and NaBH(OAc)$_3$ (244 mg, 1.15 mmol, 5 eq.). The solution was stirred for 16 h at rt and concentrated under vacuum. The residue was diluted with MeOH (5 mL), filtered and subjected to reverse phase preparative HPLC (Prep-C18, 5 μM XBridge column, 19×150 mm, Waters; gradient elution of 2% MeCN in water to 18% MeCN in water over a 6 min period, where both solvents contain 0.1% FA). The eluents were concentrated under vacuum and H$_2$O (10 mL) and 1 M HCl (aq. 1 mL) were added. The solution was lyophilized to provide the title compound as a dark green solid (15.5 mg, 17%). NMR (300 MHz, CD$_3$OD) δ 7.40 (s, 1H), 5.08-5.00 (m, 1H), 4.22 (s, 3H), 4.06 (s, 3H), 3.89-3.68 (m, 2H), 3.60-3.52 (m, 3H), 3.40-3.33 (m, 1H), 3.32-3.21 (m, 2H), 3.03-2.98 (m, 3H), 2.47-2.30 (m, 4H), 2.25-1.70 (m, 4H). LCMS (ES) [M+1]$^+$ m/z 357.5.

Example 40

(4R)—N-{2,3-dimethoxy-6H,7H,8H-cyclopenta[b]1,5-naphthyridin-9-yl}-1-methylazepan-4-amine-HCl

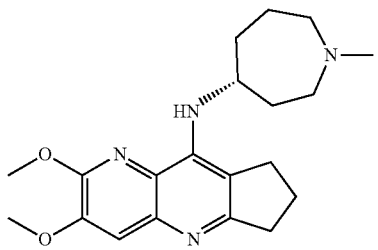

Into a 40-mL vial, was placed a mixture of (R)—N-(azepan-4-yl)-2,3-dimethoxy-7,8-dihydro-6H-cyclopenta[b][1,5]naphthyridin-9-amine—HCl (100 mg, 0.26 mmol, 1 eq.) in MeOH (10 mL), and TEA (78.8 mg, 0.78 mmol, 3 eq.), the mixture was stirred for 15 minutes at rt, HCHO (30% aqueous, 3 mL) and NaBH(OAc)$_3$ (276 mg, 1.3 mmol, 5 eq.) were added subsequently. The mixture was stirred for 16 h at 50° C. and then concentrated under vacuum. The residue was diluted with DMF (5 mL), filtered and subjected to reverse phase preparative HPLC (Prep-C18, 5 μM XBridge column, 19×150 mm, Waters; gradient elution of 4% MeCN in water to 20% MeCN in water over a 6 min period, where both solvents contain 0.1% TFA). The eluents were concentrated under vacuum, and H$_2$O (10 mL) and 1M HCl (aq., 1 mL) were added. The solution was lyophilized to provide the title compound as a light yellow solid (54 mg, 50%). $^1$H NMR (300 MHz, Methanol-d$_4$) δ 7.38 (s, 1H), 4.19 (d, J=2.8 Hz, 3H), 4.06 (s, 3H), 3.67-3.55 (m, 3H), 3.51-3.32 (m, 3H), 3.32-3.12 (m, 3H), 2.97 (d, 7=2.5 Hz, 3H), 2.51-2.27 (m, 5H), 2.19-1.94 (m, 3H). LCMS (ES) [M+1]$^+$ m/z 357.2.

Example 41

(3R)—N-[6,7-di(2H3)methoxy-1H,2H,3H-cyclopenta[b]quinolin-9-yl]piperidin-3-amine

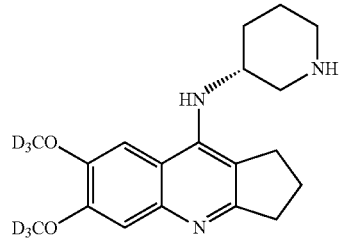

To a solution of Intermediate 1 (650 mg; 2.46 mmol; 1 eq.) in CH₂Cl₂ (6 mL) at 0° C. was added BBr₃ (6.16 mL; 1 mol/L; 6.16 mmol; 2.50 eq.). The solution was warmed to rt, concentrated, and diluted with water and sat. NaHCO₃ followed by 4N NaOH. The aqueous layer was extracted with EtOAc, acidified with concentrated HCl to pH=5, and filtered to give 9-chloro-1H,2H,3H-cyclopenta[b]quinoline-6,7-diol as yellow solid (299 mg, 52%). LCMS (ES) [M+1]⁺ m/z 235.4, 237.6.

To a suspension of 9-chloro-4-(chlorohydrogenio)-1H,2H,3H-4/4-cyclopenta[b]quinoline-6,7-diol (600 e mg; 2.20 mmol; 1 eq.) and cesium fluoride (2 002.14 mg; 13.18 mmol; 6 eq.) in DMF (18 mL) was added iodo(²H3)methane (0.55 mL; 8.79 mmol; 4 eq.). After 4 h at rt, the mixture was heated at 55° C. for 2 h, and cooled to rt. Water and EtOAc were added, the solution was filtered, and the organic layer was separated, the aqueous layer was extracted with EtOAc and the organic layers were combined, dried and concentrated to give 9-chloro-6,7-bis(²H3)methoxy-1H,2H,3H-cyclopenta[b]quinoline (160 mg, 27%). LCMS (ES) [M+1]⁺ m/z 269.4, 271.8.

To a solution of 9-chloro-6,7-bis(²H3)methoxy-1H,2H,3H-cyclopenta[b]quinoline (160 mg; 0.59 mmol; 1 eq.) in Dioxane (5 mL) was added tert-butyl (3R)-3-aminopiperidine-1-carboxylate (178.19 mg; 0.89 mmol; 1.50 eq.) followed by BrettPhos G1 precatalyst (47.38 mg; 0.06 mmol; 0.10 eq.) and NaOtBu (171.01 mg; 1.78 mmol; 3 eq.). The mixture was degassed with N₂ for 5 min, sealed and heated at 100° C. for 1 h. The mixture was cooled and diluted with water and EtOAc, organic layer was separated and concentrated to give tert-butyl (3R)-3-{[6,7-bis(²H3)methoxy-1H,2H,3H-cyclopenta[b]quinolin-9-yl]amino}piperidine-1-carboxylate, which was used without purification (250 mg, 97%). LCMS (ES) [M+1]⁺ m/z 433.8.

To a solution of tert-butyl (3R)-3-{[6,7-bis(²H3)methoxy-1H,2H,3H-cyclopenta[b]quinolin-9-yl]amino}piperidine-1-carboxylate (250 mg; 0.58 mmol; 1 eq.) in CH₂Cl₂ (2 mL) was added TFA (2 mL). The mixture was stirred for 1 hr at ambient temperature, and was concentrated to remove TFA, the residue was diluted with AcCN/1N HCl and subjected to reverse phase preparative HPLC (Waters XSelect CSH C18 column, 0.1% aqueous HCl/acetonitrile gradient) to provide title compound as off white solid. (165 mg, 86%). ¹H NMR (400 MHz, DMSO-d₆) δ 9.33 (s, 2H), 8.17 (d, J=8 Hz, 1H), 7.96 (s, 1H), 7.21 (s, 1H), 4.60-4.53 (m, 1H), 3.40-3.29 (m, 1H), 3.27-3.05 (m, 5H), 2.74 (s, 1H), 2.14 (p, J=7.5 Hz, 2H), 2.01 (d, J=10.2 Hz, 1H), 1.97-1.84 (m, 2H), 1.79 (d, J=13.3 Hz, 1H). LCMS (ES) [M+1]⁺ m/z 334.02.

Example 42

(3R)—N-[6,7-di(2H3)ethoxy-1H,2H,3H-cyclopenta[b]quinolin-9-yl]piperidin-3-amine

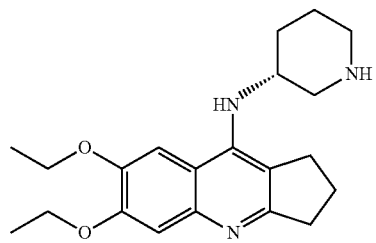

To a solution of 9-chloro-1H,2H,3H-cyclopenta[b]quinoline-6,7-diol (125 mg; 0.53 mmol; 1 eq.) in DMF (2 mL) was added K₂CO₃ (365.98 mg; 2.65 mmol; 5 eq.) and iodoethane (0.17 mL; 2.12 mmol; 4 eq.). The mixture was stirred at rt for 2 h, and was heated at 55° C. for 55 h, the dark solution was diluted with water and extracted with EtOAc, organic layers was concentrated and subjected to column purification (CH₂Cl₂/EtOAc=100:0 to 50:50) to give 9-chloro-6,7-diethoxy-1H,2H,3H-cyclopenta[b]quinoline (25 mg, 16%). LCMS (ES) [M+1]⁺ m/z 291.5, 293.8.

To a solution of 9-chloro-6,7-diethoxy-1H,2H,3H-cyclopenta[b]quinoline (25 mg; 0.09 mmol; 1 eq.) and tert-butyl (3R)-3-aminopiperidine-1-carboxylate (25.74 mg; 0.13 mmol; 1.50 eq.) in dioxane (1.5 mL) was added Brettphos precatalyst (6.84 mg; 0.01 mmol; 0.10 eq.) and NaOtBu (24.70 mg; 0.26 mmol; 3 eq.). The mixture was heated at 100° C. for 1 h, cooled and diluted with water and EtOAc, organic layer was separated and the aqueous layer was extracted with additional EtOAc. The organic layers were combined, washed with brine, dried and concentrated to give tert-butyl (3R)-3-{[6,7-di(²H3)ethoxy-1H,2H,3H-cyclopenta[b]quinolin-9-yl]amino}piperidine-1-carboxylate as crude product, which was diluted with CH₂Cl₂ (1 mL) and TFA (1.5 mL), stirred for 1.5 h, concentrated, and purified by preparative HPLC to give the title compound (11 mg, 36%). ¹H NMR (400 MHz, DMSO-d₆) δ 9.50 (s, 2H), 8.20 (s, 1H), 7.99 (s, 1H), 7.28 (s, 1H), 4.63-4.54 (m, 1H), 4.26 (q, J=6.9 Hz, 2H), 4.13 (q, J=6.9 Hz, 2H), 3.41-3.32 (m, 1H), 3.32 (s, 1H), 3.21 (d, J=12.6 Hz, 1H), 3.10 (dt, J=19.5, 7.7 Hz, 3H), 2.72 (d, J=10.9 Hz, 1H), 2.13 (p, J=7.5 Hz, 2H), 2.04-1.76 (m, 4H), 1.38 (dt, J=12.8, 6.9 Hz, 6H). LCMS (ES) [M+1]⁺ m/z 356.1.

Example 43

(3R)—N-{6-ethoxy-7-methoxy-1H,2H,3H-cyclopenta[b]quinolin-9-yl}piperidin-3-amine

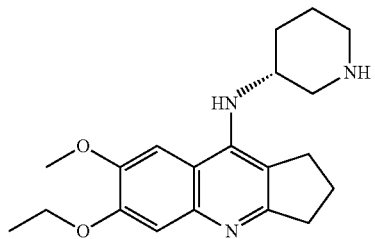

Intermediate 1-b (500 mg; 2 mmol; 1 eq.) was suspended in N,N-dimethylformamide (20 ml). Iodoethane (0.32 mL; 4 mmol; 2 eq.) and potassium carbonate (829.02 mg; 6.01 mmol; 3 eq.) were added and the reaction was stirred at 100° C. After 3 h, the mixture was partitioned into EtOAc and water. The phases were separated, the aqueous phase was extracted with EtOAc, and the combined organic phases were then washed with water and NaCl (aq.). After drying over Na₂SO₄ and evaporation, the residue was purified by silica gel chromatography (0-50% EtOAc/CH₂Cl₂) to give an off-white solid of 9-chloro-6-ethoxy-7-methoxy-1H,2H,3H-cyclopenta[b]quinoline (0.38 g, 68%). ¹H NMR (400 MHz, Chloroform-d) δ 7.38-7.33 (m, 2H), 4.25 (q, J=7.0 Hz, 2H), 4.03 (s, 3H), 3.15 (dt, J=18.4, 7.6 Hz, 4H), 2.22 (p, J=7.6 Hz, 2H), 1.55 (t, J=7.0 Hz, 3H). LCMS (ES) [M+1]⁺ m/z 277.5.

9-chloro-6-ethoxy-7-methoxy-1H,2H,3H-cyclopenta[b]quinoline (0.38 g; 1.37 mmol; 1 eq.) was partly dissolved in 1,4-dioxane (9 ml) and the mixture was purged with argon gas. Tert-butyl (3R)-3-aminopiperidine-1-carboxylate (0.33 g; 1.64 mmol; 1.20 eq.), BrettPhos Pd G1 (32.79 mg; 0.04 mmol; 0.03 eq.) and then NaOtBu (0.53 g; 5.47 mmol; 4 eq.) were added. The reaction was stirred in a heat block at 110° C. After 2 h, the reaction was cooled and filtered through Celite, rinsing with warm EtOAc. The filtrate was evaporated and purified by silica gel chromatography (0-10% MeOH/CH$_2$Cl$_2$) to give a glassy residue of tert-butyl (3R)-3-({6-ethoxy-7-methoxy-1H,2H,3H-cyclopenta[b]quinolin-9-yl}amino)piperidine-1-carboxylate (0.6 g, 99%). $^1$H NMR (400 MHz, Chloroform-d) δ 7.32 (s, 1H), 6.96 (s, 1H), 4.23 (q, J=7.0 Hz, 3H), 3.98 (s, 3H), 3.91-3.75 (m, 2H), 3.56-3.49 (m, 1H), 3.37-3.29 (m, 1H), 3.27-3.20 (m, 1H), 3.14-2.99 (m, 4H), 2.16 (p, J=7.5 Hz, 2H), 2.02-1.95 (m, 1H), 1.53 (t, J=7.0 Hz, 4H), 1.43 (d, J=20.8 Hz, 9H). LCMS (ES) [M+1]$^+$ m/z 442.0. tert-butyl (3R)-3-({6-ethoxy-7-methoxy-1H,2H,3H-cyclopenta[b]quinolin-9-yl}amino) piperidine-1-carboxylate (0.60 g; 1.36 mmol; 1 eq.) was dissolved in CH$_2$Cl$_2$ (6 ml). Trifluoroacetic acid (3.40 mL; 0.40 mol/L; 1.36 mmol; 1 eq.) was added slowly. After 2 h, the reaction solution was evaporated to dryness. It was resuspended in toluene (20 ml) and evaporated to dryness again. The residue was purified by reverse phase chromatography (Waters XSelect CSH C18 column, 0.1% aqueous HCl/acetonitrile gradient) to give a white solid of (3R)—N-{6-ethoxy-7-methoxy-1H,2H,3H-cyclopenta[b]quinolin-9-yl}piperidin-3-amine—2HCl (0.56 g, 62%). $^1$H NMR (400 MHz, DMSO-J6) δ 9.51 (s, 2H), 8.31 (s, 1H), 8.04 (s, 1H), 7.30 (s, 1H), 4.62 (s, 1H), 4.16 (s, 2H), 4.01 (s, 3H), 3.30-3.03 (m, 7H), 2.76 (s, 1H), 2.17 (s, 2H), 2.09-1.76 (m, 4H), 1.43 (s, 3H). LCMS (ES) [M+1]$^+$ m/z 341.9.

Example 44

(3S,5R)—N-{6,7-dimethoxy-1H,2H,3H-cyclopenta[b]quinolin-9-yl}-5-methylpiperidin-3-amine

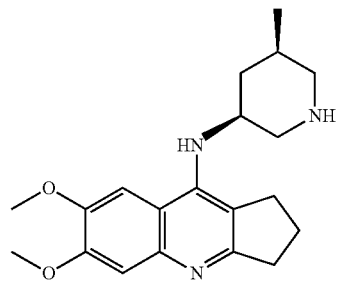

Into a 40-mL vial purged and maintained under N$_2$, was placed a mixture of (cis)-tert-butyl-3-amino-5-methylpiperidine-1-carboxylate (1 g, 4.67 mmol, 1 eq.), dioxane (20 mL), 9-chloro-6,7-dimethoxy-1H,2H,3H-cyclopenta[b]quinoline (1.2 g, 4.67 mmol, 1 eq.), t-BuONa (1.3 g, 14 mmol, 3.0 eq.) and 3rd Generation BrettPhos precatalyst (211.5 mg, 0.23 mmol, 0.05 eq.). The solution was stirred for 2 hr at 90° C. The mixtures were combined and concentrated under vacuum. The residue was purified by column chromatography on silica gel eluted with EtOAc to provide (±)-tert-butyl (3S,5R)-3-([6,7-dimethoxy-1H,2H, 3H-cyclopenta[b]quinolin-9-yl]amino)-5-methylpiperidine-1-carboxylate as yellow oil (1.2 g, 58%). LCMS (ES) [M+1]$^+$ m/z 442.3.

Into a 50-mL round-bottom flask, was placed a mixture of (±)-tert-butyl (3S,5R)-3-([6,7-dimethoxy-1H,2H,3H-cyclopenta[b]quinolin-9-yl]amino)-5-methylpiperidine-1-carboxylate (1.2 g, 2.72 mmol, 1 eq.), CH$_2$Cl$_2$ (20 mL), 4 M HCl/dioxane (10.2 mL, 40.8 mmol, 15 eq.). The solution was stirred for 5 h at rt. The solids were filtered out to provide a racemic mixture of N-{6,7-dimethoxy-1H,2H,3H-cyclopenta[b]quinolin-9-yl}-5-methylpiperidin-3-amine as white solid 780 mg (75.95%). LCMS (ES) [M-2HCl+1]$^+$ m/z 342.2.

The mixture was separated by Pre-Chair-HPLC with the following conditions: Column, CHIRALCEL OD-3, 4.6*50 mm, 3.0 um; mobile phase, A: n-Hexane (0.2% MIPA); B: EtOH/MeOH=l/l; Detector, 190 nm to 500 nm to provide 273.8 mg (49.29%) of (3R,5S)—N-[6, 7-dimethoxy-1H, 2H, 3H-cyclopenta[b]quinolin-9-yl]-5methylpiperidin-3-amine as off-white solid and 279.2 mg (36%) of (3S,5R)—N-[6, 7-dimethoxy-1H,2H,3H-cyclopenta[b]quinolin-9-yl]-5-methylpiperidin-3-amine as off-white solid. $^1$H NMR (300 MHz, DMSO-d$_6$): 10.0-9.50 (br, 1H), 7.66 (s, 1H), 7.19 (s, 1H), 6.70 (br, 1H), 4.29-4.29 (m, 1H), 3.94 (s, 3H), 3.88 (s, 3H), 3.33-3.30 (m, 1H), 3.22-3.19 (m, 2H), 3.08-3.06 (m, 1H), 3.03-2.94 (m, 3H), 2.41-2.28 (m, 1H), 2.14-2.01 (m, 4H), 1.53-1.41 (m, 1H), 0.89 (m, 3H). LCMS (ES) [M+1]$^+$ m/z 342.2.

Example 45

(3R,5R)—N-{6,7-dimethoxy-1H,2H,3H-cyclopenta[b]quinolin-9-yl}-5-methylpiperidin-3-amine

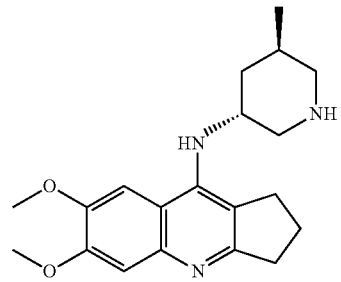 [SMILES: COc1cc2nc3c(c(N[C@H]4CNC[C@H](C)C4)c2cc1OC)CCC3]

Into a 250-mL round-bottom flask, was placed a solution of 1,5-dimethyl (2R)-2-aminopentanedioate (9.8 g, 55.94 mmol, 1 eq.) in MeOH (100 mL), TEA (17.0 g, 167.82 mmol, 3 eq.), Boc$_2$O (14.7 g, 67.13 mmol, 1.2 eq.). The solution was stirred for 16 hr at rt. The mixture was concentrated, diluted with 200 mL of CH$_2$Cl$_2$, and washed with brine. The mixture was dried over anhydrous Na$_2$SO$_4$, concentrated, and applied onto a silica gel column with CH$_2$Cl$_2$/MeOH (30:1) to provide 1,5-dimethyl (2R)-2-[[(tert-butoxy)carbonyl]amino]pentanedioate 10 g (64.9%) as colorless oil. LCMS (ES) [M+1]$^+$ m/z 276.1.

Into a 500-mL 3-necked round-bottom flask, was placed a solution of 1,5-dimethyl (2R)-2-[[(tert-butoxy)carbonyl]amino]pentanedioate (10 g, 36.32 mmol, 1 eq.) in THF (100 mL). This was followed with LiHMDS (36.3 mL, 72.6 mmol, 2 eq.) dropwise with stirring at −78° C. The solution was stirred for 0.5 hr at −78° C. To this MeI (7.7 g, 54.49 mmol, 1.5 eq.) was added. The solution was stirred for 2 hr at −78° C. The reaction was then quenched with 100 mL of NH$_4$Cl. The solution was extracted with EtOAc and the organic layers combined and dried over anhydrous Na$_2$SO$_4$, concentrated, and applied onto a silica gel column with CH$_2$Cl$_2$/MeOH (100:1) to provide the 1,5-dimethyl (2R)-2-[[(tert-butoxy)carbonyl]amino]-4-methylpentanedioate 6.7 g (63.75%) as white solid. LCMS (ES) [M+1]$^+$ m/z 290.2.

Into a 100-mL round-bottom flask, was placed a solution of 1,5-dimethyl (2R)-2-[[(tert-butoxy)carbonyl]amino]-4-methylpentanedioate (3 g, 10.37 mmol, 1 eq.) in EtOH (15 mL), a solution of CaCl$_2$ (4.6 g, 41.48 mmol, 4 eq.) in H$_2$O (15 mL). This was followed with NaBH$_4$ (3.1 g, 82.95 mmol, 8 eq.) at 0° C. The solution was stirred for 16 hr at rt. The reaction was then quenched with 50 mL of 10% Na$_2$CO$_3$. The solution was extracted with EtOAc and the organic layers combined. The mixture was washed with brine. The mixture was dried over anhydrous Na$_2$SO$_4$ and concentrated to provide the crude tert-butyl N-[(2R)-1,5-dihydroxy-4-methylpentan-2-yl]carbamate 2.1 g (86.81%) as colorless oil without further purification. LCMS (ES) [M+1]$^+$ m/z 234.2.

Into a 100-mL 3-necked round-bottom flask, was placed a solution of tert-butyl N-[(2R)-1,5-dihydroxy-4-methylpentan-2-yl]carbamate (2.1 g, 9 mmol, 1 eq.) in CH$_2$Cl$_2$ (25 mL), TEA (3.6 g, 36 mmol, 4 eq.). This was followed with MsCl (3.1 g, 27 mmol, 3 eq.) dropwise with stirring at 0° C. The solution was stirred for 1 hr at 0° C. The solution was diluted with 30 mL of CH$_2$Cl$_2$. The mixture was washed with brine. The mixture was dried over anhydrous Na$_2$SO$_4$ and concentrated to provide the crude N-[(2R)-1,5-bis(methanesulfonyloxy)-4-methylpentan-2-yl]carbamate 2.9 g (82.7%) as colorless oil. LCMS (ES) [M+1]$^+$ m/z 390.1.

Into a 100-mL round-bottom flask, was placed tert-butyl N-[(2R)-1,5-bis(methanesulfonyloxy)-4-methylpentan-2-yl]carbamate (2.9 g, 7.46 mmol, 1 eq.), 1-phenylmethanamine (30 mL). The solution was stirred for 16 hr at 70° C. The solution was cooled to rt and diluted with 100 mL of EA. The mixture was washed with 2×100 ml of 1N NaOH and 2×100 mL of brine. The mixture was dried over anhydrous Na$_2$SO$_4$, and applied onto a silica gel column with EtOAc/petroleum ether (1:50) to provide the tert-butyl N-[(3R,5R)-1-benzyl-5-methylpiperidin-3-yl]carbamate 1.4 g (61.7%) as colorless oil. LCMS (ES) [M+1]$^+$ m/z 305.2.

Into a 100-mL round-bottom flask, was placed a solution of tert-butyl N-[(3R,5R)-1-benzyl-5-methylpiperidin-3-yl]carbamate (1.4 g, 4.60 mmol, 1 eq.) in dioxane (10 mL), HCl in 1,4-dioxane (10 mL, 4 mol/L). The solution was stirred for 1 hr at rt. The solution was diluted with 20 mL of H$_2$O. The pH value of the solution was adjusted to 7-8 with Na$_2$CO$_3$ (10%). The mixture was concentrated and applied onto a silica gel column with CH$_2$Cl$_2$/MeOH (4:1) to provide (3R,5R)-1-benzyl-5-methylpiperidin-3-amine 540 mg (57.5%) as colorless oil. LCMS (ES) [M+1]$^+$ m/z 205.2.

Into a 100-mL round-bottom flask purged and maintained under N$_2$, was placed a solution of (3R,5R)-1-benzyl-5-methylpiperidin-3-amine (464.8 mg, 2.28 mmol, 1.2 eq.) in dioxane (5 mL), 9-chloro-6,7-dimethoxy-1H,2H,3H-cyclopenta[b]quinoline (500 mg, 1.90 mmol, 1 eq.), t-BuONa (728.8 mg, 7.58 mmol, 4 eq.), BrettPhos Pd G3 (85.9 mg, 0.09 mmol, 0.05 eq.). The solution was stirred for 4 hr at 90° C. under N$_2$ atmosphere. The mixture was filtered, concentrated, and applied onto a silica gel column with EtOAc to provide (3R,5R)-1-benzyl-N-[6,7-dimethoxy-1H,2H,3H-cyclopenta[b]quinolin-9-yl]-5-methylpiperidin-3-amine 400 mg (48.9%) as light yellow solid. LCMS (ES) [M+1]$^+$ m/z 432.3.

Into a 50-mL pressure tank reactor, was placed a solution of (3R,5R)-1-benzyl-N-[6,7-dimethoxy-1H,2H,3H-cyclopenta[b]quinolin-9-yl]-5-methylpiperidin-3-amine (400 mg, 0.93 mmol, 1 eq.) in MeOH (10 mL), 10% Pd/C (40 mg, 10% w/w), HCl (67.6 mg, 1.85 mmol, 2 eq.). The solution was stirred for 16 hr at rt under H$_2$ atmosphere (20 atm). The solution was filtered and diluted with 10 mL of H$_2$O. The pH value of the solution was adjusted to 7-8 with Na$_2$CO$_3$ (10%). The crude product was purified by Flash-Prep-HPLC with the following conditions (IntelFlash-1): Column, silica gel; mobile phase, H$_2$O:MeCN=10:1 increasing to H$_2$O:MeCN=1:1 with 10 min; Detector, UV. to provide the title compound product 78 mg (24.6%) as off-white solid. $^1$H NMR (300 MHz, DMSO-d$_6$) δ 7.28 (s, 1H), 7.14 (s, 1H), 5.84-5.64 (m, 1H), 3.86 (d, J=7.1 Hz, 7H), 3.03-2.93 (m, 2H), 2.90-2.71 (m, 5H), 2.46 (s, 1H), 2.20 (dd, J=11.8, 8.3 Hz, 1H), 2.02 (p, J=7.4 Hz, 2H), 1.75 (d, J=12.6 Hz, 2H), 1.39-1.19 (m, 1H), 0.79 (d, J=6.3 Hz, 3H). LCMS (ES) [M+1]$^+$ m/z 342.2.

Example 46 and Example 47

(3R)—N-{6,7-dimethoxy-1H,2H,3H-cyclopenta[b]quinolin-9-yl}-5,5-difluoropiperidin-3-amine

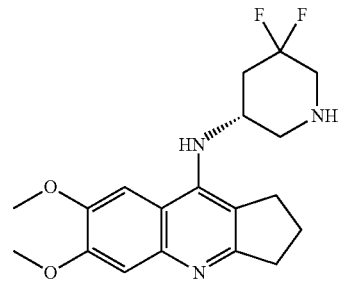

(3S)—N-{6,7-dimethoxy-1H,2H,3H-cyclopenta[b]quinolin-9-yl}-5,5-difluoropiperidin-3-amine

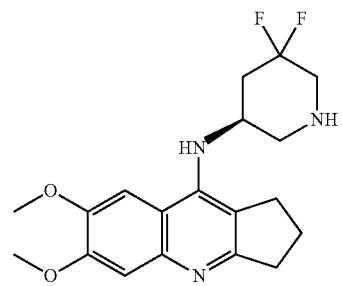

Into a 50-mL round-bottom flask, was placed tert-butyl N-(5,5-difluoropiperidin-3-yl)carbamate (1.2 g, 5.08 mmol, 1 eq.), CH$_2$Cl$_2$ (20 mL), benzaldehyde (646.8 mg, 6.09 mmol, 1.20 eq.), AcOH (2 mL) and NaBH(OAc)$_3$ (2.2 g, 10.16 mmol, 2 eq.). The solution was stirred for 16 h at rt. The mixture was concentrated and purified by column chromatography on silica gel eluted with EtOAc/petroleum ether (1/10) to provide the title compound as yellow oil (965 mg, 58%). LCMS (ES) [M+1]$^+$ m/z 327.3.

Into a 25-mL round-bottom flask, was placed a mixture of tert-butyl N-(1-benzyl-5,5-difluoropiperidin-3-yl)carbamate (965 mg, 2.96 mmol, 1 eeq.), CH$_2$Cl$_2$ (10 mL) and 4M HCl/dioxane (3.7 mL, 14.8 mmol, 5 eq.). The solution was stirred for 6 h at rt. The mixture was concentrated and water was added (5.0 ml), basified with 2 N Na$_2$CO$_3$ aqueous solution (pH 7~8). The residue was purified by column chromatography on silica gel eluted with EtOAc/petroleum ether (1/1) to provide the title compound as yellow oil (654 mg, 97.7%). LCMS (ES) [M+1]$^+$ m/z 227.3.

Into a 40-mL vial purged and maintained under $N_2$, was placed a mixture of 1-benzyl-5,5-difluoropiperidin-3-amine (653.8 mg, 2.89 mmol, 2 eq.), 9-chloro-6,7-dimethoxy-1H,2H,3H-cyclopenta[b]quinoline (381 mg, 1.44 mmol, 1 eq.), dioxane (20 mL), t-BuONa (416.5 mg, 4.33 mmol, 3.0 eq.) and 3rd Generation BrettPhos precatalyst (65.5 mg, 0.07 mmol, 0.05 eq.). The solution was stirred for 2 h at 90° C. The residue was purified by column chromatography on silica gel eluted with EtOAc provide the title compound as yellow solid (507 mg 77%). LCMS (ES) [M+1]$^+$ m/z 454.1.

Into a 50-mL sealed tube, was placed a mixture of 1-benzyl-N-[6,7-dimethoxy-1H,2H,3H-cyclopenta[b]quinolin-9-yl]-5,5-difluoropiperidin-3-amine (507 mg, 1.12 mmol, 1 eq.), MeOH (10 mL), 10% Pd/C (50 mg, 0.42 eq.), HCl (122.3 mg, 3.35 mmol, 3 eq.). The mixture was degassed and purged with $H_2$ for several time and then stirred for 8 h at rt under $H_2$. The solids were filtered out. The mixture was concentrated to provide the title compound as off-white solid 350 mg (78.30%). LCMS (ES) [M−HCl+1]$^+$ m/z 364.4.

The mixture was separated by Pre-Chair-HPLC with the following conditions: Column, CHIRALCEL OD-3, 4.6*50 mm, 3.0 um; mobile phase, A: n-Hexane (0.2% MIPA); B: EtOH; Detector, 190 nm to 500 nm to provide 56.3 mg (14.28%) of (3R)—N-[6,7-dimethoxy-1H,2H,3H-cyclopenta[b]quinolin-9-yl]-5,5-difluoropiperidin-3-amine as white solid and 23.62 mg (6.7%) of (3S)—N-[6,7-dimethoxy-1H,2H,3H-cyclopenta[b]quinolin-9-yl]-5,5-difluoropiperidin-3-amine (3R)—N-{6,7-dimethoxy-1H,2H,3H-cyclopenta[b]quinolin-9-yl}-5,5-difluoropiperidin-3-amine: $^1$H NMR (300 MHz, DMSO-$d_6$): 8.18 (br, 1H), 7.44 (s, 1H), 7.15 (s, 1H), 6.03-6.00 (br, 1H), 4.03-3.97 (m, 1H), 3.90 (s, 1H), 3.86 (s, 1H), 3.14-2.96 (m, 4H), 2.91-2.83 (m, 2H), 2.79-2.73 (m, 1H), 2.58-2.51 (m, 1H), 2.41-2.21 (m, 1H), 2.18-2.15 (m, 1), 2.12-2.09 (m, 3H). LCMS (ES) [M+1]$^+$ m/z 364.2.

(3S)—N-{6,7-dimethoxy-1H,2H,3H-cyclopenta[b]quinolin-9-yl}-5,5-difluoropiperidin-3-amine: $^1$H NMR (300 MHz, DMSO-$d_6$): 8.25-8.20 (br, 1H), 7.42 (s, 1H), 7.15 (s, 1H), 5.93-5.87 (br, 1H), 4.01-3.98 (m, 1H), 3.90 (s, 3H), 3.86 (s, 3H), 3.18-2.96 (m, 4H), 2.90-2.80 (m, 2H), 2.78-2.73 (m, 1H), 2.69-2.58 (m, 1H), 2.43-2.27 (m, 1H), 2.22-2.12 (m, 3H). LCMS (ES) [M+1]$^+$ m/z 364.2.

Example 48

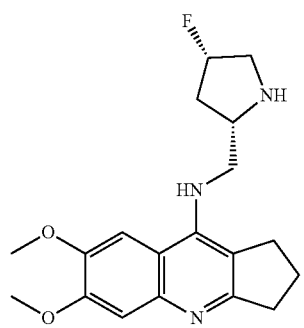

N-{[(2S,4S)-4-fluoropyrrolidin-2-yl]methyl}-6,7-dimethoxy-1H,2H,3H-cyclopenta[b]quinolin-9-amine Into a 40-mL vial purged and maintained under $N_2$, was placed a mixture of 1-[(2S,4S)-1-benzyl-4-fluoropyrrolidin-2-yl]methanamine (200 mg, 0.48 mmol, 0.5 eq., 50% w/w), dioxane (5.0 mL), 9-chloro-6,7-dimethoxy-1H,2H,3H-cyclopenta[b]quinoline (278.6 mg, 1.06 mmol, 1.1 eq.), t-BuONa (276.8 mg, 2.88 mmol, 3 eq.) and 3rd Generation BrettPhos precatalyst (43.5 mg, 0.05 mmol, 0.05 eq.). The solution was stirred for 2 hours at 90° C. in an oil bath. The reactions were conducted for 2 batches (200 mg×2, total 400 mg) in parallel. The mixture was concentrated and purified by flash column eluted with $CH_2Cl_2$/MeOH (10/1) to provide 342 mg (82%) of N-[[(2S,4S)-1-benzyl-4-fluoropyrrolidin-2-yl]methyl]-6,7-dimethoxy-1H,2H,3H-cyclopenta[b]quinolin-9-amine as yellow solid. LCMS (ES) [M+1]$^+$ m/z 436.3.

Into a 30-mL pressure tank reactor, was placed a mixture of N-[[(2S,4S)-1-benzyl-4-fluoropyrrolidin-2-yl]methyl]-6,7-dimethoxy-1H,2H,3H-cyclopenta[b]quinolin-9-amine (300 mg, 0.69 mmol, 1 eq.), MeOH (4.0 mL), Pd/C (60 mg, 10% w/w), Conc. HCl (0.20 mL). The solution was stirred for 24 hours at rt under $H_2$. The mixture was filtered, concentrated, and subjected to reverse phase preparative HPLC (Prep-C18, SunFire column, 19×150 mm, Waters; gradient elution of 11% MeCN in water to 21% MeCN in water over a 5 min period, where water phase contain 0.05% TFA) to provide 187.8 mg (48%) of N-[[(2S,4S)-4-fluoropyrrolidin-2-yl]methyl]-6,7-dimethoxy-1H,2H,3H-cyclopenta[b]quinolin-9-amine-(TLA)$_2$ as white solid. $^1$H NMR (300 MHz, DMSO-$d_6$, ppm): 14.20 (br, 1H), 10.15 (br, 1H), 9.75 (br, 1H), 8.43 (s, 1H), 7.71 (s, 1H), 7.29 (s, 1H), 5.48 (d, J=52.8 Hz, 1H), 4.08 (d, J=2.7 Hz, 3H), 3.95 (s, 6H), 3.74-3.63 (m, 1H), 3.52-3.20 (m, 3H), 3.18-3.11 (m, 2H), 2.63-2.55 (m, 1H), 2.32-2.08 (m, 3H). LCMS (ES) [M+1]$^+$ m/z 346.1.

Example 49

(3R,5S)—N-{6,7-dimethoxy-1H,2H,3H-cyclopenta[b]quinolin-9-yl}-5-fluoropiperidin-3-amine

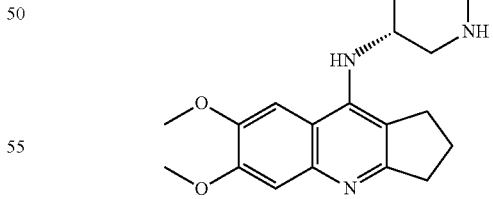

Into a 500-mL round-bottom flask, was placed a mixture of ethyl (2S,4R)-4-hydroxypyrrolidine-2-carboxylate hydrochloride (10.0 g, 51.11 mmol, 1 eq.), BnBr (9.6 g, 0.06 mmol, 1.1 eq.), DIEA (16.5 g, 0.13 mmol, 2.5 eq.) and toluene (150 mL). The solution was stirred for 6 hours at 110° C. in an oil bath. The reaction was then quenched with 200 mL of saturated aqueous $NaHCO_3$, extracted with EtOAc, the combined organic layers were washed with brine, dried over anhydrous $Na_2SO_4$ and concentrated to provide 14.3 g of ethyl (2S,4R)-1-benzyl-4-hydroxypyrrolidine-2-carboxylate as crude brown oil. LCMS (ES) [M+1]+ m/z 250.2.

Into a 500-mL 3-necked round-bottom flask purged and maintained under $N_2$, was placed a solution of ethyl (2S,4R)-1-benzyl-4-hydroxypyrrolidine-2-carboxylate (13.0 g, 52.14 mmol, 1 eq.) in $CH_2Cl_2$ (300 mL). This was followed with DAST (21.0 g, 130 mmol, 2.5 eq.) dropwise with stirring at −78° C. The solution was stirred for 16 hours at rt. The reaction was then quenched with 200 mL of saturated aqueous $Na_2CO_3$ solution, extracted with $CH_2Cl_2$, the combined organic layers were dried over anhydrous $Na_2SO_4$, concentrated, and purified by flash column eluted with EtOAc/petroleum ether (1/4) to provide 7.45 g (57%) of ethyl (2S,4S)-1-benzyl-4-fluoropyrrolidine-2-carboxylate as yellow oil. LCMS (ES) [M+1]+ m/z 252.2.

Into a 500-mL 3-necked round-bottom flask purged and maintained under $N_2$, was placed a solution of ethyl (2S,4S)-1-benzyl-4-fluoropyrrolidine-2-carboxylate (7.45 g, 29.65 mmol, 1 eq.) in THF (200 mL), DIBAL-H (90 mL, 89.1 mmol, 3.0 eq., 1M in hexane) was added dropwise at 0° C. The solution was stirred for 45 minutes at 0° C. in a water/ice bath. The reaction was quenched with 150 mL saturated aqueous potassium sodium tartrate solution and stirred for 1 hour at rt. The mixture was extracted with EtOAc. The combined organic layers were washed with brine, dried over anhydrous $Na_2SO_4$, concentrated, and purified by flash column eluted with EtOAc/petroleum ether (1/2) to provide 4.70 g (76%) of [(2S,4S)-1-benzyl-4-fluoropyrrolidin-2-yl] as light yellow oil. LCMS (ES) [M+1]+ m/z 210.2.

Into a 250-mL 3-necked round-bottom flask purged and maintained under $N_2$, was placed a solution of [(2S,4S)-1-benzyl-4-fluoropyrrolidin-2-yl]methanol (2 g, 9.56 mmol, 1 eq.) in $CH_2Cl_2$ (160 mL), to which were added $Bu_4NN_3$ (2.98 g, 10.48 mmol, 1.10 eq.) and XtalFluor-E (2.40 g, 10.48 mmol, 1.10 eq.) at −78° C. The solution was stirred for 4 hours at −78° C. in a liquid nitrogen bath. The reaction was then quenched with 100 mL of 3.75M aqueous NaOH solution at −78° C. The solution was extracted with $CH_2Cl_2$, the combined organic layers were dried over anhydrous $Na_2SO_4$, concentrated, and purified by flash column eluted with EtOAc/petroleum ether (1/4) to provide 1.21 g crude mixture of (3R,5S)-3-azido-1-benzyl-5-fluoropiperidine and (2S,4S)-2-(azidomethyl)-1-benzyl-4-fluoropyrrolidine as yellow oil. LCMS (ES) [M+1]+ m/z 235.2.

Into a 40-mL vial purged and maintained under $N_2$, was placed a mixture of (3R,5S)-3-azido-1-benzyl-5-fluoropiperidine (0.50 g, 2.13 mmol, 0.5 eq.) and (2S,4S)-2-(azidomethyl)-1-benzyl-4-fluoropyrrolidine (0.50 g, 2.13 mmol, 0.5 eq.) in THF (20 mL), to which were added $PPh_3$ (1.7 g, 0.01 mmol, 1.5 eq.) and $H_2O$ (0.538 g, 29.86 mmol, 7.0 eq.). The solution was stirred for 4 hours at 80° C. in an oil bath. The mixture was concentrated and purified by flash column eluted with $CH_2Cl_2$/MeOH (10/1) to provide 582 mg (66%) mixture of (3R,5S)-1-benzyl-5-fluoropiperidin-3-amine and 1-[(2S,4S)-1-benzyl-4-fluoropyrrolidin-2-yl]methanamine as light yellow oil. LCMS (ES) [M+1]+ m/z 209.2.

Into a 40-mL vial purged and maintained under $N_2$, was placed a mixture (3R,5S)-1-benzyl-5-fluoropiperidin-3-amine (200 mg, 0.48 mmol, 0.5 eq., 50% w/w), dioxane (5.0 mL), 9-chloro-6,7-dimethoxy-1H,2H,3H-cyclopenta[b]quinoline (278.6 mg, 1.06 mmol, 1.1 eq.), t-BuONa (276.8 mg, 2.88 mmol, 3.0 eq.) and 3rd Generation BrettPhos precatalyst (43.5 mg, 0.05 mmol, 0.05 eq.). The solution was stirred for 2 hours at 90° C. in an oil bath. The reactions were conducted for 2 batches (200 mg×2, total 400 mg) in parallel. The mixtures were concentrated and purified by flash column eluted with $CH_2Cl_2$/MeOH (10/1) to provide 258 mg (62%) of (3R,5S)-1-benzyl-N-[6,7-dimethoxy-1H,2H,3H-cyclopenta[b]quinolin-9-yl]-5-fluoropiperidin-3-amine as yellow solid. LCMS (ES) [M+1]+ m/z 436.3.

Into a 30-mL pressure tank reactor, was placed a mixture of (3R,5S)-1-benzyl-N-[6,7-dimethoxy-1H,2H,3H-cyclopenta[b]quinolin-9-yl]-5-fluoropiperidin-3-amine (200 mg, 0.46 mmol, 1 eq.), MeOH (4.0 mL), Pd/C (50 mg, 10% w/w) and Conc. HCl (0.2 mL, 0.01 mmol, 0.01 eq.). The solution was stirred for 48 hours at rt under $H_2$ atmosphere. The mixture was filtered through a pad of celite, the filter cake was washed with MeOH (2×10 mL). The filtrate was concentrated and subjected to reverse phase preparative HPLC (Prep-C18, SunFire column, 19×150 mm, Waters; gradient elution of 2% MeCN in water to 18% MeCN in water over a 7-min period, where water phase contain 0.05% TFA) to provide 89.9 mg (34%) of (3R,5S)—N-[6,7-dimethoxy-1H,2H,3H-cyclopenta[b]quinolin-9-yl]-5-fluoropiperidin-3-amine—(TFA)$_2$ as white solid. $^1$H NMR (300 MHz, DMSO-$d_6$, ppm): 14.16 (br, 1H), 9.57 (br, 2H), 7.75 (d, d, J=9.0 Hz, 1H), 7.68 (s, 1H), 7.24 (s, 1H), 5.14-4.96 (m, 1H), 4.68-4.62 (m, 1H), 3.95 (s, 6H), 3.69-3.62 (m, 1H), 3.53-3.48 (m, 1H), 3.30-3.03 (m, 6H), 2.60-2.55 (m, 1H), 2.24-2.10 (m, 3H). LCMS (ES) [M+1]+ m/z 346.1.

Example 50 and Example 51

(3R)—N-{6,7-dimethoxy-1H,2H,3H-cyclopenta[b]quinolin-9-yl}-5,5-dimethylpiperidin-3-amine

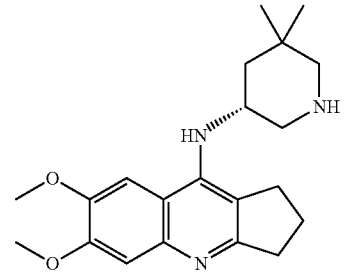

(3S)—N-{6,7-dimethoxy-1H,2H,3H-cyclopenta[b]quinolin-9-yl}-5,5-dimethylpiperidin-3-amine

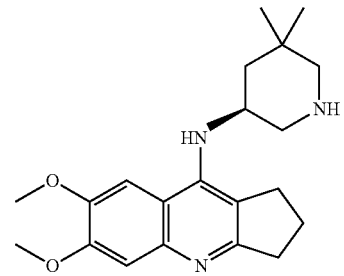 [SMILES: COc1cc2nc3c(c(N[C@@H]4CNCC(C)(C)C4)c2cc1OC)CCC3]

Into a 500-mL 3-necked round-bottom flask purged and maintained under $N_2$, was placed a solution of 2-methylpropanenitrile (10 g, 144.70 mmol, 1 eq.) in THF (300 mL). This was followed with LDA (79.6 mL, 159.20 mmol, 1.1 eq.) dropwise with stirring at −78° C. The solution was stirred for 30 min. To this was added 3-bromoprop-1-ene (21.0 g, 173.64 mmol, 1.2 eq.) at −78° C. The solution was stirred for 16 hr at rt, then quenched with 200 mL of NH₄Cl. The solution was extracted with Et₂O and the organic layers combined. The mixture was washed with ×200 mL of brine. The mixture was dried over anhydrous Na₂SO₄ and concentrated to provide the title compound 5.1 g (32.3%) as light yellow oil.

Into a 250-mL 3-necked round-bottom flask, was placed a solution of 2,2-dimethylpent-4-enenitrile (5.1 g, 46.72 mmol, 1 eq.) in Et₂O (100 mL). This was followed with LiAlH₄ (4.4 g, 116.79 mmol, 2.5 eq.) in several batches at 0° C. The solution was stirred for 4 hr at rt, quenched with 4.4 mL H₂O, 13.2 mL 10% NaOH, and then 4.4 mL H₂O. The solids were filtered out. The solution was extracted with Et₂O and the organic layers combined and dried over anhydrous Na₂SO₄ and concentrated to provide the title compound 2.6 g (49.2%) as yellow oil.

Into a 100-mL round-bottom flask, was placed a solution of 2,2-dimethylpent-4-en-1-amine (2.5 g, 22.08 mmol, 1 eq.) in MeOH (30 mL), benzaldehyde (2.6 g, 24.29 mmol, 1.1 eq.), NaBH₄ (1.3 g, 33.13 mmol, 1.5 eq.). The solution was stirred for 16 hr at rt. The reaction was then quenched with 20 mL of 10% NaOH. The solution was diluted with 100 mL of H₂O. The solution was extracted with EtOAc and the organic layers combined and dried over anhydrous Na₂SO₄, concentrated, and applied onto a silica gel column with EtOAc/petroleum ether (1:4) to provide the title compound 2.6 g (57.9%) as colorless oil. LCMS (ES) [M+1]⁺ m/z 204.2.

Into a 100-mL round-bottom flask, was placed a solution of benzyl(2,2-dimethylpent-4-en-1-yl)amine (2.3 g, 11.31 mmol, 1 eq.) in MeCN (30 mL), NCS (1.5 g, 11.31 mmol, 1 eq.). The solution was stirred for 2 hr at rt. To this was added NaN₃ (0.9 g, 13.57 mmol, 1.2 eq.), NaI (1.8 g, 11.88 mmol, 1.05 eq.). The solution was stirred for 16 hr at 60° C. The reaction was then quenched with 100 mL of 10% NaOH. The solution was extracted with Et₂O and the organic layers combined. The mixture was washed with brine. The solid was dried in an oven under reduced pressure to provide the crude title compound 2.8 g as colorless oil. LCMS (ES) [M+1]⁺ m/z 245.2.

Into a 100-mL round-bottom flask, was placed a solution of 5-azido-1-benzyl-3,3-dimethylpiperidine (2.8 g, 11.46 mmol, 1 eq.) in THF (30 mL), PPh₃ (4.5 g, 17.19 mmol, 1.5 eq.), H₂O (1.4 g, 80.22 mmol, 7 eq.). The solution was stirred for 3 hr at 80° C. The mixture was concentrated and applied onto a silica gel column with CH₂Cl₂/MeOH (10:1) to provide the title compound 2.1 g (83.9%) as light-yellow oil. LCMS (ES) [M+1]⁺ m/z 219.2.

Into a 100-mL round-bottom flask purged and maintained under N₂, was placed a solution of 1-benzyl-5,5-dimethylpiperidin-3-amine (1.7 g, 7.96 mmol, 1.50 eq.) in dioxane (15 mL), 9-chloro-6,7-dimethoxy-1H,2H,3H-cyclopenta[b]quinoline (1.4 g, 5.31 mmol, 1 eq.), t-BuONa (2.0 g, 21.23 mmol, 4 eq.), BrettPhos Pd G3 (0.2 g, 0.27 mmol, 0.05 eq. The solution was stirred for 3 hr at 90° C. under N₂ atmosphere. The mixture was cooled to rt and filtered. The mixture was concentrated and applied onto a silica gel column with EtOAc/petroleum ether (9:1) to provide the title compound 2.1 g (88.77%) as a light yellow solid. LCMS (ES) [M+1]⁺ m/z 446.3.

Into a 50-mL sealed tube, was placed a solution of 1-benzyl-N-[6,7-dimethoxy-1H,2H,3H-cyclopenta[b]quinolin-9-yl]-5,5-dimethylpiperidin-3-amine (1 g, 2.24 mmol, 1 eq.) in MeOH (20 mL), Pd/C (100 mg, 10% w/w), HCl (163.6 mg, 4.49 mmol, 2 eq.). The solution was stirred for 16 min at rt under H₂ atmosphere (20 atm). The solids were filtered out. The solution was diluted with 10 mL of H₂O. NaOH (10%) was employed to adjust the pH to 7-8. The crude product was purified by Flash-Prep-HPLC with the following conditions (IntelFlash-1): Column, C18 silica gel; mobile phase, H₂O: MeCN=10:1 increasing to H₂O: MeCN=2:1 within 10 min; Detector, UV, provided a mixture of the title compounds 400 mg (50.1%) as white solid. LCMS (ES) [M+1]⁺ m/z 356.2.

The mixture was separated by Pre-Chair-HPLC with the following conditions: Column, CHIRALCEL OD-3, 4.6*50 mm, 3.0 um; mobile phase, A: n-Hexane (0.2% MIPA); B: EtOH/MeOH=1/1; Detector, 190 nm to 500 nm to provide. 91.6 mg (22.9%) of (R)—N-(5,5-dimethylpiperidin-3-yl)-6,7-dimethoxy-2,3-dihydro-1H-cyclopenta[b]quinolin-9-amine-(CO₂H)₂ as off-white solid and 86.6 mg (21.6%) of (S)—N-(5,5-dimethylpiperidin-3-yl)-6,7-dimethoxy-2,3-dihydro-1H-cyclopenta[b]quinolin-9-amine as off-white solid.

(3R)—N-{6,7-dimethoxy-1H,2H,3H-cyclopenta[b]quinolin-9-yl}-5,5-dimethylpiperidin-3-amine: NMR (300 MHz, DMSO-d₆) δ 8.27 (d, J=2.7 Hz, 2H), 7.47 (s, 1H), 7.26-7.08 (m, 1H), 5.98 (d, J=12.9 Hz, 1H), 4.11 (d, J=21.8 Hz, 1H), 3.91 (s, 3H), 3.86 (s, 3H), 3.26-3.10 (m, 2H), 3.02 (dt, J=14.7, 7.1 Hz, 1H), 2.96-2.82 (m, 2H), 2.73 (s, 1H), 2.59 (s, 1H), 2.43 (s, 1H), 2.05 (p, J=7.3 Hz, 2H), 1.76 (d, J=12.5 Hz, 1H), 1.49 (t, J=12.2 Hz, 1H), 1.08 (s, 3H), 0.95 (d, J=1.6 Hz, 3H). LCMS (ES) [M-2HCOOH+1]⁺ m/z 356.2

(3S)—N-{6,7-dimethoxy-1H,2H,3H-cyclopenta[b]quinolin-9-yl}-5,5-dimethylpiperidin-3-amine: ¹H NMR (300 MHz, DMSO-d₆) δ 7.43 (s, 1H), 7.11 (s, 1H), 5.63 (d, J=9.7 Hz, 1H), 3.90 (s, 1H), 3.89 (s, 3H), 3.84 (s, 3H), 3.21-2.92 (m, 3H), 2.84 (t, J=7.7 Hz, 2H), 2.50 (s, 1H), 2.38 (t, J=11.2 Hz, 1H), 2.27 (d, J=12.3 Hz, 1H), 2.03 (p, J=7.3 Hz, 2H), 1.71 (d, J=12.8 Hz, 1H), 1.40 (t, J=12.1 Hz, 1H), 1.04 (s, 3H), 0.89 (s, 3H). LCMS (ES) [M+1]⁺ m/z 356.3.

Example 52

(3R,5R)—N-{6,7-dimethoxy-1H,2H,3H-cyclopenta[b]quinolin-9-yl}-5-fluoropiperidin-3-amine

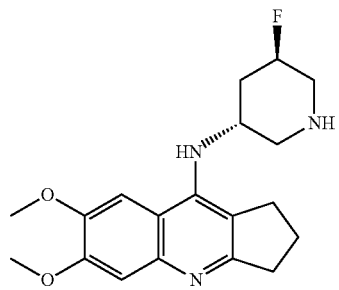

Into a 250-mL round-bottom flask, was placed a mixture of methyl (2S,4S)-4-hydroxypyrrolidine-2-carboxylate hydrochloride (10.9 g, 60.0 mmol, 1 eq.), toluene (60 mL), N-ethyl-N-isopropylpropan-2-amine (15.5 g, 120 mmol, 2 eq.), (bromomethyl)benzene (11.3 g, 66.1 mmol, 1.10 eq.). The solution was stirred for 6 hours at 110° C., concentrated, and applied onto a silica gel column with EtOAc/petroleum ether (1:3) to provide 11.0 g (78%) of methyl (2S,4S)-1-benzyl-4-hydroxypyrrolidine-2-carboxylate as light yellow oil. LCMS (ES) [M+1]⁺ m/z 236.1.

Into a 250-mL 3-necked round-bottom flask, was placed a mixture of methyl (2S,4S)-1-benzyl-4-hydroxypyrrolidine-2-carboxylate (10.0 g, 42.5 mmol, 1 eq.), CH$_2$Cl$_2$ (85 mL), N,N-diethyl-1,1,1-trifluoro-sulfanamine (17.1 g, 106 mmol, 2.50 eq.). The solution was stirred for hr at −78° C. The reaction was then quenched with saturated aq. Na$_2$CO$_3$. The pH value of the solution was adjusted to 9 with saturated Na$_2$CO$_3$ aqueous. The mixture was washed with brine, the organic layer dried over Na$_2$SO$_4$, filtered, concentrated, and applied onto a silica gel column with EtOAc/petroleum ether (1:5) to provide 5.50 g (55%) of methyl (2S,4R)-1-benzyl-4-fluoropyrrolidine-2-carboxylate as light yellow oil. LCMS (ES) [M+1]$^+$ m/z 238.1.

Into a 250-mL round-bottom flask, was placed a mixture of methyl (2S,4R)-1-benzyl-4-fluoropyrrolidine-2-carboxylate (5.50 g, 23.2 mmol, 1 eq.), tetrahydrofuran (47 mL), lithium aluminium tetrahydride (1.30 g, 34.8 mmol, 1.50 eq.). The solution was stirred for 2 hr at 0° C. The reaction was then quenched with water (1.25 mL) and 3.75 M NaOH aqueous (1.25 mL). The mixture was dried over anhydrous Na$_2$SO$_4$, filtered, and concentrated to provide 3.89 g (80%) of [(2S,4R)-1-benzyl-4-fluoropyrrolidin-2-yl]MeOH as colorless oil. LCMS (ES) [M+1]$^+$ m/z 210.2.

Into a 1000-mL 3-necked round-bottom flask, was placed a mixture of [(2S,4R)-1-benzyl-4-fluoropyrrolidin-2-yl]MeOH (3.90 g, 18.6 mmol, 1 eq.), CH$_2$Cl$_2$ (373 mL), tetrabutylammonium azide (5.80 g, 20.4 mmol, 1.10 eq.), XtalFluor-E (4.70 g, 20.4 mmol, 1.10 eq.). The solution was stirred for 30 minutes at −78° C. and then allowed the temperature warm to rt. The solution was diluted with 20 mL of 3.75 M NaOH. The mixture was washed with 5×40 ml of brine. The mixture was dried over anhydrous Na$_2$SO$_4$, filtered, and concentrated to provide 2.20 g (50%) of (3R,5R)-3-azido-1-benzyl-5-fluoropiperidine as light yellow oil. LCMS (ES) [M+1]$^+$ m/z 235.1.

Into a 50-mL round-bottom flask, was placed a mixture of (3R,5R)-3-azido-1-benzyl-5-fluoropiperidine (2 g, 8.54 mmol, 1 eq.), tetrahydrofuran (17 mL), triphenylphosphane (3.40 g, 13.0 mmol, 1.50 eq.), water (1.10 g, 59.9 mmol, 7 eq.). The solution was stirred for 5 hr at 70° C. The mixture was dried over anhydrous Na$_2$SO$_4$, concentrated, and applied onto a silica gel column with EtOAc/petroleum ether (1:1) to provide 1.30 g (73%) of (3R,5R)-1-benzyl-5-fluoropiperidin-3-amine as grey solid. LCMS (ES) [M+1]$^+$ m/z 209.1.

Into a 50-mL round-bottom flask, was placed a mixture of (3R,5R)-1-benzyl-5-fluoropiperidin-3-amine (200 mg, 0.96 mmol, 1 eq.), dioxane (10 mL), 9-chloro-6,7-dimethoxy-1H,2H,3H-cyclopenta[b] quinoline (279 mg, 1.06 mmol, 1.10 eq.), sodium 2-methylpropan-2-olate (185 mg, 1.92 mmol, 2 eq.), 3G Brettphos Precatalyst (44 mg, 0.05 mmol, 0.05 eq.). The solution was stirred for 2 hr at 90° C., filtered, concentrated, and applied onto a silica gel column with EtOAc/petroleum ether (1:1) to provide 235 mg (56%) of (5R)-1-benzyl-N-[6,7-dimethoxy-1H,2H,3H-cyclopenta[b]quinolin-9-yl]-5-fluoropiperidin-3-amine as white solid. LCMS (ES) [M+1]$^+$ m/z 436.3.

Into a 50-mL vial, was placed a mixture of (3R,5R)-1-benzyl-N-[6,7-dimethoxy-1H,2H,3H-cyclopenta [b]quinolin-9-yl]-5-fluoropiperidin-3-amine (200 mg, 0.46 mmol, 1 eq.), MeOH (10 mL), 2M hydrogen chloride aqueous (1.15 mL, 4.60 mmol, 5 eq.), Pd/C (20 mg). The solution was stirred for 6 hr at rt, filtered, concentrated, filtered again, and subjected to reverse phase preparative HPLC (Prep-C18, 5 µM XBridge column, 19×150 mm, Waters; gradient elution of 2% MeCN in water to 18% MeCN in water over a 6 min period, where the aqueous phase contains 0.1% FA) to provide 119.7 mg (60%) of (3R,5R)—N-[6,7-dimethoxy-1H,2H,3H-cyclopenta[b]quinolin-9-yl]-5-fluoropiperidin-3-amine bis(formic acid) as a light green solid. NMR (300 MHz, DMSO-cfe): δ 8.27 (s, 2H), 7.46 (s, 1H), 7.19 (s, 1H), 6.01 (d, J=10.2 Hz, 1H), 4.97-4.81 (m, 1H), 4.16-4.07 (m, 1H), 3.90-3.86 (m, 6H), 3.19-2.99 (m, 4H), 2.91-2.86 (m, 2H), 2.79-2.60 (m, 2H), 2.27-2.21 (m, 1H), 2.15-1.80 (m, 3H), 1.25-1.20 (m, 1H). LCMS (ES) [M+1]$^+$ m/z 346.3.

Biological Examples

Example 1

Determination of G9a Enzymatic Activity Assay

The G9a AlphaLISA assay was used to detect the methyl modifications of a biotinylated histone H3 peptide by the compounds. These modifications are done by the histone methyl transferase activity of the G9a enzyme. The assay consists of reading a chemiluminescent signal at 615 nm; this signal is generated by a laser excitation at 680 nm that transfers a reactive singlet oxygen between the donor beads and acceptor beads. Donor beads are streptavidin conjugated and bind to the biotin on the peptide. Acceptor beads are conjugated with an antibody that recognizes the specific G9a methyl mark on the peptide. If there is a methyl mark on the peptide, the acceptor beads will bind to the peptide. Upon binding, the acceptor beads will be in close proximity (<200 nm) of the donor beads and when the donor beads are excited, the transfer of the oxygen can occur and a strong signal will be generated. If there is no methyl mark, the interaction between beads will not occur and signal will be at background levels.

For the assay, the following buffer was used to set up reactions: 50 mM Tris-HCl pH9, 50 mM NaCl, 0.01% Tween-20 and 1 mM DTT (added fresh prior to starting the reactions). The assay is set up by adding a final concentration of 0.15 nM G9a, 15 uM S-adenosyl-methionine and 100 nM biotinylated histone 3 peptide (1-21). The reaction is incubated at rt for 1 hour and subsequently quenched with the acceptor beads (anti-H3k9me2 AlphaLISA acceptor beads, Perkin Elmer #AL117) at a final concentration of 20 ug/mL. The acceptor beads are incubated for 1 hour. After 1 hour, the donor beads are added at a final concentration of 20 ug/mL (Alpha Streptavidin donor beads, PerkinElmer #6760002). Donor beads are incubated for 0.5 hours. Both donor and acceptor beads are resuspended in AlphaLISA 5X Epigenetics Buffer 1 Kit (PerkinElmer #AL008) prior to addition to the reaction. All manipulations and incubations with the donor and acceptor beads are done in subdued light. Signal is detected in an EnVision plate reader in Alpha mode. See *ACS Med. Chem. Lett.* 2014; 5(2):205-9.

Percent inhibition was calculated for each compound dilution and the concentration that produced 50% inhibition was calculated. This value is presented as the pIC$_{50}$, which is the negative log of the IC$_{50}$ value in molar. The pIC$_{50}$ values for a representative number of compounds of the disclosure are provided in Table B below.

TABLE B

| No. | pIC$_{50}$ |
| --- | --- |
| 1 | 5.97 |
| 2 | 5 |
| 3 | 5.53 |
| 4 | 5.57 |
| 5 | 7.44 |
| 6 | 5 |
| 7 | 7.52 |
| 8 | 7.27 |
| 9 | 7.31 |
| 10 | 7.66 |
| 11 | 7.49 |

TABLE B-continued

| No. | pIC$_{50}$ |
|---|---|
| 12 | 5.5 |
| 13 | 7.22 |
| 14 | 5.55 |
| 15 | 7.67 |
| 16 | 7.27 |
| 17 | 5.5 |
| 18 | 6.21 |
| 19 | 5 |
| 20 | 7.53 |
| 21 | 5.3 |
| 22 | 6.21 |
| 23 | 7.05 |
| 24 | 6.11 |
| 25 | 5.87 |
| 26 | 7.53 |
| 27 | 8.08 |
| 28 | 6.66 |
| 29 | 6.81 |
| 30 | 7.83 |
| 31 | 6.23 |
| 32 | 5 |
| 33 | 5.78 |
| 34 | 5.7 |
| 35 | 7.94 |
| 36 | 5.42 |
| 37 | 6.85 |
| 38 | 5.24 |
| 39 | 7.27 |
| 40 | 5.76 |
| 41 | 5.32 |
| 42 | 5.48 |
| 43 | 6.72 |
| 44 | 5.49 |
| 45 | 7.07 |
| 46 | 6.75 |
| 47 | 7.1 |
| 48 | 7.58 |
| 49 | 5.63 |
| 50 | 5.53 |
| 51 | 6.45 |
| 52 | 6.39 |
| 53 | 6.54 |
| 54 | 6.24 |
| 55 | 6.05 |
| 56 | 6.45 |
| 57 | 6.72 |
| 58 | 6.12 |
| 59 | 5.3 |
| 60 | 7.4 |
| 61 | 6.7 |
| 62 | 7.5 |
| 63 | 7.5 |
| 64 | 7.6 |
| 65 | 7.4 |
| 66 | 7.3 |
| 67 | 7 |
| 68 | 6.9 |
| 69 | 7.1 |
| 134 | 6.8 |

TABLE B-continued

| No. | pIC$_{50}$ |
|---|---|
| 149 | 7.2 |
| 163 | 6.8 |
| 164 | 6.2 |
| 402 | 7.1 |
| 286 | 8 |
| 403 | 7.5 |
| 404 | 6.6 |
| 165 | 7 |
| 405 | 7.9 |
| 406 | <5 |
| 407 | 7 |
| 408 | 6.9 |
| 409 | 7.9 |
| 410 | <5 |
| 411 | 6.3 |
| 412 | 6.5 |
| 413 | <5 |
| 414 | 7.2 |
| 415 | <5 |
| 416 | 6.9 |

Example 2

Safety Pharmacological Profiling

Certain compounds were screened in a safety pharmacological profiling against a panel of receptors, enzymes and transporters. The compounds were each evaluated at 10 μM (in duplicate) for ligand binding to membranes of cells expressing different G protein coupled receptors (GPCRs) such as adrenergic α1A, muscarinic M2, mu (μ) opiate (OP3) and serotonin 5HT2A receptors. See, e.g., Michel et al., *Br. J. Pharmacol.* 1998, 98(3):883; Buckley et al., *Mol. Pharmacol.* 1989, 35(4):469; Wang et al., *FEBS Lett.* 1994, 338:217; and Saucier et al., *J. Neurochem.* 1997, 68:1998. Inhibition of acetylcholinesterase was determined spectrophotometrically in cells expressing human recombinant acetylcholinesterase. See Nadarajah, *J. Anal. Toxicol.* 1992, 16:192. Norepinephrine transporter inhibition was determined in membranes from cells expressing the norepinephrine transporter. See Galli et al., *J. Exp. Biol.* 1995, 198(Pt 10):2197. Reference compounds were used as positive controls in all assays. Specifically, prazosin, 4-DAMP ((1,1-dimethyl-4-diphenylacetoxypiperidinium iodide), DAMGO (Tyr-D-Ala-Gly-N-Me-Phe-Gly-ol) and ketanserin were used for the adrenergic α1A, muscarinic M2, μ opiate and 5HT2A receptor binding assays, respectively. Physostigmine was used in the acetylcholinesterase assay and desipramine was used in the norepinephrine transporter assay. The percent inhibition values for certain compounds are provided in Tables C and D below.

TABLE C

| Compound | Acetyl-cholinesterase | Adrenergic α1A | Muscarinic M2 |
|---|---|---|---|
| 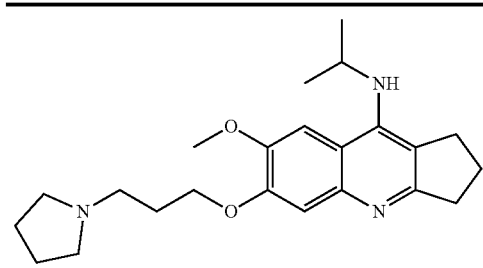 | — | 104 | 51 |

TABLE C-continued

| Compound | Acetyl-cholinesterase | Adrenergic α1A | Muscarinic M2 |
|---|---|---|---|
| | 86 | 97 | 62 |
| | 31 | 86 | 78 |
| | 19 | 88 | 65 |
| | 23 | 76 | 76 |
| | 32 | 87 | 62 |

TABLE C-continued

| Compound | Acetyl-cholinesterase | Adrenergic α1A | Muscarinic M2 |
|---|---|---|---|
| (structure: 6,7-dimethoxy cyclopenta-fused quinoline with 3-methyl-5-amino-piperidinyl substituent) | 23 | 72 | 75 |
| (structure: 6,7-dimethoxy cyclopenta-fused quinoline with azepan-3-ylamino substituent) | 13 | 83 | 80 |

TABLE D

| Compound | Mu Opiate | Serotonin 5HT2A | Norepinephrine Transporter (NET) |
|---|---|---|---|
| (structure: methoxy, pyrrolidinylpropoxy cyclopenta-fused quinoline with isopropylamino substituent) | 92 | 98 | 84 |
| (structure: methoxy, pyrrolidinylpropoxy cyclopenta-fused quinoline with ethylamino substituent) | 92 | 101 | 84 |
| (structure: 6,7-dimethoxy cyclopenta-fused quinoline with 1-isopropylpiperidin-4-ylamino substituent) | 26 | 21 | 38 |

TABLE D-continued

| Compound | Mu Opiate | Serotonin 5HT2A | Norepinephrine Transporter (NET) |
|---|---|---|---|
| 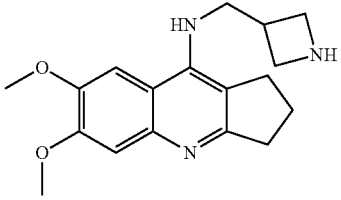 [SMILES: COc1cc2nc3c(c(NCC4CNC4)c2cc1OC)CCC3] | 12 | 54 | 57 |
| 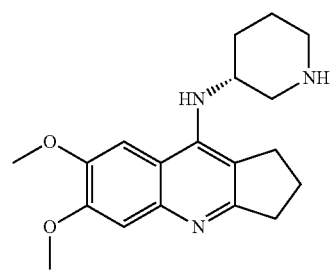 [SMILES: COc1cc2nc3c(c(N[C@@H]4CCCNC4)c2cc1OC)CCC3] | 44 | 40 | 72 |
| 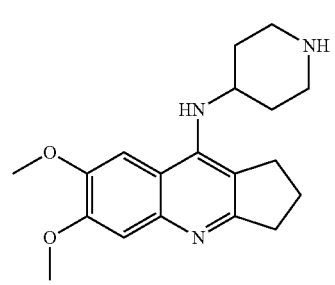 [SMILES: COc1cc2nc3c(c(NC4CCNCC4)c2cc1OC)CCC3] | 48 | 38 | 57 |
| 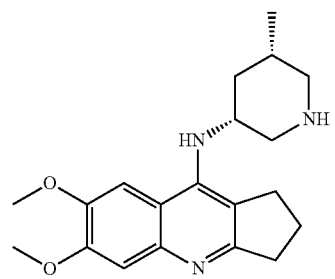 [SMILES: COc1cc2nc3c(c(N[C@H]4CNC[C@@H](C)C4)c2cc1OC)CCC3] | 23 | 27 | 33 |
| 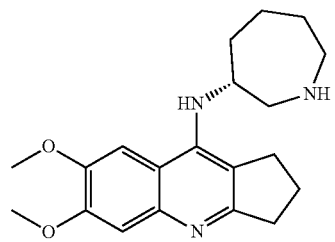 [SMILES: COc1cc2nc3c(c(N[C@@H]4CCCCNC4)c2cc1OC)CCC3] | 73 | 30 | 65 |

Example 2

Fetal Hemoglobin Induction Assay

Cryopreserved bone marrow CD34+ hematopoietic cells obtained from healthy adult human donors were used for all studies. A 21 day ex vivo serum free culture system was utilized that consists of two phases. In culture phase I (culture days 1-7), CD34+ cells were placed in media containing StemPro-34 complete media (l-glutamine, pen-strep and StemPro-34 nutrient supplement) (Invitrogen, Carlsbad, Calif.) supplemented with 50 ng/mL SCF (HumanZyme, Chicago, Ill.), 50 ng/mL FLT3-Ligand (HumanZyme) and 10 ng/mL IL-3 (HumanZyme). During the first phase of culture (days 0-7), the CD34+ cells differentiate into progenitor cell populations that include erythroblasts. After 7 days, the cells were transferred to erythropoietin (EPO; Stemcell) supplemented medium (phase 2; culture days 7-21) which is comprised of the following: StemPro-34 complete medium, 4 U/mL EPO, 3 μM mifepristone (Sigma Aldrich, St. Louis, Mo.), 10 μg/mL insulin (Sigma Aldrich), 3 U/mL heparin (Sigma Aldrich) and 0.8 mg/mL holo transferrin (Sigma Aldrich). The Compounds are added during phase 2; days 7-21 to test fetal hemoglobin production (See Blood. 2015 Jul. 30; 126(5):665-72).

Expression levels of α-, β- and γ-globin genes are assessed by quantitative PCR analyses. HbF protein levels are assessed by the human Hemoglobin F enzyme-linked immunosorbent assay (ELISA) Quantitation Kit (Bethyl Laboratory, Montgomery, Tex., USA). Percentages of cells expressing HbF are assessed by flow cytometry analysis. In brief, RNA samples were prepared and complementary DNA was synthesized, according to the manufacturer's instructions (Qiagen, Germany). The qRT-PCR analysis of human globin genes was performed using the TaqMan Gene Expression Master. The HbF induction values for certain compounds are provided in Table E below.

TABLE E

| Compound No. | Compound Conc. (nM) | Fold Induction |
|---|---|---|
| 215 | 250 | 2.1 |
| 217 | 250 | 1.0 |
| 240 | 250 | 4.1 |
| 245 | 250 | 1.1 |
| 258 | 250 | 3.0 |
| 286 | 330 | 3.3 |

Formulation Examples

The following are representative pharmaceutical formulations containing a compound of the present disclosure.

Tablet Formulation

The following ingredients are mixed intimately and pressed into single scored tablets.

| Ingredient | Quantity per tablet (mg) |
|---|---|
| Compound of this disclosure, or a pharmaceutically acceptable salt thereof | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet (mg) |
|---|---|
| Compound of this disclosure, or a pharmaceutically acceptable salt thereof | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL.

Inhalation Composition

To prepare a pharmaceutical composition for inhalation delivery, 20 mg of a compound disclosed herein is mixed with 50 mg of anhydrous citric acid and 100 mL of 0.9% NaCl (aq). The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μL of spray for each application.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I):

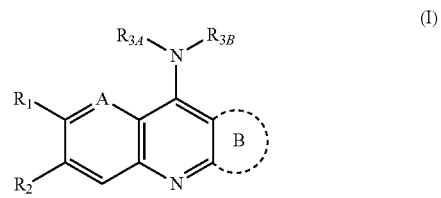

or a pharmaceutically acceptable salt thereof, wherein:

$R_1$ is alkoxy, optionally substituted with one or more $R_A$, which is deuterium;

$R_2$ is selected from the group consisting of:
cyano,
alkyl,
haloalkyl,
hydroxy,
hydroxyalkyl,
aryloxy,
heteroaryloxy,
cycloalkyl, optionally substituted with one or more hydroxy,
cycloalkoxy,
cyanoalkoxy,
alkoxy, optionally substituted with one or more $R_A$, wherein $R_A$ is independently selected from the group consisting of deuterium, hydroxy, alkoxy and (hydroxy)alkoxy, haloalkoxy,
and,
aminosulfonyl, optionally substituted with one or more alkyl;
A is CH or N;
$R_{3A}$ is
  (a) 3 to 10 membered heterocyclyl;
  (b) 3 to 10 membered heterocyclylalkyl;
  (c) 7 to 10 membered spiroheterocycloamino, optionally substituted with one or more $R_B$, independently selected from the group consisting of alkyl, aryl, wherein said aryl is optionally substituted with one or more $R_D$, and alkoxycarbonyl; wherein $R_D$ is independently halogen or alkyl;
  (d) cycloalkylalkyl, optionally substituted with one or more $R_C$, independently selected from the group consisting of amino and alkylamino;
  (e) 5 to 10 membered heteroaralkyl, optionally substituted with alkyl;
    wherein the heterocyclyl rings of (a) and (b) are independently optionally substituted with one or more $R_E$, independently selected from the group consisting of:
halogen,
hydroxy,
alkoxy,
hydroxyalkyl,
cycloalkyl,
cyanoalkyl,
aralkyl,
alkoxycarbonyl,
aminocarbonyl,
cycloalkylalkyl,
alkyl, optionally substituted with:
  (i) at least one halogen and at least one hydroxy, or
  (ii) alkoxy,
alkylcarbonyl, optionally substituted with hydroxy or benzyloxy,
alkylsulfonyl,
heteroaryl, optionally substituted with one or more $R_F$,
  wherein $R_F$ is independently selected from the group consisting of halogen, alkyl, cyano and hydroxy, heteroaralkyl, optionally substituted with one or more $R_G$,
  wherein $R_G$ is independently selected from the group consisting of halogen, alkyl, cyano and hydroxy, heterocyclyl, optionally substituted with one or more $R_H$,
  wherein $R_H$ is independently selected from the group consisting of alkyl, cyano and hydroxy,
and,
  aryl, optionally substituted with one or more $R_I$,
  wherein $R_I$ is independently selected from the group consisting of halogen, alkyl, alkoxy, cyano and hydroxy;
$R_{3B}$ is hydrogen, alkyl or —C(=O)NH$_2$;
Ring B is

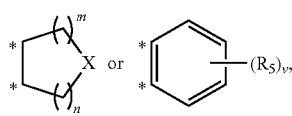

wherein the asterisks indicate the points of attachments to the pyridinyl ring of Formula (I);
m and n are independently 1, 2, 3 or 4, wherein the sum of m+n is 2, 3, 4 or 5;
X is $CR_{4A}R_{4B}$, $NR_{4C}$ or O;
  wherein $R_{4A}$, $R_{4B}$ and $R_{4C}$ are independently hydrogen or alkyl;
each $R_5$ is independently alkyl;
and,
v is 0, 1, 2, 3 or 4.
2. The compound of claim 1, wherein A is CH.
3. The compound of claim 1, wherein A is N.
4. The compound of claim 1, wherein $R_{3B}$ is hydrogen.
5. The compound of claim 1, wherein Ring B is

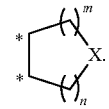

6. The compound of claim 5, wherein X is $CR_{4A}R_{4B}$.
7. The compound of claim 6, wherein $R_{4A}$ and $R_{4B}$ are each hydrogen.
8. The compound of claim 5, wherein m is 1; and n is 1.
9. The compound of claim 5, wherein m is 2; and n is 1.
10. The compound of claim 1, wherein Ring B is

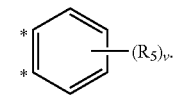

11. The compound of claim 1, wherein $R_1$ is methoxy.
12. The compound of claim 1, wherein $R_1$ and $R_2$ are each methoxy.
13. The compound of claim 1, wherein $R_1$ is methoxy; and $R_2$ is alkoxy substituted with one or more $R_A$ which is alkoxy.
14. The compound of claim 1, wherein $R_1$ is methoxy; and $R_2$ is alkoxy mono-substituted with $R_A$ which is hydroxy.
15. The compound of claim 1, wherein $R_{3A}$ is 5 to 10 membered heteroaralkyl, optionally substituted with alkyl.
16. The compound of claim 1, wherein $R_{3A}$ is cycloalkylalkyl, optionally substituted with one or more $R_C$, independently selected from amino and alkylamino.
17. The compound of claim 1, wherein $R_{3A}$ is 7 to 10 membered spiroheterocycloamino, optionally substituted with one or more $R_B$, independently selected from the group consisting of:
alkyl,
aryl, optionally substituted with one or more $R_D$,
  wherein $R_D$ is independently selected from halogen and alkyl,
and,
alkoxycarbonyl.
18. The compound of claim 1, wherein $R_{3A}$ is 3 to 10 membered heterocyclyl optionally substituted with one or more $R_E$, independently selected from the group consisting of:
halogen,
hydroxy,
alkoxy,
hydroxyalkyl,
cycloalkyl, cyanoalkyl,
aralkyl,
alkoxycarbonyl,
aminocarbonyl,
cycloalkylalkyl,
alkyl, optionally substituted with:
  (i) at least one halogen and at least one hydroxy, or
  (ii) alkoxy,
alkylcarbonyl optionally substituted with hydroxy or benzyloxy,
alkylsulfonyl,
heteroaryl, optionally substituted with one or more $R_F$,
  wherein $R_F$ is independently selected from halogen, alkyl, cyano and hydroxy,
heteroaralkyl, optionally substituted with one or more $R_G$,
  wherein $R_G$ is independently selected from halogen, alkyl, cyano and hydroxy,
heterocyclyl, optionally substituted with one or more $R_H$,
  wherein $R_H$ is independently selected from alkyl, cyano and hydroxy, and,
aryl, optionally substituted with one or more $R_I$,
  wherein $R_I$ is independently selected from halogen, alkyl, alkoxy, cyano and hydroxy.

19. The compound of claim 18, wherein $R_{3A}$ is 3 to 10 membered heterocyclyl substituted with one, two, three or four $R_E$, which is independently an unsubstituted alkyl.

20. The compound of claim 18, wherein $R_{3A}$ is 3 to 10 membered heterocyclyl independently substituted with one or more $R_E$, which is heteroaryl, optionally substituted with one or more $R_F$ independently selected from halogen, cyano and alkyl.

21. The compound of claim 18, wherein $R_{3A}$ is 3 to 10 membered heterocyclyl independently substituted with one or more $R_E$, which is heterocyclyl, optionally substituted with one or more $R_H$ independently selected from alkyl, cyano and hydroxy.

22. The compound of claim 18, wherein $R_{3A}$ is 3 to 10 membered heterocyclyl independently substituted with one or more $R_E$, which is aryl, optionally substituted with one or more $R_I$ independently selected from halogen, alkyl, alkoxy, cyano and hydroxy.

23. The compound of claim 1, wherein $R_{3A}$ is 3 to 10 membered heterocyclylalkyl optionally substituted with one or more $R_E$, independently selected from the group consisting of:
halogen,
hydroxy,
alkoxy,
hydroxyalkyl,
cycloalkyl,
cyanoalkyl,
aralkyl,
alkoxycarbonyl,
aminocarbonyl,
cycloalkylalkyl,
alkyl,
alkylcarbonyl, optionally substituted with hydroxy or benzyloxy,
alkylsulfonyl,
heteroaryl, optionally substituted with one or more $R_F$,
  wherein $R_F$ is independently selected from halogen, alkyl, cyano and hydroxy,
heteroaralkyl, optionally substituted with one or more $R_G$,
  wherein $R_G$ is independently selected from halogen, alkyl, cyano and hydroxy,
heterocyclyl, optionally substituted with one or more $R_H$,
  wherein $R_H$ is independently selected from alkyl, cyano and hydroxy,
and,
aryl, optionally substituted with one or more $R_I$,
  wherein $R_I$ is independently selected from halogen, alkyl, alkoxy, cyano and hydroxy.

24. The compound of claim 23, wherein $R_{3A}$ is 3 to 10 membered heterocyclylalkyl substituted with one or two $R_E$, independently selected from the group consisting of hydroxy, alkoxy, alkyl, cycloalkyl, heteroaryl, optionally substituted with one or two $R_F$, which is halogen, and aryl, optionally substituted with one or more $R_I$, which is halogen.

25. The compound of claim 1, wherein the compound is selected from the group consisting of:

| No | Structure | No | Structure |
|---|---|---|---|
| | | 70 | |
| | | 71 | |

-continued

| No | Structure | No | Structure |
|---|---|---|---|
| | | 72 | (structure) |
| | | 73 | (structure) |
| 5 | (structure) | 74 | (structure) |
| | | 75 | (structure) |
| 7 | (structure) | 76 | (structure) |
| 8 | (structure) | 77 | (structure) |

| No | Structure | No | Structure |
|---|---|---|---|
| 9 | 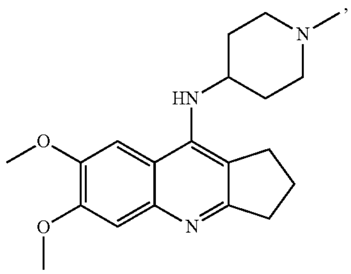 | 78 | 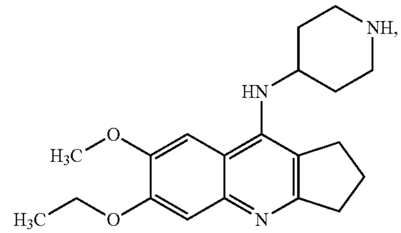 |
| 10 | 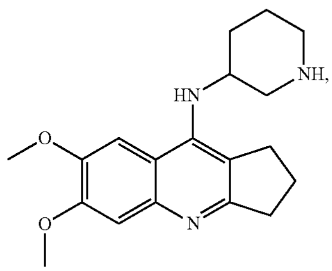 | 79 | 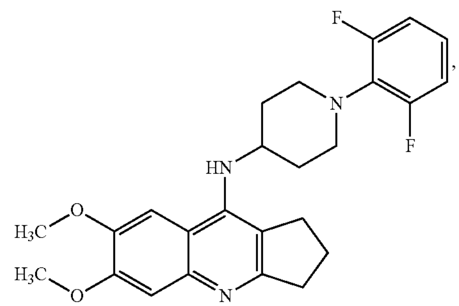 [SMILES: COc1cc2nc3c(c(NC4CCN(c5c(F)cccc5F)CC4)c2cc1OC)CCC3] |
| 11 | 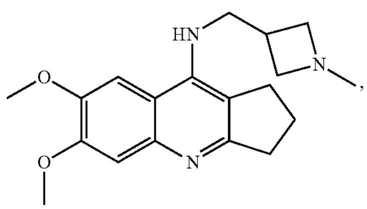 | 80 | 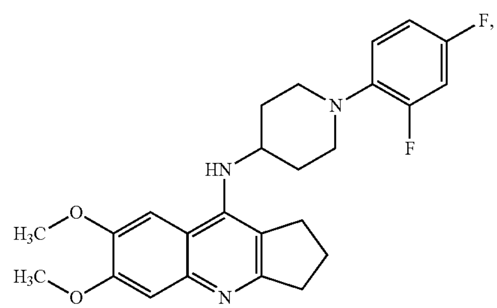 [SMILES: COc1cc2nc3c(c(NC4CCN(c5ccc(F)cc5F)CC4)c2cc1OC)CCC3] |
| 12 | 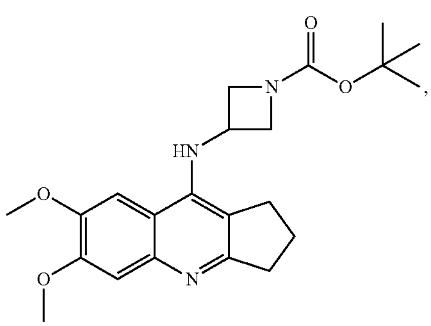 [SMILES: COc1cc2nc3c(c(NC4CN(C(=O)OC(C)(C)C)C4)c2cc1OC)CCC3] | 81 | 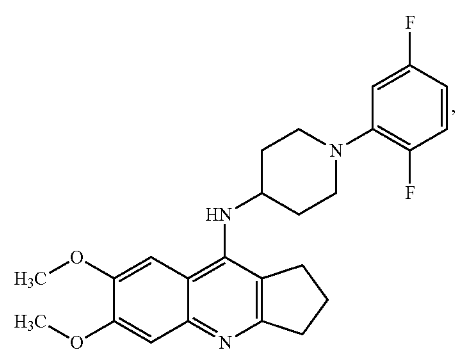 [SMILES: COc1cc2nc3c(c(NC4CCN(c5cc(F)ccc5F)CC4)c2cc1OC)CCC3] |
| 13 | 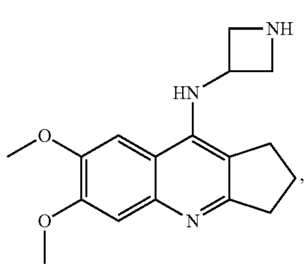 [SMILES: COc1cc2nc3c(c(NC4CNC4)c2cc1OC)CCC3] | 82 | 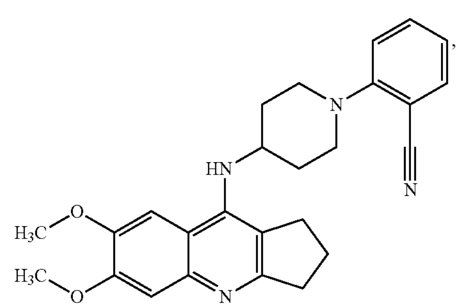 [SMILES: COc1cc2nc3c(c(NC4CCN(c5ccccc5C#N)CC4)c2cc1OC)CCC3] |

| No | Structure | No | Structure |
|---|---|---|---|
| 14 | 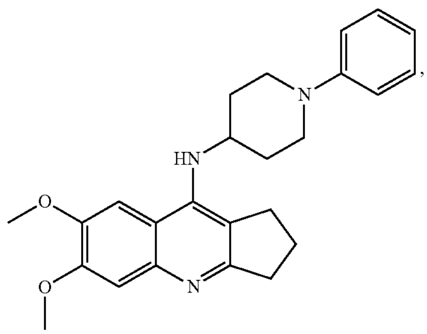 [SMILES: COc1cc2nc3c(c(NC4CCN(c5ccccc5)CC4)c2cc1OC)CCC3] | 83 | 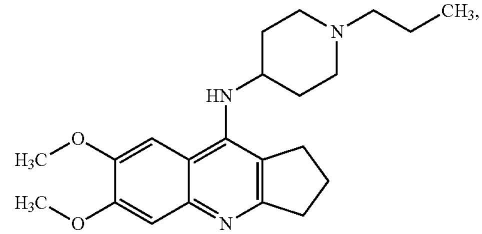 [SMILES: CCCN1CCC(Nc2c3c(nc4cc(OC)c(OC)cc24)CCC3)CC1] |
| 15 | 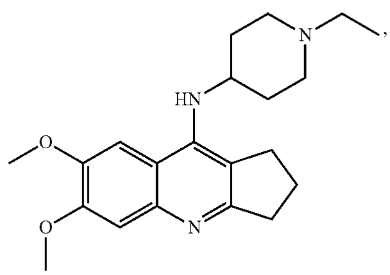 [SMILES: CCN1CCC(Nc2c3c(nc4cc(OC)c(OC)cc24)CCC3)CC1] | 84 | 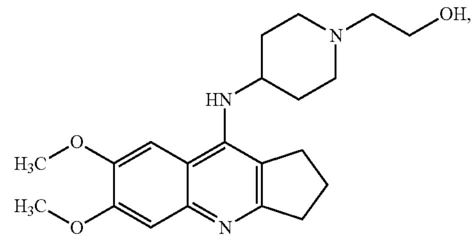 |
| 16 | 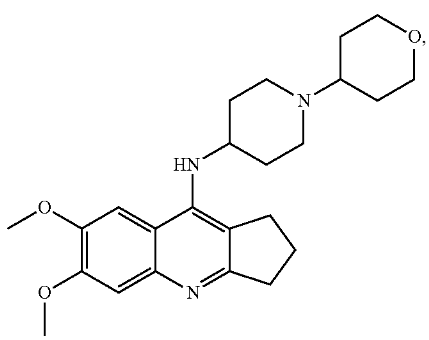 [SMILES: COc1cc2nc3c(c(NC4CCN(C5CCOCC5)CC4)c2cc1OC)CCC3] | 85 | 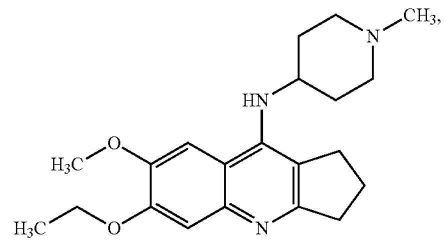 [SMILES: CCOc1cc2nc3c(c(NC4CCN(C)CC4)c2cc1OC)CCC3] |
| 17 | 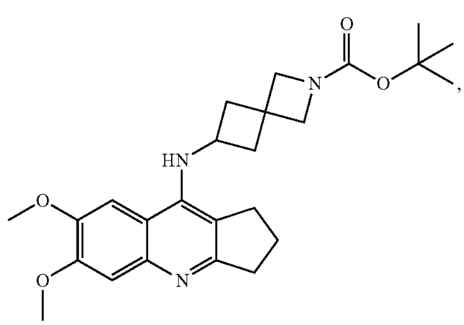 [SMILES: COc1cc2nc3c(c(NC4CC5(C4)CN(C(=O)OC(C)(C)C)C5)c2cc1OC)CCC3] | 86 | 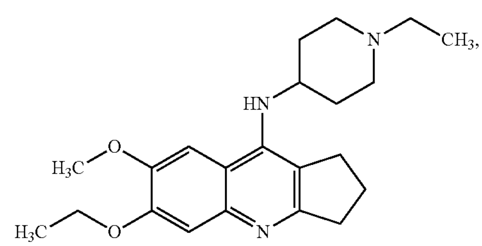 [SMILES: CCOc1cc2nc3c(c(NC4CCN(CC)CC4)c2cc1OC)CCC3] |
| 18 | 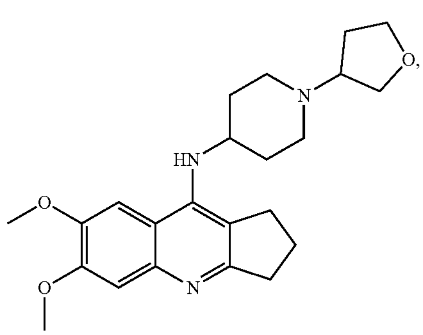 [SMILES: COc1cc2nc3c(c(NC4CCN(C5CCOC5)CC4)c2cc1OC)CCC3] | 87 | 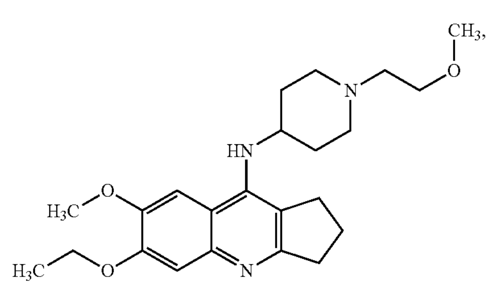 [SMILES: CCOc1cc2nc3c(c(NC4CCN(CCOC)CC4)c2cc1OC)CCC3] |

-continued

| No | Structure | No | Structure |
|---|---|---|---|
| 19 | 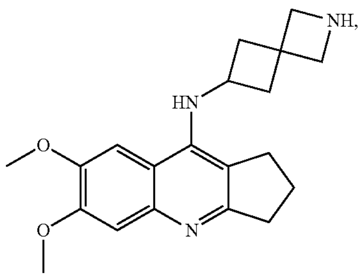 [SMILES: COc1cc2nc3c(c(NC4CC5(CNC5)C4)c2cc1OC)CCC3] | 88 | 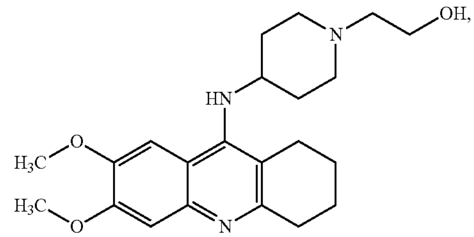 |
| 20 | 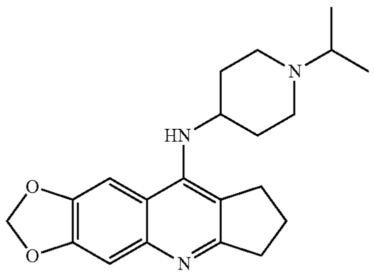 | 89 | 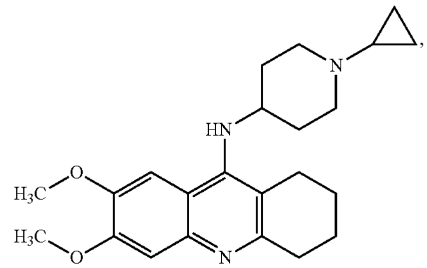 |
|  |  | 90 | |
| 22 | 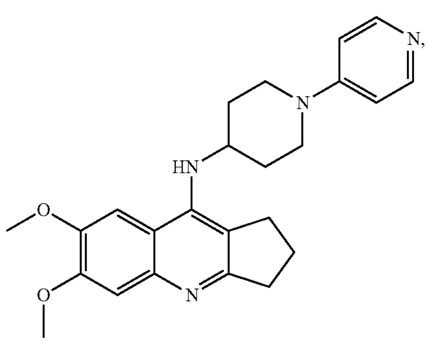 [SMILES: COc1cc2nc3c(c(NC4CCN(c5ccncc5)CC4)c2cc1OC)CCC3] | 91 | 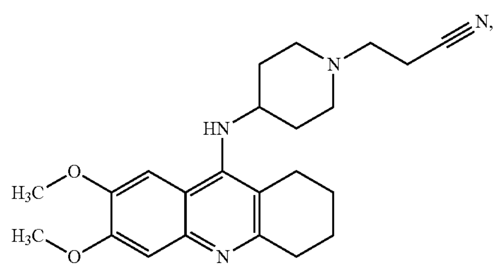 [SMILES: COc1cc2nc3c(c(NC4CCN(CCC#N)CC4)c2cc1OC)CCCC3] |
| 23 | 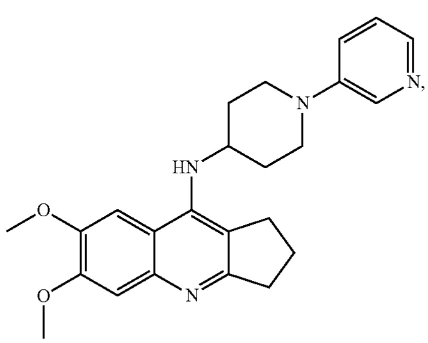 [SMILES: COc1cc2nc3c(c(NC4CCN(c5cccnc5)CC4)c2cc1OC)CCC3] | 92 | 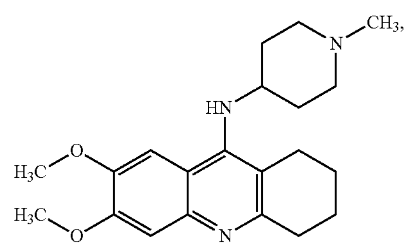 [SMILES: COc1cc2nc3c(c(NC4CCN(C)CC4)c2cc1OC)CCCC3] |

US 11,661,410 B2

305 306

-continued

| No | Structure | No | Structure |
|---|---|---|---|
| 24 | 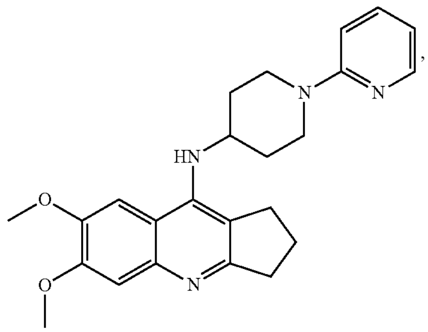 | 93 | 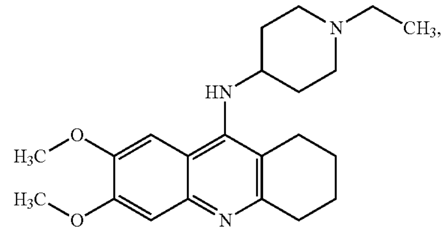 [SMILES: CCN1CCC(Nc2c3c(nc4cc(OC)c(OC)cc24)CCCC3)CC1] |
| 25 | 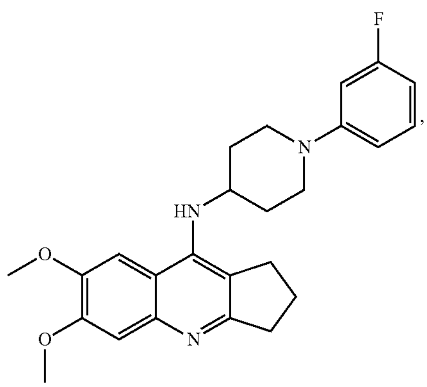 [SMILES: COc1cc2nc3c(c(NC4CCN(c5cccc(F)c5)CC4)c2cc1OC)CCC3] | 94 | 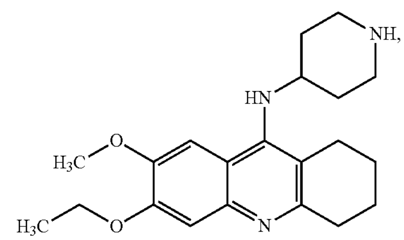 [SMILES: CCOc1cc2nc3c(c(NC4CCNCC4)c2cc1OC)CCCC3] |
| 26 | 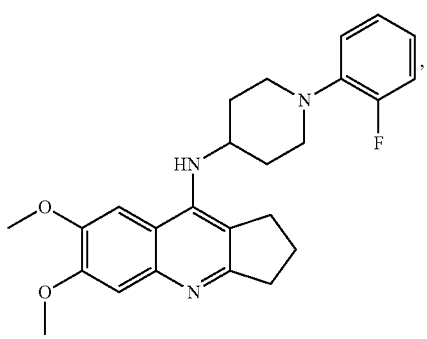 [SMILES: COc1cc2nc3c(c(NC4CCN(c5ccccc5F)CC4)c2cc1OC)CCC3] | 95 | 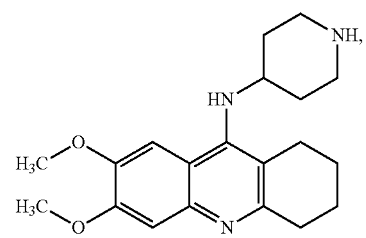 |
| 27 | 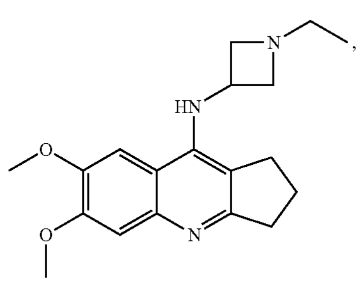 [SMILES: CCN1CC(Nc2c3c(nc4cc(OC)c(OC)cc24)CCC3)C1] | 96 | 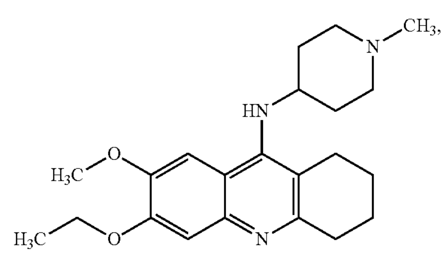 [SMILES: CCOc1cc2nc3c(c(NC4CCN(C)CC4)c2cc1OC)CCCC3] |
| 28 | 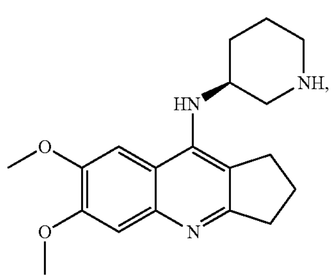 [SMILES: COc1cc2nc3c(c(N[C@H]4CCCNC4)c2cc1OC)CCC3] | 97 | 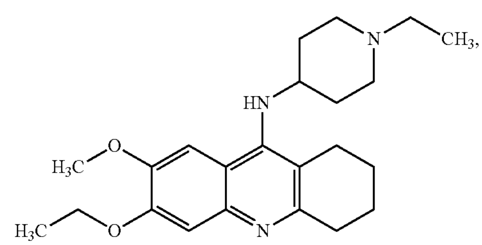 [SMILES: CCOc1cc2nc3c(c(NC4CCN(CC)CC4)c2cc1OC)CCCC3] |

| No | Structure | No | Structure |
|---|---|---|---|
| 29 | (structure) | 98 | (structure) |
| 30 | (structure) | 99 | (structure) |
| | | 100 | (structure) |
| 32 | (structure) | 101 | (structure) |
| 33 | (structure) | 102 | (structure) |

-continued

| No | Structure | No | Structure |
|---|---|---|---|
| 34 | 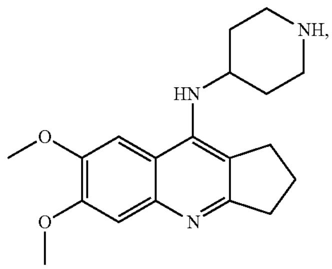 [SMILES: COc1cc2nc3c(c(NC4CCNCC4)c2cc1OC)CCC3] | 103 | 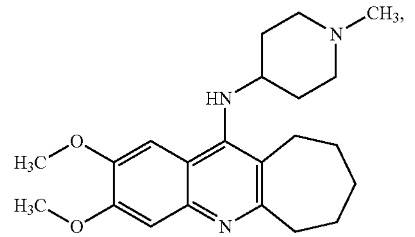 [SMILES: COc1cc2nc3c(c(NC4CCN(C)CC4)c2cc1OC)CCCCC3] |
| 35 | 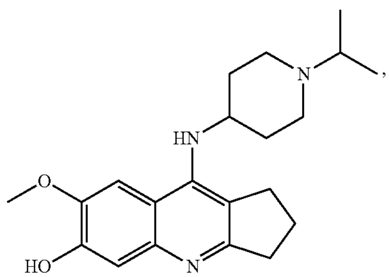 [SMILES: COc1cc2c(NC3CCN(C(C)C)CC3)c3c(nc2cc1O)CCC3] | 104 | 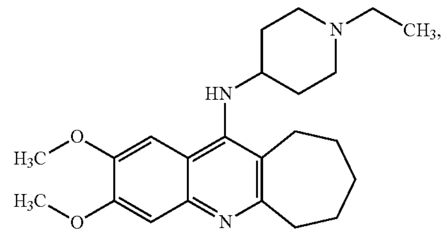 [SMILES: CCN1CCC(Nc2c3c(nc4cc(OC)c(OC)cc24)CCCCC3)CC1] |
| 36 | 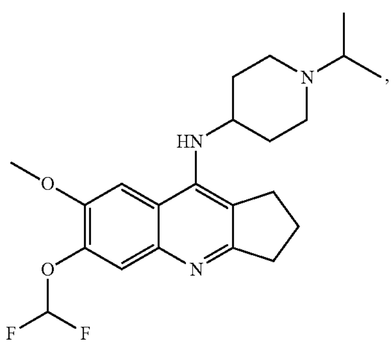 [SMILES: COc1cc2c(NC3CCN(C(C)C)CC3)c3c(nc2cc1OC(F)F)CCC3] | 105 | 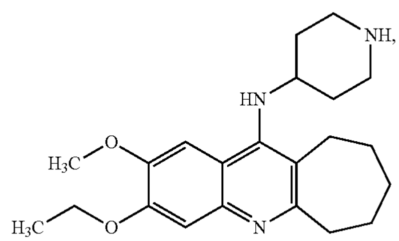 [SMILES: CCOc1cc2nc3c(c(NC4CCNCC4)c2cc1OC)CCCCC3] |
| 37 | 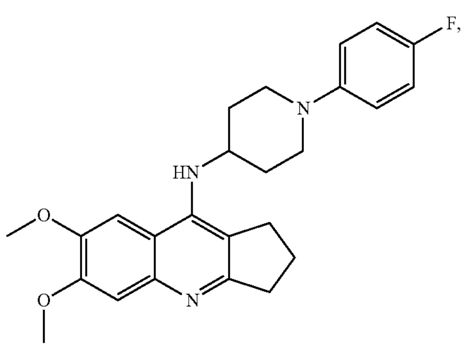 [SMILES: COc1cc2nc3c(c(NC4CCN(c5ccc(F)cc5)CC4)c2cc1OC)CCC3] | 106 | 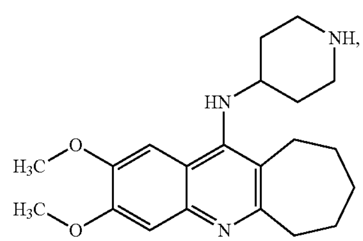 |
| 38 | 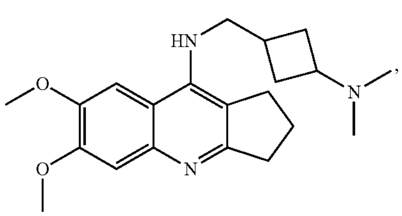 | 107 | 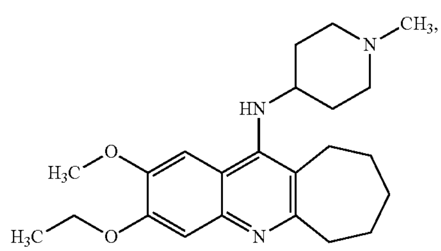 [SMILES: CCOc1cc2nc3c(c(NC4CCN(C)CC4)c2cc1OC)CCCCC3] |

-continued

| No | Structure | No | Structure |
|---|---|---|---|
| 39 | 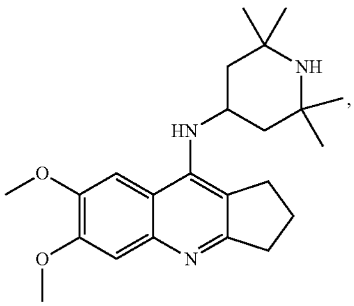 | 108 | 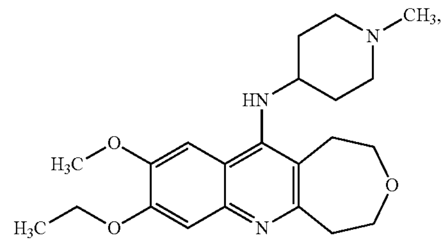 [SMILES: CCOc1cc2nc3c(c(NC4CCN(C)CC4)c2cc1OC)CCOCC3] |
| 40 | 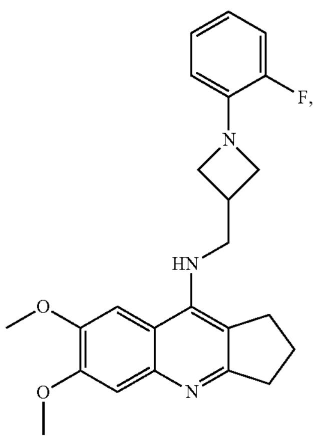 [SMILES: COc1cc2nc3c(c(NCC4CN(c5ccccc5F)C4)c2cc1OC)CCC3] | 109 | 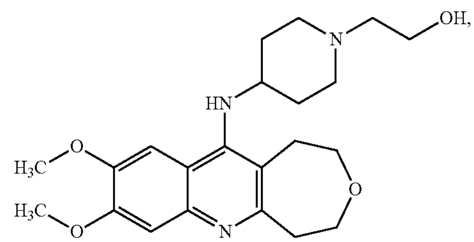 |
| 41 | 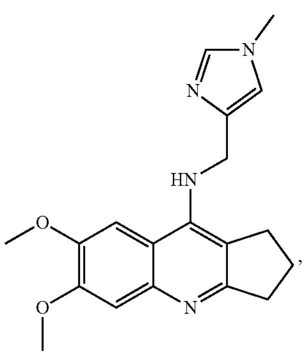 [SMILES: COc1cc2nc3c(c(NCc4cn(C)cn4)c2cc1OC)CCC3] | 110 | 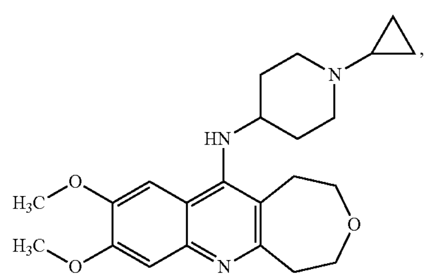 [SMILES: COc1cc2nc3c(c(NC4CCN(C5CC5)CC4)c2cc1OC)CCOCC3] |
| 42 | 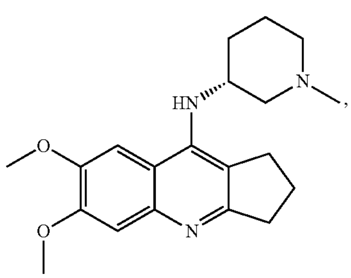 | 111 | 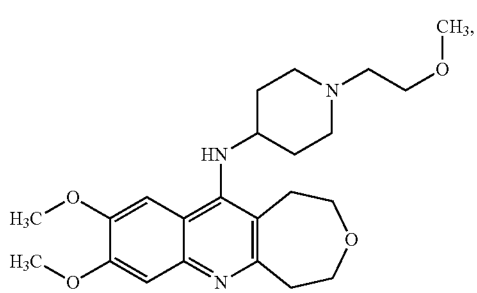 [SMILES: COCCN1CCC(Nc2c3c(nc4cc(OC)c(OC)cc24)CCOCC3)CC1] |

-continued
| No | Structure | No | Structure |
|---|---|---|---|
| 43 | 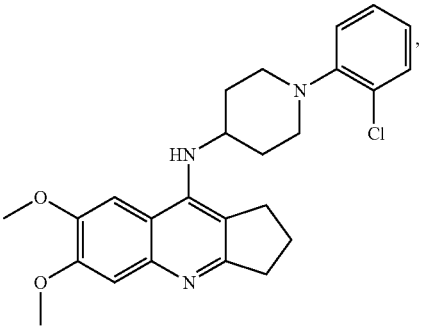 [SMILES: COc1cc2nc3c(c(NC4CCN(c5ccccc5Cl)CC4)c2cc1OC)CCC3] | 112 | 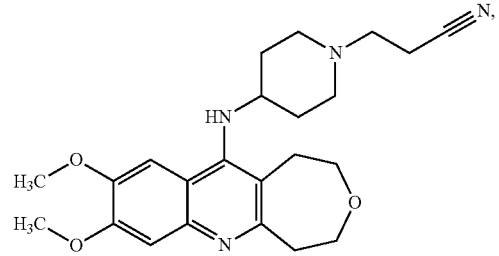 [SMILES: COc1cc2nc3c(c(NC4CCN(CCC#N)CC4)c2cc1OC)CCOCC3] |
| 44 | 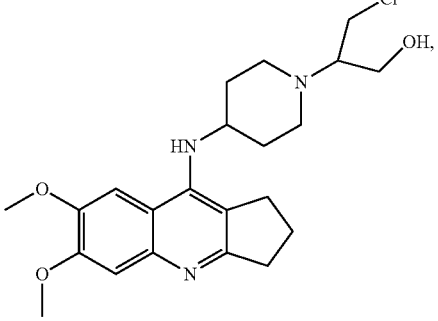 | 113 | 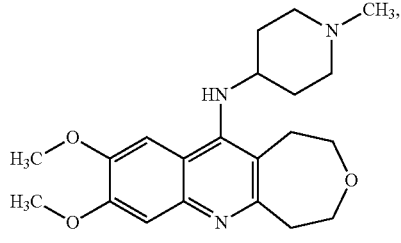 [SMILES: COc1cc2nc3c(c(NC4CCN(C)CC4)c2cc1OC)CCOCC3] |
| 45 | 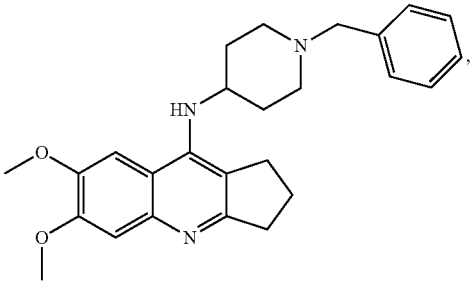 [SMILES: COc1cc2nc3c(c(NC4CCN(Cc5ccccc5)CC4)c2cc1OC)CCC3] | 114 | 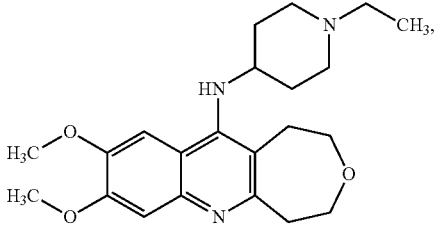 |
| 46 | 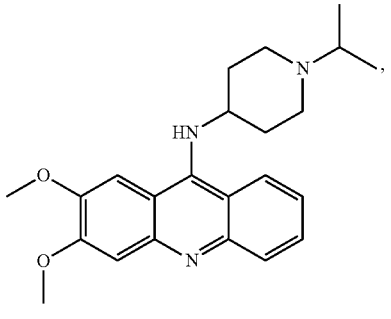 [SMILES: COc1cc2nc3ccccc3c(NC3CCN(C(C)C)CC3)c2cc1OC] | 115 | 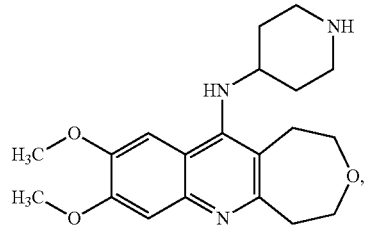 [SMILES: COc1cc2nc3c(c(NC4CCNCC4)c2cc1OC)CCOCC3] |
| 47 | 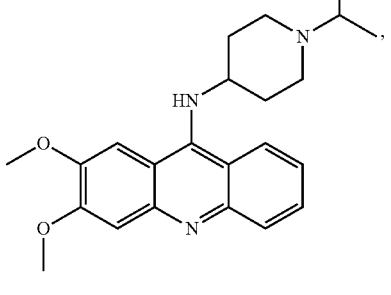 | 116 | 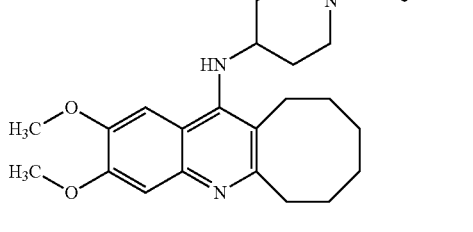 |

-continued

| No | Structure | No | Structure |
|---|---|---|---|
| 48 | 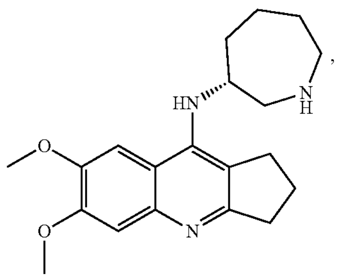 [SMILES: COc1cc2nc3c(c(N[C@@H]4CCCCNC4)c2cc1OC)CCC3] | 117 | 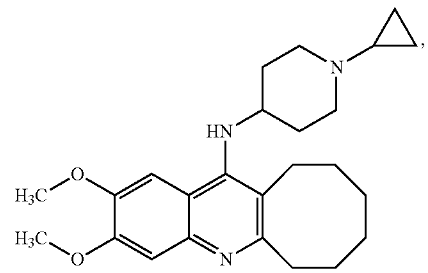 [SMILES: COc1cc2nc3c(c(NC4CCN(C5CC5)CC4)c2cc1OC)CCCCCC3] |
| 49 | 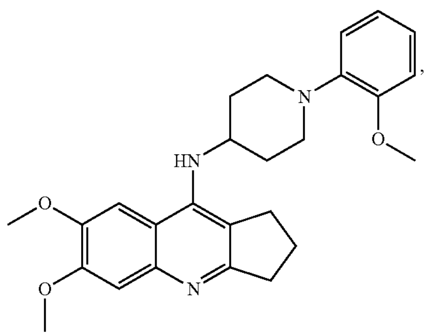 | 118 | 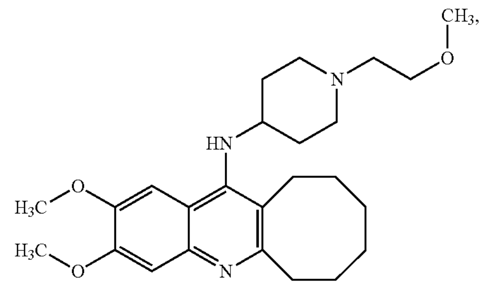 [SMILES: COCCN1CCC(Nc2c3c(nc4cc(OC)c(OC)cc24)CCCCCC3)CC1] |
| 50 | 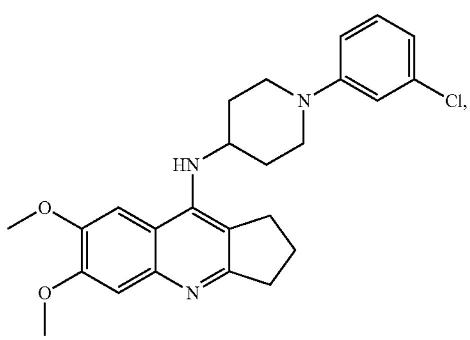 [SMILES: COc1cc2nc3c(c(NC4CCN(c5cccc(Cl)c5)CC4)c2cc1OC)CCC3] | 119 | 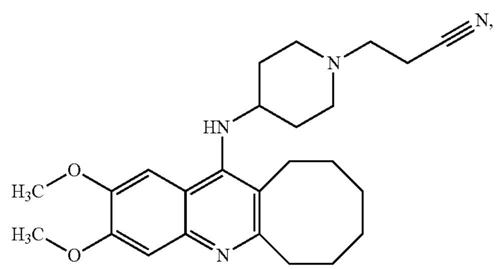 [SMILES: COc1cc2nc3c(c(NC4CCN(CCC#N)CC4)c2cc1OC)CCCCCC3] |
| 51 | 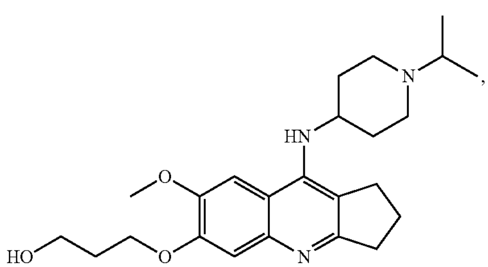 [SMILES: COc1cc2c(NC3CCN(C(C)C)CC3)c3c(nc2cc1OCCCO)CCC3] | 120 | 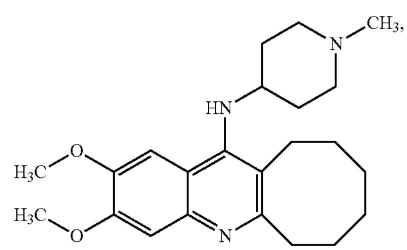 [SMILES: COc1cc2nc3c(c(NC4CCN(C)CC4)c2cc1OC)CCCCCC3] |
| 52 | 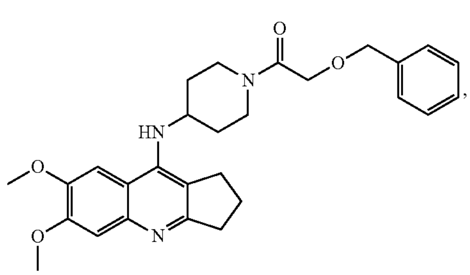 [SMILES: COc1cc2nc3c(c(NC4CCN(C(=O)COCc5ccccc5)CC4)c2cc1OC)CCC3] | 121 | 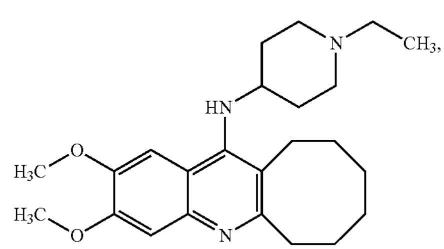 [SMILES: CCN1CCC(Nc2c3c(nc4cc(OC)c(OC)cc24)CCCCCC3)CC1] |

US 11,661,410 B2

317                                                                 318

-continued

| No | Structure | No | Structure |
|----|-----------|----|-----------|
| 53 | 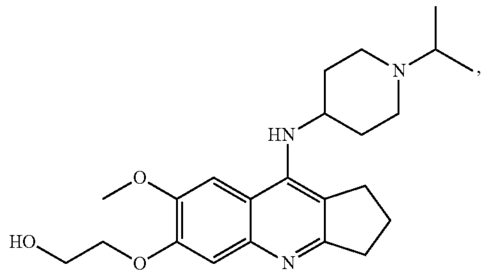 [SMILES: COc1cc2c(NC3CCN(C(C)C)CC3)c3c(nc2cc1OCCO)CCC3] | 122 | 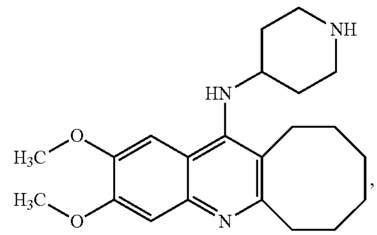 [SMILES: COc1cc2nc3c(c(NC4CCNCC4)c2cc1OC)CCCCCC3] |
| 54 | 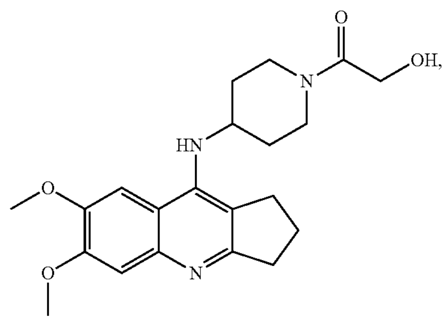 [SMILES: COc1cc2nc3c(c(NC4CCN(C(=O)CO)CC4)c2cc1OC)CCC3] | 123 | 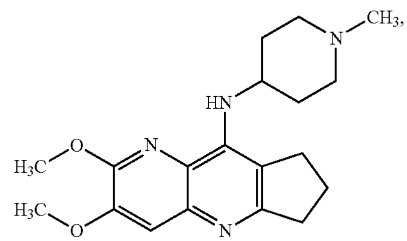 [SMILES: COc1cc2nc3c(c(NC4CCN(C)CC4)c2nc1OC)CCC3] |
| 55 | 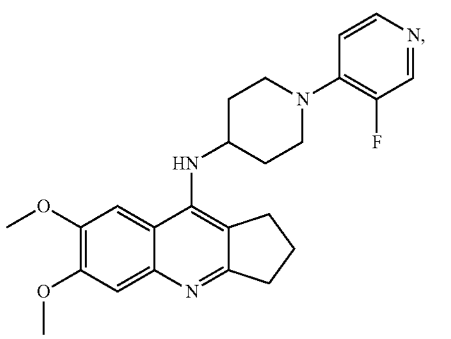 [SMILES: COc1cc2nc3c(c(NC4CCN(c5ccncc5F)CC4)c2cc1OC)CCC3] | 124 | 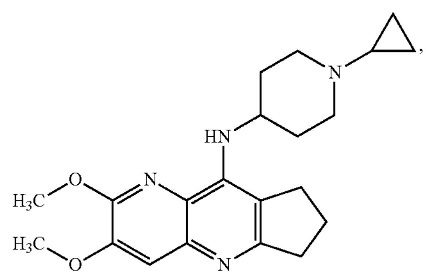 |
| 56 | 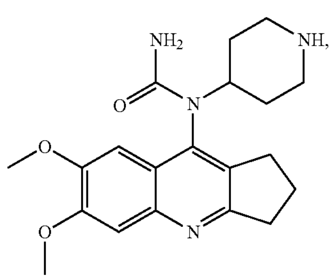 [SMILES: COc1cc2nc3c(c(N(C(N)=O)C4CCNCC4)c2cc1OC)CCC3] | 125 | 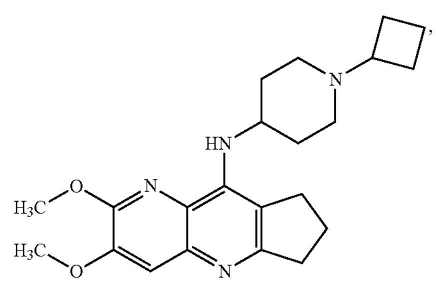 [SMILES: COc1cc2nc3c(c(NC4CCN(C5CCC5)CC4)c2nc1OC)CCC3] |
| 57 | 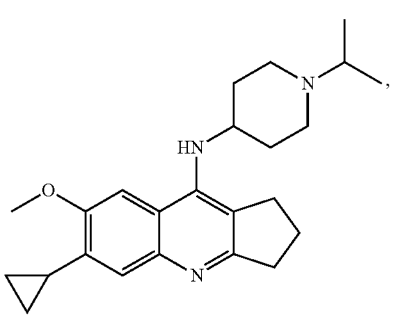 [SMILES: COc1cc2c(NC3CCN(C(C)C)CC3)c3c(nc2cc1C1CC1)CCC3] | 126 | 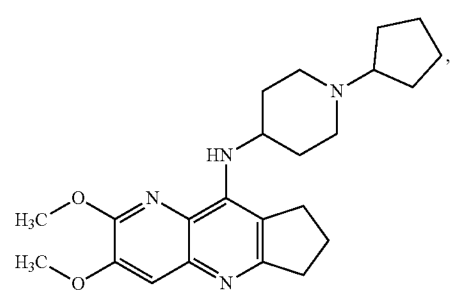 [SMILES: COc1cc2nc3c(c(NC4CCN(C5CCCC5)CC4)c2nc1OC)CCC3] |

319 320
-continued

| No | Structure | No | Structure |
|---|---|---|---|
| 58 | 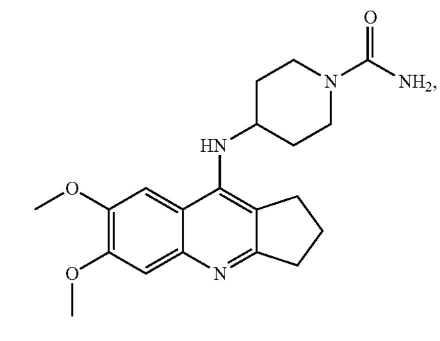 [SMILES: COc1cc2nc3c(c(NC4CCN(C(N)=O)CC4)c2cc1OC)CCC3] | 127 | 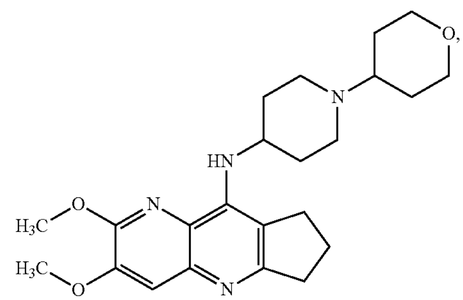 [SMILES: COc1cc2nc3c(c(NC4CCN(C5CCOCC5)CC4)c2nc1OC)CCC3] |
| 59 | 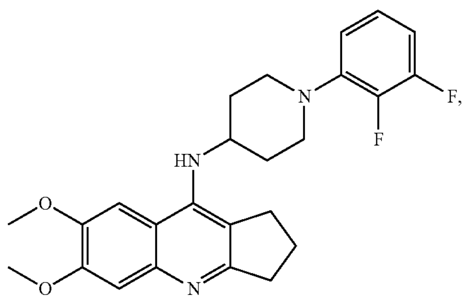 [SMILES: COc1cc2nc3c(c(NC4CCN(c5cccc(F)c5F)CC4)c2cc1OC)CCC3] | 128 | 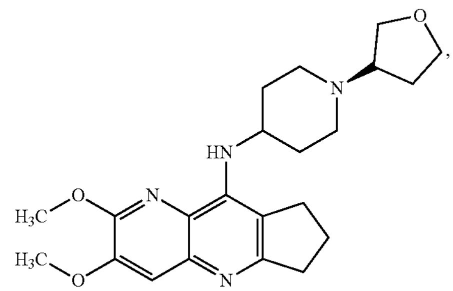 |
| 60 | 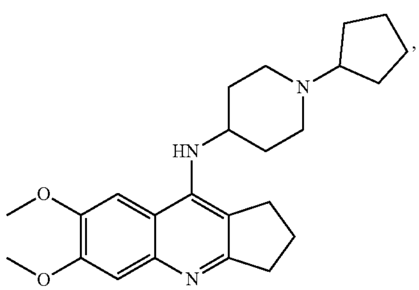 [SMILES: COc1cc2nc3c(c(NC4CCN(C5CCCC5)CC4)c2cc1OC)CCC3] | 129 | 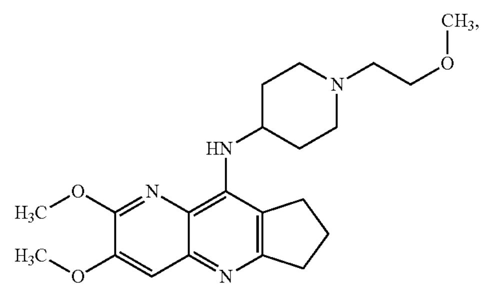 [SMILES: COCCN1CCC(Nc2c3c(nc4cc(OC)c(OC)nc24)CCC3)CC1] |
| 61 | 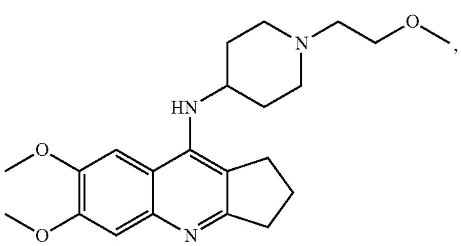 | 130 | 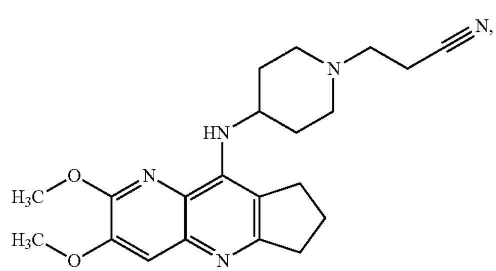 [SMILES: COc1cc2nc3c(c(NC4CCN(CCC#N)CC4)c2nc1OC)CCC3] |
| 62 | 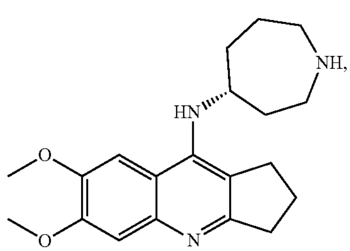 [SMILES: COc1cc2nc3c(c(N[C@@H]4CCCNCC4)c2cc1OC)CCC3] | 131 | 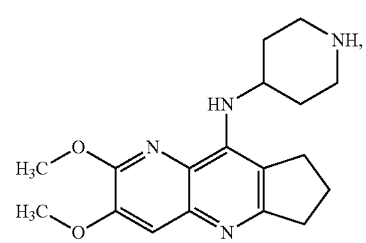 [SMILES: COc1cc2nc3c(c(NC4CCNCC4)c2nc1OC)CCC3] |

| No | Structure | No | Structure |
|---|---|---|---|
| 63 | 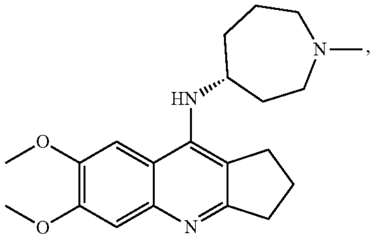 | 132 | 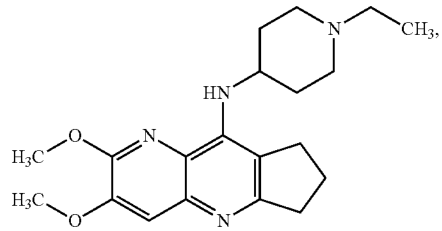 [SMILES: CCN1CCC(Nc2c3c(nc4cc(OC)c(OC)nc24)CCC3)CC1] |
| 64 | 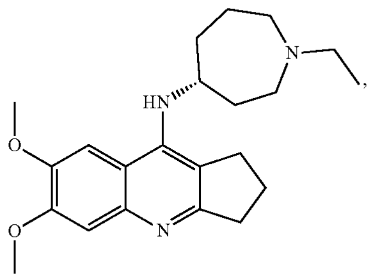 [SMILES: CCN1CCC[C@@H](Nc2c3c(nc4cc(OC)c(OC)cc24)CCC3)CC1] | 133 | 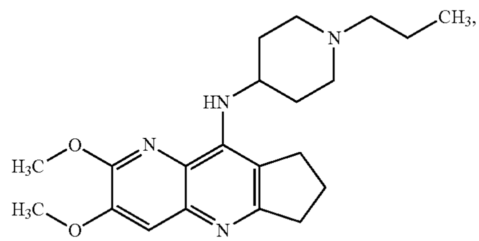 [SMILES: CCCN1CCC(Nc2c3c(nc4cc(OC)c(OC)nc24)CCC3)CC1] |
| 65 | 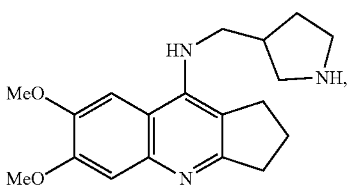 [SMILES: COc1cc2nc3c(c(NCC4CCNC4)c2cc1OC)CCC3] | 135 | 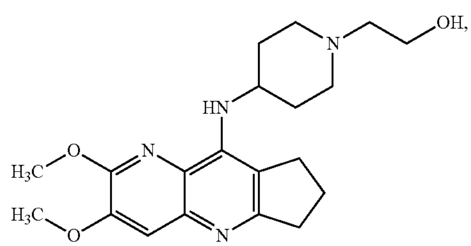 |
| 66 | 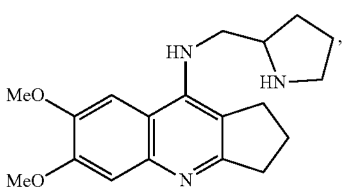 [SMILES: COc1cc2nc3c(c(NCC4CCCN4)c2cc1OC)CCC3] | 136 | 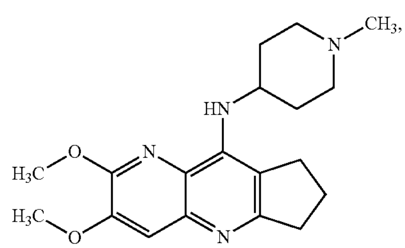 [SMILES: COc1cc2nc3c(c(NC4CCN(C)CC4)c2nc1OC)CCC3] |
| 67 | 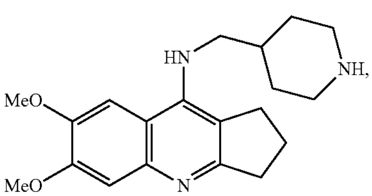 [SMILES: COc1cc2nc3c(c(NCC4CCNCC4)c2cc1OC)CCC3] | 137 | 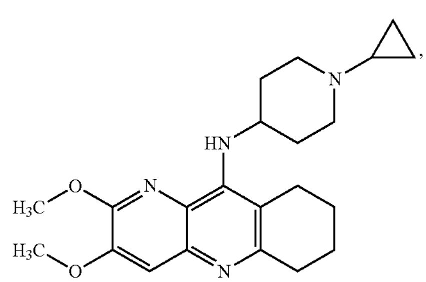 [SMILES: COc1cc2nc3c(c(NC4CCN(C5CC5)CC4)c2nc1OC)CCCC3] |
| 68 | 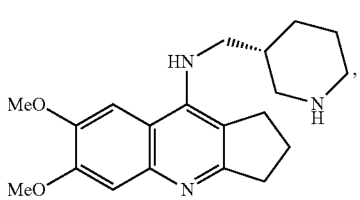 [SMILES: COc1cc2nc3c(c(NC[C@@H]4CCCNC4)c2cc1OC)CCC3] | 138 | 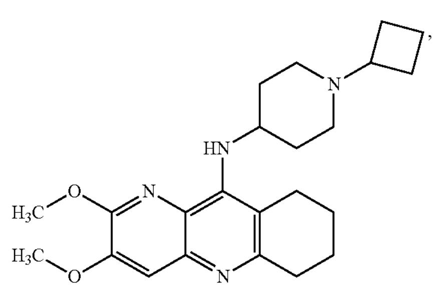 [SMILES: COc1cc2nc3c(c(NC4CCN(C5CCC5)CC4)c2nc1OC)CCCC3] |

-continued
| No | Structure | No | Structure |
|---|---|---|---|
| 69 | 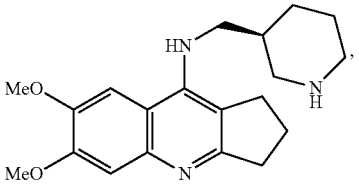 [SMILES: COc1cc2nc3c(c(NC[C@H]4CCCNC4)c2cc1OC)CCC3] | 139 | 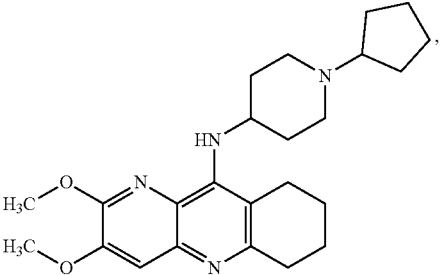 [SMILES: COc1cc2nc3c(c(NC4CCN(C5CCCC5)CC4)c2nc1OC)CCCC3] |
| 134 | 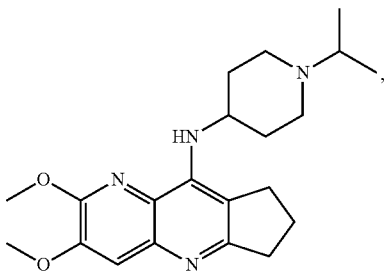 [SMILES: COc1cc2nc3c(c(NC4CCN(C(C)C)CC4)c2nc1OC)CCC3] | 140 | 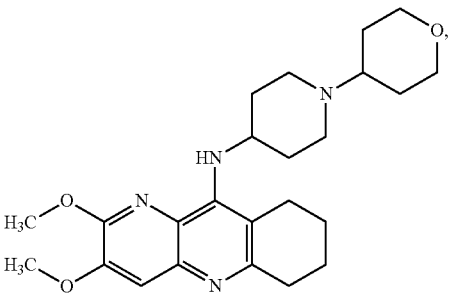 [SMILES: COc1cc2nc3c(c(NC4CCN(C5CCOCC5)CC4)c2nc1OC)CCCC3] |
| 149 | 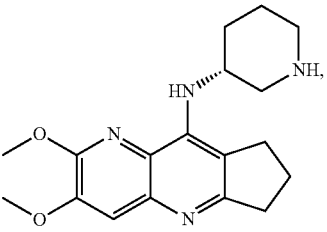 [SMILES: COc1cc2nc3c(c(N[C@@H]4CCCNC4)c2nc1OC)CCC3] | 141 | 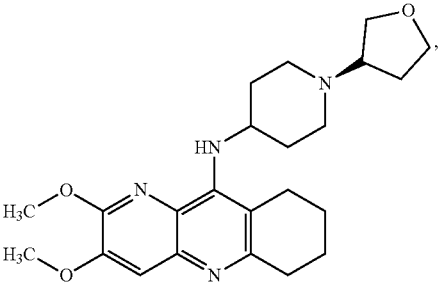 |
| 163 | 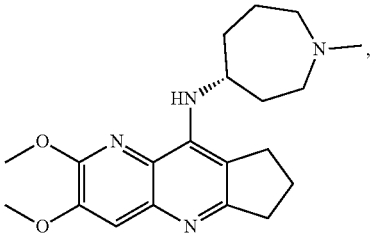 | 142 | 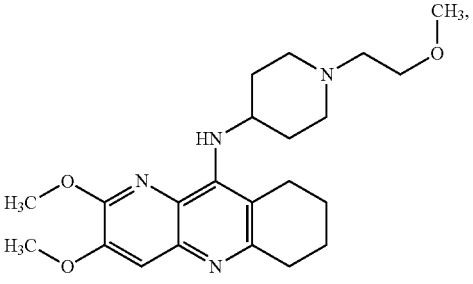 [SMILES: COCCN1CCC(Nc2c3c(nc4cc(OC)c(OC)nc24)CCCC3)CC1] |
| 164 | 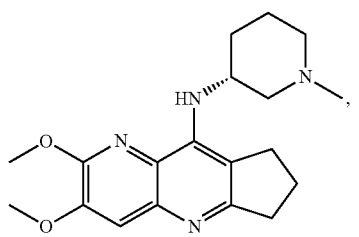 | 143 | 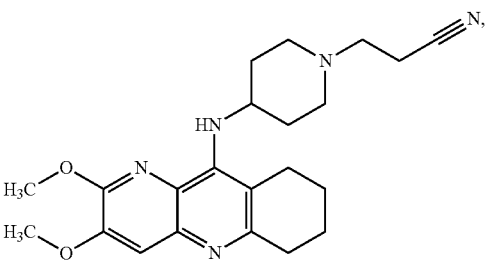 |

-continued
| No | Structure | No | Structure |
|---|---|---|---|
| 165 | 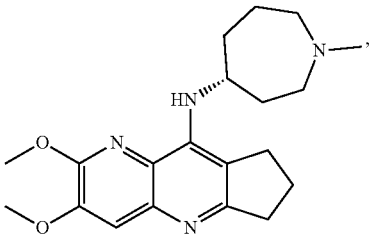 | 144 | 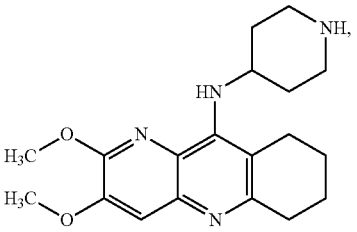 [SMILES: COc1cc2nc3c(c(NC4CCNCC4)c2nc1OC)CCCC3] |
| 286 | 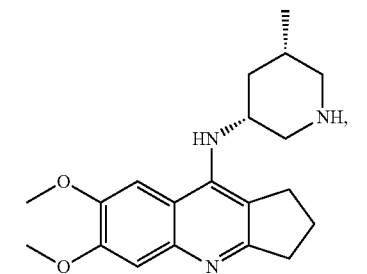 [SMILES: COc1cc2nc3c(c(N[C@H]4CNC[C@@H](C)C4)c2cc1OC)CCC3] | 145 | 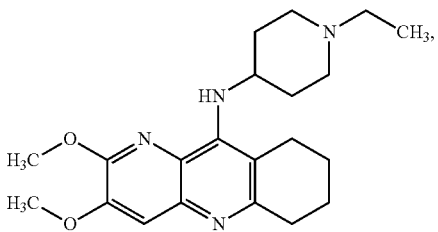 [SMILES: CCN1CCC(Nc2c3c(nc4cc(OC)c(OC)nc24)CCCC3)CC1] |
| 402 | 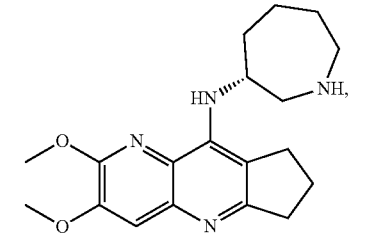 [SMILES: COc1cc2nc3c(c(N[C@@H]4CCCCNC4)c2nc1OC)CCC3] | 146 | 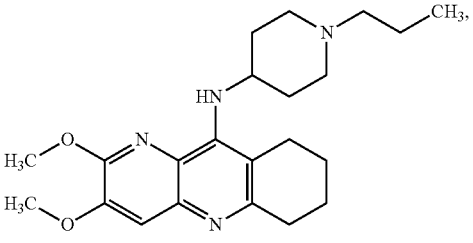 [SMILES: CCCN1CCC(Nc2c3c(nc4cc(OC)c(OC)nc24)CCCC3)CC1] |
|  |  | 147 | 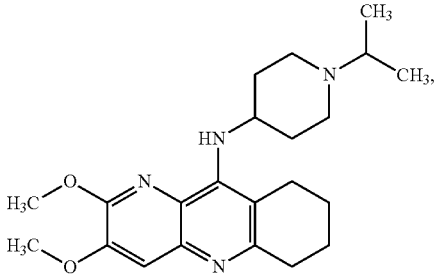 [SMILES: COc1cc2nc3c(c(NC4CCN(C(C)C)CC4)c2nc1OC)CCCC3] |
| 404 | 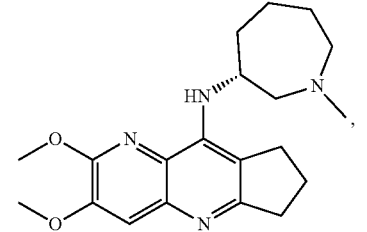 | 148 | 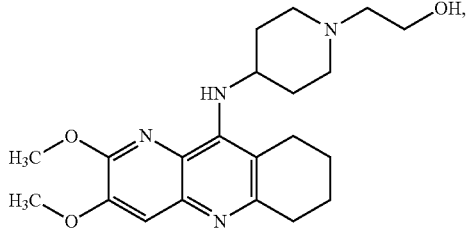 |

-continued

| No | Structure | No | Structure |
|---|---|---|---|
| 405 | 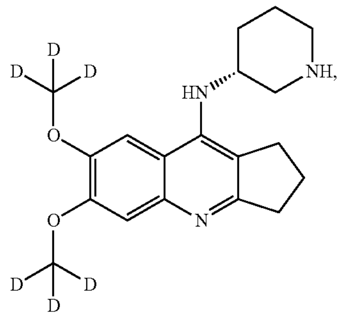 [SMILES: [2H]C([2H])([2H])Oc1cc2nc3c(c(N[C@@H]4CCCNC4)c2cc1OC([2H])([2H])[2H])CCC3] | 150 | 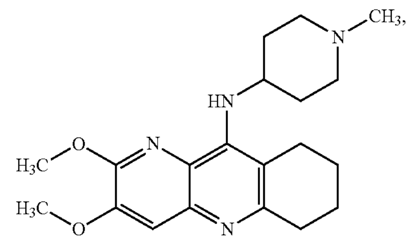 [SMILES: COc1cc2nc3c(c(NC4CCN(C)CC4)c2nc1OC)CCCC3] |
| 406 | 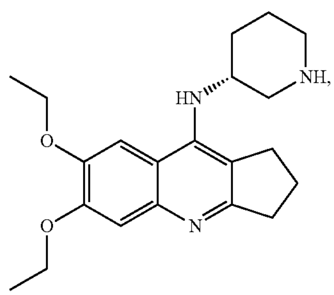 [SMILES: CCOc1cc2nc3c(c(N[C@@H]4CCCNC4)c2cc1OCC)CCC3] | 151 | 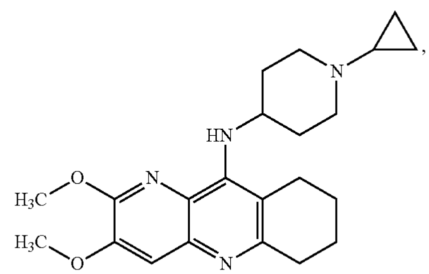 [SMILES: COc1cc2nc3c(c(NC4CCN(C5CC5)CC4)c2nc1OC)CCCC3] |
| 407 | 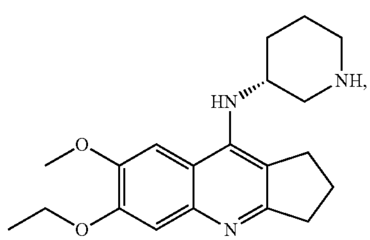 [SMILES: CCOc1cc2nc3c(c(N[C@@H]4CCCNC4)c2cc1OC)CCC3] | 152 | 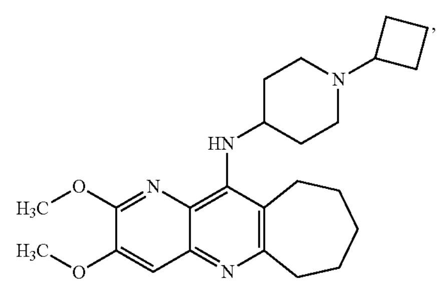 [SMILES: COc1cc2nc3c(c(NC4CCN(C5CCC5)CC4)c2nc1OC)CCCCC3] |
| 408 | 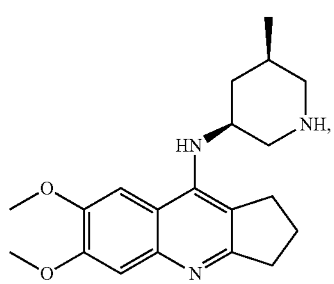 [SMILES: COc1cc2nc3c(c(N[C@@H]4CNC[C@H](C)C4)c2cc1OC)CCC3] | 153 | 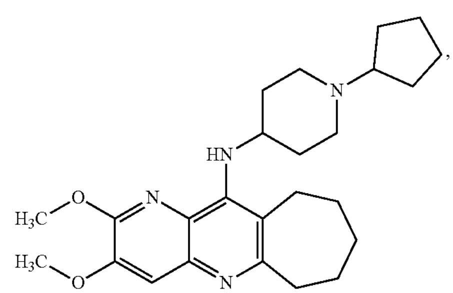 [SMILES: COc1cc2nc3c(c(NC4CCN(C5CCCC5)CC4)c2nc1OC)CCCCC3] |
| 409 | 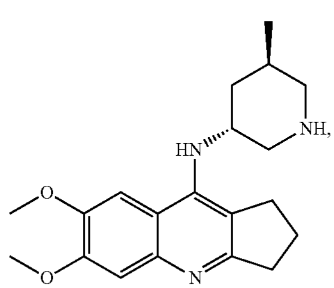 [SMILES: COc1cc2nc3c(c(N[C@H]4CNC[C@H](C)C4)c2cc1OC)CCC3] | 154 | 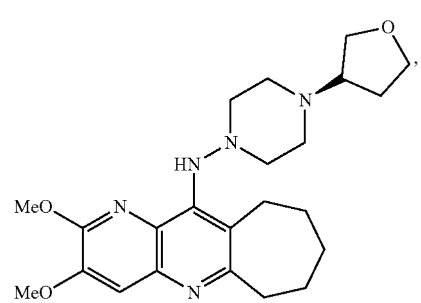 |

-continued
| No | Structure | No | Structure |
|---|---|---|---|
| 410 | 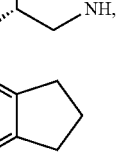 | 155 | 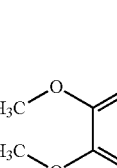 |
| 411 | 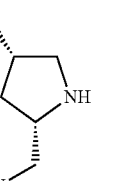 | 156 | 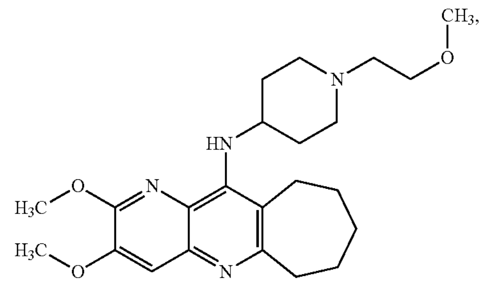 [SMILES: COCCN1CCC(Nc2c3c(nc4cc(OC)c(OC)nc24)CCCCC3)CC1] |
| 412 | 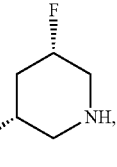 | 157 | 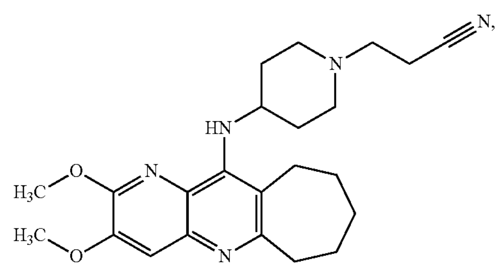 |
| 413 | 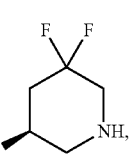 | 158 | 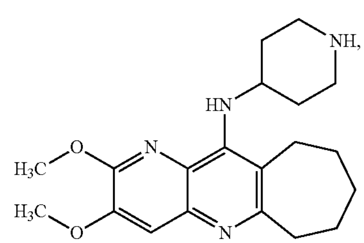 |
| 414 | 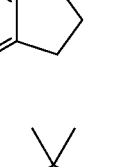 | 159 | 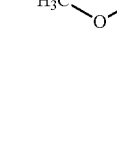 |

| No | Structure | No | Structure |
|---|---|---|---|
| 415 | 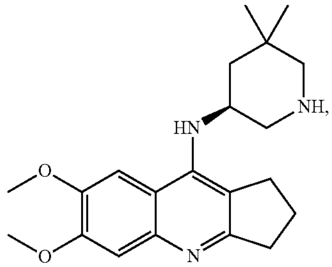 [SMILES: COc1cc2nc3c(c(N[C@@H]4CNCC(C)(C)C4)c2cc1OC)CCC3] | 160 | 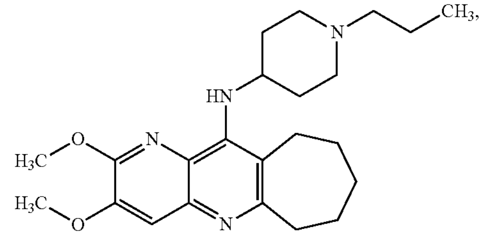 [SMILES: CCCN1CCC(Nc2c3c(nc4cc(OC)c(OC)nc24)CCCCC3)CC1] |
| 416 | 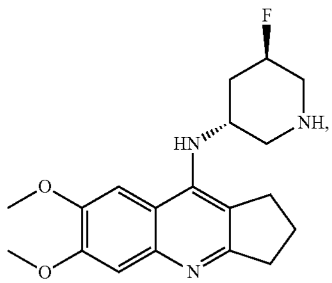 [SMILES: COc1cc2nc3c(c(N[C@H]4CNC[C@H](F)C4)c2cc1OC)CCC3] | 161 | 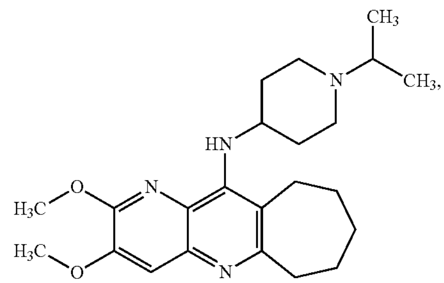 [SMILES: COc1cc2nc3c(c(NC4CCN(C(C)C)CC4)c2nc1OC)CCCCC3] |
| 162 | 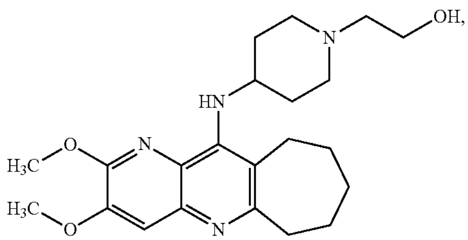 | 201 | 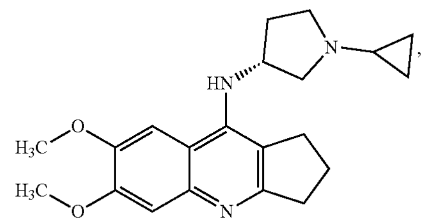 [SMILES: COc1cc2nc3c(c(N[C@@H]4CCN(C5CC5)C4)c2cc1OC)CCC3] |
| 166 | 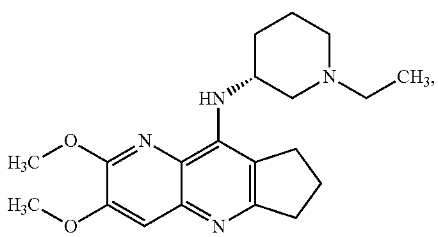 [SMILES: CCN1CCC[C@@H](Nc2c3c(nc4cc(OC)c(OC)nc24)CCC3)C1] | 202 | 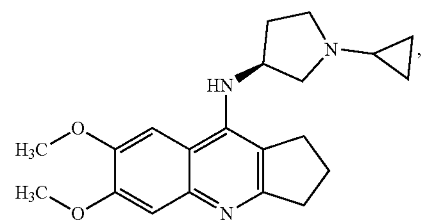 [SMILES: COc1cc2nc3c(c(N[C@H]4CCN(C5CC5)C4)c2cc1OC)CCC3] |
| 167 | 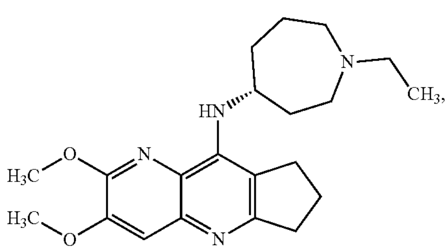 [SMILES: CCN1CCC[C@@H](Nc2c3c(nc4cc(OC)c(OC)nc24)CCC3)CC1] | 203 | 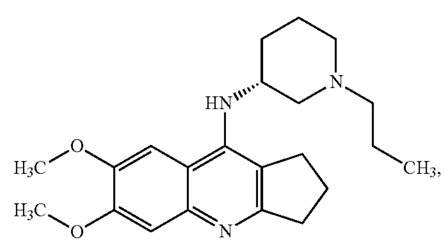 [SMILES: CCCN1CCC[C@@H](Nc2c3c(nc4cc(OC)c(OC)cc24)CCC3)C1] |
| 168 | 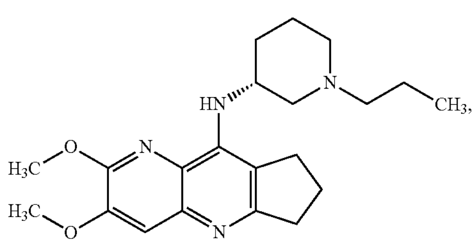 [SMILES: CCCN1CCC[C@@H](Nc2c3c(nc4cc(OC)c(OC)nc24)CCC3)C1] | 204 | 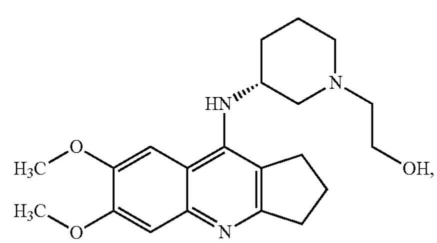 |

US 11,661,410 B2

333                                    334

-continued

| No | Structure | No | Structure |
|----|-----------|----|-----------|
| 169 | 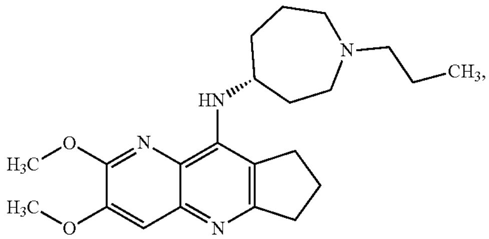 [SMILES: CCCN1CCC[C@@H](Nc2c3c(nc4cc(OC)c(OC)nc24)CCC3)CC1] | 205 | 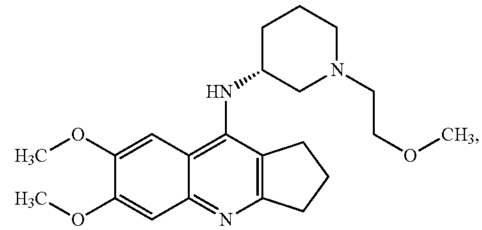 [SMILES: COCCN1CCC[C@@H](Nc2c3c(nc4cc(OC)c(OC)cc24)CCC3)C1] |
| 170 | 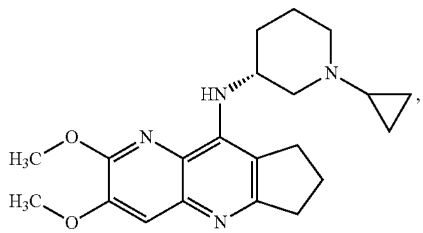 [SMILES: COc1cc2nc3c(c(N[C@@H]4CCCN(C5CC5)C4)c2nc1OC)CCC3] | 206 | 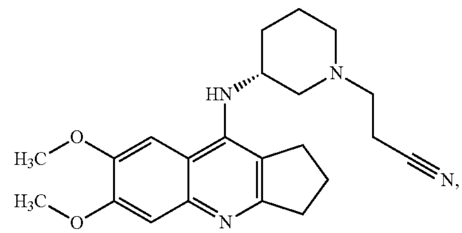 [SMILES: COc1cc2nc3c(c(N[C@@H]4CCCN(CCC#N)C4)c2cc1OC)CCC3] |
| 171 | 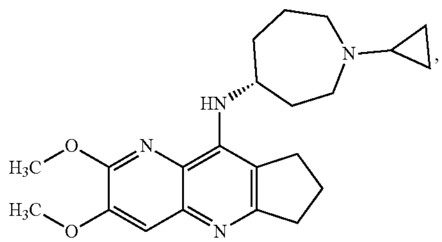 | 207 | 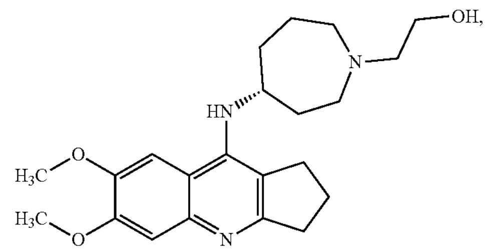 [SMILES: COc1cc2nc3c(c(N[C@@H]4CCCN(CCO)CC4)c2cc1OC)CCC3] |
| 172 | 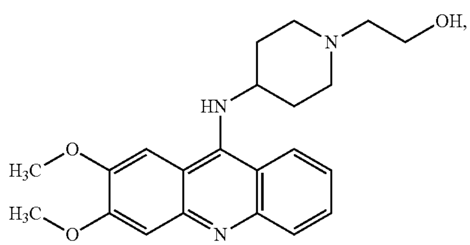 [SMILES: COc1cc2nc3ccccc3c(NC3CCN(CCO)CC3)c2cc1OC] | 208 | 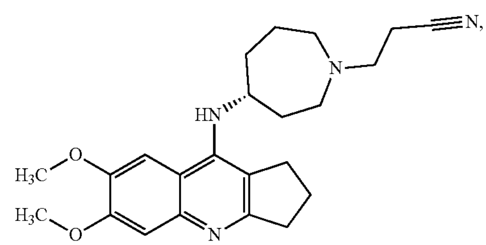 [SMILES: COc1cc2nc3c(c(N[C@@H]4CCCN(CCC#N)CC4)c2cc1OC)CCC3] |
| 173 | 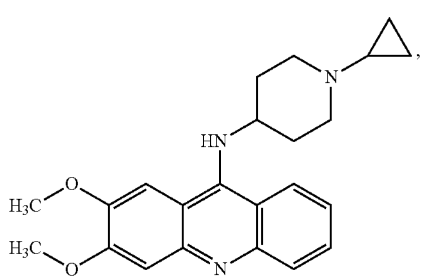 [SMILES: COc1cc2nc3ccccc3c(NC3CCN(C4CC4)CC3)c2cc1OC] | 209 | 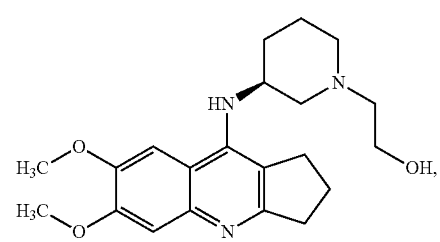 |
| 174 | 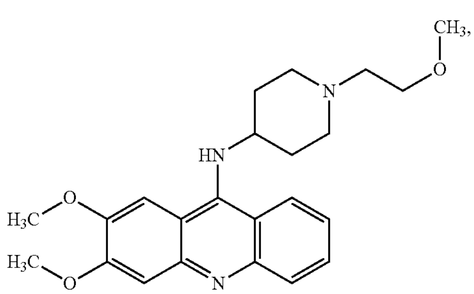 [SMILES: COCCN1CCC(Nc2c3ccccc3nc3cc(OC)c(OC)cc23)CC1] | 210 | 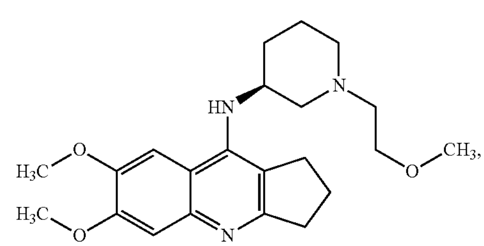 [SMILES: COCCN1CCC[C@H](Nc2c3c(nc4cc(OC)c(OC)cc24)CCC3)C1] |

335 336
-continued

| No | Structure | No | Structure |
|---|---|---|---|
| 175 | 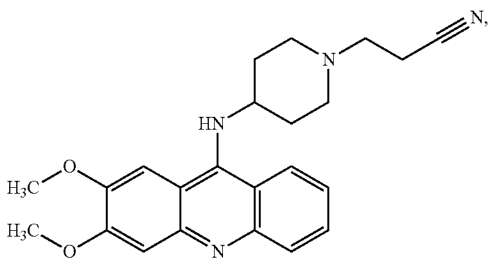 [SMILES: COc1cc2nc3ccccc3c(NC3CCN(CCC#N)CC3)c2cc1OC] | 211 | 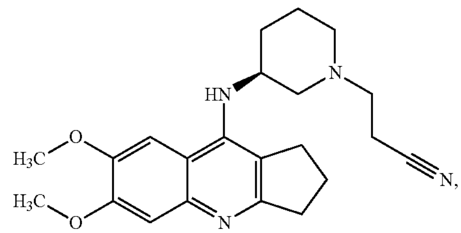 [SMILES: COc1cc2nc3c(c(N[C@H]4CCCN(CCC#N)C4)c2cc1OC)CCC3] |
| 176 | 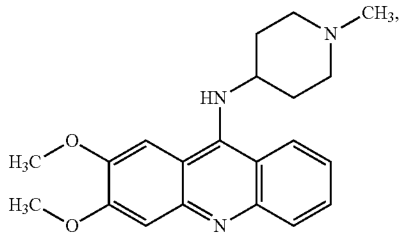 [SMILES: COc1cc2nc3ccccc3c(NC3CCN(C)CC3)c2cc1OC] | 212 | 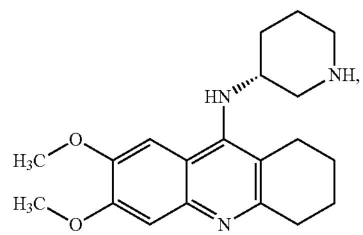 [SMILES: COc1cc2nc3c(c(N[C@@H]4CCCNC4)c2cc1OC)CCCC3] |
| 177 | 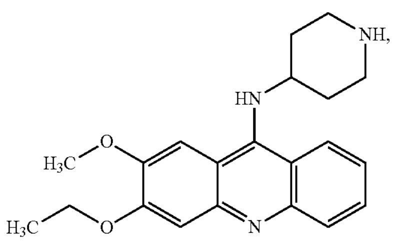 [SMILES: CCOc1cc2nc3ccccc3c(NC3CCNCC3)c2cc1OC] | 213 | 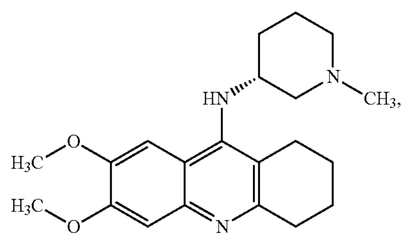 [SMILES: COc1cc2nc3c(c(N[C@@H]4CCCN(C)C4)c2cc1OC)CCCC3] |
| 178 | 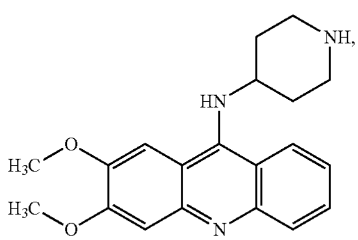 [SMILES: COc1cc2nc3ccccc3c(NC3CCNCC3)c2cc1OC] | 214 | 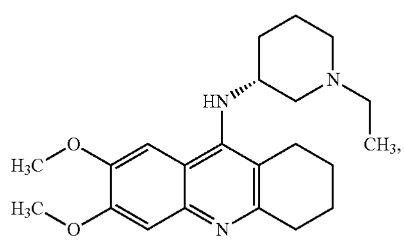 [SMILES: CCN1CCC[C@@H](Nc2c3c(nc4cc(OC)c(OC)cc24)CCCC3)C1] |
| 179 | 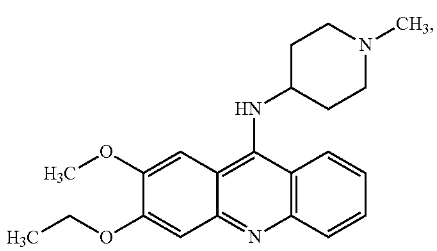 [SMILES: CCOc1cc2nc3ccccc3c(NC3CCN(C)CC3)c2cc1OC] | 215 | 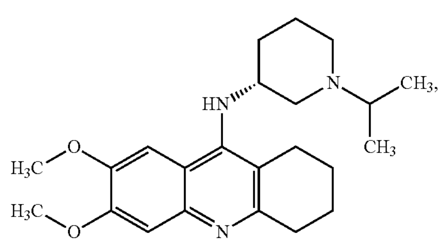 [SMILES: COc1cc2nc3c(c(N[C@@H]4CCCN(C(C)C)C4)c2cc1OC)CCCC3] |
| 180 | 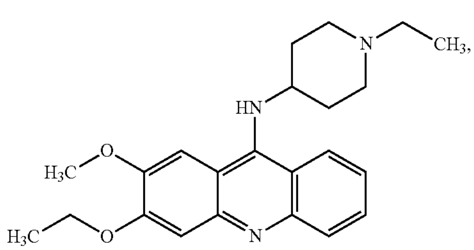 [SMILES: CCOc1cc2nc3ccccc3c(NC3CCN(CC)CC3)c2cc1OC] | 216 | 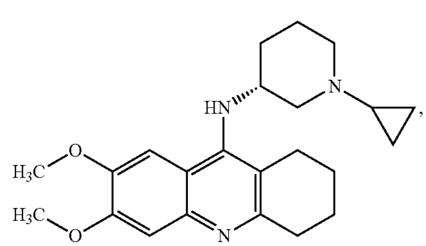 [SMILES: COc1cc2nc3c(c(N[C@@H]4CCCN(C5CC5)C4)c2cc1OC)CCCC3] |

US 11,661,410 B2

337 338

-continued

| No | Structure | No | Structure |
|---|---|---|---|
| 181 | 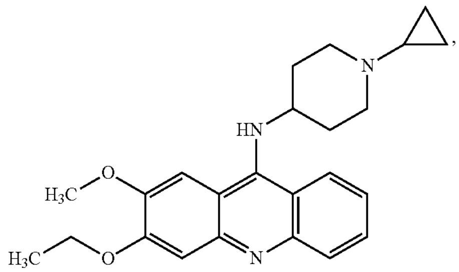 [SMILES: CCOc1cc2nc3ccccc3c(NC3CCN(C4CC4)CC3)c2cc1OC] | 217 | 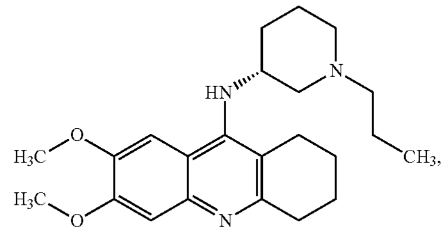 [SMILES: CCCN1CCC[C@@H](Nc2c3c(nc4cc(OC)c(OC)cc24)CCCC3)C1] |
| 182 | 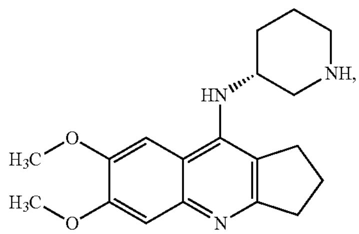 [SMILES: COc1cc2nc3c(c(N[C@@H]4CCCNC4)c2cc1OC)CCC3] | 218 | 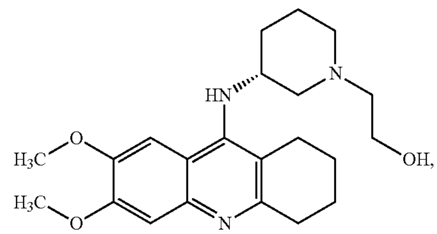 |
| 183 | 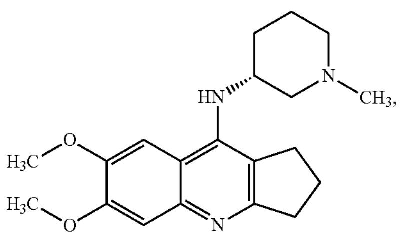 [SMILES: COc1cc2nc3c(c(N[C@@H]4CCCN(C)C4)c2cc1OC)CCC3] | 219 | 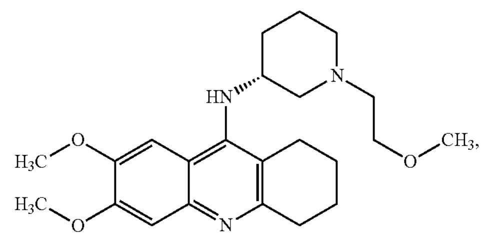 [SMILES: COCCN1CCC[C@@H](Nc2c3c(nc4cc(OC)c(OC)cc24)CCCC3)C1] |
| 184 | 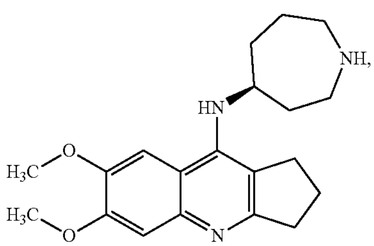 [SMILES: COc1cc2nc3c(c(N[C@H]4CCCNCC4)c2cc1OC)CCC3] | 220 | 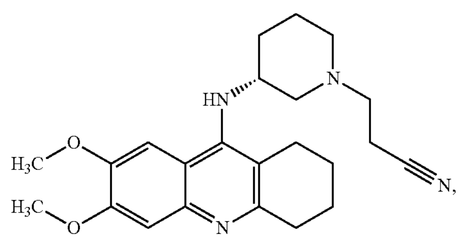 [SMILES: COc1cc2nc3c(c(N[C@@H]4CCCN(CCC#N)C4)c2cc1OC)CCCC3] |
| 185 | 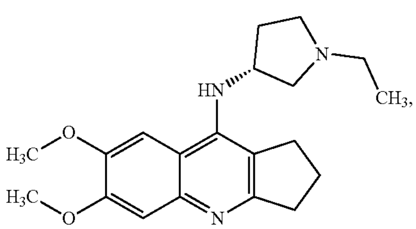 [SMILES: CCN1CC[C@@H](Nc2c3c(nc4cc(OC)c(OC)cc24)CCC3)C1] | 221 | 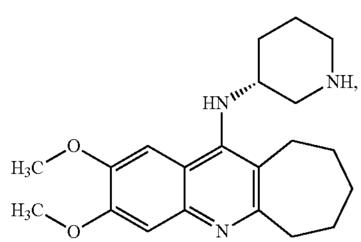 |
| 186 | 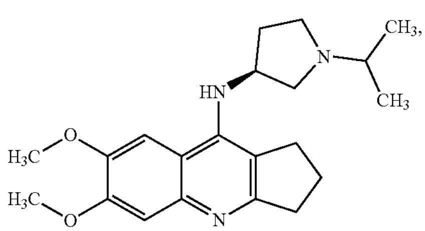 [SMILES: COc1cc2nc3c(c(N[C@H]4CCN(C(C)C)C4)c2cc1OC)CCC3] | 222 | 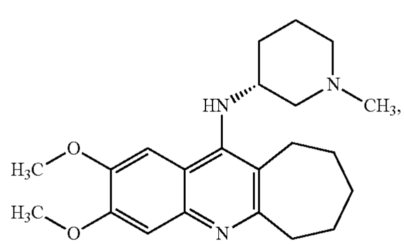 [SMILES: COc1cc2nc3c(c(N[C@@H]4CCCN(C)C4)c2cc1OC)CCCCC3] |

| No | Structure | No | Structure |
|---|---|---|---|
| 187 | 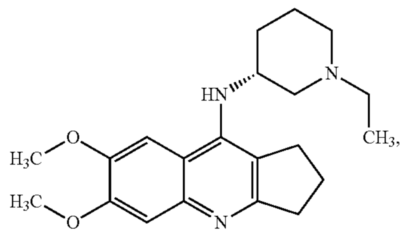 [SMILES: CCN1CCC[C@@H](Nc2c3c(nc4cc(OC)c(OC)cc24)CCC3)C1] | 223 | 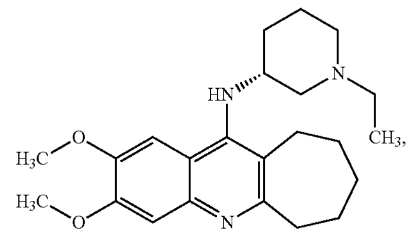 [SMILES: CCN1CCC[C@@H](Nc2c3c(nc4cc(OC)c(OC)cc24)CCCCC3)C1] |
| 188 | 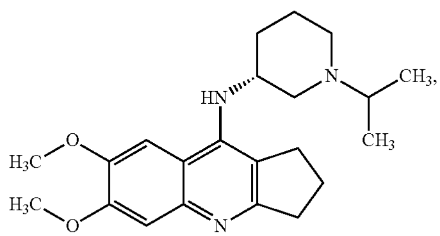 [SMILES: COc1cc2nc3c(c(N[C@@H]4CCCN(C(C)C)C4)c2cc1OC)CCC3] | 224 | 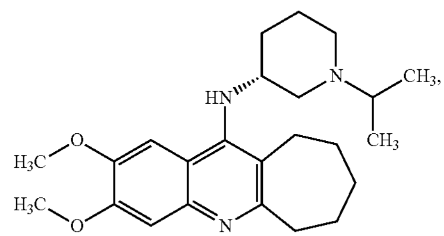 |
| 189 | 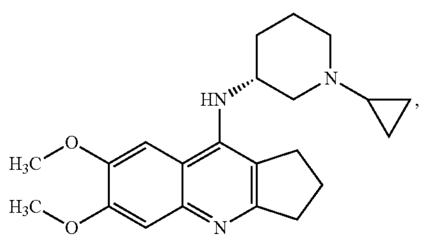 [SMILES: COc1cc2nc3c(c(N[C@@H]4CCCN(C5CC5)C4)c2cc1OC)CCC3] | 225 | 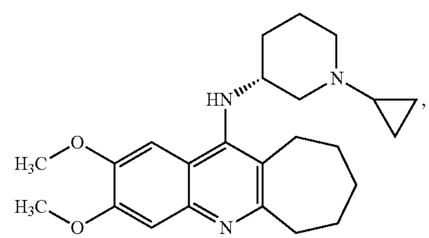 [SMILES: COc1cc2nc3c(c(N[C@@H]4CCCN(C5CC5)C4)c2cc1OC)CCCCC3] |
| 190 | 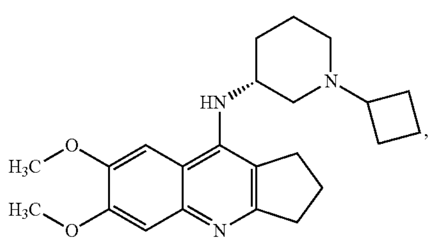 [SMILES: COc1cc2nc3c(c(N[C@@H]4CCCN(C5CCC5)C4)c2cc1OC)CCC3] | 226 | 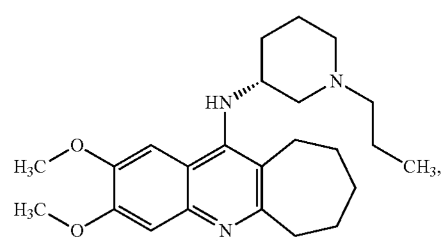 [SMILES: CCCN1CCC[C@@H](Nc2c3c(nc4cc(OC)c(OC)cc24)CCCCC3)C1] |
| 191 | 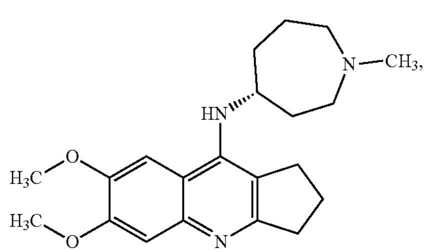 [SMILES: COc1cc2nc3c(c(N[C@@H]4CCCN(C)CC4)c2cc1OC)CCC3] | 228 | 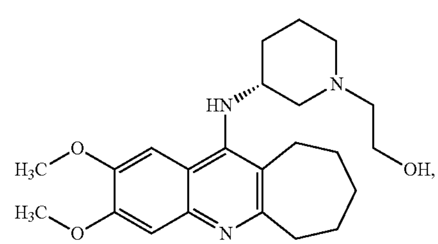 |
| 192 | 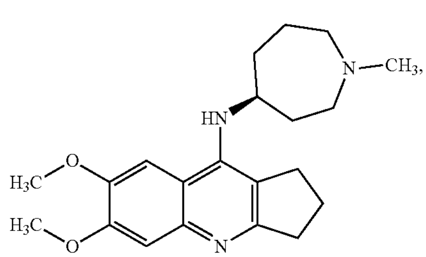 [SMILES: COc1cc2nc3c(c(N[C@H]4CCCN(C)CC4)c2cc1OC)CCC3] | 229 | 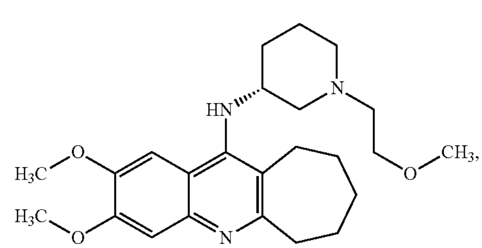 |

US 11,661,410 B2

-continued

| No | Structure | No | Structure |
|---|---|---|---|
| 193 | 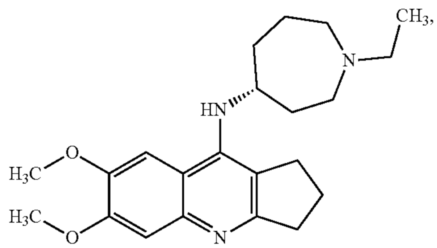 [SMILES: CCN1CCC[C@@H](Nc2c3c(nc4cc(OC)c(OC)cc24)CCC3)CC1] | 230 | 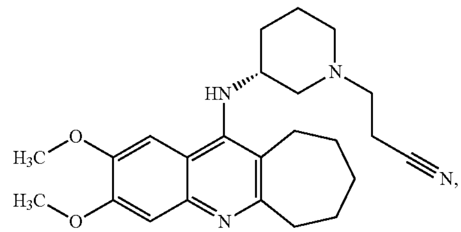 |
| 194 | 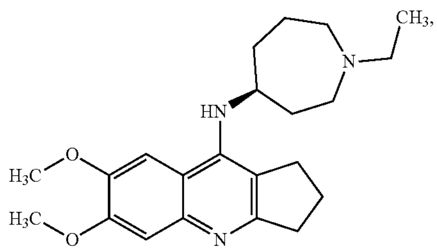 [SMILES: CCN1CCC[C@H](Nc2c3c(nc4cc(OC)c(OC)cc24)CCC3)CC1] | 231 | 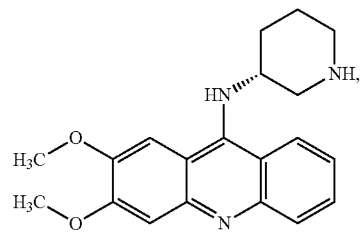 [SMILES: COc1cc2nc3ccccc3c(N[C@@H]3CCCNC3)c2cc1OC] |
| 195 | 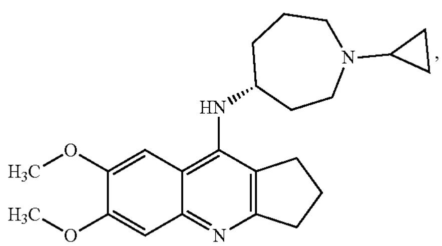 [SMILES: COc1cc2nc3c(c(N[C@@H]4CCCN(C5CC5)CC4)c2cc1OC)CCC3 ; ","] | 232 | 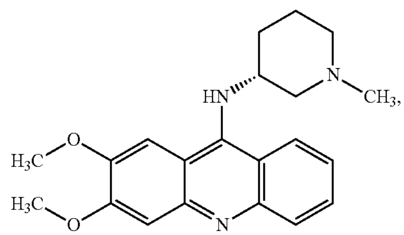 [SMILES: COc1cc2nc3ccccc3c(N[C@@H]3CCCN(C)C3)c2cc1OC] |
| 196 | 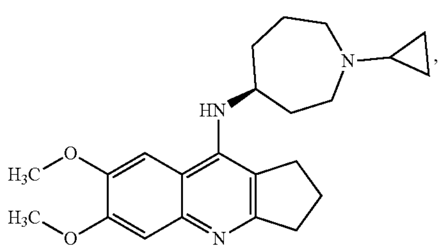 [SMILES: COc1cc2nc3c(c(N[C@H]4CCCN(C5CC5)CC4)c2cc1OC)CCC3 ; ","] | 233 | 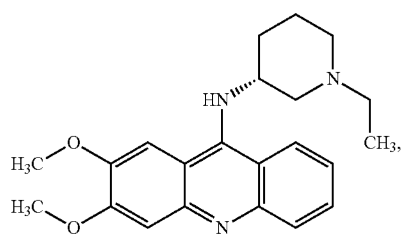 [SMILES: CCN1CCC[C@@H](Nc2c3ccccc3nc3cc(OC)c(OC)cc23)C1] |
| 197 | 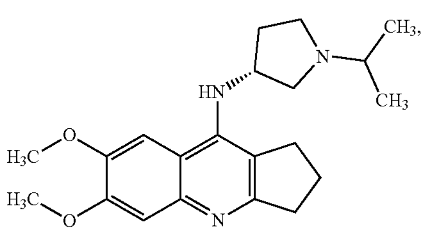 [SMILES: COc1cc2nc3c(c(N[C@@H]4CCN(C(C)C)C4)c2cc1OC)CCC3] | 234 | 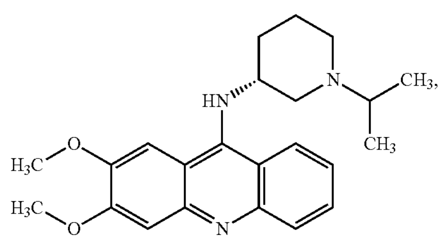 [SMILES: COc1cc2nc3ccccc3c(N[C@@H]3CCCN(C(C)C)C3)c2cc1OC] |
| 198 | 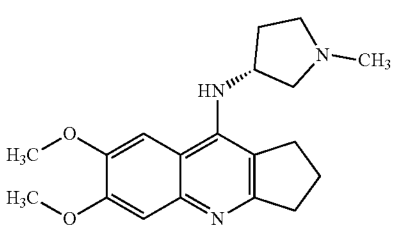 | 235 | 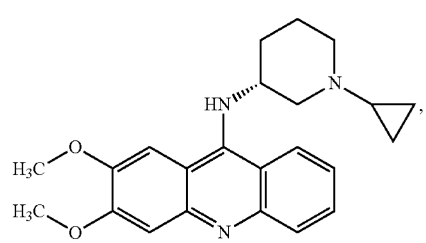 [SMILES: COc1cc2nc3ccccc3c(N[C@@H]3CCCN(C4CC4)C3)c2cc1OC] |

-continued
| No | Structure | No | Structure |
|---|---|---|---|
| 199 | 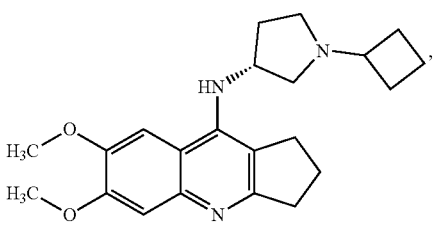 [SMILES: COc1cc2nc3c(c(N[C@@H]4CCN(C5CCC5)C4)c2cc1OC)CCC3] | 236 | 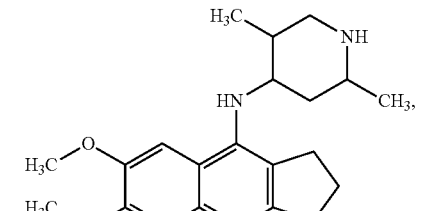 |
| 200 | 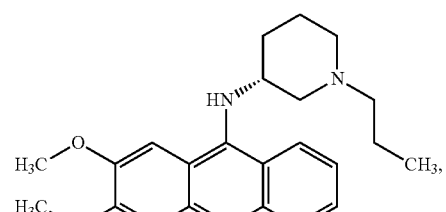 | 237 | 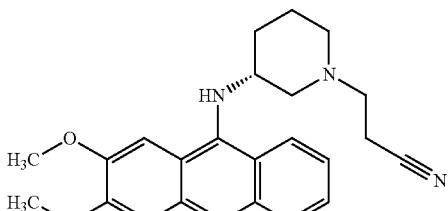 |
| 251 | 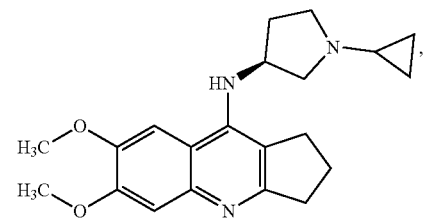 | 238 | 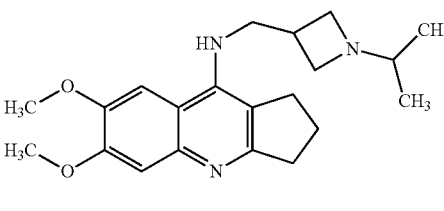 |
| 252 | 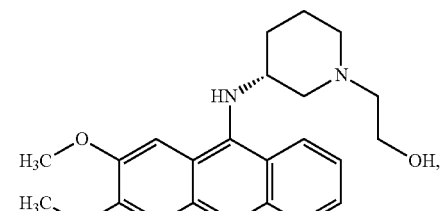 | 239 | 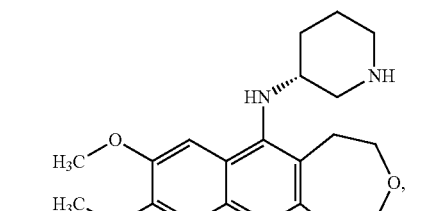 |
| 253 | 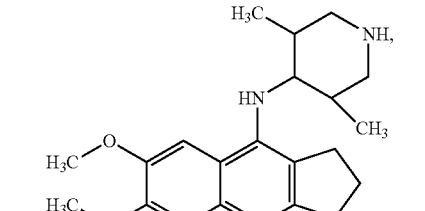 | 240 | 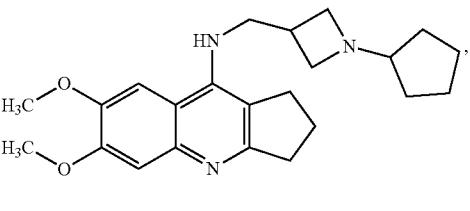 [SMILES: COc1cc2nc3c(c(NCC4CN(C5CCCC5)C4)c2cc1OC)CCC3] |
| 254 | 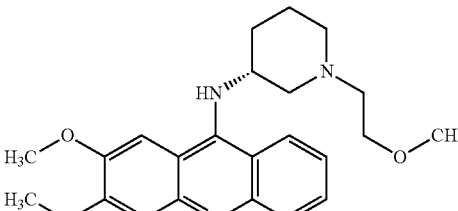 | 241 | 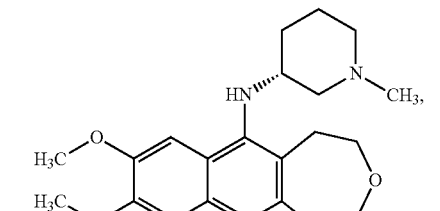 |

| No | Structure | No | Structure |
|---|---|---|---|
| 255 | 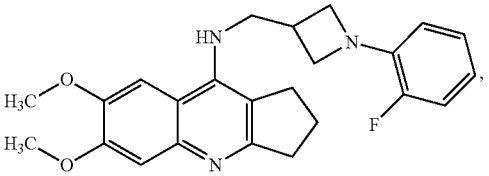 | 242 | 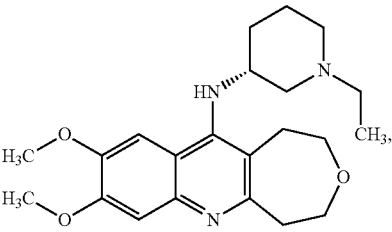 [SMILES: CCN1CCC[C@@H](Nc2c3c(nc4cc(OC)c(OC)cc24)CCOCC3)C1] |
| 256 | 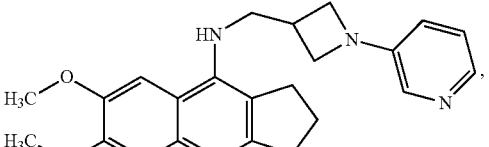 | 243 | 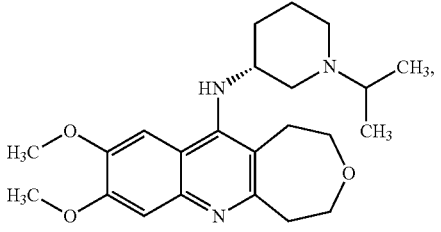 |
| 257 | 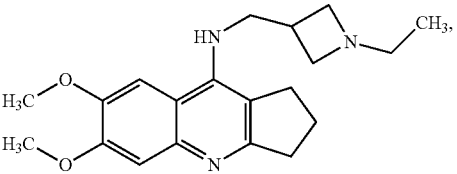 [SMILES: CCN1CC(CNc2c3c(nc4cc(OC)c(OC)cc24)CCC3)C1] | 244 | 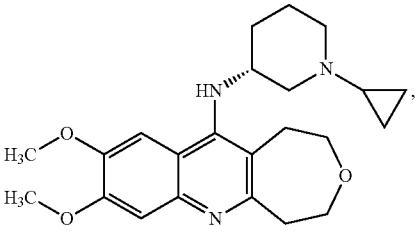 [SMILES: COc1cc2nc3c(c(N[C@@H]4CCCN(C5CC5)C4)c2cc1OC)CCOCC3] |
| 258 | 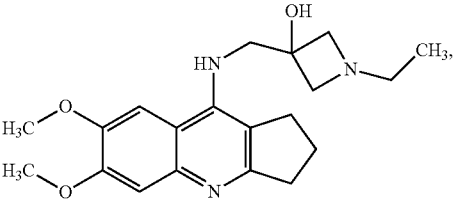 [SMILES: CCN1CC(O)(CNc2c3c(nc4cc(OC)c(OC)cc24)CCC3)C1] | 245 | 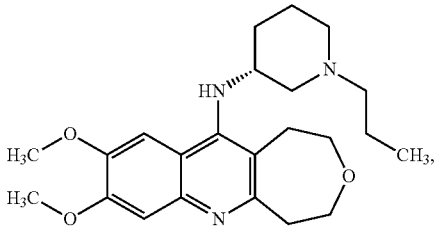 |
| 259 | 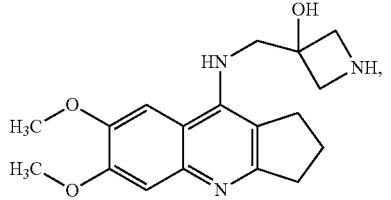 [SMILES: COc1cc2nc3c(c(NCC4(O)CNC4)c2cc1OC)CCC3] | 246 | 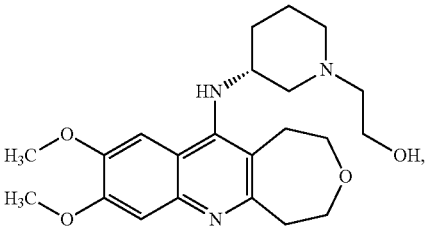 |
| 260 | 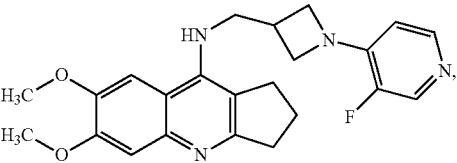 [SMILES: COc1cc2nc3c(c(NCC4CN(c5ccncc5F)C4)c2cc1OC)CCC3] | 247 | 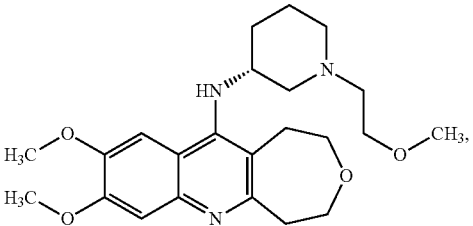 [SMILES: COCCN1CCC[C@@H](Nc2c3c(nc4cc(OC)c(OC)cc24)CCOCC3)C1] |

347                                                            348

-continued

| No | Structure | No | Structure |
|----|-----------|----|-----------|
| 261 | 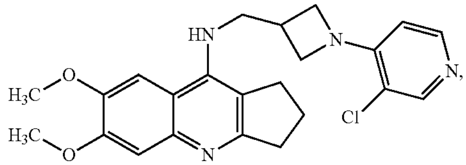 [SMILES: COc1cc2nc3c(c(NCC4CN(c5ccncc5Cl)C4)c2cc1OC)CCC3] | 248 | 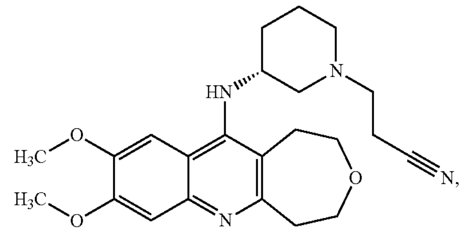 [SMILES: COc1cc2nc3c(c(N[C@@H]4CCCN(CCC#N)C4)c2cc1OC)CCOCC3] |
| 262 | 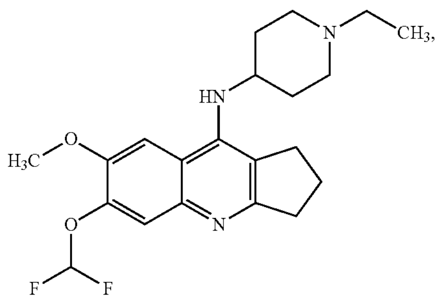 [SMILES: CCN1CCC(Nc2c3c(nc4cc(OC(F)F)c(OC)cc24)CCC3)CC1] | 249 | 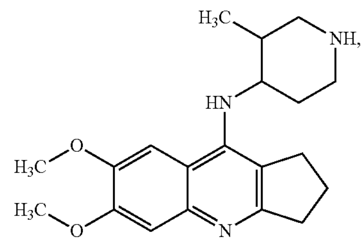 [SMILES: COc1cc2nc3c(c(NC4CCNCC4C)c2cc1OC)CCC3] |
| 263 | 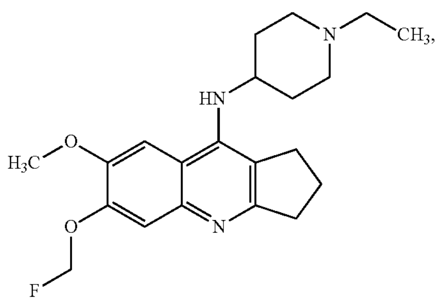 [SMILES: CCN1CCC(Nc2c3c(nc4cc(OCF)c(OC)cc24)CCC3)CC1] | 250 | 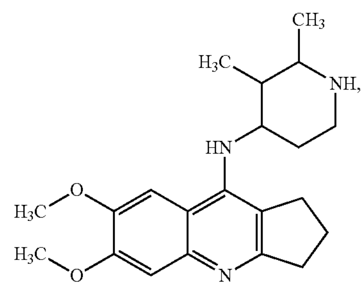 [SMILES: COc1cc2nc3c(c(NC4CCNC(C)C4C)c2cc1OC)CCC3] |
| 264 | 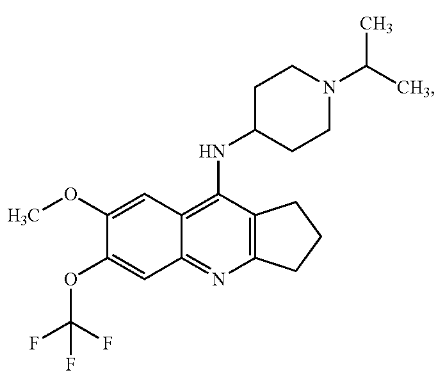 [SMILES: COc1cc2c(NC3CCN(C(C)C)CC3)c3c(nc2cc1OC(F)(F)F)CCC3] | 317 | 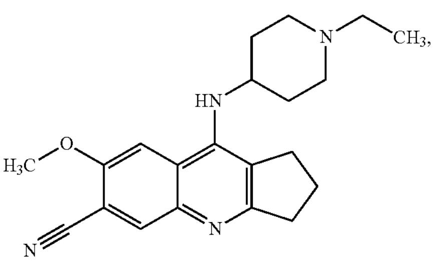 [SMILES: CCN1CCC(Nc2c3c(nc4cc(C#N)c(OC)cc24)CCC3)CC1] |
| 265 | 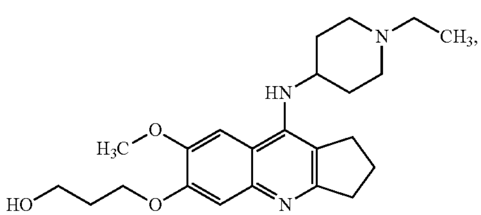 [SMILES: CCN1CCC(Nc2c3c(nc4cc(OCCCO)c(OC)cc24)CCC3)CC1] | 318 | 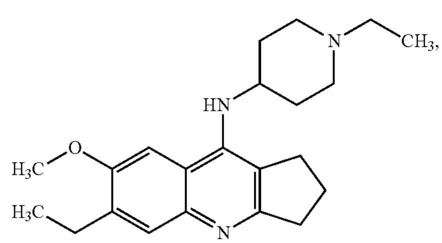 [SMILES: CCc1cc2nc3c(c(NC4CCN(CC)CC4)c2cc1OC)CCC3] |

| No | Structure | No | Structure |
|---|---|---|---|
| 266 | 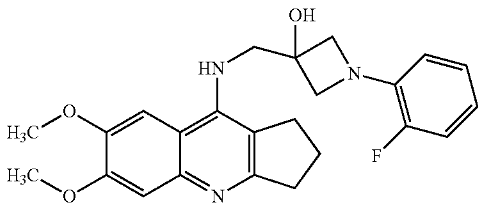 | 320 | 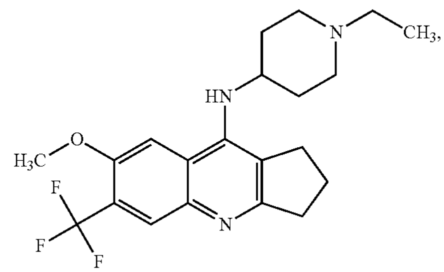 [SMILES: CCN1CCC(Nc2c3c(nc4cc(C(F)(F)F)c(OC)cc24)CCC3)CC1] |
| 267 | 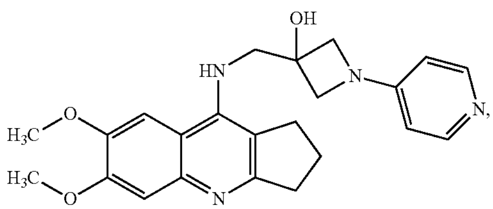 [SMILES: COc1cc2nc3c(c(NCC4(O)CN(c5ccncc5)C4)c2cc1OC)CCC3] | 290 | 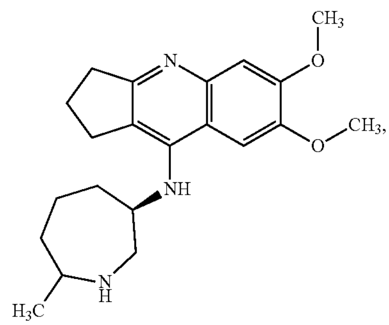 [SMILES: COc1cc2nc3c(c(N[C@@H]4CCCC(C)NC4)c2cc1OC)CCC3] |
| 268 | 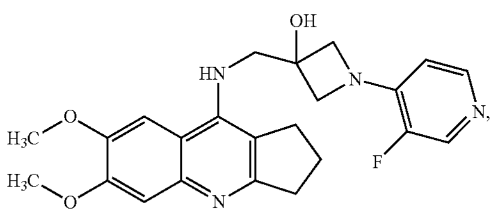 [SMILES: COc1cc2nc3c(c(NCC4(O)CN(c5ccncc5F)C4)c2cc1OC)CCC3] | 322 | 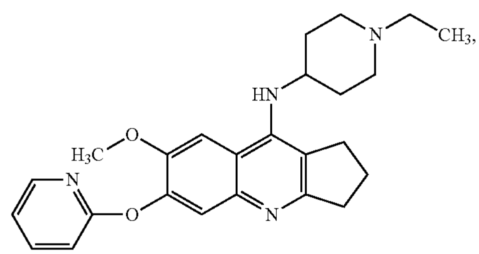 [SMILES: CCN1CCC(Nc2c3c(nc4cc(Oc5ccccn5)c(OC)cc24)CCC3)CC1] |
| 269 | 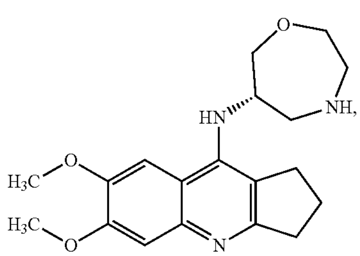 [SMILES: COc1cc2nc3c(c(N[C@H]4CNCCOC4)c2cc1OC)CCC3] | 324 | 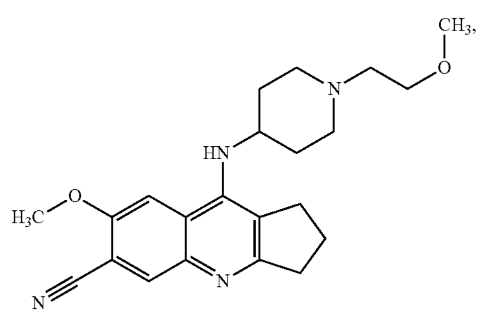 [SMILES: COCCN1CCC(Nc2c3c(nc4cc(C#N)c(OC)cc24)CCC3)CC1] |
| 270 | 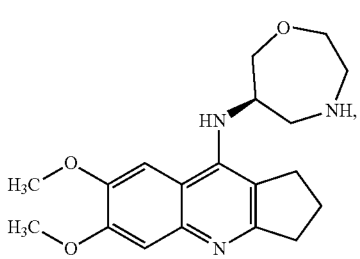 [SMILES: COc1cc2nc3c(c(N[C@@H]4CNCCOC4)c2cc1OC)CCC3] | 325 | 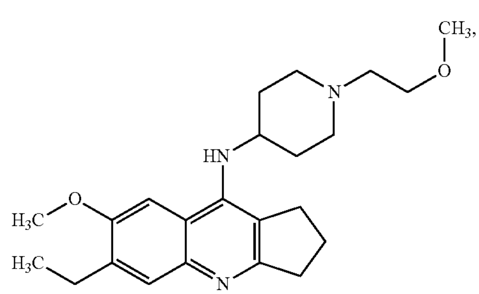 [SMILES: CCc1cc2nc3c(c(NC4CCN(CCOC)CC4)c2cc1OC)CCC3] |

-continued

| No | Structure | No | Structure |
|---|---|---|---|
| 271 | 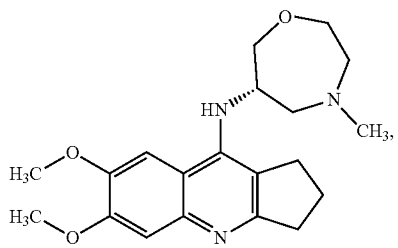 [SMILES: COc1cc2nc3c(c(N[C@@H]4COCCN(C)C4)c2cc1OC)CCC3] | 327 | 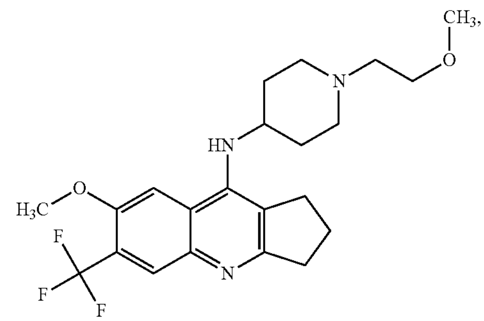 [SMILES: COCCN1CCC(Nc2c3c(nc4cc(C(F)(F)F)c(OC)cc24)CCC3)CC1] |
| 272 | 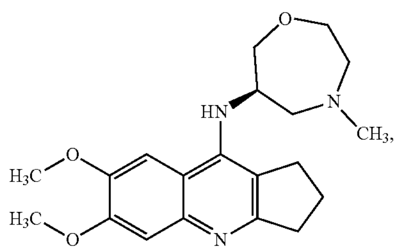 [SMILES: COc1cc2nc3c(c(N[C@H]4COCCN(C)C4)c2cc1OC)CCC3] | 281 | 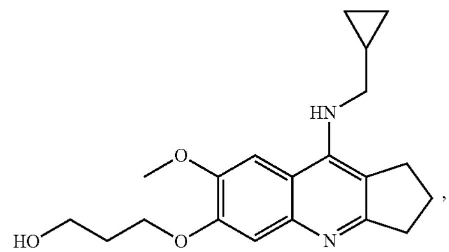 [SMILES: COc1cc2c(NCC3CC3)c3c(nc2cc1OCCCO)CCC3] |
| 273 | 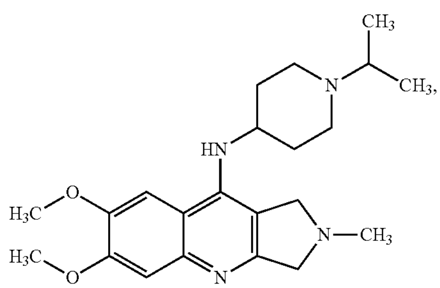 [SMILES: COc1cc2nc3c(c(NC4CCN(C(C)C)CC4)c2cc1OC)CN(C)C3] | 329 | 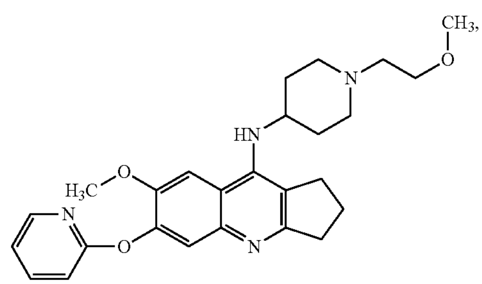 [SMILES: COCCN1CCC(Nc2c3c(nc4cc(Oc5ccccn5)c(OC)cc24)CCC3)CC1] |
| 274 | 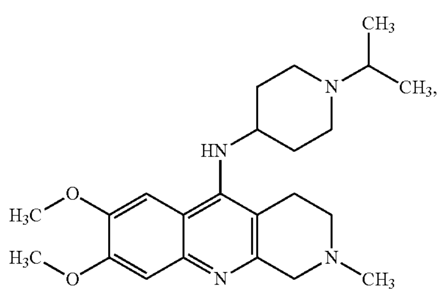 [SMILES: COc1cc2nc3c(c(NC4CCN(C(C)C)CC4)c2cc1OC)CCN(C)C3] | 330 | 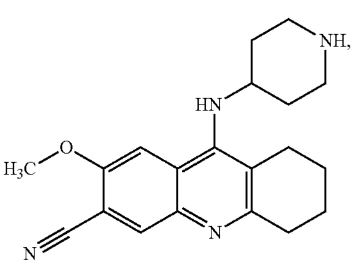 [SMILES: COc1cc2c(NC3CCNCC3)c3c(nc2cc1C#N)CCCC3] |
| 275 | 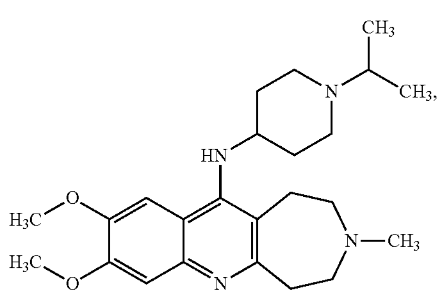 [SMILES: COc1cc2nc3c(c(NC4CCN(C(C)C)CC4)c2cc1OC)CCN(C)CC3] | 331 | 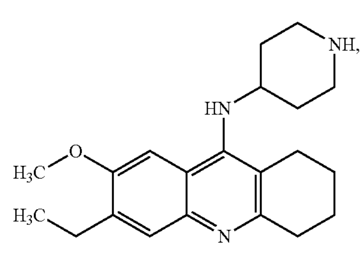 [SMILES: CCc1cc2nc3c(c(NC4CCNCC4)c2cc1OC)CCCC3] |

| No | Structure | No | Structure |
|---|---|---|---|
| 276 | 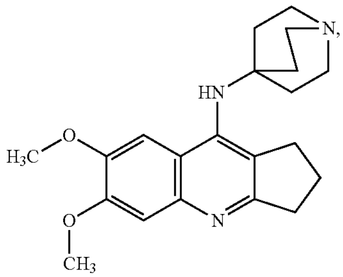 [SMILES: COc1cc2nc3c(c(NC45CCN(CC4)CC5)c2cc1OC)CCC3] | 334 | 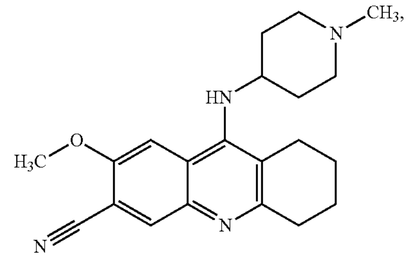 [SMILES: COc1cc2c(NC3CCN(C)CC3)c3c(nc2cc1C#N)CCCC3] |
| 277 | 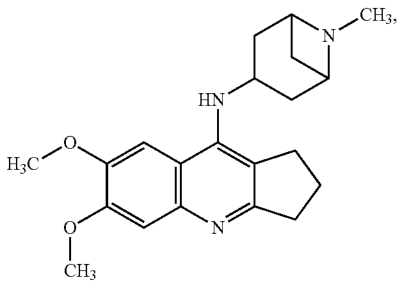 [SMILES: COc1cc2nc3c(c(NC4CC5CC(C4)N5C)c2cc1OC)CCC3] | 335 | 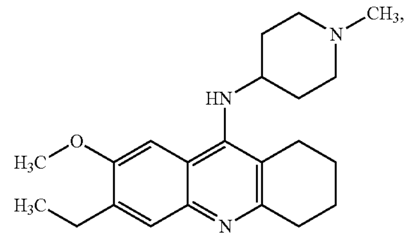 [SMILES: CCc1cc2nc3c(c(NC4CCN(C)CC4)c2cc1OC)CCCC3] |
| 278 | 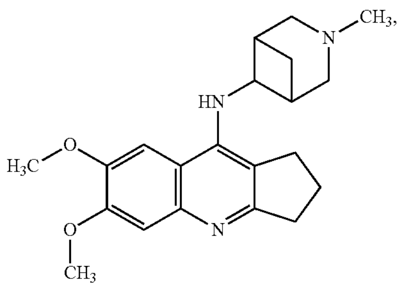 [SMILES: COc1cc2nc3c(c(NC4C5CC4CN(C)C5)c2cc1OC)CCC3] | 294 | 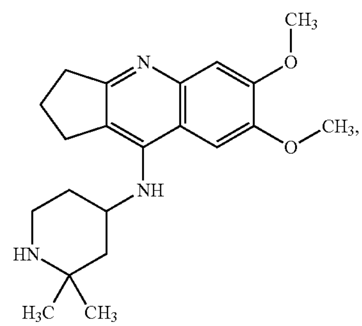 [SMILES: COc1cc2nc3c(c(NC4CCNC(C)(C)C4)c2cc1OC)CCC3] |
| 279 | 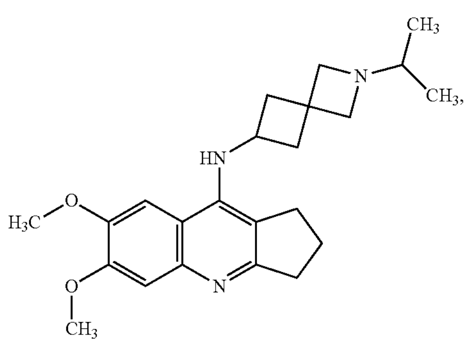 [SMILES: COc1cc2nc3c(c(NC4CC5(C4)CN(C(C)C)C5)c2cc1OC)CCC3] | 338 | 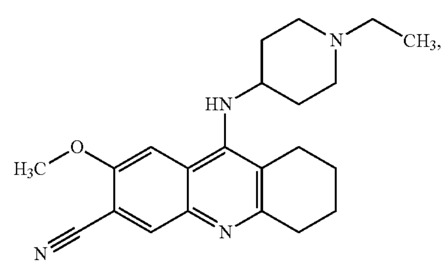 [SMILES: CCN1CCC(Nc2c3c(nc4cc(C#N)c(OC)cc24)CCCC3)CC1] |
| 280 | 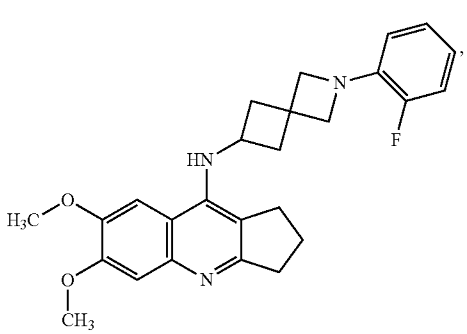 [SMILES: COc1cc2nc3c(c(NC4CC5(C4)CN(c4ccccc4F)C5)c2cc1OC)CCC3] | 339 | 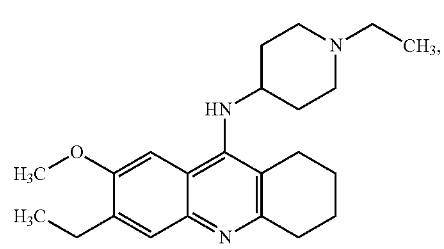 [SMILES: CCc1cc2nc3c(c(NC4CCN(CC)CC4)c2cc1OC)CCCC3] |

-continued

| No | Structure | No | Structure |
|---|---|---|---|
| 282 | 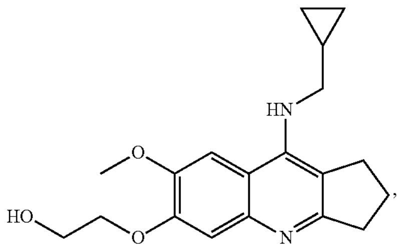 [SMILES: COc1cc2c(NCC3CC3)c3c(nc2cc1OCCO)CCC3] | 342 | 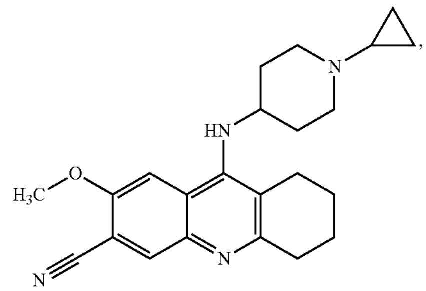 [SMILES: COc1cc2c(NC3CCN(C4CC4)CC3)c3c(nc2cc1C#N)CCCC3] |
| 283 | 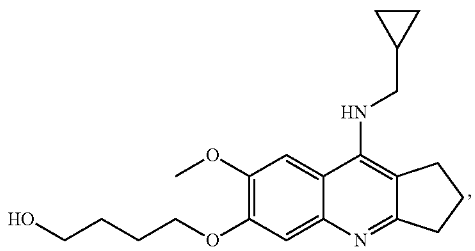 [SMILES: COc1cc2c(NCC3CC3)c3c(nc2cc1OCCCCO)CCC3] | 343 | 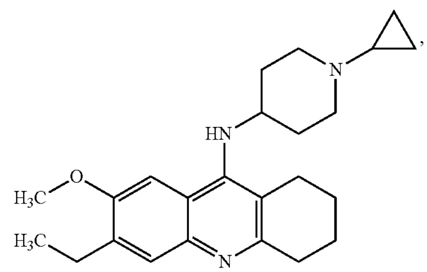 [SMILES: CCc1cc2nc3c(c(NC4CCN(C5CC5)CC4)c2cc1OC)CCCC3] |
| 284 | 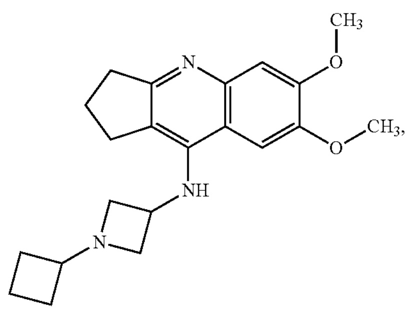 [SMILES: COc1cc2nc3c(c(NC4CN(C5CCC5)C4)c2cc1OC)CCC3] | 346 | 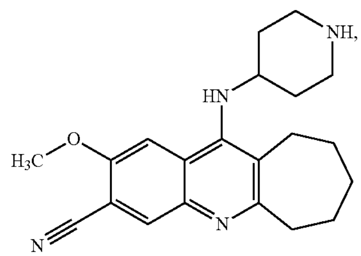 [SMILES: COc1cc2c(NC3CCNCC3)c3c(nc2cc1C#N)CCCCC3] |
| 285 | 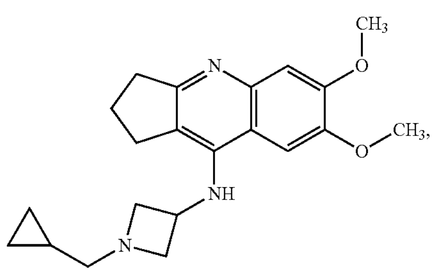 [SMILES: COc1cc2nc3c(c(NC4CN(CC5CC5)C4)c2cc1OC)CCC3] | 347 | 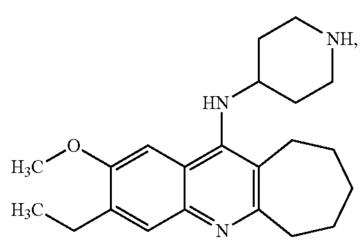 [SMILES: CCc1cc2nc3c(c(NC4CCNCC4)c2cc1OC)CCCCC3] |
| 287 | 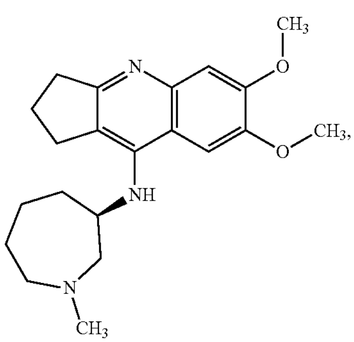 [SMILES: COc1cc2nc3c(c(N[C@@H]4CCCCN(C)C4)c2cc1OC)CCC3] | 350 | 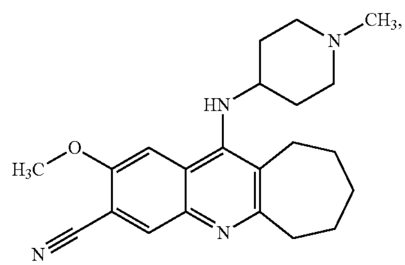 [SMILES: COc1cc2c(NC3CCN(C)CC3)c3c(nc2cc1C#N)CCCCC3] |

-continued

| No | Structure | No | Structure |
|---|---|---|---|
| 288 | 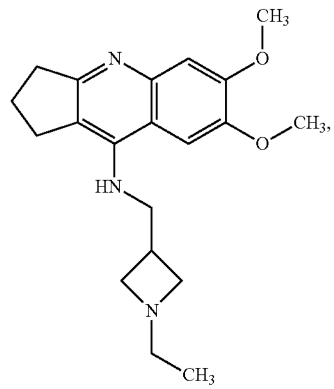 [SMILES: CCN1CC(CNc2c3c(nc4cc(OC)c(OC)cc24)CCC3)C1] | 351 | 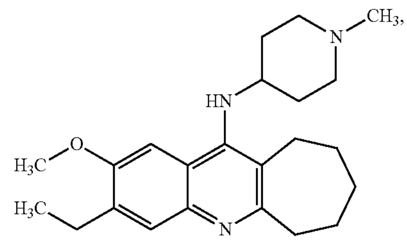 |
| 289 | 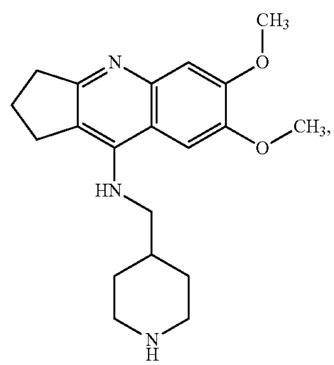 [SMILES: COc1cc2nc3c(c(NCC4CCNCC4)c2cc1OC)CCC3] | 354 | 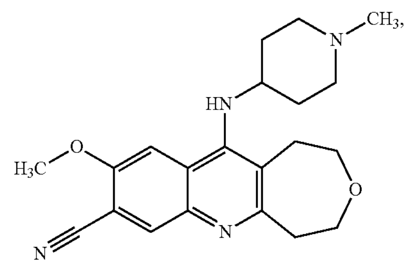 |
| 291 | 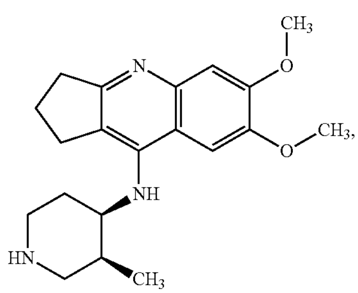 [SMILES: COc1cc2nc3c(c(N[C@@H]4CCNC[C@@H]4C)c2cc1OC)CCC3] | 355 | 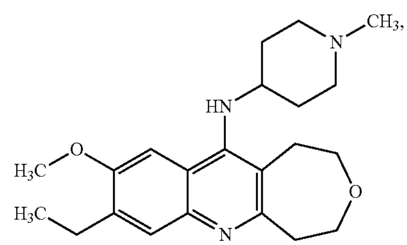 |
| 292 | 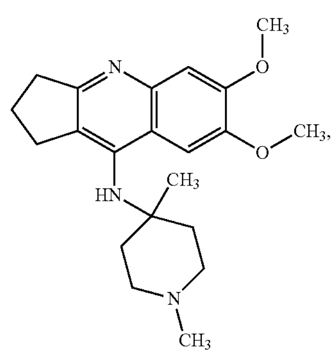 [SMILES: COc1cc2nc3c(c(NC4(C)CCN(C)CC4)c2cc1OC)CCC3] | 358 | 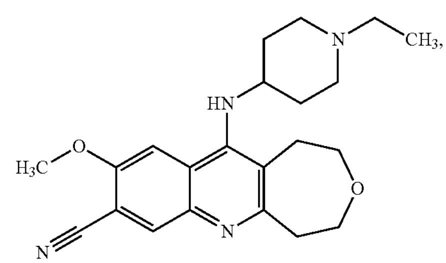 [SMILES: CCN1CCC(Nc2c3c(nc4cc(C#N)c(OC)cc24)CCOCC3)CC1] |

-continued

| No | Structure | No | Structure |
|---|---|---|---|
| 293 | 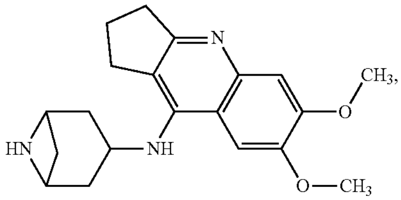 [SMILES: COc1cc2nc3c(c(NC4CC5CC(C4)N5)c2cc1OC)CCC3] | 359 | 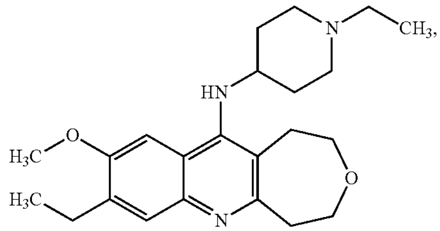 [SMILES: CCc1cc2nc3c(c(NC4CCN(CC)CC4)c2cc1OC)CCOCC3] |
| 295 | 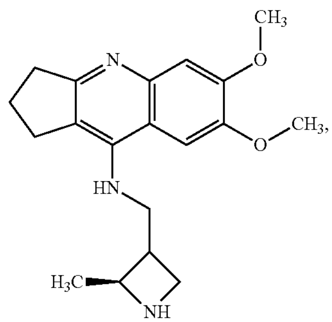 [SMILES: COc1cc2nc3c(c(NCC4CN[C@H]4C)c2cc1OC)CCC3] | 362 | 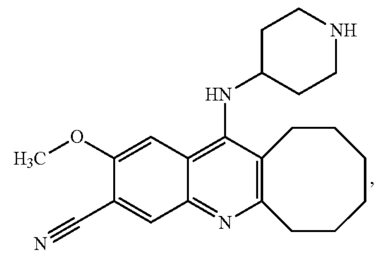 [SMILES: COc1cc2c(NC3CCNCC3)c3c(nc2cc1C#N)CCCCCC3] |
| 296 | 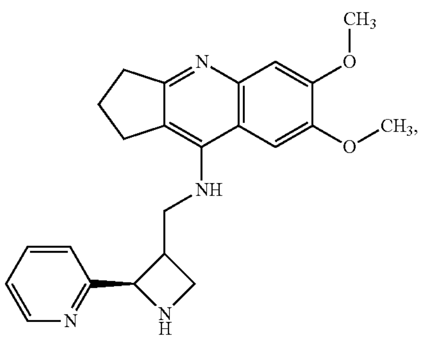 [SMILES: COc1cc2nc3c(c(NCC4CN[C@H]4c4ccccn4)c2cc1OC)CCC3] | 310 | 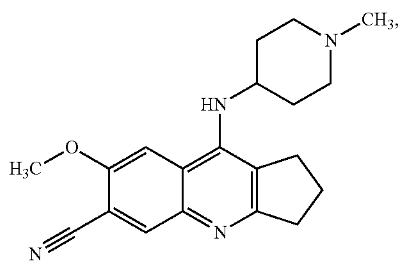 [SMILES: COc1cc2c(NC3CCN(C)CC3)c3c(nc2cc1C#N)CCC3] |
| 297 | 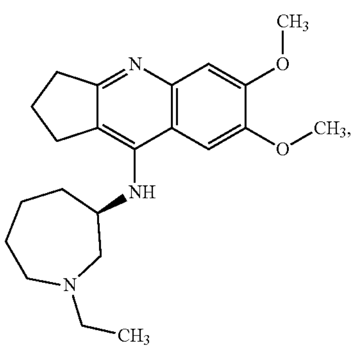 [SMILES: CCN1CCCC[C@@H](Nc2c3c(nc4cc(OC)c(OC)cc24)CCC3)C1] | 364 | 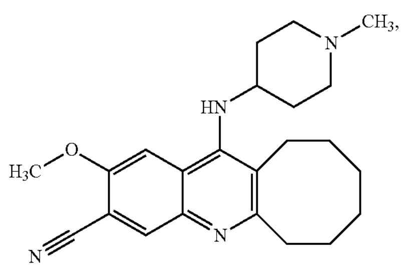 [SMILES: COc1cc2c(NC3CCN(C)CC3)c3c(nc2cc1C#N)CCCCCC3] |
| 298 | 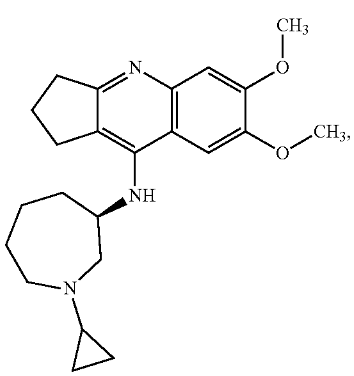 [SMILES: COc1cc2nc3c(c(N[C@@H]4CCCCN(C5CC5)C4)c2cc1OC)CCC3] | 366 | 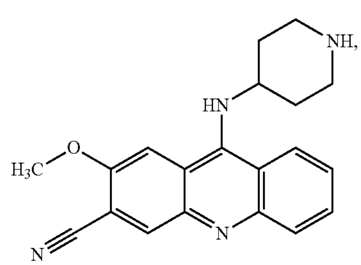 [SMILES: COc1cc2c(NC3CCNCC3)c3ccccc3nc2cc1C#N] |

-continued

| No | Structure | No | Structure |
|---|---|---|---|
| 299 | 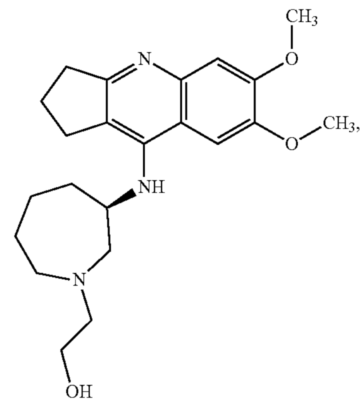 [SMILES: COc1cc2nc3c(c(N[C@@H]4CCCCN(CCO)C4)c2cc1OC)CCC3] | 367 | 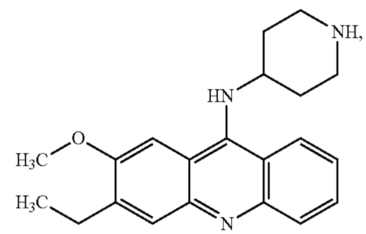 |
| 300 | 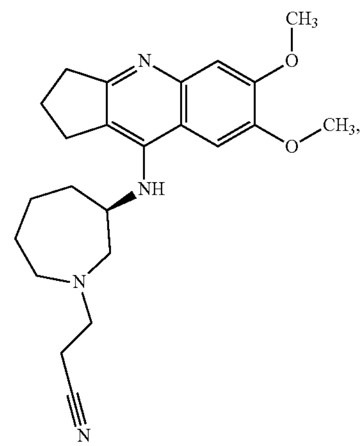 [SMILES: COc1cc2nc3c(c(N[C@@H]4CCCCN(CCC#N)C4)c2cc1OC)CCC3] | 370 | 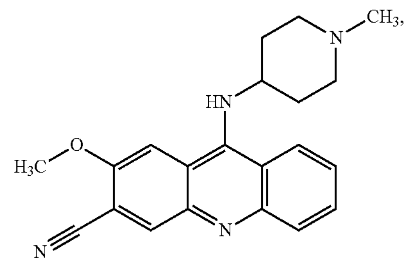 [SMILES: COc1cc2c(NC3CCN(C)CC3)c3ccccc3nc2cc1C#N] |
| 301 | 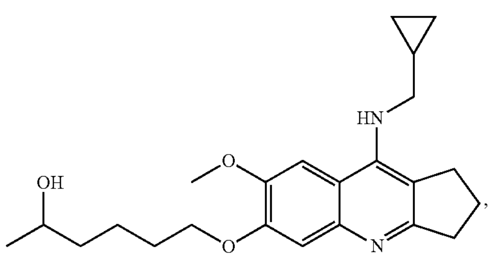 [SMILES: COc1cc2c(NCC3CC3)c3c(nc2cc1OCCCCC(C)O)CCC3] | 371 | 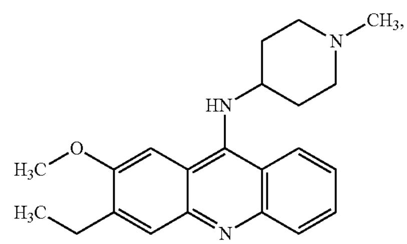 [SMILES: CCc1cc2nc3ccccc3c(NC3CCN(C)CC3)c2cc1OC] |
| 303 | 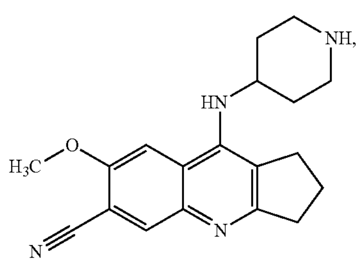 [SMILES: COc1cc2c(NC3CCNCC3)c3c(nc2cc1C#N)CCC3] | 391 | 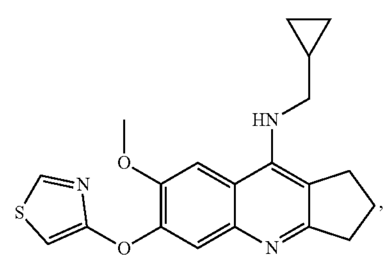 [SMILES: COc1cc2c(NCC3CC3)c3c(nc2cc1Oc1cscn1)CCC3] |

-continued

| No | Structure | No | Structure |
|---|---|---|---|
| 304 | (structure) | 392 | (structure) |
| 306 | (structure) | 393 | (structure) |
| 308 | (structure) | 394 | (structure) |
| 311 | (structure) | 395 | (structure) |
| 313 | (structure) | 396 | (structure) |

-continued

| No | Structure | No | Structure |
|---|---|---|---|
| 315 | 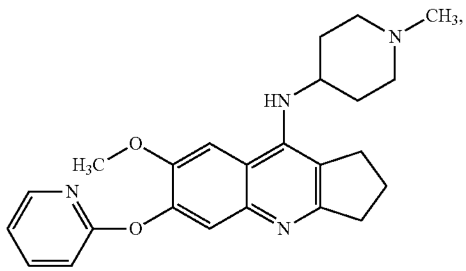 [SMILES: COc1cc2c(NC3CCN(C)CC3)c3c(nc2cc1Oc1ccccn1)CCC3] | 397 | 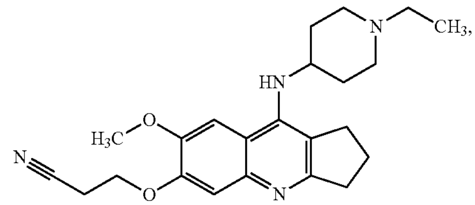 [SMILES: CCN1CCC(Nc2c3c(nc4cc(OCCC#N)c(OC)cc24)CCC3)CC1] |
| 374 | 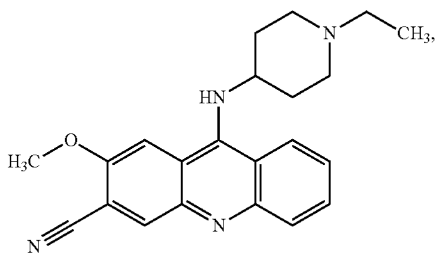 [SMILES: CCN1CCC(Nc2c3ccccc3nc3cc(C#N)c(OC)cc23)CC1] | 398 | 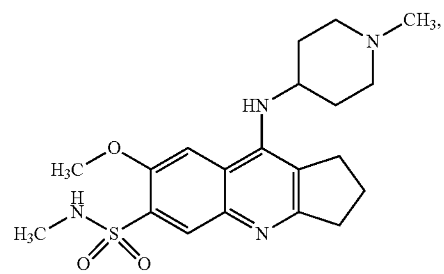 [SMILES: CNS(=O)(=O)c1cc2nc3c(c(NC4CCN(C)CC4)c2cc1OC)CCC3] |
| 375 | 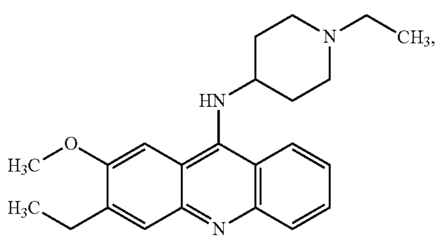 [SMILES: CCc1cc2nc3ccccc3c(NC3CCN(CC)CC3)c2cc1OC] | 399 | 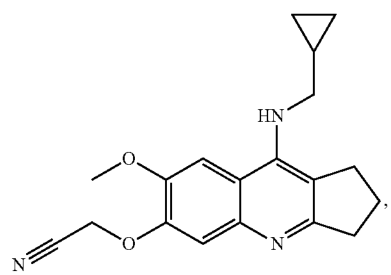 [SMILES: COc1cc2c(NCC3CC3)c3c(nc2cc1OCC#N)CCC3] |
| 378 | 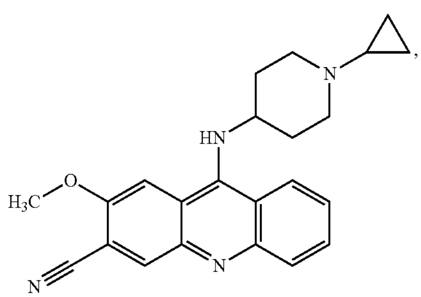 [SMILES: COc1cc2c(NC3CCN(C4CC4)CC3)c3ccccc3nc2cc1C#N] | 400 | 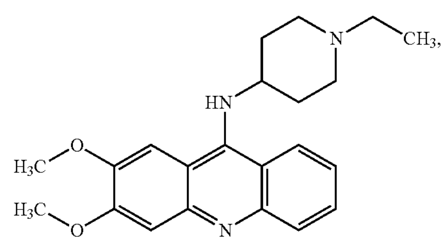 [SMILES: CCN1CCC(Nc2c3ccccc3nc3cc(OC)c(OC)cc23)CC1] |
| 379 | 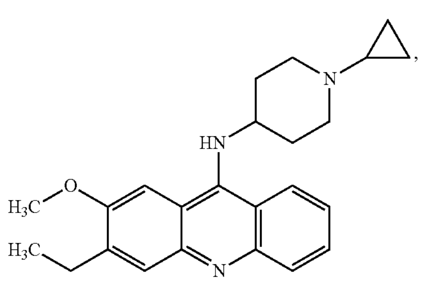 | 401 | 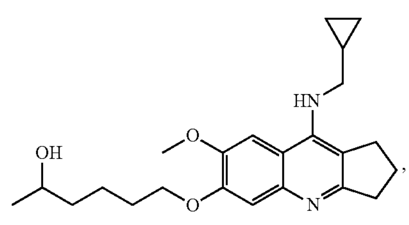 [SMILES: COc1cc2c(NCC3CC3)c3c(nc2cc1OCCCCC(C)O)CCC3] |

| No | Structure | No | Structure |
|---|---|---|---|
| 390 | 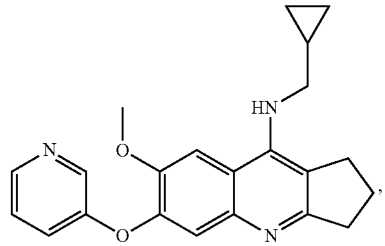 [SMILES: COc1cc2c(NCC3CC3)c3c(nc2cc1Oc1cccnc1)CCC3] | 384 | |
| 382 | 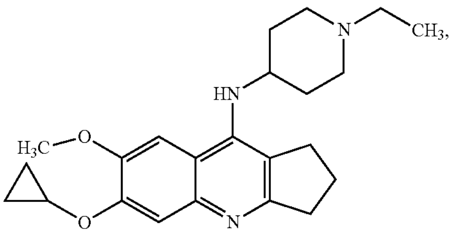 [SMILES: CCN1CCC(Nc2c3c(nc4cc(OC5CC5)c(OC)cc24)CCC3)CC1] | 385 | 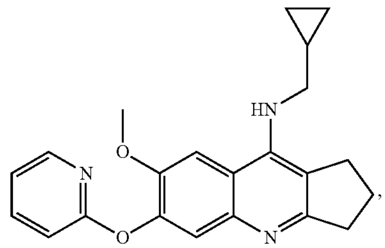 |
| 383 | 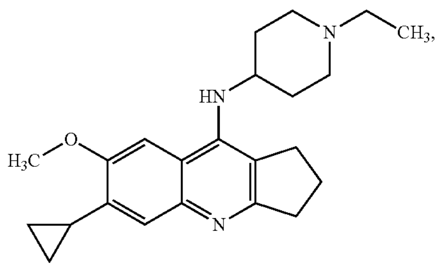 [SMILES: CCN1CCC(Nc2c3c(nc4cc(C5CC5)c(OC)cc24)CCC3)CC1] | 386 | 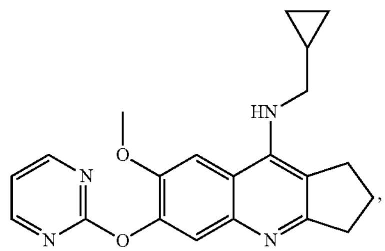 [SMILES: COc1cc2c(NCC3CC3)c3c(nc2cc1Oc1ncccn1)CCC3] |
| 388 | , and | 387 | , |
| 389 | | | | or a pharmaceutically acceptable salt thereof.

26. A pharmaceutical composition comprising a compound of claim 1, or a pharmaceutically acceptable salt thereof; and a pharmaceutically acceptable excipient.

27. A method of ameliorating or treating a hemoglobinopathy, wherein the hemoglobinopathy is sickle cell disease or beta-thalassemia, comprising administering a therapeutically effective amount of a compound of claim 1, or a pharmaceutically acceptable salt thereof, or the pharmaceutical composition of claim 26 to a subject in need thereof.

* * * * *